US007666646B2

(12) United States Patent
Jacobs et al.

(10) Patent No.: US 7,666,646 B2
(45) Date of Patent: Feb. 23, 2010

(54) CRYSTAL STRUCTURE OF HUMAN PIM-1 KINASE PROTEIN COMPLEXES AND BINDING POCKETS THEREOF, AND USES THEREOF IN DRUG DESIGN

(75) Inventors: Marc Jacobs, Roslindale, MA (US); Brian Hare, Arlington, MA (US); Lovorka Swenson, Belmont, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 76 days.

(21) Appl. No.: 11/242,666

(22) Filed: Oct. 4, 2005

(65) Prior Publication Data

US 2007/0031956 A1 Feb. 8, 2007

Related U.S. Application Data

(63) Continuation of application No. PCT/US2004/010345, filed on Apr. 1, 2004.

(60) Provisional application No. 60/460,843, filed on Apr. 4, 2003, provisional application No. 60/552,526, filed on Mar. 12, 2004.

(51) Int. Cl.
*C12N 9/12* (2006.01)
(52) U.S. Cl. .................................................. 435/194
(58) Field of Classification Search ..................... None
See application file for complete search history.

(56) References Cited

U.S. PATENT DOCUMENTS

| 4,886,646 | A | 12/1989 | Carter et al. |
| 5,096,676 | A | 3/1992 | McPherson et al. |
| 5,130,105 | A | 7/1992 | Carter et al. |
| 5,221,410 | A | 6/1993 | Kushner et al. |
| 5,400,741 | A | 3/1995 | DeTitta et al. |
| 5,884,230 | A | 3/1999 | Srinivasan et al. |
| 2004/0142864 | A1* | 7/2004 | Bremer et al. ................. 514/12 |
| 2004/0171062 | A1 | 9/2004 | Hirth et al. |

OTHER PUBLICATIONS

McPherson et al., Eur. J. Biochem. 189:1-23, 1990.*
Branden et al., "Introduction to Protein Structure Second Edition", Garland Publishing Inc., New York, 1999, pp. 374-375.*
Drenth, "Principles of X-ray Crystallography," Springer, New York, 1995, pp. 1-21.*
"Crystallization of Nucleic Acids and Proteins," Ed. Ducruix and Giege, Oxford University Press, New York, 1999 at p. 394.*
Qian et al. Acta crystallographica Section F, Structural biology and crystallization communications, (Jan. 1, 2005) vol. 61, No. Pt 1, pp. 96-99.*
Kierzek et al., Biophys Chem 91:1-20, 2001.*
Ford et al., "Fusion Tails for the Recovery and Purification of Recombinant Proteins", Prot. Exp. Purif. 2:95-107, 1991.*
Giacovazzo et al., "Fundamentals of Crystallography, Second Edition", Oxford University Press, New York, NY, 2002, p. 744.*
GenBank Accession No. P11309, Dec. 1998.*
Gonzalez et al., Eur. J. Biochem. 268, 1869-1875, 2001.*
Novagen Technical Bulletin TB045, "pET-15b Vector", Dec. 1998.*
Allen et al., "*Pim*-2 Transgene Induces Lymphoid Tumors, Exhibiting Potent Synergy with c-*myc*", *Oncogene*, 15: 1133-1141 (1997).
Amson et al., "The Human Protooncogene Product p33pim Is Expressed During Fetal Hematopoiesis and in Diverse Leukemias", *Proc. Natl. Acad. Sci. USA*, 86: 8857-8861 (1989).
Balbes et al., "A Perspective of Modem Methods in Computer-Aided Drug Design", *Rev. in Comp. Chem.*, 5: 337-379 (1994).
Bartlett et al., "CAVEAT: A Program to Facilitate the Structure-Derived Design of Biologically Active Molecules", *Mol. Recognition*, 78:182-196 (1989).
Bax et al., "The Structure of Phosphorylated GSK-3β Complexed with a Peptide, FRATtide, that Inhibits β-Catenin Phosphorylation", *Structure*, 9: 1143-1152 (2001).
Berg et al., "K-252a Inhibits Nerve Growth Factor-Induced *trk* Proto-Oncogene Tyrosine Phosphorylation and Kinase Activity", *J. Biol. Chem.*, 5: 13-16 (1992).
Bhattacharya et al., "Pim-1 Associates with Protein Complexes Necessary for Mitosis", *Chromosome*, 111: 80-95 (2002).
Blundell et al., "Knowledge-Based Prediction of Protein Structures and the Design of Novel Molecules", *Nature*, 326: 347-352 (1987).
Böhm, "The Computer Program LUDI: A New Method for the De Novo Design of Enzyme Inhibitors", *J. Comp. Aid. Molec. Design*, 6: 61-78 (1992).
Breuer et al., "Carcinogen-Induced Lymphomagenesis in *pim*-1 Transgenic Mice: Dose Dependence and Involvement of *myc* and *ras*", *Cancer Res.*, 51: 958-963 (1991).
Brünger et al., "Crystallography & NMR System: A New Software Suite for Macromolecular Structure Determination", *Acta Cryst.*, D54: 905-921 (1998).
Carson, "Ribbons 2.0", *J. Appl., Cryst.*, 24: 958-961 (1991).
Chayen, "A Novel Technique to Control the Rate of Vapour Diffusion, Giving Larger Protein Crystals", *J. Appl. Cryst.*, 30: 198-202 (1997).
Cheetham et al., "Crystal Structure of Aurora-2, an Oncogenic Serine/Threonine Kinase", *J. Biol. Chem.*, 277: 42419-42422 (2002).
Cohen et al., "Molecular Modeling Software and Methods for Medicinal Chemistry", *J. Med. Chem.*, 33: 883-894 (1990).

(Continued)

*Primary Examiner*—David J Steadman
(74) *Attorney, Agent, or Firm*—Ropes & Gray, LLP; James F. Haley, Jr.; Raymond M. Doss

(57) ABSTRACT

The present invention relates to the X-ray analysis of crystalline molecules or molecular complexes of human Pim-1. The present invention also relates to Pim-1-like binding pockets. The present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to Pim-1 protein, Pim-1 protein complexes, or homologues thereof. The invention also relates to crystallizable compositions and crystals comprising Pim-1 protein, Pim-1 protein complexes with adenosine, staurosporine or 2-(4-morpholinyl)-8-phenyl-4H-1-benzopyran-4-one and methods to produce these crystals.

1 Claim, 136 Drawing Sheets

OTHER PUBLICATIONS

Cohen, "Protein Kinases—The Major Drug Targets of the Twenty-First Century?", *Nat. Rev. Drug Discov.*, 1: 309-315 (2002).

Cory et al., "MATCHMOL, An Interactive Computer Graphics Procedure for Superposition of Molecular Models", *J. Mol. Graphics*, 2: 39-42 (1984).

D'Arcy et al., "A Novel Approach to Crystallising Proteins under Oil", *J. Cryst Growth*, 168: 175-180 (1996).

Davies et al., "Specificity and Mechanism of Action of Some Commonly Used Protein Kinase Inhibitors", *Biochem. J.*, 351: 95-105 (2000).

De Bondt et al., "Crystal Structure of Cyclin-Dependent Kinase 2", *Nature*, 363: 595-602 (1993).

Domen et al., "Analysis of *Pim*-1 Function in Mutant Mice", *Leukemia*, 7: S108-S112 (1993).

Domen et al., "*Pim*-1 Levels Determine the Size of Early B Lymphoid Compartments in Bone Marrow", *J. Exp. Med.*, 178: 1665-1673 (1993).

Dumas, "Protein Kinase Inhibitors: Emerging Pharmacophores 1997-2000", *Exp. Opin. Ther. Patents*, 11: 405-429 (2001).

Eisen et al., "HOOK: A Program for Finding Novel Molecular Architectures that Satisfy the Chemical and Steric Requirements of a Macromolecule Binding Site", *Proteins: Struct. Funct. Genet.*, 19: 199-221 (1994).

El-kholy et al., "The Phosphatidylinositol 3-Kinase Inhibitor LY294002 Potently Blocks Kv Currents via a Direct Mechanism", *FASEB J.*, 17: 720-738 (2003) [copy enclosed published online Feb. 5, 2003].

Ethier et al., "LY294002, but Not Wortmannin, Increases Intracellular Calcium and Inhibits Calcium Transients in Bovine and Human Airway Smooth Muscle Cells", *Cell Calcium*, 32: 31-38 (2002).

Feldman et al., "KID-1, A Protein Kinase Induced by Depolarization in Brain", *J. Biol. Chem.*, 273: 16535-16543 (1998).

Fetrow an et al., "New Programs for Protein Tertiary Structure Prediction", *Bio/Tech.*, 11: 479-484 (1993).

Fox et al., "Kinetic Mechanism and ATP-Binding Site Reactivity of p38γ MAP Kinase", *FEBS Lett.*, 461: 323-328 (1999).

Fox et al., "A Single Amino Acid Substitution Makes ERK2 Susceptible to Pyridinyl Imidazole Inhibitors of p38 MAP Kinase", *Prot. Sci.* 7: 2249-2255 (1998).

Friedmann et al., "Characterization of the Proto-Oncogene Pim-1: Kinase Activity and Substrate Recognition Sequence", *Arch. Biochem. Biophys.*, 298: 594-601 (1992).

Gillet et al., "SPROUT: A Program for Structure Generation", *J. Comp. Aid. Molec. Des.*, 7: 127-153 (1993).

Goodford, "A Computational Procedure for Determining Energetically Favorable Binding Sites on Biologically Important Macromolecules", *J. Med. Chem.*, 28: 849-857 (1985).

Goodsell et al., "Automated Docking of Substrates to Proteins by Simulated Annealing", *Proteins: Struct. Funct. Genet.*, 8: 195-202 (1990).

Greer, "Comparative Modeling of Homologous Proteins", *Methods Enzymol.*, 202: 239-252 (1991).

Gschwend et al., "Molecular Docking Towards Drug Discovery", *J. Mol. Recog.*, 9: 175-186 (1996).

Guex a et al., "SWISS-MODEL and the Swiss-PdbViewer: An Environment for Comparative Protein Modeling", *Electrophoresis*, 18:2714-2723 (1997).

Guida, "Software for Structure-Based Drug Design", *Curr. Opin. Struct. Biol.*, 4: 777-781 (1994).

Hanks et al., "The Protein Kinase Family: Conserved Features and Deduced Phylogeny of the Catalytic Domains", *Science*, 241: 42-52 (1988).

Hanks et al., "Protein Kinase Catalytic Domain Sequence Database: Identification of Conserved Features of Primary Structure and Classification of Family Members", *Methods Enzymol.*, 200: 38-62 (1991).

Harris et al., "Atypical Isoforms of PKC and Insulin Secretion From Pancreatic β-Cells: Evidence Using Gö 6976 and Ro 31-8220 as PKC Inhibitors", *Biochem. Biophys. Res. Comm.*, 227:672-676 (1996).

Hashimoto et al., "Potent and Preferential Inhibition of $Ca^{2+}$ / Calmodulin-Dependent Protein Kinase ll by K252a and Its Derivative, KT5926", *Biochem. Biophys. Res. Comm.*, 181: 423-429 (1991).

Higgins et al., "Using CLUSTAL for Multiple Sequence Alignments", *Methods Enzymol.*, 266: 383-402 (1996).

Hoover et al., "Recombinant Human Pim-1 Protein Exhibits Serine/Threonine Kinase Activity", *J. Biol. Chem.*, 266: 14018-14023 (1991).

Huse a et al., "The Conformational Plasticity of Protein Kinase", *Cell*, 109: 275-282 (2002).

Ishibashi et al., "Pim-1 Translocates Sorting Nexin 6/TRAF4-Associated Factor 2 from Cytoplasm to Nucleus", *FEBS Lett.*, 506: 33-38 (2001).

Johnson et al., "Knowledge-Based Protein Modeling", *Crit. Rev. Biochem. Mol. Biol.*, 29: 1-68 (1994).

Jones et al., "Improved Methods for Building Protein Models in Electron Density Maps and the Location of Errors in these Models", *Acta Cryst.*, A47: 110-119 (1991).

Koike et al, "Identification of Heterochromatin Protein 1 (HP1) as a Phosphorylation Target by Pim-1 Kinase and the Effect of Phosphorylation on the Transcriptional Repression Function of HP1", *FEBS Lett.*, 467: 17-21 (2000).

Krumenacker et al., "Prolactin Signaling to *pim*-1 Expression: A Role for Phosphatidylinositol 3-Kinase", *J. Neuroimmunology*, 113: 249-259 (2001).

Kuntz et al., "A Geometric Approach to Macromolecule-Ligand Interactions", *J. Mol. Biol.*, 161: 269-288 (1982).

Krishnan et al., "Prolactin-Regulated *pim*-1 Transcription", *Endocrine*, 20: 123-129 (2003).

Lattman, "Use of the Rotation and Translation Functions", *Methods Enzymol.*, 115: 55-77 (1985).

Lauri et al., "CAVEAT: A Program to Facilitate the Design of Organic Molecules", *J. Comp. Aid. Mol. Des.*, 8: 51-66 (1994).

Leverson et al., "Pim-1 Kinase and p100 Cooperate to Enhance c-Myb Activity", *Mol. Cell*, 2: 417-425 (1998).

Limón et al., "The Phosphatidylinositol 3-Kinase Inhibitor LY294002 Binds the Estrogen Receptor and Inhibits 17β-Estradiol-Induced Transcriptional Activity of an Estrogen Sensitive Reporter Gene", *Mol. Cell. Endocrinol.*, 200: 199-202 (2003).

Maita et al., "PAP-1, A Novel Target Protein of Phosphorylation by Pim-1 Kinase", *Eur. J. Biochem.*, 267: 5168-5178 (2000).

Manning et al., "The Protein Kinase Complement of the Human Genome", *Science*, 298: 1912-1934 (2002).

Martin, "3D Database Searching in Drug Design", *J. Med. Chem.*, 35: 2145-2154 (1992).

Meeker et al., "Characterization of the Human Pim-1 Gene: A Putative Proto-Oncogene Coding for a Tissue Specific Member of the Protein Kinase Family", *Oncogene Res.*, 1: 87-101 (1987).

Meng et al., "Automated Docking with Grid-Based Energy Evaluation", J. Comp. Chem., 13: 505-524 (1992).

Miranker a et al., "Functionality Maps of Binding Sites: A Multiple Copy Simultaneous Search Method", *Proteins: Struct. Fund. Genet.*, 11: 29-34 (1991).

Mizuno et al., "Staurosporine-Related Compounds, K252a and UCN-01, Inhibit Both cPKC and nPKC", *FEBS Lett.*, 330: 114-116 (1993).

Mochizuki et al., "Physical and Functional Interactions Between Pim-1 Kinase and Cdc25A Phosphatase", *J. Biol. Chem.*, 274: 18659-18666 (1999).

Nagarajan et al., "Localization of the Human *pim* Oncogene (*Pim*) to a Region of Chromosome 6 Involved in Translocations in Acute Leukemias", *Proc. Natl. Acad. Sci. USA*, 83: 2556-2560 (1986).

Nagata et al., "Regulation of Megakaryocytopoiesis by Thrombopoietin and Stromal Cells", *Leukemia*, 11: 435-438 (1997).

Narayana et al., "Crystal Structure of a Polyhistidine-Tagged Recombinant Catalytic Subunit of cAMP-Dependent Protein Kinase Complexed with the Peptide Inhibitor PKI(5-24) and Adenosine", *Biochemistry*, 36: 4438-4448 (1997).

Navaza, "AMoRe: an Automated Package for Molecular Replacement", *Acta Cryst.*, A50: 157-163 (1994).

Navia et al., "Use of Structural Information in Drug Design", *Curr. Opin. Struct. Biol.*, 2: 202-210 (1992).

Nishibata et al., "Automatic Creation of Drug Candidate Structures Based on Receptor Structure. Starting Point for Artificial Lead Generation", *Tetrahedron*, 47: 8985-8990 (1991).

O'Farrell et al., "Signaling Pathways Activated in a Unique Mast Cell Line Where Interleukin-3 Supports Survival and Stem Cell Factor is Required for a Proliferative Response", *Blood*, 87: 3655-3668 (1996).

Otwinowski and Minor, "Processing of X-Ray Diffraction Data Collected in Oscillation Mode", *Methods Enzymol.*, 276: 307-326 (1997).

Owen et al., "Two Structures of the Catalytic Domain of Phosphorylase Kinase: An Active Protein Kinase Complexed with Substrate Analogue and Product", *Structure*, 3: 467-482 (1995).

Pacold et al., "Crystal Structure and Functional Analysis of Ras Binding to its Effector Phosphoinositide 3-Kinase γ", *Cell*, 103: 931-943 (2000).

Padma et al., "The Human *PIM*-1 Gene Product is a Protein Serine Kinase", *Cancer Res.*, 51: 2486-2489 (1991).

Palaty et al., "Phosphorylation Site Substrate Specificity Determinants for the Pim-1 Protooncogene-Encoded Protein Kinase", *Biochem. Cell. Biol.*, 75: 153-162 (1997).

Palaty et al., "Identification of the Autophosphorylation Sites of the *Xenopus laevis* Pim-1 Proto-Oncogene-Encoded Protein Kinase", *J. Biol. Chem.*, 272: 10514-10521 (1997).

Pannu et al., "Improved Structure Refinement through Maximum Likelihood", *Acta Cryst.*, A52: 659-668 (1996).

Pav et al., "Microtube Batch Protein Crystallation: Applications to Human Immunodeficiency Virus Type 2 (HIV-2) Protease and Human Renin", *Proteins: Struct. Funct. Genet.*, 20: 98-102 (1994).

Pflugrath, "The Finer Things in X-ray Diffraction Data Collection", *Acta Cryst.*, D55: 1718-1725 (1999).

Philo, "A Method for Directly Fitting the Time Derivative of Sedimentation Velocity Data and an Alternative Algorithm for Calculating Sedimentation Coefficient Distribution Functions", *Anal. Biochem.*, 279: 151-163 (2000).

Philo, "An Improved Function for Fitting Sedimentation Velocity Data for Low-Molecular-Weight Solutes", *Biophys. J.*, 72: 435-444 (1996).

Pierce et al., "Kinase Inhibitors and the Case for $CH \cdots O$ Hydrogen Bonds in Protein-Ligand Binding", *Proteins: Struct. Funct. Genet.*, 49: 567-576 (2002).

Prade et al., "Staurosporine-Induced Conformational-Changes of cAMP-Dependent Protein Kinase Catalytic Subunit Explain Inhibitory Potential", *Structure*, 5: 1627-1637 (1997).

Rainio et al., "Cutting Edge: Transcriptional Activity of NFATc1 is Enhanced by the Pim-1 Kinase", *J. Immunol.*, 168: 1524-1527 (2002).

Redington, "Molfit: A Computer Program for Molecular Superposition", *Comput Chem.*, 16: 217-222 (1992).

Rice et al., "Torsion Angle Dynamics: Reduced Variable Conformational Sampling Enhances Crystallographic Structure Refinement", *Proteins: Struct. Funct. Genet.*, 19: 277-290 (1994).

Roversi et al., "Modelling Prior Distributions of Atoms for Macro-Molecular Refinement and Completion", *Acta Cryst.*, D56: 1316-1323 (2000).

Sakai et al., "The Kinase Domain of JAK2 Mediates Induction of Bcl-2 and Delays Cell Death in Hematopoietic Cells", *J. Biol. Chem.*, 272: 12350-12358 (1997).

Schnare et al., "Comprehensive Comparison of Structural Characteristics in Eukaryotic Cytoplasmic Large Subunit (23 S-like) Ribosomal RNA", *J. Mol. Biol.*, 256: 701-719 (1996).

Selten et al., "The Primary Structure of the Putative Oncogene *pim*-1 Shows Extensive Homology with Protein Kinases", *Cell*, 46: 603-611 (1986).

Smith et al., "Comparison of Biosequences", *Adv. In App. Math.*, 2: 482-489 (1981).

Szklarz et al., "Use of Homology Modeling in Conjunction with Site-Directed Mutagenesis for Analysis of Structure-Function Relationships of Mammalian Cytochromes P450", *Life Sci.*, 61: 2507-2520 (1997).

ter Haar et al., "Structure of GSK3β Reveals a Primed Phosphorylation Mechanism", *Nature Struct. Biol.*, 8: 593-596 (2001).

Tereshko et al., "Crystal Structures of the Catalytic Domain of Human Protein Kinase Associated with Apoptosis and Tumor Suppression", *Nature Struct. Biol.*, 8: 899-907 (2001).

van der Lugt et al., "Proviral Tagging in Eμ-myc Transgenic Mice Lacking the *Pim-1* Proto-Oncogene Leads to Compensatory Activation of *Pim-2*", *EMBO J.*, 14: 2536-2544 (1995).

van Lohuizen et al., "Predisposition to Lymphomagenesis in *pim*-1 Transgenic Mice: Cooperation with c-*myc* and N-*myc* in Murine Leukemia Virus-Induced Tumors", *Cell*, 56: 673-682 (1989).

Vlahos et al., "A Specific Inhibitor of Phosphatidylinositol 3-Kinase, 2-(4-Morpholinyl)-8-Phenyl-4H-1-Benzopyran-4-One (LY294002)", *J. Biol. Chem.*, 269: 5241-5248 (1994).

Walker et al., "Structural Insights into Phosphoinositide 3-Kinase Catalysis and Signalling", *Nature*, 402: 313-320 (1999).

Wang et al., "Pim-1: A Serine/Threonine Kinase with a Role in Cell Survival, Proliferation, Differentiation and Tumorigenesis", *J. Vet. Sci.*, 2: 167-179 (2001).

Wang et al., "Pim-1 Negatively Regulates the Activity of PTP-U2S Phosphatase and Influences Terminal Differentiation and Apoptosis of Monoblastoid Leukemia Cells", *Arch. Biochem. Biophys.*, 390: 9-18 (2001).

Wang et al., "Phosphorylation of the Cell Cycle Inhibitor $p21^{CIP1/WAF1}$ by Pim-1 Kinase", *Biochem. Biophys. Acta*, 1593: 45-55 (2002).

Winn et al., "Pim-1 Phosphorylates the DNA Binding Domain of c-Myb", *Cell Cycle*, 2: 258-262 (2003).

Wishart et al., "Constrained Multiple Sequence Alignment Using XALIGN", *Comput Appl. Biosci.*, 10: 687-688 (1994).

Xie et al., "Crystal Structure of JNK3: A Kinase Implicated in Neuronal Apoptosis", *Structure*, 6: 983-991 (1998).

Zheng et al., "Crystal Structure of the Catalytic Subunit of cAMP-Dependent Protein Kinase Complexed with MgATP and Peptide Inhibitor", *Biochemistry*, 32: 2154-2161 (1993).

"The *CCP4* Suite: Programs for Protein Crystallography", Collaborative Computational Project, No. 4, *Acta. Cryst.*, D50: 760-763 (1994).

\* cited by examiner

FIGURE 1A-1

| ATOM | Type | Resid | # | X | Y | Z | Occ | B | | |
|---|---|---|---|---|---|---|---|---|---|---|
| ATOM | 1 | CB | PRO A | 33 | -33.171 | 25.235 | 14.378 | 1.00 | 95.79 | A C |
| ATOM | 2 | CG | PRO A | 33 | -33.277 | 26.076 | 15.657 | 1.00 | 96.01 | A C |
| ATOM | 3 | C | PRO A | 33 | -31.733 | 26.730 | 12.964 | 1.00 | 95.96 | A C |
| ATOM | 4 | O | PRO A | 33 | -32.747 | 27.406 | 12.773 | 1.00 | 96.06 | A O |
| ATOM | 5 | N | PRO A | 33 | -30.986 | 25.884 | 15.170 | 1.00 | 95.87 | A N |
| ATOM | 6 | CD | PRO A | 33 | -31.899 | 25.933 | 16.328 | 1.00 | 95.61 | A C |
| ATOM | 7 | CA | PRO A | 33 | -31.750 | 25.555 | 13.940 | 1.00 | 96.01 | A C |
| ATOM | 8 | N | LEU A | 34 | -30.575 | 26.963 | 12.350 | 1.00 | 95.36 | A N |
| ATOM | 9 | CA | LEU A | 34 | -30.409 | 28.059 | 11.403 | 1.00 | 94.72 | A C |
| ATOM | 10 | CB | LEU A | 34 | -29.085 | 27.904 | 10.636 | 1.00 | 94.44 | A C |
| ATOM | 11 | CG | LEU A | 34 | -28.870 | 26.728 | 9.681 | 1.00 | 94.36 | A C |
| ATOM | 12 | CD1 | LEU A | 34 | -29.575 | 26.989 | 8.362 | 1.00 | 94.44 | A C |
| ATOM | 13 | CD2 | LEU A | 34 | -27.385 | 26.552 | 9.431 | 1.00 | 95.00 | A C |
| ATOM | 14 | C | LEU A | 34 | -31.574 | 28.151 | 10.425 | 1.00 | 94.42 | A C |
| ATOM | 15 | O | LEU A | 34 | -31.961 | 29.244 | 10.009 | 1.00 | 94.14 | A O |
| ATOM | 16 | N | GLU A | 35 | -32.133 | 26.999 | 10.068 | 1.00 | 94.17 | A N |
| ATOM | 17 | CA | GLU A | 35 | -33.256 | 26.944 | 9.138 | 1.00 | 93.91 | A C |
| ATOM | 18 | CB | GLU A | 35 | -33.519 | 25.495 | 8.704 | 1.00 | 94.02 | A C |
| ATOM | 19 | CG | GLU A | 35 | -32.270 | 24.714 | 8.310 | 1.00 | 94.85 | A C |
| ATOM | 20 | CD | GLU A | 35 | -31.586 | 24.054 | 9.499 | 1.00 | 95.64 | A C |
| ATOM | 21 | OE1 | GLU A | 35 | -31.674 | 24.601 | 10.619 | 1.00 | 96.81 | A O |
| ATOM | 22 | OE2 | GLU A | 35 | -30.949 | 22.994 | 9.312 | 1.00 | 95.28 | A O |
| ATOM | 23 | C | GLU A | 35 | -34.501 | 27.512 | 9.810 | 1.00 | 93.24 | A C |
| ATOM | 24 | O | GLU A | 35 | -35.502 | 26.819 | 9.963 | 1.00 | 93.80 | A O |
| ATOM | 25 | N | SER A | 36 | -34.433 | 28.775 | 10.215 | 1.00 | 92.32 | A N |
| ATOM | 26 | CA | SER A | 36 | -35.557 | 29.421 | 10.880 | 1.00 | 90.93 | A C |
| ATOM | 27 | CB | SER A | 36 | -35.897 | 28.674 | 12.173 | 1.00 | 91.28 | A C |
| ATOM | 28 | OG | SER A | 36 | -36.968 | 29.301 | 12.856 | 1.00 | 90.93 | A O |
| ATOM | 29 | C | SER A | 36 | -35.274 | 30.886 | 11.203 | 1.00 | 89.99 | A C |
| ATOM | 30 | O | SER A | 36 | -36.172 | 31.729 | 11.137 | 1.00 | 89.75 | A O |
| ATOM | 31 | N | GLN A | 37 | -34.027 | 31.189 | 11.554 | 1.00 | 88.38 | A N |
| ATOM | 32 | CA | GLN A | 37 | -33.649 | 32.556 | 11.896 | 1.00 | 86.71 | A C |
| ATOM | 33 | CB | GLN A | 37 | -32.488 | 32.545 | 12.885 | 1.00 | 87.32 | A C |
| ATOM | 34 | CG | GLN A | 37 | -32.639 | 31.520 | 13.984 | 1.00 | 89.05 | A C |
| ATOM | 35 | CD | GLN A | 37 | -31.403 | 31.418 | 14.847 | 1.00 | 90.11 | A C |
| ATOM | 36 | OE1 | GLN A | 37 | -31.234 | 30.455 | 15.597 | 1.00 | 91.48 | A O |
| ATOM | 37 | NE2 | GLN A | 37 | -30.531 | 32.416 | 14.751 | 1.00 | 90.30 | A N |
| ATOM | 38 | C | GLN A | 37 | -33.245 | 33.334 | 10.652 | 1.00 | 84.86 | A C |
| ATOM | 39 | O | GLN A | 37 | -33.080 | 34.553 | 10.696 | 1.00 | 85.24 | A O |
| ATOM | 40 | N | TYR A | 38 | -33.093 | 32.623 | 9.541 | 1.00 | 82.50 | A N |
| ATOM | 41 | CA | TYR A | 38 | -32.701 | 33.242 | 8.284 | 1.00 | 80.74 | A C |
| ATOM | 42 | CB | TYR A | 38 | -31.224 | 32.952 | 7.994 | 1.00 | 78.99 | A C |
| ATOM | 43 | CG | TYR A | 38 | -30.285 | 33.439 | 9.066 | 1.00 | 76.51 | A C |
| ATOM | 44 | CD1 | TYR A | 38 | -29.932 | 34.779 | 9.147 | 1.00 | 75.93 | A C |
| ATOM | 45 | CE1 | TYR A | 38 | -29.111 | 35.246 | 10.164 | 1.00 | 76.28 | A C |
| ATOM | 46 | CD2 | TYR A | 38 | -29.788 | 32.568 | 10.031 | 1.00 | 76.07 | A C |
| ATOM | 47 | CE2 | TYR A | 38 | -28.966 | 33.024 | 11.055 | 1.00 | 75.92 | A C |
| ATOM | 48 | CZ | TYR A | 38 | -28.634 | 34.365 | 11.116 | 1.00 | 75.79 | A C |
| ATOM | 49 | OH | TYR A | 38 | -27.845 | 34.836 | 12.140 | 1.00 | 76.01 | A O |
| ATOM | 50 | C | TYR A | 38 | -33.542 | 32.689 | 7.147 | 1.00 | 80.41 | A C |
| ATOM | 51 | O | TYR A | 38 | -33.943 | 31.527 | 7.173 | 1.00 | 80.41 | A O |
| ATOM | 52 | N | GLN A | 39 | -33.820 | 33.525 | 6.153 | 1.00 | 79.80 | A N |
| ATOM | 53 | CA | GLN A | 39 | -34.577 | 33.071 | 5.000 | 1.00 | 79.22 | A C |
| ATOM | 54 | CB | GLN A | 39 | -35.858 | 33.890 | 4.813 | 1.00 | 80.28 | A C |

FIGURE 1A-2

```
ATOM   55  CG  GLN A  39     -35.654  35.343   4.454  1.00 82.63      A C
ATOM   56  CD  GLN A  39     -36.950  36.021   4.039  1.00 84.05      A C
ATOM   57  OE1 GLN A  39     -36.952  37.182   3.625  1.00 84.23      A O
ATOM   58  NE2 GLN A  39     -38.061  35.295   4.148  1.00 84.07      A N
ATOM   59  C   GLN A  39     -33.667  33.193   3.784  1.00 77.93      A C
ATOM   60  O   GLN A  39     -33.318  34.294   3.352  1.00 78.00      A O
ATOM   61  N   VAL A  40     -33.271  32.042   3.252  1.00 76.24      A N
ATOM   62  CA  VAL A  40     -32.381  31.971   2.104  1.00 74.70      A C
ATOM   63  CB  VAL A  40     -32.055  30.508   1.765  1.00 75.22      A C
ATOM   64  CG1 VAL A  40     -31.516  29.802   3.000  1.00 74.95      A C
ATOM   65  CG2 VAL A  40     -33.303  29.804   1.254  1.00 76.59      A C
ATOM   66  C   VAL A  40     -32.933  32.645   0.854  1.00 73.04      A C
ATOM   67  O   VAL A  40     -34.141  32.693   0.639  1.00 73.08      A O
ATOM   68  N   GLY A  41     -32.026  33.160   0.032  1.00 71.25      A N
ATOM   69  CA  GLY A  41     -32.410  33.822  -1.197  1.00 68.73      A C
ATOM   70  C   GLY A  41     -31.636  33.245  -2.364  1.00 68.18      A C
ATOM   71  O   GLY A  41     -31.334  32.051  -2.374  1.00 67.47      A O
ATOM   72  N   PRO A  42     -31.296  34.067  -3.368  1.00 67.99      A N
ATOM   73  CD  PRO A  42     -31.718  35.470  -3.528  1.00 67.53      A C
ATOM   74  CA  PRO A  42     -30.547  33.613  -4.547  1.00 67.67      A C
ATOM   75  CB  PRO A  42     -30.735  34.762  -5.537  1.00 67.52      A C
ATOM   76  CG  PRO A  42     -30.812  35.955  -4.639  1.00 68.20      A C
ATOM   77  C   PRO A  42     -29.072  33.298  -4.295  1.00 66.70      A C
ATOM   78  O   PRO A  42     -28.484  33.747  -3.314  1.00 67.00      A O
ATOM   79  N   LEU A  43     -28.488  32.524  -5.202  1.00 65.71      A N
ATOM   80  CA  LEU A  43     -27.089  32.130  -5.118  1.00 66.09      A C
ATOM   81  CB  LEU A  43     -26.876  30.871  -5.975  1.00 66.00      A C
ATOM   82  CG  LEU A  43     -25.613  30.003  -5.928  1.00 66.51      A C
ATOM   83  CD1 LEU A  43     -25.813  28.827  -6.872  1.00 65.72      A C
ATOM   84  CD2 LEU A  43     -24.378  30.793  -6.337  1.00 67.19      A C
ATOM   85  C   LEU A  43     -26.204  33.282  -5.613  1.00 65.99      A C
ATOM   86  O   LEU A  43     -26.157  33.573  -6.809  1.00 67.02      A O
ATOM   87  N   LEU A  44     -25.511  33.943  -4.692  1.00 65.53      A N
ATOM   88  CA  LEU A  44     -24.636  35.055  -5.057  1.00 65.40      A C
ATOM   89  CB  LEU A  44     -24.092  35.737  -3.800  1.00 63.99      A C
ATOM   90  CG  LEU A  44     -25.116  36.388  -2.869  1.00 63.39      A C
ATOM   91  CD1 LEU A  44     -24.410  36.923  -1.645  1.00 63.37      A C
ATOM   92  CD2 LEU A  44     -25.839  37.506  -3.589  1.00 61.72      A C
ATOM   93  C   LEU A  44     -23.474  34.573  -5.922  1.00 65.59      A C
ATOM   94  O   LEU A  44     -23.259  35.070  -7.028  1.00 65.06      A O
ATOM   95  N   GLY A  45     -22.730  33.601  -5.410  1.00 66.90      A N
ATOM   96  CA  GLY A  45     -21.601  33.060  -6.145  1.00 68.47      A C
ATOM   97  C   GLY A  45     -21.186  31.694  -5.629  1.00 69.54      A C
ATOM   98  O   GLY A  45     -21.803  31.147  -4.711  1.00 69.30      A O
ATOM   99  N   SER A  46     -20.132  31.141  -6.215  1.00 70.26      A N
ATOM  100  CA  SER A  46     -19.638  29.831  -5.814  1.00 71.62      A C
ATOM  101  CB  SER A  46     -20.623  28.744  -6.249  1.00 72.10      A C
ATOM  102  OG  SER A  46     -20.001  27.470  -6.275  1.00 71.47      A O
ATOM  103  C   SER A  46     -18.277  29.550  -6.427  1.00 72.62      A C
ATOM  104  O   SER A  46     -17.892  30.168  -7.419  1.00 72.99      A O
ATOM  105  N   GLY A  47     -17.548  28.611  -5.837  1.00 73.55      A N
ATOM  106  CA  GLY A  47     -16.244  28.276  -6.372  1.00 75.31      A C
ATOM  107  C   GLY A  47     -15.290  27.686  -5.356  1.00 76.33      A C
ATOM  108  O   GLY A  47     -15.704  26.963  -4.447  1.00 76.20      A O
ATOM  109  N   GLY A  48     -14.006  28.000  -5.519  1.00 76.88      A N
ATOM  110  CA  GLY A  48     -12.986  27.499  -4.616  1.00 77.35      A C
```

FIGURE 1A-3

```
ATOM    111  C    GLY A  48     -13.061  28.118  -3.235  1.00 77.55      A C
ATOM    112  O    GLY A  48     -12.070  28.630  -2.715  1.00 79.09      A O
ATOM    113  N    PHE A  49     -14.251  28.082  -2.649  1.00 77.06      A N
ATOM    114  CA   PHE A  49     -14.487  28.616  -1.317  1.00 75.61      A C
ATOM    115  CB   PHE A  49     -14.386  30.149  -1.307  1.00 77.67      A C
ATOM    116  CG   PHE A  49     -15.301  30.837  -2.283  1.00 79.76      A C
ATOM    117  CD1  PHE A  49     -14.981  30.898  -3.637  1.00 80.26      A C
ATOM    118  CD2  PHE A  49     -16.482  31.433  -1.844  1.00 80.97      A C
ATOM    119  CE1  PHE A  49     -15.824  31.543  -4.544  1.00 80.88      A C
ATOM    120  CE2  PHE A  49     -17.334  32.080  -2.740  1.00 81.73      A C
ATOM    121  CZ   PHE A  49     -17.004  32.136  -4.093  1.00 82.35      A C
ATOM    122  C    PHE A  49     -15.864  28.175  -0.833  1.00 73.32      A C
ATOM    123  O    PHE A  49     -16.200  28.335   0.340  1.00 74.09      A O
ATOM    124  N    GLY A  50     -16.653  27.612  -1.745  1.00 69.75      A N
ATOM    125  CA   GLY A  50     -17.980  27.138  -1.388  1.00 65.40      A C
ATOM    126  C    GLY A  50     -19.106  27.710  -2.229  1.00 61.30      A C
ATOM    127  O    GLY A  50     -18.917  28.056  -3.398  1.00 61.23      A O
ATOM    128  N    SER A  51     -20.285  27.799  -1.624  1.00 57.06      A N
ATOM    129  CA   SER A  51     -21.463  28.331  -2.286  1.00 52.09      A C
ATOM    130  CB   SER A  51     -22.453  27.204  -2.557  1.00 52.18      A C
ATOM    131  OG   SER A  51     -21.804  26.117  -3.195  1.00 49.97      A O
ATOM    132  C    SER A  51     -22.054  29.345  -1.323  1.00 50.22      A C
ATOM    133  O    SER A  51     -22.288  29.036  -0.156  1.00 50.12      A O
ATOM    134  N    VAL A  52     -22.284  30.557  -1.809  1.00 49.24      A N
ATOM    135  CA   VAL A  52     -22.806  31.634  -0.976  1.00 48.54      A C
ATOM    136  CB   VAL A  52     -21.866  32.852  -1.031  1.00 48.09      A C
ATOM    137  CG1  VAL A  52     -22.407  33.970  -0.156  1.00 48.06      A C
ATOM    138  CG2  VAL A  52     -20.464  32.445  -0.598  1.00 45.71      A C
ATOM    139  C    VAL A  52     -24.198  32.073  -1.410  1.00 49.32      A C
ATOM    140  O    VAL A  52     -24.426  32.375  -2.583  1.00 48.66      A O
ATOM    141  N    TYR A  53     -25.123  32.126  -0.458  1.00 49.14      A N
ATOM    142  CA   TYR A  53     -26.491  32.514  -0.765  1.00 49.88      A C
ATOM    143  CB   TYR A  53     -27.482  31.430  -0.315  1.00 48.29      A C
ATOM    144  CG   TYR A  53     -27.331  30.083  -0.992  1.00 47.09      A C
ATOM    145  CD1  TYR A  53     -26.359  29.179  -0.575  1.00 46.21      A C
ATOM    146  CE1  TYR A  53     -26.225  27.933  -1.183  1.00 45.74      A C
ATOM    147  CD2  TYR A  53     -28.172  29.709  -2.042  1.00 45.58      A C
ATOM    148  CE2  TYR A  53     -28.051  28.467  -2.659  1.00 45.74      A C
ATOM    149  CZ   TYR A  53     -27.073  27.582  -2.224  1.00 46.68      A C
ATOM    150  OH   TYR A  53     -26.939  26.349  -2.820  1.00 45.40      A O
ATOM    151  C    TYR A  53     -26.878  33.812  -0.088  1.00 52.07      A C
ATOM    152  O    TYR A  53     -26.504  34.056   1.060  1.00 53.08      A O
ATOM    153  N    SER A  54     -27.633  34.644  -0.799  1.00 53.36      A N
ATOM    154  CA   SER A  54     -28.100  35.896  -0.229  1.00 54.66      A C
ATOM    155  CB   SER A  54     -28.737  36.776  -1.303  1.00 56.56      A C
ATOM    156  OG   SER A  54     -29.258  37.970  -0.738  1.00 57.39      A O
ATOM    157  C    SER A  54     -29.151  35.471   0.771  1.00 55.54      A C
ATOM    158  O    SER A  54     -29.838  34.482   0.552  1.00 57.11      A O
ATOM    159  N    GLY A  55     -29.277  36.197   1.872  1.00 56.69      A N
ATOM    160  CA   GLY A  55     -30.265  35.818   2.862  1.00 57.74      A C
ATOM    161  C    GLY A  55     -30.683  36.976   3.736  1.00 59.97      A C
ATOM    162  O    GLY A  55     -30.129  38.072   3.642  1.00 60.66      A O
ATOM    163  N    ILE A  56     -31.666  36.732   4.592  1.00 61.87      A N
ATOM    164  CA   ILE A  56     -32.166  37.756   5.493  1.00 63.96      A C
ATOM    165  CB   ILE A  56     -33.486  38.334   4.972  1.00 64.00      A C
ATOM    166  CG2  ILE A  56     -34.115  39.224   6.024  1.00 64.54      A C
```

FIGURE 1A-4

```
ATOM    167  CG1 ILE A  56     -33.225  39.092   3.670  1.00 64.20      A C
ATOM    168  CD1 ILE A  56     -34.462  39.645   3.018  1.00 66.40      A C
ATOM    169  C   ILE A  56     -32.378  37.166   6.876  1.00 65.41      A C
ATOM    170  O   ILE A  56     -32.829  36.029   7.017  1.00 65.71      A O
ATOM    171  N   ARG A  57     -32.043  37.942   7.897  1.00 67.56      A N
ATOM    172  CA  ARG A  57     -32.184  37.490   9.274  1.00 70.49      A C
ATOM    173  CB  ARG A  57     -31.038  38.047  10.124  1.00 70.48      A C
ATOM    174  CG  ARG A  57     -31.095  37.653  11.587  1.00 70.93      A C
ATOM    175  CD  ARG A  57     -30.515  38.758  12.450  1.00 72.66      A C
ATOM    176  NE  ARG A  57     -29.132  38.528  12.854  1.00 72.93      A N
ATOM    177  CZ  ARG A  57     -28.350  39.469  13.375  1.00 73.59      A C
ATOM    178  NH1 ARG A  57     -28.815  40.702  13.543  1.00 72.48      A N
ATOM    179  NH2 ARG A  57     -27.111  39.176  13.747  1.00 73.98      A N
ATOM    180  C   ARG A  57     -33.518  37.921   9.873  1.00 72.46      A C
ATOM    181  O   ARG A  57     -33.658  39.052  10.341  1.00 72.86      A O
ATOM    182  N   VAL A  58     -34.500  37.025   9.847  1.00 74.77      A N
ATOM    183  CA  VAL A  58     -35.809  37.329  10.416  1.00 76.58      A C
ATOM    184  CB  VAL A  58     -36.801  36.153  10.249  1.00 77.57      A C
ATOM    185  CG1 VAL A  58     -37.645  36.357   8.992  1.00 78.73      A C
ATOM    186  CG2 VAL A  58     -36.043  34.834  10.171  1.00 76.99      A C
ATOM    187  C   VAL A  58     -35.620  37.605  11.899  1.00 77.54      A C
ATOM    188  O   VAL A  58     -35.488  36.679  12.702  1.00 77.82      A O
ATOM    189  N   SER A  59     -35.594  38.887  12.248  1.00 77.64      A N
ATOM    190  CA  SER A  59     -35.403  39.329  13.625  1.00 77.81      A C
ATOM    191  CB  SER A  59     -34.213  38.602  14.265  1.00 77.71      A C
ATOM    192  OG  SER A  59     -33.988  39.046  15.592  1.00 77.00      A O
ATOM    193  C   SER A  59     -35.118  40.821  13.561  1.00 77.93      A C
ATOM    194  O   SER A  59     -35.281  41.550  14.541  1.00 78.40      A O
ATOM    195  N   ASP A  60     -34.680  41.255  12.385  1.00 77.28      A N
ATOM    196  CA  ASP A  60     -34.363  42.651  12.121  1.00 76.50      A C
ATOM    197  CB  ASP A  60     -33.076  43.063  12.842  1.00 76.36      A C
ATOM    198  CG  ASP A  60     -31.985  42.015  12.740  1.00 77.05      A C
ATOM    199  OD1 ASP A  60     -31.788  41.464  11.639  1.00 78.35      A O
ATOM    200  OD2 ASP A  60     -31.317  41.747  13.760  1.00 77.02      A O
ATOM    201  C   ASP A  60     -34.191  42.798  10.619  1.00 75.75      A C
ATOM    202  O   ASP A  60     -33.706  43.815  10.130  1.00 75.85      A O
ATOM    203  N   ASN A  61     -34.600  41.757   9.898  1.00 75.12      A N
ATOM    204  CA  ASN A  61     -34.509  41.718   8.443  1.00 73.88      A C
ATOM    205  CB  ASN A  61     -35.595  42.606   7.834  1.00 75.02      A C
ATOM    206  CG  ASN A  61     -36.973  41.979   7.936  1.00 76.42      A C
ATOM    207  OD1 ASN A  61     -37.350  41.136   7.116  1.00 77.77      A O
ATOM    208  ND2 ASN A  61     -37.723  42.368   8.958  1.00 77.92      A N
ATOM    209  C   ASN A  61     -33.134  42.127   7.935  1.00 71.79      A C
ATOM    210  O   ASN A  61     -32.995  42.643   6.826  1.00 72.31      A O
ATOM    211  N   LEU A  62     -32.119  41.884   8.757  1.00 68.70      A N
ATOM    212  CA  LEU A  62     -30.742  42.211   8.415  1.00 65.30      A C
ATOM    213  CB  LEU A  62     -29.824  41.876   9.582  1.00 64.78      A C
ATOM    214  CG  LEU A  62     -28.330  42.078   9.353  1.00 64.66      A C
ATOM    215  CD1 LEU A  62     -28.040  43.563   9.191  1.00 62.89      A C
ATOM    216  CD2 LEU A  62     -27.555  41.501  10.536  1.00 64.09      A C
ATOM    217  C   LEU A  62     -30.284  41.422   7.201  1.00 63.14      A C
ATOM    218  O   LEU A  62     -30.404  40.195   7.170  1.00 63.45      A O
ATOM    219  N   PRO A  63     -29.759  42.115   6.180  1.00 60.40      A N
ATOM    220  CD  PRO A  63     -29.628  43.577   6.051  1.00 59.26      A C
ATOM    221  CA  PRO A  63     -29.284  41.435   4.972  1.00 58.16      A C
ATOM    222  CB  PRO A  63     -29.052  42.587   3.996  1.00 58.42      A C
```

FIGURE 1A-5

```
ATOM    223  CG  PRO A  63     -28.656  43.712   4.903  1.00 59.05      A C
ATOM    224  C   PRO A  63     -28.001  40.666   5.282  1.00 56.23      A C
ATOM    225  O   PRO A  63     -27.017  41.251   5.740  1.00 55.75      A O
ATOM    226  N   VAL A  64     -28.015  39.358   5.046  1.00 54.00      A N
ATOM    227  CA  VAL A  64     -26.841  38.534   5.318  1.00 52.00      A C
ATOM    228  CB  VAL A  64     -27.078  37.591   6.512  1.00 51.82      A C
ATOM    229  CG1 VAL A  64     -27.487  38.390   7.737  1.00 50.74      A C
ATOM    230  CG2 VAL A  64     -28.135  36.558   6.152  1.00 50.25      A C
ATOM    231  C   VAL A  64     -26.412  37.667   4.141  1.00 51.00      A C
ATOM    232  O   VAL A  64     -27.080  37.607   3.107  1.00 51.41      A O
ATOM    233  N   ALA A  65     -25.280  36.994   4.319  1.00 49.23      A N
ATOM    234  CA  ALA A  65     -24.738  36.099   3.313  1.00 46.30      A C
ATOM    235  CB  ALA A  65     -23.413  36.625   2.788  1.00 46.31      A C
ATOM    236  C   ALA A  65     -24.539  34.774   4.011  1.00 44.81      A C
ATOM    237  O   ALA A  65     -23.964  34.717   5.095  1.00 44.20      A O
ATOM    238  N   ILE A  66     -25.032  33.711   3.391  1.00 44.29      A N
ATOM    239  CA  ILE A  66     -24.926  32.374   3.954  1.00 43.19      A C
ATOM    240  CB  ILE A  66     -26.319  31.714   4.025  1.00 42.65      A C
ATOM    241  CG2 ILE A  66     -26.231  30.355   4.694  1.00 42.79      A C
ATOM    242  CG1 ILE A  66     -27.267  32.623   4.814  1.00 43.20      A C
ATOM    243  CD1 ILE A  66     -28.670  32.087   4.931  1.00 44.11      A C
ATOM    244  C   ILE A  66     -23.979  31.541   3.098  1.00 43.39      A C
ATOM    245  O   ILE A  66     -24.244  31.277   1.921  1.00 44.79      A O
ATOM    246  N   LYS A  67     -22.872  31.130   3.704  1.00 42.07      A N
ATOM    247  CA  LYS A  67     -21.859  30.361   3.006  1.00 41.68      A C
ATOM    248  CB  LYS A  67     -20.500  31.030   3.210  1.00 42.24      A C
ATOM    249  CG  LYS A  67     -19.351  30.375   2.476  1.00 44.06      A C
ATOM    250  CD  LYS A  67     -18.080  31.203   2.646  1.00 45.96      A C
ATOM    251  CE  LYS A  67     -16.903  30.597   1.901  1.00 46.87      A C
ATOM    252  NZ  LYS A  67     -15.705  31.473   1.985  1.00 49.41      A N
ATOM    253  C   LYS A  67     -21.806  28.912   3.472  1.00 42.16      A C
ATOM    254  O   LYS A  67     -21.769  28.629   4.672  1.00 41.99      A O
ATOM    255  N   HIS A  68     -21.798  27.998   2.509  1.00 42.59      A N
ATOM    256  CA  HIS A  68     -21.755  26.575   2.802  1.00 42.14      A C
ATOM    257  CB  HIS A  68     -22.875  25.849   2.062  1.00 41.00      A C
ATOM    258  CG  HIS A  68     -24.244  26.290   2.463  1.00 38.32      A C
ATOM    259  CD2 HIS A  68     -24.972  27.373   2.100  1.00 38.85      A C
ATOM    260  ND1 HIS A  68     -25.000  25.614   3.394  1.00 38.50      A N
ATOM    261  CE1 HIS A  68     -26.135  26.263   3.593  1.00 39.33      A C
ATOM    262  NE2 HIS A  68     -26.142  27.336   2.820  1.00 38.96      A N
ATOM    263  C   HIS A  68     -20.423  26.006   2.372  1.00 43.43      A C
ATOM    264  O   HIS A  68     -19.941  26.297   1.279  1.00 43.19      A O
ATOM    265  N   VAL A  69     -19.836  25.196   3.244  1.00 46.68      A N
ATOM    266  CA  VAL A  69     -18.555  24.555   2.977  1.00 49.69      A C
ATOM    267  CB  VAL A  69     -17.421  25.213   3.793  1.00 49.99      A C
ATOM    268  CG1 VAL A  69     -16.101  24.524   3.509  1.00 50.19      A C
ATOM    269  CG2 VAL A  69     -17.322  26.687   3.443  1.00 52.29      A C
ATOM    270  C   VAL A  69     -18.658  23.089   3.373  1.00 51.34      A C
ATOM    271  O   VAL A  69     -19.041  22.772   4.494  1.00 52.67      A O
ATOM    272  N   GLU A  70     -18.334  22.196   2.446  1.00 54.79      A N
ATOM    273  CA  GLU A  70     -18.391  20.763   2.717  1.00 58.41      A C
ATOM    274  CB  GLU A  70     -18.412  19.965   1.409  1.00 61.38      A C
ATOM    275  CG  GLU A  70     -19.667  20.157   0.575  1.00 65.88      A C
ATOM    276  CD  GLU A  70     -19.536  19.565  -0.819  1.00 68.99      A C
ATOM    277  OE1 GLU A  70     -18.526  19.869  -1.498  1.00 70.26      A O
ATOM    278  OE2 GLU A  70     -20.444  18.809  -1.236  1.00 69.77      A O
```

FIGURE 1A-6

```
ATOM   279  C    GLU A  70     -17.180  20.352   3.533  1.00  59.11     A C
ATOM   280  O    GLU A  70     -16.052  20.737   3.224  1.00  58.68     A O
ATOM   281  N    LYS A  71     -17.415  19.562   4.573  1.00  60.45     A N
ATOM   282  CA   LYS A  71     -16.331  19.104   5.425  1.00  62.00     A C
ATOM   283  CB   LYS A  71     -16.877  18.161   6.491  1.00  60.54     A C
ATOM   284  CG   LYS A  71     -17.881  18.811   7.413  1.00  59.86     A C
ATOM   285  CD   LYS A  71     -18.300  17.853   8.509  1.00  60.97     A C
ATOM   286  CE   LYS A  71     -19.300  18.502   9.443  1.00  60.49     A C
ATOM   287  NZ   LYS A  71     -19.671  17.596  10.555  1.00  61.13     A N
ATOM   288  C    LYS A  71     -15.208  18.417   4.647  1.00  63.87     A C
ATOM   289  O    LYS A  71     -14.032  18.664   4.894  1.00  64.19     A O
ATOM   290  N    ASP A  72     -15.566  17.567   3.695  1.00  67.14     A N
ATOM   291  CA   ASP A  72     -14.558  16.856   2.923  1.00  70.66     A C
ATOM   292  CB   ASP A  72     -15.233  15.857   1.980  1.00  72.66     A C
ATOM   293  CG   ASP A  72     -16.146  14.888   2.719  1.00  75.38     A C
ATOM   294  OD1  ASP A  72     -15.731  14.377   3.784  1.00  75.65     A O
ATOM   295  OD2  ASP A  72     -17.273  14.632   2.237  1.00  77.05     A O
ATOM   296  C    ASP A  72     -13.643  17.778   2.129  1.00  72.22     A C
ATOM   297  O    ASP A  72     -12.528  17.398   1.777  1.00  71.95     A O
ATOM   298  N    ARG A  73     -14.105  18.999   1.875  1.00  74.78     A N
ATOM   299  CA   ARG A  73     -13.340  19.968   1.093  1.00  76.54     A C
ATOM   300  CB   ARG A  73     -14.299  20.838   0.277  1.00  78.28     A C
ATOM   301  CG   ARG A  73     -14.905  20.127  -0.918  1.00  81.43     A C
ATOM   302  CD   ARG A  73     -13.862  19.943  -2.006  1.00  84.51     A C
ATOM   303  NE   ARG A  73     -14.303  19.027  -3.055  1.00  86.97     A N
ATOM   304  CZ   ARG A  73     -13.611  18.775  -4.163  1.00  87.93     A C
ATOM   305  NH1  ARG A  73     -12.444  19.377  -4.370  1.00  87.91     A N
ATOM   306  NH2  ARG A  73     -14.081  17.918  -5.060  1.00  87.98     A N
ATOM   307  C    ARG A  73     -12.366  20.873   1.839  1.00  76.84     A C
ATOM   308  O    ARG A  73     -11.678  21.677   1.211  1.00  76.94     A O
ATOM   309  N    ILE A  74     -12.290  20.759   3.161  1.00  77.20     A N
ATOM   310  CA   ILE A  74     -11.368  21.614   3.904  1.00  78.24     A C
ATOM   311  CB   ILE A  74     -12.090  22.367   5.042  1.00  78.32     A C
ATOM   312  CG2  ILE A  74     -13.512  22.694   4.625  1.00  77.74     A C
ATOM   313  CG1  ILE A  74     -12.128  21.513   6.305  1.00  78.49     A C
ATOM   314  CD1  ILE A  74     -12.697  22.235   7.491  1.00  79.28     A C
ATOM   315  C    ILE A  74     -10.207  20.821   4.495  1.00  78.46     A C
ATOM   316  O    ILE A  74     -10.369  19.659   4.864  1.00  78.38     A O
ATOM   317  N    SER A  75      -9.039  21.455   4.588  1.00  79.23     A N
ATOM   318  CA   SER A  75      -7.857  20.792   5.133  1.00  79.94     A C
ATOM   319  CB   SER A  75      -6.721  20.807   4.108  1.00  81.39     A C
ATOM   320  OG   SER A  75      -5.612  20.051   4.572  1.00  83.58     A O
ATOM   321  C    SER A  75      -7.351  21.384   6.451  1.00  79.30     A C
ATOM   322  O    SER A  75      -6.617  20.724   7.185  1.00  79.45     A O
ATOM   323  N    ASP A  76      -7.731  22.622   6.752  1.00  78.39     A N
ATOM   324  CA   ASP A  76      -7.297  23.249   7.994  1.00  77.49     A C
ATOM   325  CB   ASP A  76      -6.724  24.636   7.730  1.00  79.74     A C
ATOM   326  CG   ASP A  76      -5.231  24.612   7.526  1.00  81.86     A C
ATOM   327  OD1  ASP A  76      -4.562  23.810   8.212  1.00  83.60     A O
ATOM   328  OD2  ASP A  76      -4.727  25.400   6.698  1.00  83.41     A O
ATOM   329  C    ASP A  76      -8.401  23.366   9.024  1.00  75.88     A C
ATOM   330  O    ASP A  76      -9.496  23.827   8.715  1.00  75.57     A O
ATOM   331  N    TRP A  77      -8.102  22.950  10.252  1.00  74.22     A N
ATOM   332  CA   TRP A  77      -9.070  23.015  11.342  1.00  72.93     A C
ATOM   333  CB   TRP A  77      -9.619  21.624  11.673  1.00  71.28     A C
ATOM   334  CG   TRP A  77     -10.092  20.810  10.504  1.00  69.10     A C
```

FIGURE 1A-7

```
ATOM    335  CD2 TRP A   77     -11.445  20.436  10.206  1.00 67.81      A C
ATOM    336  CE2 TRP A   77     -11.406  19.598   9.068  1.00 67.85      A C
ATOM    337  CE3 TRP A   77     -12.685  20.724  10.793  1.00 66.60      A C
ATOM    338  CD1 TRP A   77      -9.314  20.209   9.556  1.00 69.04      A C
ATOM    339  NE1 TRP A   77     -10.095  19.477   8.692  1.00 68.15      A N
ATOM    340  CZ2 TRP A   77     -12.560  19.045   8.504  1.00 67.97      A C
ATOM    341  CZ3 TRP A   77     -13.836  20.172  10.231  1.00 66.90      A C
ATOM    342  CH2 TRP A   77     -13.763  19.342   9.098  1.00 67.73      A C
ATOM    343  C   TRP A   77      -8.412  23.588  12.592  1.00 72.97      A C
ATOM    344  O   TRP A   77      -7.196  23.510  12.747  1.00 73.39      A O
ATOM    345  N   GLY A   78      -9.225  24.155  13.478  1.00 73.08      A N
ATOM    346  CA  GLY A   78      -8.717  24.730  14.713  1.00 74.25      A C
ATOM    347  C   GLY A   78      -9.766  24.639  15.808  1.00 75.69      A C
ATOM    348  O   GLY A   78     -10.734  23.889  15.676  1.00 76.37      A O
ATOM    349  N   ALA A   79      -9.588  25.394  16.888  1.00 76.51      A N
ATOM    350  CA  ALA A   79     -10.548  25.371  17.988  1.00 77.48      A C
ATOM    351  CB  ALA A   79     -10.252  24.193  18.912  1.00 77.36      A C
ATOM    352  C   ALA A   79     -10.519  26.678  18.777  1.00 78.43      A C
ATOM    353  O   ALA A   79      -9.616  27.495  18.507  1.00 78.47      A O
ATOM    354  OXT ALA A   79     -11.392  26.871  19.657  1.00 79.13      A O
ATOM    355  CB  THR A   84     -15.748  22.664  19.224  1.00 78.82      A C
ATOM    356  OG1 THR A   84     -15.876  23.702  18.246  1.00 79.61      A O
ATOM    357  CG2 THR A   84     -16.311  23.166  20.541  1.00 78.53      A C
ATOM    358  C   THR A   84     -13.568  22.442  18.040  1.00 77.34      A C
ATOM    359  O   THR A   84     -13.094  23.523  17.691  1.00 77.45      A O
ATOM    360  N   THR A   84     -13.586  23.179  20.378  1.00 78.70      A N
ATOM    361  CA  THR A   84     -14.263  22.291  19.387  1.00 78.49      A C
ATOM    362  N   ARG A   85     -13.520  21.356  17.282  1.00 75.82      A N
ATOM    363  CA  ARG A   85     -12.852  21.367  15.993  1.00 74.31      A C
ATOM    364  CB  ARG A   85     -12.414  19.942  15.640  1.00 76.05      A C
ATOM    365  CG  ARG A   85     -11.573  19.852  14.388  1.00 79.31      A C
ATOM    366  CD  ARG A   85     -11.155  18.422  14.095  1.00 81.12      A C
ATOM    367  NE  ARG A   85     -11.106  18.179  12.656  1.00 83.33      A N
ATOM    368  CZ  ARG A   85     -10.770  17.022  12.096  1.00 84.52      A C
ATOM    369  NH1 ARG A   85     -10.441  15.983  12.853  1.00 85.40      A N
ATOM    370  NH2 ARG A   85     -10.780  16.897  10.775  1.00 85.29      A N
ATOM    371  C   ARG A   85     -13.695  21.962  14.862  1.00 72.15      A C
ATOM    372  O   ARG A   85     -14.582  21.304  14.315  1.00 72.01      A O
ATOM    373  N   VAL A   86     -13.409  23.215  14.516  1.00 68.71      A N
ATOM    374  CA  VAL A   86     -14.127  23.906  13.447  1.00 63.49      A C
ATOM    375  CB  VAL A   86     -14.759  25.227  13.947  1.00 63.27      A C
ATOM    376  CG1 VAL A   86     -15.681  24.955  15.120  1.00 62.03      A C
ATOM    377  CG2 VAL A   86     -13.671  26.207  14.345  1.00 61.83      A C
ATOM    378  C   VAL A   86     -13.141  24.245  12.337  1.00 60.75      A C
ATOM    379  O   VAL A   86     -11.930  24.201  12.546  1.00 59.70      A O
ATOM    380  N   PRO A   87     -13.642  24.567  11.132  1.00 58.54      A N
ATOM    381  CD  PRO A   87     -15.013  24.449  10.607  1.00 56.89      A C
ATOM    382  CA  PRO A   87     -12.699  24.905  10.060  1.00 55.85      A C
ATOM    383  CB  PRO A   87     -13.603  25.068   8.829  1.00 56.33      A C
ATOM    384  CG  PRO A   87     -14.958  25.345   9.408  1.00 57.40      A C
ATOM    385  C   PRO A   87     -11.896  26.167  10.390  1.00 53.78      A C
ATOM    386  O   PRO A   87     -12.390  27.074  11.059  1.00 52.93      A O
ATOM    387  N   MET A   88     -10.651  26.209   9.926  1.00 52.50      A N
ATOM    388  CA  MET A   88      -9.774  27.343  10.181  1.00 51.02      A C
ATOM    389  CB  MET A   88      -8.480  27.200   9.374  1.00 52.08      A C
ATOM    390  CG  MET A   88      -7.449  28.292   9.643  1.00 52.96      A C
```

FIGURE 1A-8

```
ATOM    391  SD  MET A  88      -6.951  28.375  11.390  1.00 56.48      A S
ATOM    392  CE  MET A  88      -6.239  26.751  11.614  1.00 53.36      A C
ATOM    393  C   MET A  88     -10.444  28.667   9.837  1.00 49.04      A C
ATOM    394  O   MET A  88     -10.293  29.657  10.563  1.00 48.61      A O
ATOM    395  N   GLU A  89     -11.184  28.681   8.732  1.00 46.30      A N
ATOM    396  CA  GLU A  89     -11.860  29.895   8.295  1.00 44.67      A C
ATOM    397  CB  GLU A  89     -12.740  29.600   7.072  1.00 43.93      A C
ATOM    398  CG  GLU A  89     -13.417  30.830   6.463  1.00 43.39      A C
ATOM    399  CD  GLU A  89     -14.135  30.534   5.147  1.00 43.18      A C
ATOM    400  OE1 GLU A  89     -14.762  31.462   4.584  1.00 41.19      A O
ATOM    401  OE2 GLU A  89     -14.065  29.379   4.671  1.00 42.68      A O
ATOM    402  C   GLU A  89     -12.695  30.503   9.424  1.00 44.34      A C
ATOM    403  O   GLU A  89     -12.728  31.723   9.593  1.00 44.17      A O
ATOM    404  N   VAL A  90     -13.357  29.657  10.208  1.00 43.60      A N
ATOM    405  CA  VAL A  90     -14.187  30.143  11.305  1.00 42.76      A C
ATOM    406  CB  VAL A  90     -15.080  29.016  11.884  1.00 43.47      A C
ATOM    407  CG1 VAL A  90     -15.919  29.556  13.038  1.00 42.68      A C
ATOM    408  CG2 VAL A  90     -15.982  28.457  10.792  1.00 43.73      A C
ATOM    409  C   VAL A  90     -13.323  30.717  12.420  1.00 42.37      A C
ATOM    410  O   VAL A  90     -13.644  31.765  12.977  1.00 41.69      A O
ATOM    411  N   VAL A  91     -12.231  30.029  12.746  1.00 41.33      A N
ATOM    412  CA  VAL A  91     -11.329  30.496  13.791  1.00 40.55      A C
ATOM    413  CB  VAL A  91     -10.117  29.553  13.957  1.00 41.17      A C
ATOM    414  CG1 VAL A  91      -9.078  30.188  14.883  1.00 39.48      A C
ATOM    415  CG2 VAL A  91     -10.573  28.221  14.519  1.00 40.77      A C
ATOM    416  C   VAL A  91     -10.814  31.873  13.410  1.00 40.09      A C
ATOM    417  O   VAL A  91     -10.809  32.799  14.221  1.00 40.51      A O
ATOM    418  N   LEU A  92     -10.379  31.995  12.163  1.00 39.67      A N
ATOM    419  CA  LEU A  92      -9.860  33.252  11.651  1.00 39.56      A C
ATOM    420  CB  LEU A  92      -9.362  33.048  10.215  1.00 39.08      A C
ATOM    421  CG  LEU A  92      -7.876  32.702  10.021  1.00 39.30      A C
ATOM    422  CD1 LEU A  92      -7.305  31.980  11.229  1.00 36.80      A C
ATOM    423  CD2 LEU A  92      -7.717  31.879   8.765  1.00 38.72      A C
ATOM    424  C   LEU A  92     -10.907  34.366  11.716  1.00 40.30      A C
ATOM    425  O   LEU A  92     -10.676  35.398  12.341  1.00 41.08      A O
ATOM    426  N   LEU A  93     -12.059  34.159  11.088  1.00 40.47      A N
ATOM    427  CA  LEU A  93     -13.110  35.171  11.104  1.00 40.51      A C
ATOM    428  CB  LEU A  93     -14.368  34.658  10.396  1.00 39.99      A C
ATOM    429  CG  LEU A  93     -14.338  34.629   8.868  1.00 40.61      A C
ATOM    430  CD1 LEU A  93     -15.549  33.874   8.337  1.00 38.70      A C
ATOM    431  CD2 LEU A  93     -14.303  36.060   8.342  1.00 39.55      A C
ATOM    432  C   LEU A  93     -13.484  35.626  12.507  1.00 40.89      A C
ATOM    433  O   LEU A  93     -13.718  36.805  12.745  1.00 39.95      A O
ATOM    434  N   LYS A  94     -13.535  34.692  13.444  1.00 43.26      A N
ATOM    435  CA  LYS A  94     -13.918  35.033  14.807  1.00 45.18      A C
ATOM    436  CB  LYS A  94     -14.073  33.759  15.633  1.00 47.58      A C
ATOM    437  CG  LYS A  94     -14.698  33.985  16.988  1.00 52.58      A C
ATOM    438  CD  LYS A  94     -15.086  32.654  17.624  1.00 57.84      A C
ATOM    439  CE  LYS A  94     -16.143  31.947  16.795  1.00 59.20      A C
ATOM    440  NZ  LYS A  94     -17.343  32.827  16.619  1.00 63.56      A N
ATOM    441  C   LYS A  94     -12.937  35.985  15.478  1.00 44.81      A C
ATOM    442  O   LYS A  94     -13.345  36.964  16.101  1.00 44.58      A O
ATOM    443  N   LYS A  95     -11.646  35.701  15.347  1.00 44.91      A N
ATOM    444  CA  LYS A  95     -10.621  36.549  15.941  1.00 45.68      A C
ATOM    445  CB  LYS A  95      -9.238  35.917  15.755  1.00 44.91      A C
ATOM    446  CG  LYS A  95      -9.102  34.503  16.309  1.00 45.25      A C
```

FIGURE 1A-9

```
ATOM    447  CD   LYS A  95      -7.688  33.964  16.136  1.00 45.59      A C
ATOM    448  CE   LYS A  95      -6.715  34.682  17.042  1.00 48.56      A C
ATOM    449  NZ   LYS A  95      -5.323  34.232  16.780  1.00 51.97      A N
ATOM    450  C    LYS A  95     -10.610  37.936  15.303  1.00 46.74      A C
ATOM    451  O    LYS A  95     -10.144  38.907  15.907  1.00 46.99      A O
ATOM    452  N    VAL A  96     -11.149  38.026  14.091  1.00 46.87      A N
ATOM    453  CA   VAL A  96     -11.150  39.270  13.334  1.00 47.06      A C
ATOM    454  CB   VAL A  96     -10.584  38.986  11.916  1.00 46.03      A C
ATOM    455  CG1  VAL A  96     -11.663  39.178  10.851  1.00 43.98      A C
ATOM    456  CG2  VAL A  96      -9.378  39.848  11.660  1.00 46.77      A C
ATOM    457  C    VAL A  96     -12.495  39.996  13.204  1.00 48.72      A C
ATOM    458  O    VAL A  96     -12.543  41.121  12.714  1.00 48.75      A O
ATOM    459  N    SER A  97     -13.573  39.366  13.661  1.00 51.04      A N
ATOM    460  CA   SER A  97     -14.921  39.926  13.537  1.00 53.89      A C
ATOM    461  CB   SER A  97     -15.906  38.810  13.146  1.00 51.97      A C
ATOM    462  OG   SER A  97     -15.689  38.352  11.832  1.00 49.56      A O
ATOM    463  C    SER A  97     -15.522  40.709  14.706  1.00 56.73      A C
ATOM    464  O    SER A  97     -16.736  40.920  14.743  1.00 57.74      A O
ATOM    465  N    SER A  98     -14.714  41.145  15.661  1.00 60.23      A N
ATOM    466  CA   SER A  98     -15.283  41.896  16.777  1.00 64.28      A C
ATOM    467  CB   SER A  98     -14.809  41.290  18.105  1.00 65.24      A C
ATOM    468  OG   SER A  98     -13.632  40.526  17.911  1.00 68.23      A O
ATOM    469  C    SER A  98     -14.910  43.368  16.652  1.00 65.62      A C
ATOM    470  O    SER A  98     -13.775  43.714  16.316  1.00 66.05      A O
ATOM    471  N    GLY A  99     -15.895  44.221  16.901  1.00 66.83      A N
ATOM    472  CA   GLY A  99     -15.691  45.650  16.795  1.00 67.84      A C
ATOM    473  C    GLY A  99     -15.933  46.039  15.347  1.00 69.04      A C
ATOM    474  O    GLY A  99     -16.444  45.238  14.572  1.00 69.02      A O
ATOM    475  N    PHE A 100     -15.569  47.258  14.972  1.00 70.14      A N
ATOM    476  CA   PHE A 100     -15.745  47.709  13.606  1.00 69.84      A C
ATOM    477  CB   PHE A 100     -16.132  49.180  13.599  1.00 72.32      A C
ATOM    478  CG   PHE A 100     -17.460  49.438  14.199  1.00 75.41      A C
ATOM    479  CD1  PHE A 100     -17.593  50.280  15.300  1.00 76.16      A C
ATOM    480  CD2  PHE A 100     -18.588  48.814  13.678  1.00 76.39      A C
ATOM    481  CE1  PHE A 100     -18.841  50.493  15.870  1.00 77.15      A C
ATOM    482  CE2  PHE A 100     -19.842  49.018  14.237  1.00 76.59      A C
ATOM    483  CZ   PHE A 100     -19.967  49.859  15.337  1.00 76.86      A C
ATOM    484  C    PHE A 100     -14.461  47.517  12.841  1.00 67.97      A C
ATOM    485  O    PHE A 100     -13.393  47.438  13.441  1.00 67.88      A O
ATOM    486  N    SER A 101     -14.564  47.460  11.517  1.00 64.98      A N
ATOM    487  CA   SER A 101     -13.382  47.278  10.694  1.00 63.38      A C
ATOM    488  CB   SER A 101     -12.537  46.138  11.285  1.00 65.08      A C
ATOM    489  OG   SER A 101     -12.028  45.266  10.299  1.00 69.88      A O
ATOM    490  C    SER A 101     -13.706  47.026   9.218  1.00 60.01      A C
ATOM    491  O    SER A 101     -14.877  46.938   8.828  1.00 59.63      A O
ATOM    492  N    GLY A 102     -12.651  46.926   8.408  1.00 55.91      A N
ATOM    493  CA   GLY A 102     -12.796  46.702   6.975  1.00 50.67      A C
ATOM    494  C    GLY A 102     -12.839  45.257   6.478  1.00 47.46      A C
ATOM    495  O    GLY A 102     -12.438  44.971   5.350  1.00 47.26      A O
ATOM    496  N    VAL A 103     -13.333  44.350   7.319  1.00 44.81      A N
ATOM    497  CA   VAL A 103     -13.459  42.926   6.988  1.00 43.28      A C
ATOM    498  CB   VAL A 103     -12.613  42.022   7.917  1.00 42.21      A C
ATOM    499  CG1  VAL A 103     -11.176  42.492   7.943  1.00 42.53      A C
ATOM    500  CG2  VAL A 103     -13.187  42.031   9.314  1.00 41.51      A C
ATOM    501  C    VAL A 103     -14.891  42.468   7.165  1.00 42.77      A C
ATOM    502  O    VAL A 103     -15.514  42.834   8.158  1.00 43.41      A O
```

FIGURE 1A-10

```
ATOM    503  N   ILE A 104     -15.411  41.642   6.258  1.00 42.52      A N
ATOM    504  CA  ILE A 104     -16.777  41.159   6.428  1.00 42.38      A C
ATOM    505  CB  ILE A 104     -17.214  40.245   5.270  1.00 42.83      A C
ATOM    506  CG2 ILE A 104     -18.516  39.523   5.604  1.00 42.74      A C
ATOM    507  CG1 ILE A 104     -17.431  41.084   4.022  1.00 43.20      A C
ATOM    508  CD1 ILE A 104     -18.488  42.151   4.169  1.00 42.68      A C
ATOM    509  C   ILE A 104     -16.821  40.373   7.736  1.00 42.71      A C
ATOM    510  O   ILE A 104     -16.102  39.393   7.908  1.00 42.44      A O
ATOM    511  N   ARG A 105     -17.680  40.811   8.649  1.00 43.68      A N
ATOM    512  CA  ARG A 105     -17.817  40.177   9.953  1.00 46.89      A C
ATOM    513  CB  ARG A 105     -18.453  41.158  10.945  1.00 49.91      A C
ATOM    514  CG  ARG A 105     -17.541  42.300  11.369  1.00 55.20      A C
ATOM    515  CD  ARG A 105     -17.602  42.521  12.880  1.00 60.74      A C
ATOM    516  NE  ARG A 105     -18.868  43.097  13.323  1.00 65.39      A N
ATOM    517  CZ  ARG A 105     -19.241  44.346  13.064  1.00 68.49      A C
ATOM    518  NH1 ARG A 105     -18.439  45.149  12.369  1.00 70.24      A N
ATOM    519  NH2 ARG A 105     -20.423  44.786  13.477  1.00 69.79      A N
ATOM    520  C   ARG A 105     -18.619  38.881   9.955  1.00 46.16      A C
ATOM    521  O   ARG A 105     -19.619  38.760   9.253  1.00 46.76      A O
ATOM    522  N   LEU A 106     -18.167  37.914  10.747  1.00 44.71      A N
ATOM    523  CA  LEU A 106     -18.860  36.639  10.873  1.00 43.74      A C
ATOM    524  CB  LEU A 106     -17.892  35.533  11.272  1.00 43.55      A C
ATOM    525  CG  LEU A 106     -18.565  34.193  11.564  1.00 43.99      A C
ATOM    526  CD1 LEU A 106     -18.983  33.524  10.259  1.00 42.91      A C
ATOM    527  CD2 LEU A 106     -17.595  33.316  12.327  1.00 44.73      A C
ATOM    528  C   LEU A 106     -19.895  36.810  11.972  1.00 43.63      A C
ATOM    529  O   LEU A 106     -19.548  36.943  13.143  1.00 43.12      A O
ATOM    530  N   LEU A 107     -21.163  36.799  11.586  1.00 44.28      A N
ATOM    531  CA  LEU A 107     -22.261  36.984  12.521  1.00 45.34      A C
ATOM    532  CB  LEU A 107     -23.496  37.458  11.755  1.00 44.38      A C
ATOM    533  CG  LEU A 107     -23.750  38.965  11.635  1.00 42.69      A C
ATOM    534  CD1 LEU A 107     -22.488  39.750  11.857  1.00 43.28      A C
ATOM    535  CD2 LEU A 107     -24.350  39.265  10.273  1.00 45.10      A C
ATOM    536  C   LEU A 107     -22.606  35.755  13.343  1.00 46.52      A C
ATOM    537  O   LEU A 107     -22.998  35.876  14.497  1.00 45.38      A O
ATOM    538  N   ASP A 108     -22.454  34.576  12.748  1.00 48.77      A N
ATOM    539  CA  ASP A 108     -22.771  33.321  13.429  1.00 49.73      A C
ATOM    540  CB  ASP A 108     -24.282  33.254  13.695  1.00 52.96      A C
ATOM    541  CG  ASP A 108     -24.684  32.118  14.633  1.00 54.08      A C
ATOM    542  OD1 ASP A 108     -25.896  32.017  14.934  1.00 56.93      A O
ATOM    543  OD2 ASP A 108     -23.814  31.334  15.069  1.00 53.91      A O
ATOM    544  C   ASP A 108     -22.356  32.170  12.520  1.00 49.88      A C
ATOM    545  O   ASP A 108     -21.912  32.392  11.391  1.00 50.52      A O
ATOM    546  N   TRP A 109     -22.499  30.947  13.011  1.00 49.69      A N
ATOM    547  CA  TRP A 109     -22.156  29.769  12.232  1.00 51.14      A C
ATOM    548  CB  TRP A 109     -20.649  29.570  12.198  1.00 50.06      A C
ATOM    549  CG  TRP A 109     -20.066  29.339  13.544  1.00 50.48      A C
ATOM    550  CD2 TRP A 109     -19.750  28.076  14.131  1.00 50.62      A C
ATOM    551  CE2 TRP A 109     -19.214  28.332  15.410  1.00 50.70      A C
ATOM    552  CE3 TRP A 109     -19.867  26.747  13.700  1.00 51.80      A C
ATOM    553  CD1 TRP A 109     -19.729  30.284  14.462  1.00 50.14      A C
ATOM    554  NE1 TRP A 109     -19.212  29.690  15.586  1.00 50.64      A N
ATOM    555  CZ2 TRP A 109     -18.794  27.311  16.267  1.00 51.85      A C
ATOM    556  CZ3 TRP A 109     -19.449  25.726  14.555  1.00 52.57      A C
ATOM    557  CH2 TRP A 109     -18.917  26.018  15.825  1.00 51.75      A C
ATOM    558  C   TRP A 109     -22.804  28.520  12.821  1.00 53.01      A C
```

FIGURE 1A-11

```
ATOM    559  O   TRP A 109     -23.112  28.470  14.014  1.00 53.43      A O
ATOM    560  N   PHE A 110     -23.002  27.513  11.975  1.00 53.79      A N
ATOM    561  CA  PHE A 110     -23.611  26.264  12.404  1.00 54.18      A C
ATOM    562  CB  PHE A 110     -25.087  26.204  11.994  1.00 54.42      A C
ATOM    563  CG  PHE A 110     -25.903  27.361  12.493  1.00 55.23      A C
ATOM    564  CD1 PHE A 110     -25.954  28.550  11.779  1.00 54.45      A C
ATOM    565  CD2 PHE A 110     -26.609  27.268  13.689  1.00 56.39      A C
ATOM    566  CE1 PHE A 110     -26.693  29.629  12.245  1.00 56.25      A C
ATOM    567  CE2 PHE A 110     -27.352  28.344  14.164  1.00 57.19      A C
ATOM    568  CZ  PHE A 110     -27.394  29.527  13.438  1.00 56.67      A C
ATOM    569  C   PHE A 110     -22.888  25.096  11.782  1.00 53.44      A C
ATOM    570  O   PHE A 110     -22.248  25.233  10.742  1.00 53.55      A O
ATOM    571  N   GLU A 111     -22.987  23.945  12.433  1.00 54.58      A N
ATOM    572  CA  GLU A 111     -22.369  22.735  11.923  1.00 55.57      A C
ATOM    573  CB  GLU A 111     -21.493  22.076  12.989  1.00 56.61      A C
ATOM    574  CG  GLU A 111     -21.049  20.664  12.626  1.00 58.61      A C
ATOM    575  CD  GLU A 111     -19.950  20.149  13.533  1.00 61.24      A C
ATOM    576  OE1 GLU A 111     -19.963  20.496  14.736  1.00 62.28      A O
ATOM    577  OE2 GLU A 111     -19.079  19.391  13.048  1.00 62.31      A O
ATOM    578  C   GLU A 111     -23.475  21.778  11.493  1.00 55.24      A C
ATOM    579  O   GLU A 111     -24.520  21.683  12.139  1.00 54.84      A O
ATOM    580  N   ARG A 112     -23.241  21.089  10.385  1.00 54.19      A N
ATOM    581  CA  ARG A 112     -24.196  20.135   9.854  1.00 54.11      A C
ATOM    582  CB  ARG A 112     -24.784  20.637   8.539  1.00 51.40      A C
ATOM    583  CG  ARG A 112     -25.931  21.591   8.691  1.00 48.34      A C
ATOM    584  CD  ARG A 112     -26.275  22.141   7.337  1.00 47.18      A C
ATOM    585  NE  ARG A 112     -27.523  22.883   7.353  1.00 47.49      A N
ATOM    586  CZ  ARG A 112     -28.074  23.414   6.270  1.00 46.63      A C
ATOM    587  NH1 ARG A 112     -27.473  23.282   5.094  1.00 43.99      A N
ATOM    588  NH2 ARG A 112     -29.228  24.065   6.361  1.00 45.48      A N
ATOM    589  C   ARG A 112     -23.488  18.821   9.606  1.00 54.93      A C
ATOM    590  O   ARG A 112     -22.261  18.758   9.595  1.00 55.67      A O
ATOM    591  N   PRO A 113     -24.258  17.751   9.396  1.00 55.57      A N
ATOM    592  CD  PRO A 113     -25.731  17.689   9.324  1.00 56.50      A C
ATOM    593  CA  PRO A 113     -23.667  16.441   9.147  1.00 55.98      A C
ATOM    594  CB  PRO A 113     -24.802  15.691   8.463  1.00 57.21      A C
ATOM    595  CG  PRO A 113     -25.997  16.187   9.236  1.00 57.20      A C
ATOM    596  C   PRO A 113     -22.402  16.497   8.304  1.00 55.93      A C
ATOM    597  O   PRO A 113     -21.337  16.089   8.760  1.00 55.92      A O
ATOM    598  N   ASP A 114     -22.506  17.026   7.088  1.00 56.67      A N
ATOM    599  CA  ASP A 114     -21.343  17.089   6.206  1.00 57.08      A C
ATOM    600  CB  ASP A 114     -21.604  16.256   4.951  1.00 60.93      A C
ATOM    601  CG  ASP A 114     -21.820  14.787   5.261  1.00 64.77      A C
ATOM    602  OD1 ASP A 114     -22.920  14.439   5.748  1.00 66.56      A O
ATOM    603  OD2 ASP A 114     -20.883  13.986   5.022  1.00 65.83      A O
ATOM    604  C   ASP A 114     -20.853  18.474   5.779  1.00 55.31      A C
ATOM    605  O   ASP A 114     -20.155  18.603   4.770  1.00 55.47      A O
ATOM    606  N   SER A 115     -21.190  19.511   6.535  1.00 52.18      A N
ATOM    607  CA  SER A 115     -20.742  20.841   6.152  1.00 48.97      A C
ATOM    608  CB  SER A 115     -21.517  21.308   4.921  1.00 47.33      A C
ATOM    609  OG  SER A 115     -22.870  21.582   5.250  1.00 44.00      A O
ATOM    610  C   SER A 115     -20.919  21.862   7.261  1.00 47.68      A C
ATOM    611  O   SER A 115     -21.535  21.577   8.291  1.00 46.90      A O
ATOM    612  N   PHE A 116     -20.369  23.051   7.038  1.00 45.33      A N
ATOM    613  CA  PHE A 116     -20.499  24.148   7.988  1.00 44.49      A C
ATOM    614  CB  PHE A 116     -19.130  24.625   8.480  1.00 46.82      A C
```

FIGURE 1A-12

```
ATOM    615  CG  PHE A 116     -18.515  23.743   9.527  1.00 48.10      A C
ATOM    616  CD1 PHE A 116     -17.701  22.680   9.169  1.00 48.55      A C
ATOM    617  CD2 PHE A 116     -18.762  23.977  10.876  1.00 49.05      A C
ATOM    618  CE1 PHE A 116     -17.140  21.865  10.142  1.00 50.25      A C
ATOM    619  CE2 PHE A 116     -18.207  23.169  11.856  1.00 48.64      A C
ATOM    620  CZ  PHE A 116     -17.397  22.113  11.491  1.00 49.41      A C
ATOM    621  C   PHE A 116     -21.208  25.296   7.289  1.00 42.69      A C
ATOM    622  O   PHE A 116     -21.015  25.517   6.095  1.00 42.96      A O
ATOM    623  N   VAL A 117     -22.028  26.023   8.033  1.00 39.96      A N
ATOM    624  CA  VAL A 117     -22.758  27.145   7.474  1.00 40.41      A C
ATOM    625  CB  VAL A 117     -24.286  26.940   7.640  1.00 40.95      A C
ATOM    626  CG1 VAL A 117     -25.053  28.158   7.137  1.00 39.29      A C
ATOM    627  CG2 VAL A 117     -24.712  25.704   6.870  1.00 41.63      A C
ATOM    628  C   VAL A 117     -22.316  28.428   8.177  1.00 40.88      A C
ATOM    629  O   VAL A 117     -22.380  28.536   9.406  1.00 39.39      A O
ATOM    630  N   LEU A 118     -21.859  29.396   7.393  1.00 41.45      A N
ATOM    631  CA  LEU A 118     -21.396  30.658   7.950  1.00 41.72      A C
ATOM    632  CB  LEU A 118     -20.007  30.996   7.400  1.00 42.61      A C
ATOM    633  CG  LEU A 118     -18.890  29.967   7.591  1.00 43.65      A C
ATOM    634  CD1 LEU A 118     -17.591  30.504   6.995  1.00 44.33      A C
ATOM    635  CD2 LEU A 118     -18.707  29.688   9.060  1.00 43.85      A C
ATOM    636  C   LEU A 118     -22.345  31.803   7.636  1.00 40.96      A C
ATOM    637  O   LEU A 118     -22.748  31.990   6.487  1.00 41.07      A O
ATOM    638  N   ILE A 119     -22.704  32.565   8.662  1.00 39.96      A N
ATOM    639  CA  ILE A 119     -23.584  33.707   8.481  1.00 40.59      A C
ATOM    640  CB  ILE A 119     -24.610  33.824   9.640  1.00 40.83      A C
ATOM    641  CG2 ILE A 119     -25.619  34.920   9.331  1.00 39.99      A C
ATOM    642  CG1 ILE A 119     -25.334  32.487   9.849  1.00 39.27      A C
ATOM    643  CD1 ILE A 119     -26.075  31.976   8.635  1.00 38.82      A C
ATOM    644  C   ILE A 119     -22.704  34.962   8.454  1.00 41.54      A C
ATOM    645  O   ILE A 119     -22.149  35.377   9.476  1.00 42.72      A O
ATOM    646  N   LEU A 120     -22.564  35.555   7.275  1.00 41.85      A N
ATOM    647  CA  LEU A 120     -21.748  36.750   7.124  1.00 41.21      A C
ATOM    648  CB  LEU A 120     -20.797  36.615   5.929  1.00 38.40      A C
ATOM    649  CG  LEU A 120     -19.605  35.658   5.919  1.00 37.07      A C
ATOM    650  CD1 LEU A 120     -18.926  35.677   7.276  1.00 36.81      A C
ATOM    651  CD2 LEU A 120     -20.055  34.272   5.560  1.00 38.22      A C
ATOM    652  C   LEU A 120     -22.609  37.974   6.892  1.00 41.91      A C
ATOM    653  O   LEU A 120     -23.762  37.856   6.496  1.00 43.29      A O
ATOM    654  N   GLU A 121     -22.035  39.147   7.137  1.00 43.65      A N
ATOM    655  CA  GLU A 121     -22.730  40.406   6.897  1.00 46.99      A C
ATOM    656  CB  GLU A 121     -21.873  41.608   7.321  1.00 46.59      A C
ATOM    657  CG  GLU A 121     -21.534  41.722   8.794  1.00 49.20      A C
ATOM    658  CD  GLU A 121     -20.804  43.029   9.116  1.00 52.40      A C
ATOM    659  OE1 GLU A 121     -19.729  43.271   8.525  1.00 52.33      A O
ATOM    660  OE2 GLU A 121     -21.306  43.815   9.957  1.00 53.64      A O
ATOM    661  C   GLU A 121     -22.900  40.489   5.384  1.00 48.53      A C
ATOM    662  O   GLU A 121     -22.247  39.750   4.639  1.00 49.12      A O
ATOM    663  N   ARG A 122     -23.775  41.375   4.925  1.00 49.24      A N
ATOM    664  CA  ARG A 122     -23.942  41.566   3.490  1.00 52.01      A C
ATOM    665  CB  ARG A 122     -25.018  40.653   2.895  1.00 52.86      A C
ATOM    666  CG  ARG A 122     -25.216  40.893   1.388  1.00 54.65      A C
ATOM    667  CD  ARG A 122     -26.173  39.892   0.755  1.00 56.31      A C
ATOM    668  NE  ARG A 122     -27.437  39.817   1.480  1.00 59.26      A N
ATOM    669  CZ  ARG A 122     -28.623  40.146   0.974  1.00 59.74      A C
ATOM    670  NH1 ARG A 122     -28.723  40.580  -0.276  1.00 60.61      A N
```

FIGURE 1A-13

| ATOM | 671 | NH2 | ARG | A | 122 | -29.712 | 40.036 | 1.722 | 1.00 | 58.53 | A | N |
|---|---|---|---|---|---|---|---|---|---|---|---|---|
| ATOM | 672 | C | ARG | A | 122 | -24.293 | 43.007 | 3.191 | 1.00 | 52.93 | A | C |
| ATOM | 673 | O | ARG | A | 122 | -25.431 | 43.426 | 3.362 | 1.00 | 54.79 | A | O |
| ATOM | 674 | N | PRO | A | 123 | -23.305 | 43.798 | 2.762 | 1.00 | 53.77 | A | N |
| ATOM | 675 | CD | PRO | A | 123 | -21.867 | 43.491 | 2.627 | 1.00 | 54.28 | A | C |
| ATOM | 676 | CA | PRO | A | 123 | -23.592 | 45.199 | 2.452 | 1.00 | 53.19 | A | C |
| ATOM | 677 | CB | PRO | A | 123 | -22.202 | 45.826 | 2.376 | 1.00 | 54.38 | A | C |
| ATOM | 678 | CG | PRO | A | 123 | -21.335 | 44.693 | 1.889 | 1.00 | 54.55 | A | C |
| ATOM | 679 | C | PRO | A | 123 | -24.357 | 45.252 | 1.133 | 1.00 | 53.04 | A | C |
| ATOM | 680 | O | PRO | A | 123 | -24.296 | 44.314 | 0.342 | 1.00 | 52.85 | A | O |
| ATOM | 681 | N | GLU | A | 124 | -25.092 | 46.332 | 0.902 | 1.00 | 52.71 | A | N |
| ATOM | 682 | CA | GLU | A | 124 | -25.863 | 46.459 | -0.327 | 1.00 | 52.18 | A | C |
| ATOM | 683 | CB | GLU | A | 124 | -27.176 | 45.674 | -0.213 | 1.00 | 54.02 | A | C |
| ATOM | 684 | CG | GLU | A | 124 | -27.390 | 44.639 | -1.315 | 1.00 | 58.68 | A | C |
| ATOM | 685 | CD | GLU | A | 124 | -26.796 | 43.269 | -0.979 | 1.00 | 61.90 | A | C |
| ATOM | 686 | OE1 | GLU | A | 124 | -27.411 | 42.534 | -0.172 | 1.00 | 63.67 | A | O |
| ATOM | 687 | OE2 | GLU | A | 124 | -25.718 | 42.925 | -1.518 | 1.00 | 62.39 | A | O |
| ATOM | 688 | C | GLU | A | 124 | -26.159 | 47.930 | -0.578 | 1.00 | 49.74 | A | C |
| ATOM | 689 | O | GLU | A | 124 | -26.609 | 48.637 | 0.318 | 1.00 | 49.58 | A | O |
| ATOM | 690 | N | PRO | A | 125 | -25.908 | 48.411 | -1.803 | 1.00 | 47.32 | A | N |
| ATOM | 691 | CD | PRO | A | 125 | -25.955 | 49.841 | -2.138 | 1.00 | 47.03 | A | C |
| ATOM | 692 | CA | PRO | A | 125 | -25.364 | 47.641 | -2.926 | 1.00 | 45.92 | A | C |
| ATOM | 693 | CB | PRO | A | 125 | -25.570 | 48.566 | -4.136 | 1.00 | 44.66 | A | C |
| ATOM | 694 | CG | PRO | A | 125 | -26.267 | 49.796 | -3.593 | 1.00 | 46.55 | A | C |
| ATOM | 695 | C | PRO | A | 125 | -23.881 | 47.348 | -2.724 | 1.00 | 44.00 | A | C |
| ATOM | 696 | O | PRO | A | 125 | -23.222 | 48.003 | -1.924 | 1.00 | 43.25 | A | O |
| ATOM | 697 | N | VAL | A | 126 | -23.366 | 46.374 | -3.467 | 1.00 | 42.34 | A | N |
| ATOM | 698 | CA | VAL | A | 126 | -21.961 | 46.008 | -3.393 | 1.00 | 41.41 | A | C |
| ATOM | 699 | CB | VAL | A | 126 | -21.679 | 44.922 | -2.326 | 1.00 | 41.07 | A | C |
| ATOM | 700 | CG1 | VAL | A | 126 | -22.010 | 45.441 | -0.957 | 1.00 | 41.52 | A | C |
| ATOM | 701 | CG2 | VAL | A | 126 | -22.476 | 43.665 | -2.636 | 1.00 | 40.26 | A | C |
| ATOM | 702 | C | VAL | A | 126 | -21.471 | 45.454 | -4.710 | 1.00 | 40.68 | A | C |
| ATOM | 703 | O | VAL | A | 126 | -22.252 | 44.982 | -5.533 | 1.00 | 40.93 | A | O |
| ATOM | 704 | N | GLN | A | 127 | -20.158 | 45.513 | -4.887 | 1.00 | 40.21 | A | N |
| ATOM | 705 | CA | GLN | A | 127 | -19.507 | 44.984 | -6.070 | 1.00 | 38.82 | A | C |
| ATOM | 706 | CB | GLN | A | 127 | -19.505 | 46.009 | -7.200 | 1.00 | 36.46 | A | C |
| ATOM | 707 | CG | GLN | A | 127 | -19.217 | 45.385 | -8.547 | 1.00 | 35.90 | A | C |
| ATOM | 708 | CD | GLN | A | 127 | -19.135 | 46.404 | -9.658 | 1.00 | 38.05 | A | C |
| ATOM | 709 | OE1 | GLN | A | 127 | -19.220 | 46.055 | -10.837 | 1.00 | 38.97 | A | O |
| ATOM | 710 | NE2 | GLN | A | 127 | -18.957 | 47.672 | -9.292 | 1.00 | 34.86 | A | N |
| ATOM | 711 | C | GLN | A | 127 | -18.078 | 44.678 | -5.655 | 1.00 | 38.98 | A | C |
| ATOM | 712 | O | GLN | A | 127 | -17.470 | 45.462 | -4.919 | 1.00 | 39.35 | A | O |
| ATOM | 713 | N | ASP | A | 128 | -17.543 | 43.540 | -6.099 | 1.00 | 37.62 | A | N |
| ATOM | 714 | CA | ASP | A | 128 | -16.178 | 43.205 | -5.744 | 1.00 | 36.16 | A | C |
| ATOM | 715 | CB | ASP | A | 128 | -15.952 | 41.682 | -5.795 | 1.00 | 37.07 | A | C |
| ATOM | 716 | CG | ASP | A | 128 | -15.957 | 41.110 | -7.203 | 1.00 | 39.81 | A | C |
| ATOM | 717 | OD1 | ASP | A | 128 | -16.424 | 39.957 | -7.358 | 1.00 | 41.86 | A | O |
| ATOM | 718 | OD2 | ASP | A | 128 | -15.481 | 41.776 | -8.149 | 1.00 | 42.24 | A | O |
| ATOM | 719 | C | ASP | A | 128 | -15.236 | 43.981 | -6.662 | 1.00 | 36.40 | A | C |
| ATOM | 720 | O | ASP | A | 128 | -15.627 | 44.412 | -7.752 | 1.00 | 35.70 | A | O |
| ATOM | 721 | N | LEU | A | 129 | -14.007 | 44.186 | -6.205 | 1.00 | 35.04 | A | N |
| ATOM | 722 | CA | LEU | A | 129 | -13.035 | 44.951 | -6.966 | 1.00 | 33.71 | A | C |
| ATOM | 723 | CB | LEU | A | 129 | -11.720 | 45.056 | -6.189 | 1.00 | 32.07 | A | C |
| ATOM | 724 | CG | LEU | A | 129 | -11.108 | 46.444 | -5.991 | 1.00 | 30.48 | A | C |
| ATOM | 725 | CD1 | LEU | A | 129 | -9.649 | 46.278 | -5.585 | 1.00 | 26.97 | A | C |
| ATOM | 726 | CD2 | LEU | A | 129 | -11.221 | 47.273 | -7.251 | 1.00 | 27.52 | A | C |

FIGURE 1A-14

```
ATOM    727  C   LEU A 129     -12.766  44.368  -8.344  1.00 33.91      A C
ATOM    728  O   LEU A 129     -12.484  45.106  -9.287  1.00 33.12      A O
ATOM    729  N   PHE A 130     -12.834  43.048  -8.462  1.00 35.04      A N
ATOM    730  CA  PHE A 130     -12.588  42.413  -9.754  1.00 38.48      A C
ATOM    731  CB  PHE A 130     -12.668  40.890  -9.645  1.00 40.55      A C
ATOM    732  CG  PHE A 130     -12.443  40.181 -10.952  1.00 42.99      A C
ATOM    733  CD1 PHE A 130     -11.165  40.025 -11.460  1.00 44.18      A C
ATOM    734  CD2 PHE A 130     -13.521  39.710 -11.698  1.00 43.96      A C
ATOM    735  CE1 PHE A 130     -10.956  39.413 -12.693  1.00 45.48      A C
ATOM    736  CE2 PHE A 130     -13.324  39.095 -12.935  1.00 44.49      A C
ATOM    737  CZ  PHE A 130     -12.038  38.947 -13.433  1.00 44.67      A C
ATOM    738  C   PHE A 130     -13.608  42.893 -10.784  1.00 39.95      A C
ATOM    739  O   PHE A 130     -13.239  43.347 -11.865  1.00 40.62      A O
ATOM    740  N   ASP A 131     -14.891  42.790 -10.452  1.00 40.49      A N
ATOM    741  CA  ASP A 131     -15.931  43.239 -11.369  1.00 42.13      A C
ATOM    742  CB  ASP A 131     -17.316  42.882 -10.830  1.00 43.63      A C
ATOM    743  CG  ASP A 131     -17.556  41.392 -10.792  1.00 46.47      A C
ATOM    744  OD1 ASP A 131     -17.073  40.692 -11.713  1.00 46.94      A O
ATOM    745  OD2 ASP A 131     -18.237  40.923  -9.850  1.00 48.31      A O
ATOM    746  C   ASP A 131     -15.863  44.747 -11.606  1.00 42.03      A C
ATOM    747  O   ASP A 131     -16.100  45.226 -12.719  1.00 42.47      A O
ATOM    748  N   PHE A 132     -15.537  45.492 -10.555  1.00 41.20      A N
ATOM    749  CA  PHE A 132     -15.459  46.942 -10.649  1.00 40.96      A C
ATOM    750  CB  PHE A 132     -15.214  47.532  -9.259  1.00 40.11      A C
ATOM    751  CG  PHE A 132     -15.223  49.034  -9.217  1.00 40.24      A C
ATOM    752  CD1 PHE A 132     -14.075  49.760  -9.517  1.00 39.81      A C
ATOM    753  CD2 PHE A 132     -16.372  49.722  -8.841  1.00 39.07      A C
ATOM    754  CE1 PHE A 132     -14.067  51.157  -9.438  1.00 42.38      A C
ATOM    755  CE2 PHE A 132     -16.378  51.116  -8.759  1.00 40.58      A C
ATOM    756  CZ  PHE A 132     -15.219  51.836  -9.057  1.00 41.61      A C
ATOM    757  C   PHE A 132     -14.373  47.369 -11.623  1.00 42.28      A C
ATOM    758  O   PHE A 132     -14.592  48.249 -12.460  1.00 42.94      A O
ATOM    759  N   ILE A 133     -13.206  46.739 -11.529  1.00 42.38      A N
ATOM    760  CA  ILE A 133     -12.098  47.066 -12.419  1.00 42.65      A C
ATOM    761  CB  ILE A 133     -10.784  46.434 -11.907  1.00 41.75      A C
ATOM    762  CG2 ILE A 133      -9.701  46.523 -12.961  1.00 38.96      A C
ATOM    763  CG1 ILE A 133     -10.346  47.156 -10.630  1.00 42.25      A C
ATOM    764  CD1 ILE A 133      -9.208  46.487  -9.897  1.00 44.38      A C
ATOM    765  C   ILE A 133     -12.405  46.586 -13.835  1.00 43.75      A C
ATOM    766  O   ILE A 133     -12.109  47.269 -14.813  1.00 42.64      A O
ATOM    767  N   THR A 134     -13.012  45.411 -13.934  1.00 45.80      A N
ATOM    768  CA  THR A 134     -13.380  44.840 -15.222  1.00 47.23      A C
ATOM    769  CB  THR A 134     -14.023  43.441 -15.020  1.00 46.61      A C
ATOM    770  OG1 THR A 134     -13.025  42.525 -14.546  1.00 46.27      A O
ATOM    771  CG2 THR A 134     -14.625  42.915 -16.321  1.00 45.06      A C
ATOM    772  C   THR A 134     -14.345  45.757 -15.991  1.00 48.73      A C
ATOM    773  O   THR A 134     -14.287  45.832 -17.216  1.00 49.59      A O
ATOM    774  N   GLU A 135     -15.221  46.460 -15.277  1.00 50.03      A N
ATOM    775  CA  GLU A 135     -16.181  47.362 -15.921  1.00 52.24      A C
ATOM    776  CB  GLU A 135     -17.454  47.502 -15.080  1.00 52.45      A C
ATOM    777  CG  GLU A 135     -18.316  46.262 -15.007  1.00 54.34      A C
ATOM    778  CD  GLU A 135     -19.550  46.482 -14.161  1.00 55.38      A C
ATOM    779  OE1 GLU A 135     -20.291  45.498 -13.929  1.00 56.41      A O
ATOM    780  OE2 GLU A 135     -19.775  47.640 -13.732  1.00 53.57      A O
ATOM    781  C   GLU A 135     -15.650  48.768 -16.193  1.00 53.27      A C
ATOM    782  O   GLU A 135     -15.912  49.337 -17.254  1.00 54.08      A O
```

FIGURE 1A-15

```
ATOM    783  N   ARG A 136     -14.923  49.336 -15.234  1.00 51.80      A N
ATOM    784  CA  ARG A 136     -14.398  50.686 -15.402  1.00 51.30      A C
ATOM    785  CB  ARG A 136     -14.433  51.450 -14.089  1.00 53.99      A C
ATOM    786  CG  ARG A 136     -15.781  51.684 -13.457  1.00 56.96      A C
ATOM    787  CD  ARG A 136     -15.568  52.787 -12.441  1.00 59.02      A C
ATOM    788  NE  ARG A 136     -16.735  53.076 -11.628  1.00 60.30      A N
ATOM    789  CZ  ARG A 136     -16.844  54.159 -10.866  1.00 60.06      A C
ATOM    790  NH1 ARG A 136     -15.852  55.046 -10.827  1.00 57.80      A N
ATOM    791  NH2 ARG A 136     -17.942  54.352 -10.143  1.00 60.23      A N
ATOM    792  C   ARG A 136     -12.969  50.753 -15.904  1.00 49.84      A C
ATOM    793  O   ARG A 136     -12.485  51.831 -16.231  1.00 50.31      A O
ATOM    794  N   GLY A 137     -12.281  49.619 -15.940  1.00 48.73      A N
ATOM    795  CA  GLY A 137     -10.896  49.632 -16.382  1.00 46.25      A C
ATOM    796  C   GLY A 137      -9.995  50.228 -15.308  1.00 43.89      A C
ATOM    797  O   GLY A 137     -10.391  50.327 -14.145  1.00 42.31      A O
ATOM    798  N   ALA A 138      -8.787  50.630 -15.696  1.00 41.58      A N
ATOM    799  CA  ALA A 138      -7.829  51.214 -14.765  1.00 39.50      A C
ATOM    800  CB  ALA A 138      -6.631  51.745 -15.526  1.00 38.37      A C
ATOM    801  C   ALA A 138      -8.468  52.328 -13.944  1.00 39.08      A C
ATOM    802  O   ALA A 138      -9.287  53.100 -14.454  1.00 40.34      A O
ATOM    803  N   LEU A 139      -8.085  52.414 -12.674  1.00 37.49      A N
ATOM    804  CA  LEU A 139      -8.630  53.418 -11.771  1.00 36.03      A C
ATOM    805  CB  LEU A 139      -8.804  52.828 -10.371  1.00 33.89      A C
ATOM    806  CG  LEU A 139      -9.534  51.493 -10.230  1.00 35.16      A C
ATOM    807  CD1 LEU A 139      -9.629  51.130  -8.745  1.00 32.91      A C
ATOM    808  CD2 LEU A 139     -10.928  51.595 -10.848  1.00 33.06      A C
ATOM    809  C   LEU A 139      -7.743  54.647 -11.660  1.00 36.58      A C
ATOM    810  O   LEU A 139      -6.513  54.547 -11.730  1.00 36.36      A O
ATOM    811  N   GLN A 140      -8.374  55.807 -11.489  1.00 34.62      A N
ATOM    812  CA  GLN A 140      -7.638  57.050 -11.316  1.00 36.04      A C
ATOM    813  CB  GLN A 140      -8.592  58.238 -11.245  1.00 37.52      A C
ATOM    814  CG  GLN A 140      -9.425  58.420 -12.506  1.00 44.14      A C
ATOM    815  CD  GLN A 140     -10.424  59.566 -12.399  1.00 47.38      A C
ATOM    816  OE1 GLN A 140     -11.261  59.752 -13.286  1.00 49.91      A O
ATOM    817  NE2 GLN A 140     -10.338  60.341 -11.312  1.00 45.77      A N
ATOM    818  C   GLN A 140      -6.914  56.872  -9.990  1.00 35.45      A C
ATOM    819  O   GLN A 140      -7.433  56.221  -9.086  1.00 35.46      A O
ATOM    820  N   GLU A 141      -5.728  57.454  -9.870  1.00 34.91      A N
ATOM    821  CA  GLU A 141      -4.928  57.292  -8.663  1.00 35.54      A C
ATOM    822  CB  GLU A 141      -3.559  57.945  -8.872  1.00 33.61      A C
ATOM    823  CG  GLU A 141      -2.849  57.317 -10.075  1.00 34.48      A C
ATOM    824  CD  GLU A 141      -1.377  57.649 -10.172  1.00 34.92      A C
ATOM    825  OE1 GLU A 141      -0.767  57.307 -11.206  1.00 37.90      A O
ATOM    826  OE2 GLU A 141      -0.822  58.241  -9.227  1.00 34.50      A O
ATOM    827  C   GLU A 141      -5.561  57.731  -7.354  1.00 35.34      A C
ATOM    828  O   GLU A 141      -5.286  57.155  -6.304  1.00 37.17      A O
ATOM    829  N   GLU A 142      -6.422  58.734  -7.411  1.00 35.69      A N
ATOM    830  CA  GLU A 142      -7.096  59.208  -6.213  1.00 34.86      A C
ATOM    831  CB  GLU A 142      -7.918  60.453  -6.549  1.00 36.40      A C
ATOM    832  CG  GLU A 142      -8.914  60.859  -5.490  1.00 41.18      A C
ATOM    833  CD  GLU A 142      -9.624  62.156  -5.840  1.00 43.46      A C
ATOM    834  OE1 GLU A 142      -9.035  63.237  -5.607  1.00 45.28      A O
ATOM    835  OE2 GLU A 142     -10.763  62.089  -6.356  1.00 43.37      A O
ATOM    836  C   GLU A 142      -8.005  58.096  -5.688  1.00 32.39      A C
ATOM    837  O   GLU A 142      -8.090  57.856  -4.490  1.00 32.11      A O
ATOM    838  N   LEU A 143      -8.679  57.410  -6.594  1.00 31.13      A N
```

FIGURE 1A-16

```
ATOM    839  CA   LEU A 143     -9.571  56.329  -6.202  1.00 31.68      A C
ATOM    840  CB   LEU A 143    -10.453  55.947  -7.390  1.00 30.38      A C
ATOM    841  CG   LEU A 143    -11.520  54.878  -7.213  1.00 31.57      A C
ATOM    842  CD1  LEU A 143    -12.446  55.239  -6.066  1.00 32.39      A C
ATOM    843  CD2  LEU A 143    -12.284  54.740  -8.518  1.00 30.05      A C
ATOM    844  C    LEU A 143     -8.737  55.133  -5.736  1.00 30.95      A C
ATOM    845  O    LEU A 143     -9.025  54.521  -4.708  1.00 31.34      A O
ATOM    846  N    ALA A 144     -7.690  54.813  -6.486  1.00 29.35      A N
ATOM    847  CA   ALA A 144     -6.825  53.695  -6.126  1.00 29.38      A C
ATOM    848  CB   ALA A 144     -5.758  53.495  -7.185  1.00 26.00      A C
ATOM    849  C    ALA A 144     -6.179  53.956  -4.767  1.00 29.15      A C
ATOM    850  O    ALA A 144     -5.957  53.025  -3.993  1.00 28.70      A O
ATOM    851  N    ARG A 145     -5.906  55.229  -4.476  1.00 29.20      A N
ATOM    852  CA   ARG A 145     -5.277  55.608  -3.214  1.00 30.72      A C
ATOM    853  CB   ARG A 145     -4.936  57.102  -3.195  1.00 31.95      A C
ATOM    854  CG   ARG A 145     -3.742  57.429  -2.299  1.00 35.79      A C
ATOM    855  CD   ARG A 145     -3.500  58.932  -2.066  1.00 35.64      A C
ATOM    856  NE   ARG A 145     -4.037  59.814  -3.098  1.00 41.74      A N
ATOM    857  CZ   ARG A 145     -3.447  60.123  -4.250  1.00 42.74      A C
ATOM    858  NH1  ARG A 145     -2.263  59.625  -4.576  1.00 42.23      A N
ATOM    859  NH2  ARG A 145     -4.045  60.970  -5.072  1.00 45.88      A N
ATOM    860  C    ARG A 145     -6.205  55.309  -2.051  1.00 30.15      A C
ATOM    861  O    ARG A 145     -5.797  54.723  -1.046  1.00 30.68      A O
ATOM    862  N    SER A 146     -7.456  55.723  -2.192  1.00 29.59      A N
ATOM    863  CA   SER A 146     -8.451  55.512  -1.148  1.00 30.04      A C
ATOM    864  CB   SER A 146     -9.757  56.214  -1.535  1.00 29.80      A C
ATOM    865  OG   SER A 146    -10.822  55.813  -0.695  1.00 32.64      A O
ATOM    866  C    SER A 146     -8.689  54.020  -0.932  1.00 29.85      A C
ATOM    867  O    SER A 146     -8.732  53.545   0.206  1.00 28.62      A O
ATOM    868  N    PHE A 147     -8.834  53.287  -2.035  1.00 29.40      A N
ATOM    869  CA   PHE A 147     -9.057  51.849  -1.972  1.00 29.31      A C
ATOM    870  CB   PHE A 147     -9.305  51.281  -3.382  1.00 30.27      A C
ATOM    871  CG   PHE A 147    -10.703  51.532  -3.909  1.00 32.52      A C
ATOM    872  CD1  PHE A 147    -11.125  50.953  -5.104  1.00 30.99      A C
ATOM    873  CD2  PHE A 147    -11.610  52.325  -3.196  1.00 30.39      A C
ATOM    874  CE1  PHE A 147    -12.424  51.154  -5.581  1.00 29.58      A C
ATOM    875  CE2  PHE A 147    -12.905  52.530  -3.667  1.00 31.05      A C
ATOM    876  CZ   PHE A 147    -13.311  51.941  -4.861  1.00 31.71      A C
ATOM    877  C    PHE A 147     -7.879  51.118  -1.326  1.00 29.36      A C
ATOM    878  O    PHE A 147     -8.058  50.331  -0.393  1.00 28.72      A O
ATOM    879  N    PHE A 148     -6.676  51.390  -1.823  1.00 27.89      A N
ATOM    880  CA   PHE A 148     -5.474  50.748  -1.314  1.00 28.44      A C
ATOM    881  CB   PHE A 148     -4.248  51.240  -2.098  1.00 27.56      A C
ATOM    882  CG   PHE A 148     -3.018  50.398  -1.895  1.00 29.31      A C
ATOM    883  CD1  PHE A 148     -3.003  49.061  -2.284  1.00 28.64      A C
ATOM    884  CD2  PHE A 148     -1.872  50.939  -1.317  1.00 29.34      A C
ATOM    885  CE1  PHE A 148     -1.863  48.269  -2.102  1.00 28.55      A C
ATOM    886  CE2  PHE A 148     -0.725  50.154  -1.131  1.00 28.09      A C
ATOM    887  CZ   PHE A 148     -0.722  48.819  -1.525  1.00 26.51      A C
ATOM    888  C    PHE A 148     -5.319  51.065   0.175  1.00 27.72      A C
ATOM    889  O    PHE A 148     -5.057  50.172   0.991  1.00 27.58      A O
ATOM    890  N    TRP A 149     -5.489  52.337   0.525  1.00 26.46      A N
ATOM    891  CA   TRP A 149     -5.377  52.758   1.916  1.00 27.15      A C
ATOM    892  CB   TRP A 149     -5.735  54.244   2.054  1.00 27.07      A C
ATOM    893  CG   TRP A 149     -5.566  54.776   3.440  1.00 27.44      A C
ATOM    894  CD2  TRP A 149     -4.356  55.282   4.027  1.00 28.29      A C
```

FIGURE 1A-17

```
ATOM    895  CE2 TRP A 149      -4.652  55.622   5.358  1.00 27.87      A C
ATOM    896  CE3 TRP A 149      -3.050  55.476   3.554  1.00 29.66      A C
ATOM    897  CD1 TRP A 149      -6.511  54.832   4.408  1.00 27.87      A C
ATOM    898  NE1 TRP A 149      -5.974  55.337   5.566  1.00 27.58      A N
ATOM    899  CZ2 TRP A 149      -3.692  56.153   6.230  1.00 30.01      A C
ATOM    900  CZ3 TRP A 149      -2.094  56.001   4.418  1.00 31.11      A C
ATOM    901  CH2 TRP A 149      -2.422  56.332   5.743  1.00 30.52      A C
ATOM    902  C   TRP A 149      -6.292  51.904   2.800  1.00 27.70      A C
ATOM    903  O   TRP A 149      -5.843  51.360   3.814  1.00 26.51      A O
ATOM    904  N   GLN A 150      -7.559  51.758   2.405  1.00 26.97      A N
ATOM    905  CA  GLN A 150      -8.499  50.967   3.197  1.00 27.64      A C
ATOM    906  CB  GLN A 150      -9.924  51.087   2.639  1.00 27.64      A C
ATOM    907  CG  GLN A 150     -10.531  52.477   2.781  1.00 29.11      A C
ATOM    908  CD  GLN A 150     -11.975  52.528   2.325  1.00 32.37      A C
ATOM    909  OE1 GLN A 150     -12.803  51.711   2.738  1.00 33.04      A O
ATOM    910  NE2 GLN A 150     -12.286  53.491   1.474  1.00 32.60      A N
ATOM    911  C   GLN A 150      -8.097  49.497   3.274  1.00 28.91      A C
ATOM    912  O   GLN A 150      -8.328  48.836   4.292  1.00 28.31      A O
ATOM    913  N   VAL A 151      -7.516  48.970   2.200  1.00 28.46      A N
ATOM    914  CA  VAL A 151      -7.085  47.582   2.232  1.00 30.71      A C
ATOM    915  CB  VAL A 151      -6.577  47.108   0.865  1.00 31.71      A C
ATOM    916  CG1 VAL A 151      -5.932  45.744   1.005  1.00 31.67      A C
ATOM    917  CG2 VAL A 151      -7.749  47.028  -0.119  1.00 33.89      A C
ATOM    918  C   VAL A 151      -5.961  47.461   3.255  1.00 30.47      A C
ATOM    919  O   VAL A 151      -5.901  46.498   4.015  1.00 29.97      A O
ATOM    920  N   LEU A 152      -5.080  48.454   3.287  1.00 30.38      A N
ATOM    921  CA  LEU A 152      -3.977  48.437   4.238  1.00 31.04      A C
ATOM    922  CB  LEU A 152      -3.024  49.594   3.950  1.00 31.42      A C
ATOM    923  CG  LEU A 152      -1.962  49.218   2.915  1.00 33.37      A C
ATOM    924  CD1 LEU A 152      -1.637  50.418   2.083  1.00 34.79      A C
ATOM    925  CD2 LEU A 152      -0.709  48.673   3.627  1.00 31.32      A C
ATOM    926  C   LEU A 152      -4.448  48.496   5.688  1.00 31.47      A C
ATOM    927  O   LEU A 152      -3.875  47.825   6.560  1.00 32.88      A O
ATOM    928  N   GLU A 153      -5.475  49.300   5.958  1.00 28.51      A N
ATOM    929  CA  GLU A 153      -5.993  49.398   7.316  1.00 28.60      A C
ATOM    930  CB  GLU A 153      -7.065  50.487   7.424  1.00 28.63      A C
ATOM    931  CG  GLU A 153      -6.528  51.906   7.363  1.00 30.20      A C
ATOM    932  CD  GLU A 153      -5.752  52.304   8.609  1.00 30.76      A C
ATOM    933  OE1 GLU A 153      -4.654  52.862   8.447  1.00 31.11      A O
ATOM    934  OE2 GLU A 153      -6.238  52.078   9.741  1.00 31.44      A O
ATOM    935  C   GLU A 153      -6.606  48.066   7.709  1.00 27.63      A C
ATOM    936  O   GLU A 153      -6.524  47.648   8.862  1.00 27.01      A O
ATOM    937  N   ALA A 154      -7.214  47.394   6.739  1.00 27.72      A N
ATOM    938  CA  ALA A 154      -7.865  46.113   6.994  1.00 28.64      A C
ATOM    939  CB  ALA A 154      -8.772  45.740   5.814  1.00 25.00      A C
ATOM    940  C   ALA A 154      -6.849  45.011   7.241  1.00 29.79      A C
ATOM    941  O   ALA A 154      -7.039  44.146   8.099  1.00 29.36      A O
ATOM    942  N   VAL A 155      -5.763  45.042   6.480  1.00 31.28      A N
ATOM    943  CA  VAL A 155      -4.732  44.035   6.630  1.00 31.67      A C
ATOM    944  CB  VAL A 155      -3.736  44.104   5.468  1.00 31.42      A C
ATOM    945  CG1 VAL A 155      -2.624  43.120   5.676  1.00 35.39      A C
ATOM    946  CG2 VAL A 155      -4.461  43.763   4.176  1.00 31.51      A C
ATOM    947  C   VAL A 155      -4.048  44.239   7.970  1.00 32.30      A C
ATOM    948  O   VAL A 155      -3.751  43.267   8.668  1.00 33.13      A O
ATOM    949  N   ARG A 156      -3.824  45.496   8.346  1.00 30.46      A N
ATOM    950  CA  ARG A 156      -3.205  45.780   9.637  1.00 30.53      A C
```

FIGURE 1A-18

```
ATOM    951  CB   ARG A 156      -3.004   47.283    9.850  1.00 28.53      A C
ATOM    952  CG   ARG A 156      -1.916   47.897    8.982  1.00 29.04      A C
ATOM    953  CD   ARG A 156      -1.830   49.389    9.230  1.00 28.05      A C
ATOM    954  NE   ARG A 156      -1.597   49.683   10.640  1.00 27.71      A N
ATOM    955  CZ   ARG A 156      -1.737   50.886   11.189  1.00 28.51      A C
ATOM    956  NH1  ARG A 156      -2.116   51.927   10.451  1.00 27.84      A N
ATOM    957  NH2  ARG A 156      -1.496   51.049   12.482  1.00 28.52      A N
ATOM    958  C    ARG A 156      -4.117   45.244   10.722  1.00 31.26      A C
ATOM    959  O    ARG A 156      -3.652   44.678   11.703  1.00 31.87      A O
ATOM    960  N    HIS A 157      -5.422   45.428   10.533  1.00 32.57      A N
ATOM    961  CA   HIS A 157      -6.416   44.954   11.488  1.00 34.30      A C
ATOM    962  CB   HIS A 157      -7.830   45.244   10.974  1.00 34.75      A C
ATOM    963  CG   HIS A 157      -8.908   44.562   11.758  1.00 38.53      A C
ATOM    964  CD2  HIS A 157      -9.812   43.615   11.397  1.00 38.29      A C
ATOM    965  ND1  HIS A 157      -9.142   44.823   13.093  1.00 40.22      A N
ATOM    966  CE1  HIS A 157     -10.141   44.068   13.520  1.00 38.11      A C
ATOM    967  NE2  HIS A 157     -10.564   43.328   12.510  1.00 39.40      A N
ATOM    968  C    HIS A 157      -6.255   43.457   11.712  1.00 34.05      A C
ATOM    969  O    HIS A 157      -6.095   43.023   12.839  1.00 34.54      A O
ATOM    970  N    CYS A 158      -6.287   42.676   10.632  1.00 33.34      A N
ATOM    971  CA   CYS A 158      -6.140   41.221   10.726  1.00 32.06      A C
ATOM    972  CB   CYS A 158      -6.160   40.586    9.337  1.00 31.07      A C
ATOM    973  SG   CYS A 158      -7.675   40.824    8.422  1.00 34.98      A S
ATOM    974  C    CYS A 158      -4.845   40.813   11.415  1.00 32.56      A C
ATOM    975  O    CYS A 158      -4.848   39.958   12.301  1.00 31.24      A O
ATOM    976  N    HIS A 159      -3.733   41.412   10.989  1.00 33.90      A N
ATOM    977  CA   HIS A 159      -2.425   41.101   11.566  1.00 35.83      A C
ATOM    978  CB   HIS A 159      -1.333   41.909   10.866  1.00 37.68      A C
ATOM    979  CG   HIS A 159      -1.022   41.423    9.482  1.00 42.89      A C
ATOM    980  CD2  HIS A 159       0.119   41.472    8.754  1.00 44.16      A C
ATOM    981  ND1  HIS A 159      -1.962   40.815    8.675  1.00 46.47      A N
ATOM    982  CE1  HIS A 159      -1.415   40.513    7.511  1.00 45.44      A C
ATOM    983  NE2  HIS A 159      -0.153   40.902    7.532  1.00 45.62      A N
ATOM    984  C    HIS A 159      -2.435   41.388   13.056  1.00 36.31      A C
ATOM    985  O    HIS A 159      -2.009   40.568   13.860  1.00 35.42      A O
ATOM    986  N    ASN A 160      -2.950   42.550   13.418  1.00 38.20      A N
ATOM    987  CA   ASN A 160      -3.041   42.942   14.810  1.00 40.64      A C
ATOM    988  CB   ASN A 160      -3.672   44.326   14.893  1.00 44.28      A C
ATOM    989  CG   ASN A 160      -3.608   44.911   16.278  1.00 50.19      A C
ATOM    990  OD1  ASN A 160      -4.317   44.473   17.191  1.00 53.38      A O
ATOM    991  ND2  ASN A 160      -2.748   45.912   16.451  1.00 53.81      A N
ATOM    992  C    ASN A 160      -3.881   41.918   15.590  1.00 41.56      A C
ATOM    993  O    ASN A 160      -3.693   41.729   16.791  1.00 39.72      A O
ATOM    994  N    CME A 161      -4.797   41.248   14.894  1.00 41.66      A N
ATOM    995  CA   CME A 161      -5.658   40.256   15.523  1.00 41.26      A C
ATOM    996  C    CME A 161      -5.074   38.849   15.441  1.00 39.56      A C
ATOM    997  CB   CME A 161      -7.045   40.269   14.874  1.00 44.58      A C
ATOM    998  SG   CME A 161      -8.106   41.675   15.306  1.00 48.71      A S
ATOM    999  S1   CME A 161      -8.208   41.714   17.450  1.00 63.10      A S
ATOM   1000  C1   CME A 161      -7.508   43.318   17.982  1.00 61.90      A C
ATOM   1001  C2   CME A 161      -8.594   44.086   18.735  1.00 66.41      A C
ATOM   1002  O1   CME A 161      -8.606   45.481   18.378  1.00 67.54      A O
ATOM   1003  O    CME A 161      -5.719   37.890   15.853  1.00 38.26      A O
ATOM   1004  N    GLY A 162      -3.861   38.735   14.900  1.00 37.87      A N
ATOM   1005  CA   GLY A 162      -3.201   37.444   14.782  1.00 35.74      A C
ATOM   1006  C    GLY A 162      -3.587   36.637   13.554  1.00 36.04      A C
```

FIGURE 1A-19

```
ATOM   1007  O    GLY A 162      -3.298  35.438  13.466  1.00 36.09      A O
ATOM   1008  N    VAL A 163      -4.230  37.292  12.593  1.00 34.77      A N
ATOM   1009  CA   VAL A 163      -4.662  36.616  11.381  1.00 33.02      A C
ATOM   1010  CB   VAL A 163      -6.163  36.777  11.197  1.00 33.05      A C
ATOM   1011  CG1  VAL A 163      -6.601  36.125   9.899  1.00 32.86      A C
ATOM   1012  CG2  VAL A 163      -6.888  36.174  12.388  1.00 33.86      A C
ATOM   1013  C    VAL A 163      -3.974  37.085  10.099  1.00 34.02      A C
ATOM   1014  O    VAL A 163      -3.790  38.281   9.869  1.00 33.49      A O
ATOM   1015  N    LEU A 164      -3.611  36.126   9.257  1.00 34.37      A N
ATOM   1016  CA   LEU A 164      -2.964  36.418   7.981  1.00 34.89      A C
ATOM   1017  CB   LEU A 164      -1.640  35.666   7.920  1.00 35.78      A C
ATOM   1018  CG   LEU A 164      -0.616  36.048   6.860  1.00 37.54      A C
ATOM   1019  CD1  LEU A 164      -0.115  37.462   7.119  1.00 37.00      A C
ATOM   1020  CD2  LEU A 164       0.536  35.049   6.907  1.00 39.22      A C
ATOM   1021  C    LEU A 164      -3.924  35.916   6.894  1.00 34.36      A C
ATOM   1022  O    LEU A 164      -4.237  34.722   6.841  1.00 36.04      A O
ATOM   1023  N    HIS A 165      -4.407  36.808   6.036  1.00 33.55      A N
ATOM   1024  CA   HIS A 165      -5.358  36.399   4.996  1.00 31.81      A C
ATOM   1025  CB   HIS A 165      -5.948  37.641   4.323  1.00 31.48      A C
ATOM   1026  CG   HIS A 165      -7.061  37.353   3.359  1.00 30.10      A C
ATOM   1027  CD2  HIS A 165      -8.387  37.612   3.429  1.00 29.57      A C
ATOM   1028  ND1  HIS A 165      -6.852  36.764   2.130  1.00 28.84      A N
ATOM   1029  CE1  HIS A 165      -8.000  36.676   1.485  1.00 29.55      A C
ATOM   1030  NE2  HIS A 165      -8.947  37.184   2.250  1.00 28.68      A N
ATOM   1031  C    HIS A 165      -4.768  35.450   3.948  1.00 33.67      A C
ATOM   1032  O    HIS A 165      -5.389  34.444   3.598  1.00 34.16      A O
ATOM   1033  N    ARG A 166      -3.580  35.769   3.442  1.00 33.74      A N
ATOM   1034  CA   ARG A 166      -2.901  34.929   2.449  1.00 34.00      A C
ATOM   1035  CB   ARG A 166      -2.796  33.496   2.947  1.00 34.85      A C
ATOM   1036  CG   ARG A 166      -2.045  33.357   4.242  1.00 38.62      A C
ATOM   1037  CD   ARG A 166      -2.360  32.015   4.849  1.00 42.19      A C
ATOM   1038  NE   ARG A 166      -1.266  31.073   4.695  1.00 42.06      A N
ATOM   1039  CZ   ARG A 166      -1.398  29.762   4.859  1.00 43.51      A C
ATOM   1040  NH1  ARG A 166      -2.585  29.246   5.172  1.00 40.24      A N
ATOM   1041  NH2  ARG A 166      -0.338  28.971   4.730  1.00 43.30      A N
ATOM   1042  C    ARG A 166      -3.496  34.894   1.051  1.00 34.98      A C
ATOM   1043  O    ARG A 166      -2.962  34.210   0.181  1.00 36.36      A O
ATOM   1044  N    ASP A 167      -4.591  35.602   0.816  1.00 34.53      A N
ATOM   1045  CA   ASP A 167      -5.162  35.598  -0.521  1.00 36.40      A C
ATOM   1046  CB   ASP A 167      -6.208  34.486  -0.632  1.00 39.34      A C
ATOM   1047  CG   ASP A 167      -6.544  34.133  -2.076  1.00 41.91      A C
ATOM   1048  OD1  ASP A 167      -5.651  34.235  -2.947  1.00 42.15      A O
ATOM   1049  OD2  ASP A 167      -7.704  33.735  -2.331  1.00 44.45      A O
ATOM   1050  C    ASP A 167      -5.767  36.956  -0.878  1.00 36.51      A C
ATOM   1051  O    ASP A 167      -6.870  37.042  -1.418  1.00 35.57      A O
ATOM   1052  N    ILE A 168      -5.026  38.018  -0.569  1.00 36.07      A N
ATOM   1053  CA   ILE A 168      -5.468  39.371  -0.861  1.00 35.99      A C
ATOM   1054  CB   ILE A 168      -4.530  40.405  -0.199  1.00 38.45      A C
ATOM   1055  CG2  ILE A 168      -4.923  41.820  -0.613  1.00 37.35      A C
ATOM   1056  CG1  ILE A 168      -4.576  40.259   1.323  1.00 37.67      A C
ATOM   1057  CD1  ILE A 168      -3.450  40.983   2.021  1.00 37.95      A C
ATOM   1058  C    ILE A 168      -5.428  39.556  -2.377  1.00 36.21      A C
ATOM   1059  O    ILE A 168      -4.399  39.318  -3.005  1.00 36.83      A O
ATOM   1060  N    LYS A 169      -6.554  39.963  -2.958  1.00 35.75      A N
ATOM   1061  CA   LYS A 169      -6.666  40.193  -4.399  1.00 36.29      A C
ATOM   1062  CB   LYS A 169      -6.523  38.880  -5.184  1.00 37.33      A C
```

FIGURE 1A-20

```
ATOM   1063  CG  LYS A 169      -7.656  37.898  -4.973  1.00 40.26      A C
ATOM   1064  CD  LYS A 169      -7.490  36.635  -5.800  1.00 42.71      A C
ATOM   1065  CE  LYS A 169      -8.612  35.657  -5.469  1.00 45.20      A C
ATOM   1066  NZ  LYS A 169      -8.528  34.383  -6.238  1.00 49.93      A N
ATOM   1067  C   LYS A 169      -8.023  40.838  -4.699  1.00 36.42      A C
ATOM   1068  O   LYS A 169      -8.918  40.839  -3.844  1.00 34.37      A O
ATOM   1069  N   ASP A 170      -8.180  41.373  -5.909  1.00 35.91      A N
ATOM   1070  CA  ASP A 170      -9.416  42.057  -6.279  1.00 37.63      A C
ATOM   1071  CB  ASP A 170      -9.405  42.444  -7.771  1.00 36.26      A C
ATOM   1072  CG  ASP A 170      -9.007  41.296  -8.683  1.00 35.59      A C
ATOM   1073  OD1 ASP A 170      -8.982  40.132  -8.240  1.00 37.22      A O
ATOM   1074  OD2 ASP A 170      -8.716  41.565  -9.862  1.00 38.04      A O
ATOM   1075  C   ASP A 170     -10.697  41.300  -5.945  1.00 38.50      A C
ATOM   1076  O   ASP A 170     -11.616  41.869  -5.354  1.00 39.90      A O
ATOM   1077  N   GLU A 171     -10.750  40.026  -6.313  1.00 38.22      A N
ATOM   1078  CA  GLU A 171     -11.917  39.182  -6.060  1.00 40.07      A C
ATOM   1079  CB  GLU A 171     -11.690  37.779  -6.629  1.00 43.50      A C
ATOM   1080  CG  GLU A 171     -11.531  37.746  -8.138  1.00 51.40      A C
ATOM   1081  CD  GLU A 171     -11.067  36.392  -8.657  1.00 55.72      A C
ATOM   1082  OE1 GLU A 171      -9.898  36.019  -8.403  1.00 58.56      A O
ATOM   1083  OE2 GLU A 171     -11.875  35.701  -9.318  1.00 58.36      A O
ATOM   1084  C   GLU A 171     -12.288  39.050  -4.592  1.00 37.88      A C
ATOM   1085  O   GLU A 171     -13.444  38.798  -4.272  1.00 39.07      A O
ATOM   1086  N   ASN A 172     -11.316  39.210  -3.700  1.00 36.72      A N
ATOM   1087  CA  ASN A 172     -11.591  39.080  -2.277  1.00 34.84      A C
ATOM   1088  CB  ASN A 172     -10.493  38.255  -1.597  1.00 33.95      A C
ATOM   1089  CG  ASN A 172     -10.536  36.791  -2.014  1.00 35.75      A C
ATOM   1090  OD1 ASN A 172     -11.614  36.255  -2.281  1.00 36.01      A O
ATOM   1091  ND2 ASN A 172      -9.377  36.135  -2.061  1.00 32.53      A N
ATOM   1092  C   ASN A 172     -11.790  40.406  -1.570  1.00 34.79      A C
ATOM   1093  O   ASN A 172     -11.710  40.492  -0.337  1.00 36.01      A O
ATOM   1094  N   ILE A 173     -12.064  41.438  -2.362  1.00 34.41      A N
ATOM   1095  CA  ILE A 173     -12.311  42.776  -1.842  1.00 33.58      A C
ATOM   1096  CB  ILE A 173     -11.247  43.762  -2.347  1.00 34.06      A C
ATOM   1097  CG2 ILE A 173     -11.564  45.171  -1.863  1.00 31.76      A C
ATOM   1098  CG1 ILE A 173      -9.862  43.310  -1.874  1.00 33.08      A C
ATOM   1099  CD1 ILE A 173      -8.731  44.155  -2.396  1.00 31.22      A C
ATOM   1100  C   ILE A 173     -13.704  43.240  -2.309  1.00 34.69      A C
ATOM   1101  O   ILE A 173     -13.979  43.309  -3.510  1.00 33.81      A O
ATOM   1102  N   LEU A 174     -14.578  43.534  -1.351  1.00 34.57      A N
ATOM   1103  CA  LEU A 174     -15.936  43.988  -1.636  1.00 36.37      A C
ATOM   1104  CB  LEU A 174     -16.935  43.335  -0.688  1.00 36.56      A C
ATOM   1105  CG  LEU A 174     -17.777  42.185  -1.213  1.00 37.78      A C
ATOM   1106  CD1 LEU A 174     -16.896  41.140  -1.863  1.00 38.44      A C
ATOM   1107  CD2 LEU A 174     -18.572  41.604  -0.052  1.00 38.08      A C
ATOM   1108  C   LEU A 174     -16.045  45.480  -1.457  1.00 37.08      A C
ATOM   1109  O   LEU A 174     -15.502  46.036  -0.495  1.00 36.65      A O
ATOM   1110  N   ILE A 175     -16.757  46.128  -2.373  1.00 36.94      A N
ATOM   1111  CA  ILE A 175     -16.947  47.567  -2.285  1.00 38.73      A C
ATOM   1112  CB  ILE A 175     -16.634  48.273  -3.616  1.00 38.83      A C
ATOM   1113  CG2 ILE A 175     -16.609  49.781  -3.401  1.00 37.29      A C
ATOM   1114  CG1 ILE A 175     -15.289  47.813  -4.163  1.00 38.35      A C
ATOM   1115  CD1 ILE A 175     -15.064  48.237  -5.587  1.00 39.97      A C
ATOM   1116  C   ILE A 175     -18.392  47.910  -1.926  1.00 40.86      A C
ATOM   1117  O   ILE A 175     -19.340  47.491  -2.599  1.00 42.27      A O
ATOM   1118  N   ASP A 176     -18.563  48.662  -0.852  1.00 41.41      A N
```

FIGURE 1A-21

```
ATOM   1119  CA  ASP A 176     -19.887  49.105  -0.446  1.00 42.09      A C
ATOM   1120  CB  ASP A 176     -19.898  49.305   1.071  1.00 42.04      A C
ATOM   1121  CG  ASP A 176     -21.154  49.967   1.570  1.00 44.89      A C
ATOM   1122  OD1 ASP A 176     -21.450  49.810   2.778  1.00 43.98      A O
ATOM   1123  OD2 ASP A 176     -21.829  50.656   0.770  1.00 45.38      A O
ATOM   1124  C   ASP A 176     -20.051  50.427  -1.205  1.00 42.45      A C
ATOM   1125  O   ASP A 176     -19.579  51.470  -0.752  1.00 41.94      A O
ATOM   1126  N   LEU A 177     -20.696  50.368  -2.372  1.00 42.39      A N
ATOM   1127  CA  LEU A 177     -20.885  51.548  -3.222  1.00 43.16      A C
ATOM   1128  CB  LEU A 177     -21.768  51.220  -4.431  1.00 41.21      A C
ATOM   1129  CG  LEU A 177     -21.314  50.291  -5.565  1.00 40.68      A C
ATOM   1130  CD1 LEU A 177     -19.788  50.316  -5.718  1.00 35.16      A C
ATOM   1131  CD2 LEU A 177     -21.814  48.895  -5.282  1.00 39.32      A C
ATOM   1132  C   LEU A 177     -21.426  52.834  -2.594  1.00 45.22      A C
ATOM   1133  O   LEU A 177     -21.061  53.926  -3.028  1.00 46.52      A O
ATOM   1134  N   ASN A 178     -22.290  52.728  -1.591  1.00 45.69      A N
ATOM   1135  CA  ASN A 178     -22.849  53.931  -0.975  1.00 46.91      A C
ATOM   1136  CB  ASN A 178     -24.241  53.633  -0.413  1.00 48.88      A C
ATOM   1137  CG  ASN A 178     -25.291  53.457  -1.505  1.00 51.18      A C
ATOM   1138  OD1 ASN A 178     -26.437  53.104  -1.226  1.00 53.57      A O
ATOM   1139  ND2 ASN A 178     -24.904  53.708  -2.754  1.00 52.84      A N
ATOM   1140  C   ASN A 178     -21.989  54.594   0.107  1.00 47.21      A C
ATOM   1141  O   ASN A 178     -21.963  55.826   0.208  1.00 47.38      A O
ATOM   1142  N   ARG A 179     -21.290  53.800   0.916  1.00 46.57      A N
ATOM   1143  CA  ARG A 179     -20.452  54.382   1.967  1.00 46.14      A C
ATOM   1144  CB  ARG A 179     -20.489  53.522   3.234  1.00 47.75      A C
ATOM   1145  CG  ARG A 179     -21.808  52.805   3.451  1.00 51.15      A C
ATOM   1146  CD  ARG A 179     -22.088  52.548   4.921  1.00 53.20      A C
ATOM   1147  NE  ARG A 179     -22.544  53.766   5.581  1.00 57.25      A N
ATOM   1148  CZ  ARG A 179     -23.262  53.788   6.700  1.00 58.29      A C
ATOM   1149  NH1 ARG A 179     -23.606  52.648   7.289  1.00 59.75      A N
ATOM   1150  NH2 ARG A 179     -23.648  54.948   7.223  1.00 58.17      A N
ATOM   1151  C   ARG A 179     -19.006  54.545   1.506  1.00 44.47      A C
ATOM   1152  O   ARG A 179     -18.219  55.235   2.146  1.00 44.33      A O
ATOM   1153  N   GLY A 180     -18.666  53.914   0.387  1.00 42.12      A N
ATOM   1154  CA  GLY A 180     -17.310  54.009  -0.130  1.00 41.39      A C
ATOM   1155  C   GLY A 180     -16.284  53.218   0.672  1.00 39.63      A C
ATOM   1156  O   GLY A 180     -15.092  53.515   0.618  1.00 38.24      A O
ATOM   1157  N   GLU A 181     -16.746  52.206   1.401  1.00 37.87      A N
ATOM   1158  CA  GLU A 181     -15.867  51.380   2.219  1.00 37.67      A C
ATOM   1159  CB  GLU A 181     -16.477  51.186   3.606  1.00 36.35      A C
ATOM   1160  CG  GLU A 181     -17.341  52.340   4.058  1.00 39.49      A C
ATOM   1161  CD  GLU A 181     -17.762  52.223   5.505  1.00 40.40      A C
ATOM   1162  OE1 GLU A 181     -18.158  51.108   5.914  1.00 41.29      A O
ATOM   1163  OE2 GLU A 181     -17.702  53.248   6.224  1.00 39.82      A O
ATOM   1164  C   GLU A 181     -15.612  50.005   1.603  1.00 36.81      A C
ATOM   1165  O   GLU A 181     -16.522  49.394   1.043  1.00 36.23      A O
ATOM   1166  N   LEU A 182     -14.373  49.522   1.717  1.00 35.53      A N
ATOM   1167  CA  LEU A 182     -14.024  48.208   1.199  1.00 34.27      A C
ATOM   1168  CB  LEU A 182     -12.652  48.223   0.528  1.00 33.44      A C
ATOM   1169  CG  LEU A 182     -12.320  49.350  -0.446  1.00 36.60      A C
ATOM   1170  CD1 LEU A 182     -11.160  48.901  -1.333  1.00 35.63      A C
ATOM   1171  CD2 LEU A 182     -13.531  49.697  -1.298  1.00 36.56      A C
ATOM   1172  C   LEU A 182     -13.991  47.225   2.360  1.00 34.23      A C
ATOM   1173  O   LEU A 182     -13.700  47.607   3.497  1.00 32.59      A O
ATOM   1174  N   LYS A 183     -14.286  45.963   2.064  1.00 34.21      A N
```

FIGURE 1A-22

```
ATOM   1175  CA   LYS A 183     -14.279  44.908   3.071  1.00 36.94       A C
ATOM   1176  CB   LYS A 183     -15.712  44.609   3.526  1.00 39.85       A C
ATOM   1177  CG   LYS A 183     -16.364  45.770   4.239  1.00 43.30       A C
ATOM   1178  CD   LYS A 183     -17.748  45.415   4.743  1.00 46.84       A C
ATOM   1179  CE   LYS A 183     -18.381  46.621   5.415  1.00 49.08       A C
ATOM   1180  NZ   LYS A 183     -17.464  47.177   6.451  1.00 49.66       A N
ATOM   1181  C    LYS A 183     -13.622  43.629   2.544  1.00 36.53       A C
ATOM   1182  O    LYS A 183     -13.924  43.177   1.441  1.00 36.20       A O
ATOM   1183  N    LEU A 184     -12.723  43.050   3.335  1.00 36.01       A N
ATOM   1184  CA   LEU A 184     -12.032  41.823   2.944  1.00 36.20       A C
ATOM   1185  CB   LEU A 184     -10.796  41.615   3.810  1.00 36.61       A C
ATOM   1186  CG   LEU A 184      -9.444  42.046   3.249  1.00 40.20       A C
ATOM   1187  CD1  LEU A 184      -9.538  43.434   2.635  1.00 41.67       A C
ATOM   1188  CD2  LEU A 184      -8.424  42.023   4.374  1.00 40.75       A C
ATOM   1189  C    LEU A 184     -12.922  40.601   3.087  1.00 36.03       A C
ATOM   1190  O    LEU A 184     -13.683  40.502   4.048  1.00 34.41       A O
ATOM   1191  N    ILE A 185     -12.824  39.669   2.142  1.00 34.66       A N
ATOM   1192  CA   ILE A 185     -13.616  38.451   2.228  1.00 36.73       A C
ATOM   1193  CB   ILE A 185     -14.809  38.451   1.252  1.00 36.43       A C
ATOM   1194  CG2  ILE A 185     -15.750  39.605   1.575  1.00 38.39       A C
ATOM   1195  CG1  ILE A 185     -14.298  38.526  -0.184  1.00 36.83       A C
ATOM   1196  CD1  ILE A 185     -15.374  38.290  -1.220  1.00 36.70       A C
ATOM   1197  C    ILE A 185     -12.807  37.197   1.936  1.00 37.85       A C
ATOM   1198  O    ILE A 185     -11.715  37.259   1.358  1.00 37.03       A O
ATOM   1199  N    ASP A 186     -13.386  36.065   2.337  1.00 38.30       A N
ATOM   1200  CA   ASP A 186     -12.828  34.733   2.153  1.00 39.90       A C
ATOM   1201  CB   ASP A 186     -12.754  34.378   0.664  1.00 42.64       A C
ATOM   1202  CG   ASP A 186     -12.156  32.991   0.430  1.00 48.97       A C
ATOM   1203  OD1  ASP A 186     -12.648  32.024   1.061  1.00 48.12       A O
ATOM   1204  OD2  ASP A 186     -11.193  32.862  -0.372  1.00 53.28       A O
ATOM   1205  C    ASP A 186     -11.477  34.450   2.798  1.00 40.25       A C
ATOM   1206  O    ASP A 186     -10.435  34.494   2.141  1.00 39.75       A O
ATOM   1207  N    PHE A 187     -11.502  34.138   4.088  1.00 40.33       A N
ATOM   1208  CA   PHE A 187     -10.286  33.808   4.809  1.00 40.39       A C
ATOM   1209  CB   PHE A 187     -10.405  34.240   6.266  1.00 39.07       A C
ATOM   1210  CG   PHE A 187     -10.339  35.731   6.472  1.00 37.24       A C
ATOM   1211  CD1  PHE A 187     -11.394  36.549   6.094  1.00 35.91       A C
ATOM   1212  CD2  PHE A 187      -9.227  36.308   7.077  1.00 33.83       A C
ATOM   1213  CE1  PHE A 187     -11.344  37.920   6.319  1.00 35.51       A C
ATOM   1214  CE2  PHE A 187      -9.172  37.674   7.305  1.00 34.20       A C
ATOM   1215  CZ   PHE A 187     -10.227  38.481   6.929  1.00 34.86       A C
ATOM   1216  C    PHE A 187     -10.048  32.300   4.748  1.00 41.22       A C
ATOM   1217  O    PHE A 187      -9.362  31.738   5.597  1.00 42.04       A O
ATOM   1218  N    GLY A 188     -10.611  31.653   3.733  1.00 42.01       A N
ATOM   1219  CA   GLY A 188     -10.482  30.212   3.592  1.00 42.20       A C
ATOM   1220  C    GLY A 188      -9.097  29.688   3.289  1.00 43.07       A C
ATOM   1221  O    GLY A 188      -8.860  28.483   3.340  1.00 45.54       A O
ATOM   1222  N    SER A 189      -8.176  30.578   2.956  1.00 42.90       A N
ATOM   1223  CA   SER A 189      -6.809  30.166   2.662  1.00 42.57       A C
ATOM   1224  CB   SER A 189      -6.384  30.683   1.287  1.00 43.22       A C
ATOM   1225  OG   SER A 189      -7.227  30.191   0.259  1.00 46.25       A O
ATOM   1226  C    SER A 189      -5.907  30.769   3.724  1.00 41.36       A C
ATOM   1227  O    SER A 189      -4.695  30.638   3.668  1.00 41.93       A O
ATOM   1228  N    GLY A 190      -6.521  31.439   4.692  1.00 40.98       A N
ATOM   1229  CA   GLY A 190      -5.765  32.089   5.740  1.00 41.85       A C
ATOM   1230  C    GLY A 190      -5.037  31.171   6.696  1.00 42.01       A C
```

FIGURE 1A-23

```
ATOM   1231  O    GLY A 190      -5.044  29.952   6.548  1.00 41.06      A O
ATOM   1232  N    ALA A 191      -4.401  31.782   7.688  1.00 41.59      A N
ATOM   1233  CA   ALA A 191      -3.652  31.051   8.701  1.00 40.28      A C
ATOM   1234  CB   ALA A 191      -2.354  30.524   8.117  1.00 37.96      A C
ATOM   1235  C    ALA A 191      -3.357  32.002   9.838  1.00 39.49      A C
ATOM   1236  O    ALA A 191      -3.342  33.221   9.650  1.00 40.16      A O
ATOM   1237  N    LEU A 192      -3.143  31.450  11.023  1.00 39.39      A N
ATOM   1238  CA   LEU A 192      -2.823  32.265  12.181  1.00 38.58      A C
ATOM   1239  CB   LEU A 192      -2.691  31.379  13.420  1.00 37.99      A C
ATOM   1240  CG   LEU A 192      -3.965  30.645  13.850  1.00 38.01      A C
ATOM   1241  CD1  LEU A 192      -3.620  29.566  14.883  1.00 38.49      A C
ATOM   1242  CD2  LEU A 192      -4.964  31.648  14.423  1.00 35.85      A C
ATOM   1243  C    LEU A 192      -1.492  32.946  11.876  1.00 38.77      A C
ATOM   1244  O    LEU A 192      -0.611  32.356  11.241  1.00 38.52      A O
ATOM   1245  N    LEU A 193      -1.345  34.194  12.298  1.00 38.21      A N
ATOM   1246  CA   LEU A 193      -0.094  34.892  12.053  1.00 38.89      A C
ATOM   1247  CB   LEU A 193      -0.234  36.377  12.375  1.00 37.34      A C
ATOM   1248  CG   LEU A 193       1.036  37.197  12.100  1.00 37.45      A C
ATOM   1249  CD1  LEU A 193       1.298  37.230  10.590  1.00 34.06      A C
ATOM   1250  CD2  LEU A 193       0.874  38.626  12.654  1.00 35.69      A C
ATOM   1251  C    LEU A 193       1.008  34.302  12.929  1.00 39.70      A C
ATOM   1252  O    LEU A 193       0.806  34.079  14.124  1.00 39.90      A O
ATOM   1253  N    LYS A 194       2.164  34.037  12.330  1.00 39.29      A N
ATOM   1254  CA   LYS A 194       3.299  33.513  13.077  1.00 39.82      A C
ATOM   1255  CB   LYS A 194       3.381  31.981  12.971  1.00 39.34      A C
ATOM   1256  CG   LYS A 194       3.790  31.458  11.607  1.00 38.88      A C
ATOM   1257  CD   LYS A 194       3.663  29.948  11.521  1.00 37.53      A C
ATOM   1258  CE   LYS A 194       4.045  29.470  10.123  1.00 39.74      A C
ATOM   1259  NZ   LYS A 194       3.984  27.993   9.954  1.00 41.23      A N
ATOM   1260  C    LYS A 194       4.546  34.152  12.494  1.00 39.86      A C
ATOM   1261  O    LYS A 194       4.521  34.646  11.362  1.00 39.26      A O
ATOM   1262  N    ASP A 195       5.631  34.140  13.266  1.00 41.38      A N
ATOM   1263  CA   ASP A 195       6.893  34.731  12.835  1.00 41.25      A C
ATOM   1264  CB   ASP A 195       7.637  35.308  14.033  1.00 42.85      A C
ATOM   1265  CG   ASP A 195       6.919  36.491  14.646  1.00 45.61      A C
ATOM   1266  OD1  ASP A 195       6.904  36.606  15.892  1.00 45.35      A O
ATOM   1267  OD2  ASP A 195       6.379  37.316  13.876  1.00 49.06      A O
ATOM   1268  C    ASP A 195       7.801  33.757  12.111  1.00 41.44      A C
ATOM   1269  O    ASP A 195       8.742  34.176  11.452  1.00 42.15      A O
ATOM   1270  N    THR A 196       7.534  32.461  12.230  1.00 41.74      A N
ATOM   1271  CA   THR A 196       8.372  31.479  11.554  1.00 41.77      A C
ATOM   1272  CB   THR A 196       8.334  30.107  12.269  1.00 42.52      A C
ATOM   1273  OG1  THR A 196       6.978  29.683  12.453  1.00 43.11      A O
ATOM   1274  CG2  THR A 196       9.022  30.207  13.622  1.00 42.93      A C
ATOM   1275  C    THR A 196       7.961  31.321  10.095  1.00 42.68      A C
ATOM   1276  O    THR A 196       6.962  31.887   9.658  1.00 44.35      A O
ATOM   1277  N    VAL A 197       8.729  30.543   9.344  1.00 43.09      A N
ATOM   1278  CA   VAL A 197       8.467  30.337   7.927  1.00 42.66      A C
ATOM   1279  CB   VAL A 197       9.684  29.640   7.259  1.00 43.70      A C
ATOM   1280  CG1  VAL A 197       9.847  28.226   7.815  1.00 43.29      A C
ATOM   1281  CG2  VAL A 197       9.518  29.618   5.747  1.00 42.96      A C
ATOM   1282  C    VAL A 197       7.196  29.544   7.626  1.00 42.78      A C
ATOM   1283  O    VAL A 197       6.746  28.735   8.433  1.00 44.36      A O
ATOM   1284  N    TYR A 198       6.606  29.803   6.461  1.00 42.45      A N
ATOM   1285  CA   TYR A 198       5.404  29.098   6.014  1.00 42.25      A C
ATOM   1286  CB   TYR A 198       4.360  30.086   5.468  1.00 38.12      A C
```

FIGURE 1A-24

```
ATOM   1287  CG   TYR A 198       3.578  30.826   6.533  1.00 35.12      A C
ATOM   1288  CD1  TYR A 198       2.468  30.242   7.145  1.00 32.85      A C
ATOM   1289  CE1  TYR A 198       1.751  30.912   8.142  1.00 30.42      A C
ATOM   1290  CD2  TYR A 198       3.958  32.105   6.947  1.00 33.80      A C
ATOM   1291  CE2  TYR A 198       3.250  32.782   7.945  1.00 32.07      A C
ATOM   1292  CZ   TYR A 198       2.147  32.178   8.534  1.00 32.62      A C
ATOM   1293  OH   TYR A 198       1.428  32.848   9.502  1.00 35.03      A O
ATOM   1294  C    TYR A 198       5.872  28.178   4.891  1.00 44.22      A C
ATOM   1295  O    TYR A 198       6.731  28.566   4.099  1.00 45.17      A O
ATOM   1296  N    THR A 199       5.327  26.969   4.812  1.00 45.87      A N
ATOM   1297  CA   THR A 199       5.743  26.046   3.760  1.00 48.44      A C
ATOM   1298  CB   THR A 199       6.505  24.844   4.333  1.00 47.60      A C
ATOM   1299  OG1  THR A 199       5.656  24.117   5.231  1.00 48.02      A O
ATOM   1300  CG2  THR A 199       7.743  25.320   5.066  1.00 46.04      A C
ATOM   1301  C    THR A 199       4.574  25.536   2.941  1.00 50.70      A C
ATOM   1302  O    THR A 199       4.741  24.698   2.060  1.00 51.37      A O
ATOM   1303  N    ASP A 200       3.387  26.044   3.241  1.00 52.71      A N
ATOM   1304  CA   ASP A 200       2.194  25.654   2.506  1.00 54.80      A C
ATOM   1305  CB   ASP A 200       1.203  24.944   3.425  1.00 57.40      A C
ATOM   1306  CG   ASP A 200       0.618  25.873   4.473  1.00 60.34      A C
ATOM   1307  OD1  ASP A 200       1.408  26.445   5.261  1.00 60.91      A O
ATOM   1308  OD2  ASP A 200      -0.626  26.032   4.505  1.00 60.97      A O
ATOM   1309  C    ASP A 200       1.559  26.928   1.981  1.00 55.09      A C
ATOM   1310  O    ASP A 200       1.691  27.988   2.590  1.00 55.33      A O
ATOM   1311  N    PHE A 201       0.875  26.825   0.850  1.00 55.23      A N
ATOM   1312  CA   PHE A 201       0.207  27.975   0.266  1.00 54.97      A C
ATOM   1313  CB   PHE A 201       1.225  28.931  -0.359  1.00 54.41      A C
ATOM   1314  CG   PHE A 201       0.605  30.040  -1.171  1.00 52.42      A C
ATOM   1315  CD1  PHE A 201       0.327  29.860  -2.521  1.00 51.29      A C
ATOM   1316  CD2  PHE A 201       0.299  31.264  -0.582  1.00 52.75      A C
ATOM   1317  CE1  PHE A 201      -0.247  30.885  -3.278  1.00 53.19      A C
ATOM   1318  CE2  PHE A 201      -0.274  32.296  -1.328  1.00 52.44      A C
ATOM   1319  CZ   PHE A 201      -0.547  32.104  -2.682  1.00 53.31      A C
ATOM   1320  C    PHE A 201      -0.783  27.525  -0.783  1.00 56.67      A C
ATOM   1321  O    PHE A 201      -0.409  26.901  -1.773  1.00 58.10      A O
ATOM   1322  N    ASP A 202      -2.052  27.839  -0.560  1.00 58.05      A N
ATOM   1323  CA   ASP A 202      -3.086  27.468  -1.502  1.00 59.48      A C
ATOM   1324  CB   ASP A 202      -4.047  26.465  -0.859  1.00 62.49      A C
ATOM   1325  CG   ASP A 202      -4.985  25.832  -1.870  1.00 65.65      A C
ATOM   1326  OD1  ASP A 202      -4.479  25.284  -2.876  1.00 68.35      A O
ATOM   1327  OD2  ASP A 202      -6.220  25.879  -1.660  1.00 66.12      A O
ATOM   1328  C    ASP A 202      -3.829  28.721  -1.943  1.00 58.96      A C
ATOM   1329  O    ASP A 202      -5.023  28.686  -2.220  1.00 58.21      A O
ATOM   1330  N    GLY A 203      -3.106  29.833  -2.004  1.00 58.93      A N
ATOM   1331  CA   GLY A 203      -3.712  31.082  -2.417  1.00 58.91      A C
ATOM   1332  C    GLY A 203      -3.799  31.155  -3.927  1.00 58.64      A C
ATOM   1333  O    GLY A 203      -4.063  30.149  -4.575  1.00 59.68      A O
ATOM   1334  N    THR A 204      -3.583  32.342  -4.485  1.00 57.14      A N
ATOM   1335  CA   THR A 204      -3.626  32.540  -5.930  1.00 55.54      A C
ATOM   1336  CB   THR A 204      -4.418  33.816  -6.286  1.00 54.80      A C
ATOM   1337  OG1  THR A 204      -5.691  33.790  -5.628  1.00 52.27      A O
ATOM   1338  CG2  THR A 204      -4.649  33.900  -7.788  1.00 53.52      A C
ATOM   1339  C    THR A 204      -2.182  32.679  -6.411  1.00 56.19      A C
ATOM   1340  O    THR A 204      -1.474  33.605  -6.001  1.00 56.16      A O
ATOM   1341  N    ARG A 205      -1.749  31.765  -7.278  1.00 55.77      A N
ATOM   1342  CA   ARG A 205      -0.371  31.770  -7.771  1.00 56.34      A C
```

FIGURE 1A-25

```
ATOM   1343  CB  ARG A 205      -0.170  30.656  -8.807  1.00 56.25      A C
ATOM   1344  CG  ARG A 205       1.293  30.248  -8.941  1.00 58.10      A C
ATOM   1345  CD  ARG A 205       1.521  29.131  -9.956  1.00 57.55      A C
ATOM   1346  NE  ARG A 205       2.942  28.793 -10.058  1.00 56.29      A N
ATOM   1347  CZ  ARG A 205       3.629  28.149  -9.119  1.00 56.06      A C
ATOM   1348  NH1 ARG A 205       3.028  27.763  -8.002  1.00 55.25      A N
ATOM   1349  NH2 ARG A 205       4.923  27.899  -9.291  1.00 54.78      A N
ATOM   1350  C   ARG A 205       0.124  33.101  -8.349  1.00 56.38      A C
ATOM   1351  O   ARG A 205       1.173  33.611  -7.952  1.00 57.42      A O
ATOM   1352  N   VAL A 206      -0.624  33.660  -9.291  1.00 55.34      A N
ATOM   1353  CA  VAL A 206      -0.250  34.921  -9.910  1.00 52.95      A C
ATOM   1354  CB  VAL A 206      -1.334  35.329 -10.962  1.00 53.38      A C
ATOM   1355  CG1 VAL A 206      -1.387  36.837 -11.155  1.00 55.30      A C
ATOM   1356  CG2 VAL A 206      -1.009  34.662 -12.289  1.00 50.83      A C
ATOM   1357  C   VAL A 206       0.000  36.026  -8.873  1.00 50.97      A C
ATOM   1358  O   VAL A 206       0.674  37.009  -9.169  1.00 52.03      A O
ATOM   1359  N   TYR A 207      -0.528  35.855  -7.660  1.00 48.29      A N
ATOM   1360  CA  TYR A 207      -0.336  36.825  -6.567  1.00 45.77      A C
ATOM   1361  CB  TYR A 207      -1.651  37.087  -5.804  1.00 44.52      A C
ATOM   1362  CG  TYR A 207      -2.613  38.094  -6.406  1.00 43.56      A C
ATOM   1363  CD1 TYR A 207      -3.474  37.746  -7.455  1.00 43.38      A C
ATOM   1364  CE1 TYR A 207      -4.384  38.667  -7.980  1.00 42.87      A C
ATOM   1365  CD2 TYR A 207      -2.684  39.392  -5.901  1.00 44.41      A C
ATOM   1366  CE2 TYR A 207      -3.587  40.323  -6.415  1.00 45.21      A C
ATOM   1367  CZ  TYR A 207      -4.438  39.958  -7.454  1.00 46.64      A C
ATOM   1368  OH  TYR A 207      -5.345  40.891  -7.943  1.00 49.10      A O
ATOM   1369  C   TYR A 207       0.700  36.322  -5.538  1.00 44.78      A C
ATOM   1370  O   TYR A 207       0.861  36.929  -4.471  1.00 43.46      A O
ATOM   1371  N   SER A 208       1.381  35.218  -5.847  1.00 42.94      A N
ATOM   1372  CA  SER A 208       2.378  34.637  -4.937  1.00 41.95      A C
ATOM   1373  CB  SER A 208       2.430  33.113  -5.112  1.00 42.07      A C
ATOM   1374  OG  SER A 208       3.050  32.758  -6.341  1.00 44.16      A O
ATOM   1375  C   SER A 208       3.779  35.228  -5.153  1.00 39.97      A C
ATOM   1376  O   SER A 208       4.191  35.498  -6.280  1.00 40.64      A O
ATOM   1377  N   PRO A 209       4.537  35.414  -4.066  1.00 38.50      A N
ATOM   1378  CD  PRO A 209       4.225  35.019  -2.680  1.00 36.25      A C
ATOM   1379  CA  PRO A 209       5.884  35.982  -4.160  1.00 39.03      A C
ATOM   1380  CB  PRO A 209       6.194  36.333  -2.715  1.00 37.44      A C
ATOM   1381  CG  PRO A 209       5.558  35.195  -1.977  1.00 36.18      A C
ATOM   1382  C   PRO A 209       6.941  35.050  -4.775  1.00 40.30      A C
ATOM   1383  O   PRO A 209       6.761  33.837  -4.841  1.00 38.77      A O
ATOM   1384  N   PRO A 210       8.067  35.624  -5.230  1.00 41.29      A N
ATOM   1385  CD  PRO A 210       8.412  37.056  -5.173  1.00 41.34      A C
ATOM   1386  CA  PRO A 210       9.153  34.849  -5.836  1.00 41.56      A C
ATOM   1387  CB  PRO A 210      10.230  35.905  -6.096  1.00 41.58      A C
ATOM   1388  CG  PRO A 210       9.451  37.172  -6.253  1.00 42.62      A C
ATOM   1389  C   PRO A 210       9.660  33.730  -4.915  1.00 41.99      A C
ATOM   1390  O   PRO A 210       9.893  32.610  -5.367  1.00 42.50      A O
ATOM   1391  N   GLU A 211       9.832  34.041  -3.629  1.00 41.80      A N
ATOM   1392  CA  GLU A 211      10.316  33.063  -2.656  1.00 41.56      A C
ATOM   1393  CB  GLU A 211      10.460  33.694  -1.265  1.00 40.51      A C
ATOM   1394  CG  GLU A 211       9.190  34.343  -0.729  1.00 40.35      A C
ATOM   1395  CD  GLU A 211       9.050  35.790  -1.175  1.00 40.59      A C
ATOM   1396  OE1 GLU A 211       9.462  36.108  -2.310  1.00 40.81      A O
ATOM   1397  OE2 GLU A 211       8.524  36.611  -0.396  1.00 38.17      A O
ATOM   1398  C   GLU A 211       9.420  31.833  -2.558  1.00 42.93      A C
```

FIGURE 1A-26

```
ATOM   1399  O    GLU A 211       9.881  30.765  -2.179  1.00 43.46      A O
ATOM   1400  N    TRP A 212       8.140  31.968  -2.875  1.00 43.87      A N
ATOM   1401  CA   TRP A 212       7.268  30.804  -2.816  1.00 45.89      A C
ATOM   1402  CB   TRP A 212       5.799  31.209  -2.678  1.00 44.93      A C
ATOM   1403  CG   TRP A 212       4.844  30.087  -3.012  1.00 45.90      A C
ATOM   1404  CD2  TRP A 212       4.615  28.891  -2.249  1.00 45.90      A C
ATOM   1405  CE2  TRP A 212       3.644  28.132  -2.943  1.00 46.11      A C
ATOM   1406  CE3  TRP A 212       5.138  28.387  -1.048  1.00 44.35      A C
ATOM   1407  CD1  TRP A 212       4.028  30.003  -4.106  1.00 45.66      A C
ATOM   1408  NE1  TRP A 212       3.303  28.835  -4.070  1.00 46.67      A N
ATOM   1409  CZ2  TRP A 212       3.182  26.894  -2.476  1.00 44.29      A C
ATOM   1410  CZ3  TRP A 212       4.679  27.154  -0.582  1.00 43.39      A C
ATOM   1411  CH2  TRP A 212       3.709  26.423  -1.298  1.00 43.70      A C
ATOM   1412  C    TRP A 212       7.442  29.989  -4.087  1.00 48.49      A C
ATOM   1413  O    TRP A 212       7.482  28.759  -4.045  1.00 49.01      A O
ATOM   1414  N    ILE A 213       7.536  30.687  -5.215  1.00 50.82      A N
ATOM   1415  CA   ILE A 213       7.697  30.050  -6.518  1.00 53.85      A C
ATOM   1416  CB   ILE A 213       7.704  31.113  -7.658  1.00 54.33      A C
ATOM   1417  CG2  ILE A 213       7.812  30.441  -9.009  1.00 54.52      A C
ATOM   1418  CG1  ILE A 213       6.424  31.950  -7.616  1.00 55.71      A C
ATOM   1419  CD1  ILE A 213       5.150  31.170  -7.875  1.00 57.18      A C
ATOM   1420  C    ILE A 213       9.007  29.260  -6.588  1.00 55.61      A C
ATOM   1421  O    ILE A 213       9.045  28.149  -7.117  1.00 56.62      A O
ATOM   1422  N    ARG A 214      10.070  29.829  -6.028  1.00 57.11      A N
ATOM   1423  CA   ARG A 214      11.392  29.212  -6.063  1.00 58.32      A C
ATOM   1424  CB   ARG A 214      12.456  30.297  -6.201  1.00 59.98      A C
ATOM   1425  CG   ARG A 214      12.298  31.166  -7.427  1.00 63.19      A C
ATOM   1426  CD   ARG A 214      13.450  32.142  -7.533  1.00 65.99      A C
ATOM   1427  NE   ARG A 214      14.730  31.458  -7.393  1.00 69.47      A N
ATOM   1428  CZ   ARG A 214      15.909  32.030  -7.611  1.00 72.34      A C
ATOM   1429  NH1  ARG A 214      15.968  33.304  -7.986  1.00 72.66      A N
ATOM   1430  NH2  ARG A 214      17.029  31.332  -7.449  1.00 73.16      A N
ATOM   1431  C    ARG A 214      11.804  28.292  -4.920  1.00 58.28      A C
ATOM   1432  O    ARG A 214      12.529  27.331  -5.145  1.00 59.11      A O
ATOM   1433  N    TYR A 215      11.363  28.579  -3.699  1.00 57.89      A N
ATOM   1434  CA   TYR A 215      11.758  27.758  -2.559  1.00 56.71      A C
ATOM   1435  CB   TYR A 215      12.629  28.590  -1.617  1.00 55.81      A C
ATOM   1436  CG   TYR A 215      13.732  29.350  -2.324  1.00 57.72      A C
ATOM   1437  CD1  TYR A 215      14.696  28.680  -3.084  1.00 58.14      A C
ATOM   1438  CE1  TYR A 215      15.706  29.378  -3.751  1.00 58.16      A C
ATOM   1439  CD2  TYR A 215      13.807  30.741  -2.247  1.00 58.08      A C
ATOM   1440  CE2  TYR A 215      14.814  31.449  -2.909  1.00 58.25      A C
ATOM   1441  CZ   TYR A 215      15.757  30.761  -3.659  1.00 58.77      A C
ATOM   1442  OH   TYR A 215      16.745  31.456  -4.320  1.00 59.43      A O
ATOM   1443  C    TYR A 215      10.596  27.160  -1.775  1.00 56.42      A C
ATOM   1444  O    TYR A 215      10.797  26.503  -0.752  1.00 57.33      A O
ATOM   1445  N    HIS A 216       9.382  27.370  -2.259  1.00 55.65      A N
ATOM   1446  CA   HIS A 216       8.208  26.865  -1.566  1.00 55.76      A C
ATOM   1447  CB   HIS A 216       8.107  25.343  -1.693  1.00 59.30      A C
ATOM   1448  CG   HIS A 216       7.788  24.876  -3.080  1.00 64.70      A C
ATOM   1449  CD2  HIS A 216       6.614  24.509  -3.648  1.00 66.31      A C
ATOM   1450  ND1  HIS A 216       8.737  24.803  -4.079  1.00 66.85      A N
ATOM   1451  CE1  HIS A 216       8.160  24.413  -5.203  1.00 67.73      A C
ATOM   1452  NE2  HIS A 216       6.873  24.229  -4.969  1.00 68.11      A N
ATOM   1453  C    HIS A 216       8.224  27.266  -0.096  1.00 53.64      A C
ATOM   1454  O    HIS A 216       7.912  26.466   0.779  1.00 53.38      A O
```

FIGURE 1A-27

```
ATOM   1455  N    ARG A 217       8.607  28.511   0.165  1.00 51.34      A N
ATOM   1456  CA   ARG A 217       8.627  29.050   1.521  1.00 49.68      A C
ATOM   1457  CB   ARG A 217       9.850  28.540   2.299  1.00 51.09      A C
ATOM   1458  CG   ARG A 217      11.187  28.756   1.620  1.00 54.13      A C
ATOM   1459  CD   ARG A 217      12.275  27.885   2.262  1.00 56.02      A C
ATOM   1460  NE   ARG A 217      12.679  28.347   3.590  1.00 57.63      A N
ATOM   1461  CZ   ARG A 217      12.726  27.577   4.676  1.00 57.75      A C
ATOM   1462  NH1  ARG A 217      12.386  26.293   4.608  1.00 56.48      A N
ATOM   1463  NH2  ARG A 217      13.125  28.091   5.833  1.00 57.35      A N
ATOM   1464  C    ARG A 217       8.595  30.582   1.509  1.00 46.90      A C
ATOM   1465  O    ARG A 217       9.125  31.226   0.599  1.00 46.93      A O
ATOM   1466  N    TYR A 218       7.959  31.156   2.524  1.00 43.17      A N
ATOM   1467  CA   TYR A 218       7.839  32.602   2.648  1.00 39.29      A C
ATOM   1468  CB   TYR A 218       6.745  33.117   1.706  1.00 38.39      A C
ATOM   1469  CG   TYR A 218       5.398  32.487   1.975  1.00 35.47      A C
ATOM   1470  CD1  TYR A 218       4.483  33.085   2.841  1.00 34.99      A C
ATOM   1471  CE1  TYR A 218       3.267  32.469   3.141  1.00 33.86      A C
ATOM   1472  CD2  TYR A 218       5.065  31.253   1.413  1.00 36.77      A C
ATOM   1473  CE2  TYR A 218       3.853  30.625   1.710  1.00 36.30      A C
ATOM   1474  CZ   TYR A 218       2.964  31.237   2.567  1.00 36.25      A C
ATOM   1475  OH   TYR A 218       1.762  30.626   2.830  1.00 37.87      A O
ATOM   1476  C    TYR A 218       7.457  32.948   4.068  1.00 38.43      A C
ATOM   1477  O    TYR A 218       7.143  32.068   4.870  1.00 37.63      A O
ATOM   1478  N    HIS A 219       7.484  34.241   4.371  1.00 37.53      A N
ATOM   1479  CA   HIS A 219       7.092  34.721   5.681  1.00 36.66      A C
ATOM   1480  CB   HIS A 219       8.235  35.511   6.322  1.00 39.29      A C
ATOM   1481  CG   HIS A 219       9.345  34.637   6.817  1.00 41.62      A C
ATOM   1482  CD2  HIS A 219       9.666  34.227   8.067  1.00 42.15      A C
ATOM   1483  ND1  HIS A 219      10.214  33.986   5.967  1.00 42.93      A N
ATOM   1484  CE1  HIS A 219      11.019  33.211   6.673  1.00 42.13      A C
ATOM   1485  NE2  HIS A 219      10.706  33.338   7.949  1.00 42.12      A N
ATOM   1486  C    HIS A 219       5.814  35.554   5.533  1.00 35.29      A C
ATOM   1487  O    HIS A 219       5.547  36.117   4.474  1.00 32.86      A O
ATOM   1488  N    GLY A 220       5.028  35.606   6.602  1.00 33.97      A N
ATOM   1489  CA   GLY A 220       3.753  36.300   6.577  1.00 34.01      A C
ATOM   1490  C    GLY A 220       3.662  37.722   6.068  1.00 34.47      A C
ATOM   1491  O    GLY A 220       3.120  37.990   5.001  1.00 33.07      A O
ATOM   1492  N    ARG A 221       4.199  38.641   6.849  1.00 35.68      A N
ATOM   1493  CA   ARG A 221       4.152  40.047   6.527  1.00 35.47      A C
ATOM   1494  CB   ARG A 221       4.778  40.821   7.680  1.00 38.94      A C
ATOM   1495  CG   ARG A 221       4.218  40.383   9.033  1.00 45.41      A C
ATOM   1496  CD   ARG A 221       4.659  41.299  10.167  1.00 50.82      A C
ATOM   1497  NE   ARG A 221       4.134  40.871  11.466  1.00 54.97      A N
ATOM   1498  CZ   ARG A 221       4.514  39.764  12.103  1.00 57.35      A C
ATOM   1499  NH1  ARG A 221       5.426  38.960  11.560  1.00 56.85      A N
ATOM   1500  NH2  ARG A 221       3.996  39.467  13.293  1.00 57.68      A N
ATOM   1501  C    ARG A 221       4.769  40.456   5.195  1.00 34.82      A C
ATOM   1502  O    ARG A 221       4.202  41.294   4.490  1.00 35.58      A O
ATOM   1503  N    SER A 222       5.906  39.870   4.832  1.00 32.20      A N
ATOM   1504  CA   SER A 222       6.547  40.236   3.576  1.00 31.50      A C
ATOM   1505  CB   SER A 222       8.034  39.861   3.592  1.00 30.38      A C
ATOM   1506  OG   SER A 222       8.215  38.469   3.749  1.00 35.60      A O
ATOM   1507  C    SER A 222       5.857  39.629   2.352  1.00 31.01      A C
ATOM   1508  O    SER A 222       5.859  40.224   1.273  1.00 30.92      A O
ATOM   1509  N    ALA A 223       5.269  38.449   2.507  1.00 30.00      A N
ATOM   1510  CA   ALA A 223       4.558  37.849   1.386  1.00 30.04      A C
```

FIGURE 1A-28

```
ATOM 1511  CB   ALA A 223    4.157  36.405   1.698  1.00 26.80   A C
ATOM 1512  C    ALA A 223    3.313  38.709   1.181  1.00 30.81   A C
ATOM 1513  O    ALA A 223    2.960  39.059   0.047  1.00 32.87   A O
ATOM 1514  N    ALA A 224    2.665  39.069   2.286  1.00 28.37   A N
ATOM 1515  CA   ALA A 224    1.461  39.888   2.214  1.00 28.82   A C
ATOM 1516  CB   ALA A 224    0.948  40.189   3.610  1.00 25.83   A C
ATOM 1517  C    ALA A 224    1.738  41.191   1.465  1.00 29.93   A C
ATOM 1518  O    ALA A 224    0.941  41.625   0.628  1.00 30.60   A O
ATOM 1519  N    VAL A 225    2.879  41.806   1.759  1.00 29.82   A N
ATOM 1520  CA   VAL A 225    3.244  43.060   1.117  1.00 27.98   A C
ATOM 1521  CB   VAL A 225    4.563  43.612   1.702  1.00 27.45   A C
ATOM 1522  CG1  VAL A 225    5.176  44.649   0.761  1.00 25.52   A C
ATOM 1523  CG2  VAL A 225    4.283  44.226   3.072  1.00 28.24   A C
ATOM 1524  C    VAL A 225    3.379  42.881  -0.381  1.00 28.65   A C
ATOM 1525  O    VAL A 225    2.997  43.761  -1.150  1.00 29.94   A O
ATOM 1526  N    TRP A 226    3.920  41.737  -0.794  1.00 29.04   A N
ATOM 1527  CA   TRP A 226    4.093  41.450  -2.214  1.00 28.73   A C
ATOM 1528  CB   TRP A 226    4.854  40.123  -2.402  1.00 26.66   A C
ATOM 1529  CG   TRP A 226    4.825  39.614  -3.806  1.00 26.75   A C
ATOM 1530  CD2  TRP A 226    5.818  39.825  -4.816  1.00 25.91   A C
ATOM 1531  CE2  TRP A 226    5.336  39.230  -6.009  1.00 26.88   A C
ATOM 1532  CE3  TRP A 226    7.070  40.455  -4.831  1.00 26.80   A C
ATOM 1533  CD1  TRP A 226    3.808  38.911  -4.410  1.00 26.73   A C
ATOM 1534  NE1  TRP A 226    4.109  38.680  -5.734  1.00 26.97   A N
ATOM 1535  CZ2  TRP A 226    6.067  39.252  -7.208  1.00 25.75   A C
ATOM 1536  CZ3  TRP A 226    7.793  40.473  -6.023  1.00 27.87   A C
ATOM 1537  CH2  TRP A 226    7.287  39.873  -7.194  1.00 25.98   A C
ATOM 1538  C    TRP A 226    2.741  41.405  -2.936  1.00 28.31   A C
ATOM 1539  O    TRP A 226    2.586  41.998  -4.000  1.00 30.20   A O
ATOM 1540  N    SER A 227    1.765  40.710  -2.357  1.00 27.18   A N
ATOM 1541  CA   SER A 227    0.445  40.620  -2.975  1.00 28.89   A C
ATOM 1542  CB   SER A 227   -0.439  39.631  -2.201  1.00 28.07   A C
ATOM 1543  OG   SER A 227   -0.852  40.163  -0.953  1.00 31.28   A O
ATOM 1544  C    SER A 227   -0.191  42.018  -2.987  1.00 29.43   A C
ATOM 1545  O    SER A 227   -0.969  42.362  -3.877  1.00 28.11   A O
ATOM 1546  N    LEU A 228    0.155  42.822  -1.990  1.00 29.44   A N
ATOM 1547  CA   LEU A 228   -0.352  44.182  -1.903  1.00 30.04   A C
ATOM 1548  CB   LEU A 228    0.135  44.834  -0.609  1.00 31.55   A C
ATOM 1549  CG   LEU A 228   -0.884  45.233   0.463  1.00 33.80   A C
ATOM 1550  CD1  LEU A 228   -2.235  44.550   0.241  1.00 32.29   A C
ATOM 1551  CD2  LEU A 228   -0.297  44.886   1.837  1.00 33.43   A C
ATOM 1552  C    LEU A 228    0.185  44.942  -3.108  1.00 29.75   A C
ATOM 1553  O    LEU A 228   -0.479  45.825  -3.659  1.00 28.67   A O
ATOM 1554  N    GLY A 229    1.396  44.578  -3.518  1.00 29.14   A N
ATOM 1555  CA   GLY A 229    2.007  45.225  -4.667  1.00 29.41   A C
ATOM 1556  C    GLY A 229    1.317  44.840  -5.969  1.00 28.94   A C
ATOM 1557  O    GLY A 229    1.166  45.668  -6.871  1.00 29.04   A O
ATOM 1558  N    ILE A 230    0.907  43.578  -6.068  1.00 29.31   A N
ATOM 1559  CA   ILE A 230    0.216  43.080  -7.255  1.00 29.40   A C
ATOM 1560  CB   ILE A 230   -0.023  41.567  -7.170  1.00 29.10   A C
ATOM 1561  CG2  ILE A 230   -0.705  41.086  -8.429  1.00 28.94   A C
ATOM 1562  CG1  ILE A 230    1.304  40.831  -6.977  1.00 30.50   A C
ATOM 1563  CD1  ILE A 230    2.237  40.870  -8.191  1.00 30.11   A C
ATOM 1564  C    ILE A 230   -1.143  43.774  -7.332  1.00 29.22   A C
ATOM 1565  O    ILE A 230   -1.561  44.248  -8.388  1.00 27.30   A O
ATOM 1566  N    LEU A 231   -1.819  43.834  -6.189  1.00 29.38   A N
```

FIGURE 1A-29

```
ATOM   1567  CA   LEU A 231      -3.126  44.473  -6.099  1.00 29.78      A C
ATOM   1568  CB   LEU A 231      -3.626  44.444  -4.647  1.00 28.18      A C
ATOM   1569  CG   LEU A 231      -4.932  45.202  -4.390  1.00 30.16      A C
ATOM   1570  CD1  LEU A 231      -6.073  44.519  -5.138  1.00 27.14      A C
ATOM   1571  CD2  LEU A 231      -5.220  45.268  -2.896  1.00 28.35      A C
ATOM   1572  C    LEU A 231      -3.069  45.920  -6.591  1.00 29.76      A C
ATOM   1573  O    LEU A 231      -3.856  46.322  -7.441  1.00 30.72      A O
ATOM   1574  N    LEU A 232      -2.126  46.692  -6.055  1.00 31.37      A N
ATOM   1575  CA   LEU A 232      -1.966  48.093  -6.419  1.00 29.70      A C
ATOM   1576  CB   LEU A 232      -0.766  48.708  -5.690  1.00 28.80      A C
ATOM   1577  CG   LEU A 232      -0.892  50.183  -5.255  1.00 33.43      A C
ATOM   1578  CD1  LEU A 232       0.485  50.814  -5.269  1.00 28.62      A C
ATOM   1579  CD2  LEU A 232      -1.837  50.977  -6.173  1.00 28.98      A C
ATOM   1580  C    LEU A 232      -1.781  48.251  -7.923  1.00 30.14      A C
ATOM   1581  O    LEU A 232      -2.409  49.113  -8.550  1.00 31.91      A O
ATOM   1582  N    TYR A 233      -0.923  47.424  -8.506  1.00 28.82      A N
ATOM   1583  CA   TYR A 233      -0.674  47.500  -9.938  1.00 29.03      A C
ATOM   1584  CB   TYR A 233       0.417  46.495 -10.341  1.00 28.69      A C
ATOM   1585  CG   TYR A 233       0.758  46.498 -11.818  1.00 29.97      A C
ATOM   1586  CD1  TYR A 233      -0.056  45.842 -12.737  1.00 28.70      A C
ATOM   1587  CE1  TYR A 233       0.224  45.865 -14.100  1.00 29.68      A C
ATOM   1588  CD2  TYR A 233       1.879  47.183 -12.302  1.00 30.67      A C
ATOM   1589  CE2  TYR A 233       2.173  47.217 -13.674  1.00 30.89      A C
ATOM   1590  CZ   TYR A 233       1.331  46.552 -14.565  1.00 31.96      A C
ATOM   1591  OH   TYR A 233       1.567  46.588 -15.920  1.00 31.46      A O
ATOM   1592  C    TYR A 233      -1.985  47.206 -10.658  1.00 29.59      A C
ATOM   1593  O    TYR A 233      -2.362  47.914 -11.590  1.00 31.47      A O
ATOM   1594  N    ASP A 234      -2.683  46.172 -10.198  1.00 29.70      A N
ATOM   1595  CA   ASP A 234      -3.964  45.767 -10.768  1.00 31.81      A C
ATOM   1596  CB   ASP A 234      -4.596  44.675  -9.911  1.00 33.38      A C
ATOM   1597  CG   ASP A 234      -5.845  44.081 -10.540  1.00 36.99      A C
ATOM   1598  OD1  ASP A 234      -6.751  43.694  -9.776  1.00 41.87      A O
ATOM   1599  OD2  ASP A 234      -5.925  43.980 -11.782  1.00 37.30      A O
ATOM   1600  C    ASP A 234      -4.912  46.957 -10.818  1.00 33.23      A C
ATOM   1601  O    ASP A 234      -5.601  47.165 -11.815  1.00 32.83      A O
ATOM   1602  N    MET A 235      -4.937  47.734  -9.735  1.00 33.37      A N
ATOM   1603  CA   MET A 235      -5.799  48.905  -9.646  1.00 33.84      A C
ATOM   1604  CB   MET A 235      -5.808  49.469  -8.216  1.00 34.04      A C
ATOM   1605  CG   MET A 235      -6.643  48.661  -7.231  1.00 35.41      A C
ATOM   1606  SD   MET A 235      -6.847  49.482  -5.637  1.00 38.92      A S
ATOM   1607  CE   MET A 235      -5.328  49.186  -4.882  1.00 36.56      A C
ATOM   1608  C    MET A 235      -5.455  50.032 -10.610  1.00 33.28      A C
ATOM   1609  O    MET A 235      -6.335  50.583 -11.248  1.00 33.36      A O
ATOM   1610  N    VAL A 236      -4.184  50.381 -10.735  1.00 33.08      A N
ATOM   1611  CA   VAL A 236      -3.848  51.489 -11.611  1.00 31.48      A C
ATOM   1612  CB   VAL A 236      -2.711  52.323 -10.992  1.00 29.51      A C
ATOM   1613  CG1  VAL A 236      -3.136  52.772  -9.593  1.00 26.83      A C
ATOM   1614  CG2  VAL A 236      -1.428  51.525 -10.931  1.00 26.01      A C
ATOM   1615  C    VAL A 236      -3.538  51.153 -13.069  1.00 33.38      A C
ATOM   1616  O    VAL A 236      -3.406  52.055 -13.891  1.00 33.89      A O
ATOM   1617  N    CYS A 237      -3.444  49.867 -13.388  1.00 34.36      A N
ATOM   1618  CA   CYS A 237      -3.173  49.425 -14.754  1.00 37.16      A C
ATOM   1619  CB   CYS A 237      -1.901  48.571 -14.808  1.00 36.82      A C
ATOM   1620  SG   CYS A 237      -0.368  49.510 -14.603  1.00 40.55      A S
ATOM   1621  C    CYS A 237      -4.352  48.608 -15.286  1.00 40.02      A C
ATOM   1622  O    CYS A 237      -4.461  48.354 -16.492  1.00 39.93      A O
```

FIGURE 1A-30

```
ATOM   1623  N    GLY A 238      -5.229  48.192 -14.377  1.00 41.45      A N
ATOM   1624  CA   GLY A 238      -6.392  47.421 -14.769  1.00 42.44      A C
ATOM   1625  C    GLY A 238      -6.103  45.969 -15.085  1.00 43.65      A C
ATOM   1626  O    GLY A 238      -6.838  45.343 -15.837  1.00 44.52      A O
ATOM   1627  N    ASP A 239      -5.040  45.427 -14.505  1.00 44.83      A N
ATOM   1628  CA   ASP A 239      -4.672  44.040 -14.740  1.00 45.73      A C
ATOM   1629  CB   ASP A 239      -4.430  43.828 -16.231  1.00 49.44      A C
ATOM   1630  CG   ASP A 239      -4.775  42.431 -16.681  1.00 52.88      A C
ATOM   1631  OD1  ASP A 239      -4.811  42.209 -17.914  1.00 54.21      A O
ATOM   1632  OD2  ASP A 239      -5.010  41.560 -15.807  1.00 54.96      A O
ATOM   1633  C    ASP A 239      -3.405  43.708 -13.954  1.00 45.17      A C
ATOM   1634  O    ASP A 239      -2.605  44.597 -13.667  1.00 43.18      A O
ATOM   1635  N    ILE A 240      -3.224  42.438 -13.600  1.00 44.12      A N
ATOM   1636  CA   ILE A 240      -2.041  42.046 -12.851  1.00 44.11      A C
ATOM   1637  CB   ILE A 240      -2.163  40.621 -12.252  1.00 45.03      A C
ATOM   1638  CG2  ILE A 240      -3.298  40.602 -11.234  1.00 43.74      A C
ATOM   1639  CG1  ILE A 240      -2.371  39.574 -13.350  1.00 46.17      A C
ATOM   1640  CD1  ILE A 240      -3.770  39.540 -13.934  1.00 49.52      A C
ATOM   1641  C    ILE A 240      -0.814  42.141 -13.741  1.00 44.06      A C
ATOM   1642  O    ILE A 240      -0.909  42.026 -14.958  1.00 44.62      A O
ATOM   1643  N    PRO A 241       0.358  42.366 -13.138  1.00 44.08      A N
ATOM   1644  CD   PRO A 241       0.526  42.567 -11.686  1.00 44.01      A C
ATOM   1645  CA   PRO A 241       1.645  42.501 -13.826  1.00 45.17      A C
ATOM   1646  CB   PRO A 241       2.501  43.201 -12.781  1.00 44.01      A C
ATOM   1647  CG   PRO A 241       2.040  42.526 -11.519  1.00 43.19      A C
ATOM   1648  C    PRO A 241       2.325  41.233 -14.335  1.00 46.15      A C
ATOM   1649  O    PRO A 241       2.969  41.255 -15.378  1.00 46.04      A O
ATOM   1650  N    PHE A 242       2.194  40.139 -13.595  1.00 47.32      A N
ATOM   1651  CA   PHE A 242       2.845  38.894 -13.971  1.00 47.77      A C
ATOM   1652  CB   PHE A 242       3.797  38.458 -12.859  1.00 44.58      A C
ATOM   1653  CG   PHE A 242       4.706  39.549 -12.383  1.00 43.74      A C
ATOM   1654  CD1  PHE A 242       5.501  40.254 -13.284  1.00 43.12      A C
ATOM   1655  CD2  PHE A 242       4.783  39.865 -11.032  1.00 43.56      A C
ATOM   1656  CE1  PHE A 242       6.362  41.260 -12.846  1.00 42.67      A C
ATOM   1657  CE2  PHE A 242       5.643  40.870 -10.577  1.00 42.21      A C
ATOM   1658  CZ   PHE A 242       6.434  41.568 -11.486  1.00 43.87      A C
ATOM   1659  C    PHE A 242       1.864  37.773 -14.250  1.00 50.58      A C
ATOM   1660  O    PHE A 242       0.860  37.621 -13.551  1.00 50.52      A O
ATOM   1661  N    GLU A 243       2.174  36.979 -15.269  1.00 53.46      A N
ATOM   1662  CA   GLU A 243       1.329  35.861 -15.650  1.00 57.46      A C
ATOM   1663  CB   GLU A 243       0.872  36.031 -17.101  1.00 60.72      A C
ATOM   1664  CG   GLU A 243      -0.209  35.057 -17.530  1.00 67.16      A C
ATOM   1665  CD   GLU A 243      -1.402  35.048 -16.574  1.00 71.20      A C
ATOM   1666  OE1  GLU A 243      -2.021  36.120 -16.366  1.00 72.18      A O
ATOM   1667  OE2  GLU A 243      -1.718  33.963 -16.032  1.00 72.59      A O
ATOM   1668  C    GLU A 243       2.064  34.527 -15.475  1.00 58.57      A C
ATOM   1669  O    GLU A 243       1.479  33.547 -15.009  1.00 59.52      A O
ATOM   1670  N    HIS A 244       3.346  34.494 -15.831  1.00 58.69      A N
ATOM   1671  CA   HIS A 244       4.132  33.268 -15.711  1.00 59.32      A C
ATOM   1672  CB   HIS A 244       4.823  32.951 -17.041  1.00 61.16      A C
ATOM   1673  CG   HIS A 244       3.889  32.923 -18.208  1.00 64.11      A C
ATOM   1674  CD2  HIS A 244       3.015  31.977 -18.628  1.00 65.01      A C
ATOM   1675  ND1  HIS A 244       3.733  33.994 -19.062  1.00 65.34      A N
ATOM   1676  CE1  HIS A 244       2.802  33.712 -19.957  1.00 65.53      A C
ATOM   1677  NE2  HIS A 244       2.349  32.494 -19.714  1.00 66.38      A N
ATOM   1678  C    HIS A 244       5.176  33.318 -14.598  1.00 58.34      A C
```

FIGURE 1A-31

```
ATOM   1679  O    HIS A 244       5.700  34.378 -14.258  1.00 57.57      A O
ATOM   1680  N    ASP A 245       5.477  32.149 -14.044  1.00 57.24      A N
ATOM   1681  CA   ASP A 245       6.449  32.023 -12.969  1.00 55.63      A C
ATOM   1682  CB   ASP A 245       6.726  30.544 -12.699  1.00 55.72      A C
ATOM   1683  CG   ASP A 245       5.507  29.808 -12.167  1.00 57.48      A C
ATOM   1684  OD1  ASP A 245       4.402  30.392 -12.172  1.00 58.01      A O
ATOM   1685  OD2  ASP A 245       5.651  28.640 -11.743  1.00 57.36      A O
ATOM   1686  C    ASP A 245       7.757  32.749 -13.265  1.00 54.41      A C
ATOM   1687  O    ASP A 245       8.339  33.373 -12.378  1.00 53.46      A O
ATOM   1688  N    GLU A 246       8.218  32.669 -14.510  1.00 54.03      A N
ATOM   1689  CA   GLU A 246       9.466  33.327 -14.905  1.00 53.90      A C
ATOM   1690  CB   GLU A 246       9.774  33.088 -16.393  1.00 54.95      A C
ATOM   1691  CG   GLU A 246       9.805  31.642 -16.837  1.00 59.76      A C
ATOM   1692  CD   GLU A 246       8.445  30.969 -16.756  1.00 63.31      A C
ATOM   1693  OE1  GLU A 246       7.441  31.593 -17.162  1.00 64.50      A O
ATOM   1694  OE2  GLU A 246       8.382  29.809 -16.295  1.00 65.65      A O
ATOM   1695  C    GLU A 246       9.376  34.835 -14.668  1.00 52.01      A C
ATOM   1696  O    GLU A 246      10.337  35.464 -14.224  1.00 51.71      A O
ATOM   1697  N    GLU A 247       8.221  35.412 -14.988  1.00 50.73      A N
ATOM   1698  CA   GLU A 247       8.011  36.845 -14.814  1.00 49.15      A C
ATOM   1699  CB   GLU A 247       6.687  37.277 -15.437  1.00 50.68      A C
ATOM   1700  CG   GLU A 247       6.630  37.180 -16.942  1.00 52.81      A C
ATOM   1701  CD   GLU A 247       5.229  37.414 -17.454  1.00 55.13      A C
ATOM   1702  OE1  GLU A 247       4.344  36.589 -17.142  1.00 56.25      A O
ATOM   1703  OE2  GLU A 247       5.006  38.423 -18.155  1.00 57.35      A O
ATOM   1704  C    GLU A 247       8.008  37.206 -13.339  1.00 46.35      A C
ATOM   1705  O    GLU A 247       8.549  38.238 -12.951  1.00 45.63      A O
ATOM   1706  N    ILE A 248       7.397  36.359 -12.518  1.00 43.56      A N
ATOM   1707  CA   ILE A 248       7.356  36.619 -11.092  1.00 42.53      A C
ATOM   1708  CB   ILE A 248       6.499  35.567 -10.339  1.00 40.76      A C
ATOM   1709  CG2  ILE A 248       6.545  35.823  -8.826  1.00 37.81      A C
ATOM   1710  CG1  ILE A 248       5.052  35.629 -10.848  1.00 38.01      A C
ATOM   1711  CD1  ILE A 248       4.106  34.691 -10.145  1.00 35.15      A C
ATOM   1712  C    ILE A 248       8.770  36.631 -10.534  1.00 43.86      A C
ATOM   1713  O    ILE A 248       9.134  37.540  -9.791  1.00 42.81      A O
ATOM   1714  N    ILE A 249       9.584  35.646 -10.908  1.00 46.59      A N
ATOM   1715  CA   ILE A 249      10.957  35.607 -10.393  1.00 48.80      A C
ATOM   1716  CB   ILE A 249      11.641  34.216 -10.571  1.00 49.46      A C
ATOM   1717  CG2  ILE A 249      10.817  33.135  -9.893  1.00 48.12      A C
ATOM   1718  CG1  ILE A 249      11.826  33.898 -12.056  1.00 52.41      A C
ATOM   1719  CD1  ILE A 249      12.559  32.582 -12.318  1.00 56.39      A C
ATOM   1720  C    ILE A 249      11.850  36.665 -11.024  1.00 49.20      A C
ATOM   1721  O    ILE A 249      12.844  37.058 -10.420  1.00 48.98      A O
ATOM   1722  N    ARG A 250      11.510  37.125 -12.228  1.00 50.02      A N
ATOM   1723  CA   ARG A 250      12.316  38.158 -12.884  1.00 51.98      A C
ATOM   1724  CB   ARG A 250      11.889  38.345 -14.345  1.00 53.16      A C
ATOM   1725  CG   ARG A 250      13.002  38.077 -15.351  1.00 55.24      A C
ATOM   1726  CD   ARG A 250      13.591  39.345 -15.976  1.00 56.12      A C
ATOM   1727  NE   ARG A 250      12.721  39.887 -17.016  1.00 58.75      A N
ATOM   1728  CZ   ARG A 250      13.050  40.869 -17.858  1.00 60.36      A C
ATOM   1729  NH1  ARG A 250      14.249  41.442 -17.803  1.00 60.35      A N
ATOM   1730  NH2  ARG A 250      12.166  41.284 -18.761  1.00 59.20      A N
ATOM   1731  C    ARG A 250      12.166  39.479 -12.133  1.00 52.30      A C
ATOM   1732  O    ARG A 250      13.118  40.253 -12.010  1.00 51.53      A O
ATOM   1733  N    GLY A 251      10.961  39.726 -11.633  1.00 52.54      A N
ATOM   1734  CA   GLY A 251      10.718  40.942 -10.886  1.00 54.08      A C
```

FIGURE 1A-32

```
ATOM   1735  C    GLY A 251      10.581  42.195 -11.735  1.00 54.35      A C
ATOM   1736  O    GLY A 251      10.210  43.241 -11.208  1.00 55.96      A O
ATOM   1737  N    GLN A 252      10.890  42.126 -13.028  1.00 53.37      A N
ATOM   1738  CA   GLN A 252      10.754  43.308 -13.881  1.00 51.24      A C
ATOM   1739  CB   GLN A 252      11.314  43.040 -15.279  1.00 54.94      A C
ATOM   1740  CG   GLN A 252      12.797  42.809 -15.314  1.00 60.65      A C
ATOM   1741  CD   GLN A 252      13.554  44.030 -15.770  1.00 63.68      A C
ATOM   1742  OE1  GLN A 252      14.790  44.069 -15.725  1.00 67.10      A O
ATOM   1743  NE2  GLN A 252      12.819  45.039 -16.217  1.00 64.32      A N
ATOM   1744  C    GLN A 252       9.285  43.673 -14.007  1.00 47.89      A C
ATOM   1745  O    GLN A 252       8.456  42.840 -14.372  1.00 47.19      A O
ATOM   1746  N    VAL A 253       8.952  44.915 -13.700  1.00 44.04      A N
ATOM   1747  CA   VAL A 253       7.574  45.336 -13.823  1.00 40.99      A C
ATOM   1748  CB   VAL A 253       6.999  45.787 -12.452  1.00 40.04      A C
ATOM   1749  CG1  VAL A 253       8.108  46.315 -11.590  1.00 42.49      A C
ATOM   1750  CG2  VAL A 253       5.909  46.842 -12.635  1.00 38.06      A C
ATOM   1751  C    VAL A 253       7.467  46.432 -14.867  1.00 39.88      A C
ATOM   1752  O    VAL A 253       8.087  47.489 -14.762  1.00 40.31      A O
ATOM   1753  N    PHE A 254       6.692  46.143 -15.903  1.00 38.47      A N
ATOM   1754  CA   PHE A 254       6.473  47.063 -17.006  1.00 38.09      A C
ATOM   1755  CB   PHE A 254       6.606  46.297 -18.341  1.00 39.78      A C
ATOM   1756  CG   PHE A 254       6.055  47.041 -19.531  1.00 43.02      A C
ATOM   1757  CD1  PHE A 254       4.702  46.941 -19.872  1.00 44.05      A C
ATOM   1758  CD2  PHE A 254       6.871  47.895 -20.273  1.00 43.12      A C
ATOM   1759  CE1  PHE A 254       4.174  47.688 -20.933  1.00 44.40      A C
ATOM   1760  CE2  PHE A 254       6.353  48.646 -21.333  1.00 42.14      A C
ATOM   1761  CZ   PHE A 254       5.005  48.543 -21.661  1.00 43.52      A C
ATOM   1762  C    PHE A 254       5.083  47.693 -16.868  1.00 37.93      A C
ATOM   1763  O    PHE A 254       4.113  47.009 -16.540  1.00 38.43      A O
ATOM   1764  N    PHE A 255       4.983  48.997 -17.101  1.00 37.10      A N
ATOM   1765  CA   PHE A 255       3.693  49.653 -16.995  1.00 37.10      A C
ATOM   1766  CB   PHE A 255       3.835  50.984 -16.257  1.00 35.60      A C
ATOM   1767  CG   PHE A 255       4.100  50.815 -14.796  1.00 34.11      A C
ATOM   1768  CD1  PHE A 255       5.381  50.563 -14.334  1.00 32.58      A C
ATOM   1769  CD2  PHE A 255       3.041  50.801 -13.890  1.00 35.04      A C
ATOM   1770  CE1  PHE A 255       5.605  50.294 -12.995  1.00 34.38      A C
ATOM   1771  CE2  PHE A 255       3.252  50.530 -12.545  1.00 33.03      A C
ATOM   1772  CZ   PHE A 255       4.531  50.275 -12.094  1.00 34.57      A C
ATOM   1773  C    PHE A 255       3.027  49.836 -18.345  1.00 38.35      A C
ATOM   1774  O    PHE A 255       3.570  50.466 -19.248  1.00 39.65      A O
ATOM   1775  N    ARG A 256       1.844  49.256 -18.472  1.00 40.83      A N
ATOM   1776  CA   ARG A 256       1.082  49.309 -19.707  1.00 43.82      A C
ATOM   1777  CB   ARG A 256       0.285  48.013 -19.863  1.00 45.87      A C
ATOM   1778  CG   ARG A 256      -0.735  47.778 -18.759  1.00 47.82      A C
ATOM   1779  CD   ARG A 256      -1.363  46.391 -18.886  1.00 50.28      A C
ATOM   1780  NE   ARG A 256      -0.545  45.342 -18.274  1.00 51.16      A N
ATOM   1781  CZ   ARG A 256      -0.713  44.042 -18.498  1.00 51.86      A C
ATOM   1782  NH1  ARG A 256      -1.662  43.630 -19.328  1.00 51.40      A N
ATOM   1783  NH2  ARG A 256       0.054  43.153 -17.877  1.00 50.88      A N
ATOM   1784  C    ARG A 256       0.134  50.499 -19.698  1.00 43.97      A C
ATOM   1785  O    ARG A 256      -0.531  50.789 -20.686  1.00 43.91      A O
ATOM   1786  N    GLN A 257       0.087  51.183 -18.564  1.00 44.59      A N
ATOM   1787  CA   GLN A 257      -0.778  52.339 -18.385  1.00 44.56      A C
ATOM   1788  CB   GLN A 257      -1.910  51.983 -17.424  1.00 47.73      A C
ATOM   1789  CG   GLN A 257      -2.924  53.075 -17.227  1.00 52.66      A C
ATOM   1790  CD   GLN A 257      -3.963  53.077 -18.319  1.00 55.97      A C
```

FIGURE 1A-33

```
ATOM 1791  OE1  GLN A 257   -3.641  53.155  -19.506  1.00  60.22  A O
ATOM 1792  NE2  GLN A 257   -5.224  52.989  -17.925  1.00  57.29  A N
ATOM 1793  C    GLN A 257    0.035  53.485  -17.798  1.00  42.63  A C
ATOM 1794  O    GLN A 257    1.106  53.282  -17.237  1.00  41.65  A O
ATOM 1795  N    ARG A 258   -0.487  54.693  -17.915  1.00  41.08  A N
ATOM 1796  CA   ARG A 258    0.197  55.864  -17.389  1.00  39.55  A C
ATOM 1797  CB   ARG A 258   -0.399  57.115  -18.030  1.00  39.54  A C
ATOM 1798  CG   ARG A 258    0.516  58.310  -18.048  1.00  39.65  A C
ATOM 1799  CD   ARG A 258    0.880  58.841  -16.677  1.00  38.97  A C
ATOM 1800  NE   ARG A 258    2.214  59.416  -16.772  1.00  43.61  A N
ATOM 1801  CZ   ARG A 258    2.716  60.334  -15.960  1.00  44.90  A C
ATOM 1802  NH1  ARG A 258    1.990  60.810  -14.956  1.00  44.37  A N
ATOM 1803  NH2  ARG A 258    3.950  60.778  -16.169  1.00  45.57  A N
ATOM 1804  C    ARG A 258    0.030  55.962  -15.871  1.00  37.84  A C
ATOM 1805  O    ARG A 258   -1.084  56.141  -15.401  1.00  38.78  A O
ATOM 1806  N    VAL A 259    1.112  55.843  -15.106  1.00  34.70  A N
ATOM 1807  CA   VAL A 259    1.005  55.977  -13.654  1.00  35.02  A C
ATOM 1808  CB   VAL A 259    0.932  54.574  -12.917  1.00  34.62  A C
ATOM 1809  CG1  VAL A 259    1.000  53.454  -13.911  1.00  35.15  A C
ATOM 1810  CG2  VAL A 259    2.008  54.439  -11.870  1.00  33.47  A C
ATOM 1811  C    VAL A 259    2.137  56.850  -13.110  1.00  34.29  A C
ATOM 1812  O    VAL A 259    3.276  56.781  -13.566  1.00  35.06  A O
ATOM 1813  N    SER A 260    1.810  57.691  -12.141  1.00  32.72  A N
ATOM 1814  CA   SER A 260    2.790  58.604  -11.578  1.00  34.11  A C
ATOM 1815  CB   SER A 260    2.178  59.385  -10.414  1.00  31.50  A C
ATOM 1816  OG   SER A 260    1.709  58.502   -9.412  1.00  32.89  A O
ATOM 1817  C    SER A 260    4.065  57.917  -11.119  1.00  35.22  A C
ATOM 1818  O    SER A 260    4.068  56.731  -10.784  1.00  36.19  A O
ATOM 1819  N    PSR A 261    5.152  58.681  -11.116  1.00  36.27  A N
ATOM 1820  CA   PSR A 261    6.444  58.179  -10.690  1.00  36.55  A C
ATOM 1821  CB   PSR A 261    7.496  59.286  -10.791  1.00  37.30  A C
ATOM 1822  OG   PSR A 261    7.670  59.587  -12.171  1.00  43.48  A O
ATOM 1823  C    PSR A 261    6.349  57.666   -9.258  1.00  36.02  A C
ATOM 1824  O    PSR A 261    6.872  56.610   -8.945  1.00  36.34  A O
ATOM 1825  P    PSR A 261    7.258  60.992  -12.776  1.00  47.24  A P
ATOM 1826  O1   PSR A 261    7.996  62.078  -12.123  1.00  45.73  A O
ATOM 1827  O2   PSR A 261    7.487  61.003  -14.295  1.00  46.52  A O
ATOM 1828  O3   PSR A 261    5.734  61.105  -12.561  1.00  46.41  A O
ATOM 1829  N    GLU A 262    5.666  58.407   -8.394  1.00  37.22  A N
ATOM 1830  CA   GLU A 262    5.521  57.994   -7.002  1.00  39.04  A C
ATOM 1831  CB   GLU A 262    4.757  59.041   -6.205  1.00  43.32  A C
ATOM 1832  CG   GLU A 262    5.432  60.384   -6.172  1.00  50.59  A C
ATOM 1833  CD   GLU A 262    4.782  61.326   -5.186  1.00  57.26  A C
ATOM 1834  OE1  GLU A 262    3.531  61.463   -5.215  1.00  61.12  A O
ATOM 1835  OE2  GLU A 262    5.525  61.935   -4.384  1.00  61.01  A O
ATOM 1836  C    GLU A 262    4.816  56.651   -6.868  1.00  36.91  A C
ATOM 1837  O    GLU A 262    5.218  55.817   -6.061  1.00  37.02  A O
ATOM 1838  N    CYS A 263    3.771  56.443   -7.663  1.00  35.35  A N
ATOM 1839  CA   CYS A 263    3.029  55.187   -7.621  1.00  34.69  A C
ATOM 1840  CB   CYS A 263    1.759  55.282   -8.472  1.00  33.75  A C
ATOM 1841  SG   CYS A 263    0.528  53.987   -8.165  1.00  34.55  A S
ATOM 1842  C    CYS A 263    3.919  54.054   -8.136  1.00  34.61  A C
ATOM 1843  O    CYS A 263    4.013  52.989   -7.509  1.00  33.80  A O
ATOM 1844  N    GLN A 264    4.573  54.277   -9.274  1.00  34.11  A N
ATOM 1845  CA   GLN A 264    5.458  53.253   -9.833  1.00  33.15  A C
ATOM 1846  CB   GLN A 264    6.177  53.760  -11.091  1.00  31.97  A C
```

FIGURE 1A-34

```
ATOM  1847  CG   GLN A 264       5.340  53.769 -12.367  1.00 32.36      A C
ATOM  1848  CD   GLN A 264       6.202  53.961 -13.616  1.00 33.61      A C
ATOM  1849  OE1  GLN A 264       7.407  53.689 -13.595  1.00 36.85      A O
ATOM  1850  NE2  GLN A 264       5.591  54.407 -14.708  1.00 29.45      A N
ATOM  1851  C    GLN A 264       6.495  52.869  -8.785  1.00 32.22      A C
ATOM  1852  O    GLN A 264       6.847  51.689  -8.636  1.00 32.96      A O
ATOM  1853  N    HIS A 265       6.976  53.863  -8.045  1.00 31.19      A N
ATOM  1854  CA   HIS A 265       7.987  53.597  -7.023  1.00 32.17      A C
ATOM  1855  CB   HIS A 265       8.567  54.909  -6.473  1.00 32.44      A C
ATOM  1856  CG   HIS A 265       9.489  54.719  -5.308  1.00 37.25      A C
ATOM  1857  CD2  HIS A 265      10.842  54.627  -5.244  1.00 37.59      A C
ATOM  1858  ND1  HIS A 265       9.034  54.556  -4.016  1.00 36.63      A N
ATOM  1859  CE1  HIS A 265      10.065  54.371  -3.208  1.00 38.61      A C
ATOM  1860  NE2  HIS A 265      11.173  54.409  -3.928  1.00 38.75      A N
ATOM  1861  C    HIS A 265       7.440  52.737  -5.882  1.00 31.92      A C
ATOM  1862  O    HIS A 265       8.098  51.791  -5.454  1.00 32.05      A O
ATOM  1863  N    LEU A 266       6.243  53.048  -5.390  1.00 29.30      A N
ATOM  1864  CA   LEU A 266       5.689  52.250  -4.313  1.00 29.02      A C
ATOM  1865  CB   LEU A 266       4.365  52.839  -3.830  1.00 27.57      A C
ATOM  1866  CG   LEU A 266       3.602  52.079  -2.731  1.00 25.85      A C
ATOM  1867  CD1  LEU A 266       4.497  51.805  -1.527  1.00 20.26      A C
ATOM  1868  CD2  LEU A 266       2.391  52.914  -2.305  1.00 23.77      A C
ATOM  1869  C    LEU A 266       5.484  50.819  -4.811  1.00 29.60      A C
ATOM  1870  O    LEU A 266       5.880  49.860  -4.149  1.00 28.99      A O
ATOM  1871  N    ILE A 267       4.884  50.679  -5.990  1.00 29.64      A N
ATOM  1872  CA   ILE A 267       4.638  49.364  -6.552  1.00 28.48      A C
ATOM  1873  CB   ILE A 267       4.011  49.469  -7.962  1.00 27.24      A C
ATOM  1874  CG2  ILE A 267       4.034  48.112  -8.656  1.00 26.16      A C
ATOM  1875  CG1  ILE A 267       2.570  49.964  -7.841  1.00 27.71      A C
ATOM  1876  CD1  ILE A 267       1.838  50.139  -9.160  1.00 24.12      A C
ATOM  1877  C    ILE A 267       5.933  48.560  -6.614  1.00 30.34      A C
ATOM  1878  O    ILE A 267       6.012  47.453  -6.078  1.00 31.34      A O
ATOM  1879  N    ARG A 268       6.953  49.117  -7.257  1.00 31.40      A N
ATOM  1880  CA   ARG A 268       8.230  48.420  -7.371  1.00 31.84      A C
ATOM  1881  CB   ARG A 268       9.218  49.259  -8.183  1.00 32.59      A C
ATOM  1882  CG   ARG A 268       8.901  49.200  -9.665  1.00 34.16      A C
ATOM  1883  CD   ARG A 268       9.820  50.053 -10.505  1.00 35.56      A C
ATOM  1884  NE   ARG A 268       9.600  49.767 -11.918  1.00 38.19      A N
ATOM  1885  CZ   ARG A 268       9.287  50.685 -12.827  1.00 38.93      A C
ATOM  1886  NH1  ARG A 268       9.163  51.958 -12.463  1.00 37.34      A N
ATOM  1887  NH2  ARG A 268       9.083  50.329 -14.094  1.00 37.13      A N
ATOM  1888  C    ARG A 268       8.816  48.057  -6.017  1.00 30.74      A C
ATOM  1889  O    ARG A 268       9.395  46.977  -5.850  1.00 30.02      A O
ATOM  1890  N    TRP A 269       8.649  48.948  -5.044  1.00 30.52      A N
ATOM  1891  CA   TRP A 269       9.152  48.700  -3.703  1.00 30.64      A C
ATOM  1892  CB   TRP A 269       8.939  49.945  -2.842  1.00 32.44      A C
ATOM  1893  CG   TRP A 269       9.695  49.942  -1.550  1.00 35.34      A C
ATOM  1894  CD2  TRP A 269       9.566  50.887  -0.482  1.00 35.39      A C
ATOM  1895  CE2  TRP A 269      10.483  50.506   0.527  1.00 35.12      A C
ATOM  1896  CE3  TRP A 269       8.766  52.019  -0.278  1.00 35.66      A C
ATOM  1897  CD1  TRP A 269      10.658  49.048  -1.158  1.00 36.30      A C
ATOM  1898  NE1  TRP A 269      11.135  49.383   0.089  1.00 35.88      A N
ATOM  1899  CZ2  TRP A 269      10.620  51.218   1.723  1.00 35.01      A C
ATOM  1900  CZ3  TRP A 269       8.902  52.728   0.912  1.00 35.51      A C
ATOM  1901  CH2  TRP A 269       9.824  52.324   1.897  1.00 36.86      A C
ATOM  1902  C    TRP A 269       8.441  47.474  -3.105  1.00 30.79      A C
```

FIGURE 1A-35

```
ATOM   1903  O    TRP A 269       9.096  46.550  -2.609  1.00 30.58      A  O
ATOM   1904  N    CYS A 270       7.111  47.453  -3.163  1.00 29.63      A  N
ATOM   1905  CA   CYS A 270       6.353  46.308  -2.638  1.00 31.31      A  C
ATOM   1906  CB   CYS A 270       4.838  46.507  -2.779  1.00 30.49      A  C
ATOM   1907  SG   CYS A 270       4.121  47.771  -1.739  1.00 29.16      A  S
ATOM   1908  C    CYS A 270       6.716  45.028  -3.378  1.00 31.37      A  C
ATOM   1909  O    CYS A 270       6.647  43.942  -2.808  1.00 31.72      A  O
ATOM   1910  N    LEU A 271       7.079  45.154  -4.651  1.00 31.04      A  N
ATOM   1911  CA   LEU A 271       7.439  43.982  -5.441  1.00 32.09      A  C
ATOM   1912  CB   LEU A 271       6.943  44.133  -6.880  1.00 30.32      A  C
ATOM   1913  CG   LEU A 271       5.430  44.282  -7.046  1.00 30.65      A  C
ATOM   1914  CD1  LEU A 271       5.080  44.393  -8.526  1.00 29.92      A  C
ATOM   1915  CD2  LEU A 271       4.722  43.084  -6.406  1.00 30.95      A  C
ATOM   1916  C    LEU A 271       8.941  43.698  -5.443  1.00 32.63      A  C
ATOM   1917  O    LEU A 271       9.441  43.022  -6.337  1.00 33.86      A  O
ATOM   1918  N    ALA A 272       9.666  44.210  -4.453  1.00 32.88      A  N
ATOM   1919  CA   ALA A 272      11.102  43.945  -4.390  1.00 33.73      A  C
ATOM   1920  CB   ALA A 272      11.712  44.551  -3.132  1.00 30.62      A  C
ATOM   1921  C    ALA A 272      11.288  42.433  -4.389  1.00 34.72      A  C
ATOM   1922  O    ALA A 272      10.568  41.709  -3.709  1.00 35.00      A  O
ATOM   1923  N    LEU A 273      12.257  41.966  -5.162  1.00 36.82      A  N
ATOM   1924  CA   LEU A 273      12.544  40.546  -5.279  1.00 38.18      A  C
ATOM   1925  CB   LEU A 273      13.626  40.357  -6.342  1.00 35.60      A  C
ATOM   1926  CG   LEU A 273      13.273  39.407  -7.487  1.00 38.06      A  C
ATOM   1927  CD1  LEU A 273      11.810  39.531  -7.880  1.00 36.55      A  C
ATOM   1928  CD2  LEU A 273      14.172  39.719  -8.670  1.00 35.63      A  C
ATOM   1929  C    LEU A 273      12.961  39.902  -3.950  1.00 38.58      A  C
ATOM   1930  O    LEU A 273      12.546  38.789  -3.628  1.00 39.68      A  O
ATOM   1931  N    ARG A 274      13.780  40.603  -3.181  1.00 39.35      A  N
ATOM   1932  CA   ARG A 274      14.236  40.093  -1.897  1.00 42.41      A  C
ATOM   1933  CB   ARG A 274      15.628  40.654  -1.582  1.00 46.64      A  C
ATOM   1934  CG   ARG A 274      16.320  39.987  -0.409  1.00 54.41      A  C
ATOM   1935  CD   ARG A 274      17.568  40.764   0.005  1.00 61.03      A  C
ATOM   1936  NE   ARG A 274      18.253  40.144   1.140  1.00 65.54      A  N
ATOM   1937  CZ   ARG A 274      19.104  40.781   1.942  1.00 68.54      A  C
ATOM   1938  NH1  ARG A 274      19.382  42.066   1.742  1.00 69.86      A  N
ATOM   1939  NH2  ARG A 274      19.680  40.133   2.949  1.00 69.00      A  N
ATOM   1940  C    ARG A 274      13.231  40.522  -0.824  1.00 41.21      A  C
ATOM   1941  O    ARG A 274      12.984  41.708  -0.629  1.00 42.03      A  O
ATOM   1942  N    PRO A 275      12.636  39.556  -0.119  1.00 40.69      A  N
ATOM   1943  CD   PRO A 275      12.857  38.109  -0.291  1.00 40.83      A  C
ATOM   1944  CA   PRO A 275      11.649  39.812   0.935  1.00 40.87      A  C
ATOM   1945  CB   PRO A 275      11.548  38.461   1.635  1.00 40.32      A  C
ATOM   1946  CG   PRO A 275      11.694  37.504   0.489  1.00 41.14      A  C
ATOM   1947  C    PRO A 275      11.967  40.946   1.909  1.00 42.07      A  C
ATOM   1948  O    PRO A 275      11.098  41.771   2.209  1.00 41.99      A  O
ATOM   1949  N    SER A 276      13.203  40.994   2.403  1.00 41.82      A  N
ATOM   1950  CA   SER A 276      13.584  42.030   3.358  1.00 41.94      A  C
ATOM   1951  CB   SER A 276      14.918  41.680   4.044  1.00 43.82      A  C
ATOM   1952  OG   SER A 276      16.009  41.650   3.136  1.00 45.28      A  O
ATOM   1953  C    SER A 276      13.660  43.419   2.735  1.00 41.43      A  C
ATOM   1954  O    SER A 276      13.666  44.425   3.456  1.00 42.73      A  O
ATOM   1955  N    ASP A 277      13.708  43.487   1.405  1.00 39.45      A  N
ATOM   1956  CA   ASP A 277      13.762  44.781   0.721  1.00 39.07      A  C
ATOM   1957  CB   ASP A 277      14.435  44.642  -0.645  1.00 40.19      A  C
ATOM   1958  CG   ASP A 277      15.953  44.578  -0.556  1.00 40.20      A  C
```

FIGURE 1A-36

```
ATOM   1959  OD1 ASP A 277      16.584  44.085  -1.516  1.00 40.93      A O
ATOM   1960  OD2 ASP A 277      16.516  45.031   0.462  1.00 42.38      A O
ATOM   1961  C   ASP A 277      12.361  45.381   0.528  1.00 39.70      A C
ATOM   1962  O   ASP A 277      12.221  46.481   0.000  1.00 40.28      A O
ATOM   1963  N   ARG A 278      11.324  44.662   0.945  1.00 37.62      A N
ATOM   1964  CA  ARG A 278       9.974  45.181   0.790  1.00 36.84      A C
ATOM   1965  CB  ARG A 278       8.962  44.034   0.718  1.00 32.73      A C
ATOM   1966  CG  ARG A 278       9.117  43.197  -0.540  1.00 31.87      A C
ATOM   1967  CD  ARG A 278       8.243  41.947  -0.541  1.00 29.54      A C
ATOM   1968  NE  ARG A 278       8.814  40.978  -1.469  1.00 31.25      A N
ATOM   1969  CZ  ARG A 278       8.600  39.666  -1.445  1.00 30.79      A C
ATOM   1970  NH1 ARG A 278       7.806  39.122  -0.532  1.00 25.69      A N
ATOM   1971  NH2 ARG A 278       9.222  38.892  -2.325  1.00 30.91      A N
ATOM   1972  C   ARG A 278       9.647  46.102   1.953  1.00 36.76      A C
ATOM   1973  O   ARG A 278      10.227  45.988   3.029  1.00 37.02      A O
ATOM   1974  N   PRO A 279       8.726  47.047   1.743  1.00 35.68      A N
ATOM   1975  CD  PRO A 279       8.012  47.372   0.495  1.00 37.47      A C
ATOM   1976  CA  PRO A 279       8.351  47.973   2.808  1.00 35.02      A C
ATOM   1977  CB  PRO A 279       7.595  49.062   2.057  1.00 35.64      A C
ATOM   1978  CG  PRO A 279       6.898  48.283   0.986  1.00 36.36      A C
ATOM   1979  C   PRO A 279       7.477  47.316   3.858  1.00 35.20      A C
ATOM   1980  O   PRO A 279       6.871  46.270   3.617  1.00 36.51      A O
ATOM   1981  N   THR A 280       7.431  47.936   5.030  1.00 35.39      A N
ATOM   1982  CA  THR A 280       6.584  47.472   6.119  1.00 34.83      A C
ATOM   1983  CB  THR A 280       7.115  47.921   7.498  1.00 36.91      A C
ATOM   1984  OG1 THR A 280       7.189  49.352   7.528  1.00 37.55      A O
ATOM   1985  CG2 THR A 280       8.504  47.348   7.771  1.00 35.19      A C
ATOM   1986  C   THR A 280       5.288  48.234   5.860  1.00 34.91      A C
ATOM   1987  O   THR A 280       5.280  49.189   5.080  1.00 33.92      A O
ATOM   1988  N   PHE A 281       4.200  47.827   6.506  1.00 36.78      A N
ATOM   1989  CA  PHE A 281       2.920  48.507   6.328  1.00 36.78      A C
ATOM   1990  CB  PHE A 281       1.879  47.898   7.250  1.00 37.22      A C
ATOM   1991  CG  PHE A 281       1.576  46.471   6.944  1.00 40.21      A C
ATOM   1992  CD1 PHE A 281       1.235  45.590   7.959  1.00 42.91      A C
ATOM   1993  CD2 PHE A 281       1.627  46.000   5.637  1.00 41.13      A C
ATOM   1994  CE1 PHE A 281       0.950  44.263   7.673  1.00 44.48      A C
ATOM   1995  CE2 PHE A 281       1.344  44.675   5.341  1.00 41.80      A C
ATOM   1996  CZ  PHE A 281       1.005  43.804   6.355  1.00 42.76      A C
ATOM   1997  C   PHE A 281       3.074  49.985   6.642  1.00 37.43      A C
ATOM   1998  O   PHE A 281       2.524  50.840   5.943  1.00 36.72      A O
ATOM   1999  N   GLU A 282       3.839  50.278   7.691  1.00 36.23      A N
ATOM   2000  CA  GLU A 282       4.062  51.647   8.103  1.00 36.89      A C
ATOM   2001  CB  GLU A 282       4.900  51.688   9.386  1.00 38.21      A C
ATOM   2002  CG  GLU A 282       5.187  53.093   9.901  1.00 42.14      A C
ATOM   2003  CD  GLU A 282       6.152  53.104  11.080  1.00 45.10      A C
ATOM   2004  OE1 GLU A 282       7.120  52.313  11.063  1.00 47.22      A O
ATOM   2005  OE2 GLU A 282       5.958  53.913  12.015  1.00 45.12      A O
ATOM   2006  C   GLU A 282       4.754  52.419   6.996  1.00 36.11      A C
ATOM   2007  O   GLU A 282       4.390  53.551   6.703  1.00 35.95      A O
ATOM   2008  N   GLU A 283       5.756  51.810   6.376  1.00 36.13      A N
ATOM   2009  CA  GLU A 283       6.478  52.476   5.299  1.00 37.36      A C
ATOM   2010  CB  GLU A 283       7.709  51.664   4.910  1.00 38.74      A C
ATOM   2011  CG  GLU A 283       8.771  51.649   5.991  1.00 39.19      A C
ATOM   2012  CD  GLU A 283       9.980  50.837   5.602  1.00 40.21      A C
ATOM   2013  OE1 GLU A 283       9.835  49.613   5.416  1.00 39.48      A O
ATOM   2014  OE2 GLU A 283      11.075  51.424   5.479  1.00 43.29      A O
```

FIGURE 1A-37

```
ATOM 2015  C    GLU A 283    5.602  52.727   4.078  1.00 36.38      A C
ATOM 2016  O    GLU A 283    5.787  53.710   3.373  1.00 38.78      A O
ATOM 2017  N    ILE A 284    4.647  51.839   3.825  1.00 35.00      A N
ATOM 2018  CA   ILE A 284    3.738  52.010   2.701  1.00 32.48      A C
ATOM 2019  CB   ILE A 284    2.900  50.747   2.470  1.00 30.83      A C
ATOM 2020  CG2  ILE A 284    1.720  51.047   1.558  1.00 28.46      A C
ATOM 2021  CG1  ILE A 284    3.784  49.648   1.883  1.00 28.96      A C
ATOM 2022  CD1  ILE A 284    3.081  48.325   1.750  1.00 27.87      A C
ATOM 2023  C    ILE A 284    2.801  53.173   3.004  1.00 33.80      A C
ATOM 2024  O    ILE A 284    2.624  54.080   2.182  1.00 33.93      A O
ATOM 2025  N    GLN A 285    2.212  53.156   4.194  1.00 32.53      A N
ATOM 2026  CA   GLN A 285    1.294  54.217   4.572  1.00 33.24      A C
ATOM 2027  CB   GLN A 285    0.507  53.812   5.826  1.00 32.92      A C
ATOM 2028  CG   GLN A 285   -0.432  52.636   5.552  1.00 30.72      A C
ATOM 2029  CD   GLN A 285   -1.547  52.485   6.574  1.00 31.68      A C
ATOM 2030  OE1  GLN A 285   -1.316  52.075   7.713  1.00 29.72      A O
ATOM 2031  NE2  GLN A 285   -2.769  52.815   6.166  1.00 28.89      A N
ATOM 2032  C    GLN A 285    1.981  55.570   4.746  1.00 34.19      A C
ATOM 2033  O    GLN A 285    1.317  56.606   4.747  1.00 35.02      A O
ATOM 2034  N    ASN A 286    3.307  55.573   4.873  1.00 33.74      A N
ATOM 2035  CA   ASN A 286    4.032  56.834   4.995  1.00 33.86      A C
ATOM 2036  CB   ASN A 286    5.145  56.736   6.050  1.00 33.45      A C
ATOM 2037  CG   ASN A 286    4.633  56.976   7.467  1.00 33.36      A C
ATOM 2038  OD1  ASN A 286    5.122  56.376   8.421  1.00 36.12      A O
ATOM 2039  ND2  ASN A 286    3.659  57.863   7.606  1.00 31.81      A N
ATOM 2040  C    ASN A 286    4.639  57.226   3.651  1.00 35.02      A C
ATOM 2041  O    ASN A 286    5.297  58.256   3.539  1.00 37.55      A O
ATOM 2042  N    HIS A 287    4.428  56.402   2.631  1.00 33.15      A N
ATOM 2043  CA   HIS A 287    4.970  56.700   1.311  1.00 32.89      A C
ATOM 2044  CB   HIS A 287    4.721  55.522   0.358  1.00 29.47      A C
ATOM 2045  CG   HIS A 287    5.468  55.626  -0.936  1.00 28.62      A C
ATOM 2046  CD2  HIS A 287    6.627  55.055  -1.342  1.00 25.27      A C
ATOM 2047  ND1  HIS A 287    5.049  56.426  -1.979  1.00 27.58      A N
ATOM 2048  CE1  HIS A 287    5.915  56.339  -2.972  1.00 24.42      A C
ATOM 2049  NE2  HIS A 287    6.882  55.515  -2.612  1.00 25.04      A N
ATOM 2050  C    HIS A 287    4.338  57.982   0.748  1.00 33.79      A C
ATOM 2051  O    HIS A 287    3.172  58.276   1.005  1.00 35.09      A O
ATOM 2052  N    PRO A 288    5.106  58.765  -0.023  1.00 33.24      A N
ATOM 2053  CD   PRO A 288    6.543  58.619  -0.309  1.00 32.00      A C
ATOM 2054  CA   PRO A 288    4.585  60.005  -0.599  1.00 33.56      A C
ATOM 2055  CB   PRO A 288    5.720  60.473  -1.502  1.00 32.33      A C
ATOM 2056  CG   PRO A 288    6.925  60.013  -0.759  1.00 32.97      A C
ATOM 2057  C    PRO A 288    3.292  59.834  -1.365  1.00 34.21      A C
ATOM 2058  O    PRO A 288    2.406  60.668  -1.261  1.00 34.89      A O
ATOM 2059  N    TRP A 289    3.181  58.755  -2.132  1.00 35.31      A N
ATOM 2060  CA   TRP A 289    1.976  58.512  -2.931  1.00 35.13      A C
ATOM 2061  CB   TRP A 289    2.175  57.305  -3.856  1.00 33.08      A C
ATOM 2062  CG   TRP A 289    1.049  57.126  -4.821  1.00 32.33      A C
ATOM 2063  CD2  TRP A 289   -0.029  56.181  -4.724  1.00 31.80      A C
ATOM 2064  CE2  TRP A 289   -0.865  56.391  -5.842  1.00 32.43      A C
ATOM 2065  CE3  TRP A 289   -0.367  55.180  -3.801  1.00 31.76      A C
ATOM 2066  CD1  TRP A 289    0.826  57.847  -5.955  1.00 30.36      A C
ATOM 2067  NE1  TRP A 289   -0.319  57.411  -6.573  1.00 32.75      A N
ATOM 2068  CZ2  TRP A 289   -2.025  55.633  -6.065  1.00 32.15      A C
ATOM 2069  CZ3  TRP A 289   -1.521  54.424  -4.022  1.00 30.78      A C
ATOM 2070  CH2  TRP A 289   -2.334  54.657  -5.147  1.00 31.98      A C
```

FIGURE 1A-38

```
ATOM   2071  C   TRP A 289       0.730  58.273  -2.090  1.00 35.77      A C
ATOM   2072  O   TRP A 289      -0.390  58.469  -2.564  1.00 34.98      A O
ATOM   2073  N   MET A 290       0.930  57.848  -0.846  1.00 37.42      A N
ATOM   2074  CA  MET A 290      -0.176  57.553   0.061  1.00 40.50      A C
ATOM   2075  CB  MET A 290       0.244  56.451   1.037  1.00 38.83      A C
ATOM   2076  CG  MET A 290       0.396  55.060   0.412  1.00 41.30      A C
ATOM   2077  SD  MET A 290      -1.187  54.258   0.044  1.00 43.91      A S
ATOM   2078  CE  MET A 290      -1.484  53.466   1.545  1.00 45.70      A C
ATOM   2079  C   MET A 290      -0.742  58.730   0.865  1.00 41.96      A C
ATOM   2080  O   MET A 290      -1.656  58.541   1.670  1.00 42.54      A O
ATOM   2081  N   GLN A 291      -0.220  59.937   0.657  1.00 43.44      A N
ATOM   2082  CA  GLN A 291      -0.708  61.096   1.416  1.00 45.49      A C
ATOM   2083  CB  GLN A 291       0.405  62.140   1.539  1.00 45.69      A C
ATOM   2084  CG  GLN A 291       1.704  61.575   2.120  1.00 50.80      A C
ATOM   2085  CD  GLN A 291       1.488  60.699   3.371  1.00 53.61      A C
ATOM   2086  OE1 GLN A 291       1.037  61.178   4.419  1.00 54.52      A O
ATOM   2087  NE2 GLN A 291       1.813  59.409   3.254  1.00 51.81      A N
ATOM   2088  C   GLN A 291      -1.983  61.746   0.856  1.00 45.37      A C
ATOM   2089  O   GLN A 291      -2.274  61.648  -0.340  1.00 44.98      A O
ATOM   2090  N   ASP A 292      -2.748  62.393   1.734  1.00 44.99      A N
ATOM   2091  CA  ASP A 292      -3.989  63.065   1.337  1.00 46.00      A C
ATOM   2092  CB  ASP A 292      -3.706  64.114   0.255  1.00 48.62      A C
ATOM   2093  CG  ASP A 292      -2.675  65.131   0.685  1.00 52.60      A C
ATOM   2094  OD1 ASP A 292      -2.888  65.780   1.730  1.00 55.79      A O
ATOM   2095  OD2 ASP A 292      -1.654  65.285  -0.023  1.00 54.82      A O
ATOM   2096  C   ASP A 292      -5.065  62.110   0.816  1.00 44.29      A C
ATOM   2097  O   ASP A 292      -5.781  62.430  -0.127  1.00 43.49      A O
ATOM   2098  N   VAL A 293      -5.180  60.941   1.428  1.00 42.87      A N
ATOM   2099  CA  VAL A 293      -6.179  59.971   1.003  1.00 42.69      A C
ATOM   2100  CB  VAL A 293      -6.008  58.648   1.757  1.00 42.44      A C
ATOM   2101  CG1 VAL A 293      -6.099  58.897   3.258  1.00 43.10      A C
ATOM   2102  CG2 VAL A 293      -7.077  57.666   1.326  1.00 44.50      A C
ATOM   2103  C   VAL A 293      -7.581  60.500   1.287  1.00 42.56      A C
ATOM   2104  O   VAL A 293      -7.812  61.135   2.310  1.00 42.96      A O
ATOM   2105  N   LEU A 294      -8.515  60.240   0.384  1.00 42.46      A N
ATOM   2106  CA  LEU A 294      -9.888  60.691   0.575  1.00 43.08      A C
ATOM   2107  CB  LEU A 294     -10.699  60.558  -0.716  1.00 41.63      A C
ATOM   2108  CG  LEU A 294     -10.348  61.443  -1.902  1.00 42.01      A C
ATOM   2109  CD1 LEU A 294     -11.255  61.096  -3.077  1.00 43.39      A C
ATOM   2110  CD2 LEU A 294     -10.513  62.896  -1.512  1.00 40.37      A C
ATOM   2111  C   LEU A 294     -10.554  59.832   1.625  1.00 44.00      A C
ATOM   2112  O   LEU A 294     -10.097  58.731   1.908  1.00 44.04      A O
ATOM   2113  N   LEU A 295     -11.635  60.344   2.201  1.00 45.58      A N
ATOM   2114  CA  LEU A 295     -12.398  59.596   3.186  1.00 46.90      A C
ATOM   2115  CB  LEU A 295     -13.216  60.537   4.068  1.00 49.61      A C
ATOM   2116  CG  LEU A 295     -12.475  61.125   5.268  1.00 53.00      A C
ATOM   2117  CD1 LEU A 295     -11.200  61.818   4.809  1.00 55.31      A C
ATOM   2118  CD2 LEU A 295     -13.394  62.099   5.991  1.00 54.46      A C
ATOM   2119  C   LEU A 295     -13.333  58.677   2.412  1.00 45.89      A C
ATOM   2120  O   LEU A 295     -13.627  58.918   1.248  1.00 44.99      A O
ATOM   2121  N   PRO A 296     -13.803  57.602   3.047  1.00 46.28      A N
ATOM   2122  CD  PRO A 296     -13.426  57.088   4.377  1.00 45.84      A C
ATOM   2123  CA  PRO A 296     -14.705  56.676   2.357  1.00 46.82      A C
ATOM   2124  CB  PRO A 296     -15.118  55.722   3.468  1.00 46.68      A C
ATOM   2125  CG  PRO A 296     -13.854  55.638   4.294  1.00 46.30      A C
ATOM   2126  C   PRO A 296     -15.901  57.330   1.662  1.00 48.34      A C
```

FIGURE 1A-39

```
ATOM   2127  O    PRO A 296     -16.122  57.111   0.468  1.00 47.03      A O
ATOM   2128  N    GLN A 297     -16.665  58.134   2.401  1.00 50.55      A N
ATOM   2129  CA   GLN A 297     -17.845  58.792   1.831  1.00 52.11      A C
ATOM   2130  CB   GLN A 297     -18.599  59.585   2.906  1.00 55.20      A C
ATOM   2131  CG   GLN A 297     -20.063  59.878   2.551  1.00 59.51      A C
ATOM   2132  CD   GLN A 297     -20.912  58.611   2.428  1.00 62.56      A C
ATOM   2133  OE1  GLN A 297     -21.025  57.830   3.376  1.00 64.01      A O
ATOM   2134  NE2  GLN A 297     -21.512  58.407   1.257  1.00 63.73      A N
ATOM   2135  C    GLN A 297     -17.472  59.709   0.669  1.00 50.84      A C
ATOM   2136  O    GLN A 297     -18.130  59.693  -0.369  1.00 51.76      A O
ATOM   2137  N    GLU A 298     -16.421  60.504   0.846  1.00 49.24      A N
ATOM   2138  CA   GLU A 298     -15.944  61.400  -0.206  1.00 48.85      A C
ATOM   2139  CB   GLU A 298     -14.665  62.120   0.233  1.00 50.08      A C
ATOM   2140  CG   GLU A 298     -14.870  63.228   1.243  1.00 53.68      A C
ATOM   2141  CD   GLU A 298     -13.576  63.916   1.641  1.00 56.15      A C
ATOM   2142  OE1  GLU A 298     -13.648  65.078   2.097  1.00 59.06      A O
ATOM   2143  OE2  GLU A 298     -12.491  63.302   1.517  1.00 55.91      A O
ATOM   2144  C    GLU A 298     -15.634  60.576  -1.449  1.00 48.61      A C
ATOM   2145  O    GLU A 298     -15.914  60.991  -2.574  1.00 50.16      A O
ATOM   2146  N    THR A 299     -15.046  59.404  -1.232  1.00 46.95      A N
ATOM   2147  CA   THR A 299     -14.689  58.515  -2.323  1.00 45.43      A C
ATOM   2148  CB   THR A 299     -13.978  57.242  -1.799  1.00 44.41      A C
ATOM   2149  OG1  THR A 299     -12.806  57.616  -1.063  1.00 44.50      A O
ATOM   2150  CG2  THR A 299     -13.576  56.337  -2.951  1.00 41.18      A C
ATOM   2151  C    THR A 299     -15.956  58.116  -3.060  1.00 45.01      A C
ATOM   2152  O    THR A 299     -15.998  58.114  -4.288  1.00 43.48      A O
ATOM   2153  N    ALA A 300     -16.995  57.789  -2.299  1.00 45.52      A N
ATOM   2154  CA   ALA A 300     -18.265  57.379  -2.885  1.00 47.38      A C
ATOM   2155  CB   ALA A 300     -19.207  56.917  -1.798  1.00 47.69      A C
ATOM   2156  C    ALA A 300     -18.931  58.476  -3.714  1.00 49.07      A C
ATOM   2157  O    ALA A 300     -19.393  58.216  -4.821  1.00 48.90      A O
ATOM   2158  N    GLU A 301     -18.979  59.700  -3.196  1.00 49.46      A N
ATOM   2159  CA   GLU A 301     -19.628  60.767  -3.949  1.00 51.35      A C
ATOM   2160  CB   GLU A 301     -19.850  62.014  -3.086  1.00 52.64      A C
ATOM   2161  CG   GLU A 301     -19.526  61.837  -1.625  1.00 58.23      A C
ATOM   2162  CD   GLU A 301     -20.355  62.735  -0.728  1.00 60.33      A C
ATOM   2163  OE1  GLU A 301     -21.533  62.393  -0.468  1.00 61.44      A O
ATOM   2164  OE2  GLU A 301     -19.828  63.783  -0.289  1.00 61.57      A O
ATOM   2165  C    GLU A 301     -18.871  61.154  -5.205  1.00 50.37      A C
ATOM   2166  O    GLU A 301     -19.480  61.364  -6.257  1.00 50.57      A O
ATOM   2167  N    ILE A 302     -17.549  61.238  -5.105  1.00 49.01      A N
ATOM   2168  CA   ILE A 302     -16.740  61.618  -6.256  1.00 46.50      A C
ATOM   2169  CB   ILE A 302     -15.304  61.983  -5.843  1.00 46.05      A C
ATOM   2170  CG2  ILE A 302     -14.539  62.526  -7.041  1.00 44.65      A C
ATOM   2171  CG1  ILE A 302     -15.324  63.033  -4.739  1.00 45.36      A C
ATOM   2172  CD1  ILE A 302     -13.946  63.396  -4.228  1.00 43.12      A C
ATOM   2173  C    ILE A 302     -16.642  60.526  -7.317  1.00 46.77      A C
ATOM   2174  O    ILE A 302     -16.766  60.803  -8.509  1.00 46.44      A O
ATOM   2175  N    HIS A 303     -16.449  59.282  -6.879  1.00 47.32      A N
ATOM   2176  CA   HIS A 303     -16.258  58.161  -7.798  1.00 46.13      A C
ATOM   2177  CB   HIS A 303     -14.915  57.490  -7.503  1.00 43.92      A C
ATOM   2178  CG   HIS A 303     -13.735  58.400  -7.637  1.00 40.96      A C
ATOM   2179  CD2  HIS A 303     -12.990  59.034  -6.702  1.00 39.46      A C
ATOM   2180  ND1  HIS A 303     -13.211  58.764  -8.858  1.00 40.55      A N
ATOM   2181  CE1  HIS A 303     -12.192  59.585  -8.669  1.00 40.10      A C
ATOM   2182  NE2  HIS A 303     -12.037  59.765  -7.369  1.00 38.16      A N
```

FIGURE 1A-40

| | | | | | | | | | | | |
|---|---|---|---|---|---|---|---|---|---|---|---|
| ATOM | 2183 | C | HIS | A | 303 | -17.298 | 57.059 | -7.869 | 1.00 | 47.55 | A C |
| ATOM | 2184 | O | HIS | A | 303 | -17.369 | 56.362 | -8.871 | 1.00 | 46.87 | A O |
| ATOM | 2185 | N | LEU | A | 304 | -18.102 | 56.879 | -6.832 | 1.00 | 50.27 | A N |
| ATOM | 2186 | CA | LEU | A | 304 | -19.055 | 55.782 | -6.871 | 1.00 | 53.75 | A C |
| ATOM | 2187 | CB | LEU | A | 304 | -18.945 | 54.974 | -5.581 | 1.00 | 52.58 | A C |
| ATOM | 2188 | CG | LEU | A | 304 | -17.532 | 54.498 | -5.247 | 1.00 | 52.64 | A C |
| ATOM | 2189 | CD1 | LEU | A | 304 | -17.553 | 53.725 | -3.938 | 1.00 | 51.38 | A C |
| ATOM | 2190 | CD2 | LEU | A | 304 | -17.000 | 53.633 | -6.377 | 1.00 | 50.53 | A C |
| ATOM | 2191 | C | LEU | A | 304 | -20.512 | 56.133 | -7.140 | 1.00 | 57.27 | A C |
| ATOM | 2192 | O | LEU | A | 304 | -21.220 | 55.361 | -7.795 | 1.00 | 58.13 | A O |
| ATOM | 2193 | N | HIS | A | 305 | -20.967 | 57.277 | -6.639 | 1.00 | 59.77 | A N |
| ATOM | 2194 | CA | HIS | A | 305 | -22.356 | 57.678 | -6.854 | 1.00 | 62.72 | A C |
| ATOM | 2195 | CB | HIS | A | 305 | -22.753 | 58.824 | -5.908 | 1.00 | 63.91 | A C |
| ATOM | 2196 | CG | HIS | A | 305 | -22.703 | 58.460 | -4.452 | 1.00 | 65.66 | A C |
| ATOM | 2197 | CD2 | HIS | A | 305 | -22.583 | 59.232 | -3.344 | 1.00 | 65.80 | A C |
| ATOM | 2198 | ND1 | HIS | A | 305 | -22.820 | 57.161 | -4.001 | 1.00 | 66.63 | A N |
| ATOM | 2199 | CE1 | HIS | A | 305 | -22.773 | 57.149 | -2.679 | 1.00 | 65.63 | A C |
| ATOM | 2200 | NE2 | HIS | A | 305 | -22.630 | 58.392 | -2.256 | 1.00 | 65.61 | A N |
| ATOM | 2201 | C | HIS | A | 305 | -22.579 | 58.101 | -8.307 | 1.00 | 63.21 | A C |
| ATOM | 2202 | O | HIS | A | 305 | -23.418 | 57.462 | -8.984 | 1.00 | 62.66 | A O |
| ATOM | 2203 | OXT | HIS | A | 305 | -21.906 | 59.059 | -8.751 | 1.00 | 64.32 | A O |
| TER | | 1 | HIS | A | 305 | | | | | | A |
| HET | 2204 | O | HOH | W | 1 | 4.729 | 45.185 | 8.432 | 1.00 | 36.65 | W O |
| HET | 2205 | O | HOH | W | 2 | 8.337 | 38.878 | 6.694 | 1.00 | 29.30 | W O |
| HET | 2206 | O | HOH | W | 3 | -15.034 | 38.244 | 5.973 | 1.00 | 30.95 | W O |
| HET | 2207 | O | HOH | W | 4 | -2.862 | 39.196 | 5.414 | 1.00 | 32.31 | W O |
| HET | 2208 | O | HOH | W | 5 | 6.054 | 34.433 | 9.050 | 1.00 | 33.57 | W O |
| HET | 2209 | O | HOH | W | 6 | 3.237 | 37.372 | -8.066 | 1.00 | 30.25 | W O |
| HET | 2210 | O | HOH | W | 7 | -7.881 | 33.380 | 2.673 | 1.00 | 38.15 | W O |
| HET | 2211 | O | HOH | W | 8 | -17.583 | 44.864 | 8.863 | 1.00 | 44.55 | W O |
| HET | 2212 | O | HOH | W | 9 | 0.775 | 39.030 | -11.265 | 1.00 | 36.93 | W O |
| HET | 2213 | O | HOH | W | 10 | 9.335 | 40.074 | -14.685 | 1.00 | 43.50 | W O |
| HET | 2214 | O | HOH | W | 11 | -19.621 | 41.536 | -7.696 | 1.00 | 33.51 | W O |
| HET | 2215 | O | HOH | W | 12 | -11.064 | 26.602 | 6.568 | 1.00 | 43.48 | W O |
| HET | 2216 | O | HOH | W | 13 | -14.208 | 33.995 | 5.025 | 1.00 | 30.27 | W O |
| HET | 2217 | O | HOH | W | 14 | 5.736 | 37.612 | 9.167 | 1.00 | 48.52 | W O |
| HET | 2218 | O | HOH | W | 15 | -10.471 | 53.328 | -17.070 | 1.00 | 48.31 | W O |
| HET | 2219 | O | HOH | W | 16 | -11.358 | 55.717 | -12.222 | 1.00 | 43.92 | W O |
| HET | 2220 | O | HOH | W | 17 | -16.003 | 33.941 | 0.645 | 1.00 | 45.72 | W O |
| HET | 2221 | O | HOH | W | 18 | -8.614 | 42.805 | -12.192 | 1.00 | 53.74 | W O |
| HET | 2222 | O | HOH | W | 19 | -3.431 | 54.815 | 10.359 | 1.00 | 29.09 | W O |
| HET | 2223 | O | HOH | W | 20 | 4.243 | 48.144 | 9.917 | 1.00 | 37.03 | W O |
| HET | 2224 | O | HOH | W | 21 | -15.795 | 36.095 | 4.235 | 1.00 | 32.05 | W O |
| HET | 2225 | O | HOH | W | 22 | 1.775 | 48.883 | 10.671 | 1.00 | 36.50 | W O |
| HET | 2226 | O | HOH | W | 23 | -2.046 | 38.097 | 0.599 | 1.00 | 36.51 | W O |
| HET | 2227 | O | HOH | W | 24 | -7.600 | 59.349 | -2.247 | 1.00 | 40.11 | W O |
| HET | 2228 | O | HOH | W | 25 | 15.256 | 42.922 | -3.737 | 1.00 | 34.53 | W O |
| HET | 2229 | O | HOH | W | 26 | -4.869 | 59.163 | -12.225 | 1.00 | 48.39 | W O |
| HET | 2230 | O | HOH | W | 27 | -12.953 | 49.826 | 4.770 | 1.00 | 40.74 | W O |
| HET | 2231 | O | HOH | W | 28 | -10.464 | 49.746 | 6.029 | 1.00 | 32.90 | W O |
| HET | 2232 | O | HOH | W | 29 | -10.506 | 56.045 | 2.224 | 1.00 | 39.16 | W O |
| HET | 2233 | O | HOH | W | 30 | 8.105 | 55.304 | 3.245 | 1.00 | 42.00 | W O |
| HET | 2234 | O | HOH | W | 31 | -4.327 | 54.719 | -13.591 | 1.00 | 46.02 | W O |
| HET | 2235 | O | HOH | W | 32 | -6.059 | 62.619 | 4.254 | 1.00 | 62.75 | W O |
| HET | 2236 | O | HOH | W | 33 | -2.736 | 59.731 | 3.907 | 1.00 | 46.12 | W O |
| HET | 2237 | O | HOH | W | 34 | -6.764 | 39.019 | -10.922 | 1.00 | 53.57 | W O |

FIGURE 1A-41

```
HET  2238  O    HOH  W  35  -25.044  22.956    4.085  1.00  44.71  W O
HET  2239  O    HOH  W  36   14.715  38.285    2.631  1.00  55.84  W O
HET  2240  O    HOH  W  37   11.001  46.043   -8.013  1.00  42.10  W O
HET  2241  O    HOH  W  38    3.450  26.324    7.066  1.00  53.95  W O
HET  2242  O    HOH  W  39   -9.091  46.586  -16.814  1.00  56.14  W O
HET  2243  O    HOH  W  40   -4.024  36.587   -4.048  1.00  54.77  W O
HET  2244  O    HOH  W  41  -11.752  41.569   15.549  1.00  66.78  W O
HET  2245  O    HOH  W  42   -8.812  52.840    9.523  1.00  39.92  W O
HET  2246  O    HOH  W  43    5.247  25.652   -6.395  1.00  59.41  W O
HET  2247  O    HOH  W  44    8.208  50.015   10.135  1.00  43.70  W O
HET  2248  O    HOH  W  45  -12.430  33.563   -2.836  1.00  49.91  W O
HET  2249  O    HOH  W  46   15.754  39.773  -12.048  1.00  51.85  W O
HET  2250  O    HOH  W  48    9.576  24.077    1.510  1.00  48.03  W O
HET  2251  O    HOH  W  49  -29.791  30.650   -7.362  1.00  41.79  W O
HET  2252  O    HOH  W  50   -8.219  50.900  -18.374  1.00  54.04  W O
HET  2253  O    HOH  W  51  -31.835  29.438   -3.076  1.00  46.44  W O
HET  2254  O    HOH  W  52   -0.291  35.831   -0.130  1.00  49.24  W O
HET  2255  O    HOH  W  53  -23.920  50.333    5.123  1.00  69.84  W O
HET  2256  O    HOH  W  54   -8.705  25.244    4.369  1.00  70.95  W O
HET  2257  O    HOH  W  55    7.699  65.340  -13.336  1.00  73.43  W O
HET  2258  O    HOH  W  56  -18.668  17.137    3.217  1.00  71.39  W O
HET  2259  O    HOH  W  57   -5.891  27.604    4.689  1.00  44.14  W O
HET  2260  O    HOH  W  58    3.976  63.972   -3.122  1.00  59.85  W O
HET  2261  O    HOH  W  59  -24.721  56.614    9.542  1.00  73.38  W O
HET  2262  O    HOH  W  60   -6.171  61.666   -2.733  1.00  36.34  W O
HET  2263  O    HOH  W  61   -2.392  34.230   15.975  1.00  52.99  W O
HET  2264  O    HOH  W  62  -16.013  18.503   13.049  1.00  62.20  W O
HET  2265  O    HOH  W  63   11.124  43.448   -8.738  1.00  32.24  W O
HET  2266  O    HOH  W  64   -1.732  38.022    3.562  1.00  33.45  W O
HET  2267  O    HOH  W  65    8.642  36.390    2.403  1.00  41.53  W O
HET  2268  O    HOH  W  66   -7.050  26.613    1.351  1.00  61.53  W O
HET  2269  O    HOH  W  67   -7.171  63.951   -4.127  1.00  50.66  W O
HET  2270  O    HOH  W  68  -17.323  35.775    2.290  1.00  59.03  W O
HET  2271  O    HOH  W  69    1.399  37.061   -1.834  1.00  58.10  W O
HET  2272  O    HOH  W  70    1.126  61.747  -12.741  1.00  46.10  W O
HET  2273  O    HOH  W  71  -17.674  25.405   -4.968  1.00  51.21  W O
HET  2274  O    HOH  W  72  -19.485  24.431   -2.758  1.00  48.93  W O
HET  2275  O    HOH  W  73  -24.283  50.294    0.323  1.00  84.16  W O
HET  2276  O    HOH  W  74   -1.055  62.318   -3.009  1.00  47.94  W O
HET  2277  O    HOH  W  75    2.981  45.368   10.620  1.00  69.95  W O
HET  2278  O    HOH  W  76    9.636  62.038  -15.040  1.00  46.37  W O
HET  2279  O    HOH  W  77  -13.384  57.328  -11.070  1.00  37.08  W O
HET  2280  O    HOH  W  78   10.237  53.331   -9.999  1.00  61.83  W O
HET  2281  O    HOH  W  79    7.191  43.535    4.588  1.00  38.92  W O
HET  2282  O    HOH  W  80  -15.831  58.660    5.321  1.00  51.03  W O
HET  2283  O    HOH  W  81  -18.532  37.417   -8.010  1.00  89.56  W O
HET  2284  O    HOH  W  82  -14.112  35.296   -3.400  1.00  49.35  W O
HET  2285  O5'  ADE  Z   1  -16.339  36.219   -4.866  1.00  92.13  Z O
HET  2286  C5'  ADE  Z   1  -17.619  35.660   -4.722  1.00  91.01  Z C
HET  2287  C4'  ADE  Z   1  -18.711  36.734   -4.721  1.00  90.47  Z C
HET  2288  O4'  ADE  Z   1  -19.703  36.424   -3.759  1.00  89.54  Z O
HET  2289  C1'  ADE  Z   1  -20.212  37.595   -3.129  1.00  88.81  Z C
HET  2290  C2'  ADE  Z   1  -19.483  38.766   -3.796  1.00  90.11  Z C
HET  2291  C3'  ADE  Z   1  -18.223  38.128   -4.344  1.00  90.49  Z C
HET  2292  O3'  ADE  Z   1  -17.746  38.829   -5.506  1.00  91.87  Z O
HET  2293  N9   ADE  Z   1  -19.913  37.547   -1.682  1.00  86.36  Z N
```

FIGURE 1A-42

```
HET  2294  C4   ADE Z  1   -20.494  38.379  -0.732  1.00  85.38  Z C
HET  2295  N3   ADE Z  1   -21.418  39.353  -0.867  1.00  84.24  Z N
HET  2296  C2   ADE Z  1   -21.794  39.981   0.251  1.00  84.14  Z C
HET  2297  N1   ADE Z  1   -21.320  39.711   1.479  1.00  83.50  Z N
HET  2298  C6   ADE Z  1   -20.401  38.741   1.595  1.00  83.78  Z C
HET  2299  N6   ADE Z  1   -19.937  38.487   2.830  1.00  84.36  Z N
HET  2300  C5   ADE Z  1   -19.949  38.036   0.520  1.00  84.41  Z C
HET  2301  N7   ADE Z  1   -19.039  37.003   0.337  1.00  84.56  Z N
HET  2302  C8   ADE Z  1   -19.064  36.756  -0.990  1.00  85.21  Z C
HET  2303  O2'  ADE Z  1   -20.235  39.239  -4.880  1.00  90.38  Z O
END
```

FIGURE 2A-1

| ATOM | Type | Resid | # | X | Y | Z | Occ | B | | |
|---|---|---|---|---|---|---|---|---|---|---|
| ATOM | 1 | CB | PRO A | 33 | -33.439 | 25.955 | 13.809 | 1.00 | 68.92 | A C |
| ATOM | 2 | CG | PRO A | 33 | -33.315 | 26.836 | 15.047 | 1.00 | 68.97 | A C |
| ATOM | 3 | C | PRO A | 33 | -31.734 | 27.170 | 12.421 | 1.00 | 68.56 | A C |
| ATOM | 4 | O | PRO A | 33 | -32.381 | 28.222 | 12.521 | 1.00 | 68.72 | A O |
| ATOM | 5 | N | PRO A | 33 | -31.146 | 26.095 | 14.528 | 1.00 | 68.98 | A N |
| ATOM | 6 | CD | PRO A | 33 | -31.966 | 26.480 | 15.691 | 1.00 | 69.03 | A C |
| ATOM | 7 | CA | PRO A | 33 | -32.004 | 25.970 | 13.323 | 1.00 | 68.82 | A C |
| ATOM | 8 | N | LEU A | 34 | -30.721 | 27.000 | 11.578 | 1.00 | 68.12 | A N |
| ATOM | 9 | CA | LEU A | 34 | -30.288 | 28.011 | 10.620 | 1.00 | 67.49 | A C |
| ATOM | 10 | CB | LEU A | 34 | -28.977 | 27.545 | 9.988 | 1.00 | 67.61 | A C |
| ATOM | 11 | CG | LEU A | 34 | -28.851 | 27.574 | 8.469 | 1.00 | 67.72 | A C |
| ATOM | 12 | CD1 | LEU A | 34 | -28.538 | 28.979 | 7.986 | 1.00 | 67.76 | A C |
| ATOM | 13 | CD2 | LEU A | 34 | -27.760 | 26.625 | 8.045 | 1.00 | 67.71 | A C |
| ATOM | 14 | C | LEU A | 34 | -31.353 | 28.226 | 9.541 | 1.00 | 66.97 | A C |
| ATOM | 15 | O | LEU A | 34 | -31.439 | 29.290 | 8.926 | 1.00 | 66.98 | A O |
| ATOM | 16 | N | GLU A | 35 | -32.175 | 27.207 | 9.339 | 1.00 | 66.24 | A N |
| ATOM | 17 | CA | GLU A | 35 | -33.220 | 27.244 | 8.333 | 1.00 | 65.51 | A C |
| ATOM | 18 | CB | GLU A | 35 | -33.728 | 25.817 | 8.083 | 1.00 | 65.93 | A C |
| ATOM | 19 | CG | GLU A | 35 | -33.029 | 24.719 | 8.887 | 1.00 | 66.52 | A C |
| ATOM | 20 | CD | GLU A | 35 | -32.191 | 23.822 | 8.001 | 1.00 | 66.93 | A C |
| ATOM | 21 | OE1 | GLU A | 35 | -32.634 | 23.543 | 6.870 | 1.00 | 67.42 | A O |
| ATOM | 22 | OE2 | GLU A | 35 | -31.116 | 23.361 | 8.435 | 1.00 | 67.11 | A O |
| ATOM | 23 | C | GLU A | 35 | -34.380 | 28.141 | 8.746 | 1.00 | 64.68 | A C |
| ATOM | 24 | O | GLU A | 35 | -35.136 | 28.641 | 7.901 | 1.00 | 64.75 | A O |
| ATOM | 25 | N | SER A | 36 | -34.530 | 28.335 | 10.050 | 1.00 | 63.45 | A N |
| ATOM | 26 | CA | SER A | 36 | -35.620 | 29.150 | 10.573 | 1.00 | 62.08 | A C |
| ATOM | 27 | CB | SER A | 36 | -36.034 | 28.606 | 11.953 | 1.00 | 62.37 | A C |
| ATOM | 28 | OG | SER A | 36 | -36.762 | 29.576 | 12.702 | 1.00 | 62.40 | A O |
| ATOM | 29 | C | SER A | 36 | -35.310 | 30.645 | 10.683 | 1.00 | 60.89 | A C |
| ATOM | 30 | O | SER A | 36 | -36.130 | 31.499 | 10.335 | 1.00 | 60.77 | A O |
| ATOM | 31 | N | GLN A | 37 | -34.109 | 30.956 | 11.150 | 1.00 | 59.40 | A N |
| ATOM | 32 | CA | GLN A | 37 | -33.743 | 32.348 | 11.350 | 1.00 | 57.86 | A C |
| ATOM | 33 | CB | GLN A | 37 | -32.798 | 32.462 | 12.546 | 1.00 | 58.03 | A C |
| ATOM | 34 | CG | GLN A | 37 | -31.761 | 31.371 | 12.597 | 1.00 | 58.32 | A C |
| ATOM | 35 | CD | GLN A | 37 | -31.032 | 31.353 | 13.918 | 1.00 | 58.47 | A C |
| ATOM | 36 | OE1 | GLN A | 37 | -30.785 | 32.414 | 14.498 | 1.00 | 58.28 | A O |
| ATOM | 37 | NE2 | GLN A | 37 | -30.661 | 30.157 | 14.396 | 1.00 | 58.51 | A N |
| ATOM | 38 | C | GLN A | 37 | -33.167 | 33.118 | 10.161 | 1.00 | 56.54 | A C |
| ATOM | 39 | O | GLN A | 37 | -32.866 | 34.296 | 10.281 | 1.00 | 56.47 | A O |
| ATOM | 40 | N | TYR A | 38 | -32.995 | 32.468 | 9.020 | 1.00 | 54.98 | A N |
| ATOM | 41 | CA | TYR A | 38 | -32.456 | 33.143 | 7.837 | 1.00 | 53.50 | A C |
| ATOM | 42 | CB | TYR A | 38 | -30.997 | 32.740 | 7.613 | 1.00 | 52.98 | A C |
| ATOM | 43 | CG | TYR A | 38 | -30.069 | 33.229 | 8.697 | 1.00 | 52.22 | A C |
| ATOM | 44 | CD1 | TYR A | 38 | -29.668 | 34.561 | 8.753 | 1.00 | 51.93 | A C |
| ATOM | 45 | CE1 | TYR A | 38 | -28.889 | 35.028 | 9.804 | 1.00 | 51.81 | A C |
| ATOM | 46 | CD2 | TYR A | 38 | -29.661 | 32.377 | 9.715 | 1.00 | 51.99 | A C |
| ATOM | 47 | CE2 | TYR A | 38 | -28.888 | 32.830 | 10.763 | 1.00 | 51.86 | A C |
| ATOM | 48 | CZ | TYR A | 38 | -28.507 | 34.154 | 10.805 | 1.00 | 51.71 | A C |
| ATOM | 49 | OH | TYR A | 38 | -27.749 | 34.603 | 11.856 | 1.00 | 51.56 | A O |
| ATOM | 50 | C | TYR A | 38 | -33.254 | 32.797 | 6.595 | 1.00 | 52.72 | A C |
| ATOM | 51 | O | TYR A | 38 | -33.608 | 31.637 | 6.363 | 1.00 | 52.69 | A O |
| ATOM | 52 | N | GLN A | 39 | -33.543 | 33.811 | 5.794 | 1.00 | 51.74 | A N |
| ATOM | 53 | CA | GLN A | 39 | -34.261 | 33.585 | 4.555 | 1.00 | 50.71 | A C |
| ATOM | 54 | CB | GLN A | 39 | -35.319 | 34.656 | 4.333 | 1.00 | 51.43 | A C |

FIGURE 2A-2

| | | | | | | | | | | |
|---|---|---|---|---|---|---|---|---|---|---|
| ATOM | 55 | CG | GLN | A | 39 | -36.030 | 34.527 | 2.999 | 1.00 52.66 | A C |
| ATOM | 56 | CD | GLN | A | 39 | -37.264 | 35.401 | 2.909 | 1.00 53.46 | A C |
| ATOM | 57 | OE1 | GLN | A | 39 | -37.255 | 36.560 | 3.332 | 1.00 53.97 | A O |
| ATOM | 58 | NE2 | GLN | A | 39 | -38.334 | 34.855 | 2.339 | 1.00 53.96 | A N |
| ATOM | 59 | C | GLN | A | 39 | -33.234 | 33.620 | 3.430 | 1.00 49.42 | A C |
| ATOM | 60 | O | GLN | A | 39 | -32.733 | 34.675 | 3.062 | 1.00 49.37 | A O |
| ATOM | 61 | N | VAL | A | 40 | -32.926 | 32.446 | 2.894 | 1.00 47.91 | A N |
| ATOM | 62 | CA | VAL | A | 40 | -31.945 | 32.314 | 1.832 | 1.00 46.36 | A C |
| ATOM | 63 | CB | VAL | A | 40 | -31.645 | 30.833 | 1.543 | 1.00 46.34 | A C |
| ATOM | 64 | CG1 | VAL | A | 40 | -30.395 | 30.720 | 0.680 | 1.00 46.31 | A C |
| ATOM | 65 | CG2 | VAL | A | 40 | -31.481 | 30.096 | 2.856 | 1.00 46.19 | A C |
| ATOM | 66 | C | VAL | A | 40 | -32.370 | 32.998 | 0.538 | 1.00 45.26 | A C |
| ATOM | 67 | O | VAL | A | 40 | -33.548 | 33.015 | 0.197 | 1.00 45.28 | A O |
| ATOM | 68 | N | GLY | A | 41 | -31.395 | 33.580 | -0.163 | 1.00 43.81 | A N |
| ATOM | 69 | CA | GLY | A | 41 | -31.644 | 34.243 | -1.436 | 1.00 41.79 | A C |
| ATOM | 70 | C | GLY | A | 41 | -30.846 | 33.595 | -2.559 | 1.00 40.51 | A C |
| ATOM | 71 | O | GLY | A | 41 | -30.505 | 32.418 | -2.478 | 1.00 40.47 | A O |
| ATOM | 72 | N | PRO | A | 42 | -30.522 | 34.334 | -3.625 | 1.00 39.41 | A N |
| ATOM | 73 | CD | PRO | A | 42 | -30.857 | 35.734 | -3.931 | 1.00 39.12 | A C |
| ATOM | 74 | CA | PRO | A | 42 | -29.757 | 33.728 | -4.718 | 1.00 38.62 | A C |
| ATOM | 75 | CB | PRO | A | 42 | -29.892 | 34.758 | -5.836 | 1.00 38.61 | A C |
| ATOM | 76 | CG | PRO | A | 42 | -29.923 | 36.038 | -5.090 | 1.00 38.85 | A C |
| ATOM | 77 | C | PRO | A | 42 | -28.295 | 33.421 | -4.395 | 1.00 37.83 | A C |
| ATOM | 78 | O | PRO | A | 42 | -27.740 | 33.943 | -3.432 | 1.00 37.64 | A O |
| ATOM | 79 | N | LEU | A | 43 | -27.679 | 32.580 | -5.223 | 1.00 36.89 | A N |
| ATOM | 80 | CA | LEU | A | 43 | -26.279 | 32.212 | -5.056 | 1.00 36.00 | A C |
| ATOM | 81 | CB | LEU | A | 43 | -25.952 | 30.986 | -5.921 | 1.00 35.82 | A C |
| ATOM | 82 | CG | LEU | A | 43 | -24.510 | 30.459 | -5.937 | 1.00 35.60 | A C |
| ATOM | 83 | CD1 | LEU | A | 43 | -24.213 | 29.726 | -4.628 | 1.00 35.30 | A C |
| ATOM | 84 | CD2 | LEU | A | 43 | -24.320 | 29.507 | -7.118 | 1.00 35.38 | A C |
| ATOM | 85 | C | LEU | A | 43 | -25.391 | 33.380 | -5.485 | 1.00 35.42 | A C |
| ATOM | 86 | O | LEU | A | 43 | -25.494 | 33.855 | -6.615 | 1.00 35.43 | A O |
| ATOM | 87 | N | LEU | A | 44 | -24.527 | 33.849 | -4.590 | 1.00 34.64 | A N |
| ATOM | 88 | CA | LEU | A | 44 | -23.618 | 34.940 | -4.930 | 1.00 33.82 | A C |
| ATOM | 89 | CB | LEU | A | 44 | -23.145 | 35.663 | -3.666 | 1.00 33.55 | A C |
| ATOM | 90 | CG | LEU | A | 44 | -24.244 | 36.441 | -2.935 | 1.00 33.61 | A C |
| ATOM | 91 | CD1 | LEU | A | 44 | -23.702 | 37.021 | -1.636 | 1.00 32.90 | A C |
| ATOM | 92 | CD2 | LEU | A | 44 | -24.776 | 37.552 | -3.846 | 1.00 33.31 | A C |
| ATOM | 93 | C | LEU | A | 44 | -22.416 | 34.398 | -5.704 | 1.00 33.40 | A C |
| ATOM | 94 | O | LEU | A | 44 | -21.790 | 35.122 | -6.467 | 1.00 33.46 | A O |
| ATOM | 95 | N | GLY | A | 45 | -22.100 | 33.119 | -5.510 | 1.00 32.91 | A N |
| ATOM | 96 | CA | GLY | A | 45 | -20.984 | 32.512 | -6.221 | 1.00 31.85 | A C |
| ATOM | 97 | C | GLY | A | 45 | -20.533 | 31.251 | -5.523 | 1.00 31.40 | A C |
| ATOM | 98 | O | GLY | A | 45 | -20.986 | 30.963 | -4.416 | 1.00 31.33 | A O |
| ATOM | 99 | N | SER | A | 46 | -19.663 | 30.484 | -6.160 | 1.00 30.95 | A N |
| ATOM | 100 | CA | SER | A | 46 | -19.149 | 29.270 | -5.541 | 1.00 31.12 | A C |
| ATOM | 101 | CB | SER | A | 46 | -20.060 | 28.069 | -5.818 | 1.00 31.08 | A C |
| ATOM | 102 | OG | SER | A | 46 | -19.862 | 27.571 | -7.133 | 1.00 30.98 | A O |
| ATOM | 103 | C | SER | A | 46 | -17.770 | 28.995 | -6.101 | 1.00 31.17 | A C |
| ATOM | 104 | O | SER | A | 46 | -17.409 | 29.512 | -7.161 | 1.00 31.22 | A O |
| ATOM | 105 | N | GLY | A | 47 | -16.997 | 28.182 | -5.393 | 1.00 31.38 | A N |
| ATOM | 106 | CA | GLY | A | 47 | -15.659 | 27.860 | -5.856 | 1.00 31.42 | A C |
| ATOM | 107 | C | GLY | A | 47 | -14.839 | 27.186 | -4.778 | 1.00 31.58 | A C |
| ATOM | 108 | O | GLY | A | 47 | -15.379 | 26.403 | -3.989 | 1.00 31.44 | A O |
| ATOM | 109 | N | GLY | A | 48 | -13.543 | 27.503 | -4.731 | 1.00 31.56 | A N |
| ATOM | 110 | CA | GLY | A | 48 | -12.656 | 26.909 | -3.740 | 1.00 31.63 | A C |

FIGURE 2A-3

```
ATOM    111  C   GLY A  48     -13.153  27.090  -2.322  1.00 31.67      A C
ATOM    112  O   GLY A  48     -12.999  26.214  -1.483  1.00 31.97      A O
ATOM    113  N   PHE A  49     -13.765  28.236  -2.063  1.00 31.50      A N
ATOM    114  CA  PHE A  49     -14.303  28.573  -0.749  1.00 31.43      A C
ATOM    115  CB  PHE A  49     -14.489  30.090  -0.680  1.00 31.47      A C
ATOM    116  CG  PHE A  49     -15.107  30.659  -1.926  1.00 31.48      A C
ATOM    117  CD1 PHE A  49     -14.300  31.130  -2.963  1.00 31.34      A C
ATOM    118  CD2 PHE A  49     -16.490  30.604  -2.116  1.00 31.40      A C
ATOM    119  CE1 PHE A  49     -14.861  31.531  -4.186  1.00 31.27      A C
ATOM    120  CE2 PHE A  49     -17.066  30.998  -3.325  1.00 31.39      A C
ATOM    121  CZ  PHE A  49     -16.249  31.462  -4.368  1.00 31.51      A C
ATOM    122  C   PHE A  49     -15.646  27.898  -0.409  1.00 31.30      A C
ATOM    123  O   PHE A  49     -16.083  27.943   0.735  1.00 31.81      A O
ATOM    124  N   GLY A  50     -16.311  27.293  -1.391  1.00 30.90      A N
ATOM    125  CA  GLY A  50     -17.599  26.659  -1.127  1.00 30.18      A C
ATOM    126  C   GLY A  50     -18.704  27.375  -1.888  1.00 29.87      A C
ATOM    127  O   GLY A  50     -18.472  27.853  -3.000  1.00 30.04      A O
ATOM    128  N   SER A  51     -19.900  27.470  -1.315  1.00 29.34      A N
ATOM    129  CA  SER A  51     -20.999  28.146  -2.004  1.00 29.12      A C
ATOM    130  CB  SER A  51     -22.106  27.146  -2.358  1.00 28.80      A C
ATOM    131  OG  SER A  51     -21.643  26.178  -3.279  1.00 28.08      A O
ATOM    132  C   SER A  51     -21.551  29.250  -1.120  1.00 29.20      A C
ATOM    133  O   SER A  51     -21.849  29.021   0.043  1.00 29.11      A O
ATOM    134  N   VAL A  52     -21.678  30.452  -1.671  1.00 29.54      A N
ATOM    135  CA  VAL A  52     -22.155  31.591  -0.898  1.00 29.85      A C
ATOM    136  CB  VAL A  52     -21.088  32.713  -0.884  1.00 29.80      A C
ATOM    137  CG1 VAL A  52     -21.565  33.903  -0.040  1.00 29.58      A C
ATOM    138  CG2 VAL A  52     -19.784  32.164  -0.338  1.00 29.49      A C
ATOM    139  C   VAL A  52     -23.467  32.151  -1.433  1.00 30.22      A C
ATOM    140  O   VAL A  52     -23.580  32.465  -2.621  1.00 30.11      A O
ATOM    141  N   TYR A  53     -24.446  32.286  -0.539  1.00 30.75      A N
ATOM    142  CA  TYR A  53     -25.766  32.799  -0.894  1.00 31.44      A C
ATOM    143  CB  TYR A  53     -26.880  31.821  -0.503  1.00 30.67      A C
ATOM    144  CG  TYR A  53     -26.828  30.465  -1.154  1.00 30.19      A C
ATOM    145  CD1 TYR A  53     -25.973  29.480  -0.675  1.00 29.90      A C
ATOM    146  CE1 TYR A  53     -25.915  28.236  -1.273  1.00 29.83      A C
ATOM    147  CD2 TYR A  53     -27.631  30.169  -2.257  1.00 29.85      A C
ATOM    148  CE2 TYR A  53     -27.579  28.920  -2.870  1.00 29.73      A C
ATOM    149  CZ  TYR A  53     -26.717  27.962  -2.370  1.00 29.54      A C
ATOM    150  OH  TYR A  53     -26.625  26.733  -2.970  1.00 29.75      A O
ATOM    151  C   TYR A  53     -26.089  34.096  -0.190  1.00 32.49      A C
ATOM    152  O   TYR A  53     -25.651  34.342   0.943  1.00 32.55      A O
ATOM    153  N   SER A  54     -26.896  34.908  -0.860  1.00 33.79      A N
ATOM    154  CA  SER A  54     -27.355  36.156  -0.296  1.00 35.19      A C
ATOM    155  CB  SER A  54     -28.025  37.010  -1.364  1.00 35.34      A C
ATOM    156  OG  SER A  54     -28.544  38.202  -0.801  1.00 36.05      A O
ATOM    157  C   SER A  54     -28.392  35.691   0.714  1.00 36.20      A C
ATOM    158  O   SER A  54     -28.929  34.593   0.585  1.00 36.05      A O
ATOM    159  N   GLY A  55     -28.658  36.510   1.724  1.00 37.36      A N
ATOM    160  CA  GLY A  55     -29.634  36.138   2.728  1.00 38.63      A C
ATOM    161  C   GLY A  55     -30.111  37.324   3.539  1.00 39.79      A C
ATOM    162  O   GLY A  55     -29.612  38.444   3.402  1.00 39.69      A O
ATOM    163  N   ILE A  56     -31.098  37.075   4.386  1.00 40.98      A N
ATOM    164  CA  ILE A  56     -31.648  38.105   5.240  1.00 42.29      A C
ATOM    165  CB  ILE A  56     -32.880  38.754   4.597  1.00 42.65      A C
ATOM    166  CG2 ILE A  56     -32.460  39.669   3.455  1.00 42.38      A C
```

FIGURE 2A-4

| | | | | | | | | | | |
|---|---|---|---|---|---|---|---|---|---|---|
| ATOM | 167 | CG1 | ILE | A | 56 | -33.807 | 37.674 | 4.051 | 1.00 43.32 | A C |
| ATOM | 168 | CD1 | ILE | A | 56 | -34.942 | 38.233 | 3.194 | 1.00 43.93 | A C |
| ATOM | 169 | C | ILE | A | 56 | -32.029 | 37.438 | 6.546 | 1.00 42.98 | A C |
| ATOM | 170 | O | ILE | A | 56 | -32.676 | 36.397 | 6.553 | 1.00 43.15 | A O |
| ATOM | 171 | N | ARG | A | 57 | -31.592 | 38.015 | 7.653 | 1.00 43.89 | A N |
| ATOM | 172 | CA | ARG | A | 57 | -31.903 | 37.445 | 8.950 | 1.00 45.13 | A C |
| ATOM | 173 | CB | ARG | A | 57 | -31.023 | 38.071 | 10.029 | 1.00 45.11 | A C |
| ATOM | 174 | CG | ARG | A | 57 | -31.164 | 37.417 | 11.379 | 1.00 45.41 | A C |
| ATOM | 175 | CD | ARG | A | 57 | -30.741 | 38.377 | 12.459 | 1.00 45.80 | A C |
| ATOM | 176 | NE | ARG | A | 57 | -29.322 | 38.306 | 12.776 | 1.00 46.07 | A N |
| ATOM | 177 | CZ | ARG | A | 57 | -28.614 | 39.332 | 13.233 | 1.00 46.15 | A C |
| ATOM | 178 | NH1 | ARG | A | 57 | -29.191 | 40.513 | 13.417 | 1.00 46.30 | A N |
| ATOM | 179 | NH2 | ARG | A | 57 | -27.331 | 39.174 | 13.514 | 1.00 46.43 | A N |
| ATOM | 180 | C | ARG | A | 57 | -33.372 | 37.734 | 9.240 | 1.00 45.85 | A C |
| ATOM | 181 | O | ARG | A | 57 | -33.755 | 38.885 | 9.443 | 1.00 45.97 | A O |
| ATOM | 182 | N | VAL | A | 58 | -34.192 | 36.688 | 9.241 | 1.00 46.69 | A N |
| ATOM | 183 | CA | VAL | A | 58 | -35.623 | 36.837 | 9.487 | 1.00 47.53 | A C |
| ATOM | 184 | CB | VAL | A | 58 | -36.290 | 35.473 | 9.712 | 1.00 47.64 | A C |
| ATOM | 185 | CG1 | VAL | A | 58 | -37.806 | 35.642 | 9.740 | 1.00 47.75 | A C |
| ATOM | 186 | CG2 | VAL | A | 58 | -35.868 | 34.504 | 8.615 | 1.00 47.80 | A C |
| ATOM | 187 | C | VAL | A | 58 | -35.891 | 37.705 | 10.713 | 1.00 48.02 | A C |
| ATOM | 188 | O | VAL | A | 58 | -36.840 | 38.483 | 10.746 | 1.00 48.17 | A O |
| ATOM | 189 | N | SER | A | 59 | -35.037 | 37.565 | 11.718 | 1.00 48.55 | A N |
| ATOM | 190 | CA | SER | A | 59 | -35.170 | 38.325 | 12.953 | 1.00 48.90 | A C |
| ATOM | 191 | CB | SER | A | 59 | -33.950 | 38.067 | 13.847 | 1.00 49.18 | A C |
| ATOM | 192 | OG | SER | A | 59 | -34.014 | 38.843 | 15.029 | 1.00 49.98 | A O |
| ATOM | 193 | C | SER | A | 59 | -35.347 | 39.833 | 12.747 | 1.00 48.85 | A C |
| ATOM | 194 | O | SER | A | 59 | -36.371 | 40.396 | 13.132 | 1.00 48.96 | A O |
| ATOM | 195 | N | ASP | A | 60 | -34.360 | 40.488 | 12.139 | 1.00 48.60 | A N |
| ATOM | 196 | CA | ASP | A | 60 | -34.439 | 41.936 | 11.936 | 1.00 48.13 | A C |
| ATOM | 197 | CB | ASP | A | 60 | -33.460 | 42.639 | 12.884 | 1.00 48.62 | A C |
| ATOM | 198 | CG | ASP | A | 60 | -32.017 | 42.207 | 12.670 | 1.00 49.10 | A C |
| ATOM | 199 | OD1 | ASP | A | 60 | -31.762 | 41.000 | 12.515 | 1.00 49.38 | A O |
| ATOM | 200 | OD2 | ASP | A | 60 | -31.126 | 43.079 | 12.674 | 1.00 49.88 | A O |
| ATOM | 201 | C | ASP | A | 60 | -34.193 | 42.413 | 10.511 | 1.00 47.56 | A C |
| ATOM | 202 | O | ASP | A | 60 | -33.898 | 43.584 | 10.295 | 1.00 47.60 | A O |
| ATOM | 203 | N | ASN | A | 61 | -34.317 | 41.509 | 9.545 | 1.00 46.70 | A N |
| ATOM | 204 | CA | ASN | A | 61 | -34.096 | 41.841 | 8.139 | 1.00 45.86 | A C |
| ATOM | 205 | CB | ASN | A | 61 | -35.055 | 42.946 | 7.691 | 1.00 46.59 | A C |
| ATOM | 206 | CG | ASN | A | 61 | -36.497 | 42.514 | 7.764 | 1.00 47.48 | A C |
| ATOM | 207 | OD1 | ASN | A | 61 | -36.867 | 41.453 | 7.247 | 1.00 47.82 | A O |
| ATOM | 208 | ND2 | ASN | A | 61 | -37.327 | 43.329 | 8.407 | 1.00 47.61 | A N |
| ATOM | 209 | C | ASN | A | 61 | -32.663 | 42.259 | 7.820 | 1.00 44.63 | A C |
| ATOM | 210 | O | ASN | A | 61 | -32.395 | 42.845 | 6.768 | 1.00 44.56 | A O |
| ATOM | 211 | N | LEU | A | 62 | -31.745 | 41.962 | 8.729 | 1.00 43.14 | A N |
| ATOM | 212 | CA | LEU | A | 62 | -30.348 | 42.293 | 8.508 | 1.00 41.54 | A C |
| ATOM | 213 | CB | LEU | A | 62 | -29.511 | 41.908 | 9.718 | 1.00 41.34 | A C |
| ATOM | 214 | CG | LEU | A | 62 | -28.013 | 42.167 | 9.554 | 1.00 41.11 | A C |
| ATOM | 215 | CD1 | LEU | A | 62 | -27.767 | 43.667 | 9.480 | 1.00 40.46 | A C |
| ATOM | 216 | CD2 | LEU | A | 62 | -27.249 | 41.552 | 10.725 | 1.00 40.72 | A C |
| ATOM | 217 | C | LEU | A | 62 | -29.862 | 41.490 | 7.317 | 1.00 40.50 | A C |
| ATOM | 218 | O | LEU | A | 62 | -30.001 | 40.265 | 7.295 | 1.00 40.43 | A O |
| ATOM | 219 | N | PRO | A | 63 | -29.308 | 42.164 | 6.299 | 1.00 39.40 | A N |
| ATOM | 220 | CD | PRO | A | 63 | -29.262 | 43.620 | 6.081 | 1.00 39.19 | A C |
| ATOM | 221 | CA | PRO | A | 63 | -28.811 | 41.439 | 5.125 | 1.00 38.48 | A C |
| ATOM | 222 | CB | PRO | A | 63 | -28.570 | 42.547 | 4.102 | 1.00 38.60 | A C |

FIGURE 2A-5

```
ATOM    223  CG   PRO A  63     -28.269  43.740   4.955  1.00 39.02      A C
ATOM    224  C    PRO A  63     -27.543  40.677   5.483  1.00 37.43      A C
ATOM    225  O    PRO A  63     -26.662  41.206   6.159  1.00 37.41      A O
ATOM    226  N    VAL A  64     -27.466  39.425   5.049  1.00 36.31      A N
ATOM    227  CA   VAL A  64     -26.307  38.590   5.336  1.00 35.09      A C
ATOM    228  CB   VAL A  64     -26.625  37.577   6.445  1.00 35.05      A C
ATOM    229  CG1  VAL A  64     -26.970  38.302   7.728  1.00 34.98      A C
ATOM    230  CG2  VAL A  64     -27.772  36.673   6.005  1.00 34.82      A C
ATOM    231  C    VAL A  64     -25.851  37.796   4.117  1.00 34.54      A C
ATOM    232  O    VAL A  64     -26.457  37.868   3.054  1.00 34.17      A O
ATOM    233  N    ALA A  65     -24.765  37.046   4.292  1.00 34.00      A N
ATOM    234  CA   ALA A  65     -24.228  36.180   3.252  1.00 33.60      A C
ATOM    235  CB   ALA A  65     -22.891  36.693   2.735  1.00 33.40      A C
ATOM    236  C    ALA A  65     -24.053  34.854   3.956  1.00 33.40      A C
ATOM    237  O    ALA A  65     -23.492  34.798   5.043  1.00 33.32      A O
ATOM    238  N    ILE A  66     -24.553  33.790   3.342  1.00 33.33      A N
ATOM    239  CA   ILE A  66     -24.481  32.462   3.932  1.00 33.38      A C
ATOM    240  CB   ILE A  66     -25.898  31.831   3.953  1.00 33.21      A C
ATOM    241  CG2  ILE A  66     -25.898  30.534   4.734  1.00 33.04      A C
ATOM    242  CG1  ILE A  66     -26.876  32.825   4.595  1.00 33.16      A C
ATOM    243  CD1  ILE A  66     -28.348  32.397   4.581  1.00 33.04      A C
ATOM    244  C    ILE A  66     -23.486  31.583   3.165  1.00 33.63      A C
ATOM    245  O    ILE A  66     -23.674  31.282   1.985  1.00 33.48      A O
ATOM    246  N    LYS A  67     -22.416  31.184   3.847  1.00 33.92      A N
ATOM    247  CA   LYS A  67     -21.382  30.370   3.228  1.00 34.25      A C
ATOM    248  CB   LYS A  67     -20.002  30.952   3.539  1.00 34.08      A C
ATOM    249  CG   LYS A  67     -18.918  30.383   2.655  1.00 34.44      A C
ATOM    250  CD   LYS A  67     -17.617  31.147   2.810  1.00 34.86      A C
ATOM    251  CE   LYS A  67     -16.739  30.521   3.847  1.00 34.71      A C
ATOM    252  NZ   LYS A  67     -16.095  29.292   3.308  1.00 35.10      A N
ATOM    253  C    LYS A  67     -21.430  28.910   3.660  1.00 34.52      A C
ATOM    254  O    LYS A  67     -21.423  28.596   4.848  1.00 34.17      A O
ATOM    255  N    HIS A  68     -21.476  28.023   2.672  1.00 35.19      A N
ATOM    256  CA   HIS A  68     -21.529  26.592   2.917  1.00 35.89      A C
ATOM    257  CB   HIS A  68     -22.645  25.942   2.097  1.00 35.28      A C
ATOM    258  CG   HIS A  68     -24.020  26.387   2.478  1.00 34.61      A C
ATOM    259  CD2  HIS A  68     -24.722  27.495   2.145  1.00 34.36      A C
ATOM    260  ND1  HIS A  68     -24.827  25.663   3.328  1.00 34.18      A N
ATOM    261  CE1  HIS A  68     -25.965  26.307   3.505  1.00 34.20      A C
ATOM    262  NE2  HIS A  68     -25.928  27.422   2.798  1.00 34.00      A N
ATOM    263  C    HIS A  68     -20.214  25.976   2.512  1.00 36.91      A C
ATOM    264  O    HIS A  68     -19.699  26.240   1.422  1.00 36.68      A O
ATOM    265  N    VAL A  69     -19.677  25.151   3.399  1.00 38.31      A N
ATOM    266  CA   VAL A  69     -18.422  24.461   3.141  1.00 40.00      A C
ATOM    267  CB   VAL A  69     -17.286  24.997   4.033  1.00 39.98      A C
ATOM    268  CG1  VAL A  69     -15.958  24.527   3.494  1.00 40.26      A C
ATOM    269  CG2  VAL A  69     -17.337  26.523   4.104  1.00 40.71      A C
ATOM    270  C    VAL A  69     -18.616  22.987   3.477  1.00 40.89      A C
ATOM    271  O    VAL A  69     -19.063  22.659   4.573  1.00 40.99      A O
ATOM    272  N    GLU A  70     -18.301  22.104   2.535  1.00 42.36      A N
ATOM    273  CA   GLU A  70     -18.420  20.666   2.776  1.00 43.87      A C
ATOM    274  CB   GLU A  70     -18.400  19.894   1.454  1.00 44.27      A C
ATOM    275  CG   GLU A  70     -19.759  19.742   0.803  1.00 45.30      A C
ATOM    276  CD   GLU A  70     -19.686  19.046  -0.551  1.00 46.08      A C
ATOM    277  OE1  GLU A  70     -18.990  18.007  -0.650  1.00 46.54      A O
ATOM    278  OE2  GLU A  70     -20.332  19.528  -1.514  1.00 46.11      A O
```

FIGURE 2A-6

| | | | | | | | | | | | |
|---|---|---|---|---|---|---|---|---|---|---|---|
| ATOM | 279 | C | GLU | A | 70 | -17.234 | 20.250 | 3.633 | 1.00 | 44.66 | A C |
| ATOM | 280 | O | GLU | A | 70 | -16.110 | 20.675 | 3.381 | 1.00 | 44.49 | A O |
| ATOM | 281 | N | LYS | A | 71 | -17.479 | 19.431 | 4.651 | 1.00 | 45.90 | A N |
| ATOM | 282 | CA | LYS | A | 71 | -16.400 | 18.992 | 5.529 | 1.00 | 47.31 | A C |
| ATOM | 283 | CB | LYS | A | 71 | -16.949 | 18.126 | 6.658 | 1.00 | 46.85 | A C |
| ATOM | 284 | CG | LYS | A | 71 | -17.920 | 18.850 | 7.558 | 1.00 | 46.43 | A C |
| ATOM | 285 | CD | LYS | A | 71 | -18.305 | 17.982 | 8.729 | 1.00 | 46.14 | A C |
| ATOM | 286 | CE | LYS | A | 71 | -19.343 | 18.652 | 9.590 | 1.00 | 45.89 | A C |
| ATOM | 287 | NZ | LYS | A | 71 | -19.714 | 17.797 | 10.737 | 1.00 | 45.59 | A N |
| ATOM | 288 | C | LYS | A | 71 | -15.286 | 18.240 | 4.804 | 1.00 | 48.59 | A C |
| ATOM | 289 | O | LYS | A | 71 | -14.116 | 18.375 | 5.157 | 1.00 | 48.66 | A O |
| ATOM | 290 | N | ASP | A | 72 | -15.633 | 17.459 | 3.787 | 1.00 | 50.27 | A N |
| ATOM | 291 | CA | ASP | A | 72 | -14.611 | 16.716 | 3.063 | 1.00 | 52.14 | A C |
| ATOM | 292 | CB | ASP | A | 72 | -15.238 | 15.718 | 2.082 | 1.00 | 52.48 | A C |
| ATOM | 293 | CG | ASP | A | 72 | -15.959 | 14.573 | 2.785 | 1.00 | 53.21 | A C |
| ATOM | 294 | OD1 | ASP | A | 72 | -15.439 | 14.072 | 3.809 | 1.00 | 53.55 | A O |
| ATOM | 295 | OD2 | ASP | A | 72 | -17.042 | 14.160 | 2.304 | 1.00 | 53.54 | A O |
| ATOM | 296 | C | ASP | A | 72 | -13.668 | 17.625 | 2.295 | 1.00 | 53.32 | A C |
| ATOM | 297 | O | ASP | A | 72 | -12.601 | 17.193 | 1.872 | 1.00 | 53.54 | A O |
| ATOM | 298 | N | ARG | A | 73 | -14.042 | 18.888 | 2.130 | 1.00 | 54.74 | A N |
| ATOM | 299 | CA | ARG | A | 73 | -13.214 | 19.810 | 1.362 | 1.00 | 56.06 | A C |
| ATOM | 300 | CB | ARG | A | 73 | -14.088 | 20.604 | 0.388 | 1.00 | 56.50 | A C |
| ATOM | 301 | CG | ARG | A | 73 | -14.924 | 19.733 | -0.536 | 1.00 | 57.29 | A C |
| ATOM | 302 | CD | ARG | A | 73 | -15.725 | 20.577 | -1.518 | 1.00 | 58.16 | A C |
| ATOM | 303 | NE | ARG | A | 73 | -16.679 | 19.784 | -2.294 | 1.00 | 58.87 | A N |
| ATOM | 304 | CZ | ARG | A | 73 | -17.522 | 20.295 | -3.189 | 1.00 | 59.30 | A C |
| ATOM | 305 | NH1 | ARG | A | 73 | -18.363 | 19.508 | -3.857 | 1.00 | 59.21 | A N |
| ATOM | 306 | NH2 | ARG | A | 73 | -17.524 | 21.603 | -3.417 | 1.00 | 59.81 | A N |
| ATOM | 307 | C | ARG | A | 73 | -12.353 | 20.775 | 2.154 | 1.00 | 56.75 | A C |
| ATOM | 308 | O | ARG | A | 73 | -11.815 | 21.726 | 1.585 | 1.00 | 56.86 | A O |
| ATOM | 309 | N | ILE | A | 74 | -12.208 | 20.546 | 3.453 | 1.00 | 57.56 | A N |
| ATOM | 310 | CA | ILE | A | 74 | -11.385 | 21.438 | 4.263 | 1.00 | 58.53 | A C |
| ATOM | 311 | CB | ILE | A | 74 | -12.231 | 22.189 | 5.318 | 1.00 | 58.60 | A C |
| ATOM | 312 | CG2 | ILE | A | 74 | -13.104 | 23.224 | 4.629 | 1.00 | 58.81 | A C |
| ATOM | 313 | CG1 | ILE | A | 74 | -13.096 | 21.208 | 6.107 | 1.00 | 58.64 | A C |
| ATOM | 314 | CD1 | ILE | A | 74 | -14.107 | 21.874 | 7.020 | 1.00 | 58.46 | A C |
| ATOM | 315 | C | ILE | A | 74 | -10.237 | 20.724 | 4.960 | 1.00 | 59.19 | A C |
| ATOM | 316 | O | ILE | A | 74 | -10.450 | 19.818 | 5.766 | 1.00 | 59.25 | A O |
| ATOM | 317 | N | SER | A | 75 | -9.016 | 21.152 | 4.644 | 1.00 | 59.89 | A N |
| ATOM | 318 | CA | SER | A | 75 | -7.809 | 20.567 | 5.220 | 1.00 | 60.47 | A C |
| ATOM | 319 | CB | SER | A | 75 | -6.652 | 20.725 | 4.246 | 1.00 | 60.82 | A C |
| ATOM | 320 | OG | SER | A | 75 | -6.383 | 22.103 | 4.038 | 1.00 | 61.38 | A O |
| ATOM | 321 | C | SER | A | 75 | -7.405 | 21.198 | 6.551 | 1.00 | 60.76 | A C |
| ATOM | 322 | O | SER | A | 75 | -6.926 | 20.505 | 7.457 | 1.00 | 60.92 | A O |
| ATOM | 323 | N | ASP | A | 76 | -7.589 | 22.510 | 6.671 | 1.00 | 60.92 | A N |
| ATOM | 324 | CA | ASP | A | 76 | -7.209 | 23.202 | 7.894 | 1.00 | 61.04 | A C |
| ATOM | 325 | CB | ASP | A | 76 | -6.692 | 24.602 | 7.574 | 1.00 | 61.37 | A C |
| ATOM | 326 | CG | ASP | A | 76 | -5.366 | 24.581 | 6.838 | 1.00 | 61.74 | A C |
| ATOM | 327 | OD1 | ASP | A | 76 | -4.659 | 25.613 | 6.865 | 1.00 | 61.86 | A O |
| ATOM | 328 | OD2 | ASP | A | 76 | -5.033 | 23.541 | 6.227 | 1.00 | 62.00 | A O |
| ATOM | 329 | C | ASP | A | 76 | -8.312 | 23.308 | 8.923 | 1.00 | 60.97 | A C |
| ATOM | 330 | O | ASP | A | 76 | -9.289 | 24.018 | 8.727 | 1.00 | 61.09 | A O |
| ATOM | 331 | N | TRP | A | 77 | -8.144 | 22.605 | 10.033 | 1.00 | 60.89 | A N |
| ATOM | 332 | CA | TRP | A | 77 | -9.127 | 22.645 | 11.099 | 1.00 | 60.78 | A C |
| ATOM | 333 | CB | TRP | A | 77 | -9.537 | 21.234 | 11.519 | 1.00 | 60.45 | A C |
| ATOM | 334 | CG | TRP | A | 77 | -10.025 | 20.394 | 10.390 | 1.00 | 60.09 | A C |

FIGURE 2A-7

| | | | | | | | | | | |
|---|---|---|---|---|---|---|---|---|---|---|
| ATOM | 335 | CD2 | TRP | A | 77 | -11.385 | 20.076 | 10.084 | 1.00 59.81 | A C |
| ATOM | 336 | CE2 | TRP | A | 77 | -11.371 | 19.253 | 8.937 | 1.00 59.71 | A C |
| ATOM | 337 | CE3 | TRP | A | 77 | -12.617 | 20.405 | 10.668 | 1.00 59.60 | A C |
| ATOM | 338 | CD1 | TRP | A | 77 | -9.264 | 19.774 | 9.445 | 1.00 59.93 | A C |
| ATOM | 339 | NE1 | TRP | A | 77 | -10.063 | 19.085 | 8.569 | 1.00 59.73 | A N |
| ATOM | 340 | CZ2 | TRP | A | 77 | -12.537 | 18.750 | 8.361 | 1.00 59.76 | A C |
| ATOM | 341 | CZ3 | TRP | A | 77 | -13.783 | 19.904 | 10.095 | 1.00 59.65 | A C |
| ATOM | 342 | CH2 | TRP | A | 77 | -13.732 | 19.084 | 8.952 | 1.00 59.77 | A C |
| ATOM | 343 | C | TRP | A | 77 | -8.513 | 23.362 | 12.278 | 1.00 60.90 | A C |
| ATOM | 344 | O | TRP | A | 77 | -7.346 | 23.153 | 12.600 | 1.00 61.00 | A O |
| ATOM | 345 | N | GLY | A | 78 | -9.299 | 24.215 | 12.918 | 1.00 61.07 | A N |
| ATOM | 346 | CA | GLY | A | 78 | -8.799 | 24.945 | 14.061 | 1.00 61.42 | A C |
| ATOM | 347 | C | GLY | A | 78 | -9.405 | 24.381 | 15.321 | 1.00 61.62 | A C |
| ATOM | 348 | O | GLY | A | 78 | -10.061 | 23.340 | 15.282 | 1.00 61.78 | A O |
| ATOM | 349 | N | ALA | A | 79 | -9.190 | 25.068 | 16.438 | 1.00 61.73 | A N |
| ATOM | 350 | CA | ALA | A | 79 | -9.722 | 24.634 | 17.721 | 1.00 61.83 | A C |
| ATOM | 351 | CB | ALA | A | 79 | -8.580 | 24.194 | 18.641 | 1.00 62.02 | A C |
| ATOM | 352 | C | ALA | A | 79 | -10.510 | 25.762 | 18.365 | 1.00 61.82 | A C |
| ATOM | 353 | O | ALA | A | 79 | -11.682 | 25.595 | 18.700 | 1.00 61.94 | A O |
| ATOM | 354 | N | THR | A | 84 | -14.032 | 22.352 | 20.209 | 1.00 55.01 | A N |
| ATOM | 355 | CA | THR | A | 84 | -14.503 | 21.591 | 19.052 | 1.00 55.04 | A C |
| ATOM | 356 | CB | THR | A | 84 | -16.007 | 21.811 | 18.832 | 1.00 55.22 | A C |
| ATOM | 357 | OG1 | THR | A | 84 | -16.336 | 23.168 | 19.155 | 1.00 55.51 | A O |
| ATOM | 358 | CG2 | THR | A | 84 | -16.826 | 20.861 | 19.708 | 1.00 55.41 | A C |
| ATOM | 359 | C | THR | A | 84 | -13.767 | 21.927 | 17.754 | 1.00 54.81 | A C |
| ATOM | 360 | O | THR | A | 84 | -13.342 | 23.064 | 17.537 | 1.00 55.01 | A O |
| ATOM | 361 | N | ARG | A | 85 | -13.624 | 20.923 | 16.893 | 1.00 54.44 | A N |
| ATOM | 362 | CA | ARG | A | 85 | -12.940 | 21.074 | 15.611 | 1.00 53.97 | A C |
| ATOM | 363 | CB | ARG | A | 85 | -12.596 | 19.696 | 15.034 | 1.00 54.65 | A C |
| ATOM | 364 | CG | ARG | A | 85 | -11.117 | 19.328 | 15.083 | 1.00 55.59 | A C |
| ATOM | 365 | CD | ARG | A | 85 | -10.925 | 17.824 | 14.869 | 1.00 56.41 | A C |
| ATOM | 366 | NE | ARG | A | 85 | -11.457 | 17.338 | 13.592 | 1.00 57.05 | A N |
| ATOM | 367 | CZ | ARG | A | 85 | -10.772 | 17.298 | 12.452 | 1.00 57.22 | A C |
| ATOM | 368 | NH1 | ARG | A | 85 | -9.513 | 17.715 | 12.412 | 1.00 57.38 | A N |
| ATOM | 369 | NH2 | ARG | A | 85 | -11.344 | 16.827 | 11.351 | 1.00 57.40 | A N |
| ATOM | 370 | C | ARG | A | 85 | -13.822 | 21.827 | 14.625 | 1.00 53.23 | A C |
| ATOM | 371 | O | ARG | A | 85 | -14.961 | 21.437 | 14.368 | 1.00 53.19 | A O |
| ATOM | 372 | N | VAL | A | 86 | -13.293 | 22.908 | 14.068 | 1.00 52.13 | A N |
| ATOM | 373 | CA | VAL | A | 86 | -14.050 | 23.710 | 13.114 | 1.00 50.76 | A C |
| ATOM | 374 | CB | VAL | A | 86 | -14.654 | 24.969 | 13.796 | 1.00 50.65 | A C |
| ATOM | 375 | CG1 | VAL | A | 86 | -15.601 | 24.559 | 14.909 | 1.00 50.45 | A C |
| ATOM | 376 | CG2 | VAL | A | 86 | -13.540 | 25.842 | 14.362 | 1.00 50.51 | A C |
| ATOM | 377 | C | VAL | A | 86 | -13.085 | 24.161 | 12.037 | 1.00 49.79 | A C |
| ATOM | 378 | O | VAL | A | 86 | -11.874 | 24.106 | 12.230 | 1.00 49.92 | A O |
| ATOM | 379 | N | PRO | A | 87 | -13.599 | 24.587 | 10.877 | 1.00 48.80 | A N |
| ATOM | 380 | CD | PRO | A | 87 | -14.972 | 24.533 | 10.351 | 1.00 48.54 | A C |
| ATOM | 381 | CA | PRO | A | 87 | -12.656 | 25.032 | 9.850 | 1.00 47.88 | A C |
| ATOM | 382 | CB | PRO | A | 87 | -13.564 | 25.352 | 8.654 | 1.00 48.06 | A C |
| ATOM | 383 | CG | PRO | A | 87 | -14.918 | 25.560 | 9.261 | 1.00 48.23 | A C |
| ATOM | 384 | C | PRO | A | 87 | -11.847 | 26.241 | 10.339 | 1.00 46.97 | A C |
| ATOM | 385 | O | PRO | A | 87 | -12.386 | 27.141 | 10.989 | 1.00 46.90 | A O |
| ATOM | 386 | N | MET | A | 88 | -10.551 | 26.248 | 10.037 | 1.00 45.91 | A N |
| ATOM | 387 | CA | MET | A | 88 | -9.664 | 27.333 | 10.456 | 1.00 44.68 | A C |
| ATOM | 388 | CB | MET | A | 88 | -8.346 | 27.269 | 9.679 | 1.00 45.30 | A C |
| ATOM | 389 | CG | MET | A | 88 | -7.308 | 28.280 | 10.144 | 1.00 45.70 | A C |
| ATOM | 390 | SD | MET | A | 88 | -6.866 | 28.003 | 11.872 | 1.00 46.79 | A S |

FIGURE 2A-8

```
ATOM   391  CE  MET A  88      -6.391  26.274  11.794  1.00 46.29      A C
ATOM   392  C   MET A  88     -10.311  28.689  10.226  1.00 43.44      A C
ATOM   393  O   MET A  88     -10.157  29.618  11.013  1.00 43.21      A O
ATOM   394  N   GLU A  89     -11.040  28.785   9.129  1.00 42.03      A N
ATOM   395  CA  GLU A  89     -11.715  30.009   8.750  1.00 40.61      A C
ATOM   396  CB  GLU A  89     -12.585  29.699   7.549  1.00 41.03      A C
ATOM   397  CG  GLU A  89     -13.228  30.868   6.902  1.00 41.52      A C
ATOM   398  CD  GLU A  89     -13.997  30.446   5.663  1.00 42.00      A C
ATOM   399  OE1 GLU A  89     -14.537  31.340   4.985  1.00 42.19      A O
ATOM   400  OE2 GLU A  89     -14.053  29.226   5.365  1.00 41.93      A O
ATOM   401  C   GLU A  89     -12.547  30.591   9.897  1.00 39.49      A C
ATOM   402  O   GLU A  89     -12.577  31.806  10.095  1.00 39.29      A O
ATOM   403  N   VAL A  90     -13.231  29.727  10.645  1.00 38.21      A N
ATOM   404  CA  VAL A  90     -14.038  30.186  11.774  1.00 36.90      A C
ATOM   405  CB  VAL A  90     -14.880  29.046  12.380  1.00 36.82      A C
ATOM   406  CG1 VAL A  90     -15.593  29.538  13.630  1.00 36.60      A C
ATOM   407  CG2 VAL A  90     -15.892  28.562  11.374  1.00 36.74      A C
ATOM   408  C   VAL A  90     -13.128  30.756  12.868  1.00 36.07      A C
ATOM   409  O   VAL A  90     -13.424  31.793  13.446  1.00 35.65      A O
ATOM   410  N   VAL A  91     -12.026  30.072  13.155  1.00 35.18      A N
ATOM   411  CA  VAL A  91     -11.096  30.556  14.166  1.00 34.84      A C
ATOM   412  CB  VAL A  91      -9.894  29.606  14.315  1.00 35.00      A C
ATOM   413  CG1 VAL A  91      -8.841  30.236  15.226  1.00 35.09      A C
ATOM   414  CG2 VAL A  91     -10.360  28.276  14.879  1.00 35.26      A C
ATOM   415  C   VAL A  91     -10.582  31.940  13.761  1.00 34.31      A C
ATOM   416  O   VAL A  91     -10.641  32.898  14.535  1.00 34.33      A O
ATOM   417  N   LEU A  92     -10.081  32.024  12.534  1.00 33.56      A N
ATOM   418  CA  LEU A  92      -9.549  33.256  11.980  1.00 33.00      A C
ATOM   419  CB  LEU A  92      -9.141  33.020  10.520  1.00 32.51      A C
ATOM   420  CG  LEU A  92      -7.713  32.549  10.192  1.00 32.18      A C
ATOM   421  CD1 LEU A  92      -7.012  31.958  11.403  1.00 31.53      A C
ATOM   422  CD2 LEU A  92      -7.769  31.567   9.048  1.00 31.77      A C
ATOM   423  C   LEU A  92     -10.538  34.410  12.069  1.00 32.91      A C
ATOM   424  O   LEU A  92     -10.201  35.474  12.578  1.00 32.63      A O
ATOM   425  N   LEU A  93     -11.760  34.191  11.586  1.00 33.05      A N
ATOM   426  CA  LEU A  93     -12.789  35.228  11.598  1.00 33.47      A C
ATOM   427  CB  LEU A  93     -14.053  34.739  10.876  1.00 33.56      A C
ATOM   428  CG  LEU A  93     -14.013  34.692   9.341  1.00 33.94      A C
ATOM   429  CD1 LEU A  93     -15.231  33.928   8.808  1.00 33.80      A C
ATOM   430  CD2 LEU A  93     -13.987  36.112   8.780  1.00 33.68      A C
ATOM   431  C   LEU A  93     -13.146  35.706  12.998  1.00 33.77      A C
ATOM   432  O   LEU A  93     -13.391  36.886  13.203  1.00 33.73      A O
ATOM   433  N   LYS A  94     -13.177  34.798  13.968  1.00 34.45      A N
ATOM   434  CA  LYS A  94     -13.503  35.202  15.334  1.00 35.21      A C
ATOM   435  CB  LYS A  94     -13.636  33.986  16.251  1.00 35.52      A C
ATOM   436  CG  LYS A  94     -14.974  33.270  16.141  1.00 36.06      A C
ATOM   437  CD  LYS A  94     -14.950  31.981  16.945  1.00 36.89      A C
ATOM   438  CE  LYS A  94     -16.340  31.440  17.174  1.00 37.33      A C
ATOM   439  NZ  LYS A  94     -17.144  32.391  18.012  1.00 37.99      A N
ATOM   440  C   LYS A  94     -12.435  36.127  15.878  1.00 35.50      A C
ATOM   441  O   LYS A  94     -12.741  37.068  16.611  1.00 35.68      A O
ATOM   442  N   LYS A  95     -11.181  35.872  15.508  1.00 35.78      A N
ATOM   443  CA  LYS A  95     -10.083  36.701  15.980  1.00 36.18      A C
ATOM   444  CB  LYS A  95      -8.743  36.033  15.647  1.00 35.98      A C
ATOM   445  CG  LYS A  95      -8.494  34.748  16.444  1.00 36.09      A C
ATOM   446  CD  LYS A  95      -7.226  33.993  16.025  1.00 36.13      A C
```

FIGURE 2A-9

```
ATOM    447  CE   LYS A  95      -5.959  34.779  16.308  1.00 36.29       A C
ATOM    448  NZ   LYS A  95      -5.821  35.133  17.751  1.00 36.28       A N
ATOM    449  C    LYS A  95     -10.138  38.128  15.416  1.00 36.64       A C
ATOM    450  O    LYS A  95      -9.753  39.086  16.092  1.00 36.69       A O
ATOM    451  N    VAL A  96     -10.656  38.281  14.200  1.00 37.03       A N
ATOM    452  CA   VAL A  96     -10.717  39.601  13.590  1.00 37.73       A C
ATOM    453  CB   VAL A  96     -10.241  39.566  12.130  1.00 37.66       A C
ATOM    454  CG1  VAL A  96      -8.867  38.956  12.043  1.00 37.48       A C
ATOM    455  CG2  VAL A  96     -11.246  38.790  11.279  1.00 37.52       A C
ATOM    456  C    VAL A  96     -12.085  40.258  13.572  1.00 38.49       A C
ATOM    457  O    VAL A  96     -12.190  41.424  13.191  1.00 38.58       A O
ATOM    458  N    SER A  97     -13.129  39.533  13.971  1.00 39.28       A N
ATOM    459  CA   SER A  97     -14.483  40.088  13.929  1.00 40.19       A C
ATOM    460  CB   SER A  97     -15.509  38.958  13.808  1.00 40.00       A C
ATOM    461  OG   SER A  97     -15.458  38.366  12.519  1.00 39.39       A O
ATOM    462  C    SER A  97     -14.897  41.028  15.064  1.00 41.07       A C
ATOM    463  O    SER A  97     -15.915  41.725  14.969  1.00 41.39       A O
ATOM    464  N    SER A  98     -14.126  41.068  16.139  1.00 41.73       A N
ATOM    465  CA   SER A  98     -14.486  41.956  17.233  1.00 42.41       A C
ATOM    466  CB   SER A  98     -13.639  41.631  18.462  1.00 42.78       A C
ATOM    467  OG   SER A  98     -13.859  42.585  19.484  1.00 43.94       A O
ATOM    468  C    SER A  98     -14.282  43.418  16.818  1.00 42.37       A C
ATOM    469  O    SER A  98     -13.293  43.751  16.168  1.00 42.65       A O
ATOM    470  N    GLY A  99     -15.227  44.280  17.182  1.00 42.31       A N
ATOM    471  CA   GLY A  99     -15.118  45.694  16.845  1.00 41.86       A C
ATOM    472  C    GLY A  99     -15.305  45.988  15.371  1.00 41.57       A C
ATOM    473  O    GLY A  99     -15.478  45.067  14.571  1.00 41.87       A O
ATOM    474  N    PHE A 100     -15.275  47.272  15.017  1.00 41.03       A N
ATOM    475  CA   PHE A 100     -15.434  47.713  13.632  1.00 40.33       A C
ATOM    476  CB   PHE A 100     -15.827  49.189  13.582  1.00 40.99       A C
ATOM    477  CG   PHE A 100     -17.192  49.479  14.126  1.00 41.73       A C
ATOM    478  CD1  PHE A 100     -17.406  50.592  14.938  1.00 41.99       A C
ATOM    479  CD2  PHE A 100     -18.273  48.660  13.808  1.00 41.84       A C
ATOM    480  CE1  PHE A 100     -18.681  50.888  15.426  1.00 42.19       A C
ATOM    481  CE2  PHE A 100     -19.549  48.944  14.288  1.00 42.06       A C
ATOM    482  CZ   PHE A 100     -19.754  50.063  15.102  1.00 42.30       A C
ATOM    483  C    PHE A 100     -14.121  47.552  12.894  1.00 39.54       A C
ATOM    484  O    PHE A 100     -13.057  47.666  13.495  1.00 39.72       A O
ATOM    485  N    SER A 101     -14.195  47.296  11.592  1.00 38.36       A N
ATOM    486  CA   SER A 101     -12.994  47.157  10.780  1.00 37.27       A C
ATOM    487  CB   SER A 101     -12.172  45.958  11.244  1.00 37.31       A C
ATOM    488  OG   SER A 101     -12.832  44.745  10.920  1.00 37.09       A O
ATOM    489  C    SER A 101     -13.372  46.975   9.313  1.00 36.44       A C
ATOM    490  O    SER A 101     -14.558  46.894   8.970  1.00 36.24       A O
ATOM    491  N    GLY A 102     -12.357  46.920   8.457  1.00 35.27       A N
ATOM    492  CA   GLY A 102     -12.591  46.726   7.040  1.00 33.84       A C
ATOM    493  C    GLY A 102     -12.633  45.257   6.637  1.00 32.89       A C
ATOM    494  O    GLY A 102     -12.278  44.909   5.516  1.00 32.64       A O
ATOM    495  N    VAL A 103     -13.024  44.373   7.547  1.00 32.12       A N
ATOM    496  CA   VAL A 103     -13.128  42.964   7.186  1.00 31.80       A C
ATOM    497  CB   VAL A 103     -12.074  42.093   7.938  1.00 31.86       A C
ATOM    498  CG1  VAL A 103     -11.738  42.705   9.244  1.00 32.33       A C
ATOM    499  CG2  VAL A 103     -12.595  40.687   8.157  1.00 31.62       A C
ATOM    500  C    VAL A 103     -14.548  42.464   7.450  1.00 31.43       A C
ATOM    501  O    VAL A 103     -15.156  42.823   8.450  1.00 31.27       A O
ATOM    502  N    ILE A 104     -15.091  41.672   6.528  1.00 31.21       A N
```

FIGURE 2A-10

| | | | | | | | | | | |
|---|---|---|---|---|---|---|---|---|---|---|
| ATOM | 503 | CA  | ILE | A | 104 | -16.437 | 41.129 |  6.696 | 1.00 31.16 | A C |
| ATOM | 504 | CB  | ILE | A | 104 | -16.855 | 40.257 |  5.487 | 1.00 31.04 | A C |
| ATOM | 505 | CG2 | ILE | A | 104 | -17.980 | 39.284 |  5.883 | 1.00 30.79 | A C |
| ATOM | 506 | CG1 | ILE | A | 104 | -17.250 | 41.164 |  4.319 | 1.00 30.76 | A C |
| ATOM | 507 | CD1 | ILE | A | 104 | -18.254 | 42.219 |  4.672 | 1.00 30.20 | A C |
| ATOM | 508 | C   | ILE | A | 104 | -16.475 | 40.285 |  7.962 | 1.00 31.51 | A C |
| ATOM | 509 | O   | ILE | A | 104 | -15.673 | 39.359 |  8.135 | 1.00 31.24 | A O |
| ATOM | 510 | N   | ARG | A | 105 | -17.423 | 40.605 |  8.838 | 1.00 32.01 | A N |
| ATOM | 511 | CA  | ARG | A | 105 | -17.551 | 39.917 | 10.112 | 1.00 32.87 | A C |
| ATOM | 512 | CB  | ARG | A | 105 | -18.081 | 40.917 | 11.141 | 1.00 34.12 | A C |
| ATOM | 513 | CG  | ARG | A | 105 | -17.152 | 42.118 | 11.283 | 1.00 36.17 | A C |
| ATOM | 514 | CD  | ARG | A | 105 | -17.761 | 43.273 | 12.058 | 1.00 37.77 | A C |
| ATOM | 515 | NE  | ARG | A | 105 | -17.777 | 43.036 | 13.500 | 1.00 39.50 | A N |
| ATOM | 516 | CZ  | ARG | A | 105 | -18.066 | 43.975 | 14.399 | 1.00 40.13 | A C |
| ATOM | 517 | NH1 | ARG | A | 105 | -18.366 | 45.211 | 14.000 | 1.00 40.23 | A N |
| ATOM | 518 | NH2 | ARG | A | 105 | -18.038 | 43.685 | 15.697 | 1.00 40.33 | A N |
| ATOM | 519 | C   | ARG | A | 105 | -18.385 | 38.628 | 10.143 | 1.00 32.79 | A C |
| ATOM | 520 | O   | ARG | A | 105 | -19.327 | 38.447 |  9.363 | 1.00 32.53 | A O |
| ATOM | 521 | N   | LEU | A | 106 | -18.009 | 37.731 | 11.050 | 1.00 32.73 | A N |
| ATOM | 522 | CA  | LEU | A | 106 | -18.717 | 36.477 | 11.239 | 1.00 33.02 | A C |
| ATOM | 523 | CB  | LEU | A | 106 | -17.792 | 35.404 | 11.798 | 1.00 32.58 | A C |
| ATOM | 524 | CG  | LEU | A | 106 | -18.431 | 34.019 | 11.916 | 1.00 32.64 | A C |
| ATOM | 525 | CD1 | LEU | A | 106 | -18.755 | 33.497 | 10.508 | 1.00 32.96 | A C |
| ATOM | 526 | CD2 | LEU | A | 106 | -17.482 | 33.064 | 12.625 | 1.00 32.62 | A C |
| ATOM | 527 | C   | LEU | A | 106 | -19.819 | 36.741 | 12.253 | 1.00 33.41 | A C |
| ATOM | 528 | O   | LEU | A | 106 | -19.536 | 37.051 | 13.401 | 1.00 33.51 | A O |
| ATOM | 529 | N   | LEU | A | 107 | -21.072 | 36.612 | 11.838 | 1.00 33.88 | A N |
| ATOM | 530 | CA  | LEU | A | 107 | -22.176 | 36.863 | 12.750 | 1.00 34.65 | A C |
| ATOM | 531 | CB  | LEU | A | 107 | -23.394 | 37.365 | 11.974 | 1.00 34.53 | A C |
| ATOM | 532 | CG  | LEU | A | 107 | -23.176 | 38.691 | 11.237 | 1.00 34.41 | A C |
| ATOM | 533 | CD1 | LEU | A | 107 | -24.401 | 39.048 | 10.417 | 1.00 34.44 | A C |
| ATOM | 534 | CD2 | LEU | A | 107 | -22.872 | 39.778 | 12.239 | 1.00 34.23 | A C |
| ATOM | 535 | C   | LEU | A | 107 | -22.548 | 35.631 | 13.553 | 1.00 35.22 | A C |
| ATOM | 536 | O   | LEU | A | 107 | -22.978 | 35.737 | 14.700 | 1.00 35.12 | A O |
| ATOM | 537 | N   | ASP | A | 108 | -22.365 | 34.460 | 12.958 | 1.00 36.06 | A N |
| ATOM | 538 | CA  | ASP | A | 108 | -22.708 | 33.209 | 13.624 | 1.00 36.90 | A C |
| ATOM | 539 | CB  | ASP | A | 108 | -24.205 | 33.213 | 13.935 | 1.00 37.46 | A C |
| ATOM | 540 | CG  | ASP | A | 108 | -24.648 | 32.029 | 14.779 | 1.00 38.23 | A C |
| ATOM | 541 | OD1 | ASP | A | 108 | -23.818 | 31.423 | 15.495 | 1.00 38.69 | A O |
| ATOM | 542 | OD2 | ASP | A | 108 | -25.856 | 31.722 | 14.734 | 1.00 38.50 | A O |
| ATOM | 543 | C   | ASP | A | 108 | -22.357 | 32.056 | 12.697 | 1.00 37.29 | A C |
| ATOM | 544 | O   | ASP | A | 108 | -22.089 | 32.266 | 11.514 | 1.00 37.28 | A O |
| ATOM | 545 | N   | TRP | A | 109 | -22.331 | 30.842 | 13.227 | 1.00 37.91 | A N |
| ATOM | 546 | CA  | TRP | A | 109 | -22.028 | 29.684 | 12.395 | 1.00 38.69 | A C |
| ATOM | 547 | CB  | TRP | A | 109 | -20.515 | 29.452 | 12.320 | 1.00 39.09 | A C |
| ATOM | 548 | CG  | TRP | A | 109 | -19.894 | 29.175 | 13.636 | 1.00 39.90 | A C |
| ATOM | 549 | CD2 | TRP | A | 109 | -19.622 | 27.890 | 14.198 | 1.00 40.32 | A C |
| ATOM | 550 | CE2 | TRP | A | 109 | -19.089 | 28.103 | 15.486 | 1.00 40.37 | A C |
| ATOM | 551 | CE3 | TRP | A | 109 | -19.780 | 26.574 | 13.739 | 1.00 40.84 | A C |
| ATOM | 552 | CD1 | TRP | A | 109 | -19.524 | 30.090 | 14.573 | 1.00 40.10 | A C |
| ATOM | 553 | NE1 | TRP | A | 109 | -19.039 | 29.456 | 15.688 | 1.00 40.22 | A N |
| ATOM | 554 | CZ2 | TRP | A | 109 | -18.710 | 27.050 | 16.328 | 1.00 40.75 | A C |
| ATOM | 555 | CZ3 | TRP | A | 109 | -19.403 | 25.521 | 14.576 | 1.00 41.01 | A C |
| ATOM | 556 | CH2 | TRP | A | 109 | -18.873 | 25.770 | 15.859 | 1.00 40.98 | A C |
| ATOM | 557 | C   | TRP | A | 109 | -22.729 | 28.428 | 12.915 | 1.00 38.94 | A C |
| ATOM | 558 | O   | TRP | A | 109 | -23.078 | 28.343 | 14.093 | 1.00 38.92 | A O |

FIGURE 2A-11

```
ATOM   559  N   PHE A 110     -22.942  27.463  12.023  1.00 39.18      A N
ATOM   560  CA  PHE A 110     -23.613  26.212  12.373  1.00 39.31      A C
ATOM   561  CB  PHE A 110     -25.037  26.165  11.806  1.00 39.30      A C
ATOM   562  CG  PHE A 110     -25.888  27.332  12.186  1.00 39.38      A C
ATOM   563  CD1 PHE A 110     -25.712  28.563  11.572  1.00 39.32      A C
ATOM   564  CD2 PHE A 110     -26.873  27.199  13.163  1.00 39.49      A C
ATOM   565  CE1 PHE A 110     -26.505  29.652  11.921  1.00 39.52      A C
ATOM   566  CE2 PHE A 110     -27.672  28.278  13.522  1.00 39.64      A C
ATOM   567  CZ  PHE A 110     -27.488  29.511  12.899  1.00 39.69      A C
ATOM   568  C   PHE A 110     -22.874  25.026  11.799  1.00 39.34      A C
ATOM   569  O   PHE A 110     -22.283  25.114  10.729  1.00 39.31      A O
ATOM   570  N   GLU A 111     -22.913  23.909  12.508  1.00 39.48      A N
ATOM   571  CA  GLU A 111     -22.278  22.710  11.997  1.00 39.70      A C
ATOM   572  CB  GLU A 111     -21.418  22.042  13.063  1.00 40.04      A C
ATOM   573  CG  GLU A 111     -20.896  20.688  12.640  1.00 40.67      A C
ATOM   574  CD  GLU A 111     -19.868  20.146  13.601  1.00 41.41      A C
ATOM   575  OE1 GLU A 111     -19.837  20.606  14.765  1.00 41.68      A O
ATOM   576  OE2 GLU A 111     -19.091  19.255  13.196  1.00 41.93      A O
ATOM   577  C   GLU A 111     -23.382  21.759  11.551  1.00 39.60      A C
ATOM   578  O   GLU A 111     -24.382  21.581  12.250  1.00 39.69      A O
ATOM   579  N   ARG A 112     -23.215  21.185  10.369  1.00 39.21      A N
ATOM   580  CA  ARG A 112     -24.181  20.238   9.843  1.00 39.07      A C
ATOM   581  CB  ARG A 112     -24.729  20.693   8.489  1.00 38.63      A C
ATOM   582  CG  ARG A 112     -25.865  21.686   8.598  1.00 38.34      A C
ATOM   583  CD  ARG A 112     -26.246  22.214   7.227  1.00 38.34      A C
ATOM   584  NE  ARG A 112     -27.520  22.924   7.249  1.00 38.14      A N
ATOM   585  CZ  ARG A 112     -28.092  23.456   6.174  1.00 38.13      A C
ATOM   586  NH1 ARG A 112     -27.495  23.366   4.988  1.00 38.10      A N
ATOM   587  NH2 ARG A 112     -29.269  24.060   6.280  1.00 37.73      A N
ATOM   588  C   ARG A 112     -23.466  18.908   9.695  1.00 39.19      A C
ATOM   589  O   ARG A 112     -22.231  18.839   9.737  1.00 39.21      A O
ATOM   590  N   PRO A 113     -24.233  17.827   9.525  1.00 39.21      A N
ATOM   591  CD  PRO A 113     -25.705  17.716   9.444  1.00 39.33      A C
ATOM   592  CA  PRO A 113     -23.594  16.524   9.383  1.00 39.13      A C
ATOM   593  CB  PRO A 113     -24.740  15.636   8.891  1.00 39.39      A C
ATOM   594  CG  PRO A 113     -25.936  16.218   9.627  1.00 39.29      A C
ATOM   595  C   PRO A 113     -22.400  16.532   8.431  1.00 39.06      A C
ATOM   596  O   PRO A 113     -21.300  16.162   8.819  1.00 39.14      A O
ATOM   597  N   ASP A 114     -22.609  16.982   7.197  1.00 38.70      A N
ATOM   598  CA  ASP A 114     -21.540  16.974   6.211  1.00 38.37      A C
ATOM   599  CB  ASP A 114     -22.022  16.212   4.978  1.00 39.38      A C
ATOM   600  CG  ASP A 114     -22.562  14.832   5.332  1.00 40.35      A C
ATOM   601  OD1 ASP A 114     -21.793  14.039   5.924  1.00 41.11      A O
ATOM   602  OD2 ASP A 114     -23.748  14.543   5.032  1.00 40.78      A O
ATOM   603  C   ASP A 114     -20.985  18.332   5.793  1.00 37.67      A C
ATOM   604  O   ASP A 114     -20.269  18.432   4.795  1.00 37.73      A O
ATOM   605  N   SER A 115     -21.295  19.377   6.550  1.00 36.60      A N
ATOM   606  CA  SER A 115     -20.792  20.695   6.199  1.00 35.59      A C
ATOM   607  CB  SER A 115     -21.556  21.235   4.989  1.00 35.38      A C
ATOM   608  OG  SER A 115     -22.868  21.621   5.370  1.00 34.97      A O
ATOM   609  C   SER A 115     -20.914  21.700   7.334  1.00 34.97      A C
ATOM   610  O   SER A 115     -21.532  21.431   8.368  1.00 34.57      A O
ATOM   611  N   PHE A 116     -20.307  22.864   7.120  1.00 34.29      A N
ATOM   612  CA  PHE A 116     -20.374  23.963   8.074  1.00 33.70      A C
ATOM   613  CB  PHE A 116     -18.984  24.389   8.555  1.00 33.83      A C
ATOM   614  CG  PHE A 116     -18.398  23.492   9.608  1.00 34.03      A C
```

FIGURE 2A-12

```
ATOM    615  CD1 PHE A 116     -17.595  22.416   9.252  1.00 33.94      A C
ATOM    616  CD2 PHE A 116     -18.627  23.748  10.962  1.00 34.05      A C
ATOM    617  CE1 PHE A 116     -17.018  21.609  10.225  1.00 34.19      A C
ATOM    618  CE2 PHE A 116     -18.055  22.945  11.950  1.00 34.09      A C
ATOM    619  CZ  PHE A 116     -17.249  21.876  11.581  1.00 34.16      A C
ATOM    620  C   PHE A 116     -21.013  25.136   7.358  1.00 33.12      A C
ATOM    621  O   PHE A 116     -20.787  25.341   6.171  1.00 33.09      A O
ATOM    622  N   VAL A 117     -21.812  25.901   8.084  1.00 32.45      A N
ATOM    623  CA  VAL A 117     -22.470  27.058   7.521  1.00 31.89      A C
ATOM    624  CB  VAL A 117     -24.013  26.901   7.556  1.00 32.02      A C
ATOM    625  CG1 VAL A 117     -24.673  28.117   6.927  1.00 31.74      A C
ATOM    626  CG2 VAL A 117     -24.431  25.622   6.808  1.00 32.06      A C
ATOM    627  C   VAL A 117     -22.072  28.298   8.317  1.00 31.56      A C
ATOM    628  O   VAL A 117     -22.214  28.343   9.537  1.00 31.13      A O
ATOM    629  N   LEU A 118     -21.546  29.298   7.618  1.00 31.34      A N
ATOM    630  CA  LEU A 118     -21.140  30.549   8.255  1.00 30.93      A C
ATOM    631  CB  LEU A 118     -19.696  30.907   7.887  1.00 31.05      A C
ATOM    632  CG  LEU A 118     -18.534  30.213   8.610  1.00 31.05      A C
ATOM    633  CD1 LEU A 118     -18.587  28.734   8.361  1.00 31.25      A C
ATOM    634  CD2 LEU A 118     -17.207  30.782   8.114  1.00 30.81      A C
ATOM    635  C   LEU A 118     -22.056  31.682   7.831  1.00 30.62      A C
ATOM    636  O   LEU A 118     -22.351  31.856   6.646  1.00 30.45      A O
ATOM    637  N   ILE A 119     -22.512  32.446   8.811  1.00 30.45      A N
ATOM    638  CA  ILE A 119     -23.376  33.577   8.549  1.00 30.67      A C
ATOM    639  CB  ILE A 119     -24.457  33.726   9.639  1.00 30.64      A C
ATOM    640  CG2 ILE A 119     -25.346  34.901   9.311  1.00 30.60      A C
ATOM    641  CG1 ILE A 119     -25.297  32.443   9.729  1.00 30.66      A C
ATOM    642  CD1 ILE A 119     -26.075  32.115   8.452  1.00 30.87      A C
ATOM    643  C   ILE A 119     -22.449  34.781   8.560  1.00 30.93      A C
ATOM    644  O   ILE A 119     -21.815  35.087   9.569  1.00 31.06      A O
ATOM    645  N   LEU A 120     -22.365  35.453   7.423  1.00 31.23      A N
ATOM    646  CA  LEU A 120     -21.482  36.597   7.271  1.00 31.60      A C
ATOM    647  CB  LEU A 120     -20.576  36.380   6.058  1.00 30.95      A C
ATOM    648  CG  LEU A 120     -19.188  35.762   6.174  1.00 30.88      A C
ATOM    649  CD1 LEU A 120     -18.974  35.044   7.472  1.00 30.93      A C
ATOM    650  CD2 LEU A 120     -18.994  34.851   4.997  1.00 30.81      A C
ATOM    651  C   LEU A 120     -22.221  37.899   7.082  1.00 32.18      A C
ATOM    652  O   LEU A 120     -23.319  37.937   6.543  1.00 32.32      A O
ATOM    653  N   GLU A 121     -21.586  38.974   7.513  1.00 33.05      A N
ATOM    654  CA  GLU A 121     -22.124  40.313   7.363  1.00 33.94      A C
ATOM    655  CB  GLU A 121     -21.144  41.293   8.014  1.00 34.67      A C
ATOM    656  CG  GLU A 121     -21.410  42.767   7.812  1.00 36.60      A C
ATOM    657  CD  GLU A 121     -20.232  43.632   8.267  1.00 37.60      A C
ATOM    658  OE1 GLU A 121     -19.384  43.124   9.037  1.00 38.07      A O
ATOM    659  OE2 GLU A 121     -20.159  44.820   7.856  1.00 38.28      A O
ATOM    660  C   GLU A 121     -22.228  40.582   5.858  1.00 33.99      A C
ATOM    661  O   GLU A 121     -21.428  40.057   5.087  1.00 34.01      A O
ATOM    662  N   ARG A 122     -23.227  41.356   5.435  1.00 34.19      A N
ATOM    663  CA  ARG A 122     -23.370  41.703   4.019  1.00 34.49      A C
ATOM    664  CB  ARG A 122     -24.358  40.790   3.277  1.00 34.48      A C
ATOM    665  CG  ARG A 122     -24.607  41.257   1.820  1.00 34.21      A C
ATOM    666  CD  ARG A 122     -25.413  40.266   0.960  1.00 34.35      A C
ATOM    667  NE  ARG A 122     -26.796  40.060   1.406  1.00 34.16      A N
ATOM    668  CZ  ARG A 122     -27.833  40.825   1.062  1.00 34.07      A C
ATOM    669  NH1 ARG A 122     -27.670  41.870   0.259  1.00 33.41      A N
ATOM    670  NH2 ARG A 122     -29.043  40.536   1.525  1.00 33.88      A N
```

FIGURE 2A-13

| | | | | | | | | | | |
|---|---|---|---|---|---|---|---|---|---|---|
| ATOM | 671 | C | ARG | A | 122 | -23.813 | 43.144 | 3.798 | 1.00 34.69 | A C |
| ATOM | 672 | O | ARG | A | 122 | -24.970 | 43.492 | 4.020 | 1.00 34.71 | A O |
| ATOM | 673 | N | PRO | A | 123 | -22.888 | 44.008 | 3.368 | 1.00 34.85 | A N |
| ATOM | 674 | CD | PRO | A | 123 | -21.425 | 43.827 | 3.251 | 1.00 34.89 | A C |
| ATOM | 675 | CA | PRO | A | 123 | -23.276 | 45.401 | 3.133 | 1.00 34.79 | A C |
| ATOM | 676 | CB | PRO | A | 123 | -21.930 | 46.124 | 3.070 | 1.00 35.07 | A C |
| ATOM | 677 | CG | PRO | A | 123 | -21.002 | 45.074 | 2.511 | 1.00 35.17 | A C |
| ATOM | 678 | C | PRO | A | 123 | -24.060 | 45.480 | 1.823 | 1.00 34.69 | A C |
| ATOM | 679 | O | PRO | A | 123 | -24.087 | 44.518 | 1.054 | 1.00 34.34 | A O |
| ATOM | 680 | N | GLU | A | 124 | -24.713 | 46.609 | 1.579 | 1.00 34.77 | A N |
| ATOM | 681 | CA | GLU | A | 124 | -25.489 | 46.784 | 0.348 | 1.00 35.02 | A C |
| ATOM | 682 | CB | GLU | A | 124 | -26.862 | 46.094 | 0.459 | 1.00 36.04 | A C |
| ATOM | 683 | CG | GLU | A | 124 | -27.581 | 46.337 | 1.777 | 1.00 37.93 | A C |
| ATOM | 684 | CD | GLU | A | 124 | -29.034 | 45.844 | 1.789 | 1.00 39.23 | A C |
| ATOM | 685 | OE1 | GLU | A | 124 | -29.344 | 44.767 | 1.201 | 1.00 39.72 | A O |
| ATOM | 686 | OE2 | GLU | A | 124 | -29.868 | 46.546 | 2.410 | 1.00 39.79 | A O |
| ATOM | 687 | C | GLU | A | 124 | -25.691 | 48.262 | 0.047 | 1.00 34.31 | A C |
| ATOM | 688 | O | GLU | A | 124 | -25.906 | 49.061 | 0.964 | 1.00 34.48 | A O |
| ATOM | 689 | N | PRO | A | 125 | -25.585 | 48.656 | -1.237 | 1.00 33.33 | A N |
| ATOM | 690 | CD | PRO | A | 125 | -25.800 | 50.054 | -1.662 | 1.00 33.19 | A C |
| ATOM | 691 | CA | PRO | A | 125 | -25.286 | 47.807 | -2.393 | 1.00 32.63 | A C |
| ATOM | 692 | CB | PRO | A | 125 | -25.786 | 48.647 | -3.560 | 1.00 32.64 | A C |
| ATOM | 693 | CG | PRO | A | 125 | -25.391 | 50.030 | -3.125 | 1.00 32.70 | A C |
| ATOM | 694 | C | PRO | A | 125 | -23.774 | 47.553 | -2.470 | 1.00 32.07 | A C |
| ATOM | 695 | O | PRO | A | 125 | -22.976 | 48.376 | -2.018 | 1.00 32.01 | A O |
| ATOM | 696 | N | VAL | A | 126 | -23.388 | 46.439 | -3.084 | 1.00 31.29 | A N |
| ATOM | 697 | CA | VAL | A | 126 | -21.988 | 46.066 | -3.170 | 1.00 30.60 | A C |
| ATOM | 698 | CB | VAL | A | 126 | -21.651 | 44.989 | -2.093 | 1.00 30.57 | A C |
| ATOM | 699 | CG1 | VAL | A | 126 | -20.239 | 44.437 | -2.296 | 1.00 30.71 | A C |
| ATOM | 700 | CG2 | VAL | A | 126 | -21.798 | 45.581 | -0.714 | 1.00 30.38 | A C |
| ATOM | 701 | C | VAL | A | 126 | -21.599 | 45.495 | -4.518 | 1.00 30.03 | A C |
| ATOM | 702 | O | VAL | A | 126 | -22.437 | 44.940 | -5.236 | 1.00 30.30 | A O |
| ATOM | 703 | N | GLN | A | 127 | -20.320 | 45.649 | -4.845 | 1.00 28.98 | A N |
| ATOM | 704 | CA | GLN | A | 127 | -19.726 | 45.106 | -6.056 | 1.00 28.19 | A C |
| ATOM | 705 | CB | GLN | A | 127 | -19.652 | 46.150 | -7.174 | 1.00 27.89 | A C |
| ATOM | 706 | CG | GLN | A | 127 | -19.255 | 45.512 | -8.500 | 1.00 27.90 | A C |
| ATOM | 707 | CD | GLN | A | 127 | -19.174 | 46.488 | -9.655 | 1.00 28.17 | A C |
| ATOM | 708 | OE1 | GLN | A | 127 | -19.439 | 46.124 | -10.810 | 1.00 28.40 | A O |
| ATOM | 709 | NE2 | GLN | A | 127 | -18.794 | 47.724 | -9.364 | 1.00 27.53 | A N |
| ATOM | 710 | C | GLN | A | 127 | -18.305 | 44.719 | -5.633 | 1.00 27.84 | A C |
| ATOM | 711 | O | GLN | A | 127 | -17.663 | 45.480 | -4.910 | 1.00 27.39 | A O |
| ATOM | 712 | N | ASP | A | 128 | -17.813 | 43.550 | -6.046 | 1.00 27.59 | A N |
| ATOM | 713 | CA | ASP | A | 128 | -16.456 | 43.186 | -5.659 | 1.00 27.34 | A C |
| ATOM | 714 | CB | ASP | A | 128 | -16.230 | 41.660 | -5.766 | 1.00 27.80 | A C |
| ATOM | 715 | CG | ASP | A | 128 | -16.163 | 41.135 | -7.197 | 1.00 28.21 | A C |
| ATOM | 716 | OD1 | ASP | A | 128 | -16.262 | 39.900 | -7.340 | 1.00 28.62 | A O |
| ATOM | 717 | OD2 | ASP | A | 128 | -15.994 | 41.905 | -8.169 | 1.00 28.57 | A O |
| ATOM | 718 | C | ASP | A | 128 | -15.473 | 44.010 | -6.504 | 1.00 27.10 | A C |
| ATOM | 719 | O | ASP | A | 128 | -15.857 | 44.545 | -7.548 | 1.00 26.77 | A O |
| ATOM | 720 | N | LEU | A | 129 | -14.231 | 44.156 | -6.037 | 1.00 26.87 | A N |
| ATOM | 721 | CA | LEU | A | 129 | -13.234 | 44.957 | -6.750 | 1.00 26.56 | A C |
| ATOM | 722 | CB | LEU | A | 129 | -11.922 | 45.015 | -5.965 | 1.00 26.28 | A C |
| ATOM | 723 | CG | LEU | A | 129 | -11.112 | 46.320 | -5.887 | 1.00 26.39 | A C |
| ATOM | 724 | CD1 | LEU | A | 129 | -9.676 | 46.018 | -5.463 | 1.00 25.84 | A C |
| ATOM | 725 | CD2 | LEU | A | 129 | -11.120 | 47.037 | -7.202 | 1.00 26.46 | A C |
| ATOM | 726 | C | LEU | A | 129 | -12.949 | 44.416 | -8.141 | 1.00 26.64 | A C |

FIGURE 2A-14

```
ATOM    727  O    LEU A 129     -12.657  45.168  -9.073  1.00 26.09      A O
ATOM    728  N    PHE A 130     -13.021  43.105  -8.289  1.00 27.17      A N
ATOM    729  CA   PHE A 130     -12.749  42.511  -9.595  1.00 27.99      A C
ATOM    730  CB   PHE A 130     -12.849  40.990  -9.521  1.00 28.39      A C
ATOM    731  CG   PHE A 130     -12.559  40.303 -10.822  1.00 29.22      A C
ATOM    732  CD1  PHE A 130     -11.255  40.020 -11.200  1.00 29.28      A C
ATOM    733  CD2  PHE A 130     -13.597  39.943 -11.677  1.00 29.49      A C
ATOM    734  CE1  PHE A 130     -10.986  39.387 -12.417  1.00 29.75      A C
ATOM    735  CE2  PHE A 130     -13.339  39.310 -12.896  1.00 29.64      A C
ATOM    736  CZ   PHE A 130     -12.033  39.032 -13.265  1.00 29.74      A C
ATOM    737  C    PHE A 130     -13.727  43.041 -10.641  1.00 28.02      A C
ATOM    738  O    PHE A 130     -13.313  43.526 -11.696  1.00 28.02      A O
ATOM    739  N    ASP A 131     -15.025  42.955 -10.342  1.00 28.08      A N
ATOM    740  CA   ASP A 131     -16.051  43.435 -11.269  1.00 28.00      A C
ATOM    741  CB   ASP A 131     -17.451  43.148 -10.733  1.00 27.93      A C
ATOM    742  CG   ASP A 131     -17.791  41.697 -10.762  1.00 27.83      A C
ATOM    743  OD1  ASP A 131     -17.000  40.901 -11.311  1.00 28.42      A O
ATOM    744  OD2  ASP A 131     -18.855  41.346 -10.235  1.00 28.38      A O
ATOM    745  C    ASP A 131     -15.942  44.929 -11.520  1.00 27.87      A C
ATOM    746  O    ASP A 131     -16.134  45.395 -12.648  1.00 27.99      A O
ATOM    747  N    PHE A 132     -15.654  45.678 -10.461  1.00 27.74      A N
ATOM    748  CA   PHE A 132     -15.532  47.122 -10.565  1.00 27.76      A C
ATOM    749  CB   PHE A 132     -15.323  47.706  -9.165  1.00 27.40      A C
ATOM    750  CG   PHE A 132     -15.245  49.206  -9.125  1.00 27.37      A C
ATOM    751  CD1  PHE A 132     -14.028  49.862  -9.321  1.00 27.25      A C
ATOM    752  CD2  PHE A 132     -16.378  49.965  -8.873  1.00 27.22      A C
ATOM    753  CE1  PHE A 132     -13.948  51.257  -9.260  1.00 27.03      A C
ATOM    754  CE2  PHE A 132     -16.306  51.354  -8.812  1.00 27.10      A C
ATOM    755  CZ   PHE A 132     -15.092  52.001  -9.004  1.00 26.79      A C
ATOM    756  C    PHE A 132     -14.389  47.475 -11.527  1.00 28.30      A C
ATOM    757  O    PHE A 132     -14.547  48.331 -12.387  1.00 28.07      A O
ATOM    758  N    ILE A 133     -13.255  46.785 -11.427  1.00 28.73      A N
ATOM    759  CA   ILE A 133     -12.143  47.069 -12.330  1.00 29.51      A C
ATOM    760  CB   ILE A 133     -10.820  46.462 -11.782  1.00 28.91      A C
ATOM    761  CG2  ILE A 133      -9.747  46.478 -12.843  1.00 28.85      A C
ATOM    762  CG1  ILE A 133     -10.362  47.256 -10.559  1.00 28.66      A C
ATOM    763  CD1  ILE A 133      -9.219  46.629  -9.781  1.00 28.30      A C
ATOM    764  C    ILE A 133     -12.427  46.569 -13.765  1.00 30.48      A C
ATOM    765  O    ILE A 133     -12.010  47.196 -14.747  1.00 30.46      A O
ATOM    766  N    THR A 134     -13.135  45.450 -13.895  1.00 31.43      A N
ATOM    767  CA   THR A 134     -13.468  44.932 -15.221  1.00 32.53      A C
ATOM    768  CB   THR A 134     -14.183  43.562 -15.115  1.00 32.56      A C
ATOM    769  OG1  THR A 134     -13.296  42.605 -14.520  1.00 32.82      A O
ATOM    770  CG2  THR A 134     -14.607  43.061 -16.491  1.00 32.45      A C
ATOM    771  C    THR A 134     -14.380  45.929 -15.966  1.00 33.35      A C
ATOM    772  O    THR A 134     -14.239  46.137 -17.168  1.00 33.60      A O
ATOM    773  N    GLU A 135     -15.302  46.563 -15.251  1.00 34.33      A N
ATOM    774  CA   GLU A 135     -16.206  47.517 -15.883  1.00 35.30      A C
ATOM    775  CB   GLU A 135     -17.483  47.667 -15.055  1.00 36.19      A C
ATOM    776  CG   GLU A 135     -18.297  46.375 -14.986  1.00 37.87      A C
ATOM    777  CD   GLU A 135     -19.604  46.544 -14.239  1.00 38.91      A C
ATOM    778  OE1  GLU A 135     -20.334  45.533 -14.113  1.00 39.56      A O
ATOM    779  OE2  GLU A 135     -19.897  47.681 -13.783  1.00 39.16      A O
ATOM    780  C    GLU A 135     -15.596  48.896 -16.111  1.00 35.43      A C
ATOM    781  O    GLU A 135     -15.851  49.539 -17.133  1.00 35.27      A O
ATOM    782  N    ARG A 136     -14.783  49.352 -15.168  1.00 35.14      A N
```

FIGURE 2A-15

```
ATOM    783  CA  ARG A 136     -14.186  50.665 -15.302  1.00 34.79      A C
ATOM    784  CB  ARG A 136     -14.171  51.355 -13.952  1.00 35.73      A C
ATOM    785  CG  ARG A 136     -15.540  51.687 -13.409  1.00 36.89      A C
ATOM    786  CD  ARG A 136     -15.406  52.944 -12.562  1.00 38.05      A C
ATOM    787  NE  ARG A 136     -16.626  53.280 -11.845  1.00 38.72      A N
ATOM    788  CZ  ARG A 136     -16.766  54.376 -11.110  1.00 39.04      A C
ATOM    789  NH1 ARG A 136     -15.757  55.238 -11.009  1.00 38.90      A N
ATOM    790  NH2 ARG A 136     -17.907  54.596 -10.466  1.00 39.24      A N
ATOM    791  C   ARG A 136     -12.779  50.709 -15.879  1.00 34.01      A C
ATOM    792  O   ARG A 136     -12.303  51.780 -16.258  1.00 33.91      A O
ATOM    793  N   GLY A 137     -12.108  49.563 -15.947  1.00 33.27      A N
ATOM    794  CA  GLY A 137     -10.743  49.549 -16.451  1.00 32.29      A C
ATOM    795  C   GLY A 137      -9.830  50.158 -15.392  1.00 31.65      A C
ATOM    796  O   GLY A 137     -10.206  50.218 -14.221  1.00 31.68      A O
ATOM    797  N   ALA A 138      -8.650  50.631 -15.784  1.00 30.81      A N
ATOM    798  CA  ALA A 138      -7.719  51.216 -14.823  1.00 30.02      A C
ATOM    799  CB  ALA A 138      -6.494  51.780 -15.549  1.00 29.90      A C
ATOM    800  C   ALA A 138      -8.401  52.311 -13.997  1.00 29.62      A C
ATOM    801  O   ALA A 138      -9.228  53.074 -14.516  1.00 29.65      A O
ATOM    802  N   LEU A 139      -8.047  52.381 -12.715  1.00 28.60      A N
ATOM    803  CA  LEU A 139      -8.625  53.359 -11.806  1.00 28.07      A C
ATOM    804  CB  LEU A 139      -8.825  52.741 -10.418  1.00 27.41      A C
ATOM    805  CG  LEU A 139      -9.512  51.379 -10.260  1.00 27.45      A C
ATOM    806  CD1 LEU A 139      -9.646  51.042  -8.761  1.00 26.68      A C
ATOM    807  CD2 LEU A 139     -10.879  51.402 -10.930  1.00 27.01      A C
ATOM    808  C   LEU A 139      -7.737  54.594 -11.656  1.00 27.82      A C
ATOM    809  O   LEU A 139      -6.507  54.482 -11.657  1.00 27.46      A O
ATOM    810  N   GLN A 140      -8.360  55.767 -11.530  1.00 27.62      A N
ATOM    811  CA  GLN A 140      -7.612  57.001 -11.320  1.00 27.81      A C
ATOM    812  CB  GLN A 140      -8.556  58.193 -11.114  1.00 29.02      A C
ATOM    813  CG  GLN A 140      -9.529  58.391 -12.273  1.00 31.34      A C
ATOM    814  CD  GLN A 140     -10.434  59.602 -12.077  1.00 32.76      A C
ATOM    815  OE1 GLN A 140     -11.440  59.753 -12.778  1.00 34.01      A O
ATOM    816  NE2 GLN A 140     -10.056  60.495 -11.154  1.00 33.05      A N
ATOM    817  C   GLN A 140      -6.806  56.780 -10.044  1.00 27.15      A C
ATOM    818  O   GLN A 140      -7.257  56.086  -9.124  1.00 26.33      A O
ATOM    819  N   GLU A 141      -5.624  57.380  -9.980  1.00 26.89      A N
ATOM    820  CA  GLU A 141      -4.768  57.196  -8.818  1.00 26.91      A C
ATOM    821  CB  GLU A 141      -3.416  57.879  -9.045  1.00 27.02      A C
ATOM    822  CG  GLU A 141      -2.710  57.308 -10.280  1.00 27.85      A C
ATOM    823  CD  GLU A 141      -1.213  57.555 -10.323  1.00 27.69      A C
ATOM    824  OE1 GLU A 141      -0.606  57.267 -11.365  1.00 28.06      A O
ATOM    825  OE2 GLU A 141      -0.635  58.027  -9.329  1.00 28.68      A O
ATOM    826  C   GLU A 141      -5.404  57.638  -7.505  1.00 26.82      A C
ATOM    827  O   GLU A 141      -5.169  57.013  -6.474  1.00 26.63      A O
ATOM    828  N   GLU A 142      -6.224  58.686  -7.543  1.00 26.73      A N
ATOM    829  CA  GLU A 142      -6.887  59.175  -6.336  1.00 26.67      A C
ATOM    830  CB  GLU A 142      -7.725  60.424  -6.651  1.00 27.44      A C
ATOM    831  CG  GLU A 142      -8.559  60.931  -5.482  1.00 28.70      A C
ATOM    832  CD  GLU A 142      -9.275  62.239  -5.792  1.00 29.58      A C
ATOM    833  OE1 GLU A 142      -8.696  63.315  -5.514  1.00 30.25      A O
ATOM    834  OE2 GLU A 142     -10.406  62.189  -6.324  1.00 29.89      A O
ATOM    835  C   GLU A 142      -7.788  58.086  -5.766  1.00 26.11      A C
ATOM    836  O   GLU A 142      -7.861  57.877  -4.551  1.00 26.22      A O
ATOM    837  N   LEU A 143      -8.482  57.395  -6.654  1.00 25.37      A N
ATOM    838  CA  LEU A 143      -9.378  56.326  -6.250  1.00 24.70      A C
```

FIGURE 2A-16

```
ATOM    839  CB   LEU A 143     -10.318  55.982   -7.417  1.00 24.13      A C
ATOM    840  CG   LEU A 143     -11.365  54.899   -7.174  1.00 23.61      A C
ATOM    841  CD1  LEU A 143     -12.233  55.256   -5.978  1.00 23.29      A C
ATOM    842  CD2  LEU A 143     -12.201  54.740   -8.431  1.00 23.71      A C
ATOM    843  C    LEU A 143      -8.563  55.101   -5.808  1.00 24.34      A C
ATOM    844  O    LEU A 143      -8.845  54.502   -4.775  1.00 24.32      A O
ATOM    845  N    ALA A 144      -7.538  54.743   -6.579  1.00 24.18      A N
ATOM    846  CA   ALA A 144      -6.696  53.600   -6.217  1.00 23.80      A C
ATOM    847  CB   ALA A 144      -5.603  53.391   -7.266  1.00 23.28      A C
ATOM    848  C    ALA A 144      -6.060  53.840   -4.840  1.00 23.65      A C
ATOM    849  O    ALA A 144      -5.931  52.906   -4.048  1.00 23.41      A O
ATOM    850  N    ARG A 145      -5.677  55.090   -4.560  1.00 23.37      A N
ATOM    851  CA   ARG A 145      -5.038  55.431   -3.282  1.00 23.53      A C
ATOM    852  CB   ARG A 145      -4.576  56.898   -3.270  1.00 23.85      A C
ATOM    853  CG   ARG A 145      -3.951  57.346   -1.939  1.00 24.90      A C
ATOM    854  CD   ARG A 145      -3.069  58.595   -2.104  1.00 26.20      A C
ATOM    855  NE   ARG A 145      -3.763  59.588   -2.899  1.00 27.51      A N
ATOM    856  CZ   ARG A 145      -3.339  60.075   -4.061  1.00 27.28      A C
ATOM    857  NH1  ARG A 145      -2.188  59.680   -4.587  1.00 27.00      A N
ATOM    858  NH2  ARG A 145      -4.111  60.924   -4.719  1.00 27.33      A N
ATOM    859  C    ARG A 145      -5.980  55.177   -2.117  1.00 23.25      A C
ATOM    860  O    ARG A 145      -5.604  54.539   -1.133  1.00 23.05      A O
ATOM    861  N    SER A 146      -7.210  55.669   -2.243  1.00 23.12      A N
ATOM    862  CA   SER A 146      -8.225  55.486   -1.207  1.00 23.05      A C
ATOM    863  CB   SER A 146      -9.504  56.213   -1.602  1.00 23.13      A C
ATOM    864  OG   SER A 146     -10.562  55.852   -0.729  1.00 24.07      A O
ATOM    865  C    SER A 146      -8.536  54.006   -0.983  1.00 22.61      A C
ATOM    866  O    SER A 146      -8.632  53.548    0.156  1.00 22.47      A O
ATOM    867  N    PHE A 147      -8.706  53.271   -2.081  1.00 22.23      A N
ATOM    868  CA   PHE A 147      -8.998  51.847   -2.016  1.00 22.01      A C
ATOM    869  CB   PHE A 147      -9.301  51.307   -3.416  1.00 22.33      A C
ATOM    870  CG   PHE A 147     -10.707  51.565   -3.888  1.00 22.73      A C
ATOM    871  CD1  PHE A 147     -11.183  50.948   -5.043  1.00 22.51      A C
ATOM    872  CD2  PHE A 147     -11.567  52.402   -3.168  1.00 22.92      A C
ATOM    873  CE1  PHE A 147     -12.489  51.151   -5.474  1.00 22.69      A C
ATOM    874  CE2  PHE A 147     -12.880  52.614   -3.594  1.00 23.07      A C
ATOM    875  CZ   PHE A 147     -13.339  51.982   -4.753  1.00 23.07      A C
ATOM    876  C    PHE A 147      -7.810  51.076   -1.421  1.00 21.83      A C
ATOM    877  O    PHE A 147      -7.971  50.272   -0.501  1.00 21.25      A O
ATOM    878  N    PHE A 148      -6.620  51.335   -1.953  1.00 21.29      A N
ATOM    879  CA   PHE A 148      -5.429  50.664   -1.476  1.00 21.53      A C
ATOM    880  CB   PHE A 148      -4.201  51.110   -2.287  1.00 21.33      A C
ATOM    881  CG   PHE A 148      -2.989  50.251   -2.056  1.00 21.35      A C
ATOM    882  CD1  PHE A 148      -3.027  48.879   -2.333  1.00 21.37      A C
ATOM    883  CD2  PHE A 148      -1.814  50.799   -1.570  1.00 21.27      A C
ATOM    884  CE1  PHE A 148      -1.914  48.078   -2.129  1.00 20.70      A C
ATOM    885  CE2  PHE A 148      -0.694  49.996   -1.367  1.00 21.22      A C
ATOM    886  CZ   PHE A 148      -0.749  48.635   -1.648  1.00 20.74      A C
ATOM    887  C    PHE A 148      -5.213  50.947    0.012  1.00 21.51      A C
ATOM    888  O    PHE A 148      -4.889  50.049    0.776  1.00 21.45      A O
ATOM    889  N    TRP A 149      -5.411  52.197    0.418  1.00 21.90      A N
ATOM    890  CA   TRP A 149      -5.251  52.596    1.822  1.00 22.04      A C
ATOM    891  CB   TRP A 149      -5.561  54.085    1.980  1.00 22.07      A C
ATOM    892  CG   TRP A 149      -5.422  54.590    3.385  1.00 22.78      A C
ATOM    893  CD2  TRP A 149      -4.237  55.121    3.992  1.00 23.01      A C
ATOM    894  CE2  TRP A 149      -4.579  55.520    5.302  1.00 23.40      A C
```

FIGURE 2A-17

```
ATOM    895  CE3 TRP A 149      -2.918  55.303   3.550  1.00 23.62      A C
ATOM    896  CD1 TRP A 149      -6.405  54.677   4.324  1.00 22.84      A C
ATOM    897  NE1 TRP A 149      -5.909  55.238   5.481  1.00 23.12      A N
ATOM    898  CZ2 TRP A 149      -3.648  56.095   6.187  1.00 23.63      A C
ATOM    899  CZ3 TRP A 149      -1.982  55.878   4.435  1.00 24.05      A C
ATOM    900  CH2 TRP A 149      -2.362  56.265   5.740  1.00 23.42      A C
ATOM    901  C   TRP A 149      -6.163  51.785   2.738  1.00 22.12      A C
ATOM    902  O   TRP A 149      -5.726  51.290   3.780  1.00 21.89      A O
ATOM    903  N   GLN A 150      -7.429  51.654   2.344  1.00 22.26      A N
ATOM    904  CA  GLN A 150      -8.392  50.889   3.127  1.00 22.41      A C
ATOM    905  CB  GLN A 150      -9.803  51.043   2.556  1.00 22.54      A C
ATOM    906  CG  GLN A 150     -10.406  52.413   2.770  1.00 22.82      A C
ATOM    907  CD  GLN A 150     -11.848  52.474   2.313  1.00 23.43      A C
ATOM    908  OE1 GLN A 150     -12.697  51.735   2.803  1.00 23.47      A O
ATOM    909  NE2 GLN A 150     -12.129  53.353   1.363  1.00 23.65      A N
ATOM    910  C   GLN A 150      -8.024  49.415   3.181  1.00 22.59      A C
ATOM    911  O   GLN A 150      -8.209  48.767   4.214  1.00 22.53      A O
ATOM    912  N   VAL A 151      -7.519  48.867   2.077  1.00 22.52      A N
ATOM    913  CA  VAL A 151      -7.113  47.466   2.099  1.00 22.70      A C
ATOM    914  CB  VAL A 151      -6.680  46.973   0.690  1.00 22.72      A C
ATOM    915  CG1 VAL A 151      -6.020  45.596   0.771  1.00 22.46      A C
ATOM    916  CG2 VAL A 151      -7.916  46.903  -0.220  1.00 22.47      A C
ATOM    917  C   VAL A 151      -5.956  47.347   3.100  1.00 22.82      A C
ATOM    918  O   VAL A 151      -5.935  46.427   3.918  1.00 22.81      A O
ATOM    919  N   LEU A 152      -5.013  48.288   3.065  1.00 22.73      A N
ATOM    920  CA  LEU A 152      -3.897  48.224   3.997  1.00 22.93      A C
ATOM    921  CB  LEU A 152      -2.924  49.374   3.759  1.00 23.30      A C
ATOM    922  CG  LEU A 152      -1.911  49.149   2.665  1.00 23.90      A C
ATOM    923  CD1 LEU A 152      -1.403  50.460   2.243  1.00 24.55      A C
ATOM    924  CD2 LEU A 152      -0.757  48.293   3.145  1.00 24.86      A C
ATOM    925  C   LEU A 152      -4.378  48.260   5.432  1.00 22.83      A C
ATOM    926  O   LEU A 152      -3.897  47.498   6.257  1.00 23.16      A O
ATOM    927  N   GLU A 153      -5.322  49.143   5.736  1.00 22.70      A N
ATOM    928  CA  GLU A 153      -5.820  49.220   7.104  1.00 23.02      A C
ATOM    929  CB  GLU A 153      -6.823  50.367   7.262  1.00 23.29      A C
ATOM    930  CG  GLU A 153      -6.186  51.754   7.164  1.00 23.74      A C
ATOM    931  CD  GLU A 153      -5.348  52.118   8.387  1.00 24.40      A C
ATOM    932  OE1 GLU A 153      -4.345  52.846   8.225  1.00 24.48      A O
ATOM    933  OE2 GLU A 153      -5.699  51.696   9.512  1.00 24.53      A O
ATOM    934  C   GLU A 153      -6.471  47.901   7.517  1.00 22.98      A C
ATOM    935  O   GLU A 153      -6.323  47.470   8.666  1.00 22.88      A O
ATOM    936  N   ALA A 154      -7.175  47.257   6.583  1.00 22.62      A N
ATOM    937  CA  ALA A 154      -7.842  45.981   6.876  1.00 22.66      A C
ATOM    938  CB  ALA A 154      -8.746  45.573   5.706  1.00 21.87      A C
ATOM    939  C   ALA A 154      -6.816  44.872   7.160  1.00 22.42      A C
ATOM    940  O   ALA A 154      -6.973  44.082   8.094  1.00 22.27      A O
ATOM    941  N   VAL A 155      -5.770  44.828   6.347  1.00 22.30      A N
ATOM    942  CA  VAL A 155      -4.739  43.833   6.508  1.00 22.31      A C
ATOM    943  CB  VAL A 155      -3.797  43.823   5.284  1.00 22.15      A C
ATOM    944  CG1 VAL A 155      -2.674  42.828   5.497  1.00 22.05      A C
ATOM    945  CG2 VAL A 155      -4.603  43.455   4.020  1.00 22.27      A C
ATOM    946  C   VAL A 155      -3.964  44.082   7.801  1.00 22.49      A C
ATOM    947  O   VAL A 155      -3.610  43.132   8.494  1.00 22.68      A O
ATOM    948  N   ARG A 156      -3.708  45.342   8.147  1.00 22.68      A N
ATOM    949  CA  ARG A 156      -2.993  45.623   9.404  1.00 23.10      A C
ATOM    950  CB  ARG A 156      -2.704  47.117   9.562  1.00 23.00      A C
```

FIGURE 2A-18

```
ATOM    951  CG   ARG A 156      -1.595  47.654   8.660  1.00 23.08      A C
ATOM    952  CD   ARG A 156      -1.428  49.162   8.886  1.00 23.24      A C
ATOM    953  NE   ARG A 156      -1.144  49.441  10.283  1.00 22.74      A N
ATOM    954  CZ   ARG A 156      -1.387  50.597  10.889  1.00 22.80      A C
ATOM    955  NH1  ARG A 156      -1.924  51.608  10.220  1.00 22.84      A N
ATOM    956  NH2  ARG A 156      -1.119  50.725  12.188  1.00 22.72      A N
ATOM    957  C    ARG A 156      -3.832  45.152  10.589  1.00 23.52      A C
ATOM    958  O    ARG A 156      -3.303  44.646  11.576  1.00 23.39      A O
ATOM    959  N    HIS A 157      -5.147  45.323  10.476  1.00 24.13      A N
ATOM    960  CA   HIS A 157      -6.068  44.910  11.521  1.00 24.89      A C
ATOM    961  CB   HIS A 157      -7.504  45.291  11.143  1.00 25.37      A C
ATOM    962  CG   HIS A 157      -8.538  44.704  12.051  1.00 26.01      A C
ATOM    963  CD2  HIS A 157      -9.407  43.679  11.869  1.00 26.49      A C
ATOM    964  ND1  HIS A 157      -8.712  45.129  13.350  1.00 26.55      A N
ATOM    965  CE1  HIS A 157      -9.641  44.388  13.933  1.00 26.77      A C
ATOM    966  NE2  HIS A 157     -10.077  43.501  13.057  1.00 26.95      A N
ATOM    967  C    HIS A 157      -5.968  43.399  11.723  1.00 25.23      A C
ATOM    968  O    HIS A 157      -5.881  42.928  12.859  1.00 24.91      A O
ATOM    969  N    CYS A 158      -5.975  42.640  10.626  1.00 25.47      A N
ATOM    970  CA   CYS A 158      -5.868  41.186  10.728  1.00 25.77      A C
ATOM    971  CB   CYS A 158      -5.938  40.523   9.345  1.00 25.84      A C
ATOM    972  SG   CYS A 158      -7.492  40.682   8.434  1.00 26.06      A S
ATOM    973  C    CYS A 158      -4.542  40.783  11.382  1.00 26.20      A C
ATOM    974  O    CYS A 158      -4.527  39.968  12.307  1.00 25.99      A O
ATOM    975  N    HIS A 159      -3.435  41.328  10.871  1.00 26.76      A N
ATOM    976  CA   HIS A 159      -2.111  41.011  11.401  1.00 27.67      A C
ATOM    977  CB   HIS A 159      -1.020  41.763  10.618  1.00 27.99      A C
ATOM    978  CG   HIS A 159      -0.772  41.221   9.246  1.00 28.87      A C
ATOM    979  CD2  HIS A 159       0.321  41.265   8.452  1.00 29.15      A C
ATOM    980  ND1  HIS A 159      -1.740  40.554   8.522  1.00 29.69      A N
ATOM    981  CE1  HIS A 159      -1.253  40.208   7.347  1.00 29.22      A C
ATOM    982  NE2  HIS A 159      -0.003  40.628   7.277  1.00 29.53      A N
ATOM    983  C    HIS A 159      -2.058  41.415  12.872  1.00 28.14      A C
ATOM    984  O    HIS A 159      -1.470  40.733  13.694  1.00 27.98      A O
ATOM    985  N    ASN A 160      -2.701  42.522  13.196  1.00 28.86      A N
ATOM    986  CA   ASN A 160      -2.688  42.984  14.558  1.00 29.86      A C
ATOM    987  CB   ASN A 160      -3.398  44.322  14.677  1.00 30.87      A C
ATOM    988  CG   ASN A 160      -3.241  44.945  16.042  1.00 32.19      A C
ATOM    989  OD1  ASN A 160      -3.959  45.885  16.382  1.00 33.38      A O
ATOM    990  ND2  ASN A 160      -2.278  44.470  16.817  1.00 32.64      A N
ATOM    991  C    ASN A 160      -3.403  41.977  15.438  1.00 29.85      A C
ATOM    992  O    ASN A 160      -3.140  41.890  16.629  1.00 30.12      A O
ATOM    993  N    CME A 161      -4.337  41.243  14.849  1.00 29.80      A N
ATOM    994  CA   CME A 161      -5.127  40.260  15.569  1.00 29.55      A C
ATOM    995  C    CME A 161      -4.588  38.849  15.406  1.00 28.35      A C
ATOM    996  CB   CME A 161      -6.588  40.321  15.090  1.00 31.48      A C
ATOM    997  SG   CME A 161      -7.474  41.840  15.643  1.00 34.40      A S
ATOM    998  S1   CME A 161      -7.352  41.854  17.770  1.00 37.86      A S
ATOM    999  C1   CME A 161      -6.214  43.203  18.227  1.00 37.87      A C
ATOM   1000  C2   CME A 161      -6.474  43.832  19.605  1.00 39.27      A C
ATOM   1001  O1   CME A 161      -7.859  44.341  19.774  1.00 40.16      A O
ATOM   1002  O    CME A 161      -5.273  37.892  15.736  1.00 27.93      A O
ATOM   1003  N    GLY A 162      -3.373  38.717  14.884  1.00 27.18      A N
ATOM   1004  CA   GLY A 162      -2.783  37.398  14.735  1.00 26.05      A C
ATOM   1005  C    GLY A 162      -3.266  36.556  13.561  1.00 25.55      A C
ATOM   1006  O    GLY A 162      -3.088  35.335  13.569  1.00 25.27      A O
```

FIGURE 2A-19

```
ATOM 1007  N    VAL A 163      -3.858  37.195  12.548  1.00 24.73      A N
ATOM 1008  CA   VAL A 163      -4.374  36.487  11.372  1.00 24.04      A C
ATOM 1009  CB   VAL A 163      -5.901  36.722  11.202  1.00 24.03      A C
ATOM 1010  CG1  VAL A 163      -6.429  35.931  10.021  1.00 24.06      A C
ATOM 1011  CG2  VAL A 163      -6.635  36.340  12.471  1.00 23.84      A C
ATOM 1012  C    VAL A 163      -3.710  36.917  10.071  1.00 23.75      A C
ATOM 1013  O    VAL A 163      -3.544  38.114   9.803  1.00 23.66      A O
ATOM 1014  N    LEU A 164      -3.351  35.933   9.260  1.00 23.53      A N
ATOM 1015  CA   LEU A 164      -2.735  36.169   7.956  1.00 23.83      A C
ATOM 1016  CB   LEU A 164      -1.455  35.331   7.820  1.00 23.93      A C
ATOM 1017  CG   LEU A 164      -0.553  35.607   6.611  1.00 24.18      A C
ATOM 1018  CD1  LEU A 164       0.058  36.994   6.769  1.00 24.02      A C
ATOM 1019  CD2  LEU A 164       0.553  34.537   6.509  1.00 23.86      A C
ATOM 1020  C    LEU A 164      -3.770  35.715   6.911  1.00 23.79      A C
ATOM 1021  O    LEU A 164      -4.161  34.540   6.893  1.00 23.70      A O
ATOM 1022  N    HIS A 165      -4.222  36.632   6.059  1.00 23.49      A N
ATOM 1023  CA   HIS A 165      -5.227  36.288   5.040  1.00 23.37      A C
ATOM 1024  CB   HIS A 165      -5.720  37.562   4.336  1.00 22.79      A C
ATOM 1025  CG   HIS A 165      -6.879  37.334   3.414  1.00 22.16      A C
ATOM 1026  CD2  HIS A 165      -8.194  37.630   3.550  1.00 21.64      A C
ATOM 1027  ND1  HIS A 165      -6.751  36.713   2.190  1.00 21.78      A N
ATOM 1028  CE1  HIS A 165      -7.937  36.639   1.612  1.00 21.67      A C
ATOM 1029  NE2  HIS A 165      -8.829  37.189   2.417  1.00 21.74      A N
ATOM 1030  C    HIS A 165      -4.752  35.284   3.977  1.00 23.71      A C
ATOM 1031  O    HIS A 165      -5.455  34.306   3.681  1.00 24.00      A O
ATOM 1032  N    ARG A 166      -3.582  35.555   3.394  1.00 23.83      A N
ATOM 1033  CA   ARG A 166      -2.942  34.724   2.361  1.00 24.15      A C
ATOM 1034  CB   ARG A 166      -2.679  33.309   2.901  1.00 24.59      A C
ATOM 1035  CG   ARG A 166      -1.624  33.290   4.019  1.00 25.45      A C
ATOM 1036  CD   ARG A 166      -1.045  31.893   4.266  1.00 26.07      A C
ATOM 1037  NE   ARG A 166      -2.040  30.933   4.734  1.00 26.62      A N
ATOM 1038  CZ   ARG A 166      -1.772  29.655   4.995  1.00 27.27      A C
ATOM 1039  NH1  ARG A 166      -0.533  29.191   4.828  1.00 27.01      A N
ATOM 1040  NH2  ARG A 166      -2.730  28.842   5.439  1.00 27.00      A N
ATOM 1041  C    ARG A 166      -3.598  34.651   0.970  1.00 24.11      A C
ATOM 1042  O    ARG A 166      -3.130  33.927   0.082  1.00 24.10      A O
ATOM 1043  N    ASP A 167      -4.667  35.401   0.757  1.00 23.95      A N
ATOM 1044  CA   ASP A 167      -5.266  35.401  -0.566  1.00 24.06      A C
ATOM 1045  CB   ASP A 167      -6.361  34.337  -0.642  1.00 24.45      A C
ATOM 1046  CG   ASP A 167      -6.821  34.073  -2.059  1.00 25.40      A C
ATOM 1047  OD1  ASP A 167      -6.038  34.298  -3.024  1.00 25.51      A O
ATOM 1048  OD2  ASP A 167      -7.978  33.627  -2.202  1.00 26.01      A O
ATOM 1049  C    ASP A 167      -5.798  36.788  -0.942  1.00 23.71      A C
ATOM 1050  O    ASP A 167      -6.859  36.919  -1.544  1.00 23.57      A O
ATOM 1051  N    ILE A 168      -5.041  37.826  -0.591  1.00 23.53      A N
ATOM 1052  CA   ILE A 168      -5.431  39.196  -0.906  1.00 23.06      A C
ATOM 1053  CB   ILE A 168      -4.439  40.210  -0.311  1.00 22.56      A C
ATOM 1054  CG2  ILE A 168      -4.818  41.633  -0.739  1.00 21.68      A C
ATOM 1055  CG1  ILE A 168      -4.405  40.071   1.213  1.00 21.67      A C
ATOM 1056  CD1  ILE A 168      -3.255  40.823   1.849  1.00 20.82      A C
ATOM 1057  C    ILE A 168      -5.452  39.390  -2.417  1.00 23.41      A C
ATOM 1058  O    ILE A 168      -4.453  39.146  -3.090  1.00 23.37      A O
ATOM 1059  N    LYS A 169      -6.591  39.832  -2.942  1.00 23.53      A N
ATOM 1060  CA   LYS A 169      -6.754  40.079  -4.380  1.00 23.92      A C
ATOM 1061  CB   LYS A 169      -6.668  38.766  -5.173  1.00 24.05      A C
ATOM 1062  CG   LYS A 169      -7.670  37.699  -4.745  1.00 24.69      A C
```

FIGURE 2A-20

```
ATOM   1063  CD   LYS A 169      -7.669  36.518  -5.726  1.00 25.08      A C
ATOM   1064  CE   LYS A 169      -8.667  35.450  -5.296  1.00 25.61      A C
ATOM   1065  NZ   LYS A 169      -8.604  34.267  -6.208  1.00 26.17      A N
ATOM   1066  C    LYS A 169      -8.114  40.755  -4.615  1.00 24.05      A C
ATOM   1067  O    LYS A 169      -8.980  40.735  -3.729  1.00 23.81      A O
ATOM   1068  N    ASP A 170      -8.302  41.331  -5.800  1.00 24.07      A N
ATOM   1069  CA   ASP A 170      -9.537  42.044  -6.121  1.00 24.31      A C
ATOM   1070  CB   ASP A 170      -9.494  42.594  -7.563  1.00 24.22      A C
ATOM   1071  CG   ASP A 170      -9.203  41.517  -8.606  1.00 24.66      A C
ATOM   1072  OD1  ASP A 170      -9.267  40.310  -8.285  1.00 24.57      A O
ATOM   1073  OD2  ASP A 170      -8.911  41.889  -9.761  1.00 25.02      A O
ATOM   1074  C    ASP A 170     -10.815  41.243  -5.913  1.00 24.39      A C
ATOM   1075  O    ASP A 170     -11.824  41.804  -5.504  1.00 24.45      A O
ATOM   1076  N    GLU A 171     -10.768  39.941  -6.186  1.00 24.63      A N
ATOM   1077  CA   GLU A 171     -11.929  39.070  -6.022  1.00 25.10      A C
ATOM   1078  CB   GLU A 171     -11.649  37.680  -6.582  1.00 26.33      A C
ATOM   1079  CG   GLU A 171     -11.608  37.592  -8.087  1.00 28.10      A C
ATOM   1080  CD   GLU A 171     -11.209  36.212  -8.544  1.00 29.44      A C
ATOM   1081  OE1  GLU A 171     -10.098  35.777  -8.202  1.00 30.78      A O
ATOM   1082  OE2  GLU A 171     -12.001  35.546  -9.239  1.00 30.62      A O
ATOM   1083  C    GLU A 171     -12.354  38.897  -4.576  1.00 24.83      A C
ATOM   1084  O    GLU A 171     -13.481  38.473  -4.309  1.00 24.83      A O
ATOM   1085  N    ASN A 172     -11.445  39.192  -3.649  1.00 24.23      A N
ATOM   1086  CA   ASN A 172     -11.739  39.055  -2.233  1.00 23.92      A C
ATOM   1087  CB   ASN A 172     -10.660  38.221  -1.538  1.00 23.71      A C
ATOM   1088  CG   ASN A 172     -10.676  36.796  -2.003  1.00 23.57      A C
ATOM   1089  OD1  ASN A 172     -11.746  36.277  -2.336  1.00 23.91      A O
ATOM   1090  ND2  ASN A 172      -9.510  36.143  -2.034  1.00 23.03      A N
ATOM   1091  C    ASN A 172     -11.896  40.377  -1.528  1.00 23.72      A C
ATOM   1092  O    ASN A 172     -11.675  40.465  -0.320  1.00 23.71      A O
ATOM   1093  N    ILE A 173     -12.266  41.402  -2.294  1.00 23.46      A N
ATOM   1094  CA   ILE A 173     -12.491  42.733  -1.757  1.00 23.41      A C
ATOM   1095  CB   ILE A 173     -11.414  43.719  -2.247  1.00 23.08      A C
ATOM   1096  CG2  ILE A 173     -11.792  45.139  -1.864  1.00 22.39      A C
ATOM   1097  CG1  ILE A 173     -10.057  43.336  -1.654  1.00 22.89      A C
ATOM   1098  CD1  ILE A 173      -8.882  44.082  -2.257  1.00 22.07      A C
ATOM   1099  C    ILE A 173     -13.878  43.239  -2.192  1.00 23.82      A C
ATOM   1100  O    ILE A 173     -14.187  43.320  -3.386  1.00 23.90      A O
ATOM   1101  N    LEU A 174     -14.715  43.556  -1.212  1.00 24.24      A N
ATOM   1102  CA   LEU A 174     -16.058  44.065  -1.471  1.00 24.64      A C
ATOM   1103  CB   LEU A 174     -17.035  43.509  -0.440  1.00 24.77      A C
ATOM   1104  CG   LEU A 174     -17.855  42.269  -0.793  1.00 25.22      A C
ATOM   1105  CD1  LEU A 174     -17.107  41.381  -1.780  1.00 24.66      A C
ATOM   1106  CD2  LEU A 174     -18.215  41.540   0.488  1.00 24.62      A C
ATOM   1107  C    LEU A 174     -16.059  45.581  -1.369  1.00 24.89      A C
ATOM   1108  O    LEU A 174     -15.370  46.154  -0.509  1.00 24.41      A O
ATOM   1109  N    ILE A 175     -16.816  46.229  -2.250  1.00 25.04      A N
ATOM   1110  CA   ILE A 175     -16.935  47.684  -2.206  1.00 25.60      A C
ATOM   1111  CB   ILE A 175     -16.651  48.355  -3.579  1.00 25.15      A C
ATOM   1112  CG2  ILE A 175     -16.826  49.866  -3.471  1.00 24.78      A C
ATOM   1113  CG1  ILE A 175     -15.243  48.050  -4.061  1.00 24.53      A C
ATOM   1114  CD1  ILE A 175     -15.080  48.402  -5.499  1.00 23.83      A C
ATOM   1115  C    ILE A 175     -18.366  48.090  -1.834  1.00 26.42      A C
ATOM   1116  O    ILE A 175     -19.311  47.756  -2.548  1.00 26.56      A O
ATOM   1117  N    ASP A 176     -18.533  48.792  -0.715  1.00 27.26      A N
ATOM   1118  CA   ASP A 176     -19.850  49.300  -0.355  1.00 28.12      A C
```

FIGURE 2A-21

```
ATOM   1119  CB   ASP A 176     -19.902  49.627   1.139  1.00 28.61      A C
ATOM   1120  CG   ASP A 176     -21.196  50.313   1.546  1.00 29.25      A C
ATOM   1121  OD1  ASP A 176     -21.517  50.308   2.755  1.00 29.11      A O
ATOM   1122  OD2  ASP A 176     -21.882  50.872   0.656  1.00 29.67      A O
ATOM   1123  C    ASP A 176     -19.930  50.578  -1.216  1.00 28.68      A C
ATOM   1124  O    ASP A 176     -19.284  51.592  -0.921  1.00 28.54      A O
ATOM   1125  N    LEU A 177     -20.689  50.495  -2.306  1.00 29.26      A N
ATOM   1126  CA   LEU A 177     -20.843  51.596  -3.256  1.00 30.07      A C
ATOM   1127  CB   LEU A 177     -21.668  51.117  -4.452  1.00 29.99      A C
ATOM   1128  CG   LEU A 177     -21.013  49.980  -5.251  1.00 30.29      A C
ATOM   1129  CD1  LEU A 177     -22.023  49.412  -6.256  1.00 30.03      A C
ATOM   1130  CD2  LEU A 177     -19.744  50.490  -5.953  1.00 29.15      A C
ATOM   1131  C    LEU A 177     -21.423  52.912  -2.731  1.00 30.74      A C
ATOM   1132  O    LEU A 177     -21.175  53.964  -3.321  1.00 31.10      A O
ATOM   1133  N    ASN A 178     -22.186  52.877  -1.640  1.00 31.31      A N
ATOM   1134  CA   ASN A 178     -22.751  54.112  -1.096  1.00 32.02      A C
ATOM   1135  CB   ASN A 178     -24.139  53.855  -0.487  1.00 32.79      A C
ATOM   1136  CG   ASN A 178     -25.212  53.606  -1.550  1.00 34.17      A C
ATOM   1137  OD1  ASN A 178     -26.338  53.210  -1.225  1.00 35.14      A O
ATOM   1138  ND2  ASN A 178     -24.873  53.845  -2.825  1.00 34.30      A N
ATOM   1139  C    ASN A 178     -21.847  54.788  -0.058  1.00 31.94      A C
ATOM   1140  O    ASN A 178     -21.724  56.015  -0.051  1.00 31.88      A O
ATOM   1141  N    ARG A 179     -21.205  53.997   0.802  1.00 31.86      A N
ATOM   1142  CA   ARG A 179     -20.322  54.558   1.829  1.00 31.75      A C
ATOM   1143  CB   ARG A 179     -20.428  53.732   3.118  1.00 32.63      A C
ATOM   1144  CG   ARG A 179     -21.823  53.182   3.355  1.00 33.83      A C
ATOM   1145  CD   ARG A 179     -22.181  53.089   4.822  1.00 34.88      A C
ATOM   1146  NE   ARG A 179     -22.184  54.421   5.405  1.00 36.30      A N
ATOM   1147  CZ   ARG A 179     -23.036  54.836   6.339  1.00 36.94      A C
ATOM   1148  NH1  ARG A 179     -23.973  54.022   6.809  1.00 37.37      A N
ATOM   1149  NH2  ARG A 179     -22.951  56.077   6.801  1.00 37.27      A N
ATOM   1150  C    ARG A 179     -18.854  54.645   1.386  1.00 31.29      A C
ATOM   1151  O    ARG A 179     -18.034  55.297   2.043  1.00 31.07      A O
ATOM   1152  N    GLY A 180     -18.530  54.001   0.263  1.00 30.77      A N
ATOM   1153  CA   GLY A 180     -17.165  54.021  -0.243  1.00 30.01      A C
ATOM   1154  C    GLY A 180     -16.180  53.234   0.616  1.00 29.59      A C
ATOM   1155  O    GLY A 180     -14.992  53.562   0.648  1.00 29.54      A O
ATOM   1156  N    GLU A 181     -16.663  52.195   1.296  1.00 28.70      A N
ATOM   1157  CA   GLU A 181     -15.816  51.379   2.168  1.00 28.23      A C
ATOM   1158  CB   GLU A 181     -16.490  51.203   3.537  1.00 28.40      A C
ATOM   1159  CG   GLU A 181     -16.910  52.533   4.145  1.00 29.31      A C
ATOM   1160  CD   GLU A 181     -17.706  52.420   5.437  1.00 29.31      A C
ATOM   1161  OE1  GLU A 181     -18.210  51.331   5.762  1.00 29.98      A O
ATOM   1162  OE2  GLU A 181     -17.848  53.449   6.127  1.00 29.79      A O
ATOM   1163  C    GLU A 181     -15.521  50.009   1.574  1.00 27.60      A C
ATOM   1164  O    GLU A 181     -16.409  49.377   0.997  1.00 27.21      A O
ATOM   1165  N    LEU A 182     -14.268  49.561   1.704  1.00 26.81      A N
ATOM   1166  CA   LEU A 182     -13.891  48.247   1.202  1.00 26.15      A C
ATOM   1167  CB   LEU A 182     -12.516  48.274   0.514  1.00 25.73      A C
ATOM   1168  CG   LEU A 182     -12.230  49.250  -0.641  1.00 26.23      A C
ATOM   1169  CD1  LEU A 182     -11.150  48.655  -1.555  1.00 25.40      A C
ATOM   1170  CD2  LEU A 182     -13.470  49.531  -1.437  1.00 25.65      A C
ATOM   1171  C    LEU A 182     -13.877  47.250   2.364  1.00 25.73      A C
ATOM   1172  O    LEU A 182     -13.591  47.612   3.505  1.00 25.26      A O
ATOM   1173  N    LYS A 183     -14.202  45.995   2.066  1.00 25.60      A N
ATOM   1174  CA   LYS A 183     -14.231  44.936   3.078  1.00 25.63      A C
```

FIGURE 2A-22

```
ATOM   1175  CB  LYS A 183     -15.669  44.548   3.416  1.00 26.14      A C
ATOM   1176  CG  LYS A 183     -16.574  45.687   3.812  1.00 27.11      A C
ATOM   1177  CD  LYS A 183     -16.336  46.098   5.235  1.00 27.92      A C
ATOM   1178  CE  LYS A 183     -17.516  46.882   5.768  1.00 28.38      A C
ATOM   1179  NZ  LYS A 183     -17.219  47.277   7.173  1.00 29.66      A N
ATOM   1180  C   LYS A 183     -13.518  43.699   2.544  1.00 25.27      A C
ATOM   1181  O   LYS A 183     -13.714  43.313   1.396  1.00 25.00      A O
ATOM   1182  N   LEU A 184     -12.712  43.073   3.388  1.00 25.19      A N
ATOM   1183  CA  LEU A 184     -11.967  41.876   3.017  1.00 25.40      A C
ATOM   1184  CB  LEU A 184     -10.695  41.790   3.858  1.00 26.03      A C
ATOM   1185  CG  LEU A 184      -9.342  41.805   3.153  1.00 27.30      A C
ATOM   1186  CD1 LEU A 184      -9.228  40.583   2.255  1.00 27.60      A C
ATOM   1187  CD2 LEU A 184      -9.184  43.092   2.327  1.00 27.66      A C
ATOM   1188  C   LEU A 184     -12.814  40.608   3.243  1.00 25.12      A C
ATOM   1189  O   LEU A 184     -13.433  40.446   4.295  1.00 24.62      A O
ATOM   1190  N   ILE A 185     -12.830  39.708   2.263  1.00 24.77      A N
ATOM   1191  CA  ILE A 185     -13.593  38.480   2.409  1.00 24.64      A C
ATOM   1192  CB  ILE A 185     -14.814  38.430   1.469  1.00 24.43      A C
ATOM   1193  CG2 ILE A 185     -15.838  39.496   1.869  1.00 24.08      A C
ATOM   1194  CG1 ILE A 185     -14.339  38.556   0.019  1.00 23.87      A C
ATOM   1195  CD1 ILE A 185     -15.427  38.429  -0.980  1.00 23.55      A C
ATOM   1196  C   ILE A 185     -12.753  37.261   2.086  1.00 24.95      A C
ATOM   1197  O   ILE A 185     -11.679  37.363   1.488  1.00 24.98      A O
ATOM   1198  N   ASP A 186     -13.277  36.110   2.490  1.00 25.30      A N
ATOM   1199  CA  ASP A 186     -12.665  34.813   2.271  1.00 25.60      A C
ATOM   1200  CB  ASP A 186     -12.505  34.532   0.776  1.00 25.82      A C
ATOM   1201  CG  ASP A 186     -12.151  33.071   0.500  1.00 26.48      A C
ATOM   1202  OD1 ASP A 186     -12.348  32.244   1.419  1.00 26.81      A O
ATOM   1203  OD2 ASP A 186     -11.698  32.742  -0.624  1.00 26.64      A O
ATOM   1204  C   ASP A 186     -11.338  34.557   2.970  1.00 25.92      A C
ATOM   1205  O   ASP A 186     -10.252  34.773   2.409  1.00 25.67      A O
ATOM   1206  N   PHE A 187     -11.436  34.065   4.198  1.00 26.16      A N
ATOM   1207  CA  PHE A 187     -10.252  33.720   4.963  1.00 26.58      A C
ATOM   1208  CB  PHE A 187     -10.422  34.145   6.414  1.00 26.34      A C
ATOM   1209  CG  PHE A 187     -10.247  35.615   6.623  1.00 26.11      A C
ATOM   1210  CD1 PHE A 187     -11.187  36.519   6.138  1.00 26.12      A C
ATOM   1211  CD2 PHE A 187      -9.112  36.102   7.257  1.00 25.65      A C
ATOM   1212  CE1 PHE A 187     -10.991  37.898   6.279  1.00 26.11      A C
ATOM   1213  CE2 PHE A 187      -8.910  37.463   7.403  1.00 25.71      A C
ATOM   1214  CZ  PHE A 187      -9.847  38.367   6.913  1.00 25.92      A C
ATOM   1215  C   PHE A 187      -9.993  32.227   4.890  1.00 26.86      A C
ATOM   1216  O   PHE A 187      -9.288  31.668   5.726  1.00 27.56      A O
ATOM   1217  N   GLY A 188     -10.536  31.589   3.863  1.00 27.02      A N
ATOM   1218  CA  GLY A 188     -10.383  30.151   3.714  1.00 27.29      A C
ATOM   1219  C   GLY A 188      -9.004  29.597   3.418  1.00 27.40      A C
ATOM   1220  O   GLY A 188      -8.809  28.387   3.479  1.00 27.56      A O
ATOM   1221  N   SER A 189      -8.049  30.453   3.074  1.00 27.51      A N
ATOM   1222  CA  SER A 189      -6.691  29.991   2.802  1.00 27.44      A C
ATOM   1223  CB  SER A 189      -6.234  30.441   1.414  1.00 27.86      A C
ATOM   1224  OG  SER A 189      -7.155  30.066   0.398  1.00 28.90      A O
ATOM   1225  C   SER A 189      -5.767  30.609   3.842  1.00 27.22      A C
ATOM   1226  O   SER A 189      -4.545  30.482   3.752  1.00 27.37      A O
ATOM   1227  N   GLY A 190      -6.360  31.287   4.819  1.00 26.86      A N
ATOM   1228  CA  GLY A 190      -5.576  31.963   5.836  1.00 26.90      A C
ATOM   1229  C   GLY A 190      -4.891  31.073   6.852  1.00 27.00      A C
ATOM   1230  O   GLY A 190      -4.921  29.841   6.756  1.00 27.23      A O
```

FIGURE 2A-23

```
ATOM   1231  N    ALA A 191      -4.267  31.698   7.841  1.00 26.68      A N
ATOM   1232  CA   ALA A 191      -3.566  30.953   8.875  1.00 26.62      A C
ATOM   1233  CB   ALA A 191      -2.235  30.423   8.337  1.00 26.29      A C
ATOM   1234  C    ALA A 191      -3.305  31.885  10.022  1.00 26.66      A C
ATOM   1235  O    ALA A 191      -3.453  33.100   9.886  1.00 26.69      A O
ATOM   1236  N    LEU A 192      -2.931  31.322  11.163  1.00 26.77      A N
ATOM   1237  CA   LEU A 192      -2.603  32.149  12.297  1.00 26.99      A C
ATOM   1238  CB   LEU A 192      -2.411  31.287  13.541  1.00 27.51      A C
ATOM   1239  CG   LEU A 192      -3.706  30.600  13.983  1.00 28.39      A C
ATOM   1240  CD1  LEU A 192      -3.416  29.509  15.018  1.00 28.76      A C
ATOM   1241  CD2  LEU A 192      -4.651  31.664  14.551  1.00 28.47      A C
ATOM   1242  C    LEU A 192      -1.287  32.767  11.858  1.00 26.85      A C
ATOM   1243  O    LEU A 192      -0.490  32.112  11.184  1.00 26.76      A O
ATOM   1244  N    LEU A 193      -1.073  34.031  12.189  1.00 26.72      A N
ATOM   1245  CA   LEU A 193       0.165  34.699  11.822  1.00 26.89      A C
ATOM   1246  CB   LEU A 193       0.013  36.215  11.985  1.00 26.83      A C
ATOM   1247  CG   LEU A 193       1.224  37.102  11.659  1.00 26.55      A C
ATOM   1248  CD1  LEU A 193       1.522  37.049  10.175  1.00 26.12      A C
ATOM   1249  CD2  LEU A 193       0.937  38.540  12.092  1.00 26.36      A C
ATOM   1250  C    LEU A 193       1.264  34.177  12.749  1.00 27.26      A C
ATOM   1251  O    LEU A 193       1.015  33.901  13.924  1.00 27.02      A O
ATOM   1252  N    LYS A 194       2.470  34.034  12.206  1.00 27.62      A N
ATOM   1253  CA   LYS A 194       3.618  33.550  12.958  1.00 28.03      A C
ATOM   1254  CB   LYS A 194       3.719  32.019  12.863  1.00 27.97      A C
ATOM   1255  CG   LYS A 194       3.995  31.497  11.461  1.00 28.29      A C
ATOM   1256  CD   LYS A 194       4.050  29.978  11.436  1.00 28.43      A C
ATOM   1257  CE   LYS A 194       4.348  29.485  10.019  1.00 28.62      A C
ATOM   1258  NZ   LYS A 194       4.405  27.993   9.922  1.00 28.98      A N
ATOM   1259  C    LYS A 194       4.854  34.196  12.349  1.00 28.21      A C
ATOM   1260  O    LYS A 194       4.784  34.730  11.237  1.00 28.30      A O
ATOM   1261  N    ASP A 195       5.978  34.146  13.067  1.00 28.55      A N
ATOM   1262  CA   ASP A 195       7.227  34.745  12.589  1.00 28.83      A C
ATOM   1263  CB   ASP A 195       7.972  35.403  13.753  1.00 28.94      A C
ATOM   1264  CG   ASP A 195       7.156  36.501  14.411  1.00 29.24      A C
ATOM   1265  OD1  ASP A 195       6.877  36.409  15.625  1.00 29.48      A O
ATOM   1266  OD2  ASP A 195       6.780  37.463  13.709  1.00 29.73      A O
ATOM   1267  C    ASP A 195       8.133  33.738  11.884  1.00 29.01      A C
ATOM   1268  O    ASP A 195       9.121  34.120  11.253  1.00 29.03      A O
ATOM   1269  N    THR A 196       7.785  32.458  11.982  1.00 28.98      A N
ATOM   1270  CA   THR A 196       8.548  31.394  11.333  1.00 29.17      A C
ATOM   1271  CB   THR A 196       8.425  30.076  12.119  1.00 29.10      A C
ATOM   1272  OG1  THR A 196       7.047  29.826  12.418  1.00 29.14      A O
ATOM   1273  CG2  THR A 196       9.215  30.155  13.429  1.00 29.14      A C
ATOM   1274  C    THR A 196       8.060  31.176   9.893  1.00 29.44      A C
ATOM   1275  O    THR A 196       7.008  31.698   9.492  1.00 29.59      A O
ATOM   1276  N    VAL A 197       8.811  30.386   9.130  1.00 29.46      A N
ATOM   1277  CA   VAL A 197       8.509  30.126   7.724  1.00 29.50      A C
ATOM   1278  CB   VAL A 197       9.722  29.452   7.029  1.00 29.43      A C
ATOM   1279  CG1  VAL A 197       9.906  28.016   7.548  1.00 29.43      A C
ATOM   1280  CG2  VAL A 197       9.529  29.462   5.513  1.00 29.43      A C
ATOM   1281  C    VAL A 197       7.250  29.299   7.444  1.00 29.57      A C
ATOM   1282  O    VAL A 197       6.877  28.431   8.219  1.00 30.06      A O
ATOM   1283  N    TYR A 198       6.588  29.601   6.333  1.00 29.70      A N
ATOM   1284  CA   TYR A 198       5.387  28.881   5.902  1.00 29.70      A C
ATOM   1285  CB   TYR A 198       4.299  29.856   5.412  1.00 28.46      A C
ATOM   1286  CG   TYR A 198       3.576  30.631   6.494  1.00 27.20      A C
```

FIGURE 2A-24

```
ATOM   1287  CD1  TYR A 198       2.447  30.101   7.120  1.00 26.71      A C
ATOM   1288  CE1  TYR A 198       1.752  30.816   8.098  1.00 26.00      A C
ATOM   1289  CD2  TYR A 198       4.004  31.906   6.875  1.00 26.46      A C
ATOM   1290  CE2  TYR A 198       3.321  32.629   7.850  1.00 26.06      A C
ATOM   1291  CZ   TYR A 198       2.189  32.076   8.457  1.00 26.08      A C
ATOM   1292  OH   TYR A 198       1.479  32.786   9.401  1.00 25.24      A O
ATOM   1293  C    TYR A 198       5.822  28.008   4.726  1.00 30.38      A C
ATOM   1294  O    TYR A 198       6.531  28.473   3.830  1.00 30.51      A O
ATOM   1295  N    THR A 199       5.399  26.750   4.726  1.00 31.31      A N
ATOM   1296  CA   THR A 199       5.747  25.832   3.651  1.00 32.20      A C
ATOM   1297  CB   THR A 199       6.479  24.610   4.198  1.00 32.48      A C
ATOM   1298  OG1  THR A 199       5.698  24.039   5.252  1.00 32.75      A O
ATOM   1299  CG2  THR A 199       7.837  25.012   4.744  1.00 32.63      A C
ATOM   1300  C    THR A 199       4.487  25.367   2.950  1.00 32.68      A C
ATOM   1301  O    THR A 199       4.540  24.535   2.044  1.00 32.83      A O
ATOM   1302  N    ASP A 200       3.349  25.901   3.384  1.00 33.37      A N
ATOM   1303  CA   ASP A 200       2.062  25.563   2.779  1.00 34.01      A C
ATOM   1304  CB   ASP A 200       1.104  24.971   3.817  1.00 34.59      A C
ATOM   1305  CG   ASP A 200       0.554  26.024   4.774  1.00 35.51      A C
ATOM   1306  OD1  ASP A 200       1.366  26.665   5.475  1.00 35.77      A O
ATOM   1307  OD2  ASP A 200      -0.685  26.211   4.829  1.00 35.95      A O
ATOM   1308  C    ASP A 200       1.437  26.827   2.197  1.00 34.03      A C
ATOM   1309  O    ASP A 200       1.568  27.912   2.766  1.00 33.96      A O
ATOM   1310  N    PHE A 201       0.774  26.679   1.055  1.00 33.88      A N
ATOM   1311  CA   PHE A 201       0.104  27.791   0.403  1.00 33.84      A C
ATOM   1312  CB   PHE A 201       1.089  28.637  -0.397  1.00 33.43      A C
ATOM   1313  CG   PHE A 201       0.439  29.783  -1.141  1.00 33.14      A C
ATOM   1314  CD1  PHE A 201       0.295  29.745  -2.525  1.00 33.02      A C
ATOM   1315  CD2  PHE A 201      -0.034  30.897  -0.451  1.00 32.97      A C
ATOM   1316  CE1  PHE A 201      -0.310  30.800  -3.214  1.00 33.37      A C
ATOM   1317  CE2  PHE A 201      -0.641  31.956  -1.123  1.00 33.22      A C
ATOM   1318  CZ   PHE A 201      -0.781  31.914  -2.508  1.00 33.44      A C
ATOM   1319  C    PHE A 201      -0.979  27.283  -0.533  1.00 34.14      A C
ATOM   1320  O    PHE A 201      -0.741  26.391  -1.330  1.00 34.51      A O
ATOM   1321  N    ASP A 202      -2.171  27.850  -0.435  1.00 34.43      A N
ATOM   1322  CA   ASP A 202      -3.251  27.443  -1.308  1.00 34.78      A C
ATOM   1323  CB   ASP A 202      -4.184  26.451  -0.593  1.00 35.64      A C
ATOM   1324  CG   ASP A 202      -5.264  25.892  -1.522  1.00 36.39      A C
ATOM   1325  OD1  ASP A 202      -4.918  25.404  -2.621  1.00 36.72      A O
ATOM   1326  OD2  ASP A 202      -6.459  25.942  -1.156  1.00 36.92      A O
ATOM   1327  C    ASP A 202      -4.024  28.669  -1.780  1.00 34.57      A C
ATOM   1328  O    ASP A 202      -5.203  28.582  -2.119  1.00 34.70      A O
ATOM   1329  N    GLY A 203      -3.352  29.814  -1.810  1.00 34.12      A N
ATOM   1330  CA   GLY A 203      -4.006  31.028  -2.266  1.00 33.44      A C
ATOM   1331  C    GLY A 203      -3.955  31.113  -3.778  1.00 32.86      A C
ATOM   1332  O    GLY A 203      -3.810  30.100  -4.444  1.00 33.00      A O
ATOM   1333  N    THR A 204      -4.064  32.316  -4.326  1.00 32.36      A N
ATOM   1334  CA   THR A 204      -4.032  32.495  -5.771  1.00 31.79      A C
ATOM   1335  CB   THR A 204      -4.807  33.751  -6.173  1.00 31.69      A C
ATOM   1336  OG1  THR A 204      -6.141  33.656  -5.654  1.00 31.30      A O
ATOM   1337  CG2  THR A 204      -4.854  33.889  -7.699  1.00 31.39      A C
ATOM   1338  C    THR A 204      -2.590  32.606  -6.246  1.00 31.57      A C
ATOM   1339  O    THR A 204      -1.852  33.493  -5.811  1.00 31.64      A O
ATOM   1340  N    ARG A 205      -2.199  31.722  -7.157  1.00 31.12      A N
ATOM   1341  CA   ARG A 205      -0.826  31.687  -7.635  1.00 31.00      A C
ATOM   1342  CB   ARG A 205      -0.636  30.506  -8.602  1.00 31.60      A C
```

FIGURE 2A-25

```
ATOM   1343  CG   ARG A 205       0.825  30.044  -8.716  1.00 32.44      A C
ATOM   1344  CD   ARG A 205       0.988  28.873  -9.679  1.00 32.79      A C
ATOM   1345  NE   ARG A 205       2.388  28.479  -9.867  1.00 33.35      A N
ATOM   1346  CZ   ARG A 205       3.131  27.821  -8.974  1.00 33.54      A C
ATOM   1347  NH1  ARG A 205       2.629  27.467  -7.796  1.00 33.59      A N
ATOM   1348  NH2  ARG A 205       4.381  27.493  -9.271  1.00 33.29      A N
ATOM   1349  C    ARG A 205      -0.250  32.974  -8.250  1.00 30.49      A C
ATOM   1350  O    ARG A 205       0.847  33.396  -7.867  1.00 30.40      A O
ATOM   1351  N    VAL A 206      -0.964  33.603  -9.183  1.00 29.68      A N
ATOM   1352  CA   VAL A 206      -0.453  34.825  -9.807  1.00 28.80      A C
ATOM   1353  CB   VAL A 206      -1.357  35.310 -10.987  1.00 29.01      A C
ATOM   1354  CG1  VAL A 206      -1.281  34.314 -12.144  1.00 28.69      A C
ATOM   1355  CG2  VAL A 206      -2.810  35.486 -10.526  1.00 28.52      A C
ATOM   1356  C    VAL A 206      -0.274  35.960  -8.793  1.00 28.47      A C
ATOM   1357  O    VAL A 206       0.239  37.022  -9.139  1.00 28.31      A O
ATOM   1358  N    TYR A 207      -0.711  35.734  -7.550  1.00 28.00      A N
ATOM   1359  CA   TYR A 207      -0.554  36.717  -6.466  1.00 27.56      A C
ATOM   1360  CB   TYR A 207      -1.872  36.952  -5.709  1.00 27.64      A C
ATOM   1361  CG   TYR A 207      -2.832  37.937  -6.351  1.00 27.74      A C
ATOM   1362  CD1  TYR A 207      -3.679  37.553  -7.394  1.00 27.49      A C
ATOM   1363  CE1  TYR A 207      -4.540  38.461  -7.990  1.00 27.71      A C
ATOM   1364  CD2  TYR A 207      -2.874  39.261  -5.920  1.00 27.63      A C
ATOM   1365  CE2  TYR A 207      -3.728  40.175  -6.501  1.00 27.78      A C
ATOM   1366  CZ   TYR A 207      -4.558  39.772  -7.535  1.00 28.00      A C
ATOM   1367  OH   TYR A 207      -5.399  40.701  -8.100  1.00 28.64      A O
ATOM   1368  C    TYR A 207       0.490  36.239  -5.445  1.00 27.20      A C
ATOM   1369  O    TYR A 207       0.760  36.941  -4.461  1.00 26.90      A O
ATOM   1370  N    SER A 208       1.045  35.040  -5.666  1.00 26.65      A N
ATOM   1371  CA   SER A 208       2.047  34.458  -4.765  1.00 26.59      A C
ATOM   1372  CB   SER A 208       2.019  32.918  -4.829  1.00 26.62      A C
ATOM   1373  OG   SER A 208       2.493  32.434  -6.074  1.00 26.37      A O
ATOM   1374  C    SER A 208       3.438  34.970  -5.127  1.00 26.58      A C
ATOM   1375  O    SER A 208       3.734  35.186  -6.304  1.00 26.75      A O
ATOM   1376  N    PRO A 209       4.317  35.134  -4.123  1.00 26.45      A N
ATOM   1377  CD   PRO A 209       4.056  34.765  -2.719  1.00 26.39      A C
ATOM   1378  CA   PRO A 209       5.689  35.632  -4.289  1.00 26.44      A C
ATOM   1379  CB   PRO A 209       6.080  36.006  -2.862  1.00 26.39      A C
ATOM   1380  CG   PRO A 209       5.421  34.906  -2.061  1.00 26.41      A C
ATOM   1381  C    PRO A 209       6.704  34.685  -4.933  1.00 26.67      A C
ATOM   1382  O    PRO A 209       6.528  33.466  -4.942  1.00 26.62      A O
ATOM   1383  N    PRO A 210       7.803  35.249  -5.468  1.00 26.89      A N
ATOM   1384  CD   PRO A 210       8.196  36.664  -5.349  1.00 26.95      A C
ATOM   1385  CA   PRO A 210       8.865  34.469  -6.117  1.00 26.93      A C
ATOM   1386  CB   PRO A 210       9.940  35.513  -6.432  1.00 26.80      A C
ATOM   1387  CG   PRO A 210       9.227  36.796  -6.431  1.00 27.26      A C
ATOM   1388  C    PRO A 210       9.433  33.377  -5.206  1.00 27.10      A C
ATOM   1389  O    PRO A 210       9.798  32.304  -5.690  1.00 27.00      A O
ATOM   1390  N    GLU A 211       9.529  33.668  -3.904  1.00 27.30      A N
ATOM   1391  CA   GLU A 211      10.078  32.711  -2.937  1.00 27.78      A C
ATOM   1392  CB   GLU A 211      10.343  33.364  -1.563  1.00 26.90      A C
ATOM   1393  CG   GLU A 211       9.130  34.001  -0.907  1.00 26.71      A C
ATOM   1394  CD   GLU A 211       8.943  35.475  -1.279  1.00 26.25      A C
ATOM   1395  OE1  GLU A 211       9.382  35.897  -2.376  1.00 25.69      A O
ATOM   1396  OE2  GLU A 211       8.336  36.201  -0.468  1.00 25.74      A O
ATOM   1397  C    GLU A 211       9.172  31.498  -2.781  1.00 28.33      A C
ATOM   1398  O    GLU A 211       9.660  30.397  -2.532  1.00 28.53      A O
```

FIGURE 2A-26

```
ATOM   1399  N    TRP A 212       7.860  31.675  -2.911  1.00 28.92      A N
ATOM   1400  CA   TRP A 212       6.985  30.509  -2.830  1.00 29.60      A C
ATOM   1401  CB   TRP A 212       5.515  30.906  -2.693  1.00 29.49      A C
ATOM   1402  CG   TRP A 212       4.583  29.768  -3.022  1.00 29.33      A C
ATOM   1403  CD2  TRP A 212       4.369  28.577  -2.249  1.00 29.28      A C
ATOM   1404  CE2  TRP A 212       3.457  27.766  -2.972  1.00 29.36      A C
ATOM   1405  CE3  TRP A 212       4.859  28.115  -1.017  1.00 29.26      A C
ATOM   1406  CD1  TRP A 212       3.820  29.636  -4.143  1.00 29.41      A C
ATOM   1407  NE1  TRP A 212       3.136  28.437  -4.122  1.00 29.58      A N
ATOM   1408  CZ2  TRP A 212       3.026  26.517  -2.504  1.00 29.00      A C
ATOM   1409  CZ3  TRP A 212       4.424  26.865  -0.550  1.00 29.11      A C
ATOM   1410  CH2  TRP A 212       3.516  26.085  -1.299  1.00 29.20      A C
ATOM   1411  C    TRP A 212       7.155  29.675  -4.110  1.00 30.34      A C
ATOM   1412  O    TRP A 212       7.253  28.447  -4.050  1.00 30.63      A O
ATOM   1413  N    ILE A 213       7.192  30.350  -5.261  1.00 31.07      A N
ATOM   1414  CA   ILE A 213       7.345  29.678  -6.554  1.00 31.91      A C
ATOM   1415  CB   ILE A 213       7.394  30.697  -7.725  1.00 31.71      A C
ATOM   1416  CG2  ILE A 213       7.481  29.957  -9.051  1.00 31.88      A C
ATOM   1417  CG1  ILE A 213       6.162  31.604  -7.722  1.00 31.73      A C
ATOM   1418  CD1  ILE A 213       4.873  30.931  -8.109  1.00 31.95      A C
ATOM   1419  C    ILE A 213       8.630  28.829  -6.626  1.00 32.67      A C
ATOM   1420  O    ILE A 213       8.596  27.668  -7.027  1.00 32.77      A O
ATOM   1421  N    ARG A 214       9.755  29.410  -6.218  1.00 33.55      A N
ATOM   1422  CA   ARG A 214      11.055  28.737  -6.277  1.00 34.24      A C
ATOM   1423  CB   ARG A 214      12.177  29.773  -6.354  1.00 35.12      A C
ATOM   1424  CG   ARG A 214      12.044  30.797  -7.455  1.00 36.90      A C
ATOM   1425  CD   ARG A 214      13.166  31.817  -7.352  1.00 38.19      A C
ATOM   1426  NE   ARG A 214      14.464  31.213  -7.637  1.00 40.06      A N
ATOM   1427  CZ   ARG A 214      15.639  31.755  -7.309  1.00 40.87      A C
ATOM   1428  NH1  ARG A 214      15.689  32.923  -6.677  1.00 41.10      A N
ATOM   1429  NH2  ARG A 214      16.772  31.125  -7.613  1.00 41.19      A N
ATOM   1430  C    ARG A 214      11.419  27.779  -5.148  1.00 34.32      A C
ATOM   1431  O    ARG A 214      12.094  26.788  -5.390  1.00 34.37      A O
ATOM   1432  N    TYR A 215      10.990  28.067  -3.922  1.00 34.42      A N
ATOM   1433  CA   TYR A 215      11.366  27.233  -2.782  1.00 34.25      A C
ATOM   1434  CB   TYR A 215      12.304  28.014  -1.873  1.00 34.94      A C
ATOM   1435  CG   TYR A 215      13.384  28.740  -2.612  1.00 35.73      A C
ATOM   1436  CD1  TYR A 215      14.349  28.038  -3.341  1.00 36.29      A C
ATOM   1437  CE1  TYR A 215      15.356  28.711  -4.036  1.00 36.71      A C
ATOM   1438  CD2  TYR A 215      13.447  30.133  -2.593  1.00 36.01      A C
ATOM   1439  CE2  TYR A 215      14.447  30.817  -3.286  1.00 36.56      A C
ATOM   1440  CZ   TYR A 215      15.395  30.099  -4.002  1.00 36.93      A C
ATOM   1441  OH   TYR A 215      16.382  30.773  -4.686  1.00 38.16      A O
ATOM   1442  C    TYR A 215      10.242  26.736  -1.919  1.00 33.88      A C
ATOM   1443  O    TYR A 215      10.484  26.049  -0.931  1.00 33.85      A O
ATOM   1444  N    HIS A 216       9.016  27.088  -2.268  1.00 33.44      A N
ATOM   1445  CA   HIS A 216       7.886  26.694  -1.450  1.00 33.09      A C
ATOM   1446  CB   HIS A 216       7.646  25.185  -1.538  1.00 33.56      A C
ATOM   1447  CG   HIS A 216       6.808  24.792  -2.716  1.00 34.88      A C
ATOM   1448  CD2  HIS A 216       6.589  25.416  -3.900  1.00 35.15      A C
ATOM   1449  ND1  HIS A 216       6.050  23.639  -2.748  1.00 35.35      A N
ATOM   1450  CE1  HIS A 216       5.402  23.572  -3.898  1.00 35.35      A C
ATOM   1451  NE2  HIS A 216       5.712  24.638  -4.615  1.00 35.49      A N
ATOM   1452  C    HIS A 216       8.088  27.128  -0.002  1.00 32.37      A C
ATOM   1453  O    HIS A 216       7.748  26.407   0.922  1.00 32.60      A O
ATOM   1454  N    ARG A 217       8.652  28.317   0.182  1.00 31.57      A N
```

FIGURE 2A-27

```
ATOM 1455  CA   ARG A 217      8.889  28.880   1.518  1.00 30.76      A C
ATOM 1456  CB   ARG A 217     10.343  28.648   1.973  1.00 30.71      A C
ATOM 1457  CG   ARG A 217     10.766  27.200   2.189  1.00 30.70      A C
ATOM 1458  CD   ARG A 217     12.302  27.099   2.300  1.00 30.60      A C
ATOM 1459  NE   ARG A 217     12.848  27.823   3.451  1.00 30.82      A N
ATOM 1460  CZ   ARG A 217     12.770  27.401   4.711  1.00 30.65      A C
ATOM 1461  NH1  ARG A 217     12.167  26.252   4.987  1.00 31.00      A N
ATOM 1462  NH2  ARG A 217     13.283  28.128   5.696  1.00 30.57      A N
ATOM 1463  C    ARG A 217      8.662  30.393   1.449  1.00 29.98      A C
ATOM 1464  O    ARG A 217      9.102  31.044   0.498  1.00 30.07      A O
ATOM 1465  N    TYR A 218      8.002  30.951   2.460  1.00 29.02      A N
ATOM 1466  CA   TYR A 218      7.764  32.391   2.507  1.00 27.95      A C
ATOM 1467  CB   TYR A 218      6.624  32.788   1.559  1.00 27.52      A C
ATOM 1468  CG   TYR A 218      5.277  32.204   1.934  1.00 27.07      A C
ATOM 1469  CD1  TYR A 218      4.385  32.904   2.760  1.00 26.70      A C
ATOM 1470  CE1  TYR A 218      3.149  32.359   3.112  1.00 26.51      A C
ATOM 1471  CD2  TYR A 218      4.895  30.941   1.472  1.00 27.02      A C
ATOM 1472  CE2  TYR A 218      3.664  30.389   1.820  1.00 26.80      A C
ATOM 1473  CZ   TYR A 218      2.797  31.099   2.637  1.00 26.82      A C
ATOM 1474  OH   TYR A 218      1.580  30.538   2.969  1.00 26.94      A O
ATOM 1475  C    TYR A 218      7.405  32.801   3.918  1.00 27.50      A C
ATOM 1476  O    TYR A 218      6.998  31.972   4.731  1.00 27.62      A O
ATOM 1477  N    HIS A 219      7.576  34.080   4.219  1.00 26.81      A N
ATOM 1478  CA   HIS A 219      7.208  34.568   5.528  1.00 26.29      A C
ATOM 1479  CB   HIS A 219      8.365  35.339   6.170  1.00 26.16      A C
ATOM 1480  CG   HIS A 219      9.426  34.436   6.727  1.00 26.51      A C
ATOM 1481  CD2  HIS A 219      9.603  33.929   7.971  1.00 26.77      A C
ATOM 1482  ND1  HIS A 219     10.405  33.865   5.944  1.00 27.13      A N
ATOM 1483  CE1  HIS A 219     11.141  33.047   6.676  1.00 26.96      A C
ATOM 1484  NE2  HIS A 219     10.675  33.067   7.911  1.00 26.74      A N
ATOM 1485  C    HIS A 219      5.928  35.385   5.356  1.00 25.76      A C
ATOM 1486  O    HIS A 219      5.684  35.961   4.302  1.00 25.37      A O
ATOM 1487  N    GLY A 220      5.103  35.375   6.390  1.00 25.33      A N
ATOM 1488  CA   GLY A 220      3.813  36.027   6.339  1.00 25.21      A C
ATOM 1489  C    GLY A 220      3.672  37.437   5.819  1.00 25.15      A C
ATOM 1490  O    GLY A 220      3.052  37.675   4.782  1.00 24.85      A O
ATOM 1491  N    ARG A 221      4.250  38.375   6.556  1.00 25.21      A N
ATOM 1492  CA   ARG A 221      4.163  39.775   6.226  1.00 25.18      A C
ATOM 1493  CB   ARG A 221      4.799  40.564   7.368  1.00 26.41      A C
ATOM 1494  CG   ARG A 221      4.350  40.007   8.736  1.00 28.87      A C
ATOM 1495  CD   ARG A 221      4.942  40.735   9.946  1.00 30.80      A C
ATOM 1496  NE   ARG A 221      4.481  40.198  11.242  1.00 32.45      A N
ATOM 1497  CZ   ARG A 221      5.076  39.206  11.920  1.00 33.77      A C
ATOM 1498  NH1  ARG A 221      6.169  38.612  11.433  1.00 34.15      A N
ATOM 1499  NH2  ARG A 221      4.618  38.833  13.124  1.00 34.26      A N
ATOM 1500  C    ARG A 221      4.759  40.144   4.869  1.00 24.52      A C
ATOM 1501  O    ARG A 221      4.129  40.872   4.088  1.00 24.35      A O
ATOM 1502  N    SER A 222      5.947  39.636   4.562  1.00 23.44      A N
ATOM 1503  CA   SER A 222      6.562  39.983   3.288  1.00 22.87      A C
ATOM 1504  CB   SER A 222      8.043  39.588   3.295  1.00 22.75      A C
ATOM 1505  OG   SER A 222      8.197  38.182   3.332  1.00 23.38      A O
ATOM 1506  C    SER A 222      5.817  39.347   2.090  1.00 22.47      A C
ATOM 1507  O    SER A 222      5.828  39.885   0.989  1.00 22.59      A O
ATOM 1508  N    ALA A 223      5.181  38.202   2.298  1.00 21.84      A N
ATOM 1509  CA   ALA A 223      4.424  37.581   1.217  1.00 21.55      A C
ATOM 1510  CB   ALA A 223      4.029  36.142   1.585  1.00 21.28      A C
```

FIGURE 2A-28

```
ATOM 1511  C    ALA A 223   3.164  38.430   1.011  1.00  21.38   A C
ATOM 1512  O    ALA A 223   2.698  38.601  -0.121  1.00  20.82   A O
ATOM 1513  N    ALA A 224   2.619  38.961   2.111  1.00  20.87   A N
ATOM 1514  CA   ALA A 224   1.419  39.788   2.022  1.00  20.64   A C
ATOM 1515  CB   ALA A 224   0.908  40.112   3.397  1.00  20.36   A C
ATOM 1516  C    ALA A 224   1.704  41.077   1.254  1.00  20.54   A C
ATOM 1517  O    ALA A 224   0.891  41.516   0.433  1.00  20.69   A O
ATOM 1518  N    VAL A 225   2.866  41.669   1.523  1.00  20.31   A N
ATOM 1519  CA   VAL A 225   3.280  42.908   0.881  1.00  19.98   A C
ATOM 1520  CB   VAL A 225   4.631  43.412   1.496  1.00  19.99   A C
ATOM 1521  CG1  VAL A 225   5.232  44.549   0.661  1.00  19.15   A C
ATOM 1522  CG2  VAL A 225   4.380  43.893   2.928  1.00  19.94   A C
ATOM 1523  C    VAL A 225   3.397  42.697  -0.629  1.00  20.24   A C
ATOM 1524  O    VAL A 225   2.993  43.564  -1.411  1.00  20.22   A O
ATOM 1525  N    TRP A 226   3.942  41.550  -1.045  1.00  20.02   A N
ATOM 1526  CA   TRP A 226   4.051  41.248  -2.471  1.00  19.92   A C
ATOM 1527  CB   TRP A 226   4.753  39.896  -2.691  1.00  20.44   A C
ATOM 1528  CG   TRP A 226   4.700  39.401  -4.124  1.00  20.89   A C
ATOM 1529  CD2  TRP A 226   5.729  39.536  -5.118  1.00  21.22   A C
ATOM 1530  CE2  TRP A 226   5.238  38.954  -6.314  1.00  21.15   A C
ATOM 1531  CE3  TRP A 226   7.018  40.093  -5.113  1.00  21.45   A C
ATOM 1532  CD1  TRP A 226   3.657  38.756  -4.740  1.00  21.03   A C
ATOM 1533  NE1  TRP A 226   3.975  38.484  -6.057  1.00  21.38   A N
ATOM 1534  CZ2  TRP A 226   5.989  38.913  -7.492  1.00  21.46   A C
ATOM 1535  CZ3  TRP A 226   7.767  40.052  -6.292  1.00  22.03   A C
ATOM 1536  CH2  TRP A 226   7.245  39.464  -7.465  1.00  21.80   A C
ATOM 1537  C    TRP A 226   2.654  41.195  -3.099  1.00  19.83   A C
ATOM 1538  O    TRP A 226   2.425  41.775  -4.150  1.00  19.96   A O
ATOM 1539  N    SER A 227   1.718  40.493  -2.468  1.00  19.51   A N
ATOM 1540  CA   SER A 227   0.377  40.409  -3.033  1.00  19.57   A C
ATOM 1541  CB   SER A 227  -0.491  39.459  -2.215  1.00  19.33   A C
ATOM 1542  OG   SER A 227  -0.858  40.041  -0.983  1.00  20.33   A O
ATOM 1543  C    SER A 227  -0.256  41.801  -3.088  1.00  19.65   A C
ATOM 1544  O    SER A 227  -1.063  42.086  -3.970  1.00  19.43   A O
ATOM 1545  N    LEU A 228   0.106  42.666  -2.140  1.00  19.63   A N
ATOM 1546  CA   LEU A 228  -0.416  44.026  -2.134  1.00  19.91   A C
ATOM 1547  CB   LEU A 228  -0.080  44.729  -0.805  1.00  19.98   A C
ATOM 1548  CG   LEU A 228  -0.911  44.251   0.400  1.00  20.23   A C
ATOM 1549  CD1  LEU A 228  -0.355  44.818   1.703  1.00  20.22   A C
ATOM 1550  CD2  LEU A 228  -2.377  44.680   0.202  1.00  20.05   A C
ATOM 1551  C    LEU A 228   0.174  44.790  -3.331  1.00  19.92   A C
ATOM 1552  O    LEU A 228  -0.466  45.678  -3.883  1.00  19.91   A O
ATOM 1553  N    GLY A 229   1.384  44.428  -3.747  1.00  19.78   A N
ATOM 1554  CA   GLY A 229   1.981  45.086  -4.897  1.00  19.76   A C
ATOM 1555  C    GLY A 229   1.259  44.691  -6.178  1.00  19.93   A C
ATOM 1556  O    GLY A 229   1.076  45.514  -7.086  1.00  19.49   A O
ATOM 1557  N    ILE A 230   0.840  43.428  -6.248  1.00  20.24   A N
ATOM 1558  CA   ILE A 230   0.116  42.911  -7.409  1.00  20.77   A C
ATOM 1559  CB   ILE A 230  -0.160  41.391  -7.276  1.00  21.07   A C
ATOM 1560  CG2  ILE A 230  -0.964  40.900  -8.481  1.00  20.87   A C
ATOM 1561  CG1  ILE A 230   1.155  40.616  -7.157  1.00  21.31   A C
ATOM 1562  CD1  ILE A 230   2.017  40.655  -8.412  1.00  21.99   A C
ATOM 1563  C    ILE A 230  -1.231  43.634  -7.451  1.00  20.96   A C
ATOM 1564  O    ILE A 230  -1.671  44.119  -8.496  1.00  20.41   A O
ATOM 1565  N    LEU A 231  -1.870  43.709  -6.288  1.00  21.10   A N
ATOM 1566  CA   LEU A 231  -3.160  44.371  -6.167  1.00  21.66   A C
```

FIGURE 2A-29

```
ATOM   1567  CB   LEU A 231      -3.641  44.313  -4.717  1.00 21.59      A C
ATOM   1568  CG   LEU A 231      -4.923  45.102  -4.418  1.00 21.98      A C
ATOM   1569  CD1  LEU A 231      -6.115  44.467  -5.156  1.00 21.81      A C
ATOM   1570  CD2  LEU A 231      -5.162  45.126  -2.900  1.00 21.45      A C
ATOM   1571  C    LEU A 231      -3.115  45.834  -6.622  1.00 21.80      A C
ATOM   1572  O    LEU A 231      -3.990  46.292  -7.352  1.00 22.19      A O
ATOM   1573  N    LEU A 232      -2.096  46.563  -6.188  1.00 21.72      A N
ATOM   1574  CA   LEU A 232      -1.969  47.969  -6.531  1.00 21.57      A C
ATOM   1575  CB   LEU A 232      -0.797  48.594  -5.764  1.00 21.93      A C
ATOM   1576  CG   LEU A 232      -0.896  50.072  -5.358  1.00 23.20      A C
ATOM   1577  CD1  LEU A 232       0.518  50.660  -5.169  1.00 22.55      A C
ATOM   1578  CD2  LEU A 232      -1.698  50.861  -6.385  1.00 22.62      A C
ATOM   1579  C    LEU A 232      -1.754  48.138  -8.037  1.00 21.43      A C
ATOM   1580  O    LEU A 232      -2.353  49.020  -8.673  1.00 21.28      A O
ATOM   1581  N    TYR A 233      -0.893  47.306  -8.610  1.00 20.83      A N
ATOM   1582  CA   TYR A 233      -0.646  47.376 -10.041  1.00 20.65      A C
ATOM   1583  CB   TYR A 233       0.419  46.338 -10.442  1.00 20.34      A C
ATOM   1584  CG   TYR A 233       0.724  46.267 -11.937  1.00 20.14      A C
ATOM   1585  CD1  TYR A 233      -0.163  45.657 -12.813  1.00 19.91      A C
ATOM   1586  CE1  TYR A 233       0.066  45.643 -14.197  1.00 20.15      A C
ATOM   1587  CD2  TYR A 233       1.874  46.864 -12.467  1.00 19.65      A C
ATOM   1588  CE2  TYR A 233       2.120  46.864 -13.851  1.00 20.41      A C
ATOM   1589  CZ   TYR A 233       1.199  46.251 -14.712  1.00 20.36      A C
ATOM   1590  OH   TYR A 233       1.389  46.271 -16.079  1.00 20.44      A O
ATOM   1591  C    TYR A 233      -1.982  47.102 -10.741  1.00 20.78      A C
ATOM   1592  O    TYR A 233      -2.356  47.794 -11.684  1.00 21.23      A O
ATOM   1593  N    ASP A 234      -2.694  46.090 -10.267  1.00 20.79      A N
ATOM   1594  CA   ASP A 234      -3.992  45.709 -10.822  1.00 21.48      A C
ATOM   1595  CB   ASP A 234      -4.617  44.623  -9.950  1.00 21.66      A C
ATOM   1596  CG   ASP A 234      -5.945  44.118 -10.491  1.00 22.42      A C
ATOM   1597  OD1  ASP A 234      -6.869  43.947  -9.678  1.00 22.96      A O
ATOM   1598  OD2  ASP A 234      -6.072  43.871 -11.709  1.00 22.23      A O
ATOM   1599  C    ASP A 234      -4.924  46.922 -10.849  1.00 21.94      A C
ATOM   1600  O    ASP A 234      -5.552  47.210 -11.869  1.00 22.08      A O
ATOM   1601  N    MET A 235      -4.994  47.629  -9.724  1.00 22.03      A N
ATOM   1602  CA   MET A 235      -5.841  48.795  -9.611  1.00 22.98      A C
ATOM   1603  CB   MET A 235      -5.795  49.385  -8.195  1.00 23.37      A C
ATOM   1604  CG   MET A 235      -6.540  48.647  -7.137  1.00 24.11      A C
ATOM   1605  SD   MET A 235      -6.343  49.513  -5.592  1.00 25.96      A S
ATOM   1606  CE   MET A 235      -7.036  48.337  -4.560  1.00 25.71      A C
ATOM   1607  C    MET A 235      -5.458  49.906 -10.579  1.00 23.19      A C
ATOM   1608  O    MET A 235      -6.322  50.483 -11.221  1.00 23.42      A O
ATOM   1609  N    VAL A 236      -4.174  50.205 -10.706  1.00 23.39      A N
ATOM   1610  CA   VAL A 236      -3.798  51.309 -11.575  1.00 23.80      A C
ATOM   1611  CB   VAL A 236      -2.532  52.041 -11.051  1.00 23.52      A C
ATOM   1612  CG1  VAL A 236      -2.825  52.640  -9.667  1.00 23.41      A C
ATOM   1613  CG2  VAL A 236      -1.353  51.085 -11.003  1.00 22.95      A C
ATOM   1614  C    VAL A 236      -3.612  50.991 -13.039  1.00 24.33      A C
ATOM   1615  O    VAL A 236      -3.553  51.916 -13.848  1.00 24.47      A O
ATOM   1616  N    CYS A 237      -3.526  49.711 -13.394  1.00 24.96      A N
ATOM   1617  CA   CYS A 237      -3.351  49.351 -14.797  1.00 25.93      A C
ATOM   1618  CB   CYS A 237      -2.098  48.499 -14.978  1.00 26.03      A C
ATOM   1619  SG   CYS A 237      -0.572  49.426 -14.693  1.00 27.34      A S
ATOM   1620  C    CYS A 237      -4.557  48.615 -15.360  1.00 26.45      A C
ATOM   1621  O    CYS A 237      -4.694  48.478 -16.574  1.00 26.36      A O
ATOM   1622  N    GLY A 238      -5.431  48.142 -14.477  1.00 26.89      A N
```

FIGURE 2A-30

```
ATOM   1623  CA  GLY A 238      -6.610  47.439 -14.941  1.00 27.79      A C
ATOM   1624  C   GLY A 238      -6.442  45.939 -15.046  1.00 28.38      A C
ATOM   1625  O   GLY A 238      -7.397  45.237 -15.343  1.00 28.58      A O
ATOM   1626  N   ASP A 239      -5.235  45.441 -14.809  1.00 29.03      A N
ATOM   1627  CA  ASP A 239      -4.984  44.005 -14.859  1.00 29.80      A C
ATOM   1628  CB  ASP A 239      -4.803  43.556 -16.311  1.00 30.68      A C
ATOM   1629  CG  ASP A 239      -5.241  42.115 -16.538  1.00 32.06      A C
ATOM   1630  OD1 ASP A 239      -5.477  41.377 -15.545  1.00 31.91      A O
ATOM   1631  OD2 ASP A 239      -5.342  41.714 -17.732  1.00 33.33      A O
ATOM   1632  C   ASP A 239      -3.722  43.672 -14.046  1.00 29.86      A C
ATOM   1633  O   ASP A 239      -2.946  44.567 -13.725  1.00 29.61      A O
ATOM   1634  N   ILE A 240      -3.526  42.397 -13.710  1.00 30.02      A N
ATOM   1635  CA  ILE A 240      -2.357  41.996 -12.940  1.00 30.43      A C
ATOM   1636  CB  ILE A 240      -2.521  40.590 -12.330  1.00 30.48      A C
ATOM   1637  CG2 ILE A 240      -3.612  40.608 -11.306  1.00 30.30      A C
ATOM   1638  CG1 ILE A 240      -2.824  39.557 -13.417  1.00 30.75      A C
ATOM   1639  CD1 ILE A 240      -3.172  38.174 -12.853  1.00 30.65      A C
ATOM   1640  C   ILE A 240      -1.107  42.051 -13.816  1.00 30.71      A C
ATOM   1641  O   ILE A 240      -1.185  41.935 -15.041  1.00 30.63      A O
ATOM   1642  N   PRO A 241       0.065  42.248 -13.195  1.00 30.90      A N
ATOM   1643  CD  PRO A 241       0.263  42.401 -11.740  1.00 30.69      A C
ATOM   1644  CA  PRO A 241       1.345  42.340 -13.903  1.00 31.22      A C
ATOM   1645  CB  PRO A 241       2.256  42.988 -12.864  1.00 30.69      A C
ATOM   1646  CG  PRO A 241       1.780  42.365 -11.599  1.00 30.54      A C
ATOM   1647  C   PRO A 241       1.941  41.048 -14.445  1.00 31.70      A C
ATOM   1648  O   PRO A 241       2.576  41.052 -15.499  1.00 31.53      A O
ATOM   1649  N   PHE A 242       1.734  39.948 -13.730  1.00 32.38      A N
ATOM   1650  CA  PHE A 242       2.315  38.673 -14.130  1.00 33.18      A C
ATOM   1651  CB  PHE A 242       3.289  38.173 -13.056  1.00 32.46      A C
ATOM   1652  CG  PHE A 242       4.217  39.224 -12.527  1.00 32.00      A C
ATOM   1653  CD1 PHE A 242       5.030  39.957 -13.387  1.00 32.01      A C
ATOM   1654  CD2 PHE A 242       4.326  39.442 -11.156  1.00 31.90      A C
ATOM   1655  CE1 PHE A 242       5.948  40.892 -12.888  1.00 31.67      A C
ATOM   1656  CE2 PHE A 242       5.239  40.377 -10.645  1.00 31.75      A C
ATOM   1657  CZ  PHE A 242       6.051  41.099 -11.518  1.00 31.72      A C
ATOM   1658  C   PHE A 242       1.283  37.588 -14.358  1.00 34.17      A C
ATOM   1659  O   PHE A 242       0.263  37.536 -13.677  1.00 34.02      A O
ATOM   1660  N   GLU A 243       1.578  36.701 -15.306  1.00 35.68      A N
ATOM   1661  CA  GLU A 243       0.690  35.592 -15.621  1.00 37.17      A C
ATOM   1662  CB  GLU A 243       0.191  35.718 -17.058  1.00 38.37      A C
ATOM   1663  CG  GLU A 243      -0.773  34.623 -17.429  1.00 40.46      A C
ATOM   1664  CD  GLU A 243      -1.981  34.597 -16.509  1.00 41.75      A C
ATOM   1665  OE1 GLU A 243      -2.484  33.479 -16.244  1.00 42.90      A O
ATOM   1666  OE2 GLU A 243      -2.434  35.683 -16.058  1.00 42.14      A O
ATOM   1667  C   GLU A 243       1.381  34.229 -15.420  1.00 37.44      A C
ATOM   1668  O   GLU A 243       0.783  33.290 -14.885  1.00 37.69      A O
ATOM   1669  N   HIS A 244       2.640  34.125 -15.832  1.00 37.59      A N
ATOM   1670  CA  HIS A 244       3.371  32.871 -15.687  1.00 37.73      A C
ATOM   1671  CB  HIS A 244       4.007  32.488 -17.022  1.00 38.67      A C
ATOM   1672  CG  HIS A 244       3.034  32.488 -18.157  1.00 39.71      A C
ATOM   1673  CD2 HIS A 244       2.018  31.643 -18.455  1.00 40.05      A C
ATOM   1674  ND1 HIS A 244       2.972  33.508 -19.084  1.00 40.21      A N
ATOM   1675  CE1 HIS A 244       1.955  33.293 -19.902  1.00 40.42      A C
ATOM   1676  NE2 HIS A 244       1.360  32.169 -19.541  1.00 40.43      A N
ATOM   1677  C   HIS A 244       4.439  32.912 -14.607  1.00 37.28      A C
ATOM   1678  O   HIS A 244       4.936  33.980 -14.240  1.00 37.01      A O
```

FIGURE 2A-31

```
ATOM   1679  N   ASP A 245       4.781  31.729 -14.106  1.00 36.91      A N
ATOM   1680  CA  ASP A 245       5.797  31.580 -13.075  1.00 36.71      A C
ATOM   1681  CB  ASP A 245       6.093  30.099 -12.831  1.00 36.91      A C
ATOM   1682  CG  ASP A 245       4.953  29.376 -12.153  1.00 37.13      A C
ATOM   1683  OD1 ASP A 245       3.974  30.034 -11.757  1.00 37.37      A O
ATOM   1684  OD2 ASP A 245       5.042  28.139 -12.004  1.00 37.45      A O
ATOM   1685  C   ASP A 245       7.099  32.284 -13.449  1.00 36.37      A C
ATOM   1686  O   ASP A 245       7.727  32.910 -12.603  1.00 36.07      A O
ATOM   1687  N   GLU A 246       7.505  32.181 -14.711  1.00 36.32      A N
ATOM   1688  CA  GLU A 246       8.752  32.809 -15.150  1.00 36.57      A C
ATOM   1689  CB  GLU A 246       9.075  32.449 -16.603  1.00 37.61      A C
ATOM   1690  CG  GLU A 246       8.785  31.014 -16.942  1.00 39.64      A C
ATOM   1691  CD  GLU A 246       7.297  30.766 -17.042  1.00 40.62      A C
ATOM   1692  OE1 GLU A 246       6.653  31.497 -17.822  1.00 41.69      A O
ATOM   1693  OE2 GLU A 246       6.772  29.859 -16.356  1.00 41.20      A O
ATOM   1694  C   GLU A 246       8.723  34.325 -15.009  1.00 35.88      A C
ATOM   1695  O   GLU A 246       9.747  34.941 -14.737  1.00 35.51      A O
ATOM   1696  N   GLU A 247       7.557  34.929 -15.203  1.00 35.34      A N
ATOM   1697  CA  GLU A 247       7.459  36.381 -15.063  1.00 35.07      A C
ATOM   1698  CB  GLU A 247       6.144  36.896 -15.628  1.00 35.57      A C
ATOM   1699  CG  GLU A 247       5.958  36.634 -17.090  1.00 36.98      A C
ATOM   1700  CD  GLU A 247       4.575  37.029 -17.539  1.00 37.87      A C
ATOM   1701  OE1 GLU A 247       3.590  36.422 -17.061  1.00 38.25      A O
ATOM   1702  OE2 GLU A 247       4.469  37.959 -18.356  1.00 38.77      A O
ATOM   1703  C   GLU A 247       7.545  36.766 -13.593  1.00 34.05      A C
ATOM   1704  O   GLU A 247       8.173  37.764 -13.244  1.00 33.72      A O
ATOM   1705  N   ILE A 248       6.913  35.970 -12.739  1.00 33.26      A N
ATOM   1706  CA  ILE A 248       6.937  36.242 -11.309  1.00 32.78      A C
ATOM   1707  CB  ILE A 248       6.109  35.200 -10.501  1.00 32.24      A C
ATOM   1708  CG2 ILE A 248       6.351  35.386  -9.001  1.00 31.56      A C
ATOM   1709  CG1 ILE A 248       4.625  35.348 -10.834  1.00 31.76      A C
ATOM   1710  CD1 ILE A 248       3.726  34.293 -10.212  1.00 31.59      A C
ATOM   1711  C   ILE A 248       8.368  36.233 -10.798  1.00 32.81      A C
ATOM   1712  O   ILE A 248       8.795  37.176 -10.114  1.00 32.44      A O
ATOM   1713  N   ILE A 249       9.128  35.191 -11.135  1.00 33.07      A N
ATOM   1714  CA  ILE A 249      10.497  35.145 -10.642  1.00 33.44      A C
ATOM   1715  CB  ILE A 249      11.117  33.701 -10.688  1.00 33.72      A C
ATOM   1716  CG2 ILE A 249      10.148  32.695 -10.069  1.00 33.43      A C
ATOM   1717  CG1 ILE A 249      11.446  33.281 -12.111  1.00 33.87      A C
ATOM   1718  CD1 ILE A 249      12.115  31.923 -12.160  1.00 34.83      A C
ATOM   1719  C   ILE A 249      11.416  36.158 -11.324  1.00 33.55      A C
ATOM   1720  O   ILE A 249      12.393  36.577 -10.709  1.00 33.80      A O
ATOM   1721  N   ARG A 250      11.117  36.563 -12.565  1.00 33.46      A N
ATOM   1722  CA  ARG A 250      11.944  37.568 -13.241  1.00 33.83      A C
ATOM   1723  CB  ARG A 250      11.529  37.731 -14.712  1.00 33.99      A C
ATOM   1724  CG  ARG A 250      12.342  38.754 -15.452  1.00 34.86      A C
ATOM   1725  CD  ARG A 250      12.638  38.329 -16.849  1.00 35.54      A C
ATOM   1726  NE  ARG A 250      13.182  39.413 -17.657  1.00 36.63      A N
ATOM   1727  CZ  ARG A 250      12.489  40.321 -18.353  1.00 36.92      A C
ATOM   1728  NH1 ARG A 250      11.158  40.356 -18.396  1.00 36.47      A N
ATOM   1729  NH2 ARG A 250      13.175  41.216 -19.040  1.00 37.45      A N
ATOM   1730  C   ARG A 250      11.721  38.876 -12.480  1.00 33.88      A C
ATOM   1731  O   ARG A 250      12.645  39.673 -12.270  1.00 33.90      A O
ATOM   1732  N   GLY A 251      10.469  39.070 -12.079  1.00 33.73      A N
ATOM   1733  CA  GLY A 251      10.088  40.234 -11.310  1.00 33.72      A C
ATOM   1734  C   GLY A 251      10.156  41.591 -11.978  1.00 33.70      A C
```

FIGURE 2A-32

```
ATOM   1735  O    GLY A 251      10.078  42.604 -11.283  1.00 34.00      A O
ATOM   1736  N    GLN A 252      10.317  41.658 -13.296  1.00 33.52      A N
ATOM   1737  CA   GLN A 252      10.348  42.976 -13.932  1.00 33.25      A C
ATOM   1738  CB   GLN A 252      11.186  42.982 -15.207  1.00 33.90      A C
ATOM   1739  CG   GLN A 252      12.667  43.024 -14.915  1.00 35.25      A C
ATOM   1740  CD   GLN A 252      13.481  43.478 -16.101  1.00 36.18      A C
ATOM   1741  OE1  GLN A 252      13.279  44.580 -16.630  1.00 36.77      A O
ATOM   1742  NE2  GLN A 252      14.417  42.634 -16.531  1.00 36.67      A N
ATOM   1743  C    GLN A 252       8.940  43.439 -14.239  1.00 32.60      A C
ATOM   1744  O    GLN A 252       8.149  42.723 -14.847  1.00 32.43      A O
ATOM   1745  N    VAL A 253       8.636  44.648 -13.799  1.00 32.00      A N
ATOM   1746  CA   VAL A 253       7.317  45.216 -13.987  1.00 31.51      A C
ATOM   1747  CB   VAL A 253       6.893  46.011 -12.734  1.00 31.25      A C
ATOM   1748  CG1  VAL A 253       5.515  46.592 -12.921  1.00 30.52      A C
ATOM   1749  CG2  VAL A 253       6.939  45.102 -11.517  1.00 31.64      A C
ATOM   1750  C    VAL A 253       7.231  46.145 -15.183  1.00 31.26      A C
ATOM   1751  O    VAL A 253       7.956  47.127 -15.268  1.00 31.36      A O
ATOM   1752  N    PHE A 254       6.331  45.839 -16.098  1.00 31.20      A N
ATOM   1753  CA   PHE A 254       6.124  46.684 -17.259  1.00 31.40      A C
ATOM   1754  CB   PHE A 254       6.115  45.835 -18.537  1.00 31.58      A C
ATOM   1755  CG   PHE A 254       5.605  46.576 -19.736  1.00 32.53      A C
ATOM   1756  CD1  PHE A 254       4.237  46.610 -20.025  1.00 32.57      A C
ATOM   1757  CD2  PHE A 254       6.476  47.315 -20.538  1.00 32.61      A C
ATOM   1758  CE1  PHE A 254       3.753  47.378 -21.093  1.00 32.96      A C
ATOM   1759  CE2  PHE A 254       5.993  48.085 -21.608  1.00 32.49      A C
ATOM   1760  CZ   PHE A 254       4.639  48.116 -21.882  1.00 32.33      A C
ATOM   1761  C    PHE A 254       4.779  47.398 -17.082  1.00 31.29      A C
ATOM   1762  O    PHE A 254       3.785  46.756 -16.755  1.00 31.45      A O
ATOM   1763  N    PHE A 255       4.737  48.714 -17.279  1.00 31.00      A N
ATOM   1764  CA   PHE A 255       3.476  49.443 -17.132  1.00 31.15      A C
ATOM   1765  CB   PHE A 255       3.705  50.779 -16.421  1.00 30.06      A C
ATOM   1766  CG   PHE A 255       3.921  50.632 -14.949  1.00 29.23      A C
ATOM   1767  CD1  PHE A 255       5.179  50.319 -14.446  1.00 28.55      A C
ATOM   1768  CD2  PHE A 255       2.837  50.708 -14.066  1.00 28.82      A C
ATOM   1769  CE1  PHE A 255       5.365  50.074 -13.095  1.00 28.37      A C
ATOM   1770  CE2  PHE A 255       3.010  50.466 -12.712  1.00 28.31      A C
ATOM   1771  CZ   PHE A 255       4.273  50.146 -12.221  1.00 28.44      A C
ATOM   1772  C    PHE A 255       2.737  49.666 -18.446  1.00 31.69      A C
ATOM   1773  O    PHE A 255       3.240  50.330 -19.347  1.00 31.81      A O
ATOM   1774  N    ARG A 256       1.536  49.103 -18.542  1.00 32.57      A N
ATOM   1775  CA   ARG A 256       0.721  49.208 -19.753  1.00 33.38      A C
ATOM   1776  CB   ARG A 256      -0.159  47.950 -19.902  1.00 34.40      A C
ATOM   1777  CG   ARG A 256      -0.975  47.587 -18.653  1.00 35.95      A C
ATOM   1778  CD   ARG A 256      -1.887  46.373 -18.903  1.00 37.38      A C
ATOM   1779  NE   ARG A 256      -1.176  45.090 -18.951  1.00 38.60      A N
ATOM   1780  CZ   ARG A 256      -0.995  44.286 -17.901  1.00 38.94      A C
ATOM   1781  NH1  ARG A 256      -1.476  44.626 -16.715  1.00 39.57      A N
ATOM   1782  NH2  ARG A 256      -0.330  43.146 -18.029  1.00 38.97      A N
ATOM   1783  C    ARG A 256      -0.153  50.455 -19.780  1.00 33.11      A C
ATOM   1784  O    ARG A 256      -0.785  50.754 -20.786  1.00 33.46      A O
ATOM   1785  N    GLN A 257      -0.176  51.181 -18.669  1.00 32.72      A N
ATOM   1786  CA   GLN A 257      -0.973  52.395 -18.538  1.00 32.11      A C
ATOM   1787  CB   GLN A 257      -2.165  52.148 -17.600  1.00 33.44      A C
ATOM   1788  CG   GLN A 257      -3.142  51.069 -18.037  1.00 35.31      A C
ATOM   1789  CD   GLN A 257      -4.067  51.553 -19.132  1.00 36.64      A C
ATOM   1790  OE1  GLN A 257      -4.653  52.638 -19.028  1.00 37.18      A O
```

FIGURE 2A-33

| ATOM | 1791 | NE2 | GLN | A | 257 | -4.209 | 50.751 | -20.192 | 1.00 | 37.39 | A | N |
|------|------|-----|-----|---|-----|--------|--------|---------|------|-------|---|---|
| ATOM | 1792 | C   | GLN | A | 257 | -0.115 | 53.504 | -17.925 | 1.00 | 31.03 | A | C |
| ATOM | 1793 | O   | GLN | A | 257 | 0.894  | 53.235 | -17.276 | 1.00 | 30.46 | A | O |
| ATOM | 1794 | N   | ARG | A | 258 | -0.533 | 54.747 | -18.120 | 1.00 | 29.82 | A | N |
| ATOM | 1795 | CA  | ARG | A | 258 | 0.180  | 55.877 | -17.558 | 1.00 | 29.07 | A | C |
| ATOM | 1796 | CB  | ARG | A | 258 | -0.381 | 57.182 | -18.115 | 1.00 | 29.25 | A | C |
| ATOM | 1797 | CG  | ARG | A | 258 | 0.544  | 58.348 | -17.936 | 1.00 | 29.72 | A | C |
| ATOM | 1798 | CD  | ARG | A | 258 | 0.541  | 58.874 | -16.530 | 1.00 | 30.84 | A | C |
| ATOM | 1799 | NE  | ARG | A | 258 | 1.702  | 59.730 | -16.323 | 1.00 | 31.85 | A | N |
| ATOM | 1800 | CZ  | ARG | A | 258 | 1.953  | 60.421 | -15.214 | 1.00 | 32.93 | A | C |
| ATOM | 1801 | NH1 | ARG | A | 258 | 1.109  | 60.374 | -14.170 | 1.00 | 33.10 | A | N |
| ATOM | 1802 | NH2 | ARG | A | 258 | 3.062  | 61.158 | -15.145 | 1.00 | 32.87 | A | N |
| ATOM | 1803 | C   | ARG | A | 258 | 0.021  | 55.858 | -16.036 | 1.00 | 28.35 | A | C |
| ATOM | 1804 | O   | ARG | A | 258 | -1.093 | 55.928 | -15.532 | 1.00 | 27.92 | A | O |
| ATOM | 1805 | N   | VAL | A | 259 | 1.134  | 55.759 | -15.319 | 1.00 | 27.52 | A | N |
| ATOM | 1806 | CA  | VAL | A | 259 | 1.122  | 55.725 | -13.865 | 1.00 | 27.05 | A | C |
| ATOM | 1807 | CB  | VAL | A | 259 | 1.352  | 54.272 | -13.343 | 1.00 | 27.08 | A | C |
| ATOM | 1808 | CG1 | VAL | A | 259 | 1.436  | 54.251 | -11.799 | 1.00 | 26.35 | A | C |
| ATOM | 1809 | CG2 | VAL | A | 259 | 0.232  | 53.373 | -13.817 | 1.00 | 26.53 | A | C |
| ATOM | 1810 | C   | VAL | A | 259 | 2.242  | 56.636 | -13.354 | 1.00 | 27.10 | A | C |
| ATOM | 1811 | O   | VAL | A | 259 | 3.365  | 56.591 | -13.863 | 1.00 | 26.84 | A | O |
| ATOM | 1812 | N   | SER | A | 260 | 1.942  | 57.457 | -12.354 | 1.00 | 26.98 | A | N |
| ATOM | 1813 | CA  | SER | A | 260 | 2.940  | 58.377 | -11.809 | 1.00 | 27.48 | A | C |
| ATOM | 1814 | CB  | SER | A | 260 | 2.368  | 59.170 | -10.628 | 1.00 | 26.89 | A | C |
| ATOM | 1815 | OG  | SER | A | 260 | 2.116  | 58.330 | -9.511  | 1.00 | 26.28 | A | O |
| ATOM | 1816 | C   | SER | A | 260 | 4.205  | 57.666 | -11.360 | 1.00 | 27.95 | A | C |
| ATOM | 1817 | O   | SER | A | 260 | 4.176  | 56.489 | -11.003 | 1.00 | 28.17 | A | O |
| ATOM | 1818 | N   | PSR | A | 261 | 5.312  | 58.396 | -11.375 | 1.00 | 28.70 | A | N |
| ATOM | 1819 | CA  | PSR | A | 261 | 6.604  | 57.862 | -10.971 | 1.00 | 29.59 | A | C |
| ATOM | 1820 | CB  | PSR | A | 261 | 7.688  | 58.934 | -11.161 | 1.00 | 31.24 | A | C |
| ATOM | 1821 | OG  | PSR | A | 261 | 7.616  | 59.491 | -12.511 | 1.00 | 34.22 | A | O |
| ATOM | 1822 | C   | PSR | A | 261 | 6.567  | 57.388 | -9.511  | 1.00 | 29.22 | A | C |
| ATOM | 1823 | O   | PSR | A | 261 | 7.204  | 56.395 | -9.153  | 1.00 | 29.05 | A | O |
| ATOM | 1824 | P   | PSR | A | 261 | 6.823  | 61.050 | -12.979 | 1.00 | 37.32 | A | P |
| ATOM | 1825 | O1  | PSR | A | 261 | 7.451  | 62.297 | -12.352 | 1.00 | 36.03 | A | O |
| ATOM | 1826 | O2  | PSR | A | 261 | 7.088  | 61.056 | -14.601 | 1.00 | 35.85 | A | O |
| ATOM | 1827 | O3  | PSR | A | 261 | 5.247  | 61.006 | -12.597 | 1.00 | 35.30 | A | O |
| ATOM | 1828 | N   | GLU | A | 262 | 5.819  | 58.091 | -8.668  | 1.00 | 28.88 | A | N |
| ATOM | 1829 | CA  | GLU | A | 262 | 5.723  | 57.707 | -7.263  | 1.00 | 28.67 | A | C |
| ATOM | 1830 | CB  | GLU | A | 262 | 5.120  | 58.845 | -6.428  | 1.00 | 29.89 | A | C |
| ATOM | 1831 | CG  | GLU | A | 262 | 6.143  | 59.931 | -6.101  | 1.00 | 32.10 | A | C |
| ATOM | 1832 | CD  | GLU | A | 262 | 5.552  | 61.113 | -5.359  | 1.00 | 33.87 | A | C |
| ATOM | 1833 | OE1 | GLU | A | 262 | 6.334  | 62.036 | -5.022  | 1.00 | 35.19 | A | O |
| ATOM | 1834 | OE2 | GLU | A | 262 | 4.319  | 61.134 | -5.115  | 1.00 | 34.79 | A | O |
| ATOM | 1835 | C   | GLU | A | 262 | 4.931  | 56.420 | -7.059  | 1.00 | 27.43 | A | C |
| ATOM | 1836 | O   | GLU | A | 262 | 5.278  | 55.627 | -6.195  | 1.00 | 27.16 | A | O |
| ATOM | 1837 | N   | CYS | A | 263 | 3.877  | 56.214 | -7.848  | 1.00 | 26.30 | A | N |
| ATOM | 1838 | CA  | CYS | A | 263 | 3.082  | 54.997 | -7.738  | 1.00 | 25.26 | A | C |
| ATOM | 1839 | CB  | CYS | A | 263 | 1.778  | 55.112 | -8.535  | 1.00 | 24.74 | A | C |
| ATOM | 1840 | SG  | CYS | A | 263 | 0.611  | 53.714 | -8.325  | 1.00 | 24.55 | A | S |
| ATOM | 1841 | C   | CYS | A | 263 | 3.936  | 53.846 | -8.266  | 1.00 | 24.99 | A | C |
| ATOM | 1842 | O   | CYS | A | 263 | 4.035  | 52.804 | -7.628  | 1.00 | 24.79 | A | O |
| ATOM | 1843 | N   | GLN | A | 264 | 4.557  | 54.039 | -9.426  | 1.00 | 24.65 | A | N |
| ATOM | 1844 | CA  | GLN | A | 264 | 5.425  | 53.010 | -9.991  | 1.00 | 24.72 | A | C |
| ATOM | 1845 | CB  | GLN | A | 264 | 6.120  | 53.511 | -11.265 | 1.00 | 24.67 | A | C |
| ATOM | 1846 | CG  | GLN | A | 264 | 5.272  | 53.429 | -12.528 | 1.00 | 24.85 | A | C |

FIGURE 2A-34

| ATOM | 1847 | CD | GLN | A | 264 | 6.096 | 53.666 | -13.790 | 1.00 | 25.54 | A | C |
|------|------|-----|-----|---|-----|--------|--------|---------|------|-------|---|---|
| ATOM | 1848 | OE1 | GLN | A | 264 | 7.286 | 53.342 | -13.833 | 1.00 | 25.78 | A | O |
| ATOM | 1849 | NE2 | GLN | A | 264 | 5.462 | 54.207 | -14.827 | 1.00 | 25.21 | A | N |
| ATOM | 1850 | C | GLN | A | 264 | 6.492 | 52.624 | -8.968 | 1.00 | 24.61 | A | C |
| ATOM | 1851 | O | GLN | A | 264 | 6.845 | 51.449 | -8.821 | 1.00 | 24.48 | A | O |
| ATOM | 1852 | N | HIS | A | 265 | 7.014 | 53.618 | -8.261 | 1.00 | 24.42 | A | N |
| ATOM | 1853 | CA | HIS | A | 265 | 8.029 | 53.330 | -7.269 | 1.00 | 24.66 | A | C |
| ATOM | 1854 | CB | HIS | A | 265 | 8.601 | 54.623 | -6.685 | 1.00 | 25.32 | A | C |
| ATOM | 1855 | CG | HIS | A | 265 | 9.568 | 54.390 | -5.567 | 1.00 | 26.67 | A | C |
| ATOM | 1856 | CD2 | HIS | A | 265 | 10.894 | 54.102 | -5.579 | 1.00 | 26.96 | A | C |
| ATOM | 1857 | ND1 | HIS | A | 265 | 9.184 | 54.383 | -4.243 | 1.00 | 27.00 | A | N |
| ATOM | 1858 | CE1 | HIS | A | 265 | 10.233 | 54.102 | -3.486 | 1.00 | 27.50 | A | C |
| ATOM | 1859 | NE2 | HIS | A | 265 | 11.281 | 53.926 | -4.273 | 1.00 | 27.52 | A | N |
| ATOM | 1860 | C | HIS | A | 265 | 7.474 | 52.438 | -6.150 | 1.00 | 23.97 | A | C |
| ATOM | 1861 | O | HIS | A | 265 | 8.070 | 51.426 | -5.818 | 1.00 | 23.59 | A | O |
| ATOM | 1862 | N | LEU | A | 266 | 6.330 | 52.805 | -5.579 | 1.00 | 23.37 | A | N |
| ATOM | 1863 | CA | LEU | A | 266 | 5.741 | 51.995 | -4.511 | 1.00 | 22.89 | A | C |
| ATOM | 1864 | CB | LEU | A | 266 | 4.438 | 52.641 | -3.998 | 1.00 | 22.42 | A | C |
| ATOM | 1865 | CG | LEU | A | 266 | 3.705 | 51.916 | -2.856 | 1.00 | 22.40 | A | C |
| ATOM | 1866 | CD1 | LEU | A | 266 | 4.667 | 51.626 | -1.695 | 1.00 | 21.72 | A | C |
| ATOM | 1867 | CD2 | LEU | A | 266 | 2.539 | 52.777 | -2.365 | 1.00 | 21.68 | A | C |
| ATOM | 1868 | C | LEU | A | 266 | 5.474 | 50.563 | -5.004 | 1.00 | 22.67 | A | C |
| ATOM | 1869 | O | LEU | A | 266 | 5.739 | 49.594 | -4.291 | 1.00 | 22.60 | A | O |
| ATOM | 1870 | N | ILE | A | 267 | 4.982 | 50.424 | -6.229 | 1.00 | 22.27 | A | N |
| ATOM | 1871 | CA | ILE | A | 267 | 4.702 | 49.101 | -6.761 | 1.00 | 22.30 | A | C |
| ATOM | 1872 | CB | ILE | A | 267 | 4.013 | 49.196 | -8.137 | 1.00 | 21.95 | A | C |
| ATOM | 1873 | CG2 | ILE | A | 267 | 4.023 | 47.840 | -8.824 | 1.00 | 21.59 | A | C |
| ATOM | 1874 | CG1 | ILE | A | 267 | 2.575 | 49.693 | -7.961 | 1.00 | 21.55 | A | C |
| ATOM | 1875 | CD1 | ILE | A | 267 | 1.861 | 50.038 | -9.277 | 1.00 | 21.25 | A | C |
| ATOM | 1876 | C | ILE | A | 267 | 5.957 | 48.238 | -6.886 | 1.00 | 22.81 | A | C |
| ATOM | 1877 | O | ILE | A | 267 | 5.962 | 47.066 | -6.489 | 1.00 | 23.11 | A | O |
| ATOM | 1878 | N | ARG | A | 268 | 7.024 | 48.803 | -7.430 | 1.00 | 23.08 | A | N |
| ATOM | 1879 | CA | ARG | A | 268 | 8.249 | 48.043 | -7.592 | 1.00 | 23.64 | A | C |
| ATOM | 1880 | CB | ARG | A | 268 | 9.238 | 48.810 | -8.489 | 1.00 | 24.18 | A | C |
| ATOM | 1881 | CG | ARG | A | 268 | 8.779 | 48.872 | -9.935 | 1.00 | 24.60 | A | C |
| ATOM | 1882 | CD | ARG | A | 268 | 9.836 | 49.437 | -10.847 | 1.00 | 25.54 | A | C |
| ATOM | 1883 | NE | ARG | A | 268 | 9.482 | 49.192 | -12.247 | 1.00 | 26.34 | A | N |
| ATOM | 1884 | CZ | ARG | A | 268 | 9.052 | 50.128 | -13.092 | 1.00 | 26.56 | A | C |
| ATOM | 1885 | NH1 | ARG | A | 268 | 8.926 | 51.392 | -12.691 | 1.00 | 26.63 | A | N |
| ATOM | 1886 | NH2 | ARG | A | 268 | 8.727 | 49.793 | -14.330 | 1.00 | 26.36 | A | N |
| ATOM | 1887 | C | ARG | A | 268 | 8.890 | 47.707 | -6.257 | 1.00 | 23.61 | A | C |
| ATOM | 1888 | O | ARG | A | 268 | 9.600 | 46.710 | -6.136 | 1.00 | 23.79 | A | O |
| ATOM | 1889 | N | TRP | A | 269 | 8.634 | 48.531 | -5.248 | 1.00 | 23.51 | A | N |
| ATOM | 1890 | CA | TRP | A | 269 | 9.194 | 48.283 | -3.927 | 1.00 | 23.53 | A | C |
| ATOM | 1891 | CB | TRP | A | 269 | 9.065 | 49.557 | -3.065 | 1.00 | 23.84 | A | C |
| ATOM | 1892 | CG | TRP | A | 269 | 9.810 | 49.534 | -1.747 | 1.00 | 24.35 | A | C |
| ATOM | 1893 | CD2 | TRP | A | 269 | 9.707 | 50.496 | -0.684 | 1.00 | 24.46 | A | C |
| ATOM | 1894 | CE2 | TRP | A | 269 | 10.588 | 50.083 | 0.346 | 1.00 | 24.57 | A | C |
| ATOM | 1895 | CE3 | TRP | A | 269 | 8.958 | 51.665 | -0.502 | 1.00 | 24.77 | A | C |
| ATOM | 1896 | CD1 | TRP | A | 269 | 10.729 | 48.601 | -1.328 | 1.00 | 24.62 | A | C |
| ATOM | 1897 | NE1 | TRP | A | 269 | 11.197 | 48.927 | -0.071 | 1.00 | 24.37 | A | N |
| ATOM | 1898 | CZ2 | TRP | A | 269 | 10.738 | 50.798 | 1.540 | 1.00 | 24.59 | A | C |
| ATOM | 1899 | CZ3 | TRP | A | 269 | 9.109 | 52.381 | 0.694 | 1.00 | 25.02 | A | C |
| ATOM | 1900 | CH2 | TRP | A | 269 | 9.994 | 51.940 | 1.697 | 1.00 | 24.80 | A | C |
| ATOM | 1901 | C | TRP | A | 269 | 8.449 | 47.074 | -3.322 | 1.00 | 23.32 | A | C |
| ATOM | 1902 | O | TRP | A | 269 | 9.077 | 46.122 | -2.844 | 1.00 | 23.39 | A | O |

FIGURE 2A-35

```
ATOM   1903  N    CYS A 270       7.118  47.095  -3.367  1.00 22.88      A N
ATOM   1904  CA   CYS A 270       6.328  45.977  -2.847  1.00 22.48      A C
ATOM   1905  CB   CYS A 270       4.821  46.242  -3.016  1.00 22.41      A C
ATOM   1906  SG   CYS A 270       4.173  47.522  -1.929  1.00 23.18      A S
ATOM   1907  C    CYS A 270       6.683  44.683  -3.573  1.00 22.30      A C
ATOM   1908  O    CYS A 270       6.623  43.602  -2.987  1.00 22.05      A O
ATOM   1909  N    LEU A 271       7.066  44.792  -4.846  1.00 22.32      A N
ATOM   1910  CA   LEU A 271       7.416  43.608  -5.634  1.00 22.79      A C
ATOM   1911  CB   LEU A 271       6.852  43.740  -7.047  1.00 22.39      A C
ATOM   1912  CG   LEU A 271       5.335  43.941  -7.087  1.00 22.47      A C
ATOM   1913  CD1  LEU A 271       4.869  44.139  -8.535  1.00 21.83      A C
ATOM   1914  CD2  LEU A 271       4.649  42.714  -6.445  1.00 21.83      A C
ATOM   1915  C    LEU A 271       8.917  43.288  -5.710  1.00 23.18      A C
ATOM   1916  O    LEU A 271       9.371  42.643  -6.657  1.00 22.86      A O
ATOM   1917  N    ALA A 272       9.678  43.722  -4.710  1.00 23.63      A N
ATOM   1918  CA   ALA A 272      11.112  43.446  -4.695  1.00 24.38      A C
ATOM   1919  CB   ALA A 272      11.789  44.129  -3.490  1.00 24.22      A C
ATOM   1920  C    ALA A 272      11.271  41.937  -4.617  1.00 24.94      A C
ATOM   1921  O    ALA A 272      10.559  41.258  -3.865  1.00 24.37      A O
ATOM   1922  N    LEU A 273      12.193  41.427  -5.426  1.00 25.88      A N
ATOM   1923  CA   LEU A 273      12.487  40.008  -5.501  1.00 27.04      A C
ATOM   1924  CB   LEU A 273      13.612  39.786  -6.528  1.00 27.19      A C
ATOM   1925  CG   LEU A 273      13.279  39.024  -7.814  1.00 27.71      A C
ATOM   1926  CD1  LEU A 273      11.796  39.113  -8.123  1.00 27.34      A C
ATOM   1927  CD2  LEU A 273      14.133  39.568  -8.972  1.00 27.38      A C
ATOM   1928  C    LEU A 273      12.890  39.448  -4.135  1.00 27.55      A C
ATOM   1929  O    LEU A 273      12.421  38.387  -3.723  1.00 27.51      A O
ATOM   1930  N    ARG A 274      13.754  40.161  -3.427  1.00 28.36      A N
ATOM   1931  CA   ARG A 274      14.187  39.696  -2.116  1.00 29.64      A C
ATOM   1932  CB   ARG A 274      15.574  40.266  -1.777  1.00 31.22      A C
ATOM   1933  CG   ARG A 274      16.046  39.928  -0.356  1.00 34.10      A C
ATOM   1934  CD   ARG A 274      17.230  40.808   0.125  1.00 36.50      A C
ATOM   1935  NE   ARG A 274      18.539  40.398  -0.394  1.00 38.44      A N
ATOM   1936  CZ   ARG A 274      18.939  40.534  -1.657  1.00 39.72      A C
ATOM   1937  NH1  ARG A 274      18.139  41.077  -2.572  1.00 40.42      A N
ATOM   1938  NH2  ARG A 274      20.154  40.122  -2.012  1.00 40.52      A N
ATOM   1939  C    ARG A 274      13.159  40.130  -1.074  1.00 29.49      A C
ATOM   1940  O    ARG A 274      12.907  41.317  -0.908  1.00 29.62      A O
ATOM   1941  N    PRO A 275      12.547  39.168  -0.362  1.00 29.37      A N
ATOM   1942  CD   PRO A 275      12.807  37.720  -0.477  1.00 29.33      A C
ATOM   1943  CA   PRO A 275      11.537  39.447   0.669  1.00 29.42      A C
ATOM   1944  CB   PRO A 275      11.411  38.117   1.396  1.00 29.45      A C
ATOM   1945  CG   PRO A 275      11.654  37.117   0.293  1.00 29.48      A C
ATOM   1946  C    PRO A 275      11.897  40.584   1.630  1.00 29.65      A C
ATOM   1947  O    PRO A 275      11.075  41.468   1.893  1.00 29.60      A O
ATOM   1948  N    SER A 276      13.123  40.559   2.152  1.00 29.63      A N
ATOM   1949  CA   SER A 276      13.578  41.573   3.097  1.00 29.63      A C
ATOM   1950  CB   SER A 276      14.915  41.155   3.731  1.00 29.91      A C
ATOM   1951  OG   SER A 276      15.992  41.207   2.803  1.00 30.23      A O
ATOM   1952  C    SER A 276      13.716  42.959   2.472  1.00 29.65      A C
ATOM   1953  O    SER A 276      13.812  43.957   3.190  1.00 29.77      A O
ATOM   1954  N    ASP A 277      13.721  43.029   1.143  1.00 29.52      A N
ATOM   1955  CA   ASP A 277      13.837  44.315   0.454  1.00 29.25      A C
ATOM   1956  CB   ASP A 277      14.433  44.126  -0.939  1.00 30.03      A C
ATOM   1957  CG   ASP A 277      15.967  44.158  -0.953  1.00 30.62      A C
ATOM   1958  OD1  ASP A 277      16.551  43.717  -1.963  1.00 31.32      A O
```

FIGURE 2A-36

```
ATOM   1959  OD2 ASP A 277      16.587  44.624   0.018  1.00 30.75      A O
ATOM   1960  C   ASP A 277      12.479  45.009   0.308  1.00 28.97      A C
ATOM   1961  O   ASP A 277      12.419  46.157  -0.141  1.00 29.31      A O
ATOM   1962  N   ARG A 278      11.399  44.318   0.667  1.00 27.83      A N
ATOM   1963  CA  ARG A 278      10.059  44.888   0.558  1.00 27.29      A C
ATOM   1964  CB  ARG A 278       9.006  43.775   0.470  1.00 26.28      A C
ATOM   1965  CG  ARG A 278       9.108  42.973  -0.818  1.00 25.60      A C
ATOM   1966  CD  ARG A 278       8.281  41.683  -0.799  1.00 24.72      A C
ATOM   1967  NE  ARG A 278       8.865  40.736  -1.742  1.00 23.44      A N
ATOM   1968  CZ  ARG A 278       8.686  39.420  -1.724  1.00 23.02      A C
ATOM   1969  NH1 ARG A 278       7.913  38.844  -0.808  1.00 22.65      A N
ATOM   1970  NH2 ARG A 278       9.334  38.673  -2.601  1.00 22.37      A N
ATOM   1971  C   ARG A 278       9.753  45.787   1.737  1.00 27.20      A C
ATOM   1972  O   ARG A 278      10.350  45.656   2.801  1.00 27.45      A O
ATOM   1973  N   PRO A 279       8.818  46.725   1.563  1.00 27.16      A N
ATOM   1974  CD  PRO A 279       8.088  47.070   0.326  1.00 27.13      A C
ATOM   1975  CA  PRO A 279       8.462  47.632   2.652  1.00 27.11      A C
ATOM   1976  CB  PRO A 279       7.726  48.753   1.934  1.00 27.11      A C
ATOM   1977  CG  PRO A 279       7.030  48.019   0.831  1.00 27.27      A C
ATOM   1978  C   PRO A 279       7.575  46.990   3.707  1.00 27.37      A C
ATOM   1979  O   PRO A 279       6.885  45.994   3.438  1.00 27.41      A O
ATOM   1980  N   THR A 280       7.609  47.572   4.905  1.00 27.28      A N
ATOM   1981  CA  THR A 280       6.767  47.155   6.025  1.00 27.53      A C
ATOM   1982  CB  THR A 280       7.343  47.643   7.372  1.00 27.49      A C
ATOM   1983  OG1 THR A 280       7.508  49.062   7.315  1.00 27.40      A O
ATOM   1984  CG2 THR A 280       8.712  47.019   7.654  1.00 27.23      A C
ATOM   1985  C   THR A 280       5.466  47.930   5.773  1.00 27.87      A C
ATOM   1986  O   THR A 280       5.452  48.861   4.959  1.00 27.53      A O
ATOM   1987  N   PHE A 281       4.385  47.570   6.456  1.00 28.47      A N
ATOM   1988  CA  PHE A 281       3.126  48.277   6.266  1.00 29.10      A C
ATOM   1989  CB  PHE A 281       2.035  47.672   7.143  1.00 30.37      A C
ATOM   1990  CG  PHE A 281       1.547  46.363   6.649  1.00 31.79      A C
ATOM   1991  CD1 PHE A 281       2.339  45.231   6.752  1.00 33.01      A C
ATOM   1992  CD2 PHE A 281       0.324  46.260   6.018  1.00 32.62      A C
ATOM   1993  CE1 PHE A 281       1.917  44.011   6.227  1.00 33.47      A C
ATOM   1994  CE2 PHE A 281      -0.102  45.040   5.489  1.00 33.23      A C
ATOM   1995  CZ  PHE A 281       0.696  43.916   5.595  1.00 33.29      A C
ATOM   1996  C   PHE A 281       3.265  49.753   6.573  1.00 28.99      A C
ATOM   1997  O   PHE A 281       2.669  50.599   5.899  1.00 28.64      A O
ATOM   1998  N   GLU A 282       4.069  50.058   7.588  1.00 28.82      A N
ATOM   1999  CA  GLU A 282       4.298  51.444   7.984  1.00 28.61      A C
ATOM   2000  CB  GLU A 282       5.151  51.502   9.258  1.00 29.25      A C
ATOM   2001  CG  GLU A 282       5.550  52.906   9.694  1.00 30.72      A C
ATOM   2002  CD  GLU A 282       6.377  52.909  10.986  1.00 31.82      A C
ATOM   2003  OE1 GLU A 282       7.238  52.018  11.154  1.00 32.10      A O
ATOM   2004  OE2 GLU A 282       6.174  53.808  11.830  1.00 32.22      A O
ATOM   2005  C   GLU A 282       4.994  52.185   6.845  1.00 27.93      A C
ATOM   2006  O   GLU A 282       4.626  53.313   6.526  1.00 27.53      A O
ATOM   2007  N   GLU A 283       5.993  51.550   6.235  1.00 27.27      A N
ATOM   2008  CA  GLU A 283       6.705  52.179   5.123  1.00 27.17      A C
ATOM   2009  CB  GLU A 283       7.913  51.346   4.723  1.00 27.15      A C
ATOM   2010  CG  GLU A 283       9.014  51.390   5.749  1.00 28.08      A C
ATOM   2011  CD  GLU A 283      10.172  50.483   5.398  1.00 28.16      A C
ATOM   2012  OE1 GLU A 283       9.952  49.282   5.196  1.00 28.68      A O
ATOM   2013  OE2 GLU A 283      11.310  50.974   5.328  1.00 29.17      A O
ATOM   2014  C   GLU A 283       5.805  52.408   3.901  1.00 26.64      A C
```

FIGURE 2A-37

```
ATOM   2015  O    GLU A 283       5.973  53.388   3.170  1.00 26.50    A O
ATOM   2016  N    ILE A 284       4.853  51.507   3.677  1.00 26.15    A N
ATOM   2017  CA   ILE A 284       3.942  51.673   2.553  1.00 25.62    A C
ATOM   2018  CB   ILE A 284       3.055  50.425   2.345  1.00 25.27    A C
ATOM   2019  CG2  ILE A 284       1.925  50.735   1.322  1.00 24.83    A C
ATOM   2020  CG1  ILE A 284       3.917  49.256   1.866  1.00 24.82    A C
ATOM   2021  CD1  ILE A 284       3.135  48.009   1.616  1.00 25.07    A C
ATOM   2022  C    ILE A 284       3.034  52.882   2.796  1.00 25.78    A C
ATOM   2023  O    ILE A 284       2.889  53.739   1.918  1.00 25.89    A O
ATOM   2024  N    GLN A 285       2.440  52.959   3.989  1.00 25.49    A N
ATOM   2025  CA   GLN A 285       1.536  54.061   4.330  1.00 25.62    A C
ATOM   2026  CB   GLN A 285       0.693  53.692   5.565  1.00 25.31    A C
ATOM   2027  CG   GLN A 285      -0.267  52.526   5.295  1.00 24.96    A C
ATOM   2028  CD   GLN A 285      -1.324  52.342   6.374  1.00 25.15    A C
ATOM   2029  OE1  GLN A 285      -1.022  51.911   7.492  1.00 25.27    A O
ATOM   2030  NE2  GLN A 285      -2.570  52.671   6.042  1.00 24.40    A N
ATOM   2031  C    GLN A 285       2.214  55.422   4.541  1.00 25.81    A C
ATOM   2032  O    GLN A 285       1.546  56.460   4.597  1.00 26.16    A O
ATOM   2033  N    ASN A 286       3.534  55.423   4.663  1.00 25.78    A N
ATOM   2034  CA   ASN A 286       4.266  56.676   4.825  1.00 26.03    A C
ATOM   2035  CB   ASN A 286       5.373  56.531   5.882  1.00 25.75    A C
ATOM   2036  CG   ASN A 286       4.862  56.748   7.297  1.00 25.81    A C
ATOM   2037  OD1  ASN A 286       5.442  56.257   8.255  1.00 26.55    A O
ATOM   2038  ND2  ASN A 286       3.785  57.494   7.431  1.00 25.72    A N
ATOM   2039  C    ASN A 286       4.889  57.041   3.482  1.00 26.10    A C
ATOM   2040  O    ASN A 286       5.588  58.043   3.358  1.00 26.33    A O
ATOM   2041  N    HIS A 287       4.636  56.217   2.473  1.00 25.94    A N
ATOM   2042  CA   HIS A 287       5.196  56.476   1.158  1.00 25.88    A C
ATOM   2043  CB   HIS A 287       4.948  55.272   0.242  1.00 24.92    A C
ATOM   2044  CG   HIS A 287       5.673  55.350  -1.062  1.00 23.86    A C
ATOM   2045  CD2  HIS A 287       6.811  54.753  -1.483  1.00 23.35    A C
ATOM   2046  ND1  HIS A 287       5.258  56.161  -2.097  1.00 23.28    A N
ATOM   2047  CE1  HIS A 287       6.110  56.059  -3.101  1.00 23.25    A C
ATOM   2048  NE2  HIS A 287       7.064  55.211  -2.754  1.00 23.22    A N
ATOM   2049  C    HIS A 287       4.582  57.741   0.557  1.00 26.38    A C
ATOM   2050  O    HIS A 287       3.397  58.026   0.752  1.00 26.64    A O
ATOM   2051  N    PRO A 288       5.388  58.534  -0.161  1.00 26.74    A N
ATOM   2052  CD   PRO A 288       6.847  58.410  -0.330  1.00 26.83    A C
ATOM   2053  CA   PRO A 288       4.905  59.765  -0.783  1.00 27.08    A C
ATOM   2054  CB   PRO A 288       6.053  60.143  -1.714  1.00 27.04    A C
ATOM   2055  CG   PRO A 288       7.231  59.770  -0.904  1.00 26.92    A C
ATOM   2056  C    PRO A 288       3.594  59.596  -1.534  1.00 27.37    A C
ATOM   2057  O    PRO A 288       2.713  60.444  -1.442  1.00 27.43    A O
ATOM   2058  N    TRP A 289       3.456  58.497  -2.271  1.00 27.70    A N
ATOM   2059  CA   TRP A 289       2.241  58.273  -3.050  1.00 28.14    A C
ATOM   2060  CB   TRP A 289       2.419  57.064  -3.984  1.00 27.62    A C
ATOM   2061  CG   TRP A 289       1.271  56.888  -4.950  1.00 26.93    A C
ATOM   2062  CD2  TRP A 289       0.164  55.979  -4.821  1.00 26.51    A C
ATOM   2063  CE2  TRP A 289      -0.714  56.231  -5.898  1.00 26.48    A C
ATOM   2064  CE3  TRP A 289      -0.171  54.982  -3.898  1.00 26.39    A C
ATOM   2065  CD1  TRP A 289       1.028  57.625  -6.074  1.00 26.64    A C
ATOM   2066  NE1  TRP A 289      -0.161  57.237  -6.650  1.00 26.64    A N
ATOM   2067  CZ2  TRP A 289      -1.913  55.522  -6.077  1.00 26.18    A C
ATOM   2068  CZ3  TRP A 289      -1.372  54.270  -4.082  1.00 26.53    A C
ATOM   2069  CH2  TRP A 289      -2.221  54.548  -5.161  1.00 26.12    A C
ATOM   2070  C    TRP A 289       0.974  58.086  -2.206  1.00 28.92    A C
```

FIGURE 2A-38

```
ATOM  2071  O    TRP A 289   -0.120  58.378  -2.674  1.00  28.75      A O
ATOM  2072  N    MET A 290    1.133  57.630  -0.960  1.00  30.06      A N
ATOM  2073  CA   MET A 290    0.016  57.361  -0.038  1.00  31.36      A C
ATOM  2074  CB   MET A 290    0.432  56.231   0.906  1.00  31.08      A C
ATOM  2075  CG   MET A 290    0.583  54.885   0.216  1.00  31.48      A C
ATOM  2076  SD   MET A 290   -1.062  54.101  -0.052  1.00  32.05      A S
ATOM  2077  CE   MET A 290   -0.939  52.949   1.008  1.00  31.36      A C
ATOM  2078  C    MET A 290   -0.544  58.533   0.783  1.00  32.48      A C
ATOM  2079  O    MET A 290   -1.513  58.373   1.538  1.00  32.80      A O
ATOM  2080  N    GLN A 291    0.041  59.718   0.629  1.00  33.58      A N
ATOM  2081  CA   GLN A 291   -0.406  60.899   1.395  1.00  34.40      A C
ATOM  2082  CB   GLN A 291    0.749  61.913   1.467  1.00  34.96      A C
ATOM  2083  CG   GLN A 291    2.056  61.343   2.048  1.00  36.06      A C
ATOM  2084  CD   GLN A 291    1.803  60.403   3.252  1.00  37.05      A C
ATOM  2085  OE1  GLN A 291    1.348  60.849   4.313  1.00  37.37      A O
ATOM  2086  NE2  GLN A 291    2.079  59.098   3.074  1.00  36.71      A N
ATOM  2087  C    GLN A 291   -1.701  61.578   0.897  1.00  34.67      A C
ATOM  2088  O    GLN A 291   -2.037  61.488  -0.279  1.00  34.69      A O
ATOM  2089  N    ASP A 292   -2.437  62.235   1.796  1.00  34.87      A N
ATOM  2090  CA   ASP A 292   -3.686  62.913   1.426  1.00  35.14      A C
ATOM  2091  CB   ASP A 292   -3.414  64.020   0.409  1.00  36.16      A C
ATOM  2092  CG   ASP A 292   -2.438  65.035   0.922  1.00  37.36      A C
ATOM  2093  OD1  ASP A 292   -2.641  65.525   2.064  1.00  38.19      A O
ATOM  2094  OD2  ASP A 292   -1.471  65.327   0.188  1.00  38.33      A O
ATOM  2095  C    ASP A 292   -4.781  62.003   0.847  1.00  34.78      A C
ATOM  2096  O    ASP A 292   -5.415  62.342  -0.157  1.00  34.35      A O
ATOM  2097  N    VAL A 293   -5.009  60.863   1.486  1.00  34.32      A N
ATOM  2098  CA   VAL A 293   -6.023  59.941   1.016  1.00  33.99      A C
ATOM  2099  CB   VAL A 293   -5.897  58.561   1.721  1.00  33.83      A C
ATOM  2100  CG1  VAL A 293   -6.102  58.714   3.212  1.00  33.87      A C
ATOM  2101  CG2  VAL A 293   -6.901  57.579   1.141  1.00  33.60      A C
ATOM  2102  C    VAL A 293   -7.386  60.553   1.298  1.00  33.93      A C
ATOM  2103  O    VAL A 293   -7.553  61.305   2.254  1.00  33.93      A O
ATOM  2104  N    LEU A 294   -8.349  60.269   0.437  1.00  33.95      A N
ATOM  2105  CA   LEU A 294   -9.698  60.780   0.615  1.00  34.08      A C
ATOM  2106  CB   LEU A 294  -10.499  60.652  -0.682  1.00  33.63      A C
ATOM  2107  CG   LEU A 294  -10.109  61.419  -1.943  1.00  33.58      A C
ATOM  2108  CD1  LEU A 294  -11.087  61.068  -3.066  1.00  33.52      A C
ATOM  2109  CD2  LEU A 294  -10.131  62.901  -1.673  1.00  33.17      A C
ATOM  2110  C    LEU A 294  -10.371  59.912   1.666  1.00  34.38      A C
ATOM  2111  O    LEU A 294   -9.915  58.805   1.949  1.00  34.02      A O
ATOM  2112  N    LEU A 295  -11.459  60.421   2.235  1.00  34.95      A N
ATOM  2113  CA   LEU A 295  -12.235  59.673   3.210  1.00  35.38      A C
ATOM  2114  CB   LEU A 295  -13.074  60.619   4.070  1.00  35.64      A C
ATOM  2115  CG   LEU A 295  -12.261  61.546   4.976  1.00  36.09      A C
ATOM  2116  CD1  LEU A 295  -13.195  62.510   5.720  1.00  36.16      A C
ATOM  2117  CD2  LEU A 295  -11.454  60.708   5.949  1.00  36.04      A C
ATOM  2118  C    LEU A 295  -13.147  58.764   2.398  1.00  35.61      A C
ATOM  2119  O    LEU A 295  -13.438  59.046   1.227  1.00  35.53      A O
ATOM  2120  N    PRO A 296  -13.604  57.655   2.997  1.00  35.86      A N
ATOM  2121  CD   PRO A 296  -13.249  57.095   4.316  1.00  35.90      A C
ATOM  2122  CA   PRO A 296  -14.484  56.747   2.254  1.00  36.07      A C
ATOM  2123  CB   PRO A 296  -14.912  55.742   3.315  1.00  35.94      A C
ATOM  2124  CG   PRO A 296  -13.674  55.637   4.177  1.00  35.98      A C
ATOM  2125  C    PRO A 296  -15.670  57.473   1.633  1.00  36.55      A C
ATOM  2126  O    PRO A 296  -15.954  57.324   0.437  1.00  36.17      A O
```

FIGURE 2A-39

```
ATOM   2127  N    GLN A 297     -16.351  58.274   2.450  1.00 37.20      A N
ATOM   2128  CA   GLN A 297     -17.525  59.006   1.986  1.00 38.03      A C
ATOM   2129  CB   GLN A 297     -18.211  59.722   3.163  1.00 38.68      A C
ATOM   2130  CG   GLN A 297     -19.616  60.252   2.845  1.00 39.63      A C
ATOM   2131  CD   GLN A 297     -20.515  59.214   2.169  1.00 40.52      A C
ATOM   2132  OE1  GLN A 297     -20.974  58.248   2.793  1.00 40.84      A O
ATOM   2133  NE2  GLN A 297     -20.766  59.411   0.879  1.00 41.21      A N
ATOM   2134  C    GLN A 297     -17.202  59.980   0.849  1.00 37.98      A C
ATOM   2135  O    GLN A 297     -17.992  60.118  -0.078  1.00 38.03      A O
ATOM   2136  N    GLU A 298     -16.053  60.648   0.912  1.00 38.22      A N
ATOM   2137  CA   GLU A 298     -15.659  61.566  -0.164  1.00 38.58      A C
ATOM   2138  CB   GLU A 298     -14.349  62.289   0.148  1.00 39.26      A C
ATOM   2139  CG   GLU A 298     -14.398  63.220   1.307  1.00 40.59      A C
ATOM   2140  CD   GLU A 298     -13.078  63.922   1.519  1.00 41.53      A C
ATOM   2141  OE1  GLU A 298     -12.069  63.240   1.812  1.00 41.65      A O
ATOM   2142  OE2  GLU A 298     -13.052  65.169   1.390  1.00 42.73      A O
ATOM   2143  C    GLU A 298     -15.419  60.721  -1.400  1.00 38.37      A C
ATOM   2144  O    GLU A 298     -15.826  61.077  -2.510  1.00 38.39      A O
ATOM   2145  N    THR A 299     -14.742  59.597  -1.188  1.00 37.86      A N
ATOM   2146  CA   THR A 299     -14.426  58.685  -2.269  1.00 37.55      A C
ATOM   2147  CB   THR A 299     -13.715  57.416  -1.743  1.00 37.21      A C
ATOM   2148  OG1  THR A 299     -12.526  57.793  -1.034  1.00 36.66      A O
ATOM   2149  CG2  THR A 299     -13.353  56.497  -2.890  1.00 36.54      A C
ATOM   2150  C    THR A 299     -15.690  58.263  -3.003  1.00 37.60      A C
ATOM   2151  O    THR A 299     -15.718  58.233  -4.230  1.00 37.42      A O
ATOM   2152  N    ALA A 300     -16.739  57.932  -2.259  1.00 37.62      A N
ATOM   2153  CA   ALA A 300     -17.964  57.505  -2.914  1.00 37.98      A C
ATOM   2154  CB   ALA A 300     -18.932  56.925  -1.897  1.00 37.98      A C
ATOM   2155  C    ALA A 300     -18.608  58.679  -3.653  1.00 38.31      A C
ATOM   2156  O    ALA A 300     -19.032  58.541  -4.798  1.00 38.27      A O
ATOM   2157  N    GLU A 301     -18.656  59.837  -3.002  1.00 38.54      A N
ATOM   2158  CA   GLU A 301     -19.275  61.016  -3.601  1.00 39.05      A C
ATOM   2159  CB   GLU A 301     -19.275  62.178  -2.599  1.00 39.59      A C
ATOM   2160  CG   GLU A 301     -20.325  62.016  -1.497  1.00 40.85      A C
ATOM   2161  CD   GLU A 301     -20.060  62.885  -0.271  1.00 41.55      A C
ATOM   2162  OE1  GLU A 301     -20.840  62.780   0.704  1.00 41.99      A O
ATOM   2163  OE2  GLU A 301     -19.079  63.667  -0.275  1.00 41.81      A O
ATOM   2164  C    GLU A 301     -18.612  61.437  -4.898  1.00 38.92      A C
ATOM   2165  O    GLU A 301     -19.289  61.809  -5.852  1.00 38.90      A O
ATOM   2166  N    ILE A 302     -17.289  61.345  -4.933  1.00 38.77      A N
ATOM   2167  CA   ILE A 302     -16.509  61.726  -6.100  1.00 38.48      A C
ATOM   2168  CB   ILE A 302     -15.091  62.144  -5.691  1.00 38.47      A C
ATOM   2169  CG2  ILE A 302     -14.276  62.506  -6.921  1.00 38.22      A C
ATOM   2170  CG1  ILE A 302     -15.162  63.312  -4.709  1.00 38.37      A C
ATOM   2171  CD1  ILE A 302     -13.824  63.738  -4.178  1.00 38.32      A C
ATOM   2172  C    ILE A 302     -16.354  60.660  -7.174  1.00 38.48      A C
ATOM   2173  O    ILE A 302     -16.344  60.986  -8.359  1.00 38.78      A O
ATOM   2174  N    HIS A 303     -16.243  59.393  -6.776  1.00 38.13      A N
ATOM   2175  CA   HIS A 303     -15.998  58.320  -7.739  1.00 37.74      A C
ATOM   2176  CB   HIS A 303     -14.661  57.648  -7.406  1.00 36.62      A C
ATOM   2177  CG   HIS A 303     -13.473  58.550  -7.536  1.00 35.43      A C
ATOM   2178  CD2  HIS A 303     -12.735  59.189  -6.601  1.00 34.94      A C
ATOM   2179  ND1  HIS A 303     -12.916  58.878  -8.753  1.00 34.94      A N
ATOM   2180  CE1  HIS A 303     -11.884  59.678  -8.561  1.00 34.56      A C
ATOM   2181  NE2  HIS A 303     -11.752  59.883  -7.264  1.00 34.73      A N
ATOM   2182  C    HIS A 303     -17.045  57.225  -7.883  1.00 38.41      A C
```

FIGURE 2A-40

```
ATOM  2183  O    HIS A 303     -17.066  56.517  -8.901  1.00 38.09      A O
ATOM  2184  N    LEU A 304     -17.905  57.070  -6.881  1.00 39.14      A N
ATOM  2185  CA   LEU A 304     -18.896  56.005  -6.925  1.00 40.20      A C
ATOM  2186  CB   LEU A 304     -18.759  55.152  -5.666  1.00 39.70      A C
ATOM  2187  CG   LEU A 304     -17.344  54.647  -5.380  1.00 39.47      A C
ATOM  2188  CD1  LEU A 304     -17.310  53.968  -4.022  1.00 39.35      A C
ATOM  2189  CD2  LEU A 304     -16.908  53.691  -6.472  1.00 39.04      A C
ATOM  2190  C    LEU A 304     -20.360  56.420  -7.106  1.00 41.19      A C
ATOM  2191  O    LEU A 304     -21.153  55.664  -7.669  1.00 41.18      A O
ATOM  2192  N    HIS A 305     -20.730  57.601  -6.625  1.00 42.42      A N
ATOM  2193  CA   HIS A 305     -22.115  58.046  -6.764  1.00 43.79      A C
ATOM  2194  CB   HIS A 305     -22.369  59.304  -5.926  1.00 44.31      A C
ATOM  2195  CG   HIS A 305     -22.375  59.059  -4.447  1.00 44.92      A C
ATOM  2196  CD2  HIS A 305     -22.537  59.909  -3.402  1.00 44.99      A C
ATOM  2197  ND1  HIS A 305     -22.201  57.805  -3.897  1.00 45.29      A N
ATOM  2198  CE1  HIS A 305     -22.255  57.893  -2.578  1.00 45.20      A C
ATOM  2199  NE2  HIS A 305     -22.457  59.159  -2.253  1.00 45.15      A N
ATOM  2200  C    HIS A 305     -22.411  58.342  -8.233  1.00 44.33      A C
ATOM  2201  O    HIS A 305     -21.555  59.013  -8.863  1.00 44.78      A O
ATOM  2202  OXT  HIS A 305     -23.485  57.908  -8.724  1.00 44.44      A O
TER   1           HIS A 305                                             A
HET   2203  O    HOH W   1       5.212  44.355   7.893  1.00 35.40      W O
HET   2204  O    HOH W   2       8.417  38.986   6.811  1.00 32.60      W O
HET   2205  O    HOH W   3     -14.568  38.217   5.927  1.00 21.67      W O
HET   2206  O    HOH W   4      -2.738  38.833   5.268  1.00 22.78      W O
HET   2207  O    HOH W   5       6.255  34.464   8.951  1.00 25.09      W O
HET   2208  O    HOH W   6       2.795  36.994  -8.168  1.00 20.29      W O
HET   2209  O    HOH W   7      -7.740  33.313   2.802  1.00 21.15      W O
HET   2210  O    HOH W   8     -17.206  44.780   8.882  1.00 31.68      W O
HET   2211  O    HOH W   9       0.337  38.925 -11.388  1.00 22.82      W O
HET   2212  O    HOH W  10       8.713  39.589 -15.036  1.00 29.43      W O
HET   2213  O    HOH W  12     -10.989  26.657   6.528  1.00 51.60      W O
HET   2214  O    HOH W  13     -14.596  33.553   5.148  1.00 23.49      W O
HET   2215  O    HOH W  14       5.496  37.378   9.070  1.00 40.82      W O
HET   2216  O    HOH W  15     -10.178  53.351 -17.004  1.00 41.14      W O
HET   2217  O    HOH W  16     -11.373  55.678 -11.919  1.00 26.83      W O
HET   2218  O    HOH W  18      -9.445  42.668 -12.521  1.00 46.50      W O
HET   2219  O    HOH W  19      -3.263  54.539  10.073  1.00 19.58      W O
HET   2220  O    HOH W  20       4.586  47.817   9.766  1.00 23.38      W O
HET   2221  O    HOH W  21     -15.369  36.059   4.383  1.00 26.97      W O
HET   2222  O    HOH W  22       1.949  48.977  10.513  1.00 35.51      W O
HET   2223  O    HOH W  23      -1.967  37.821   0.519  1.00 23.92      W O
HET   2224  O    HOH W  24      -7.240  59.242  -2.232  1.00 26.36      W O
HET   2225  O    HOH W  25      15.115  42.636  -4.103  1.00 28.08      W O
HET   2226  O    HOH W  26      -4.730  58.540 -12.650  1.00 33.46      W O
HET   2227  O    HOH W  27     -12.865  49.765   4.749  1.00 26.81      W O
HET   2228  O    HOH W  28     -10.127  49.485   6.135  1.00 23.82      W O
HET   2229  O    HOH W  29     -10.440  55.854   2.097  1.00 30.94      W O
HET   2230  O    HOH W  30       8.283  54.982   3.094  1.00 22.77      W O
HET   2231  O    HOH W  31      -4.513  54.836 -13.525  1.00 36.98      W O
HET   2232  O    HOH W  32      -5.807  62.589   4.345  1.00 56.33      W O
HET   2233  O    HOH W  33      -2.797  59.486   3.720  1.00 35.39      W O
HET   2234  O    HOH W  34      -7.087  39.196 -10.078  1.00 42.59      W O
HET   2235  O    HOH W  35     -24.718  22.958   4.141  1.00 25.29      W O
HET   2236  O    HOH W  36      15.028  38.185   2.891  1.00 52.12      W O
HET   2237  O    HOH W  37      10.867  45.618  -8.219  1.00 38.83      W O
```

FIGURE 2A-41

```
HET  2238  O  HOH W  38    3.736  26.370   7.038  1.00 39.08  W O
HET  2239  O  HOH W  39   -9.277  46.706 -16.792  1.00 45.05  W O
HET  2240  O  HOH W  40   -4.278  36.322  -3.784  1.00 29.40  W O
HET  2241  O  HOH W  42   -8.188  51.639  10.340  1.00 37.57  W O
HET  2242  O  HOH W  43    4.308  24.802  -6.902  1.00 55.67  W O
HET  2243  O  HOH W  44    8.947  50.251   9.577  1.00 34.55  W O
HET  2244  O  HOH W  46   15.427  39.450 -12.597  1.00 53.94  W O
HET  2245  O  HOH W  48    9.455  24.154   1.642  1.00 37.76  W O
HET  2246  O  HOH W  49  -29.401  30.984  -6.964  1.00 39.78  W O
HET  2247  O  HOH W  50   -8.109  50.401 -18.412  1.00 40.63  W O
HET  2248  O  HOH W  51  -30.954  30.086  -3.494  1.00 31.99  W O
HET  2249  O  HOH W  52   -0.586  35.769  -0.747  1.00 34.60  W O
HET  2250  O  HOH W  53  -24.284  48.859   3.821  1.00 71.39  W O
HET  2251  O  HOH W  55    8.047  65.651 -13.476  1.00 54.19  W O
HET  2252  O  HOH W  56  -18.470  16.700   3.474  1.00 48.72  W O
HET  2253  O  HOH W  57   -5.322  26.757   3.066  1.00 54.14  W O
HET  2254  O  HOH W  58    5.025  63.559  -3.416  1.00 56.14  W O
HET  2255  O  HOH W  59  -24.745  56.608   8.909  1.00 53.88  W O
HET  2256  O  HOH W  60   -5.993  61.575  -2.626  1.00 32.62  W O
HET  2257  O  HOH W  61   -1.987  34.307  15.886  1.00 36.44  W O
HET  2258  O  HOH W  63   10.978  43.204  -8.974  1.00 23.08  W O
HET  2259  O  HOH W  64   -1.608  37.699   3.126  1.00 22.94  W O
HET  2260  O  HOH W  65    8.616  35.812   2.340  1.00 24.46  W O
HET  2261  O  HOH W  66   -7.639  27.345   0.580  1.00 45.82  W O
HET  2262  O  HOH W  67   -6.912  63.760  -4.055  1.00 47.64  W O
HET  2263  O  HOH W  69    1.745  36.696  -1.868  1.00 26.81  W O
HET  2264  O  HOH W  71  -17.429  24.985  -4.905  1.00 35.04  W O
HET  2265  O  HOH W  72  -19.600  24.497  -3.015  1.00 29.29  W O
HET  2266  O  HOH W  73  -24.271  51.032   2.229  1.00 38.47  W O
HET  2267  O  HOH W  74   -0.895  62.286  -2.569  1.00 39.95  W O
HET  2268  O  HOH W  76    9.873  61.551 -15.061  1.00 37.54  W O
HET  2269  O  HOH W  77  -13.578  57.531 -11.018  1.00 39.01  W O
HET  2270  O  HOH W  78   10.121  52.616 -10.455  1.00 44.06  W O
HET  2271  O  HOH W  79    7.327  43.491   4.160  1.00 22.80  W O
HET  2272  O  HOH W  80  -15.673  58.533   5.455  1.00 37.18  W O
HET  2273  O  HOH W  83  -11.963  33.730  -2.896  1.00 21.54  W O
HET  2274  O  HOH W  84  -18.124  23.005  -0.952  1.00 25.45  W O
HET  2275  O  HOH W  85    1.314  51.350   9.331  1.00 33.30  W O
HET  2276  O  HOH W  86    0.631  27.781  -5.580  1.00 29.86  W O
HET  2277  O  HOH W  87    0.847  36.241   3.337  1.00 18.60  W O
HET  2278  O  HOH W  88   10.456  38.307   5.314  1.00 27.40  W O
HET  2279  O  HOH W  89   12.095  47.498   4.202  1.00 44.68  W O
HET  2280  O  HOH W  90   -5.824  49.207  11.039  1.00 26.73  W O
HET  2281  O  HOH W  91    0.625  34.446   1.430  1.00 31.58  W O
HET  2282  O  HOH W  92  -23.548  29.347 -10.396  1.00 29.01  W O
HET  2283  O  HOH W  93  -19.510  41.574  -7.708  1.00 27.71  W O
HET  2284  O  HOH W  94    5.935  32.764  15.692  1.00 30.76  W O
HET  2285  O  HOH W  95    3.716  37.237  15.437  1.00 63.54  W O
HET  2286  O  HOH W  96    9.156  39.155 -17.589  1.00 34.60  W O
HET  2287  O  HOH W  97  -19.458  31.825  -9.046  1.00 30.22  W O
HET  2288  O  HOH W  98  -10.749  29.515  -1.814  1.00 48.58  W O
HET  2289  O  HOH W  99   -3.021  29.184   1.922  1.00 28.07  W O
HET  2290  O  HOH W 100  -10.659  32.330  17.462  1.00 41.13  W O
HET  2291  O  HOH W 101   -6.124  60.850  -9.621  1.00 33.81  W O
HET  2292  O  HOH W 102  -14.593  49.718   6.791  1.00 38.42  W O
HET  2293  O  HOH W 103  -20.957  43.101 -10.957  1.00 32.50  W O
```

FIGURE 2A-42

```
HET  2294  O  HOH  W  104   -3.213  32.059   -9.993  1.00  33.63  W  O
HET  2295  O  HOH  W  105   -4.224  30.052   -8.162  1.00  37.86  W  O
HET  2296  O  HOH  W  106   -2.430  34.513   -2.817  1.00  29.57  W  O
HET  2297  O  HOH  W  107  -19.920  49.497    4.394  1.00  39.12  W  O
HET  2298  O  HOH  W  108   11.612  24.185    3.333  1.00  46.30  W  O
HET  2299  O  HOH  W  109  -35.236  30.646    2.831  1.00  49.80  W  O
HET  2300  O  HOH  W  110   11.157  51.039   -5.972  1.00  45.82  W  O
HET  2301  O  HOH  W  111  -25.455  28.662   16.250  1.00  56.18  W  O
HET  2302  O  HOH  W  112   -4.133  62.224   -7.121  1.00  37.52  W  O
HET  2303  O  HOH  W  113    3.358  29.072  -14.953  1.00  40.02  W  O
HET  2304  O  HOH  W  114    5.238  56.384   11.178  1.00  38.89  W  O
HET  2305  O  HOH  W  115   -2.136  27.965   -5.144  1.00  44.79  W  O
HET  2306  O  HOH  W  116  -25.651  44.713   -3.228  1.00  39.36  W  O
HET  2307  O  HOH  W  117   -2.725  28.375   11.139  1.00  37.27  W  O
HET  2308  O  HOH  W  118    1.582  32.255   15.957  1.00  33.46  W  O
HET  2309  O  HOH  W  119  -22.441  42.820   -7.377  1.00  34.26  W  O
HET  2310  O  HOH  W  120    4.807  43.441  -15.921  1.00  30.97  W  O
HET  2311  O  HOH  W  121   -8.937  31.920   -0.415  1.00  32.42  W  O
HET  2312  O  HOH  W  122  -19.155  35.814   -8.083  1.00  51.00  W  O
HET  2313  O  HOH  W  123  -14.515  23.686   -2.506  1.00  61.58  W  O
HET  2314  O  HOH  W  124  -15.546  22.895   -5.055  1.00  50.13  W  O
HET  2315  O  HOH  W  125  -24.773  42.675    7.542  1.00  40.80  W  O
HET  2316  O  HOH  W  126   10.163  43.072    3.813  1.00  32.95  W  O
HET  2317  O  HOH  W  127   10.498  46.597  -12.786  1.00  42.87  W  O
HET  2318  O  HOH  W  128  -17.057  49.685    7.396  1.00  55.77  W  O
HET  2319  O  HOH  W  129  -28.205  28.717    2.329  1.00  47.88  W  O
HET  2320  O  HOH  W  130    9.468  57.122  -13.804  1.00  44.49  W  O
HET  2321  O  HOH  W  131    0.835  23.801    0.084  1.00  41.17  W  O
HET  2322  O  HOH  W  132  -31.146  42.444    1.157  1.00  42.73  W  O
HET  2323  O  HOH  W  133  -25.498  43.162   -0.886  1.00  28.92  W  O
HET  2324  O  HOH  W  134   -9.937  48.101    8.915  1.00  30.08  W  O
HET  2325  O  HOH  W  135   13.602  43.283   -7.503  1.00  35.13  W  O
HET  2326  O  HOH  W  136  -20.971  29.116   -9.174  1.00  29.52  W  O
HET  2327  O  HOH  W  137    6.206  29.957   15.120  1.00  39.19  W  O
HET  2328  O  HOH  W  138  -21.363  33.450   -9.815  1.00  47.38  W  O
HET  2329  O  HOH  W  140    1.498  27.566    9.993  1.00  33.91  W  O
HET  2330  O  HOH  W  141   13.608  30.494    2.649  1.00  35.06  W  O
HET  2331  O  HOH  W  142  -22.040  37.657   -7.186  1.00  31.45  W  O
HET  2332  O  HOH  W  143    0.079  29.402   11.248  1.00  35.29  W  O
HET  2333  O  HOH  W  144  -12.176  29.360   -6.291  1.00  43.13  W  O
HET  2334  O  HOH  W  145   11.867  51.888   -8.588  1.00  35.43  W  O
HET  2335  O  HOH  W  146  -22.596  58.234    8.668  1.00  43.78  W  O
HET  2336  O  HOH  W  147  -13.978  43.051   12.898  1.00  42.64  W  O
HET  2337  O  HOH  W  148   13.528  48.338    2.159  1.00  49.51  W  O
HET  2338  O  HOH  W  149   10.933  34.654    3.136  1.00  33.39  W  O
HET  2339  O  HOH  W  150   17.064  37.420    4.532  1.00  44.57  W  O
HET  2340  O  HOH  W  151  -13.621  28.198    2.952  1.00  41.29  W  O
HET  2341  O  HOH  W  152   -2.858  26.020    3.013  1.00  40.24  W  O
HET  2342  O  HOH  W  153  -31.440  37.873   -0.079  1.00  36.14  W  O
HET  2343  O  HOH  W  154  -25.576  57.215   11.651  1.00  43.17  W  O
HET  2344  O  HOH  W  155   -1.017  62.578    4.341  1.00  44.81  W  O
HET  2380  O  HOH  W  156  -14.113  31.287    2.674  1.00  40.40  W  O
HET  2381  O  HOH  W  157  -16.214  38.738   -9.405  1.00  37.08  W  O
HET  2382  O  HOH  W  158   -9.097  53.539    9.066  1.00  35.07  W  O
HET  2383  O  HOH  W  159    7.055  43.042    6.394  1.00  38.28  W  O
HET  2384  O  HOH  W  160  -19.558  39.109   -7.269  1.00  38.32  W  O
```

FIGURE 2A-43

```
HET   2385  O    HOH W  161    -2.684  56.549 -13.288  1.00 37.13      W O
HET   2386  O    HOH W  162     0.031  27.041   7.341  1.00 40.61      W O
HET   2387  O    HOH W  163     2.724  62.517 -12.063  1.00 40.62      W O
HET   2388  O    HOH W  164     3.494  33.338  16.949  1.00 42.73      W O
HET   2389  O    HOH W  165    -7.905  47.934 -18.746  1.00 42.41      W O
HET   2345  C1   STO Z    1   -17.190  35.048   1.581  1.00 24.39      Z C
HET   2346  C2   STO Z    1   -16.210  33.972   1.415  1.00 24.28      Z C
HET   2347  C3   STO Z    1   -15.849  33.457   0.091  1.00 24.49      Z C
HET   2348  C4   STO Z    1   -16.482  34.008  -1.111  1.00 24.37      Z C
HET   2349  C5   STO Z    1   -17.474  35.093  -0.955  1.00 24.69      Z C
HET   2350  N1   STO Z    1   -18.229  35.797  -1.944  1.00 24.92      Z N
HET   2351  C6   STO Z    1   -18.944  36.794  -1.236  1.00 24.88      Z C
HET   2352  C7   STO Z    1   -19.809  37.848  -1.790  1.00 25.03      Z C
HET   2353  N2   STO Z    1   -20.055  38.130  -3.130  1.00 25.52      Z N
HET   2354  C8   STO Z    1   -20.928  39.278  -3.194  1.00 25.75      Z C
HET   2355  C9   STO Z    1   -21.519  39.987  -4.363  1.00 26.03      Z C
HET   2356  C10  STO Z    1   -22.416  41.141  -4.128  1.00 25.71      Z C
HET   2357  C11  STO Z    1   -22.719  41.583  -2.747  1.00 25.67      Z C
HET   2358  C12  STO Z    1   -22.123  40.872  -1.580  1.00 25.77      Z C
HET   2359  C13  STO Z    1   -21.230  39.723  -1.826  1.00 25.50      Z C
HET   2360  C14  STO Z    1   -20.516  38.781  -0.927  1.00 25.10      Z C
HET   2361  C15  STO Z    1   -20.328  38.658   0.532  1.00 24.91      Z C
HET   2362  C16  STO Z    1   -20.835  39.482   1.605  1.00 25.07      Z C
HET   2363  N3   STO Z    1   -20.262  39.086   2.768  1.00 24.96      Z N
HET   2364  C17  STO Z    1   -19.450  37.859   2.607  1.00 24.63      Z C
HET   2365  C18  STO Z    1   -19.471  37.663   1.109  1.00 24.72      Z C
HET   2366  C19  STO Z    1   -18.770  36.707   0.205  1.00 24.66      Z C
HET   2367  C20  STO Z    1   -17.810  35.606   0.386  1.00 24.60      Z C
HET   2368  C21  STO Z    1   -18.301  35.477  -3.459  1.00 25.27      Z C
HET   2369  C22  STO Z    1   -16.936  35.811  -4.228  1.00 24.98      Z C
HET   2370  C23  STO Z    1   -17.112  37.004  -5.207  1.00 25.27      Z C
HET   2371  C24  STO Z    1   -17.971  38.083  -4.545  1.00 25.64      Z C
HET   2372  C25  STO Z    1   -19.395  37.530  -4.245  1.00 25.43      Z C
HET   2373  O1   STO Z    1   -19.428  36.151  -4.080  1.00 25.69      Z O
HET   2374  O2   STO Z    1   -21.651  40.389   1.455  1.00 25.66      Z O
HET   2375  N4   STO Z    1   -15.881  37.639  -5.707  1.00 25.27      Z N
HET   2376  C26  STO Z    1   -15.338  36.684  -6.689  1.00 24.85      Z C
HET   2377  O3   STO Z    1   -15.935  36.196  -3.283  1.00 24.52      Z O
HET   2378  C27  STO Z    1   -14.670  35.524  -3.447  1.00 23.53      Z C
HET   2379  C28  STO Z    1   -18.633  33.986  -3.730  1.00 25.05      Z C
END
```

FIGURE 3A-1

| ATOM | Type | Resid | # | X | Y | Z | Occ | B | | |
|------|------|-------|---|---|---|---|-----|---|---|---|
| ATOM | 1 | CB | PRO A 33 | -33.999 | 26.506 | 14.294 | 1.00 | 75.23 | A | C |
| ATOM | 2 | CG | PRO A 33 | -33.664 | 27.271 | 15.584 | 1.00 | 75.32 | A | C |
| ATOM | 3 | C | PRO A 33 | -32.162 | 27.277 | 12.754 | 1.00 | 75.02 | A | C |
| ATOM | 4 | O | PRO A 33 | -32.466 | 28.463 | 12.909 | 1.00 | 75.11 | A | O |
| ATOM | 5 | N | PRO A 33 | -31.694 | 26.166 | 14.927 | 1.00 | 75.33 | A | N |
| ATOM | 6 | CD | PRO A 33 | -32.423 | 26.554 | 16.149 | 1.00 | 75.36 | A | C |
| ATOM | 7 | CA | PRO A 33 | -32.605 | 26.210 | 13.756 | 1.00 | 75.18 | A | C |
| ATOM | 8 | N | LEU A 34 | -31.441 | 26.843 | 11.726 | 1.00 | 74.67 | A | N |
| ATOM | 9 | CA | LEU A 34 | -30.935 | 27.742 | 10.694 | 1.00 | 74.04 | A | C |
| ATOM | 10 | CB | LEU A 34 | -29.765 | 27.071 | 9.965 | 1.00 | 73.85 | A | C |
| ATOM | 11 | CG | LEU A 34 | -28.918 | 27.856 | 8.960 | 1.00 | 73.74 | A | C |
| ATOM | 12 | CD1 | LEU A 34 | -27.794 | 26.953 | 8.493 | 1.00 | 73.70 | A | C |
| ATOM | 13 | CD2 | LEU A 34 | -29.749 | 28.328 | 7.771 | 1.00 | 73.63 | A | C |
| ATOM | 14 | C | LEU A 34 | -32.032 | 28.111 | 9.693 | 1.00 | 73.63 | A | C |
| ATOM | 15 | O | LEU A 34 | -32.254 | 29.289 | 9.401 | 1.00 | 73.54 | A | O |
| ATOM | 16 | N | GLU A 35 | -32.708 | 27.093 | 9.172 | 1.00 | 72.96 | A | N |
| ATOM | 17 | CA | GLU A 35 | -33.776 | 27.276 | 8.193 | 1.00 | 72.25 | A | C |
| ATOM | 18 | CB | GLU A 35 | -34.377 | 25.917 | 7.818 | 1.00 | 72.86 | A | C |
| ATOM | 19 | CG | GLU A 35 | -33.953 | 24.775 | 8.736 | 1.00 | 73.58 | A | C |
| ATOM | 20 | CD | GLU A 35 | -32.701 | 24.069 | 8.245 | 1.00 | 74.04 | A | C |
| ATOM | 21 | OE1 | GLU A 35 | -32.040 | 23.386 | 9.060 | 1.00 | 74.15 | A | O |
| ATOM | 22 | OE2 | GLU A 35 | -32.387 | 24.187 | 7.039 | 1.00 | 74.29 | A | O |
| ATOM | 23 | C | GLU A 35 | -34.895 | 28.206 | 8.661 | 1.00 | 71.32 | A | C |
| ATOM | 24 | O | GLU A 35 | -35.705 | 28.663 | 7.852 | 1.00 | 71.37 | A | O |
| ATOM | 25 | N | SER A 36 | -34.942 | 28.488 | 9.959 | 1.00 | 69.96 | A | N |
| ATOM | 26 | CA | SER A 36 | -35.986 | 29.354 | 10.498 | 1.00 | 68.45 | A | C |
| ATOM | 27 | CB | SER A 36 | -36.502 | 28.794 | 11.829 | 1.00 | 68.80 | A | C |
| ATOM | 28 | OG | SER A 36 | -35.470 | 28.736 | 12.800 | 1.00 | 69.17 | A | O |
| ATOM | 29 | C | SER A 36 | -35.547 | 30.802 | 10.692 | 1.00 | 66.95 | A | C |
| ATOM | 30 | O | SER A 36 | -36.359 | 31.719 | 10.576 | 1.00 | 66.85 | A | O |
| ATOM | 31 | N | GLN A 37 | -34.268 | 31.011 | 10.984 | 1.00 | 65.11 | A | N |
| ATOM | 32 | CA | GLN A 37 | -33.758 | 32.361 | 11.204 | 1.00 | 63.22 | A | C |
| ATOM | 33 | CB | GLN A 37 | -32.515 | 32.317 | 12.082 | 1.00 | 62.94 | A | C |
| ATOM | 34 | CG | GLN A 37 | -32.804 | 32.183 | 13.549 | 1.00 | 62.87 | A | C |
| ATOM | 35 | CD | GLN A 37 | -31.540 | 32.174 | 14.365 | 1.00 | 62.68 | A | C |
| ATOM | 36 | OE1 | GLN A 37 | -30.747 | 31.236 | 14.287 | 1.00 | 62.67 | A | O |
| ATOM | 37 | NE2 | GLN A 37 | -31.335 | 33.226 | 15.146 | 1.00 | 62.61 | A | N |
| ATOM | 38 | C | GLN A 37 | -33.425 | 33.139 | 9.940 | 1.00 | 61.96 | A | C |
| ATOM | 39 | O | GLN A 37 | -33.609 | 34.356 | 9.888 | 1.00 | 61.76 | A | O |
| ATOM | 40 | N | TYR A 38 | -32.932 | 32.440 | 8.926 | 1.00 | 60.43 | A | N |
| ATOM | 41 | CA | TYR A 38 | -32.551 | 33.090 | 7.683 | 1.00 | 58.96 | A | C |
| ATOM | 42 | CB | TYR A 38 | -31.068 | 32.839 | 7.414 | 1.00 | 58.13 | A | C |
| ATOM | 43 | CG | TYR A 38 | -30.183 | 33.325 | 8.533 | 1.00 | 57.09 | A | C |
| ATOM | 44 | CD1 | TYR A 38 | -29.956 | 34.685 | 8.724 | 1.00 | 56.68 | A | C |
| ATOM | 45 | CE1 | TYR A 38 | -29.188 | 35.141 | 9.784 | 1.00 | 56.43 | A | C |
| ATOM | 46 | CD2 | TYR A 38 | -29.615 | 32.429 | 9.434 | 1.00 | 56.56 | A | C |
| ATOM | 47 | CE2 | TYR A 38 | -28.848 | 32.875 | 10.500 | 1.00 | 56.35 | A | C |
| ATOM | 48 | CZ | TYR A 38 | -28.639 | 34.231 | 10.670 | 1.00 | 56.23 | A | C |
| ATOM | 49 | OH | TYR A 38 | -27.886 | 34.680 | 11.728 | 1.00 | 56.16 | A | O |
| ATOM | 50 | C | TYR A 38 | -33.374 | 32.628 | 6.496 | 1.00 | 58.44 | A | C |
| ATOM | 51 | O | TYR A 38 | -33.705 | 31.449 | 6.371 | 1.00 | 58.74 | A | O |
| ATOM | 52 | N | GLN A 39 | -33.702 | 33.574 | 5.625 | 1.00 | 57.37 | A | N |
| ATOM | 53 | CA | GLN A 39 | -34.474 | 33.282 | 4.433 | 1.00 | 56.33 | A | C |

FIGURE 3A-2

```
ATOM     54  CB  GLN A  39     -35.581  34.318   4.266  1.00 57.05      A C
ATOM     55  CG  GLN A  39     -36.462  34.092   3.062  1.00 58.58      A C
ATOM     56  CD  GLN A  39     -37.655  35.023   3.045  1.00 60.00      A C
ATOM     57  OE1 GLN A  39     -37.511  36.239   3.190  1.00 60.34      A O
ATOM     58  NE2 GLN A  39     -38.847  34.456   2.865  1.00 60.77      A N
ATOM     59  C   GLN A  39     -33.527  33.310   3.240  1.00 55.10      A C
ATOM     60  O   GLN A  39     -33.184  34.376   2.727  1.00 55.30      A O
ATOM     61  N   VAL A  40     -33.103  32.124   2.815  1.00 53.39      A N
ATOM     62  CA  VAL A  40     -32.176  31.974   1.698  1.00 51.82      A C
ATOM     63  CB  VAL A  40     -31.921  30.490   1.407  1.00 51.51      A C
ATOM     64  CG1 VAL A  40     -31.059  30.340   0.168  1.00 51.49      A C
ATOM     65  CG2 VAL A  40     -31.244  29.848   2.604  1.00 51.76      A C
ATOM     66  C   VAL A  40     -32.596  32.655   0.397  1.00 50.93      A C
ATOM     67  O   VAL A  40     -33.767  32.651   0.022  1.00 50.89      A O
ATOM     68  N   GLY A  41     -31.615  33.233  -0.286  1.00 49.85      A N
ATOM     69  CA  GLY A  41     -31.869  33.912  -1.540  1.00 48.27      A C
ATOM     70  C   GLY A  41     -31.135  33.239  -2.683  1.00 47.46      A C
ATOM     71  O   GLY A  41     -30.822  32.049  -2.601  1.00 47.43      A O
ATOM     72  N   PRO A  42     -30.830  33.976  -3.761  1.00 46.67      A N
ATOM     73  CD  PRO A  42     -31.080  35.418  -3.942  1.00 46.50      A C
ATOM     74  CA  PRO A  42     -30.128  33.421  -4.920  1.00 46.27      A C
ATOM     75  CB  PRO A  42     -30.266  34.527  -5.957  1.00 46.12      A C
ATOM     76  CG  PRO A  42     -30.179  35.759  -5.114  1.00 46.20      A C
ATOM     77  C   PRO A  42     -28.669  33.070  -4.648  1.00 46.07      A C
ATOM     78  O   PRO A  42     -28.038  33.631  -3.748  1.00 46.12      A O
ATOM     79  N   LEU A  43     -28.140  32.136  -5.431  1.00 45.40      A N
ATOM     80  CA  LEU A  43     -26.749  31.727  -5.292  1.00 44.67      A C
ATOM     81  CB  LEU A  43     -26.469  30.500  -6.164  1.00 44.62      A C
ATOM     82  CG  LEU A  43     -25.032  29.973  -6.229  1.00 44.52      A C
ATOM     83  CD1 LEU A  43     -24.647  29.350  -4.896  1.00 44.26      A C
ATOM     84  CD2 LEU A  43     -24.920  28.943  -7.340  1.00 44.52      A C
ATOM     85  C   LEU A  43     -25.880  32.892  -5.753  1.00 44.11      A C
ATOM     86  O   LEU A  43     -26.047  33.395  -6.861  1.00 43.90      A O
ATOM     87  N   LEU A  44     -24.962  33.330  -4.901  1.00 43.73      A N
ATOM     88  CA  LEU A  44     -24.083  34.432  -5.258  1.00 43.33      A C
ATOM     89  CB  LEU A  44     -23.624  35.173  -4.003  1.00 43.20      A C
ATOM     90  CG  LEU A  44     -24.663  36.117  -3.395  1.00 43.42      A C
ATOM     91  CD1 LEU A  44     -24.155  36.666  -2.081  1.00 43.63      A C
ATOM     92  CD2 LEU A  44     -24.947  37.254  -4.363  1.00 43.17      A C
ATOM     93  C   LEU A  44     -22.880  33.940  -6.046  1.00 43.15      A C
ATOM     94  O   LEU A  44     -22.391  34.632  -6.936  1.00 42.93      A O
ATOM     95  N   GLY A  45     -22.419  32.736  -5.722  1.00 43.20      A N
ATOM     96  CA  GLY A  45     -21.272  32.161  -6.403  1.00 43.13      A C
ATOM     97  C   GLY A  45     -20.706  31.002  -5.612  1.00 43.57      A C
ATOM     98  O   GLY A  45     -21.119  30.763  -4.479  1.00 43.20      A O
ATOM     99  N   SER A  46     -19.762  30.275  -6.196  1.00 44.50      A N
ATOM    100  CA  SER A  46     -19.167  29.140  -5.505  1.00 46.13      A C
ATOM    101  CB  SER A  46     -20.056  27.910  -5.645  1.00 46.12      A C
ATOM    102  OG  SER A  46     -20.023  27.428  -6.978  1.00 46.67      A O
ATOM    103  C   SER A  46     -17.788  28.797  -6.040  1.00 47.45      A C
ATOM    104  O   SER A  46     -17.313  29.393  -7.007  1.00 47.34      A O
ATOM    105  N   GLY A  47     -17.157  27.817  -5.401  1.00 49.10      A N
ATOM    106  CA  GLY A  47     -15.834  27.380  -5.808  1.00 51.09      A C
ATOM    107  C   GLY A  47     -15.326  26.306  -4.868  1.00 52.48      A C
ATOM    108  O   GLY A  47     -16.122  25.591  -4.253  1.00 53.09      A O
ATOM    109  N   GLY A  48     -14.007  26.180  -4.753  1.00 53.41      A N
```

FIGURE 3A-3

```
ATOM    110  CA   GLY A   48     -13.449  25.183  -3.856  1.00 54.40      A C
ATOM    111  C    GLY A   48     -13.762  25.572  -2.422  1.00 55.14      A C
ATOM    112  O    GLY A   48     -13.864  24.723  -1.527  1.00 55.47      A O
ATOM    113  N    PHE A   49     -13.928  26.879  -2.224  1.00 55.12      A N
ATOM    114  CA   PHE A   49     -14.236  27.480  -0.929  1.00 54.83      A C
ATOM    115  CB   PHE A   49     -13.978  28.978  -1.013  1.00 56.58      A C
ATOM    116  CG   PHE A   49     -14.627  29.623  -2.203  1.00 58.74      A C
ATOM    117  CD1  PHE A   49     -13.988  29.632  -3.444  1.00 59.44      A C
ATOM    118  CD2  PHE A   49     -15.906  30.171  -2.100  1.00 59.34      A C
ATOM    119  CE1  PHE A   49     -14.614  30.179  -4.568  1.00 59.87      A C
ATOM    120  CE2  PHE A   49     -16.539  30.716  -3.213  1.00 59.73      A C
ATOM    121  CZ   PHE A   49     -15.893  30.722  -4.452  1.00 60.03      A C
ATOM    122  C    PHE A   49     -15.690  27.254  -0.489  1.00 53.80      A C
ATOM    123  O    PHE A   49     -16.099  27.716   0.579  1.00 53.78      A O
ATOM    124  N    GLY A   50     -16.469  26.559  -1.317  1.00 52.37      A N
ATOM    125  CA   GLY A   50     -17.860  26.299  -0.983  1.00 49.97      A C
ATOM    126  C    GLY A   50     -18.831  27.117  -1.814  1.00 48.12      A C
ATOM    127  O    GLY A   50     -18.455  27.673  -2.850  1.00 48.47      A O
ATOM    128  N    SER A   51     -20.081  27.189  -1.363  1.00 45.87      A N
ATOM    129  CA   SER A   51     -21.117  27.943  -2.064  1.00 43.41      A C
ATOM    130  CB   SER A   51     -22.274  27.019  -2.450  1.00 43.40      A C
ATOM    131  OG   SER A   51     -21.832  25.941  -3.257  1.00 43.30      A O
ATOM    132  C    SER A   51     -21.642  29.067  -1.178  1.00 41.96      A C
ATOM    133  O    SER A   51     -21.821  28.882   0.023  1.00 41.41      A O
ATOM    134  N    VAL A   52     -21.895  30.227  -1.776  1.00 40.70      A N
ATOM    135  CA   VAL A   52     -22.392  31.377  -1.030  1.00 39.61      A C
ATOM    136  CB   VAL A   52     -21.361  32.523  -1.055  1.00 39.33      A C
ATOM    137  CG1  VAL A   52     -21.878  33.722  -0.274  1.00 38.19      A C
ATOM    138  CG2  VAL A   52     -20.047  32.036  -0.473  1.00 39.20      A C
ATOM    139  C    VAL A   52     -23.716  31.882  -1.594  1.00 39.57      A C
ATOM    140  O    VAL A   52     -23.826  32.151  -2.791  1.00 39.11      A O
ATOM    141  N    TYR A   53     -24.716  32.004  -0.719  1.00 39.44      A N
ATOM    142  CA   TYR A   53     -26.047  32.469  -1.104  1.00 39.33      A C
ATOM    143  CB   TYR A   53     -27.127  31.470  -0.671  1.00 38.30      A C
ATOM    144  CG   TYR A   53     -27.014  30.088  -1.266  1.00 37.39      A C
ATOM    145  CD1  TYR A   53     -26.088  29.172  -0.778  1.00 37.03      A C
ATOM    146  CE1  TYR A   53     -25.992  27.895  -1.315  1.00 36.75      A C
ATOM    147  CD2  TYR A   53     -27.845  29.693  -2.309  1.00 36.66      A C
ATOM    148  CE2  TYR A   53     -27.758  28.421  -2.853  1.00 36.79      A C
ATOM    149  CZ   TYR A   53     -26.829  27.527  -2.352  1.00 37.05      A C
ATOM    150  OH   TYR A   53     -26.728  26.268  -2.893  1.00 37.68      A O
ATOM    151  C    TYR A   53     -26.386  33.803  -0.463  1.00 40.05      A C
ATOM    152  O    TYR A   53     -25.908  34.118   0.627  1.00 40.15      A O
ATOM    153  N    SER A   54     -27.222  34.583  -1.143  1.00 40.85      A N
ATOM    154  CA   SER A   54     -27.657  35.865  -0.612  1.00 41.51      A C
ATOM    155  CB   SER A   54     -28.249  36.741  -1.717  1.00 41.66      A C
ATOM    156  OG   SER A   54     -28.705  37.982  -1.194  1.00 42.30      A O
ATOM    157  C    SER A   54     -28.737  35.485   0.379  1.00 42.06      A C
ATOM    158  O    SER A   54     -29.268  34.382   0.308  1.00 42.10      A O
ATOM    159  N    GLY A   55     -29.065  36.376   1.304  1.00 43.11      A N
ATOM    160  CA   GLY A   55     -30.088  36.040   2.274  1.00 44.54      A C
ATOM    161  C    GLY A   55     -30.434  37.164   3.221  1.00 45.80      A C
ATOM    162  O    GLY A   55     -29.784  38.210   3.241  1.00 45.87      A O
ATOM    163  N    ILE A   56     -31.476  36.947   4.010  1.00 46.96      A N
ATOM    164  CA   ILE A   56     -31.912  37.948   4.965  1.00 48.27      A C
ATOM    165  CB   ILE A   56     -33.143  38.714   4.435  1.00 48.57      A C
```

FIGURE 3A-4

```
ATOM    166  CG2 ILE A   56     -32.752  39.546   3.221  1.00 48.29      A C
ATOM    167  CG1 ILE A   56     -34.250  37.728   4.055  1.00 49.41      A C
ATOM    168  CD1 ILE A   56     -35.501  38.391   3.486  1.00 50.04      A C
ATOM    169  C   ILE A   56     -32.246  37.293   6.297  1.00 48.63      A C
ATOM    170  O   ILE A   56     -32.825  36.209   6.344  1.00 48.75      A O
ATOM    171  N   ARG A   57     -31.853  37.949   7.380  1.00 49.30      A N
ATOM    172  CA  ARG A   57     -32.120  37.436   8.715  1.00 50.11      A C
ATOM    173  CB  ARG A   57     -31.178  38.097   9.724  1.00 49.64      A C
ATOM    174  CG  ARG A   57     -31.349  37.614  11.147  1.00 48.93      A C
ATOM    175  CD  ARG A   57     -30.877  38.671  12.128  1.00 48.83      A C
ATOM    176  NE  ARG A   57     -29.448  38.618  12.420  1.00 48.06      A N
ATOM    177  CZ  ARG A   57     -28.769  39.623  12.967  1.00 47.78      A C
ATOM    178  NH1 ARG A   57     -29.391  40.756  13.268  1.00 46.81      A N
ATOM    179  NH2 ARG A   57     -27.474  39.494  13.226  1.00 47.75      A N
ATOM    180  C   ARG A   57     -33.568  37.786   9.038  1.00 50.91      A C
ATOM    181  O   ARG A   57     -33.874  38.938   9.344  1.00 51.41      A O
ATOM    182  N   VAL A   58     -34.452  36.793   8.953  1.00 51.65      A N
ATOM    183  CA  VAL A   58     -35.878  36.986   9.219  1.00 52.14      A C
ATOM    184  CB  VAL A   58     -36.577  35.643   9.494  1.00 52.06      A C
ATOM    185  CG1 VAL A   58     -38.074  35.851   9.598  1.00 52.23      A C
ATOM    186  CG2 VAL A   58     -36.252  34.653   8.391  1.00 52.38      A C
ATOM    187  C   VAL A   58     -36.097  37.900  10.418  1.00 52.54      A C
ATOM    188  O   VAL A   58     -36.973  38.765  10.407  1.00 52.57      A O
ATOM    189  N   SER A   59     -35.282  37.695  11.446  1.00 52.98      A N
ATOM    190  CA  SER A   59     -35.338  38.482  12.670  1.00 53.29      A C
ATOM    191  CB  SER A   59     -34.070  38.226  13.496  1.00 53.65      A C
ATOM    192  OG  SER A   59     -33.918  39.186  14.529  1.00 54.30      A O
ATOM    193  C   SER A   59     -35.504  39.987  12.442  1.00 53.30      A C
ATOM    194  O   SER A   59     -36.217  40.650  13.194  1.00 53.24      A O
ATOM    195  N   ASP A   60     -34.855  40.530  11.413  1.00 53.36      A N
ATOM    196  CA  ASP A   60     -34.948  41.966  11.150  1.00 53.25      A C
ATOM    197  CB  ASP A   60     -34.017  42.729  12.106  1.00 53.02      A C
ATOM    198  CG  ASP A   60     -32.554  42.357  11.928  1.00 53.13      A C
ATOM    199  OD1 ASP A   60     -32.224  41.156  11.990  1.00 53.20      A O
ATOM    200  OD2 ASP A   60     -31.726  43.268  11.730  1.00 53.50      A O
ATOM    201  C   ASP A   60     -34.659  42.395   9.710  1.00 53.18      A C
ATOM    202  O   ASP A   60     -34.388  43.570   9.456  1.00 53.33      A O
ATOM    203  N   ASN A   61     -34.724  41.452   8.774  1.00 53.02      A N
ATOM    204  CA  ASN A   61     -34.472  41.741   7.358  1.00 52.86      A C
ATOM    205  CB  ASN A   61     -35.407  42.844   6.859  1.00 54.15      A C
ATOM    206  CG  ASN A   61     -36.861  42.504   7.064  1.00 55.77      A C
ATOM    207  OD1 ASN A   61     -37.349  41.485   6.567  1.00 56.25      A O
ATOM    208  ND2 ASN A   61     -37.569  43.356   7.804  1.00 56.12      A N
ATOM    209  C   ASN A   61     -33.033  42.159   7.068  1.00 51.79      A C
ATOM    210  O   ASN A   61     -32.734  42.653   5.979  1.00 51.86      A O
ATOM    211  N   LEU A   62     -32.147  41.974   8.040  1.00 50.12      A N
ATOM    212  CA  LEU A   62     -30.753  42.334   7.848  1.00 48.25      A C
ATOM    213  CB  LEU A   62     -29.950  42.074   9.123  1.00 48.23      A C
ATOM    214  CG  LEU A   62     -28.447  42.357   9.036  1.00 47.79      A C
ATOM    215  CD1 LEU A   62     -28.218  43.818   8.701  1.00 47.28      A C
ATOM    216  CD2 LEU A   62     -27.780  42.005  10.355  1.00 47.62      A C
ATOM    217  C   LEU A   62     -30.185  41.497   6.716  1.00 47.11      A C
ATOM    218  O   LEU A   62     -30.316  40.275   6.715  1.00 47.26      A O
ATOM    219  N   PRO A   63     -29.563  42.146   5.723  1.00 46.05      A N
ATOM    220  CD  PRO A   63     -29.397  43.598   5.535  1.00 45.82      A C
ATOM    221  CA  PRO A   63     -28.986  41.404   4.600  1.00 45.05      A C
```

FIGURE 3A-5

```
ATOM    222  CB  PRO A  63     -28.646  42.505   3.599  1.00 45.21      A C
ATOM    223  CG  PRO A  63     -28.308  43.663   4.489  1.00 45.56      A C
ATOM    224  C   PRO A  63     -27.756  40.628   5.056  1.00 43.82      A C
ATOM    225  O   PRO A  63     -26.877  41.175   5.721  1.00 43.67      A O
ATOM    226  N   VAL A  64     -27.705  39.350   4.710  1.00 42.65      A N
ATOM    227  CA  VAL A  64     -26.578  38.517   5.097  1.00 41.36      A C
ATOM    228  CB  VAL A  64     -26.951  37.568   6.259  1.00 41.15      A C
ATOM    229  CG1 VAL A  64     -27.496  38.369   7.427  1.00 41.22      A C
ATOM    230  CG2 VAL A  64     -27.963  36.537   5.789  1.00 40.39      A C
ATOM    231  C   VAL A  64     -26.082  37.673   3.936  1.00 40.59      A C
ATOM    232  O   VAL A  64     -26.655  37.684   2.848  1.00 39.92      A O
ATOM    233  N   ALA A  65     -25.000  36.948   4.182  1.00 40.29      A N
ATOM    234  CA  ALA A  65     -24.418  36.067   3.187  1.00 39.95      A C
ATOM    235  CB  ALA A  65     -23.040  36.558   2.783  1.00 39.46      A C
ATOM    236  C   ALA A  65     -24.321  34.711   3.856  1.00 39.61      A C
ATOM    237  O   ALA A  65     -23.785  34.594   4.954  1.00 39.38      A O
ATOM    238  N   ILE A  66     -24.862  33.691   3.205  1.00 39.71      A N
ATOM    239  CA  ILE A  66     -24.824  32.350   3.762  1.00 39.78      A C
ATOM    240  CB  ILE A  66     -26.224  31.693   3.722  1.00 39.83      A C
ATOM    241  CG2 ILE A  66     -26.160  30.286   4.306  1.00 40.29      A C
ATOM    242  CG1 ILE A  66     -27.212  32.546   4.528  1.00 39.94      A C
ATOM    243  CD1 ILE A  66     -28.640  32.045   4.502  1.00 39.25      A C
ATOM    244  C   ILE A  66     -23.815  31.504   2.996  1.00 39.91      A C
ATOM    245  O   ILE A  66     -23.982  31.237   1.803  1.00 39.68      A O
ATOM    246  N   LYS A  67     -22.764  31.095   3.700  1.00 39.87      A N
ATOM    247  CA  LYS A  67     -21.694  30.297   3.122  1.00 40.15      A C
ATOM    248  CB  LYS A  67     -20.347  30.903   3.520  1.00 39.91      A C
ATOM    249  CG  LYS A  67     -19.137  30.359   2.786  1.00 39.52      A C
ATOM    250  CD  LYS A  67     -17.916  31.203   3.130  1.00 40.12      A C
ATOM    251  CE  LYS A  67     -16.695  30.813   2.313  1.00 40.55      A C
ATOM    252  NZ  LYS A  67     -15.587  31.793   2.497  1.00 40.25      A N
ATOM    253  C   LYS A  67     -21.771  28.844   3.578  1.00 40.52      A C
ATOM    254  O   LYS A  67     -21.816  28.554   4.772  1.00 40.27      A O
ATOM    255  N   HIS A  68     -21.793  27.936   2.611  1.00 41.40      A N
ATOM    256  CA  HIS A  68     -21.854  26.509   2.885  1.00 42.00      A C
ATOM    257  CB  HIS A  68     -22.940  25.855   2.032  1.00 41.61      A C
ATOM    258  CG  HIS A  68     -24.326  26.247   2.427  1.00 40.94      A C
ATOM    259  CD2 HIS A  68     -25.099  27.292   2.049  1.00 41.12      A C
ATOM    260  ND1 HIS A  68     -25.054  25.553   3.368  1.00 41.10      A N
ATOM    261  CE1 HIS A  68     -26.215  26.155   3.555  1.00 41.05      A C
ATOM    262  NE2 HIS A  68     -26.267  27.213   2.766  1.00 40.88      A N
ATOM    263  C   HIS A  68     -20.509  25.906   2.545  1.00 42.96      A C
ATOM    264  O   HIS A  68     -19.916  26.244   1.523  1.00 42.84      A O
ATOM    265  N   VAL A  69     -20.030  25.016   3.406  1.00 44.62      A N
ATOM    266  CA  VAL A  69     -18.746  24.367   3.192  1.00 46.68      A C
ATOM    267  CB  VAL A  69     -17.636  25.049   4.010  1.00 46.90      A C
ATOM    268  CG1 VAL A  69     -16.292  24.445   3.654  1.00 47.50      A C
ATOM    269  CG2 VAL A  69     -17.635  26.545   3.747  1.00 47.59      A C
ATOM    270  C   VAL A  69     -18.790  22.902   3.598  1.00 48.09      A C
ATOM    271  O   VAL A  69     -19.037  22.584   4.760  1.00 48.55      A O
ATOM    272  N   GLU A  70     -18.553  22.011   2.639  1.00 49.72      A N
ATOM    273  CA  GLU A  70     -18.546  20.581   2.924  1.00 51.13      A C

ATOM    274  CB  GLU A  70     -18.512  19.768   1.626  1.00 52.32      A C
ATOM    275  CG  GLU A  70     -19.840  19.713   0.888  1.00 54.34      A C
ATOM    276  CD  GLU A  70     -19.824  18.739  -0.276  1.00 55.69      A C
```

FIGURE 3A-6

```
ATOM   277  OE1 GLU A  70     -19.531  17.543  -0.049  1.00 56.39      A O
ATOM   278  OE2 GLU A  70     -20.108  19.168  -1.418  1.00 56.29      A O
ATOM   279  C   GLU A  70     -17.314  20.260   3.758  1.00 51.41      A C
ATOM   280  O   GLU A  70     -16.226  20.767   3.482  1.00 51.30      A O
ATOM   281  N   LYS A  71     -17.489  19.423   4.778  1.00 51.81      A N
ATOM   282  CA  LYS A  71     -16.384  19.041   5.651  1.00 52.24      A C
ATOM   283  CB  LYS A  71     -16.891  18.180   6.804  1.00 51.33      A C
ATOM   284  CG  LYS A  71     -17.915  18.858   7.685  1.00 50.77      A C
ATOM   285  CD  LYS A  71     -18.343  17.928   8.804  1.00 50.35      A C
ATOM   286  CE  LYS A  71     -19.350  18.585   9.724  1.00 49.97      A C
ATOM   287  NZ  LYS A  71     -19.667  17.713  10.886  1.00 49.70      A N
ATOM   288  C   LYS A  71     -15.309  18.276   4.891  1.00 53.26      A C
ATOM   289  O   LYS A  71     -14.116  18.469   5.115  1.00 53.07      A O
ATOM   290  N   ASP A  72     -15.734  17.404   3.986  1.00 54.90      A N
ATOM   291  CA  ASP A  72     -14.789  16.617   3.210  1.00 56.76      A C
ATOM   292  CB  ASP A  72     -15.532  15.702   2.229  1.00 57.61      A C
ATOM   293  CG  ASP A  72     -16.353  14.626   2.931  1.00 58.94      A C
ATOM   294  OD1 ASP A  72     -17.087  13.888   2.235  1.00 59.46      A O
ATOM   295  OD2 ASP A  72     -16.266  14.511   4.175  1.00 59.32      A O
ATOM   296  C   ASP A  72     -13.820  17.503   2.442  1.00 57.46      A C
ATOM   297  O   ASP A  72     -12.742  17.059   2.065  1.00 58.11      A O
ATOM   298  N   ARG A  73     -14.192  18.760   2.227  1.00 58.37      A N
ATOM   299  CA  ARG A  73     -13.348  19.678   1.469  1.00 59.25      A C
ATOM   300  CB  ARG A  73     -14.216  20.489   0.505  1.00 59.89      A C
ATOM   301  CG  ARG A  73     -14.911  19.634  -0.536  1.00 61.24      A C
ATOM   302  CD  ARG A  73     -15.976  20.415  -1.284  1.00 62.70      A C
ATOM   303  NE  ARG A  73     -16.645  19.588  -2.285  1.00 63.75      A N
ATOM   304  CZ  ARG A  73     -17.674  19.993  -3.021  1.00 64.17      A C
ATOM   305  NH1 ARG A  73     -18.220  19.172  -3.910  1.00 64.29      A N
ATOM   306  NH2 ARG A  73     -18.162  21.216  -2.864  1.00 64.54      A N
ATOM   307  C   ARG A  73     -12.475  20.626   2.284  1.00 59.20      A C
ATOM   308  O   ARG A  73     -11.672  21.368   1.721  1.00 59.38      A O
ATOM   309  N   ILE A  74     -12.623  20.612   3.602  1.00 59.21      A N
ATOM   310  CA  ILE A  74     -11.820  21.491   4.440  1.00 59.33      A C
ATOM   311  CB  ILE A  74     -12.445  21.647   5.838  1.00 58.82      A C
ATOM   312  CG2 ILE A  74     -11.558  22.522   6.710  1.00 58.40      A C
ATOM   313  CG1 ILE A  74     -13.847  22.250   5.707  1.00 58.36      A C
ATOM   314  CD1 ILE A  74     -14.586  22.406   7.019  1.00 57.92      A C
ATOM   315  C   ILE A  74     -10.411  20.926   4.573  1.00 59.93      A C
ATOM   316  O   ILE A  74     -10.237  19.717   4.722  1.00 60.16      A O
ATOM   317  N   SER A  75      -9.410  21.803   4.516  1.00 60.45      A N
ATOM   318  CA  SER A  75      -8.013  21.384   4.622  1.00 60.66      A C
ATOM   319  CB  SER A  75      -7.203  21.995   3.480  1.00 60.78      A C
ATOM   320  OG  SER A  75      -7.753  21.628   2.226  1.00 60.84      A O
ATOM   321  C   SER A  75      -7.382  21.758   5.965  1.00 60.90      A C
ATOM   322  O   SER A  75      -6.552  21.014   6.494  1.00 60.88      A O
ATOM   323  N   ASP A  76      -7.775  22.911   6.506  1.00 60.99      A N
ATOM   324  CA  ASP A  76      -7.263  23.384   7.791  1.00 60.77      A C
ATOM   325  CB  ASP A  76      -6.572  24.738   7.640  1.00 61.29      A C
ATOM   326  CG  ASP A  76      -5.247  24.638   6.933  1.00 62.10      A C
ATOM   327  OD1 ASP A  76      -4.523  25.657   6.890  1.00 62.78      A O
ATOM   328  OD2 ASP A  76      -4.931  23.544   6.418  1.00 62.85      A O
ATOM   329  C   ASP A  76      -8.379  23.534   8.811  1.00 60.45      A C
ATOM   330  O   ASP A  76      -9.368  24.217   8.557  1.00 60.57      A O
ATOM   331  N   TRP A  77      -8.211  22.907   9.970  1.00 59.95      A N
ATOM   332  CA  TRP A  77      -9.208  22.991  11.028  1.00 59.65      A C
```

FIGURE 3A-7

```
ATOM    333  CB   TRP A   77      -9.661  21.591  11.453  1.00 59.18      A C
ATOM    334  CG   TRP A   77     -10.294  20.772  10.366  1.00 58.20      A C
ATOM    335  CD2  TRP A   77     -11.670  20.386  10.279  1.00 57.75      A C
ATOM    336  CE2  TRP A   77     -11.811  19.600   9.115  1.00 57.52      A C
ATOM    337  CE3  TRP A   77     -12.798  20.625  11.075  1.00 57.64      A C
ATOM    338  CD1  TRP A   77      -9.673  20.226   9.280  1.00 57.99      A C
ATOM    339  NE1  TRP A   77     -10.578  19.518   8.523  1.00 57.72      A N
ATOM    340  CZ2  TRP A   77     -13.036  19.053   8.724  1.00 57.29      A C
ATOM    341  CZ3  TRP A   77     -14.020  20.080  10.685  1.00 57.58      A C
ATOM    342  CH2  TRP A   77     -14.126  19.301   9.520  1.00 57.19      A C
ATOM    343  C    TRP A   77      -8.635  23.721  12.240  1.00 59.84      A C
ATOM    344  O    TRP A   77      -7.449  23.601  12.541  1.00 59.94      A O
ATOM    345  N    GLY A   78      -9.482  24.473  12.934  1.00 59.96      A N
ATOM    346  CA   GLY A   78      -9.032  25.203  14.107  1.00 60.19      A C
ATOM    347  C    GLY A   78      -9.793  24.779  15.347  1.00 60.30      A C
ATOM    348  O    GLY A   78     -10.607  23.859  15.286  1.00 60.64      A O
ATOM    349  N    ALA A   79      -9.536  25.444  16.470  1.00 60.12      A N
ATOM    350  CA   ALA A   79     -10.211  25.117  17.721  1.00 60.23      A C
ATOM    351  CB   ALA A   79      -9.193  24.992  18.847  1.00 60.37      A C
ATOM    352  C    ALA A   79     -11.261  26.162  18.082  1.00 60.36      A C
ATOM    353  O    ALA A   79     -11.520  26.419  19.261  1.00 60.53      A O
ATOM    354  N    THR A   84     -13.418  21.930  20.215  1.00 56.12      A N
ATOM    355  CA   THR A   84     -14.190  21.600  19.021  1.00 56.31      A C
ATOM    356  CB   THR A   84     -15.644  22.088  19.147  1.00 56.55      A C
ATOM    357  OG1  THR A   84     -15.673  23.312  19.892  1.00 55.88      A O
ATOM    358  CG2  THR A   84     -16.502  21.032  19.840  1.00 56.81      A C
ATOM    359  C    THR A   84     -13.588  22.185  17.747  1.00 56.34      A C
ATOM    360  O    THR A   84     -13.376  23.395  17.637  1.00 56.44      A O
ATOM    361  N    ARG A   85     -13.325  21.308  16.784  1.00 56.07      A N
ATOM    362  CA   ARG A   85     -12.738  21.704  15.512  1.00 55.70      A C
ATOM    363  CB   ARG A   85     -12.186  20.472  14.797  1.00 56.26      A C
ATOM    364  CG   ARG A   85     -11.210  19.659  15.630  1.00 57.07      A C
ATOM    365  CD   ARG A   85     -10.989  18.297  15.000  1.00 57.98      A C
ATOM    366  NE   ARG A   85     -10.311  18.388  13.711  1.00 58.76      A N
ATOM    367  CZ   ARG A   85     -10.507  17.545  12.702  1.00 59.06      A C
ATOM    368  NH1  ARG A   85     -11.371  16.544  12.827  1.00 59.18      A N
ATOM    369  NH2  ARG A   85      -9.833  17.697  11.569  1.00 59.13      A N
ATOM    370  C    ARG A   85     -13.758  22.399  14.617  1.00 55.04      A C
ATOM    371  O    ARG A   85     -14.948  22.096  14.667  1.00 55.19      A O
ATOM    372  N    VAL A   86     -13.277  23.329  13.797  1.00 53.87      A N
ATOM    373  CA   VAL A   86     -14.125  24.085  12.878  1.00 52.21      A C
ATOM    374  CB   VAL A   86     -14.766  25.308  13.586  1.00 51.90      A C
ATOM    375  CG1  VAL A   86     -15.730  24.849  14.666  1.00 51.57      A C
ATOM    376  CG2  VAL A   86     -13.683  26.181  14.197  1.00 51.51      A C
ATOM    377  C    VAL A   86     -13.252  24.591  11.729  1.00 51.29      A C
ATOM    378  O    VAL A   86     -12.025  24.528  11.804  1.00 51.44      A O
ATOM    379  N    PRO A   87     -13.869  25.086  10.643  1.00 50.30      A N
ATOM    380  CD   PRO A   87     -15.305  25.156  10.320  1.00 50.21      A C
ATOM    381  CA   PRO A   87     -13.059  25.587   9.527  1.00 49.25      A C
ATOM    382  CB   PRO A   87     -14.095  25.828   8.429  1.00 49.33      A C
ATOM    383  CG   PRO A   87     -15.328  26.170   9.198  1.00 49.66      A C
ATOM    384  C    PRO A   87     -12.294  26.861   9.907  1.00 48.26      A C
ATOM    385  O    PRO A   87     -12.817  27.722  10.619  1.00 48.06      A O
ATOM    386  N    MET A   88     -11.055  26.967   9.436  1.00 47.05      A N
ATOM    387  CA   MET A   88     -10.215  28.124   9.720  1.00 46.01      A C
ATOM    388  CB   MET A   88      -9.086  28.219   8.694  1.00 46.46      A C
```

FIGURE 3A-8

```
ATOM    389  CG  MET A  88      -7.735  27.773   9.217  1.00 46.81      A C
ATOM    390  SD  MET A  88      -7.268  28.645  10.725  1.00 47.64      A S
ATOM    391  CE  MET A  88      -7.116  27.279  11.871  1.00 47.45      A C
ATOM    392  C   MET A  88     -10.982  29.440   9.731  1.00 45.15      A C
ATOM    393  O   MET A  88     -10.862  30.232  10.665  1.00 45.06      A O
ATOM    394  N   GLU A  89     -11.765  29.665   8.683  1.00 43.92      A N
ATOM    395  CA  GLU A  89     -12.552  30.885   8.545  1.00 42.97      A C
ATOM    396  CB  GLU A  89     -13.647  30.688   7.498  1.00 44.25      A C
ATOM    397  CG  GLU A  89     -13.166  30.156   6.161  1.00 45.95      A C
ATOM    398  CD  GLU A  89     -14.318  29.779   5.242  1.00 46.96      A C
ATOM    399  OE1 GLU A  89     -15.160  30.661   4.948  1.00 46.95      A O
ATOM    400  OE2 GLU A  89     -14.379  28.602   4.818  1.00 46.92      A O
ATOM    401  C   GLU A  89     -13.208  31.325   9.846  1.00 41.46      A C
ATOM    402  O   GLU A  89     -13.160  32.502  10.201  1.00 41.15      A O
ATOM    403  N   VAL A  90     -13.825  30.374  10.543  1.00 40.04      A N
ATOM    404  CA  VAL A  90     -14.524  30.654  11.795  1.00 38.60      A C
ATOM    405  CB  VAL A  90     -15.300  29.419  12.299  1.00 38.25      A C
ATOM    406  CG1 VAL A  90     -16.072  29.774  13.557  1.00 37.96      A C
ATOM    407  CG2 VAL A  90     -16.243  28.919  11.222  1.00 38.04      A C
ATOM    408  C   VAL A  90     -13.595  31.115  12.907  1.00 37.86      A C
ATOM    409  O   VAL A  90     -13.903  32.070  13.614  1.00 37.85      A O
ATOM    410  N   VAL A  91     -12.468  30.432  13.071  1.00 37.25      A N
ATOM    411  CA  VAL A  91     -11.512  30.805  14.107  1.00 36.71      A C
ATOM    412  CB  VAL A  91     -10.357  29.790  14.192  1.00 36.51      A C
ATOM    413  CG1 VAL A  91      -9.332  30.254  15.205  1.00 36.25      A C
ATOM    414  CG2 VAL A  91     -10.898  28.427  14.586  1.00 36.46      A C
ATOM    415  C   VAL A  91     -10.940  32.191  13.816  1.00 36.51      A C
ATOM    416  O   VAL A  91     -10.971  33.084  14.666  1.00 36.34      A O
ATOM    417  N   LEU A  92     -10.434  32.367  12.602  1.00 35.95      A N
ATOM    418  CA  LEU A  92      -9.852  33.633  12.188  1.00 35.63      A C
ATOM    419  CB  LEU A  92      -9.350  33.517  10.746  1.00 35.03      A C
ATOM    420  CG  LEU A  92      -8.336  32.385  10.524  1.00 34.80      A C
ATOM    421  CD1 LEU A  92      -8.000  32.274   9.048  1.00 34.36      A C
ATOM    422  CD2 LEU A  92      -7.078  32.641  11.348  1.00 33.97      A C
ATOM    423  C   LEU A  92     -10.830  34.799  12.321  1.00 35.89      A C
ATOM    424  O   LEU A  92     -10.516  35.805  12.956  1.00 35.88      A O
ATOM    425  N   LEU A  93     -12.015  34.666  11.735  1.00 36.47      A N
ATOM    426  CA  LEU A  93     -13.012  35.731  11.807  1.00 37.19      A C
ATOM    427  CB  LEU A  93     -14.252  35.360  10.990  1.00 37.08      A C
ATOM    428  CG  LEU A  93     -14.096  35.470   9.472  1.00 37.32      A C
ATOM    429  CD1 LEU A  93     -15.350  34.963   8.786  1.00 37.12      A C
ATOM    430  CD2 LEU A  93     -13.820  36.918   9.089  1.00 36.90      A C
ATOM    431  C   LEU A  93     -13.417  36.071  13.239  1.00 37.96      A C
ATOM    432  O   LEU A  93     -13.746  37.217  13.539  1.00 38.01      A O
ATOM    433  N   LYS A  94     -13.395  35.082  14.123  1.00 39.01      A N
ATOM    434  CA  LYS A  94     -13.753  35.324  15.516  1.00 40.43      A C
ATOM    435  CB  LYS A  94     -13.920  34.005  16.274  1.00 40.84      A C
ATOM    436  CG  LYS A  94     -15.295  33.375  16.154  1.00 41.21      A C
ATOM    437  CD  LYS A  94     -15.388  32.130  17.022  1.00 42.02      A C
ATOM    438  CE  LYS A  94     -16.824  31.638  17.142  1.00 43.55      A C
ATOM    439  NZ  LYS A  94     -17.723  32.632  17.812  1.00 43.93      A N
ATOM    440  C   LYS A  94     -12.690  36.165  16.210  1.00 41.26      A C
ATOM    441  O   LYS A  94     -12.991  36.903  17.147  1.00 41.25      A O
ATOM    442  N   LYS A  95     -11.447  36.046  15.748  1.00 42.23      A N
ATOM    443  CA  LYS A  95     -10.344  36.799  16.335  1.00 43.35      A C
ATOM    444  CB  LYS A  95      -9.007  36.148  15.975  1.00 42.39      A C
```

FIGURE 3A-9

| ATOM | 445 | CG  | LYS A | 95  | -8.867  | 34.713 | 16.452 | 1.00 | 41.88 | A | C |
|------|-----|-----|-------|-----|---------|--------|--------|------|-------|---|---|
| ATOM | 446 | CD  | LYS A | 95  | -7.425  | 34.236 | 16.359 | 1.00 | 41.24 | A | C |
| ATOM | 447 | CE  | LYS A | 95  | -6.542  | 34.991 | 17.335 | 1.00 | 40.96 | A | C |
| ATOM | 448 | NZ  | LYS A | 95  | -5.136  | 34.528 | 17.269 | 1.00 | 41.24 | A | N |
| ATOM | 449 | C   | LYS A | 95  | -10.333 | 38.264 | 15.897 | 1.00 | 44.57 | A | C |
| ATOM | 450 | O   | LYS A | 95  | -9.951  | 39.148 | 16.667 | 1.00 | 44.22 | A | O |
| ATOM | 451 | N   | VAL A | 96  | -10.755 | 38.520 | 14.663 | 1.00 | 46.07 | A | N |
| ATOM | 452 | CA  | VAL A | 96  | -10.782 | 39.878 | 14.144 | 1.00 | 48.00 | A | C |
| ATOM | 453 | CB  | VAL A | 96  | -10.461 | 39.898 | 12.638 | 1.00 | 47.72 | A | C |
| ATOM | 454 | CG1 | VAL A | 96  | -9.016  | 39.502 | 12.421 | 1.00 | 47.78 | A | C |
| ATOM | 455 | CG2 | VAL A | 96  | -11.372 | 38.940 | 11.891 | 1.00 | 47.72 | A | C |
| ATOM | 456 | C   | VAL A | 96  | -12.124 | 40.556 | 14.382 | 1.00 | 49.75 | A | C |
| ATOM | 457 | O   | VAL A | 96  | -12.224 | 41.468 | 15.206 | 1.00 | 49.82 | A | O |
| ATOM | 458 | N   | SER A | 97  | -13.145 | 40.094 | 13.661 | 1.00 | 51.89 | A | N |
| ATOM | 459 | CA  | SER A | 97  | -14.511 | 40.623 | 13.745 | 1.00 | 53.86 | A | C |
| ATOM | 460 | CB  | SER A | 97  | -15.521 | 39.477 | 13.913 | 1.00 | 53.93 | A | C |
| ATOM | 461 | OG  | SER A | 97  | -15.629 | 38.698 | 12.734 | 1.00 | 54.06 | A | O |
| ATOM | 462 | C   | SER A | 97  | -14.741 | 41.640 | 14.855 | 1.00 | 54.86 | A | C |
| ATOM | 463 | O   | SER A | 97  | -14.812 | 42.843 | 14.598 | 1.00 | 54.69 | A | O |
| ATOM | 464 | N   | SER A | 98  | -14.864 | 41.141 | 16.084 | 1.00 | 56.00 | A | N |
| ATOM | 465 | CA  | SER A | 98  | -15.101 | 41.984 | 17.250 | 1.00 | 56.78 | A | C |
| ATOM | 466 | CB  | SER A | 98  | -14.348 | 41.433 | 18.463 | 1.00 | 57.23 | A | C |
| ATOM | 467 | OG  | SER A | 98  | -14.694 | 42.142 | 19.645 | 1.00 | 58.13 | A | O |
| ATOM | 468 | C   | SER A | 98  | -14.687 | 43.427 | 16.993 | 1.00 | 56.97 | A | C |
| ATOM | 469 | O   | SER A | 98  | -13.510 | 43.721 | 16.758 | 1.00 | 56.70 | A | O |
| ATOM | 470 | N   | GLY A | 99  | -15.674 | 44.316 | 17.018 | 1.00 | 57.31 | A | N |
| ATOM | 471 | CA  | GLY A | 99  | -15.416 | 45.722 | 16.787 | 1.00 | 57.20 | A | C |
| ATOM | 472 | C   | GLY A | 99  | -15.605 | 46.116 | 15.338 | 1.00 | 57.02 | A | C |
| ATOM | 473 | O   | GLY A | 99  | -15.755 | 45.268 | 14.457 | 1.00 | 56.92 | A | O |
| ATOM | 474 | N   | PHE A | 100 | -15.602 | 47.419 | 15.091 | 1.00 | 56.74 | A | N |
| ATOM | 475 | CA  | PHE A | 100 | -15.755 | 47.949 | 13.746 | 1.00 | 56.15 | A | C |
| ATOM | 476 | CB  | PHE A | 100 | -16.039 | 49.457 | 13.823 | 1.00 | 57.23 | A | C |
| ATOM | 477 | CG  | PHE A | 100 | -17.382 | 49.807 | 14.427 | 1.00 | 58.27 | A | C |
| ATOM | 478 | CD1 | PHE A | 100 | -17.590 | 51.062 | 15.014 | 1.00 | 58.56 | A | C |
| ATOM | 479 | CD2 | PHE A | 100 | -18.448 | 48.911 | 14.372 | 1.00 | 58.73 | A | C |
| ATOM | 480 | CE1 | PHE A | 100 | -18.848 | 51.413 | 15.536 | 1.00 | 59.14 | A | C |
| ATOM | 481 | CE2 | PHE A | 100 | -19.707 | 49.250 | 14.889 | 1.00 | 58.98 | A | C |
| ATOM | 482 | CZ  | PHE A | 100 | -19.907 | 50.501 | 15.470 | 1.00 | 59.30 | A | C |
| ATOM | 483 | C   | PHE A | 100 | -14.471 | 47.692 | 12.966 | 1.00 | 55.26 | A | C |
| ATOM | 484 | O   | PHE A | 100 | -13.401 | 47.566 | 13.562 | 1.00 | 55.13 | A | O |
| ATOM | 485 | N   | SER A | 101 | -14.576 | 47.609 | 11.642 | 1.00 | 53.94 | A | N |
| ATOM | 486 | CA  | SER A | 101 | -13.393 | 47.385 | 10.819 | 1.00 | 52.77 | A | C |
| ATOM | 487 | CB  | SER A | 101 | -12.568 | 46.211 | 11.367 | 1.00 | 53.28 | A | C |
| ATOM | 488 | OG  | SER A | 101 | -11.236 | 46.281 | 10.911 | 1.00 | 53.94 | A | O |
| ATOM | 489 | C   | SER A | 101 | -13.714 | 47.136 | 9.346  | 1.00 | 51.37 | A | C |
| ATOM | 490 | O   | SER A | 101 | -14.879 | 47.118 | 8.933  | 1.00 | 51.14 | A | O |
| ATOM | 491 | N   | GLY A | 102 | -12.661 | 46.942 | 8.557  | 1.00 | 49.52 | A | N |
| ATOM | 492 | CA  | GLY A | 102 | -12.819 | 46.694 | 7.134  | 1.00 | 46.92 | A | C |
| ATOM | 493 | C   | GLY A | 102 | -12.755 | 45.218 | 6.788  | 1.00 | 45.27 | A | C |
| ATOM | 494 | O   | GLY A | 102 | -12.297 | 44.851 | 5.707  | 1.00 | 44.33 | A | O |
| ATOM | 495 | N   | VAL A | 103 | -13.197 | 44.372 | 7.712  | 1.00 | 44.29 | A | N |
| ATOM | 496 | CA  | VAL A | 103 | -13.220 | 42.940 | 7.472  | 1.00 | 43.70 | A | C |
| ATOM | 497 | CB  | VAL A | 103 | -12.305 | 42.153 | 8.465  | 1.00 | 43.74 | A | C |
| ATOM | 498 | CG1 | VAL A | 103 | -10.873 | 42.643 | 8.368  | 1.00 | 43.81 | A | C |
| ATOM | 499 | CG2 | VAL A | 103 | -12.812 | 42.289 | 9.884  | 1.00 | 44.07 | A | C |
| ATOM | 500 | C   | VAL A | 103 | -14.658 | 42.450 | 7.629  | 1.00 | 43.05 | A | C |

FIGURE 3A-10

```
ATOM   501  O    VAL A 103     -15.349  42.834   8.574  1.00 42.67      A O
ATOM   502  N    ILE A 104     -15.118  41.622   6.696  1.00 42.53      A N
ATOM   503  CA   ILE A 104     -16.469  41.083   6.780  1.00 42.38      A C
ATOM   504  CB   ILE A 104     -16.747  40.051   5.655  1.00 42.24      A C
ATOM   505  CG2  ILE A 104     -17.739  38.996   6.125  1.00 42.60      A C
ATOM   506  CG1  ILE A 104     -17.295  40.765   4.420  1.00 42.46      A C
ATOM   507  CD1  ILE A 104     -18.660  41.383   4.606  1.00 41.93      A C
ATOM   508  C    ILE A 104     -16.629  40.413   8.137  1.00 42.45      A C
ATOM   509  O    ILE A 104     -15.749  39.679   8.584  1.00 42.84      A O
ATOM   510  N    ARG A 105     -17.752  40.669   8.794  1.00 42.44      A N
ATOM   511  CA   ARG A 105     -17.990  40.094  10.109  1.00 42.79      A C
ATOM   512  CB   ARG A 105     -18.727  41.107  10.988  1.00 44.78      A C
ATOM   513  CG   ARG A 105     -18.038  42.462  11.018  1.00 48.43      A C
ATOM   514  CD   ARG A 105     -18.544  43.360  12.136  1.00 51.14      A C
ATOM   515  NE   ARG A 105     -18.160  42.858  13.453  1.00 53.54      A N
ATOM   516  CZ   ARG A 105     -18.054  43.619  14.538  1.00 54.70      A C
ATOM   517  NH1  ARG A 105     -18.303  44.922  14.464  1.00 55.14      A N
ATOM   518  NH2  ARG A 105     -17.692  43.079  15.697  1.00 55.31      A N
ATOM   519  C    ARG A 105     -18.752  38.773  10.094  1.00 41.55      A C
ATOM   520  O    ARG A 105     -19.628  38.551   9.257  1.00 41.18      A O
ATOM   521  N    LEU A 106     -18.394  37.893  11.023  1.00 40.34      A N
ATOM   522  CA   LEU A 106     -19.053  36.603  11.151  1.00 39.37      A C
ATOM   523  CB   LEU A 106     -18.085  35.551  11.691  1.00 38.49      A C
ATOM   524  CG   LEU A 106     -18.699  34.157  11.820  1.00 37.96      A C
ATOM   525  CD1  LEU A 106     -19.006  33.616  10.431  1.00 37.17      A C
ATOM   526  CD2  LEU A 106     -17.745  33.234  12.565  1.00 37.69      A C
ATOM   527  C    LEU A 106     -20.201  36.787  12.133  1.00 39.12      A C
ATOM   528  O    LEU A 106     -19.987  36.935  13.335  1.00 38.80      A O
ATOM   529  N    LEU A 107     -21.420  36.789  11.614  1.00 39.02      A N
ATOM   530  CA   LEU A 107     -22.595  36.969  12.448  1.00 39.65      A C
ATOM   531  CB   LEU A 107     -23.795  37.335  11.570  1.00 39.17      A C
ATOM   532  CG   LEU A 107     -24.063  38.828  11.346  1.00 38.64      A C
ATOM   533  CD1  LEU A 107     -22.775  39.626  11.420  1.00 38.46      A C
ATOM   534  CD2  LEU A 107     -24.754  39.018  10.003  1.00 38.77      A C
ATOM   535  C    LEU A 107     -22.901  35.734  13.283  1.00 40.22      A C
ATOM   536  O    LEU A 107     -23.268  35.843  14.451  1.00 39.68      A O
ATOM   537  N    ASP A 108     -22.740  34.561  12.682  1.00 41.33      A N
ATOM   538  CA   ASP A 108     -23.006  33.309  13.373  1.00 42.49      A C
ATOM   539  CB   ASP A 108     -24.481  33.261  13.795  1.00 43.83      A C
ATOM   540  CG   ASP A 108     -24.850  31.978  14.522  1.00 45.09      A C
ATOM   541  OD1  ASP A 108     -23.976  31.390  15.196  1.00 45.99      A O
ATOM   542  OD2  ASP A 108     -26.028  31.569  14.431  1.00 45.66      A O
ATOM   543  C    ASP A 108     -22.667  32.143  12.454  1.00 42.56      A C
ATOM   544  O    ASP A 108     -22.482  32.326  11.255  1.00 42.66      A O
ATOM   545  N    TRP A 109     -22.570  30.946  13.018  1.00 43.16      A N
ATOM   546  CA   TRP A 109     -22.256  29.768  12.222  1.00 43.88      A C
ATOM   547  CB   TRP A 109     -20.742  29.544  12.176  1.00 43.70      A C
ATOM   548  CG   TRP A 109     -20.130  29.290  13.519  1.00 43.65      A C
ATOM   549  CD2  TRP A 109     -19.816  28.014  14.089  1.00 43.65      A C
ATOM   550  CE2  TRP A 109     -19.287  28.250  15.375  1.00 43.35      A C
ATOM   551  CE3  TRP A 109     -19.934  26.692  13.636  1.00 43.61      A C
ATOM   552  CD1  TRP A 109     -19.788  30.221  14.455  1.00 43.48      A C
ATOM   553  NE1  TRP A 109     -19.280  29.605  15.573  1.00 43.49      A N
ATOM   554  CZ2  TRP A 109     -18.874  27.213  16.217  1.00 43.56      A C
ATOM   555  CZ3  TRP A 109     -19.522  25.657  14.476  1.00 43.63      A C
ATOM   556  CH2  TRP A 109     -19.000  25.926  15.752  1.00 43.51      A C
```

FIGURE 3A-11

```
ATOM   557  C    TRP A 109     -22.943  28.527  12.785  1.00 44.28      A C
ATOM   558  O    TRP A 109     -23.217  28.452  13.985  1.00 44.47      A O
ATOM   559  N    PHE A 110     -23.224  27.562  11.910  1.00 44.49      A N
ATOM   560  CA   PHE A 110     -23.875  26.312  12.302  1.00 44.40      A C
ATOM   561  CB   PHE A 110     -25.316  26.243  11.784  1.00 45.03      A C
ATOM   562  CG   PHE A 110     -26.162  27.424  12.152  1.00 45.88      A C
ATOM   563  CD1  PHE A 110     -26.200  28.548  11.338  1.00 46.28      A C
ATOM   564  CD2  PHE A 110     -26.937  27.406  13.306  1.00 46.50      A C
ATOM   565  CE1  PHE A 110     -27.001  29.641  11.668  1.00 47.01      A C
ATOM   566  CE2  PHE A 110     -27.742  28.491  13.647  1.00 46.95      A C
ATOM   567  CZ   PHE A 110     -27.774  29.611  12.825  1.00 47.12      A C
ATOM   568  C    PHE A 110     -23.128  25.120  11.729  1.00 44.07      A C
ATOM   569  O    PHE A 110     -22.594  25.184  10.623  1.00 43.90      A O
ATOM   570  N    GLU A 111     -23.093  24.028  12.482  1.00 44.03      A N
ATOM   571  CA   GLU A 111     -22.438  22.819  12.006  1.00 44.13      A C
ATOM   572  CB   GLU A 111     -21.529  22.212  13.077  1.00 43.99      A C
ATOM   573  CG   GLU A 111     -21.121  20.778  12.765  1.00 43.47      A C
ATOM   574  CD   GLU A 111     -20.092  20.235  13.729  1.00 43.95      A C
ATOM   575  OE1  GLU A 111     -20.175  20.555  14.932  1.00 44.50      A O
ATOM   576  OE2  GLU A 111     -19.204  19.477  13.288  1.00 43.93      A O
ATOM   577  C    GLU A 111     -23.504  21.810  11.626  1.00 44.13      A C
ATOM   578  O    GLU A 111     -24.494  21.640  12.339  1.00 43.98      A O
ATOM   579  N    ARG A 112     -23.305  21.148  10.494  1.00 43.98      A N
ATOM   580  CA   ARG A 112     -24.252  20.153  10.033  1.00 43.95      A C
ATOM   581  CB   ARG A 112     -24.966  20.655   8.774  1.00 43.12      A C
ATOM   582  CG   ARG A 112     -25.557  22.033   9.002  1.00 42.57      A C
ATOM   583  CD   ARG A 112     -26.901  22.249   8.349  1.00 42.02      A C
ATOM   584  NE   ARG A 112     -26.803  22.457   6.911  1.00 41.93      A N
ATOM   585  CZ   ARG A 112     -27.768  23.002   6.178  1.00 41.48      A C
ATOM   586  NH1  ARG A 112     -28.897  23.396   6.752  1.00 41.24      A N
ATOM   587  NH2  ARG A 112     -27.608  23.153   4.872  1.00 41.49      A N
ATOM   588  C    ARG A 112     -23.491  18.863   9.779  1.00 44.48      A C
ATOM   589  O    ARG A 112     -22.271  18.874   9.620  1.00 44.46      A O
ATOM   590  N    PRO A 113     -24.202  17.729   9.760  1.00 44.90      A N
ATOM   591  CD   PRO A 113     -25.670  17.584   9.840  1.00 44.98      A C
ATOM   592  CA   PRO A 113     -23.562  16.434   9.532  1.00 44.95      A C
ATOM   593  CB   PRO A 113     -24.724  15.570   9.053  1.00 45.01      A C
ATOM   594  CG   PRO A 113     -25.854  16.076   9.912  1.00 45.06      A C
ATOM   595  C    PRO A 113     -22.381  16.440   8.563  1.00 44.84      A C
ATOM   596  O    PRO A 113     -21.299  15.970   8.906  1.00 44.74      A O
ATOM   597  N    ASP A 114     -22.576  16.989   7.367  1.00 45.06      A N
ATOM   598  CA   ASP A 114     -21.512  17.007   6.366  1.00 45.07      A C
ATOM   599  CB   ASP A 114     -21.964  16.226   5.139  1.00 46.61      A C
ATOM   600  CG   ASP A 114     -22.267  14.779   5.459  1.00 48.43      A C
ATOM   601  OD1  ASP A 114     -21.311  14.026   5.757  1.00 49.40      A O
ATOM   602  OD2  ASP A 114     -23.460  14.398   5.421  1.00 48.88      A O
ATOM   603  C    ASP A 114     -21.017  18.379   5.925  1.00 44.16      A C
ATOM   604  O    ASP A 114     -20.358  18.498   4.893  1.00 44.44      A O
ATOM   605  N    SER A 115     -21.316  19.413   6.698  1.00 42.81      A N
ATOM   606  CA   SER A 115     -20.875  20.747   6.323  1.00 41.24      A C
ATOM   607  CB   SER A 115     -21.594  21.197   5.044  1.00 41.03      A C
ATOM   608  OG   SER A 115     -22.998  21.260   5.232  1.00 40.14      A O
ATOM   609  C    SER A 115     -21.109  21.775   7.413  1.00 40.29      A C
ATOM   610  O    SER A 115     -21.759  21.500   8.425  1.00 39.77      A O
ATOM   611  N    PHE A 116     -20.556  22.963   7.193  1.00 39.27      A N
ATOM   612  CA   PHE A 116     -20.707  24.080   8.114  1.00 38.15      A C
```

FIGURE 3A-12

```
ATOM    613  CB  PHE A 116     -19.347  24.590   8.595  1.00 37.80      A C
ATOM    614  CG  PHE A 116     -18.681  23.700   9.597  1.00 37.37      A C
ATOM    615  CD1 PHE A 116     -17.838  22.672   9.186  1.00 37.07      A C
ATOM    616  CD2 PHE A 116     -18.896  23.891  10.957  1.00 37.13      A C
ATOM    617  CE1 PHE A 116     -17.217  21.849  10.117  1.00 36.45      A C
ATOM    618  CE2 PHE A 116     -18.282  23.075  11.895  1.00 36.55      A C
ATOM    619  CZ  PHE A 116     -17.440  22.052  11.474  1.00 36.83      A C
ATOM    620  C   PHE A 116     -21.402  25.197   7.367  1.00 37.04      A C
ATOM    621  O   PHE A 116     -21.240  25.333   6.160  1.00 37.55      A O
ATOM    622  N   VAL A 117     -22.181  25.994   8.079  1.00 36.15      A N
ATOM    623  CA  VAL A 117     -22.866  27.112   7.454  1.00 35.45      A C
ATOM    624  CB  VAL A 117     -24.395  26.964   7.529  1.00 35.21      A C
ATOM    625  CG1 VAL A 117     -25.062  28.159   6.866  1.00 34.90      A C
ATOM    626  CG2 VAL A 117     -24.820  25.680   6.848  1.00 35.28      A C
ATOM    627  C   VAL A 117     -22.456  28.373   8.188  1.00 35.20      A C
ATOM    628  O   VAL A 117     -22.632  28.479   9.404  1.00 35.12      A O
ATOM    629  N   LEU A 118     -21.889  29.321   7.450  1.00 34.96      A N
ATOM    630  CA  LEU A 118     -21.455  30.579   8.041  1.00 34.30      A C
ATOM    631  CB  LEU A 118     -20.020  30.914   7.617  1.00 34.25      A C
ATOM    632  CG  LEU A 118     -18.882  30.130   8.271  1.00 34.28      A C
ATOM    633  CD1 LEU A 118     -18.986  28.665   7.908  1.00 33.92      A C
ATOM    634  CD2 LEU A 118     -17.552  30.692   7.809  1.00 34.48      A C
ATOM    635  C   LEU A 118     -22.370  31.718   7.641  1.00 33.76      A C
ATOM    636  O   LEU A 118     -22.738  31.857   6.476  1.00 33.44      A O
ATOM    637  N   ILE A 119     -22.745  32.527   8.620  1.00 33.37      A N
ATOM    638  CA  ILE A 119     -23.591  33.672   8.361  1.00 33.43      A C
ATOM    639  CB  ILE A 119     -24.692  33.816   9.438  1.00 33.56      A C
ATOM    640  CG2 ILE A 119     -25.592  34.999   9.108  1.00 33.63      A C
ATOM    641  CG1 ILE A 119     -25.522  32.535   9.509  1.00 32.95      A C
ATOM    642  CD1 ILE A 119     -26.188  32.161   8.202  1.00 32.94      A C
ATOM    643  C   ILE A 119     -22.688  34.897   8.390  1.00 33.60      A C
ATOM    644  O   ILE A 119     -22.243  35.329   9.455  1.00 33.82      A O
ATOM    645  N   LEU A 120     -22.393  35.434   7.210  1.00 33.68      A N
ATOM    646  CA  LEU A 120     -21.545  36.613   7.090  1.00 33.81      A C
ATOM    647  CB  LEU A 120     -20.534  36.449   5.951  1.00 32.42      A C
ATOM    648  CG  LEU A 120     -19.390  35.436   6.032  1.00 31.75      A C
ATOM    649  CD1 LEU A 120     -18.801  35.474   7.430  1.00 31.38      A C
ATOM    650  CD2 LEU A 120     -19.875  34.047   5.693  1.00 31.01      A C
ATOM    651  C   LEU A 120     -22.411  37.825   6.792  1.00 34.85      A C
ATOM    652  O   LEU A 120     -23.500  37.694   6.240  1.00 35.02      A O
ATOM    653  N   GLU A 121     -21.928  39.008   7.150  1.00 36.10      A N
ATOM    654  CA  GLU A 121     -22.687  40.216   6.878  1.00 37.40      A C
ATOM    655  CB  GLU A 121     -22.061  41.422   7.580  1.00 37.97      A C
ATOM    656  CG  GLU A 121     -20.900  42.055   6.823  1.00 38.66      A C
ATOM    657  CD  GLU A 121     -20.249  43.197   7.584  1.00 39.42      A C
ATOM    658  OE1 GLU A 121     -19.770  42.950   8.711  1.00 40.01      A O
ATOM    659  OE2 GLU A 121     -20.215  44.335   7.060  1.00 39.26      A O
ATOM    660  C   GLU A 121     -22.659  40.435   5.371  1.00 37.96      A C
ATOM    661  O   GLU A 121     -21.763  39.943   4.682  1.00 37.98      A O
ATOM    662  N   ARG A 122     -23.646  41.159   4.857  1.00 38.94      A N
ATOM    663  CA  ARG A 122     -23.708  41.456   3.430  1.00 39.63      A C
ATOM    664  CB  ARG A 122     -24.655  40.505   2.694  1.00 39.47      A C
ATOM    665  CG  ARG A 122     -24.886  40.905   1.233  1.00 39.76      A C
ATOM    666  CD  ARG A 122     -25.607  39.827   0.428  1.00 39.91      A C
ATOM    667  NE  ARG A 122     -26.966  39.573   0.900  1.00 40.40      A N
ATOM    668  CZ  ARG A 122     -27.999  40.386   0.700  1.00 40.64      A C
```

FIGURE 3A-13

```
ATOM    669  NH1 ARG A 122     -27.844  41.518   0.029  1.00 40.48     A N
ATOM    670  NH2 ARG A 122     -29.191  40.070   1.182  1.00 40.87     A N
ATOM    671  C   ARG A 122     -24.172  42.884   3.212  1.00 40.02     A C
ATOM    672  O   ARG A 122     -25.291  43.245   3.571  1.00 40.16     A O
ATOM    673  N   PRO A 123     -23.296  43.730   2.653  1.00 40.37     A N
ATOM    674  CD  PRO A 123     -21.826  43.588   2.625  1.00 40.29     A C
ATOM    675  CA  PRO A 123     -23.690  45.120   2.411  1.00 40.78     A C
ATOM    676  CB  PRO A 123     -22.374  45.877   2.572  1.00 40.77     A C
ATOM    677  CG  PRO A 123     -21.374  44.911   2.041  1.00 40.05     A C
ATOM    678  C   PRO A 123     -24.307  45.288   1.024  1.00 41.14     A C
ATOM    679  O   PRO A 123     -23.849  44.689   0.057  1.00 41.69     A O
ATOM    680  N   GLU A 124     -25.366  46.083   0.951  1.00 41.64     A N
ATOM    681  CA  GLU A 124     -26.077  46.356  -0.292  1.00 42.34     A C
ATOM    682  CB  GLU A 124     -27.418  45.600  -0.311  1.00 43.95     A C
ATOM    683  CG  GLU A 124     -28.641  46.389  -0.837  1.00 46.92     A C
ATOM    684  CD  GLU A 124     -28.865  46.255  -2.333  1.00 48.85     A C
ATOM    685  OE1 GLU A 124     -28.046  45.580  -2.996  1.00 50.17     A O
ATOM    686  OE2 GLU A 124     -29.862  46.811  -2.862  1.00 49.28     A O
ATOM    687  C   GLU A 124     -26.327  47.862  -0.348  1.00 41.27     A C
ATOM    688  O   GLU A 124     -26.730  48.466   0.641  1.00 41.61     A O
ATOM    689  N   PRO A 125     -26.068  48.488  -1.502  1.00 40.06     A N
ATOM    690  CD  PRO A 125     -26.402  49.889  -1.813  1.00 39.60     A C
ATOM    691  CA  PRO A 125     -25.557  47.794  -2.685  1.00 39.43     A C
ATOM    692  CB  PRO A 125     -25.821  48.792  -3.806  1.00 39.62     A C
ATOM    693  CG  PRO A 125     -25.662  50.111  -3.106  1.00 39.43     A C
ATOM    694  C   PRO A 125     -24.075  47.480  -2.515  1.00 38.97     A C
ATOM    695  O   PRO A 125     -23.369  48.163  -1.773  1.00 38.90     A O
ATOM    696  N   VAL A 126     -23.614  46.440  -3.197  1.00 38.10     A N
ATOM    697  CA  VAL A 126     -22.219  46.047  -3.108  1.00 37.01     A C
ATOM    698  CB  VAL A 126     -22.004  44.996  -1.997  1.00 37.00     A C
ATOM    699  CG1 VAL A 126     -22.642  43.670  -2.405  1.00 36.38     A C
ATOM    700  CG2 VAL A 126     -20.521  44.820  -1.717  1.00 36.78     A C
ATOM    701  C   VAL A 126     -21.721  45.462  -4.423  1.00 36.45     A C
ATOM    702  O   VAL A 126     -22.506  45.011  -5.262  1.00 36.04     A O
ATOM    703  N   GLN A 127     -20.403  45.478  -4.585  1.00 35.64     A N
ATOM    704  CA  GLN A 127     -19.750  44.940  -5.770  1.00 34.71     A C
ATOM    705  CB  GLN A 127     -19.739  45.974  -6.895  1.00 33.75     A C
ATOM    706  CG  GLN A 127     -19.445  45.380  -8.256  1.00 33.43     A C
ATOM    707  CD  GLN A 127     -19.391  46.420  -9.360  1.00 33.47     A C
ATOM    708  OE1 GLN A 127     -19.526  46.094 -10.540  1.00 33.06     A O
ATOM    709  NE2 GLN A 127     -19.182  47.676  -8.985  1.00 33.86     A N
ATOM    710  C   GLN A 127     -18.319  44.619  -5.364  1.00 34.38     A C
ATOM    711  O   GLN A 127     -17.712  45.375  -4.603  1.00 34.23     A O
ATOM    712  N   ASP A 128     -17.778  43.502  -5.845  1.00 33.87     A N
ATOM    713  CA  ASP A 128     -16.406  43.166  -5.495  1.00 33.29     A C
ATOM    714  CB  ASP A 128     -16.174  41.644  -5.556  1.00 33.89     A C
ATOM    715  CG  ASP A 128     -16.219  41.075  -6.963  1.00 34.07     A C
ATOM    716  OD1 ASP A 128     -16.489  39.861  -7.081  1.00 33.80     A O
ATOM    717  OD2 ASP A 128     -15.968  41.810  -7.940  1.00 34.54     A O
ATOM    718  C   ASP A 128     -15.452  43.937  -6.407  1.00 32.83     A C
ATOM    719  O   ASP A 128     -15.820  44.318  -7.520  1.00 32.76     A O
ATOM    720  N   LEU A 129     -14.241  44.190  -5.921  1.00 31.97     A N
ATOM    721  CA  LEU A 129     -13.251  44.946  -6.674  1.00 30.87     A C
ATOM    722  CB  LEU A 129     -11.949  45.028  -5.876  1.00 30.65     A C
ATOM    723  CG  LEU A 129     -10.874  46.008  -6.362  1.00 30.12     A C
ATOM    724  CD1 LEU A 129     -11.456  47.412  -6.488  1.00 29.34     A C
```

FIGURE 3A-14

| | | | | | | | | | | |
|---|---|---|---|---|---|---|---|---|---|---|
| ATOM | 725 | CD2 | LEU | A | 129 | -9.714 | 46.005 | -5.381 | 1.00 29.33 | A C |
| ATOM | 726 | C | LEU | A | 129 | -12.980 | 44.390 | -8.068 | 1.00 30.82 | A C |
| ATOM | 727 | O | LEU | A | 129 | -12.646 | 45.137 | -8.986 | 1.00 30.41 | A O |
| ATOM | 728 | N | PHE | A | 130 | -13.130 | 43.083 | -8.235 | 1.00 31.39 | A N |
| ATOM | 729 | CA | PHE | A | 130 | -12.891 | 42.470 | -9.536 | 1.00 31.88 | A C |
| ATOM | 730 | CB | PHE | A | 130 | -13.014 | 40.954 | -9.447 | 1.00 32.83 | A C |
| ATOM | 731 | CG | PHE | A | 130 | -12.681 | 40.247 | -10.730 | 1.00 33.86 | A C |
| ATOM | 732 | CD1 | PHE | A | 130 | -11.364 | 39.924 | -11.038 | 1.00 34.05 | A C |
| ATOM | 733 | CD2 | PHE | A | 130 | -13.687 | 39.913 | -11.637 | 1.00 34.34 | A C |
| ATOM | 734 | CE1 | PHE | A | 130 | -11.049 | 39.277 | -12.228 | 1.00 34.23 | A C |
| ATOM | 735 | CE2 | PHE | A | 130 | -13.384 | 39.266 | -12.830 | 1.00 34.36 | A C |
| ATOM | 736 | CZ | PHE | A | 130 | -12.061 | 38.946 | -13.127 | 1.00 34.68 | A C |
| ATOM | 737 | C | PHE | A | 130 | -13.882 | 42.993 | -10.568 | 1.00 32.15 | A C |
| ATOM | 738 | O | PHE | A | 130 | -13.489 | 43.516 | -11.611 | 1.00 32.19 | A O |
| ATOM | 739 | N | ASP | A | 131 | -15.170 | 42.849 | -10.280 | 1.00 32.14 | A N |
| ATOM | 740 | CA | ASP | A | 131 | -16.195 | 43.319 | -11.200 | 1.00 32.37 | A C |
| ATOM | 741 | CB | ASP | A | 131 | -17.586 | 42.933 | -10.693 | 1.00 32.81 | A C |
| ATOM | 742 | CG | ASP | A | 131 | -17.777 | 41.436 | -10.619 | 1.00 33.24 | A C |
| ATOM | 743 | OD1 | ASP | A | 131 | -17.240 | 40.734 | -11.505 | 1.00 33.62 | A O |
| ATOM | 744 | OD2 | ASP | A | 131 | -18.466 | 40.966 | -9.686 | 1.00 33.02 | A O |
| ATOM | 745 | C | ASP | A | 131 | -16.119 | 44.826 | -11.399 | 1.00 32.43 | A C |
| ATOM | 746 | O | ASP | A | 131 | -16.341 | 45.325 | -12.502 | 1.00 32.49 | A O |
| ATOM | 747 | N | PHE | A | 132 | -15.810 | 45.550 | -10.328 | 1.00 32.84 | A N |
| ATOM | 748 | CA | PHE | A | 132 | -15.704 | 47.000 | -10.397 | 1.00 32.97 | A C |
| ATOM | 749 | CB | PHE | A | 132 | -15.384 | 47.568 | -9.007 | 1.00 32.67 | A C |
| ATOM | 750 | CG | PHE | A | 132 | -15.376 | 49.074 | -8.942 | 1.00 32.70 | A C |
| ATOM | 751 | CD1 | PHE | A | 132 | -14.211 | 49.794 | -9.199 | 1.00 32.57 | A C |
| ATOM | 752 | CD2 | PHE | A | 132 | -16.531 | 49.776 | -8.606 | 1.00 32.42 | A C |
| ATOM | 753 | CE1 | PHE | A | 132 | -14.196 | 51.192 | -9.120 | 1.00 32.35 | A C |
| ATOM | 754 | CE2 | PHE | A | 132 | -16.526 | 51.171 | -8.525 | 1.00 32.21 | A C |
| ATOM | 755 | CZ | PHE | A | 132 | -15.355 | 51.879 | -8.781 | 1.00 32.16 | A C |
| ATOM | 756 | C | PHE | A | 132 | -14.620 | 47.376 | -11.403 | 1.00 33.46 | A C |
| ATOM | 757 | O | PHE | A | 132 | -14.870 | 48.158 | -12.320 | 1.00 33.70 | A O |
| ATOM | 758 | N | ILE | A | 133 | -13.429 | 46.797 | -11.250 | 1.00 33.78 | A N |
| ATOM | 759 | CA | ILE | A | 133 | -12.307 | 47.081 | -12.148 | 1.00 34.01 | A C |
| ATOM | 760 | CB | ILE | A | 133 | -11.006 | 46.420 | -11.631 | 1.00 33.36 | A C |
| ATOM | 761 | CG2 | ILE | A | 133 | -9.897 | 46.547 | -12.662 | 1.00 32.84 | A C |
| ATOM | 762 | CG1 | ILE | A | 133 | -10.577 | 47.091 | -10.327 | 1.00 33.01 | A C |
| ATOM | 763 | CD1 | ILE | A | 133 | -9.326 | 46.510 | -9.707 | 1.00 33.02 | A C |
| ATOM | 764 | C | ILE | A | 133 | -12.571 | 46.626 | -13.584 | 1.00 34.68 | A C |
| ATOM | 765 | O | ILE | A | 133 | -12.196 | 47.307 | -14.540 | 1.00 34.81 | A O |
| ATOM | 766 | N | THR | A | 134 | -13.220 | 45.476 | -13.727 | 1.00 35.47 | A N |
| ATOM | 767 | CA | THR | A | 134 | -13.555 | 44.931 | -15.037 | 1.00 36.48 | A C |
| ATOM | 768 | CB | THR | A | 134 | -14.245 | 43.560 | -14.903 | 1.00 36.38 | A C |
| ATOM | 769 | OG1 | THR | A | 134 | -13.359 | 42.637 | -14.259 | 1.00 37.27 | A O |
| ATOM | 770 | CG2 | THR | A | 134 | -14.630 | 43.014 | -16.270 | 1.00 36.21 | A C |
| ATOM | 771 | C | THR | A | 134 | -14.520 | 45.889 | -15.730 | 1.00 37.17 | A C |
| ATOM | 772 | O | THR | A | 134 | -14.540 | 45.997 | -16.956 | 1.00 37.28 | A O |
| ATOM | 773 | N | GLU | A | 135 | -15.301 | 46.604 | -14.932 | 1.00 38.50 | A N |
| ATOM | 774 | CA | GLU | A | 135 | -16.281 | 47.535 | -15.464 | 1.00 39.61 | A C |
| ATOM | 775 | CB | GLU | A | 135 | -17.302 | 47.846 | -14.390 | 1.00 41.18 | A C |
| ATOM | 776 | CG | GLU | A | 135 | -18.704 | 47.993 | -14.881 | 1.00 43.78 | A C |
| ATOM | 777 | CD | GLU | A | 135 | -19.618 | 47.107 | -14.071 | 1.00 45.84 | A C |
| ATOM | 778 | OE1 | GLU | A | 135 | -19.767 | 45.918 | -14.442 | 1.00 46.46 | A O |
| ATOM | 779 | OE2 | GLU | A | 135 | -20.196 | 47.612 | -13.072 | 1.00 47.12 | A O |
| ATOM | 780 | C | GLU | A | 135 | -15.664 | 48.844 | -15.950 | 1.00 39.55 | A C |

FIGURE 3A-15

```
ATOM    781  O   GLU A 135     -15.837  49.239 -17.103  1.00 39.75      A O
ATOM    782  N   ARG A 136     -14.940  49.507 -15.055  1.00 38.81      A N
ATOM    783  CA  ARG A 136     -14.316  50.790 -15.349  1.00 38.32      A C
ATOM    784  CB  ARG A 136     -14.336  51.669 -14.102  1.00 39.53      A C
ATOM    785  CG  ARG A 136     -15.669  51.786 -13.408  1.00 40.80      A C
ATOM    786  CD  ARG A 136     -15.567  52.881 -12.357  1.00 42.79      A C
ATOM    787  NE  ARG A 136     -16.824  53.126 -11.655  1.00 43.60      A N
ATOM    788  CZ  ARG A 136     -17.027  54.155 -10.839  1.00 43.66      A C
ATOM    789  NH1 ARG A 136     -16.054  55.035 -10.627  1.00 43.18      A N
ATOM    790  NH2 ARG A 136     -18.198  54.301 -10.231  1.00 43.84      A N
ATOM    791  C   ARG A 136     -12.880  50.730 -15.845  1.00 37.47      A C
ATOM    792  O   ARG A 136     -12.330  51.753 -16.241  1.00 37.36      A O
ATOM    793  N   GLY A 137     -12.261  49.554 -15.808  1.00 36.50      A N
ATOM    794  CA  GLY A 137     -10.877  49.459 -16.241  1.00 34.82      A C
ATOM    795  C   GLY A 137      -9.964  50.109 -15.210  1.00 33.86      A C
ATOM    796  O   GLY A 137     -10.309  50.182 -14.027  1.00 33.69      A O
ATOM    797  N   ALA A 138      -8.808  50.595 -15.649  1.00 32.62      A N
ATOM    798  CA  ALA A 138      -7.862  51.226 -14.740  1.00 31.43      A C
ATOM    799  CB  ALA A 138      -6.703  51.819 -15.526  1.00 30.83      A C
ATOM    800  C   ALA A 138      -8.532  52.304 -13.891  1.00 30.88      A C
ATOM    801  O   ALA A 138      -9.243  53.164 -14.407  1.00 31.18      A O
ATOM    802  N   LEU A 139      -8.307  52.238 -12.583  1.00 30.21      A N
ATOM    803  CA  LEU A 139      -8.872  53.203 -11.653  1.00 29.62      A C
ATOM    804  CB  LEU A 139      -9.006  52.590 -10.258  1.00 29.01      A C
ATOM    805  CG  LEU A 139      -9.766  51.271 -10.104  1.00 29.60      A C
ATOM    806  CD1 LEU A 139      -9.682  50.809  -8.657  1.00 29.23      A C
ATOM    807  CD2 LEU A 139     -11.216  51.448 -10.529  1.00 29.85      A C
ATOM    808  C   LEU A 139      -7.954  54.414 -11.565  1.00 29.62      A C
ATOM    809  O   LEU A 139      -6.738  54.291 -11.702  1.00 29.07      A O
ATOM    810  N   GLN A 140      -8.539  55.585 -11.345  1.00 29.71      A N
ATOM    811  CA  GLN A 140      -7.757  56.801 -11.204  1.00 30.14      A C
ATOM    812  CB  GLN A 140      -8.669  58.018 -11.093  1.00 31.57      A C
ATOM    813  CG  GLN A 140      -9.322  58.433 -12.393  1.00 34.09      A C
ATOM    814  CD  GLN A 140     -10.351  59.529 -12.189  1.00 35.96      A C
ATOM    815  OE1 GLN A 140     -10.128  60.471 -11.414  1.00 37.35      A O
ATOM    816  NE2 GLN A 140     -11.481  59.422 -12.888  1.00 35.79      A N
ATOM    817  C   GLN A 140      -6.952  56.652  -9.925  1.00 29.78      A C
ATOM    818  O   GLN A 140      -7.416  56.057  -8.954  1.00 29.82      A O
ATOM    819  N   GLU A 141      -5.745  57.196  -9.917  1.00 29.24      A N
ATOM    820  CA  GLU A 141      -4.903  57.076  -8.749  1.00 28.82      A C
ATOM    821  CB  GLU A 141      -3.556  57.745  -9.018  1.00 28.13      A C
ATOM    822  CG  GLU A 141      -2.734  56.898  -9.989  1.00 27.94      A C
ATOM    823  CD  GLU A 141      -1.327  57.395 -10.204  1.00 27.38      A C
ATOM    824  OE1 GLU A 141      -0.679  57.800  -9.220  1.00 27.64      A O
ATOM    825  OE2 GLU A 141      -0.859  57.359 -11.360  1.00 27.40      A O
ATOM    826  C   GLU A 141      -5.535  57.568  -7.458  1.00 28.99      A C
ATOM    827  O   GLU A 141      -5.306  56.986  -6.398  1.00 29.43      A O
ATOM    828  N   GLU A 142      -6.350  58.613  -7.529  1.00 28.80      A N
ATOM    829  CA  GLU A 142      -6.991  59.111  -6.318  1.00 28.51      A C
ATOM    830  CB  GLU A 142      -7.829  60.354  -6.611  1.00 29.94      A C
ATOM    831  CG  GLU A 142      -8.749  60.722  -5.461  1.00 31.87      A C
ATOM    832  CD  GLU A 142      -9.551  61.969  -5.735  1.00 33.74      A C
ATOM    833  OE1 GLU A 142      -8.982  63.076  -5.627  1.00 34.40      A O
ATOM    834  OE2 GLU A 142     -10.750  61.839  -6.065  1.00 34.91      A O
ATOM    835  C   GLU A 142      -7.890  58.047  -5.704  1.00 27.13      A C
ATOM    836  O   GLU A 142      -7.926  57.877  -4.491  1.00 27.18      A O
```

FIGURE 3A-16

```
ATOM    837  N    LEU A 143      -8.625  57.345  -6.553  1.00 26.11      A N
ATOM    838  CA   LEU A 143      -9.529  56.297  -6.105  1.00 25.39      A C
ATOM    839  CB   LEU A 143     -10.489  55.933  -7.239  1.00 24.93      A C
ATOM    840  CG   LEU A 143     -11.494  54.803  -7.020  1.00 24.21      A C
ATOM    841  CD1  LEU A 143     -12.402  55.126  -5.850  1.00 23.68      A C
ATOM    842  CD2  LEU A 143     -12.294  54.613  -8.288  1.00 23.64      A C
ATOM    843  C    LEU A 143      -8.723  55.073  -5.677  1.00 25.26      A C
ATOM    844  O    LEU A 143      -9.037  54.431  -4.674  1.00 25.34      A O
ATOM    845  N    ALA A 144      -7.681  54.757  -6.444  1.00 24.86      A N
ATOM    846  CA   ALA A 144      -6.818  53.621  -6.132  1.00 24.21      A C
ATOM    847  CB   ALA A 144      -5.742  53.478  -7.190  1.00 23.73      A C
ATOM    848  C    ALA A 144      -6.180  53.839  -4.768  1.00 24.07      A C
ATOM    849  O    ALA A 144      -6.028  52.904  -3.984  1.00 24.37      A O
ATOM    850  N    ARG A 145      -5.813  55.086  -4.491  1.00 23.71      A N
ATOM    851  CA   ARG A 145      -5.193  55.438  -3.223  1.00 23.70      A C
ATOM    852  CB   ARG A 145      -4.748  56.908  -3.244  1.00 23.18      A C
ATOM    853  CG   ARG A 145      -4.252  57.440  -1.911  1.00 22.41      A C
ATOM    854  CD   ARG A 145      -3.305  58.616  -2.091  1.00 22.87      A C
ATOM    855  NE   ARG A 145      -3.868  59.644  -2.959  1.00 23.99      A N
ATOM    856  CZ   ARG A 145      -3.367  59.984  -4.141  1.00 24.00      A C
ATOM    857  NH1  ARG A 145      -2.281  59.384  -4.605  1.00 23.84      A N
ATOM    858  NH2  ARG A 145      -3.960  60.922  -4.866  1.00 24.70      A N
ATOM    859  C    ARG A 145      -6.156  55.192  -2.072  1.00 23.74      A C
ATOM    860  O    ARG A 145      -5.796  54.567  -1.077  1.00 23.98      A O
ATOM    861  N    SER A 146      -7.384  55.682  -2.213  1.00 24.11      A N
ATOM    862  CA   SER A 146      -8.393  55.507  -1.174  1.00 23.88      A C
ATOM    863  CB   SER A 146      -9.690  56.207  -1.571  1.00 24.01      A C
ATOM    864  OG   SER A 146     -10.724  55.906  -0.646  1.00 24.93      A O
ATOM    865  C    SER A 146      -8.672  54.030  -0.925  1.00 23.87      A C
ATOM    866  O    SER A 146      -8.721  53.579   0.220  1.00 23.67      A O
ATOM    867  N    PHE A 147      -8.857  53.278  -2.004  1.00 23.51      A N
ATOM    868  CA   PHE A 147      -9.129  51.856  -1.886  1.00 23.53      A C
ATOM    869  CB   PHE A 147      -9.444  51.254  -3.259  1.00 23.38      A C
ATOM    870  CG   PHE A 147     -10.845  51.522  -3.738  1.00 23.87      A C
ATOM    871  CD1  PHE A 147     -11.312  50.930  -4.906  1.00 24.06      A C
ATOM    872  CD2  PHE A 147     -11.707  52.355  -3.017  1.00 25.10      A C
ATOM    873  CE1  PHE A 147     -12.615  51.156  -5.351  1.00 24.66      A C
ATOM    874  CE2  PHE A 147     -13.017  52.591  -3.453  1.00 24.72      A C
ATOM    875  CZ   PHE A 147     -13.469  51.990  -4.623  1.00 25.15      A C
ATOM    876  C    PHE A 147      -7.944  51.133  -1.268  1.00 23.56      A C
ATOM    877  O    PHE A 147      -8.080  50.455  -0.249  1.00 23.49      A O
ATOM    878  N    PHE A 148      -6.779  51.291  -1.884  1.00 23.69      A N
ATOM    879  CA   PHE A 148      -5.571  50.644  -1.398  1.00 23.74      A C
ATOM    880  CB   PHE A 148      -4.364  51.110  -2.211  1.00 23.23      A C
ATOM    881  CG   PHE A 148      -3.127  50.306  -1.963  1.00 23.38      A C
ATOM    882  CD1  PHE A 148      -3.089  48.954  -2.282  1.00 23.13      A C
ATOM    883  CD2  PHE A 148      -1.999  50.894  -1.400  1.00 23.81      A C
ATOM    884  CE1  PHE A 148      -1.947  48.195  -2.044  1.00 23.27      A C
ATOM    885  CE2  PHE A 148      -0.848  50.142  -1.158  1.00 24.14      A C
ATOM    886  CZ   PHE A 148      -0.825  48.788  -1.482  1.00 23.56      A C
ATOM    887  C    PHE A 148      -5.355  50.945   0.083  1.00 23.91      A C
ATOM    888  O    PHE A 148      -5.032  50.055   0.872  1.00 24.10      A O
ATOM    889  N    TRP A 149      -5.546  52.202   0.463  1.00 24.02      A N
ATOM    890  CA   TRP A 149      -5.377  52.600   1.852  1.00 24.16      A C
ATOM    891  CB   TRP A 149      -5.640  54.098   1.999  1.00 23.86      A C
ATOM    892  CG   TRP A 149      -5.523  54.597   3.401  1.00 23.71      A C
```

FIGURE 3A-17

```
ATOM    893  CD2 TRP A 149      -4.348  55.120   4.030  1.00 24.07      A C
ATOM    894  CE2 TRP A 149      -4.705  55.478   5.348  1.00 24.16      A C
ATOM    895  CE3 TRP A 149      -3.026  55.326   3.607  1.00 24.88      A C
ATOM    896  CD1 TRP A 149      -6.512  54.649   4.334  1.00 23.75      A C
ATOM    897  NE1 TRP A 149      -6.032  55.177   5.507  1.00 24.08      A N
ATOM    898  CZ2 TRP A 149      -3.789  56.030   6.253  1.00 23.64      A C
ATOM    899  CZ3 TRP A 149      -2.110  55.878   4.510  1.00 24.22      A C
ATOM    900  CH2 TRP A 149      -2.502  56.223   5.816  1.00 23.99      A C
ATOM    901  C   TRP A 149      -6.303  51.810   2.778  1.00 24.61      A C
ATOM    902  O   TRP A 149      -5.880  51.336   3.834  1.00 24.44      A O
ATOM    903  N   GLN A 150      -7.563  51.660   2.385  1.00 24.62      A N
ATOM    904  CA  GLN A 150      -8.502  50.922   3.216  1.00 24.93      A C
ATOM    905  CB  GLN A 150      -9.916  51.028   2.652  1.00 24.65      A C
ATOM    906  CG  GLN A 150     -10.509  52.405   2.820  1.00 24.72      A C
ATOM    907  CD  GLN A 150     -11.945  52.471   2.389  1.00 24.92      A C
ATOM    908  OE1 GLN A 150     -12.796  51.745   2.909  1.00 25.73      A O
ATOM    909  NE2 GLN A 150     -12.233  53.343   1.433  1.00 24.37      A N
ATOM    910  C   GLN A 150      -8.102  49.464   3.363  1.00 25.33      A C
ATOM    911  O   GLN A 150      -8.260  48.880   4.435  1.00 25.92      A O
ATOM    912  N   VAL A 151      -7.587  48.876   2.289  1.00 25.25      A N
ATOM    913  CA  VAL A 151      -7.145  47.488   2.331  1.00 25.03      A C
ATOM    914  CB  VAL A 151      -6.720  47.010   0.922  1.00 24.97      A C
ATOM    915  CG1 VAL A 151      -6.102  45.628   0.990  1.00 24.00      A C
ATOM    916  CG2 VAL A 151      -7.940  46.990   0.006  1.00 24.08      A C
ATOM    917  C   VAL A 151      -5.973  47.390   3.318  1.00 25.35      A C
ATOM    918  O   VAL A 151      -5.902  46.462   4.124  1.00 25.04      A O
ATOM    919  N   LEU A 152      -5.067  48.363   3.263  1.00 25.21      A N
ATOM    920  CA  LEU A 152      -3.927  48.398   4.172  1.00 25.75      A C
ATOM    921  CB  LEU A 152      -3.080  49.643   3.907  1.00 26.75      A C
ATOM    922  CG  LEU A 152      -1.853  49.524   2.998  1.00 27.38      A C
ATOM    923  CD1 LEU A 152      -0.743  48.804   3.745  1.00 28.24      A C
ATOM    924  CD2 LEU A 152      -2.213  48.786   1.724  1.00 27.81      A C
ATOM    925  C   LEU A 152      -4.394  48.404   5.631  1.00 26.06      A C
ATOM    926  O   LEU A 152      -3.864  47.666   6.464  1.00 26.92      A O
ATOM    927  N   GLU A 153      -5.382  49.238   5.943  1.00 25.55      A N
ATOM    928  CA  GLU A 153      -5.894  49.310   7.305  1.00 25.01      A C
ATOM    929  CB  GLU A 153      -6.923  50.436   7.444  1.00 24.91      A C
ATOM    930  CG  GLU A 153      -6.369  51.849   7.299  1.00 24.63      A C
ATOM    931  CD  GLU A 153      -5.447  52.254   8.429  1.00 24.61      A C
ATOM    932  OE1 GLU A 153      -5.860  52.188   9.606  1.00 25.80      A O
ATOM    933  OE2 GLU A 153      -4.305  52.646   8.141  1.00 24.66      A O
ATOM    934  C   GLU A 153      -6.549  47.990   7.676  1.00 24.96      A C
ATOM    935  O   GLU A 153      -6.428  47.522   8.807  1.00 25.02      A O
ATOM    936  N   ALA A 154      -7.245  47.389   6.719  1.00 24.74      A N
ATOM    937  CA  ALA A 154      -7.927  46.121   6.960  1.00 24.40      A C
ATOM    938  CB  ALA A 154      -8.736  45.730   5.734  1.00 23.60      A C
ATOM    939  C   ALA A 154      -6.923  45.019   7.305  1.00 24.50      A C
ATOM    940  O   ALA A 154      -7.065  44.322   8.315  1.00 24.02      A O
ATOM    941  N   VAL A 155      -5.907  44.879   6.458  1.00 24.37      A N
ATOM    942  CA  VAL A 155      -4.871  43.876   6.645  1.00 23.98      A C
ATOM    943  CB  VAL A 155      -3.918  43.868   5.437  1.00 23.74      A C
ATOM    944  CG1 VAL A 155      -2.766  42.906   5.675  1.00 23.12      A C
ATOM    945  CG2 VAL A 155      -4.694  43.471   4.189  1.00 22.23      A C
ATOM    946  C   VAL A 155      -4.087  44.100   7.939  1.00 24.45      A C
ATOM    947  O   VAL A 155      -3.766  43.144   8.646  1.00 24.66      A O
ATOM    948  N   ARG A 156      -3.783  45.355   8.253  1.00 24.87      A N
```

FIGURE 3A-18

```
ATOM    949  CA   ARG A 156      -3.057  45.664   9.484  1.00 25.73      A C
ATOM    950  CB   ARG A 156      -2.835  47.169   9.620  1.00 25.57      A C
ATOM    951  CG   ARG A 156      -1.757  47.727   8.721  1.00 25.81      A C
ATOM    952  CD   ARG A 156      -1.628  49.217   8.949  1.00 26.16      A C
ATOM    953  NE   ARG A 156      -1.390  49.529  10.355  1.00 25.39      A N
ATOM    954  CZ   ARG A 156      -1.560  50.736  10.888  1.00 25.56      A C
ATOM    955  NH1  ARG A 156      -1.973  51.746  10.129  1.00 25.06      A N
ATOM    956  NH2  ARG A 156      -1.318  50.932  12.178  1.00 24.70      A N
ATOM    957  C    ARG A 156      -3.850  45.174  10.685  1.00 26.21      A C
ATOM    958  O    ARG A 156      -3.286  44.681  11.658  1.00 26.09      A O
ATOM    959  N    HIS A 157      -5.167  45.324  10.605  1.00 27.27      A N
ATOM    960  CA   HIS A 157      -6.060  44.900  11.672  1.00 28.10      A C
ATOM    961  CB   HIS A 157      -7.496  45.314  11.342  1.00 28.83      A C
ATOM    962  CG   HIS A 157      -8.492  44.906  12.381  1.00 29.71      A C
ATOM    963  CD2  HIS A 157      -9.511  44.014  12.339  1.00 29.89      A C
ATOM    964  ND1  HIS A 157      -8.483  45.417  13.661  1.00 29.64      A N
ATOM    965  CE1  HIS A 157      -9.452  44.857  14.362  1.00 30.46      A C
ATOM    966  NE2  HIS A 157     -10.091  44.001  13.584  1.00 30.34      A N
ATOM    967  C    HIS A 157      -5.980  43.385  11.850  1.00 28.43      A C
ATOM    968  O    HIS A 157      -5.838  42.890  12.964  1.00 27.78      A O
ATOM    969  N    CYS A 158      -6.080  42.656  10.743  1.00 28.85      A N
ATOM    970  CA   CYS A 158      -6.002  41.205  10.777  1.00 29.90      A C
ATOM    971  CB   CYS A 158      -6.041  40.629   9.360  1.00 29.92      A C
ATOM    972  SG   CYS A 158      -7.624  40.767   8.518  1.00 30.27      A S
ATOM    973  C    CYS A 158      -4.715  40.754  11.457  1.00 30.90      A C
ATOM    974  O    CYS A 158      -4.754  40.035  12.457  1.00 30.43      A O
ATOM    975  N    HIS A 159      -3.577  41.174  10.903  1.00 31.97      A N
ATOM    976  CA   HIS A 159      -2.274  40.805  11.451  1.00 33.00      A C
ATOM    977  CB   HIS A 159      -1.143  41.488  10.676  1.00 33.25      A C
ATOM    978  CG   HIS A 159      -1.010  41.019   9.260  1.00 33.78      A C
ATOM    979  CD2  HIS A 159      -1.756  40.155   8.531  1.00 33.93      A C
ATOM    980  ND1  HIS A 159       0.005  41.443   8.428  1.00 34.42      A N
ATOM    981  CE1  HIS A 159      -0.121  40.859   7.250  1.00 34.09      A C
ATOM    982  NE2  HIS A 159      -1.181  40.072   7.286  1.00 34.10      A N
ATOM    983  C    HIS A 159      -2.196  41.206  12.908  1.00 33.51      A C
ATOM    984  O    HIS A 159      -1.642  40.492  13.734  1.00 33.68      A O
ATOM    985  N    ASN A 160      -2.768  42.359  13.216  1.00 34.53      A N
ATOM    986  CA   ASN A 160      -2.769  42.870  14.571  1.00 35.45      A C
ATOM    987  CB   ASN A 160      -3.405  44.252  14.584  1.00 36.72      A C
ATOM    988  CG   ASN A 160      -3.126  44.998  15.856  1.00 38.28      A C
ATOM    989  OD1  ASN A 160      -3.716  44.721  16.903  1.00 38.86      A O
ATOM    990  ND2  ASN A 160      -2.205  45.945  15.781  1.00 40.04      A N
ATOM    991  C    ASN A 160      -3.520  41.940  15.522  1.00 35.76      A C
ATOM    992  O    ASN A 160      -3.279  41.950  16.727  1.00 35.78      A O
ATOM    993  N    CME A 161      -4.429  41.140  14.969  1.00 36.10      A N
ATOM    994  CA   CME A 161      -5.226  40.204  15.756  1.00 35.76      A C
ATOM    995  C    CME A 161      -4.751  38.763  15.572  1.00 34.38      A C
ATOM    996  CB   CME A 161      -6.704  40.309  15.365  1.00 37.89      A C
ATOM    997  SG   CME A 161      -7.621  41.814  15.878  1.00 42.07      A S
ATOM    998  S1   CME A 161      -7.310  42.058  17.938  1.00 45.24      A S
ATOM    999  C1   CME A 161      -6.265  43.547  18.187  1.00 45.82      A C
ATOM   1000  C2   CME A 161      -5.721  43.786  19.599  1.00 46.85      A C
ATOM   1001  O1   CME A 161      -6.751  44.150  20.537  1.00 47.93      A O
ATOM   1002  O    CME A 161      -5.466  37.823  15.904  1.00 34.21      A O
ATOM   1003  N    GLY A 162      -3.548  38.597  15.029  1.00 32.70      A N
ATOM   1004  CA   GLY A 162      -2.992  37.269  14.833  1.00 30.82      A C
```

FIGURE 3A-19

```
ATOM   1005  C    GLY A 162      -3.502  36.490  13.639  1.00 29.85      A C
ATOM   1006  O    GLY A 162      -3.221  35.300  13.514  1.00 29.76      A O
ATOM   1007  N    VAL A 163      -4.234  37.159  12.754  1.00 28.88      A N
ATOM   1008  CA   VAL A 163      -4.800  36.526  11.565  1.00 27.52      A C
ATOM   1009  CB   VAL A 163      -6.288  36.908  11.410  1.00 27.20      A C
ATOM   1010  CG1  VAL A 163      -6.884  36.230  10.190  1.00 26.57      A C
ATOM   1011  CG2  VAL A 163      -7.048  36.541  12.668  1.00 26.27      A C
ATOM   1012  C    VAL A 163      -4.078  36.924  10.277  1.00 27.64      A C
ATOM   1013  O    VAL A 163      -3.790  38.102  10.058  1.00 27.58      A O
ATOM   1014  N    LEU A 164      -3.798  35.942   9.423  1.00 27.28      A N
ATOM   1015  CA   LEU A 164      -3.137  36.195   8.144  1.00 27.55      A C
ATOM   1016  CB   LEU A 164      -1.822  35.418   8.067  1.00 27.47      A C
ATOM   1017  CG   LEU A 164      -0.903  35.729   6.884  1.00 27.86      A C
ATOM   1018  CD1  LEU A 164      -0.329  37.135   7.026  1.00 27.32      A C
ATOM   1019  CD2  LEU A 164       0.219  34.711   6.837  1.00 28.12      A C
ATOM   1020  C    LEU A 164      -4.086  35.722   7.043  1.00 27.66      A C
ATOM   1021  O    LEU A 164      -4.420  34.543   6.983  1.00 28.65      A O
ATOM   1022  N    HIS A 165      -4.521  36.628   6.175  1.00 27.14      A N
ATOM   1023  CA   HIS A 165      -5.462  36.264   5.115  1.00 27.41      A C
ATOM   1024  CB   HIS A 165      -5.946  37.526   4.393  1.00 27.04      A C
ATOM   1025  CG   HIS A 165      -7.145  37.304   3.523  1.00 26.00      A C
ATOM   1026  CD2  HIS A 165      -8.431  37.704   3.661  1.00 25.61      A C
ATOM   1027  ND1  HIS A 165      -7.092  36.583   2.350  1.00 25.86      A N
ATOM   1028  CE1  HIS A 165      -8.294  36.550   1.801  1.00 25.87      A C
ATOM   1029  NE2  HIS A 165      -9.124  37.222   2.577  1.00 25.44      A N
ATOM   1030  C    HIS A 165      -4.935  35.247   4.095  1.00 27.80      A C
ATOM   1031  O    HIS A 165      -5.617  34.276   3.772  1.00 27.85      A O
ATOM   1032  N    ARG A 166      -3.732  35.485   3.584  1.00 28.06      A N
ATOM   1033  CA   ARG A 166      -3.079  34.607   2.614  1.00 28.85      A C
ATOM   1034  CB   ARG A 166      -2.881  33.205   3.204  1.00 28.96      A C
ATOM   1035  CG   ARG A 166      -1.908  33.183   4.372  1.00 30.05      A C
ATOM   1036  CD   ARG A 166      -1.286  31.813   4.591  1.00 30.84      A C
ATOM   1037  NE   ARG A 166      -2.265  30.781   4.920  1.00 31.86      A N
ATOM   1038  CZ   ARG A 166      -1.949  29.510   5.153  1.00 32.15      A C
ATOM   1039  NH1  ARG A 166      -0.680  29.122   5.093  1.00 32.26      A N
ATOM   1040  NH2  ARG A 166      -2.896  28.626   5.439  1.00 31.89      A N
ATOM   1041  C    ARG A 166      -3.696  34.487   1.225  1.00 29.22      A C
ATOM   1042  O    ARG A 166      -3.264  33.652   0.428  1.00 29.30      A O
ATOM   1043  N    ASP A 167      -4.696  35.307   0.920  1.00 29.60      A N
ATOM   1044  CA   ASP A 167      -5.297  35.267  -0.410  1.00 30.19      A C
ATOM   1045  CB   ASP A 167      -6.369  34.175  -0.500  1.00 31.24      A C
ATOM   1046  CG   ASP A 167      -6.885  33.972  -1.927  1.00 32.27      A C
ATOM   1047  OD1  ASP A 167      -6.075  34.032  -2.879  1.00 31.88      A O
ATOM   1048  OD2  ASP A 167      -8.102  33.738  -2.096  1.00 33.01      A O
ATOM   1049  C    ASP A 167      -5.885  36.618  -0.786  1.00 29.94      A C
ATOM   1050  O    ASP A 167      -6.957  36.702  -1.375  1.00 30.11      A O
ATOM   1051  N    ILE A 168      -5.167  37.678  -0.441  1.00 29.49      A N
ATOM   1052  CA   ILE A 168      -5.610  39.024  -0.758  1.00 29.04      A C
ATOM   1053  CB   ILE A 168      -4.668  40.068  -0.136  1.00 28.62      A C
ATOM   1054  CG2  ILE A 168      -5.115  41.467  -0.527  1.00 28.12      A C
ATOM   1055  CG1  ILE A 168      -4.639  39.903   1.383  1.00 27.90      A C
ATOM   1056  CD1  ILE A 168      -3.630  40.792   2.071  1.00 27.24      A C
ATOM   1057  C    ILE A 168      -5.615  39.215  -2.274  1.00 29.41      A C
ATOM   1058  O    ILE A 168      -4.645  38.885  -2.948  1.00 29.32      A O
ATOM   1059  N    LYS A 169      -6.715  39.737  -2.803  1.00 29.95      A N
ATOM   1060  CA   LYS A 169      -6.856  40.003  -4.233  1.00 30.50      A C
```

FIGURE 3A-20

```
ATOM   1061  CB   LYS A 169      -6.806  38.708  -5.044  1.00 30.68      A C
ATOM   1062  CG   LYS A 169      -7.917  37.729  -4.752  1.00 31.56      A C
ATOM   1063  CD   LYS A 169      -7.821  36.520  -5.668  1.00 31.68      A C
ATOM   1064  CE   LYS A 169      -8.943  35.539  -5.397  1.00 32.81      A C
ATOM   1065  NZ   LYS A 169      -8.951  34.432  -6.388  1.00 33.88      A N
ATOM   1066  C    LYS A 169      -8.181  40.723  -4.462  1.00 31.04      A C
ATOM   1067  O    LYS A 169      -8.994  40.831  -3.542  1.00 30.81      A O
ATOM   1068  N    ASP A 170      -8.409  41.210  -5.678  1.00 31.62      A N
ATOM   1069  CA   ASP A 170      -9.635  41.954  -5.970  1.00 31.91      A C
ATOM   1070  CB   ASP A 170      -9.617  42.494  -7.409  1.00 32.09      A C
ATOM   1071  CG   ASP A 170      -9.363  41.416  -8.442  1.00 32.44      A C
ATOM   1072  OD1  ASP A 170      -9.453  40.218  -8.104  1.00 32.55      A O
ATOM   1073  OD2  ASP A 170      -9.083  41.774  -9.605  1.00 33.13      A O
ATOM   1074  C    ASP A 170     -10.941  41.211  -5.716  1.00 32.04      A C
ATOM   1075  O    ASP A 170     -11.917  41.817  -5.272  1.00 32.35      A O
ATOM   1076  N    GLU A 171     -10.971  39.911  -5.988  1.00 32.22      A N
ATOM   1077  CA   GLU A 171     -12.185  39.134  -5.768  1.00 32.65      A C
ATOM   1078  CB   GLU A 171     -12.010  37.704  -6.275  1.00 34.08      A C
ATOM   1079  CG   GLU A 171     -11.769  37.601  -7.767  1.00 36.63      A C
ATOM   1080  CD   GLU A 171     -11.674  36.162  -8.241  1.00 37.66      A C
ATOM   1081  OE1  GLU A 171     -12.683  35.437  -8.128  1.00 38.54      A O
ATOM   1082  OE2  GLU A 171     -10.591  35.755  -8.720  1.00 38.71      A O
ATOM   1083  C    GLU A 171     -12.585  39.098  -4.296  1.00 32.10      A C
ATOM   1084  O    GLU A 171     -13.772  39.132  -3.974  1.00 32.75      A O
ATOM   1085  N    ASN A 172     -11.601  39.031  -3.405  1.00 31.09      A N
ATOM   1086  CA   ASN A 172     -11.884  38.988  -1.976  1.00 30.05      A C
ATOM   1087  CB   ASN A 172     -10.822  38.168  -1.249  1.00 30.17      A C
ATOM   1088  CG   ASN A 172     -10.752  36.749  -1.756  1.00 30.81      A C
ATOM   1089  OD1  ASN A 172     -11.777  36.148  -2.071  1.00 31.78      A O
ATOM   1090  ND2  ASN A 172      -9.547  36.200  -1.832  1.00 30.68      A N
ATOM   1091  C    ASN A 172     -12.007  40.363  -1.331  1.00 29.26      A C
ATOM   1092  O    ASN A 172     -11.818  40.513  -0.127  1.00 29.36      A O
ATOM   1093  N    ILE A 173     -12.332  41.363  -2.140  1.00 28.28      A N
ATOM   1094  CA   ILE A 173     -12.513  42.717  -1.640  1.00 27.69      A C
ATOM   1095  CB   ILE A 173     -11.395  43.654  -2.134  1.00 27.05      A C
ATOM   1096  CG2  ILE A 173     -11.711  45.088  -1.737  1.00 26.18      A C
ATOM   1097  CG1  ILE A 173     -10.052  43.207  -1.547  1.00 26.76      A C
ATOM   1098  CD1  ILE A 173      -8.858  44.012  -2.031  1.00 26.08      A C
ATOM   1099  C    ILE A 173     -13.868  43.248  -2.109  1.00 27.91     .A C
ATOM   1100  O    ILE A 173     -14.119  43.375  -3.312  1.00 27.75      A O
ATOM   1101  N    LEU A 174     -14.739  43.539  -1.148  1.00 27.70      A N
ATOM   1102  CA   LEU A 174     -16.075  44.046  -1.429  1.00 28.50      A C
ATOM   1103  CB   LEU A 174     -17.092  43.388  -0.492  1.00 28.49      A C
ATOM   1104  CG   LEU A 174     -17.783  42.101  -0.957  1.00 28.90      A C
ATOM   1105  CD1  LEU A 174     -16.777  41.148  -1.571  1.00 27.75      A C
ATOM   1106  CD2  LEU A 174     -18.507  41.463   0.225  1.00 27.83      A C
ATOM   1107  C    LEU A 174     -16.144  45.554  -1.260  1.00 29.02      A C
ATOM   1108  O    LEU A 174     -15.508  46.115  -0.368  1.00 29.28      A O
ATOM   1109  N    ILE A 175     -16.926  46.207  -2.113  1.00 29.66      A N
ATOM   1110  CA   ILE A 175     -17.085  47.655  -2.044  1.00 30.43      A C
ATOM   1111  CB   ILE A 175     -16.798  48.327  -3.403  1.00 29.68      A C
ATOM   1112  CG2  ILE A 175     -16.890  49.835  -3.256  1.00 29.27      A C
ATOM   1113  CG1  ILE A 175     -15.413  47.932  -3.915  1.00 29.16      A C
ATOM   1114  CD1  ILE A 175     -15.116  48.459  -5.300  1.00 28.37      A C
ATOM   1115  C    ILE A 175     -18.505  48.054  -1.642  1.00 31.77      A C
ATOM   1116  O    ILE A 175     -19.470  47.753  -2.351  1.00 32.32      A O
```

FIGURE 3A-21

```
ATOM   1117  N    ASP A 176     -18.638  48.717  -0.498  1.00 32.78      A N
ATOM   1118  CA   ASP A 176     -19.943  49.188  -0.064  1.00 33.45      A C
ATOM   1119  CB   ASP A 176     -19.948  49.464   1.440  1.00 34.50      A C
ATOM   1120  CG   ASP A 176     -21.260  50.065   1.920  1.00 35.90      A C
ATOM   1121  OD1  ASP A 176     -21.466  50.133   3.154  1.00 35.90      A O
ATOM   1122  OD2  ASP A 176     -22.081  50.473   1.065  1.00 36.68      A O
ATOM   1123  C    ASP A 176     -20.121  50.477  -0.856  1.00 33.84      A C
ATOM   1124  O    ASP A 176     -19.639  51.542  -0.466  1.00 33.73      A O
ATOM   1125  N    LEU A 177     -20.800  50.355  -1.989  1.00 34.35      A N
ATOM   1126  CA   LEU A 177     -21.034  51.469  -2.897  1.00 34.94      A C
ATOM   1127  CB   LEU A 177     -21.876  50.977  -4.071  1.00 34.39      A C
ATOM   1128  CG   LEU A 177     -21.190  49.843  -4.833  1.00 34.54      A C
ATOM   1129  CD1  LEU A 177     -22.128  49.281  -5.885  1.00 34.44      A C
ATOM   1130  CD2  LEU A 177     -19.906  50.367  -5.466  1.00 34.05      A C
ATOM   1131  C    LEU A 177     -21.628  52.768  -2.341  1.00 35.39      A C
ATOM   1132  O    LEU A 177     -21.436  53.824  -2.942  1.00 35.44      A O
ATOM   1133  N    ASN A 178     -22.337  52.715  -1.215  1.00 35.79      A N
ATOM   1134  CA   ASN A 178     -22.917  53.941  -0.659  1.00 36.63      A C
ATOM   1135  CB   ASN A 178     -24.241  53.658   0.055  1.00 38.13      A C
ATOM   1136  CG   ASN A 178     -25.328  53.197  -0.891  1.00 39.81      A C
ATOM   1137  OD1  ASN A 178     -25.393  53.628  -2.048  1.00 40.82      A O
ATOM   1138  ND2  ASN A 178     -26.204  52.326  -0.399  1.00 40.44      A N
ATOM   1139  C    ASN A 178     -22.009  54.695   0.303  1.00 36.35      A C
ATOM   1140  O    ASN A 178     -21.968  55.926   0.285  1.00 36.43      A O
ATOM   1141  N    ARG A 179     -21.290  53.964   1.148  1.00 36.08      A N
ATOM   1142  CA   ARG A 179     -20.398  54.592   2.117  1.00 35.54      A C
ATOM   1143  CB   ARG A 179     -20.472  53.848   3.452  1.00 35.72      A C
ATOM   1144  CG   ARG A 179     -21.770  53.099   3.650  1.00 36.53      A C
ATOM   1145  CD   ARG A 179     -22.109  52.894   5.113  1.00 37.40      A C
ATOM   1146  NE   ARG A 179     -22.392  54.165   5.774  1.00 38.64      A N
ATOM   1147  CZ   ARG A 179     -23.242  54.309   6.788  1.00 39.22      A C
ATOM   1148  NH1  ARG A 179     -23.903  53.258   7.263  1.00 39.11      A N
ATOM   1149  NH2  ARG A 179     -23.428  55.506   7.329  1.00 39.52      A N
ATOM   1150  C    ARG A 179     -18.953  54.627   1.621  1.00 35.14      A C
ATOM   1151  O    ARG A 179     -18.092  55.246   2.244  1.00 35.38      A O
ATOM   1152  N    GLY A 180     -18.694  53.963   0.500  1.00 34.44      A N
ATOM   1153  CA   GLY A 180     -17.350  53.943  -0.051  1.00 34.03      A C
ATOM   1154  C    GLY A 180     -16.348  53.237   0.847  1.00 33.47      A C
ATOM   1155  O    GLY A 180     -15.188  53.645   0.947  1.00 32.89      A O
ATOM   1156  N    GLU A 181     -16.797  52.169   1.498  1.00 32.72      A N
ATOM   1157  CA   GLU A 181     -15.937  51.410   2.389  1.00 32.27      A C
ATOM   1158  CB   GLU A 181     -16.592  51.281   3.768  1.00 32.61      A C
ATOM   1159  CG   GLU A 181     -17.169  52.579   4.311  1.00 33.71      A C
ATOM   1160  CD   GLU A 181     -17.585  52.473   5.767  1.00 34.08      A C
ATOM   1161  OE1  GLU A 181     -18.042  51.384   6.181  1.00 34.28      A O
ATOM   1162  OE2  GLU A 181     -17.467  53.485   6.493  1.00 33.93      A O
ATOM   1163  C    GLU A 181     -15.665  50.022   1.823  1.00 31.66      A C
ATOM   1164  O    GLU A 181     -16.565  49.378   1.282  1.00 31.09      A O
ATOM   1165  N    LEU A 182     -14.419  49.568   1.944  1.00 30.96      A N
ATOM   1166  CA   LEU A 182     -14.041  48.243   1.466  1.00 30.07      A C
ATOM   1167  CB   LEU A 182     -12.640  48.267   0.851  1.00 29.41      A C
ATOM   1168  CG   LEU A 182     -12.387  49.165  -0.354  1.00 29.21      A C
ATOM   1169  CD1  LEU A 182     -11.114  48.710  -1.041  1.00 28.62      A C
ATOM   1170  CD2  LEU A 182     -13.547  49.086  -1.325  1.00 29.92      A C
ATOM   1171  C    LEU A 182     -14.058  47.239   2.615  1.00 29.82      A C
ATOM   1172  O    LEU A 182     -13.753  47.582   3.756  1.00 29.25      A O
```

FIGURE 3A-22

```
ATOM   1173  N   LYS A 183     -14.426  46.001   2.303  1.00 30.07      A N
ATOM   1174  CA  LYS A 183     -14.471  44.927   3.293  1.00 30.71      A C
ATOM   1175  CB  LYS A 183     -15.894  44.372   3.447  1.00 31.45      A C
ATOM   1176  CG  LYS A 183     -16.949  45.362   3.886  1.00 32.60      A C
ATOM   1177  CD  LYS A 183     -16.688  45.848   5.285  1.00 33.53      A C
ATOM   1178  CE  LYS A 183     -17.854  46.658   5.795  1.00 33.79      A C
ATOM   1179  NZ  LYS A 183     -17.534  47.199   7.143  1.00 35.44      A N
ATOM   1180  C   LYS A 183     -13.580  43.804   2.783  1.00 30.21      A C
ATOM   1181  O   LYS A 183     -13.539  43.540   1.586  1.00 30.64      A O
ATOM   1182  N   LEU A 184     -12.879  43.136   3.687  1.00 29.80      A N
ATOM   1183  CA  LEU A 184     -12.013  42.028   3.305  1.00 29.44      A C
ATOM   1184  CB  LEU A 184     -10.772  42.029   4.190  1.00 29.60      A C
ATOM   1185  CG  LEU A 184      -9.542  41.306   3.672  1.00 29.64      A C
ATOM   1186  CD1 LEU A 184      -9.189  41.832   2.289  1.00 29.95      A C
ATOM   1187  CD2 LEU A 184      -8.397  41.525   4.651  1.00 29.57      A C
ATOM   1188  C   LEU A 184     -12.818  40.748   3.519  1.00 29.19      A C
ATOM   1189  O   LEU A 184     -13.404  40.566   4.581  1.00 28.95      A O
ATOM   1190  N   ILE A 185     -12.853  39.862   2.527  1.00 29.26      A N
ATOM   1191  CA  ILE A 185     -13.634  38.636   2.664  1.00 29.41      A C
ATOM   1192  CB  ILE A 185     -14.868  38.643   1.747  1.00 29.37      A C
ATOM   1193  CG2 ILE A 185     -15.717  39.859   2.007  1.00 29.23      A C
ATOM   1194  CG1 ILE A 185     -14.415  38.622   0.288  1.00 28.93      A C
ATOM   1195  CD1 ILE A 185     -15.535  38.392  -0.692  1.00 29.20      A C
ATOM   1196  C   ILE A 185     -12.919  37.331   2.357  1.00 29.93      A C
ATOM   1197  O   ILE A 185     -11.859  37.306   1.736  1.00 29.95      A O
ATOM   1198  N   ASP A 186     -13.554  36.247   2.790  1.00 30.58      A N
ATOM   1199  CA  ASP A 186     -13.089  34.887   2.569  1.00 31.55      A C
ATOM   1200  CB  ASP A 186     -13.116  34.583   1.068  1.00 33.37      A C
ATOM   1201  CG  ASP A 186     -12.992  33.099   0.766  1.00 35.64      A C
ATOM   1202  OD1 ASP A 186     -13.000  32.736  -0.435  1.00 36.97      A O
ATOM   1203  OD2 ASP A 186     -12.888  32.297   1.724  1.00 36.62      A O
ATOM   1204  C   ASP A 186     -11.717  34.554   3.144  1.00 31.24      A C
ATOM   1205  O   ASP A 186     -10.704  34.627   2.449  1.00 30.97      A O
ATOM   1206  N   PHE A 187     -11.697  34.178   4.418  1.00 30.93      A N
ATOM   1207  CA  PHE A 187     -10.456  33.809   5.081  1.00 30.95      A C
ATOM   1208  CB  PHE A 187     -10.475  34.267   6.538  1.00 29.88      A C
ATOM   1209  CG  PHE A 187     -10.340  35.751   6.707  1.00 29.14      A C
ATOM   1210  CD1 PHE A 187     -11.297  36.615   6.192  1.00 29.25      A C
ATOM   1211  CD2 PHE A 187      -9.245  36.287   7.370  1.00 28.76      A C
ATOM   1212  CE1 PHE A 187     -11.162  37.998   6.336  1.00 28.89      A C
ATOM   1213  CE2 PHE A 187      -9.103  37.666   7.518  1.00 28.88      A C
ATOM   1214  CZ  PHE A 187     -10.063  38.522   7.001  1.00 28.47      A C
ATOM   1215  C   PHE A 187     -10.288  32.295   5.017  1.00 31.55      A C
ATOM   1216  O   PHE A 187      -9.692  31.686   5.904  1.00 31.88      A O
ATOM   1217  N   GLY A 188     -10.814  31.697   3.952  1.00 31.94      A N
ATOM   1218  CA  GLY A 188     -10.741  30.257   3.788  1.00 32.52      A C
ATOM   1219  C   GLY A 188      -9.357  29.673   3.585  1.00 32.98      A C
ATOM   1220  O   GLY A 188      -9.158  28.478   3.802  1.00 33.39      A O
ATOM   1221  N   SER A 189      -8.404  30.498   3.164  1.00 33.28      A N
ATOM   1222  CA  SER A 189      -7.036  30.033   2.933  1.00 33.55      A C
ATOM   1223  CB  SER A 189      -6.574  30.424   1.531  1.00 34.37      A C
ATOM   1224  OG  SER A 189      -7.604  30.229   0.577  1.00 36.56      A O
ATOM   1225  C   SER A 189      -6.109  30.675   3.953  1.00 33.58      A C
ATOM   1226  O   SER A 189      -4.887  30.542   3.874  1.00 33.11      A O
ATOM   1227  N   GLY A 190      -6.705  31.378   4.909  1.00 33.85      A N
ATOM   1228  CA  GLY A 190      -5.927  32.055   5.927  1.00 34.60      A C
```

FIGURE 3A-23

```
ATOM   1229  C    GLY A 190      -5.216  31.139   6.901  1.00 35.32       A C
ATOM   1230  O    GLY A 190      -5.149  29.921   6.712  1.00 36.21       A O
ATOM   1231  N    ALA A 191      -4.681  31.739   7.957  1.00 35.00       A N
ATOM   1232  CA   ALA A 191      -3.964  30.997   8.982  1.00 34.56       A C
ATOM   1233  CB   ALA A 191      -2.679  30.425   8.403  1.00 34.09       A C
ATOM   1234  C    ALA A 191      -3.641  31.941  10.125  1.00 34.39       A C
ATOM   1235  O    ALA A 191      -3.765  33.162   9.989  1.00 34.69       A O
ATOM   1236  N    LEU A 192      -3.241  31.379  11.258  1.00 33.84       A N
ATOM   1237  CA   LEU A 192      -2.875  32.198  12.397  1.00 33.58       A C
ATOM   1238  CB   LEU A 192      -2.724  31.338  13.646  1.00 33.29       A C
ATOM   1239  CG   LEU A 192      -3.999  30.632  14.100  1.00 33.54       A C
ATOM   1240  CD1  LEU A 192      -3.680  29.682  15.248  1.00 33.49       A C
ATOM   1241  CD2  LEU A 192      -5.032  31.674  14.517  1.00 33.20       A C
ATOM   1242  C    LEU A 192      -1.538  32.813  12.027  1.00 33.83       A C
ATOM   1243  O    LEU A 192      -0.692  32.146  11.438  1.00 34.36       A O
ATOM   1244  N    LEU A 193      -1.347  34.085  12.346  1.00 33.96       A N
ATOM   1245  CA   LEU A 193      -0.088  34.736  12.024  1.00 34.28       A C
ATOM   1246  CB   LEU A 193      -0.199  36.250  12.222  1.00 33.61       A C
ATOM   1247  CG   LEU A 193       1.056  37.054  11.870  1.00 32.92       A C
ATOM   1248  CD1  LEU A 193       1.414  36.840  10.408  1.00 32.28       A C
ATOM   1249  CD2  LEU A 193       0.817  38.527  12.153  1.00 32.72       A C
ATOM   1250  C    LEU A 193       1.028  34.186  12.905  1.00 34.91       A C
ATOM   1251  O    LEU A 193       0.839  33.974  14.106  1.00 35.27       A O
ATOM   1252  N    LYS A 194       2.185  33.945  12.298  1.00 35.05       A N
ATOM   1253  CA   LYS A 194       3.344  33.444  13.023  1.00 35.38       A C
ATOM   1254  CB   LYS A 194       3.417  31.913  12.938  1.00 35.29       A C
ATOM   1255  CG   LYS A 194       3.721  31.362  11.554  1.00 35.20       A C
ATOM   1256  CD   LYS A 194       3.690  29.840  11.542  1.00 35.06       A C
ATOM   1257  CE   LYS A 194       3.960  29.299  10.146  1.00 35.23       A C
ATOM   1258  NZ   LYS A 194       3.866  27.816  10.078  1.00 35.01       A N
ATOM   1259  C    LYS A 194       4.587  34.074  12.399  1.00 35.86       A C
ATOM   1260  O    LYS A 194       4.539  34.553  11.263  1.00 35.94       A O
ATOM   1261  N    ASP A 195       5.695  34.084  13.137  1.00 36.23       A N
ATOM   1262  CA   ASP A 195       6.930  34.671  12.631  1.00 36.25       A C
ATOM   1263  CB   ASP A 195       7.670  35.376  13.760  1.00 36.74       A C
ATOM   1264  CG   ASP A 195       6.934  36.598  14.253  1.00 37.34       A C
ATOM   1265  OD1  ASP A 195       6.777  37.556  13.465  1.00 38.25       A O
ATOM   1266  OD2  ASP A 195       6.506  36.602  15.424  1.00 37.54       A O
ATOM   1267  C    ASP A 195       7.848  33.660  11.963  1.00 36.26       A C
ATOM   1268  O    ASP A 195       8.818  34.037  11.307  1.00 36.01       A O
ATOM   1269  N    THR A 196       7.543  32.377  12.129  1.00 36.18       A N
ATOM   1270  CA   THR A 196       8.346  31.329  11.517  1.00 36.41       A C
ATOM   1271  CB   THR A 196       8.254  30.022  12.317  1.00 36.80       A C
ATOM   1272  OG1  THR A 196       6.885  29.621  12.427  1.00 37.51       A O
ATOM   1273  CG2  THR A 196       8.829  30.221  13.712  1.00 37.11       A C
ATOM   1274  C    THR A 196       7.866  31.094  10.089  1.00 36.54       A C
ATOM   1275  O    THR A 196       6.837  31.627   9.681  1.00 36.75       A O
ATOM   1276  N    VAL A 197       8.608  30.292   9.333  1.00 36.68       A N
ATOM   1277  CA   VAL A 197       8.275  30.016   7.938  1.00 36.71       A C
ATOM   1278  CB   VAL A 197       9.408  29.217   7.259  1.00 37.15       A C
ATOM   1279  CG1  VAL A 197       9.537  27.848   7.910  1.00 36.96       A C
ATOM   1280  CG2  VAL A 197       9.137  29.081   5.762  1.00 37.24       A C
ATOM   1281  C    VAL A 197       6.963  29.275   7.687  1.00 36.99       A C
ATOM   1282  O    VAL A 197       6.480  28.515   8.529  1.00 37.75       A O
ATOM   1283  N    TYR A 198       6.396  29.517   6.507  1.00 36.88       A N
ATOM   1284  CA   TYR A 198       5.157  28.884   6.061  1.00 36.68       A C
```

FIGURE 3A-24

```
ATOM   1285  CB   TYR A 198       4.168  29.943   5.567  1.00 34.64      A C
ATOM   1286  CG   TYR A 198       3.373  30.631   6.654  1.00 32.83      A C
ATOM   1287  CD1  TYR A 198       2.233  30.037   7.192  1.00 31.86      A C
ATOM   1288  CE1  TYR A 198       1.485  30.671   8.183  1.00 31.09      A C
ATOM   1289  CD2  TYR A 198       3.752  31.884   7.136  1.00 31.97      A C
ATOM   1290  CE2  TYR A 198       3.014  32.528   8.130  1.00 31.11      A C
ATOM   1291  CZ   TYR A 198       1.881  31.914   8.647  1.00 30.99      A C
ATOM   1292  OH   TYR A 198       1.157  32.540   9.634  1.00 30.01      A O
ATOM   1293  C    TYR A 198       5.535  27.962   4.902  1.00 37.66      A C
ATOM   1294  O    TYR A 198       6.197  28.391   3.956  1.00 38.18      A O
ATOM   1295  N    THR A 199       5.123  26.702   4.971  1.00 38.53      A N
ATOM   1296  CA   THR A 199       5.449  25.749   3.918  1.00 39.50      A C
ATOM   1297  CB   THR A 199       6.136  24.501   4.489  1.00 39.43      A C
ATOM   1298  OG1  THR A 199       5.300  23.908   5.491  1.00 39.58      A O
ATOM   1299  CG2  THR A 199       7.477  24.870   5.095  1.00 39.56      A C
ATOM   1300  C    THR A 199       4.226  25.301   3.139  1.00 40.54      A C
ATOM   1301  O    THR A 199       4.334  24.482   2.230  1.00 40.80      A O
ATOM   1302  N    ASP A 200       3.064  25.832   3.504  1.00 41.79      A N
ATOM   1303  CA   ASP A 200       1.818  25.490   2.821  1.00 42.62      A C
ATOM   1304  CB   ASP A 200       0.823  24.852   3.792  1.00 43.95      A C
ATOM   1305  CG   ASP A 200       0.357  25.820   4.871  1.00 45.02      A C
ATOM   1306  OD1  ASP A 200       1.202  26.253   5.685  1.00 45.44      A O
ATOM   1307  OD2  ASP A 200      -0.851  26.149   4.902  1.00 45.50      A O
ATOM   1308  C    ASP A 200       1.193  26.749   2.243  1.00 42.59      A C
ATOM   1309  O    ASP A 200       1.311  27.829   2.819  1.00 42.85      A O
ATOM   1310  N    PHE A 201       0.527  26.608   1.106  1.00 42.13      A N
ATOM   1311  CA   PHE A 201      -0.124  27.743   0.477  1.00 41.91      A C
ATOM   1312  CB   PHE A 201       0.891  28.579  -0.304  1.00 41.20      A C
ATOM   1313  CG   PHE A 201       0.285  29.757  -1.010  1.00 40.35      A C
ATOM   1314  CD1  PHE A 201      -0.009  29.696  -2.364  1.00 39.91      A C
ATOM   1315  CD2  PHE A 201      -0.017  30.921  -0.311  1.00 40.09      A C
ATOM   1316  CE1  PHE A 201      -0.596  30.777  -3.012  1.00 40.13      A C
ATOM   1317  CE2  PHE A 201      -0.603  32.006  -0.949  1.00 39.80      A C
ATOM   1318  CZ   PHE A 201      -0.893  31.935  -2.300  1.00 39.96      A C
ATOM   1319  C    PHE A 201      -1.241  27.277  -0.443  1.00 42.39      A C
ATOM   1320  O    PHE A 201      -1.026  26.478  -1.350  1.00 42.47      A O
ATOM   1321  N    ASP A 202      -2.439  27.788  -0.200  1.00 43.12      A N
ATOM   1322  CA   ASP A 202      -3.595  27.415  -0.992  1.00 43.97      A C
ATOM   1323  CB   ASP A 202      -4.554  26.595  -0.131  1.00 45.11      A C
ATOM   1324  CG   ASP A 202      -5.655  25.956  -0.940  1.00 46.25      A C
ATOM   1325  OD1  ASP A 202      -6.647  25.504  -0.329  1.00 47.27      A O
ATOM   1326  OD2  ASP A 202      -5.523  25.898  -2.184  1.00 46.39      A O
ATOM   1327  C    ASP A 202      -4.306  28.657  -1.521  1.00 43.96      A C
ATOM   1328  O    ASP A 202      -5.534  28.693  -1.610  1.00 44.11      A O
ATOM   1329  N    GLY A 203      -3.529  29.677  -1.867  1.00 43.79      A N
ATOM   1330  CA   GLY A 203      -4.112  30.903  -2.378  1.00 42.96      A C
ATOM   1331  C    GLY A 203      -4.044  30.984  -3.889  1.00 42.45      A C
ATOM   1332  O    GLY A 203      -3.849  29.971  -4.560  1.00 43.00      A O
ATOM   1333  N    THR A 204      -4.199  32.192  -4.423  1.00 41.47      A N
ATOM   1334  CA   THR A 204      -4.165  32.413  -5.861  1.00 40.29      A C
ATOM   1335  CB   THR A 204      -4.879  33.724  -6.221  1.00 39.78      A C
ATOM   1336  OG1  THR A 204      -6.166  33.752  -5.593  1.00 38.97      A O
ATOM   1337  CG2  THR A 204      -5.055  33.838  -7.728  1.00 39.77      A C
ATOM   1338  C    THR A 204      -2.720  32.482  -6.335  1.00 40.25      A C
ATOM   1339  O    THR A 204      -1.974  33.379  -5.937  1.00 40.50      A O
ATOM   1340  N    ARG A 205      -2.329  31.545  -7.194  1.00 39.52      A N
```

FIGURE 3A-25

```
ATOM   1341  CA   ARG A 205      -0.956  31.492  -7.689  1.00 39.15      A C
ATOM   1342  CB   ARG A 205      -0.807  30.392  -8.746  1.00 39.62      A C
ATOM   1343  CG   ARG A 205       0.645  29.962  -8.967  1.00 40.10      A C
ATOM   1344  CD   ARG A 205       0.751  28.750  -9.889  1.00 40.22      A C
ATOM   1345  NE   ARG A 205       2.133  28.293 -10.050  1.00 40.09      A N
ATOM   1346  CZ   ARG A 205       2.856  27.725  -9.089  1.00 39.62      A C
ATOM   1347  NH1  ARG A 205       2.334  27.533  -7.885  1.00 40.08      A N
ATOM   1348  NH2  ARG A 205       4.105  27.351  -9.329  1.00 38.81      A N
ATOM   1349  C    ARG A 205      -0.413  32.809  -8.244  1.00 38.25      A C
ATOM   1350  O    ARG A 205       0.615  33.297  -7.777  1.00 38.47      A O
ATOM   1351  N    VAL A 206      -1.090  33.386  -9.233  1.00 37.18      A N
ATOM   1352  CA   VAL A 206      -0.622  34.640  -9.823  1.00 35.71      A C
ATOM   1353  CB   VAL A 206      -1.572  35.140 -10.940  1.00 35.29      A C
ATOM   1354  CG1  VAL A 206      -1.529  34.184 -12.121  1.00 34.25      A C
ATOM   1355  CG2  VAL A 206      -2.989  35.278 -10.404  1.00 34.96      A C
ATOM   1356  C    VAL A 206      -0.434  35.760  -8.799  1.00 35.21      A C
ATOM   1357  O    VAL A 206       0.142  36.803  -9.117  1.00 34.51      A O
ATOM   1358  N    TYR A 207      -0.921  35.544  -7.576  1.00 34.63      A N
ATOM   1359  CA   TYR A 207      -0.782  36.529  -6.501  1.00 34.20      A C
ATOM   1360  CB   TYR A 207      -2.119  36.754  -5.776  1.00 34.52      A C
ATOM   1361  CG   TYR A 207      -3.036  37.791  -6.401  1.00 34.96      A C
ATOM   1362  CD1  TYR A 207      -3.834  37.485  -7.506  1.00 34.66      A C
ATOM   1363  CE1  TYR A 207      -4.686  38.436  -8.065  1.00 34.65      A C
ATOM   1364  CD2  TYR A 207      -3.112  39.080  -5.874  1.00 35.47      A C
ATOM   1365  CE2  TYR A 207      -3.958  40.039  -6.426  1.00 35.57      A C
ATOM   1366  CZ   TYR A 207      -4.745  39.711  -7.520  1.00 35.68      A C
ATOM   1367  OH   TYR A 207      -5.595  40.662  -8.051  1.00 36.14      A O
ATOM   1368  C    TYR A 207       0.262  36.073  -5.478  1.00 33.78      A C
ATOM   1369  O    TYR A 207       0.526  36.775  -4.498  1.00 32.88      A O
ATOM   1370  N    SER A 208       0.846  34.896  -5.708  1.00 33.57      A N
ATOM   1371  CA   SER A 208       1.855  34.346  -4.799  1.00 33.74      A C
ATOM   1372  CB   SER A 208       1.871  32.821  -4.874  1.00 33.93      A C
ATOM   1373  OG   SER A 208       2.313  32.381  -6.143  1.00 36.03      A O
ATOM   1374  C    SER A 208       3.245  34.890  -5.114  1.00 33.18      A C
ATOM   1375  O    SER A 208       3.560  35.190  -6.266  1.00 33.48      A O
ATOM   1376  N    PRO A 209       4.096  35.019  -4.087  1.00 32.39      A N
ATOM   1377  CD   PRO A 209       3.786  34.712  -2.679  1.00 31.88      A C
ATOM   1378  CA   PRO A 209       5.462  35.532  -4.211  1.00 32.26      A C
ATOM   1379  CB   PRO A 209       5.807  35.900  -2.776  1.00 32.19      A C
ATOM   1380  CG   PRO A 209       5.146  34.812  -2.013  1.00 31.62      A C
ATOM   1381  C    PRO A 209       6.480  34.567  -4.815  1.00 32.59      A C
ATOM   1382  O    PRO A 209       6.285  33.354  -4.813  1.00 32.26      A O
ATOM   1383  N    PRO A 210       7.595  35.108  -5.329  1.00 33.17      A N
ATOM   1384  CD   PRO A 210       7.902  36.550  -5.361  1.00 33.09      A C
ATOM   1385  CA   PRO A 210       8.680  34.339  -5.947  1.00 33.07      A C
ATOM   1386  CB   PRO A 210       9.737  35.403  -6.225  1.00 33.11      A C
ATOM   1387  CG   PRO A 210       8.932  36.629  -6.457  1.00 33.44      A C
ATOM   1388  C    PRO A 210       9.212  33.237  -5.033  1.00 33.28      A C
ATOM   1389  O    PRO A 210       9.562  32.152  -5.494  1.00 33.25      A O
ATOM   1390  N    GLU A 211       9.278  33.530  -3.737  1.00 33.69      A N
ATOM   1391  CA   GLU A 211       9.776  32.570  -2.762  1.00 33.92      A C
ATOM   1392  CB   GLU A 211       9.918  33.220  -1.380  1.00 33.90      A C
ATOM   1393  CG   GLU A 211       8.636  33.821  -0.829  1.00 34.48      A C
ATOM   1394  CD   GLU A 211       8.476  35.298  -1.159  1.00 34.06      A C
ATOM   1395  OE1  GLU A 211       8.994  35.745  -2.202  1.00 33.69      A O
ATOM   1396  OE2  GLU A 211       7.815  36.010  -0.377  1.00 34.17      A O
```

FIGURE 3A-26

```
ATOM   1397  C    GLU A 211       8.874  31.350  -2.666  1.00 34.44      A C
ATOM   1398  O    GLU A 211       9.355  30.251  -2.426  1.00 34.78      A O
ATOM   1399  N    TRP A 212       7.570  31.533  -2.851  1.00 35.20      A N
ATOM   1400  CA   TRP A 212       6.656  30.398  -2.784  1.00 36.33      A C
ATOM   1401  CB   TRP A 212       5.195  30.844  -2.747  1.00 35.94      A C
ATOM   1402  CG   TRP A 212       4.270  29.696  -3.028  1.00 35.39      A C
ATOM   1403  CD2  TRP A 212       4.048  28.556  -2.192  1.00 35.28      A C
ATOM   1404  CE2  TRP A 212       3.184  27.683  -2.893  1.00 35.01      A C
ATOM   1405  CE3  TRP A 212       4.500  28.181  -0.919  1.00 35.13      A C
ATOM   1406  CD1  TRP A 212       3.548  29.480  -4.168  1.00 35.57      A C
ATOM   1407  NE1  TRP A 212       2.893  28.272  -4.094  1.00 35.48      A N
ATOM   1408  CZ2  TRP A 212       2.762  26.463  -2.362  1.00 34.27      A C
ATOM   1409  CZ3  TRP A 212       4.078  26.962  -0.392  1.00 34.91      A C
ATOM   1410  CH2  TRP A 212       3.219  26.120  -1.116  1.00 34.22      A C
ATOM   1411  C    TRP A 212       6.837  29.489  -3.982  1.00 37.36      A C
ATOM   1412  O    TRP A 212       6.890  28.267  -3.851  1.00 37.73      A O
ATOM   1413  N    ILE A 213       6.914  30.103  -5.153  1.00 38.41      A N
ATOM   1414  CA   ILE A 213       7.072  29.377  -6.400  1.00 39.44      A C
ATOM   1415  CB   ILE A 213       6.856  30.337  -7.586  1.00 39.25      A C
ATOM   1416  CG2  ILE A 213       7.181  29.650  -8.899  1.00 39.18      A C
ATOM   1417  CG1  ILE A 213       5.403  30.823  -7.569  1.00 39.32      A C
ATOM   1418  CD1  ILE A 213       5.074  31.834  -8.629  1.00 40.07      A C
ATOM   1419  C    ILE A 213       8.428  28.679  -6.516  1.00 40.33      A C
ATOM   1420  O    ILE A 213       8.513  27.567  -7.029  1.00 40.43      A O
ATOM   1421  N    ARG A 214       9.479  29.319  -6.017  1.00 41.58      A N
ATOM   1422  CA   ARG A 214      10.825  28.753  -6.087  1.00 42.72      A C
ATOM   1423  CB   ARG A 214      11.863  29.880  -6.204  1.00 43.82      A C
ATOM   1424  CG   ARG A 214      12.109  30.357  -7.629  1.00 45.75      A C
ATOM   1425  CD   ARG A 214      12.588  31.805  -7.679  1.00 47.41      A C
ATOM   1426  NE   ARG A 214      13.881  32.039  -7.034  1.00 48.90      A N
ATOM   1427  CZ   ARG A 214      15.046  31.571  -7.476  1.00 49.68      A C
ATOM   1428  NH1  ARG A 214      15.096  30.827  -8.576  1.00 49.70      A N
ATOM   1429  NH2  ARG A 214      16.167  31.872  -6.830  1.00 49.84      A N
ATOM   1430  C    ARG A 214      11.229  27.828  -4.940  1.00 42.83      A C
ATOM   1431  O    ARG A 214      12.064  26.946  -5.131  1.00 43.32      A O
ATOM   1432  N    TYR A 215      10.653  28.012  -3.754  1.00 42.60      A N
ATOM   1433  CA   TYR A 215      11.033  27.172  -2.620  1.00 42.25      A C
ATOM   1434  CB   TYR A 215      12.023  27.919  -1.726  1.00 42.12      A C
ATOM   1435  CG   TYR A 215      13.095  28.673  -2.472  1.00 42.41      A C
ATOM   1436  CD1  TYR A 215      13.996  28.011  -3.305  1.00 42.62      A C
ATOM   1437  CE1  TYR A 215      14.987  28.711  -3.993  1.00 42.85      A C
ATOM   1438  CD2  TYR A 215      13.212  30.057  -2.343  1.00 42.69      A C
ATOM   1439  CE2  TYR A 215      14.197  30.765  -3.022  1.00 42.53      A C
ATOM   1440  CZ   TYR A 215      15.079  30.089  -3.845  1.00 42.62      A C
ATOM   1441  OH   TYR A 215      16.044  30.795  -4.520  1.00 42.87      A O
ATOM   1442  C    TYR A 215       9.880  26.696  -1.748  1.00 42.11      A C
ATOM   1443  O    TYR A 215      10.108  26.058  -0.725  1.00 42.15      A O
ATOM   1444  N    HIS A 216       8.650  26.993  -2.140  1.00 42.09      A N
ATOM   1445  CA   HIS A 216       7.507  26.600  -1.328  1.00 42.37      A C
ATOM   1446  CB   HIS A 216       7.257  25.094  -1.425  1.00 43.08      A C
ATOM   1447  CG   HIS A 216       6.530  24.681  -2.667  1.00 44.58      A C
ATOM   1448  CD2  HIS A 216       6.490  25.232  -3.904  1.00 45.23      A C
ATOM   1449  ND1  HIS A 216       5.729  23.560  -2.722  1.00 45.32      A N
ATOM   1450  CE1  HIS A 216       5.226  23.439  -3.938  1.00 45.39      A C
ATOM   1451  NE2  HIS A 216       5.673  24.441  -4.675  1.00 45.62      A N
ATOM   1452  C    HIS A 216       7.742  26.997   0.129  1.00 41.93      A C
```

FIGURE 3A-27

```
ATOM   1453  O    HIS A 216       7.442  26.243   1.052  1.00 42.06      A O
ATOM   1454  N    ARG A 217       8.297  28.189   0.318  1.00 41.27      A N
ATOM   1455  CA   ARG A 217       8.579  28.729   1.643  1.00 40.71      A C
ATOM   1456  CB   ARG A 217      10.037  28.460   2.038  1.00 41.09      A C
ATOM   1457  CG   ARG A 217      10.389  26.995   2.239  1.00 41.92      A C
ATOM   1458  CD   ARG A 217      11.901  26.792   2.297  1.00 41.89      A C
ATOM   1459  NE   ARG A 217      12.530  27.480   3.422  1.00 42.21      A N
ATOM   1460  CZ   ARG A 217      12.410  27.111   4.694  1.00 42.04      A C
ATOM   1461  NH1  ARG A 217      11.678  26.054   5.014  1.00 42.34      A N
ATOM   1462  NH2  ARG A 217      13.029  27.796   5.646  1.00 41.94      A N
ATOM   1463  C    ARG A 217       8.348  30.235   1.589  1.00 40.16      A C
ATOM   1464  O    ARG A 217       8.715  30.892   0.610  1.00 40.52      A O
ATOM   1465  N    TYR A 218       7.735  30.782   2.633  1.00 38.90      A N
ATOM   1466  CA   TYR A 218       7.484  32.217   2.688  1.00 37.27      A C
ATOM   1467  CB   TYR A 218       6.374  32.607   1.700  1.00 36.64      A C
ATOM   1468  CG   TYR A 218       5.005  32.091   2.075  1.00 35.71      A C
ATOM   1469  CD1  TYR A 218       4.218  32.758   3.014  1.00 35.45      A C
ATOM   1470  CE1  TYR A 218       2.975  32.261   3.398  1.00 34.89      A C
ATOM   1471  CD2  TYR A 218       4.512  30.911   1.523  1.00 35.74      A C
ATOM   1472  CE2  TYR A 218       3.270  30.404   1.900  1.00 35.28      A C
ATOM   1473  CZ   TYR A 218       2.509  31.083   2.838  1.00 35.06      A C
ATOM   1474  OH   TYR A 218       1.292  30.577   3.226  1.00 35.19      A O
ATOM   1475  C    TYR A 218       7.093  32.629   4.100  1.00 36.52      A C
ATOM   1476  O    TYR A 218       6.680  31.801   4.914  1.00 36.65      A O
ATOM   1477  N    HIS A 219       7.240  33.912   4.391  1.00 35.39      A N
ATOM   1478  CA   HIS A 219       6.878  34.421   5.698  1.00 34.44      A C
ATOM   1479  CB   HIS A 219       8.044  35.198   6.310  1.00 34.82      A C
ATOM   1480  CG   HIS A 219       9.128  34.316   6.846  1.00 34.67      A C
ATOM   1481  CD2  HIS A 219       9.616  34.163   8.100  1.00 34.88      A C
ATOM   1482  ND1  HIS A 219       9.812  33.417   6.058  1.00 34.80      A N
ATOM   1483  CE1  HIS A 219      10.673  32.747   6.802  1.00 34.46      A C
ATOM   1484  NE2  HIS A 219      10.575  33.180   8.045  1.00 34.36      A N
ATOM   1485  C    HIS A 219       5.646  35.295   5.548  1.00 33.68      A C
ATOM   1486  O    HIS A 219       5.489  35.990   4.553  1.00 33.27      A O
ATOM   1487  N    GLY A 220       4.772  35.237   6.545  1.00 32.98      A N
ATOM   1488  CA   GLY A 220       3.525  35.981   6.522  1.00 32.54      A C
ATOM   1489  C    GLY A 220       3.517  37.425   6.050  1.00 32.42      A C
ATOM   1490  O    GLY A 220       3.071  37.712   4.940  1.00 32.35      A O
ATOM   1491  N    ARG A 221       3.984  38.346   6.885  1.00 32.23      A N
ATOM   1492  CA   ARG A 221       3.972  39.754   6.515  1.00 31.94      A C
ATOM   1493  CB   ARG A 221       4.731  40.558   7.555  1.00 34.19      A C
ATOM   1494  CG   ARG A 221       3.815  41.306   8.465  1.00 37.69      A C
ATOM   1495  CD   ARG A 221       3.935  40.895   9.914  1.00 40.26      A C
ATOM   1496  NE   ARG A 221       3.043  41.750  10.688  1.00 43.45      A N
ATOM   1497  CZ   ARG A 221       2.757  41.591  11.974  1.00 44.83      A C
ATOM   1498  NH1  ARG A 221       3.292  40.590  12.666  1.00 45.59      A N
ATOM   1499  NH2  ARG A 221       1.939  42.451  12.571  1.00 45.09      A N
ATOM   1500  C    ARG A 221       4.516  40.079   5.127  1.00 30.70      A C
ATOM   1501  O    ARG A 221       3.896  40.821   4.368  1.00 29.95      A O
ATOM   1502  N    SER A 222       5.678  39.532   4.799  1.00 29.24      A N
ATOM   1503  CA   SER A 222       6.306  39.808   3.516  1.00 28.54      A C
ATOM   1504  CB   SER A 222       7.737  39.273   3.530  1.00 28.50      A C
ATOM   1505  OG   SER A 222       7.751  37.885   3.788  1.00 29.70      A O
ATOM   1506  C    SER A 222       5.534  39.259   2.307  1.00 27.85      A C
ATOM   1507  O    SER A 222       5.424  39.927   1.280  1.00 28.05      A O
ATOM   1508  N    ALA A 223       5.000  38.049   2.413  1.00 26.48      A N
```

FIGURE 3A-28

```
ATOM   1509  CA   ALA A 223       4.245  37.490   1.298  1.00 25.60      A C
ATOM   1510  CB   ALA A 223       3.899  36.031   1.565  1.00 25.38      A C
ATOM   1511  C    ALA A 223       2.972  38.304   1.106  1.00 24.96      A C
ATOM   1512  O    ALA A 223       2.454  38.406  -0.007  1.00 24.36      A O
ATOM   1513  N    ALA A 224       2.480  38.886   2.200  1.00 24.30      A N
ATOM   1514  CA   ALA A 224       1.270  39.702   2.169  1.00 24.04      A C
ATOM   1515  CB   ALA A 224       0.814  40.002   3.581  1.00 23.74      A C
ATOM   1516  C    ALA A 224       1.527  41.006   1.416  1.00 24.12      A C
ATOM   1517  O    ALA A 224       0.679  41.475   0.652  1.00 24.32      A O
ATOM   1518  N    VAL A 225       2.701  41.589   1.639  1.00 23.62      A N
ATOM   1519  CA   VAL A 225       3.078  42.829   0.976  1.00 23.17      A C
ATOM   1520  CB   VAL A 225       4.433  43.355   1.514  1.00 23.08      A C
ATOM   1521  CG1  VAL A 225       4.945  44.488   0.640  1.00 22.31      A C
ATOM   1522  CG2  VAL A 225       4.265  43.832   2.952  1.00 22.36      A C
ATOM   1523  C    VAL A 225       3.182  42.597  -0.528  1.00 23.51      A C
ATOM   1524  O    VAL A 225       2.798  43.456  -1.325  1.00 24.00      A O
ATOM   1525  N    TRP A 226       3.700  41.433  -0.916  1.00 23.10      A N
ATOM   1526  CA   TRP A 226       3.836  41.110  -2.332  1.00 22.42      A C
ATOM   1527  CB   TRP A 226       4.553  39.762  -2.519  1.00 22.80      A C
ATOM   1528  CG   TRP A 226       4.504  39.258  -3.940  1.00 22.67      A C
ATOM   1529  CD2  TRP A 226       5.503  39.439  -4.951  1.00 22.39      A C
ATOM   1530  CE2  TRP A 226       5.004  38.865  -6.141  1.00 22.58      A C
ATOM   1531  CE3  TRP A 226       6.772  40.033  -4.968  1.00 22.76      A C
ATOM   1532  CD1  TRP A 226       3.468  38.596  -4.543  1.00 22.71      A C
ATOM   1533  NE1  TRP A 226       3.761  38.358  -5.864  1.00 22.77      A N
ATOM   1534  CZ2  TRP A 226       5.730  38.866  -7.335  1.00 22.72      A C
ATOM   1535  CZ3  TRP A 226       7.493  40.034  -6.157  1.00 22.63      A C
ATOM   1536  CH2  TRP A 226       6.969  39.453  -7.323  1.00 22.84      A C
ATOM   1537  C    TRP A 226       2.471  41.070  -3.015  1.00 21.68      A C
ATOM   1538  O    TRP A 226       2.288  41.651  -4.083  1.00 21.46      A O
ATOM   1539  N    SER A 227       1.517  40.376  -2.403  1.00 21.15      A N
ATOM   1540  CA   SER A 227       0.187  40.294  -2.979  1.00 21.14      A C
ATOM   1541  CB   SER A 227      -0.701  39.358  -2.158  1.00 20.44      A C
ATOM   1542  OG   SER A 227      -0.784  39.778  -0.813  1.00 21.14      A O
ATOM   1543  C    SER A 227      -0.416  41.692  -3.041  1.00 21.22      A C
ATOM   1544  O    SER A 227      -1.153  42.016  -3.971  1.00 21.57      A O
ATOM   1545  N    LEU A 228      -0.102  42.525  -2.054  1.00 21.19      A N
ATOM   1546  CA   LEU A 228      -0.612  43.889  -2.055  1.00 21.17      A C
ATOM   1547  CB   LEU A 228      -0.267  44.598  -0.744  1.00 20.60      A C
ATOM   1548  CG   LEU A 228      -1.096  44.141   0.461  1.00 20.31      A C
ATOM   1549  CD1  LEU A 228      -0.554  44.781   1.733  1.00 19.66      A C
ATOM   1550  CD2  LEU A 228      -2.560  44.509   0.243  1.00 19.07      A C
ATOM   1551  C    LEU A 228       0.013  44.617  -3.238  1.00 21.13      A C
ATOM   1552  O    LEU A 228      -0.586  45.521  -3.825  1.00 21.22      A O
ATOM   1553  N    GLY A 229       1.222  44.206  -3.591  1.00 20.87      A N
ATOM   1554  CA   GLY A 229       1.891  44.809  -4.723  1.00 21.09      A C
ATOM   1555  C    GLY A 229       1.118  44.480  -5.985  1.00 21.42      A C
ATOM   1556  O    GLY A 229       0.890  45.346  -6.828  1.00 21.71      A O
ATOM   1557  N    ILE A 230       0.710  43.221  -6.120  1.00 21.80      A N
ATOM   1558  CA   ILE A 230      -0.057  42.802  -7.287  1.00 21.79      A C
ATOM   1559  CB   ILE A 230      -0.374  41.299  -7.242  1.00 21.64      A C
ATOM   1560  CG2  ILE A 230      -1.100  40.892  -8.517  1.00 21.38      A C
ATOM   1561  CG1  ILE A 230       0.913  40.488  -7.079  1.00 21.77      A C
ATOM   1562  CD1  ILE A 230       1.813  40.485  -8.302  1.00 22.62      A C
ATOM   1563  C    ILE A 230.     -1.383  43.569  -7.315  1.00 22.29      A C
ATOM   1564  O    ILE A 230      -1.819  44.044  -8.367  1.00 21.82      A O
```

FIGURE 3A-29

```
ATOM   1565  N    LEU A 231      -2.011  43.693  -6.148  1.00 22.88      A N
ATOM   1566  CA   LEU A 231      -3.288  44.390  -6.024  1.00 23.31      A C
ATOM   1567  CB   LEU A 231      -3.790  44.344  -4.573  1.00 23.06      A C
ATOM   1568  CG   LEU A 231      -5.098  45.103  -4.303  1.00 23.69      A C
ATOM   1569  CD1  LEU A 231      -6.236  44.487  -5.102  1.00 23.37      A C
ATOM   1570  CD2  LEU A 231      -5.424  45.069  -2.823  1.00 23.28      A C
ATOM   1571  C    LEU A 231      -3.219  45.841  -6.492  1.00 23.71      A C
ATOM   1572  O    LEU A 231      -4.043  46.266  -7.294  1.00 24.23      A O
ATOM   1573  N    LEU A 232      -2.243  46.600  -5.998  1.00 23.91      A N
ATOM   1574  CA   LEU A 232      -2.121  47.998  -6.394  1.00 23.68      A C
ATOM   1575  CB   LEU A 232      -0.919  48.660  -5.715  1.00 23.78      A C
ATOM   1576  CG   LEU A 232      -1.084  50.132  -5.297  1.00 24.26      A C
ATOM   1577  CD1  LEU A 232       0.279  50.712  -4.987  1.00 23.82      A C
ATOM   1578  CD2  LEU A 232      -1.762  50.949  -6.391  1.00 24.08      A C
ATOM   1579  C    LEU A 232      -1.959  48.091  -7.906  1.00 23.98      A C
ATOM   1580  O    LEU A 232      -2.595  48.925  -8.557  1.00 24.76      A O
ATOM   1581  N    TYR A 233      -1.108  47.235  -8.464  1.00 23.57      A N
ATOM   1582  CA   TYR A 233      -0.874  47.234  -9.903  1.00 23.05      A C
ATOM   1583  CB   TYR A 233       0.209  46.210 -10.276  1.00 21.64      A C
ATOM   1584  CG   TYR A 233       0.533  46.180 -11.756  1.00 20.10      A C
ATOM   1585  CD1  TYR A 233      -0.353  45.619 -12.674  1.00 18.81      A C
ATOM   1586  CE1  TYR A 233      -0.090  45.641 -14.037  1.00 18.22      A C
ATOM   1587  CD2  TYR A 233       1.704  46.762 -12.247  1.00 19.72      A C
ATOM   1588  CE2  TYR A 233       1.978  46.791 -13.616  1.00 18.55      A C
ATOM   1589  CZ   TYR A 233       1.073  46.231 -14.502  1.00 18.85      A C
ATOM   1590  OH   TYR A 233       1.314  46.281 -15.857  1.00 19.45      A O
ATOM   1591  C    TYR A 233      -2.172  46.903 -10.623  1.00 23.64      A C
ATOM   1592  O    TYR A 233      -2.495  47.502 -11.644  1.00 24.49      A O
ATOM   1593  N    ASP A 234      -2.916  45.944 -10.091  1.00 24.15      A N
ATOM   1594  CA   ASP A 234      -4.175  45.561 -10.705  1.00 25.11      A C
ATOM   1595  CB   ASP A 234      -4.845  44.461  -9.888  1.00 25.53      A C
ATOM   1596  CG   ASP A 234      -6.177  44.044 -10.460  1.00 25.90      A C
ATOM   1597  OD1  ASP A 234      -7.123  43.867  -9.670  1.00 27.09      A O
ATOM   1598  OD2  ASP A 234      -6.284  43.886 -11.693  1.00 26.17      A O
ATOM   1599  C    ASP A 234      -5.098  46.773 -10.777  1.00 26.03      A C
ATOM   1600  O    ASP A 234      -5.722  47.029 -11.810  1.00 26.29      A O
ATOM   1601  N    MET A 235      -5.168  47.521  -9.676  1.00 26.30      A N
ATOM   1602  CA   MET A 235      -6.018  48.704  -9.590  1.00 26.73      A C
ATOM   1603  CB   MET A 235      -5.997  49.289  -8.173  1.00 26.52      A C
ATOM   1604  CG   MET A 235      -6.712  48.456  -7.132  1.00 27.65      A C
ATOM   1605  SD   MET A 235      -6.914  49.309  -5.550  1.00 28.52      A S
ATOM   1606  CE   MET A 235      -5.347  49.066  -4.817  1.00 29.19      A C
ATOM   1607  C    MET A 235      -5.661  49.812 -10.568  1.00 27.41      A C
ATOM   1608  O    MET A 235      -6.544  50.365 -11.228  1.00 27.49      A O
ATOM   1609  N    VAL A 236      -4.375  50.137 -10.670  1.00 27.73      A N
ATOM   1610  CA   VAL A 236      -3.955  51.226 -11.546  1.00 27.72      A C
ATOM   1611  CB   VAL A 236      -2.703  51.933 -10.981  1.00 27.14      A C
ATOM   1612  CG1  VAL A 236      -2.978  52.384  -9.558  1.00 27.41      A C
ATOM   1613  CG2  VAL A 236      -1.504  51.007 -11.019  1.00 26.32      A C
ATOM   1614  C    VAL A 236      -3.708  50.860 -13.002  1.00 28.22      A C
ATOM   1615  O    VAL A 236      -3.545  51.746 -13.838  1.00 28.32      A O
ATOM   1616  N    CYS A 237      -3.683  49.568 -13.313  1.00 28.77      A N
ATOM   1617  CA   CYS A 237      -3.468  49.135 -14.693  1.00 29.68      A C
ATOM   1618  CB   CYS A 237      -2.238  48.240 -14.792  1.00 29.71      A C
ATOM   1619  SG   CYS A 237      -0.688  49.093 -14.510  1.00 31.28      A S
ATOM   1620  C    CYS A 237      -4.671  48.389 -15.247  1.00 30.33      A C
```

FIGURE 3A-30

```
ATOM   1621  O    CYS A 237      -4.797  48.215 -16.460  1.00 30.28      A  O
ATOM   1622  N    GLY A 238      -5.550  47.948 -14.351  1.00 30.97      A  N
ATOM   1623  CA   GLY A 238      -6.735  47.224 -14.768  1.00 32.39      A  C
ATOM   1624  C    GLY A 238      -6.494  45.738 -14.948  1.00 33.64      A  C
ATOM   1625  O    GLY A 238      -7.363  45.017 -15.442  1.00 33.64      A  O
ATOM   1626  N    ASP A 239      -5.314  45.274 -14.548  1.00 34.84      A  N
ATOM   1627  CA   ASP A 239      -4.972  43.863 -14.673  1.00 35.82      A  C
ATOM   1628  CB   ASP A 239      -4.681  43.527 -16.134  1.00 37.59      A  C
ATOM   1629  CG   ASP A 239      -5.152  42.138 -16.517  1.00 39.57      A  C
ATOM   1630  OD1  ASP A 239      -5.046  41.210 -15.679  1.00 40.53      A  O
ATOM   1631  OD2  ASP A 239      -5.622  41.974 -17.664  1.00 41.16      A  O
ATOM   1632  C    ASP A 239      -3.747  43.515 -13.827  1.00 35.63      A  C
ATOM   1633  O    ASP A 239      -3.014  44.397 -13.398  1.00 35.70      A  O
ATOM   1634  N    ILE A 240      -3.535  42.224 -13.586  1.00 35.62      A  N
ATOM   1635  CA   ILE A 240      -2.389  41.779 -12.808  1.00 35.32      A  C
ATOM   1636  CB   ILE A 240      -2.607  40.376 -12.245  1.00 35.08      A  C
ATOM   1637  CG2  ILE A 240      -3.702  40.411 -11.199  1.00 34.92      A  C
ATOM   1638  CG1  ILE A 240      -2.964  39.415 -13.376  1.00 34.86      A  C
ATOM   1639  CD1  ILE A 240      -3.117  37.980 -12.931  1.00 34.38      A  C
ATOM   1640  C    ILE A 240      -1.177  41.772 -13.724  1.00 35.52      A  C
ATOM   1641  O    ILE A 240      -1.289  41.461 -14.907  1.00 35.69      A  O
ATOM   1642  N    PRO A 241       0.002  42.111 -13.183  1.00 35.58      A  N
ATOM   1643  CD   PRO A 241       0.196  42.471 -11.768  1.00 35.29      A  C
ATOM   1644  CA   PRO A 241       1.274  42.170 -13.913  1.00 35.96      A  C
ATOM   1645  CB   PRO A 241       2.194  42.877 -12.925  1.00 35.88      A  C
ATOM   1646  CG   PRO A 241       1.695  42.373 -11.609  1.00 35.63      A  C
ATOM   1647  C    PRO A 241       1.874  40.858 -14.418  1.00 36.54      A  C
ATOM   1648  O    PRO A 241       2.406  40.810 -15.526  1.00 36.27      A  O
ATOM   1649  N    PHE A 242       1.794  39.803 -13.611  1.00 37.71      A  N
ATOM   1650  CA   PHE A 242       2.353  38.503 -13.982  1.00 38.74      A  C
ATOM   1651  CB   PHE A 242       3.301  38.005 -12.884  1.00 36.80      A  C
ATOM   1652  CG   PHE A 242       4.204  39.065 -12.327  1.00 35.67      A  C
ATOM   1653  CD1  PHE A 242       5.033  39.807 -13.163  1.00 35.12      A  C
ATOM   1654  CD2  PHE A 242       4.239  39.313 -10.958  1.00 35.33      A  C
ATOM   1655  CE1  PHE A 242       5.887  40.782 -12.643  1.00 35.01      A  C
ATOM   1656  CE2  PHE A 242       5.086  40.284 -10.426  1.00 34.83      A  C
ATOM   1657  CZ   PHE A 242       5.913  41.020 -11.271  1.00 34.99      A  C
ATOM   1658  C    PHE A 242       1.268  37.453 -14.202  1.00 40.46      A  C
ATOM   1659  O    PHE A 242       0.274  37.424 -13.478  1.00 40.61      A  O
ATOM   1660  N    GLU A 243       1.465  36.589 -15.197  1.00 42.94      A  N
ATOM   1661  CA   GLU A 243       0.507  35.522 -15.495  1.00 45.51      A  C
ATOM   1662  CB   GLU A 243      -0.114  35.708 -16.892  1.00 47.93      A  C
ATOM   1663  CG   GLU A 243       0.902  35.741 -18.043  1.00 52.26      A  C
ATOM   1664  CD   GLU A 243       0.271  35.945 -19.430  1.00 54.38      A  C
ATOM   1665  OE1  GLU A 243      -0.886  36.421 -19.512  1.00 55.09      A  O
ATOM   1666  OE2  GLU A 243       0.948  35.641 -20.444  1.00 55.53      A  O
ATOM   1667  C    GLU A 243       1.176  34.149 -15.411  1.00 45.82      A  C
ATOM   1668  O    GLU A 243       0.516  33.150 -15.127  1.00 46.16      A  O
ATOM   1669  N    HIS A 244       2.486  34.107 -15.648  1.00 45.92      A  N
ATOM   1670  CA   HIS A 244       3.237  32.852 -15.605  1.00 46.20      A  C
ATOM   1671  CB   HIS A 244       3.907  32.584 -16.956  1.00 46.96      A  C
ATOM   1672  CG   HIS A 244       2.982  32.706 -18.124  1.00 48.01      A  C
ATOM   1673  CD2  HIS A 244       3.077  33.430 -19.264  1.00 48.07      A  C
ATOM   1674  ND1  HIS A 244       1.786  32.024 -18.201  1.00 48.43      A  N
ATOM   1675  CE1  HIS A 244       1.183  32.324 -19.338  1.00 48.39      A  C
ATOM   1676  NE2  HIS A 244       1.946  33.175 -20.001  1.00 48.59      A  N
```

FIGURE 3A-31

```
ATOM   1677  C   HIS A 244       4.311  32.873 -14.525  1.00 45.97      A C
ATOM   1678  O   HIS A 244       4.801  33.934 -14.141  1.00 46.02      A O
ATOM   1679  N   ASP A 245       4.690  31.691 -14.054  1.00 45.53      A N
ATOM   1680  CA  ASP A 245       5.709  31.580 -13.024  1.00 45.15      A C
ATOM   1681  CB  ASP A 245       5.963  30.109 -12.705  1.00 45.50      A C
ATOM   1682  CG  ASP A 245       4.757  29.439 -12.075  1.00 46.41      A C
ATOM   1683  OD1 ASP A 245       4.844  28.239 -11.739  1.00 47.11      A O
ATOM   1684  OD2 ASP A 245       3.718  30.114 -11.913  1.00 46.66      A O
ATOM   1685  C   ASP A 245       7.013  32.272 -13.409  1.00 44.75      A C
ATOM   1686  O   ASP A 245       7.664  32.877 -12.562  1.00 44.33      A O
ATOM   1687  N   GLU A 246       7.394  32.191 -14.682  1.00 44.79      A N
ATOM   1688  CA  GLU A 246       8.626  32.834 -15.137  1.00 45.23      A C
ATOM   1689  CB  GLU A 246       8.806  32.703 -16.656  1.00 46.50      A C
ATOM   1690  CG  GLU A 246       8.796  31.292 -17.213  1.00 48.66      A C
ATOM   1691  CD  GLU A 246       7.408  30.676 -17.229  1.00 50.00      A C
ATOM   1692  OE1 GLU A 246       6.961  30.178 -16.173  1.00 50.50      A O
ATOM   1693  OE2 GLU A 246       6.758  30.701 -18.300  1.00 50.89      A O
ATOM   1694  C   GLU A 246       8.575  34.318 -14.790  1.00 44.45      A C
ATOM   1695  O   GLU A 246       9.495  34.855 -14.176  1.00 44.55      A O
ATOM   1696  N   GLU A 247       7.493  34.975 -15.198  1.00 43.56      A N
ATOM   1697  CA  GLU A 247       7.313  36.400 -14.942  1.00 42.74      A C
ATOM   1698  CB  GLU A 247       5.947  36.861 -15.444  1.00 43.13      A C
ATOM   1699  CG  GLU A 247       5.760  36.822 -16.946  1.00 43.62      A C
ATOM   1700  CD  GLU A 247       4.313  37.057 -17.336  1.00 44.52      A C
ATOM   1701  OE1 GLU A 247       3.470  36.195 -17.021  1.00 45.06      A O
ATOM   1702  OE2 GLU A 247       4.009  38.103 -17.942  1.00 45.42      A O
ATOM   1703  C   GLU A 247       7.431  36.724 -13.458  1.00 41.88      A C
ATOM   1704  O   GLU A 247       8.057  37.714 -13.083  1.00 42.05      A O
ATOM   1705  N   ILE A 248       6.827  35.891 -12.616  1.00 40.84      A N
ATOM   1706  CA  ILE A 248       6.871  36.107 -11.176  1.00 39.99      A C
ATOM   1707  CB  ILE A 248       5.967  35.097 -10.433  1.00 39.47      A C
ATOM   1708  CG2 ILE A 248       6.034  35.332  -8.932  1.00 38.57      A C
ATOM   1709  CG1 ILE A 248       4.523  35.254 -10.913  1.00 39.17      A C
ATOM   1710  CD1 ILE A 248       3.546  34.324 -10.236  1.00 39.05      A C
ATOM   1711  C   ILE A 248       8.291  36.031 -10.610  1.00 40.10      A C
ATOM   1712  O   ILE A 248       8.722  36.935  -9.886  1.00 39.68      A O
ATOM   1713  N   ILE A 249       9.026  34.968 -10.935  1.00 40.15      A N
ATOM   1714  CA  ILE A 249      10.387  34.839 -10.420  1.00 40.03      A C
ATOM   1715  CB  ILE A 249      10.987  33.427 -10.664  1.00 39.75      A C
ATOM   1716  CG2 ILE A 249      10.123  32.374  -9.995  1.00 39.56      A C
ATOM   1717  CG1 ILE A 249      11.111  33.153 -12.159  1.00 40.35      A C
ATOM   1718  CD1 ILE A 249      11.758  31.819 -12.476  1.00 41.06      A C
ATOM   1719  C   ILE A 249      11.318  35.883 -11.028  1.00 39.63      A C
ATOM   1720  O   ILE A 249      12.336  36.229 -10.429  1.00 39.81      A O
ATOM   1721  N   ARG A 250      10.975  36.391 -12.208  1.00 39.10      A N
ATOM   1722  CA  ARG A 250      11.817  37.405 -12.835  1.00 39.09      A C
ATOM   1723  CB  ARG A 250      11.562  37.483 -14.341  1.00 38.30      A C
ATOM   1724  CG  ARG A 250      12.608  38.315 -15.063  1.00 37.35      A C
ATOM   1725  CD  ARG A 250      12.199  38.645 -16.482  1.00 37.19      A C
ATOM   1726  NE  ARG A 250      13.108  39.620 -17.075  1.00 36.66      A N
ATOM   1727  CZ  ARG A 250      12.778  40.459 -18.052  1.00 36.72      A C
ATOM   1728  NH1 ARG A 250      11.552  40.448 -18.557  1.00 36.16      A N
ATOM   1729  NH2 ARG A 250      13.673  41.318 -18.519  1.00 36.93      A N
ATOM   1730  C   ARG A 250      11.529  38.757 -12.188  1.00 39.36      A C
ATOM   1731  O   ARG A 250      12.401  39.625 -12.116  1.00 39.77      A O
ATOM   1732  N   GLY A 251      10.291  38.925 -11.728  1.00 39.34      A N
```

FIGURE 3A-32

```
ATOM   1733  CA  GLY A 251       9.887  40.150 -11.063  1.00 39.16      A C
ATOM   1734  C   GLY A 251      10.027  41.455 -11.823  1.00 39.12      A C
ATOM   1735  O   GLY A 251      10.113  42.515 -11.207  1.00 39.50      A O
ATOM   1736  N   GLN A 252      10.047  41.396 -13.151  1.00 38.91      A N
ATOM   1737  CA  GLN A 252      10.162  42.610 -13.958  1.00 38.40      A C
ATOM   1738  CB  GLN A 252      10.737  42.289 -15.335  1.00 39.40      A C
ATOM   1739  CG  GLN A 252      11.178  43.516 -16.107  1.00 40.02      A C
ATOM   1740  CD  GLN A 252      12.538  44.010 -15.661  1.00 40.80      A C
ATOM   1741  OE1 GLN A 252      12.954  45.118 -16.008  1.00 41.78      A O
ATOM   1742  NE2 GLN A 252      13.247  43.184 -14.896  1.00 40.12      A N
ATOM   1743  C   GLN A 252       8.772  43.199 -14.138  1.00 37.66      A C
ATOM   1744  O   GLN A 252       7.881  42.537 -14.673  1.00 37.99      A O
ATOM   1745  N   VAL A 253       8.578  44.438 -13.704  1.00 36.59      A N
ATOM   1746  CA  VAL A 253       7.264  45.056 -13.831  1.00 35.43      A C
ATOM   1747  CB  VAL A 253       6.855  45.778 -12.524  1.00 34.84      A C
ATOM   1748  CG1 VAL A 253       5.449  46.332 -12.648  1.00 33.84      A C
ATOM   1749  CG2 VAL A 253       6.933  44.815 -11.356  1.00 34.62      A C
ATOM   1750  C   VAL A 253       7.189  46.046 -14.984  1.00 34.91      A C
ATOM   1751  O   VAL A 253       7.950  47.011 -15.038  1.00 34.86      A O
ATOM   1752  N   PHE A 254       6.270  45.790 -15.910  1.00 34.45      A N
ATOM   1753  CA  PHE A 254       6.062  46.664 -17.059  1.00 34.51      A C
ATOM   1754  CB  PHE A 254       6.179  45.861 -18.363  1.00 35.55      A C
ATOM   1755  CG  PHE A 254       5.645  46.583 -19.580  1.00 37.57      A C
ATOM   1756  CD1 PHE A 254       4.292  46.502 -19.920  1.00 38.13      A C
ATOM   1757  CD2 PHE A 254       6.486  47.364 -20.373  1.00 38.23      A C
ATOM   1758  CE1 PHE A 254       3.787  47.188 -21.030  1.00 38.03      A C
ATOM   1759  CE2 PHE A 254       5.990  48.056 -21.488  1.00 38.39      A C
ATOM   1760  CZ  PHE A 254       4.640  47.966 -21.815  1.00 38.27      A C
ATOM   1761  C   PHE A 254       4.674  47.300 -16.945  1.00 33.90      A C
ATOM   1762  O   PHE A 254       3.715  46.628 -16.577  1.00 34.17      A O
ATOM   1763  N   PHE A 255       4.565  48.592 -17.247  1.00 33.09      A N
ATOM   1764  CA  PHE A 255       3.274  49.272 -17.170  1.00 32.69      A C
ATOM   1765  CB  PHE A 255       3.416  50.615 -16.445  1.00 31.75      A C
ATOM   1766  CG  PHE A 255       3.705  50.475 -14.979  1.00 30.54      A C
ATOM   1767  CD1 PHE A 255       4.994  50.224 -14.531  1.00 29.60      A C
ATOM   1768  CD2 PHE A 255       2.669  50.513 -14.052  1.00 29.71      A C
ATOM   1769  CE1 PHE A 255       5.247  50.007 -13.182  1.00 29.93      A C
ATOM   1770  CE2 PHE A 255       2.911  50.298 -12.705  1.00 29.36      A C
ATOM   1771  CZ  PHE A 255       4.201  50.042 -12.267  1.00 29.80      A C
ATOM   1772  C   PHE A 255       2.630  49.480 -18.534  1.00 33.08      A C
ATOM   1773  O   PHE A 255       3.209  50.103 -19.423  1.00 32.57      A O
ATOM   1774  N   ARG A 256       1.423  48.945 -18.690  1.00 34.14      A N
ATOM   1775  CA  ARG A 256       0.681  49.051 -19.943  1.00 35.28      A C
ATOM   1776  CB  ARG A 256      -0.213  47.821 -20.121  1.00 36.35      A C
ATOM   1777  CG  ARG A 256      -1.326  47.718 -19.083  1.00 38.55      A C
ATOM   1778  CD  ARG A 256      -1.198  46.466 -18.234  1.00 40.30      A C
ATOM   1779  NE  ARG A 256      -1.338  45.248 -19.028  1.00 42.32      A N
ATOM   1780  CZ  ARG A 256      -1.175  44.017 -18.547  1.00 43.34      A C
ATOM   1781  NH1 ARG A 256      -0.864  43.830 -17.270  1.00 43.87      A N
ATOM   1782  NH2 ARG A 256      -1.323  42.970 -19.346  1.00 44.02      A N
ATOM   1783  C   ARG A 256      -0.182  50.311 -19.951  1.00 34.92      A C
ATOM   1784  O   ARG A 256      -0.829  50.632 -20.944  1.00 35.04      A O
ATOM   1785  N   GLN A 257      -0.181  51.018 -18.829  1.00 34.64      A N
ATOM   1786  CA  GLN A 257      -0.963  52.233 -18.676  1.00 34.59      A C
ATOM   1787  CB  GLN A 257      -2.154  51.971 -17.763  1.00 36.06      A C
ATOM   1788  CG  GLN A 257      -3.278  51.188 -18.383  1.00 37.80      A C
```

FIGURE 3A-33

```
ATOM   1789  CD   GLN A 257      -4.548  52.001 -18.430  1.00 39.27      A C
ATOM   1790  OE1  GLN A 257      -5.642  51.460 -18.600  1.00 40.69      A O
ATOM   1791  NE2  GLN A 257      -4.412  53.318 -18.284  1.00 39.39      A N
ATOM   1792  C    GLN A 257      -0.131  53.346 -18.068  1.00 33.66      A C
ATOM   1793  O    GLN A 257       0.972  53.116 -17.584  1.00 33.66      A O
ATOM   1794  N    ARG A 258      -0.674  54.555 -18.078  1.00 32.84      A N
ATOM   1795  CA   ARG A 258       0.033  55.691 -17.509  1.00 31.69      A C
ATOM   1796  CB   ARG A 258      -0.524  56.999 -18.075  1.00 31.07      A C
ATOM   1797  CG   ARG A 258       0.427  58.169 -17.966  1.00 31.14      A C
ATOM   1798  CD   ARG A 258       0.606  58.630 -16.540  1.00 32.07      A C
ATOM   1799  NE   ARG A 258       1.773  59.496 -16.425  1.00 33.54      A N
ATOM   1800  CZ   ARG A 258       2.046  60.262 -15.372  1.00 34.00      A C
ATOM   1801  NH1  ARG A 258       1.228  60.281 -14.326  1.00 34.22      A N
ATOM   1802  NH2  ARG A 258       3.145  61.006 -15.364  1.00 33.81      A N
ATOM   1803  C    ARG A 258      -0.119  55.674 -15.993  1.00 30.88      A C
ATOM   1804  O    ARG A 258      -1.223  55.800 -15.474  1.00 31.51      A O
ATOM   1805  N    VAL A 259       0.991  55.500 -15.289  1.00 29.87      A N
ATOM   1806  CA   VAL A 259       0.979  55.484 -13.832  1.00 28.83      A C
ATOM   1807  CB   VAL A 259       1.249  54.064 -13.279  1.00 27.94      A C
ATOM   1808  CG1  VAL A 259       1.350  54.100 -11.763  1.00 26.92      A C
ATOM   1809  CG2  VAL A 259       0.135  53.127 -13.697  1.00 26.67      A C
ATOM   1810  C    VAL A 259       2.071  56.430 -13.359  1.00 28.77      A C
ATOM   1811  O    VAL A 259       3.153  56.457 -13.930  1.00 28.78      A O
ATOM   1812  N    SER A 260       1.788  57.209 -12.321  1.00 29.04      A N
ATOM   1813  CA   SER A 260       2.769  58.161 -11.807  1.00 29.30      A C
ATOM   1814  CB   SER A 260       2.174  58.976 -10.655  1.00 28.09      A C
ATOM   1815  OG   SER A 260       1.833  58.152  -9.561  1.00 27.76      A O
ATOM   1816  C    SER A 260       4.055  57.481 -11.354  1.00 30.04      A C
ATOM   1817  O    SER A 260       4.063  56.299 -11.020  1.00 30.23      A O
ATOM   1818  N    PSR A 261       5.143  58.243 -11.353  1.00 31.10      A N
ATOM   1819  CA   PSR A 261       6.448  57.733 -10.956  1.00 31.99      A C
ATOM   1820  CB   PSR A 261       7.497  58.834 -11.079  1.00 33.03      A C
ATOM   1821  OG   PSR A 261       7.564  59.250 -12.427  1.00 36.26      A O
ATOM   1822  C    PSR A 261       6.433  57.205  -9.533  1.00 31.92      A C
ATOM   1823  O    PSR A 261       7.036  56.173  -9.233  1.00 32.44      A O
ATOM   1824  P    PSR A 261       6.915  60.633 -12.882  1.00 38.76      A P
ATOM   1825  O1   PSR A 261       7.686  61.755 -12.306  1.00 38.43      A O
ATOM   1826  O2   PSR A 261       6.949  60.688 -14.414  1.00 38.21      A O
ATOM   1827  O3   PSR A 261       5.404  60.683 -12.500  1.00 37.10      A O
ATOM   1828  N    GLU A 262       5.746  57.919  -8.652  1.00 31.67      A N
ATOM   1829  CA   GLU A 262       5.665  57.507  -7.261  1.00 31.40      A C
ATOM   1830  CB   GLU A 262       5.044  58.620  -6.419  1.00 32.56      A C
ATOM   1831  CG   GLU A 262       6.062  59.635  -5.927  1.00 34.69      A C
ATOM   1832  CD   GLU A 262       5.412  60.870  -5.344  1.00 37.15      A C
ATOM   1833  OE1  GLU A 262       4.358  60.729  -4.685  1.00 38.40      A O
ATOM   1834  OE2  GLU A 262       5.956  61.981  -5.534  1.00 37.97      A O
ATOM   1835  C    GLU A 262       4.883  56.211  -7.097  1.00 30.39      A C
ATOM   1836  O    GLU A 262       5.311  55.317  -6.365  1.00 30.61      A O
ATOM   1837  N    CYS A 263       3.750  56.094  -7.783  1.00 28.93      A N
ATOM   1838  CA   CYS A 263       2.959  54.876  -7.680  1.00 27.70      A C
ATOM   1839  CB   CYS A 263       1.639  55.012  -8.437  1.00 27.39      A C
ATOM   1840  SG   CYS A 263       0.543  53.592  -8.205  1.00 26.70      A S
ATOM   1841  C    CYS A 263       3.769  53.723  -8.252  1.00 27.04      A C
ATOM   1842  O    CYS A 263       3.809  52.632  -7.681  1.00 26.65      A O
ATOM   1843  N    GLN A 264       4.417  53.969  -9.386  1.00 26.34      A N
ATOM   1844  CA   GLN A 264       5.242  52.946 -10.005  1.00 25.65      A C
```

FIGURE 3A-34

| ATOM | 1845 | CB  | GLN | A | 264 | 5.894  | 53.472 | -11.286 | 1.00 | 25.50 | A | C |
|------|------|-----|-----|---|-----|--------|--------|---------|------|-------|---|---|
| ATOM | 1846 | CG  | GLN | A | 264 | 5.037  | 53.308 | -12.526 | 1.00 | 25.96 | A | C |
| ATOM | 1847 | CD  | GLN | A | 264 | 5.804  | 53.558 | -13.813 | 1.00 | 26.89 | A | C |
| ATOM | 1848 | OE1 | GLN | A | 264 | 6.957  | 53.144 | -13.955 | 1.00 | 26.95 | A | O |
| ATOM | 1849 | NE2 | GLN | A | 264 | 5.160  | 54.221 | -14.767 | 1.00 | 26.68 | A | N |
| ATOM | 1850 | C   | GLN | A | 264 | 6.317  | 52.533 | -9.012  | 1.00 | 25.46 | A | C |
| ATOM | 1851 | O   | GLN | A | 264 | 6.719  | 51.370 | -8.957  | 1.00 | 25.30 | A | O |
| ATOM | 1852 | N   | HIS | A | 265 | 6.769  | 53.493 | -8.212  | 1.00 | 25.49 | A | N |
| ATOM | 1853 | CA  | HIS | A | 265 | 7.801  | 53.212 | -7.230  | 1.00 | 25.46 | A | C |
| ATOM | 1854 | CB  | HIS | A | 265 | 8.397  | 54.507 | -6.677  | 1.00 | 25.94 | A | C |
| ATOM | 1855 | CG  | HIS | A | 265 | 9.339  | 54.282 | -5.536  | 1.00 | 26.84 | A | C |
| ATOM | 1856 | CD2 | HIS | A | 265 | 10.686 | 54.149 | -5.504  | 1.00 | 26.91 | A | C |
| ATOM | 1857 | ND1 | HIS | A | 265 | 8.903  | 54.073 | -4.244  | 1.00 | 27.41 | A | N |
| ATOM | 1858 | CE1 | HIS | A | 265 | 9.941  | 53.818 | -3.467  | 1.00 | 27.22 | A | C |
| ATOM | 1859 | NE2 | HIS | A | 265 | 11.035 | 53.857 | -4.208  | 1.00 | 27.42 | A | N |
| ATOM | 1860 | C   | HIS | A | 265 | 7.302  | 52.355 | -6.077  | 1.00 | 24.83 | A | C |
| ATOM | 1861 | O   | HIS | A | 265 | 7.976  | 51.412 | -5.672  | 1.00 | 24.71 | A | O |
| ATOM | 1862 | N   | LEU | A | 266 | 6.128  | 52.686 | -5.545  | 1.00 | 24.24 | A | N |
| ATOM | 1863 | CA  | LEU | A | 266 | 5.569  | 51.923 | -4.438  | 1.00 | 23.26 | A | C |
| ATOM | 1864 | CB  | LEU | A | 266 | 4.298  | 52.587 | -3.912  | 1.00 | 22.65 | A | C |
| ATOM | 1865 | CG  | LEU | A | 266 | 3.615  | 51.860 | -2.747  | 1.00 | 22.81 | A | C |
| ATOM | 1866 | CD1 | LEU | A | 266 | 4.581  | 51.697 | -1.581  | 1.00 | 21.97 | A | C |
| ATOM | 1867 | CD2 | LEU | A | 266 | 2.394  | 52.643 | -2.308  | 1.00 | 22.48 | A | C |
| ATOM | 1868 | C   | LEU | A | 266 | 5.263  | 50.501 | -4.887  | 1.00 | 23.14 | A | C |
| ATOM | 1869 | O   | LEU | A | 266 | 5.448  | 49.550 | -4.132  | 1.00 | 23.31 | A | O |
| ATOM | 1870 | N   | ILE | A | 267 | 4.804  | 50.359 | -6.124  | 1.00 | 23.22 | A | N |
| ATOM | 1871 | CA  | ILE | A | 267 | 4.477  | 49.049 | -6.665  | 1.00 | 23.41 | A | C |
| ATOM | 1872 | CB  | ILE | A | 267 | 3.807  | 49.159 | -8.047  | 1.00 | 22.37 | A | C |
| ATOM | 1873 | CG2 | ILE | A | 267 | 3.714  | 47.780 | -8.691  | 1.00 | 21.94 | A | C |
| ATOM | 1874 | CG1 | ILE | A | 267 | 2.425  | 49.793 | -7.905  | 1.00 | 21.54 | A | C |
| ATOM | 1875 | CD1 | ILE | A | 267 | 1.659  | 49.894 | -9.207  | 1.00 | 20.68 | A | C |
| ATOM | 1876 | C   | ILE | A | 267 | 5.703  | 48.156 | -6.801  | 1.00 | 24.06 | A | C |
| ATOM | 1877 | O   | ILE | A | 267 | 5.678  | 46.992 | -6.398  | 1.00 | 24.45 | A | O |
| ATOM | 1878 | N   | ARG | A | 268 | 6.772  | 48.691 | -7.379  | 1.00 | 24.72 | A | N |
| ATOM | 1879 | CA  | ARG | A | 268 | 7.985  | 47.902 | -7.557  | 1.00 | 25.19 | A | C |
| ATOM | 1880 | CB  | ARG | A | 268 | 8.983  | 48.644 | -8.455  | 1.00 | 25.28 | A | C |
| ATOM | 1881 | CG  | ARG | A | 268 | 8.531  | 48.734 | -9.902  | 1.00 | 25.54 | A | C |
| ATOM | 1882 | CD  | ARG | A | 268 | 9.643  | 49.204 | -10.812 | 1.00 | 26.16 | A | C |
| ATOM | 1883 | NE  | ARG | A | 268 | 9.285  | 49.065 | -12.222 | 1.00 | 26.81 | A | N |
| ATOM | 1884 | CZ  | ARG | A | 268 | 8.866  | 50.063 | -12.996 | 1.00 | 26.99 | A | C |
| ATOM | 1885 | NH1 | ARG | A | 268 | 8.756  | 51.291 | -12.500 | 1.00 | 27.14 | A | N |
| ATOM | 1886 | NH2 | ARG | A | 268 | 8.552  | 49.831 | -14.268 | 1.00 | 26.09 | A | N |
| ATOM | 1887 | C   | ARG | A | 268 | 8.623  | 47.570 | -6.218  | 1.00 | 25.06 | A | C |
| ATOM | 1888 | O   | ARG | A | 268 | 9.330  | 46.569 | -6.089  | 1.00 | 25.05 | A | O |
| ATOM | 1889 | N   | TRP | A | 269 | 8.359  | 48.406 | -5.219  | 1.00 | 25.01 | A | N |
| ATOM | 1890 | CA  | TRP | A | 269 | 8.910  | 48.197 | -3.887  | 1.00 | 25.45 | A | C |
| ATOM | 1891 | CB  | TRP | A | 269 | 8.738  | 49.468 | -3.049  | 1.00 | 25.08 | A | C |
| ATOM | 1892 | CG  | TRP | A | 269 | 9.518  | 49.467 | -1.764  | 1.00 | 25.17 | A | C |
| ATOM | 1893 | CD2 | TRP | A | 269 | 9.439  | 50.437 | -0.713  | 1.00 | 24.95 | A | C |
| ATOM | 1894 | CE2 | TRP | A | 269 | 10.352 | 50.042 | 0.291   | 1.00 | 24.72 | A | C |
| ATOM | 1895 | CE3 | TRP | A | 269 | 8.686  | 51.603 | -0.521  | 1.00 | 25.26 | A | C |
| ATOM | 1896 | CD1 | TRP | A | 269 | 10.451 | 48.548 | -1.368  | 1.00 | 25.27 | A | C |
| ATOM | 1897 | NE1 | TRP | A | 269 | 10.955 | 48.887 | -0.135  | 1.00 | 25.30 | A | N |
| ATOM | 1898 | CZ2 | TRP | A | 269 | 10.533 | 50.770 | 1.468   | 1.00 | 24.37 | A | C |
| ATOM | 1899 | CZ3 | TRP | A | 269 | 8.866  | 52.326 | 0.651   | 1.00 | 25.57 | A | C |
| ATOM | 1900 | CH2 | TRP | A | 269 | 9.784  | 51.904 | 1.631   | 1.00 | 24.90 | A | C |

FIGURE 3A-35

```
ATOM  1901  C    TRP A 269       8.236  47.000  -3.208  1.00 25.87      A C
ATOM  1902  O    TRP A 269       8.906  46.163  -2.601  1.00 26.33      A O
ATOM  1903  N    CYS A 270       6.914  46.921  -3.316  1.00 26.26      A N
ATOM  1904  CA   CYS A 270       6.160  45.814  -2.733  1.00 26.14      A C
ATOM  1905  CB   CYS A 270       4.654  46.072  -2.842  1.00 25.67      A C
ATOM  1906  SG   CYS A 270       4.058  47.478  -1.891  1.00 25.04      A S
ATOM  1907  C    CYS A 270       6.491  44.525  -3.473  1.00 26.43      A C
ATOM  1908  O    CYS A 270       6.431  43.439  -2.902  1.00 27.07      A O
ATOM  1909  N    LEU A 271       6.841  44.652  -4.747  1.00 26.64      A N
ATOM  1910  CA   LEU A 271       7.161  43.493  -5.566  1.00 27.00      A C
ATOM  1911  CB   LEU A 271       6.622  43.693  -6.980  1.00 26.86      A C
ATOM  1912  CG   LEU A 271       5.104  43.815  -7.087  1.00 26.70      A C
ATOM  1913  CD1  LEU A 271       4.706  44.004  -8.544  1.00 26.15      A C
ATOM  1914  CD2  LEU A 271       4.456  42.563  -6.506  1.00 26.92      A C
ATOM  1915  C    LEU A 271       8.643  43.148  -5.639  1.00 27.35      A C
ATOM  1916  O    LEU A 271       9.079  42.492  -6.582  1.00 27.32      A O
ATOM  1917  N    ALA A 272       9.418  43.583  -4.651  1.00 27.97      A N
ATOM  1918  CA   ALA A 272      10.844  43.277  -4.629  1.00 28.63      A C
ATOM  1919  CB   ALA A 272      11.499  43.914  -3.413  1.00 27.60      A C
ATOM  1920  C    ALA A 272      11.020  41.760  -4.584  1.00 29.58      A C
ATOM  1921  O    ALA A 272      10.279  41.067  -3.886  1.00 29.68      A O
ATOM  1922  N    LEU A 273      11.996  41.247  -5.332  1.00 30.65      A N
ATOM  1923  CA   LEU A 273      12.258  39.810  -5.368  1.00 31.47      A C
ATOM  1924  CB   LEU A 273      13.369  39.495  -6.373  1.00 31.72      A C
ATOM  1925  CG   LEU A 273      12.988  39.533  -7.854  1.00 32.25      A C
ATOM  1926  CD1  LEU A 273      12.004  38.420  -8.158  1.00 32.17      A C
ATOM  1927  CD2  LEU A 273      12.379  40.885  -8.196  1.00 33.84      A C
ATOM  1928  C    LEU A 273      12.639  39.271  -3.994  1.00 32.04      A C
ATOM  1929  O    LEU A 273      12.154  38.218  -3.579  1.00 32.27      A O
ATOM  1930  N    ARG A 274      13.508  39.992  -3.290  1.00 32.68      A N
ATOM  1931  CA   ARG A 274      13.933  39.577  -1.958  1.00 33.87      A C
ATOM  1932  CB   ARG A 274      15.298  40.184  -1.609  1.00 35.70      A C
ATOM  1933  CG   ARG A 274      15.995  39.491  -0.440  1.00 38.98      A C
ATOM  1934  CD   ARG A 274      17.102  40.348   0.173  1.00 41.92      A C
ATOM  1935  NE   ARG A 274      17.961  40.955  -0.840  1.00 45.22      A N
ATOM  1936  CZ   ARG A 274      18.704  40.276  -1.711  1.00 46.69      A C
ATOM  1937  NH1  ARG A 274      18.705  38.945  -1.701  1.00 47.07      A N
ATOM  1938  NH2  ARG A 274      19.442  40.934  -2.602  1.00 47.11      A N
ATOM  1939  C    ARG A 274      12.898  40.041  -0.933  1.00 33.36      A C
ATOM  1940  O    ARG A 274      12.675  41.238  -0.758  1.00 33.73      A O
ATOM  1941  N    PRO A 275      12.251  39.094  -0.242  1.00 33.09      A N
ATOM  1942  CD   PRO A 275      12.444  37.639  -0.374  1.00 32.87      A C
ATOM  1943  CA   PRO A 275      11.234  39.394   0.770  1.00 32.97      A C
ATOM  1944  CB   PRO A 275      11.046  38.050   1.465  1.00 32.82      A C
ATOM  1945  CG   PRO A 275      11.232  37.084   0.346  1.00 32.81      A C
ATOM  1946  C    PRO A 275      11.611  40.507   1.754  1.00 33.33      A C
ATOM  1947  O    PRO A 275      10.819  41.418   2.004  1.00 33.43      A O
ATOM  1948  N    SER A 276      12.819  40.433   2.310  1.00 33.50      A N
ATOM  1949  CA   SER A 276      13.277  41.433   3.272  1.00 33.47      A C
ATOM  1950  CB   SER A 276      14.606  41.003   3.906  1.00 33.83      A C
ATOM  1951  OG   SER A 276      15.670  41.033   2.968  1.00 34.30      A O
ATOM  1952  C    SER A 276      13.434  42.816   2.648  1.00 33.37      A C
ATOM  1953  O    SER A 276      13.561  43.813   3.362  1.00 33.64      A O
ATOM  1954  N    ASP A 277      13.428  42.875   1.318  1.00 33.25      A N
ATOM  1955  CA   ASP A 277      13.562  44.146   0.607  1.00 33.06      A C
ATOM  1956  CB   ASP A 277      14.195  43.924  -0.766  1.00 33.66      A C
```

FIGURE 3A-36

```
ATOM 1957  CG   ASP A 277   15.707  43.880  -0.711  1.00 33.91      A C
ATOM 1958  OD1  ASP A 277   16.324  43.506  -1.729  1.00 34.61      A O
ATOM 1959  OD2  ASP A 277   16.279  44.226   0.345  1.00 34.19      A O
ATOM 1960  C    ASP A 277   12.222  44.851   0.435  1.00 32.69      A C
ATOM 1961  O    ASP A 277   12.172  46.021   0.066  1.00 32.73      A O
ATOM 1962  N    ARG A 278   11.136  44.129   0.689  1.00 31.99      A N
ATOM 1963  CA   ARG A 278    9.809  44.709   0.571  1.00 31.22      A C
ATOM 1964  CB   ARG A 278    8.752  43.612   0.538  1.00 30.16      A C
ATOM 1965  CG   ARG A 278    8.815  42.790  -0.716  1.00 28.94      A C
ATOM 1966  CD   ARG A 278    8.087  41.478  -0.582  1.00 28.41      A C
ATOM 1967  NE   ARG A 278    8.545  40.575  -1.628  1.00 28.72      A N
ATOM 1968  CZ   ARG A 278    8.369  39.263  -1.621  1.00 28.26      A C
ATOM 1969  NH1  ARG A 278    7.732  38.680  -0.617  1.00 28.43      A N
ATOM 1970  NH2  ARG A 278    8.852  38.535  -2.614  1.00 28.84      A N
ATOM 1971  C    ARG A 278    9.585  45.606   1.767  1.00 31.37      A C
ATOM 1972  O    ARG A 278   10.251  45.459   2.790  1.00 31.58      A O
ATOM 1973  N    PRO A 279    8.648  46.555   1.652  1.00 31.21      A N
ATOM 1974  CD   PRO A 279    7.925  46.915   0.419  1.00 31.42      A C
ATOM 1975  CA   PRO A 279    8.328  47.492   2.727  1.00 31.29      A C
ATOM 1976  CB   PRO A 279    7.656  48.632   1.984  1.00 31.63      A C
ATOM 1977  CG   PRO A 279    6.895  47.902   0.928  1.00 31.46      A C
ATOM 1978  C    PRO A 279    7.416  46.918   3.798  1.00 31.81      A C
ATOM 1979  O    PRO A 279    6.770  45.886   3.604  1.00 32.40      A O
ATOM 1980  N    THR A 280    7.377  47.601   4.935  1.00 31.99      A N
ATOM 1981  CA   THR A 280    6.518  47.209   6.041  1.00 32.07      A C
ATOM 1982  CB   THR A 280    7.100  47.658   7.393  1.00 32.39      A C
ATOM 1983  OG1  THR A 280    7.248  49.084   7.397  1.00 32.72      A O
ATOM 1984  CG2  THR A 280    8.456  47.022   7.631  1.00 31.97      A C
ATOM 1985  C    THR A 280    5.226  47.974   5.797  1.00 32.00      A C
ATOM 1986  O    THR A 280    5.207  48.924   5.013  1.00 32.18      A O
ATOM 1987  N    PHE A 281    4.148  47.566   6.454  1.00 31.91      A N
ATOM 1988  CA   PHE A 281    2.874  48.251   6.284  1.00 31.72      A C
ATOM 1989  CB   PHE A 281    1.808  47.595   7.161  1.00 32.17      A C
ATOM 1990  CG   PHE A 281    1.382  46.246   6.665  1.00 32.69      A C
ATOM 1991  CD1  PHE A 281    0.625  46.130   5.507  1.00 33.31      A C
ATOM 1992  CD2  PHE A 281    1.781  45.090   7.317  1.00 33.74      A C
ATOM 1993  CE1  PHE A 281    0.276  44.887   5.004  1.00 33.55      A C
ATOM 1994  CE2  PHE A 281    1.437  43.838   6.821  1.00 34.05      A C
ATOM 1995  CZ   PHE A 281    0.684  43.737   5.662  1.00 34.12      A C
ATOM 1996  C    PHE A 281    3.046  49.719   6.636  1.00 31.64      A C
ATOM 1997  O    PHE A 281    2.433  50.595   6.026  1.00 31.49      A O
ATOM 1998  N    GLU A 282    3.908  49.977   7.614  1.00 31.87      A N
ATOM 1999  CA   GLU A 282    4.190  51.338   8.048  1.00 31.78      A C
ATOM 2000  CB   GLU A 282    5.061  51.318   9.305  1.00 32.22      A C
ATOM 2001  CG   GLU A 282    5.660  52.664   9.668  1.00 33.46      A C
ATOM 2002  CD   GLU A 282    6.317  52.660  11.035  1.00 34.27      A C
ATOM 2003  OE1  GLU A 282    7.024  51.680  11.352  1.00 34.15      A O
ATOM 2004  OE2  GLU A 282    6.128  53.642  11.788  1.00 34.77      A O
ATOM 2005  C    GLU A 282    4.891  52.104   6.938  1.00 31.66      A C
ATOM 2006  O    GLU A 282    4.559  53.257   6.668  1.00 31.68      A O
ATOM 2007  N    GLU A 283    5.856  51.456   6.292  1.00 31.63      A N
ATOM 2008  CA   GLU A 283    6.592  52.086   5.206  1.00 32.04      A C
ATOM 2009  CB   GLU A 283    7.780  51.220   4.796  1.00 32.98      A C
ATOM 2010  CG   GLU A 283    8.889  51.211   5.832  1.00 34.14      A C
ATOM 2011  CD   GLU A 283   10.079  50.381   5.413  1.00 34.85      A C
ATOM 2012  OE1  GLU A 283    9.910  49.160   5.200  1.00 34.82      A O
```

FIGURE 3A-37

```
ATOM   2013  OE2 GLU A 283      11.185  50.953   5.300  1.00 35.88      A O
ATOM   2014  C   GLU A 283       5.710  52.369   3.996  1.00 32.13      A C
ATOM   2015  O   GLU A 283       5.884  53.385   3.323  1.00 32.62      A O
ATOM   2016  N   ILE A 284       4.762  51.479   3.717  1.00 31.46      A N
ATOM   2017  CA  ILE A 284       3.869  51.686   2.588  1.00 30.84      A C
ATOM   2018  CB  ILE A 284       2.976  50.448   2.333  1.00 30.21      A C
ATOM   2019  CG2 ILE A 284       1.964  50.741   1.235  1.00 29.70      A C
ATOM   2020  CG1 ILE A 284       3.843  49.258   1.917  1.00 29.32      A C
ATOM   2021  CD1 ILE A 284       3.059  47.989   1.656  1.00 27.41      A C
ATOM   2022  C   ILE A 284       2.986  52.907   2.846  1.00 31.23      A C
ATOM   2023  O   ILE A 284       2.917  53.816   2.018  1.00 31.62      A O
ATOM   2024  N   GLN A 285       2.330  52.947   4.002  1.00 30.98      A N
ATOM   2025  CA  GLN A 285       1.453  54.071   4.324  1.00 30.83      A C
ATOM   2026  CB  GLN A 285       0.609  53.744   5.555  1.00 30.48      A C
ATOM   2027  CG  GLN A 285      -0.401  52.639   5.293  1.00 30.38      A C
ATOM   2028  CD  GLN A 285      -1.386  52.463   6.425  1.00 30.29      A C
ATOM   2029  OE1 GLN A 285      -1.051  51.936   7.489  1.00 29.83      A O
ATOM   2030  NE2 GLN A 285      -2.614  52.916   6.205  1.00 30.24      A N
ATOM   2031  C   GLN A 285       2.173  55.402   4.520  1.00 30.98      A C
ATOM   2032  O   GLN A 285       1.551  56.466   4.469  1.00 30.99      A O
ATOM   2033  N   ASN A 286       3.480  55.349   4.748  1.00 31.18      A N
ATOM   2034  CA  ASN A 286       4.255  56.572   4.918  1.00 31.36      A C
ATOM   2035  CB  ASN A 286       5.396  56.357   5.915  1.00 30.79      A C
ATOM   2036  CG  ASN A 286       4.959  56.543   7.356  1.00 30.73      A C
ATOM   2037  OD1 ASN A 286       5.636  56.097   8.279  1.00 31.60      A O
ATOM   2038  ND2 ASN A 286       3.835  57.216   7.557  1.00 30.28      A N
ATOM   2039  C   ASN A 286       4.821  56.981   3.566  1.00 31.43      A C
ATOM   2040  O   ASN A 286       5.481  58.011   3.440  1.00 31.45      A O
ATOM   2041  N   HIS A 287       4.548  56.166   2.553  1.00 31.32      A N
ATOM   2042  CA  HIS A 287       5.035  56.436   1.209  1.00 31.17      A C
ATOM   2043  CB  HIS A 287       4.754  55.240   0.300  1.00 29.93      A C
ATOM   2044  CG  HIS A 287       5.450  55.312  -1.022  1.00 29.31      A C
ATOM   2045  CD2 HIS A 287       6.549  54.671  -1.484  1.00 28.46      A C
ATOM   2046  ND1 HIS A 287       5.042  56.154  -2.033  1.00 29.09      A N
ATOM   2047  CE1 HIS A 287       5.860  56.028  -3.063  1.00 29.04      A C
ATOM   2048  NE2 HIS A 287       6.784  55.135  -2.754  1.00 28.58      A N
ATOM   2049  C   HIS A 287       4.402  57.701   0.625  1.00 31.51      A C
ATOM   2050  O   HIS A 287       3.233  58.002   0.874  1.00 32.07      A O
ATOM   2051  N   PRO A 288       5.177  58.463  -0.156  1.00 31.24      A N
ATOM   2052  CD  PRO A 288       6.610  58.276  -0.439  1.00 30.86      A C
ATOM   2053  CA  PRO A 288       4.689  59.695  -0.770  1.00 31.12      A C
ATOM   2054  CB  PRO A 288       5.828  60.082  -1.697  1.00 30.70      A C
ATOM   2055  CG  PRO A 288       7.019  59.638  -0.924  1.00 30.77      A C
ATOM   2056  C   PRO A 288       3.375  59.535  -1.514  1.00 31.08      A C
ATOM   2057  O   PRO A 288       2.497  60.387  -1.422  1.00 32.24      A O
ATOM   2058  N   TRP A 289       3.233  58.441  -2.247  1.00 30.80      A N
ATOM   2059  CA  TRP A 289       2.017  58.221  -3.016  1.00 30.53      A C
ATOM   2060  CB  TRP A 289       2.215  57.042  -3.973  1.00 29.39      A C
ATOM   2061  CG  TRP A 289       1.058  56.826  -4.892  1.00 27.91      A C
ATOM   2062  CD2 TRP A 289       0.027  55.845  -4.751  1.00 26.99      A C
ATOM   2063  CE2 TRP A 289      -0.884  56.045  -5.809  1.00 27.12      A C
ATOM   2064  CE3 TRP A 289      -0.217  54.817  -3.834  1.00 26.62      A C
ATOM   2065  CD1 TRP A 289       0.743  57.558  -5.998  1.00 27.31      A C
ATOM   2066  NE1 TRP A 289      -0.421  57.097  -6.554  1.00 27.11      A N
ATOM   2067  CZ2 TRP A 289      -2.028  55.255  -5.975  1.00 27.02      A C
ATOM   2068  CZ3 TRP A 289      -1.356  54.027  -3.998  1.00 27.10      A C
```

FIGURE 3A-38

```
ATOM  2069  CH2  TRP A 289   -2.246  54.253  -5.061  1.00 27.03   A C
ATOM  2070  C    TRP A 289    0.774  57.983  -2.154  1.00 30.97   A C
ATOM  2071  O    TRP A 289   -0.349  58.184  -2.614  1.00 30.43   A O
ATOM  2072  N    MET A 290    0.980  57.570  -0.906  1.00 32.06   A N
ATOM  2073  CA   MET A 290   -0.124  57.279   0.006  1.00 33.53   A C
ATOM  2074  CB   MET A 290    0.293  56.192   1.001  1.00 32.78   A C
ATOM  2075  CG   MET A 290    0.396  54.792   0.410  1.00 32.61   A C
ATOM  2076  SD   MET A 290   -1.205  54.057   0.012  1.00 32.41   A S
ATOM  2077  CE   MET A 290   -1.358  52.861   1.325  1.00 32.97   A C
ATOM  2078  C    MET A 290   -0.670  58.472   0.787  1.00 35.26   A C
ATOM  2079  O    MET A 290   -1.602  58.316   1.582  1.00 36.05   A O
ATOM  2080  N    GLN A 291   -0.112  59.659   0.565  1.00 36.55   A N
ATOM  2081  CA   GLN A 291   -0.566  60.848   1.287  1.00 37.83   A C
ATOM  2082  CB   GLN A 291    0.540  61.910   1.300  1.00 38.93   A C
ATOM  2083  CG   GLN A 291    1.770  61.509   2.106  1.00 41.18   A C
ATOM  2084  CD   GLN A 291    1.406  60.761   3.389  1.00 42.74   A C
ATOM  2085  OE1  GLN A 291    1.202  59.544   3.377  1.00 43.13   A O
ATOM  2086  NE2  GLN A 291    1.308  61.492   4.496  1.00 43.44   A N
ATOM  2087  C    GLN A 291   -1.861  61.468   0.765  1.00 37.92   A C
ATOM  2088  O    GLN A 291   -2.272  61.216  -0.368  1.00 38.01   A O
ATOM  2089  N    ASP A 292   -2.497  62.273   1.614  1.00 37.98   A N
ATOM  2090  CA   ASP A 292   -3.741  62.967   1.277  1.00 38.64   A C
ATOM  2091  CB   ASP A 292   -3.469  64.054   0.238  1.00 40.31   A C
ATOM  2092  CG   ASP A 292   -2.609  65.173   0.782  1.00 42.16   A C
ATOM  2093  OD1  ASP A 292   -2.072  65.951  -0.036  1.00 43.49   A O
ATOM  2094  OD2  ASP A 292   -2.477  65.281   2.026  1.00 43.28   A O
ATOM  2095  C    ASP A 292   -4.857  62.063   0.772  1.00 38.13   A C
ATOM  2096  O    ASP A 292   -5.593  62.426  -0.146  1.00 37.67   A O
ATOM  2097  N    VAL A 293   -4.984  60.891   1.380  1.00 37.74   A N
ATOM  2098  CA   VAL A 293   -6.015  59.948   0.988  1.00 36.92   A C
ATOM  2099  CB   VAL A 293   -5.874  58.620   1.760  1.00 36.63   A C
ATOM  2100  CG1  VAL A 293   -6.085  58.857   3.241  1.00 36.75   A C
ATOM  2101  CG2  VAL A 293   -6.875  57.607   1.240  1.00 36.45   A C
ATOM  2102  C    VAL A 293   -7.380  60.548   1.287  1.00 36.77   A C
ATOM  2103  O    VAL A 293   -7.520  61.363   2.194  1.00 36.28   A O
ATOM  2104  N    LEU A 294   -8.379  60.145   0.510  1.00 37.04   A N
ATOM  2105  CA   LEU A 294   -9.744  60.619   0.693  1.00 36.70   A C
ATOM  2106  CB   LEU A 294  -10.541  60.488  -0.608  1.00 36.31   A C
ATOM  2107  CG   LEU A 294  -10.184  61.373  -1.797  1.00 35.98   A C
ATOM  2108  CD1  LEU A 294  -11.121  61.055  -2.958  1.00 35.56   A C
ATOM  2109  CD2  LEU A 294  -10.299  62.833  -1.399  1.00 35.35   A C
ATOM  2110  C    LEU A 294  -10.431  59.774   1.753  1.00 36.93   A C
ATOM  2111  O    LEU A 294   -9.994  58.662   2.050  1.00 36.89   A O
ATOM  2112  N    LEU A 295  -11.511  60.308   2.317  1.00 37.27   A N
ATOM  2113  CA   LEU A 295  -12.285  59.591   3.320  1.00 37.34   A C
ATOM  2114  CB   LEU A 295  -13.111  60.571   4.150  1.00 37.61   A C
ATOM  2115  CG   LEU A 295  -12.317  61.616   4.938  1.00 38.05   A C
ATOM  2116  CD1  LEU A 295  -13.267  62.655   5.514  1.00 37.84   A C
ATOM  2117  CD2  LEU A 295  -11.525  60.933   6.044  1.00 37.79   A C
ATOM  2118  C    LEU A 295  -13.207  58.655   2.552  1.00 37.69   A C
ATOM  2119  O    LEU A 295  -13.495  58.883   1.377  1.00 37.67   A O
ATOM  2120  N    PRO A 296  -13.674  57.580   3.195  1.00 38.07   A N
ATOM  2121  CD   PRO A 296  -13.305  57.036   4.513  1.00 37.73   A C
ATOM  2122  CA   PRO A 296  -14.561  56.663   2.477  1.00 38.61   A C
ATOM  2123  CB   PRO A 296  -14.935  55.649   3.551  1.00 38.60   A C
ATOM  2124  CG   PRO A 296  -13.664  55.576   4.362  1.00 38.08   A C
```

FIGURE 3A-39

```
ATOM   2125  C    PRO A 296     -15.776  57.346   1.846  1.00 39.37      A C
ATOM   2126  O    PRO A 296     -16.075  57.124   0.672  1.00 39.15      A O
ATOM   2127  N    GLN A 297     -16.466  58.185   2.615  1.00 40.53      A N
ATOM   2128  CA   GLN A 297     -17.643  58.882   2.097  1.00 41.54      A C
ATOM   2129  CB   GLN A 297     -18.342  59.683   3.201  1.00 42.00      A C
ATOM   2130  CG   GLN A 297     -19.703  60.226   2.776  1.00 43.00      A C
ATOM   2131  CD   GLN A 297     -20.612  59.145   2.202  1.00 44.13      A C
ATOM   2132  OE1  GLN A 297     -21.048  58.235   2.910  1.00 44.03      A O
ATOM   2133  NE2  GLN A 297     -20.891  59.238   0.905  1.00 45.11      A N
ATOM   2134  C    GLN A 297     -17.277  59.806   0.942  1.00 41.76      A C
ATOM   2135  O    GLN A 297     -17.993  59.866  -0.056  1.00 42.14      A O
ATOM   2136  N    GLU A 298     -16.174  60.534   1.077  1.00 41.95      A N
ATOM   2137  CA   GLU A 298     -15.733  61.416   0.004  1.00 42.55      A C
ATOM   2138  CB   GLU A 298     -14.416  62.108   0.371  1.00 42.98      A C
ATOM   2139  CG   GLU A 298     -14.534  63.222   1.387  1.00 44.14      A C
ATOM   2140  CD   GLU A 298     -13.179  63.772   1.799  1.00 45.20      A C
ATOM   2141  OE1  GLU A 298     -13.142  64.794   2.520  1.00 46.25      A O
ATOM   2142  OE2  GLU A 298     -12.150  63.179   1.407  1.00 44.80      A O
ATOM   2143  C    GLU A 298     -15.513  60.566  -1.245  1.00 42.63      A C
ATOM   2144  O    GLU A 298     -15.956  60.915  -2.337  1.00 42.92      A O
ATOM   2145  N    THR A 299     -14.825  59.442  -1.066  1.00 42.59      A N
ATOM   2146  CA   THR A 299     -14.528  58.537  -2.167  1.00 42.62      A C
ATOM   2147  CB   THR A 299     -13.803  57.271  -1.669  1.00 42.32      A C
ATOM   2148  OG1  THR A 299     -12.682  57.648  -0.861  1.00 42.76      A O
ATOM   2149  CG2  THR A 299     -13.314  56.443  -2.843  1.00 41.47      A C
ATOM   2150  C    THR A 299     -15.809  58.117  -2.874  1.00 42.61      A C
ATOM   2151  O    THR A 299     -15.851  58.026  -4.099  1.00 42.88      A O
ATOM   2152  N    ALA A 300     -16.853  57.864  -2.096  1.00 42.68      A N
ATOM   2153  CA   ALA A 300     -18.130  57.447  -2.657  1.00 42.89      A C
ATOM   2154  CB   ALA A 300     -19.081  57.034  -1.542  1.00 42.68      A C
ATOM   2155  C    ALA A 300     -18.750  58.561  -3.483  1.00 43.19      A C
ATOM   2156  O    ALA A 300     -19.160  58.343  -4.620  1.00 43.47      A O
ATOM   2157  N    GLU A 301     -18.809  59.756  -2.905  1.00 43.41      A N
ATOM   2158  CA   GLU A 301     -19.391  60.914  -3.574  1.00 43.84      A C
ATOM   2159  CB   GLU A 301     -19.358  62.132  -2.648  1.00 44.85      A C
ATOM   2160  CG   GLU A 301     -20.431  62.139  -1.572  1.00 46.58      A C
ATOM   2161  CD   GLU A 301     -20.252  63.276  -0.574  1.00 48.06      A C
ATOM   2162  OE1  GLU A 301     -21.177  63.496   0.240  1.00 49.05      A O
ATOM   2163  OE2  GLU A 301     -19.190  63.943  -0.597  1.00 48.02      A O
ATOM   2164  C    GLU A 301     -18.710  61.278  -4.883  1.00 43.56      A C
ATOM   2165  O    GLU A 301     -19.373  61.628  -5.858  1.00 43.87      A O
ATOM   2166  N    ILE A 302     -17.387  61.192  -4.901  1.00 43.12      A N
ATOM   2167  CA   ILE A 302     -16.618  61.543  -6.085  1.00 42.30      A C
ATOM   2168  CB   ILE A 302     -15.182  61.936  -5.707  1.00 41.90      A C
ATOM   2169  CG2  ILE A 302     -14.424  62.396  -6.939  1.00 41.79      A C
ATOM   2170  CG1  ILE A 302     -15.200  63.049  -4.667  1.00 41.67      A C
ATOM   2171  CD1  ILE A 302     -13.820  63.453  -4.198  1.00 41.60      A C
ATOM   2172  C    ILE A 302     -16.522  60.453  -7.143  1.00 42.44      A C
ATOM   2173  O    ILE A 302     -16.597  60.740  -8.336  1.00 42.27      A O
ATOM   2174  N    HIS A 303     -16.363  59.205  -6.711  1.00 42.56      A N
ATOM   2175  CA   HIS A 303     -16.189  58.097  -7.649  1.00 42.80      A C
ATOM   2176  CB   HIS A 303     -14.837  57.424  -7.384  1.00 41.08      A C
ATOM   2177  CG   HIS A 303     -13.665  58.349  -7.487  1.00 39.57      A C
ATOM   2178  CD2  HIS A 303     -12.898  58.924  -6.531  1.00 38.64      A C
ATOM   2179  ND1  HIS A 303     -13.161  58.782  -8.694  1.00 38.96      A N
ATOM   2180  CE1  HIS A 303     -12.132  59.583  -8.477  1.00 38.56      A C
```

FIGURE 3A-40

```
ATOM   2181  NE2 HIS A 303     -11.953  59.686  -7.173  1.00 38.04      A N
ATOM   2182  C   HIS A 303     -17.259  57.009  -7.690  1.00 44.03      A C
ATOM   2183  O   HIS A 303     -17.271  56.199  -8.615  1.00 43.91      A O
ATOM   2184  N   LEU A 304     -18.157  56.975  -6.714  1.00 45.62      A N
ATOM   2185  CA  LEU A 304     -19.160  55.918  -6.701  1.00 47.23      A C
ATOM   2186  CB  LEU A 304     -19.076  55.177  -5.369  1.00 46.59      A C
ATOM   2187  CG  LEU A 304     -17.652  54.716  -5.045  1.00 45.72      A C
ATOM   2188  CD1 LEU A 304     -17.633  53.993  -3.712  1.00 45.64      A C
ATOM   2189  CD2 LEU A 304     -17.140  53.814  -6.156  1.00 45.10      A C
ATOM   2190  C   LEU A 304     -20.607  56.318  -6.994  1.00 48.86      A C
ATOM   2191  O   LEU A 304     -21.342  55.561  -7.628  1.00 48.95      A O
ATOM   2192  N   HIS A 305     -21.023  57.495  -6.538  1.00 50.81      A N
ATOM   2193  CA  HIS A 305     -22.391  57.948  -6.781  1.00 52.83      A C
ATOM   2194  CB  HIS A 305     -22.759  59.084  -5.817  1.00 53.66      A C
ATOM   2195  CG  HIS A 305     -22.748  58.683  -4.372  1.00 54.94      A C
ATOM   2196  CD2 HIS A 305     -22.613  57.469  -3.784  1.00 55.00      A C
ATOM   2197  ND1 HIS A 305     -22.881  59.593  -3.345  1.00 55.12      A N
ATOM   2198  CE1 HIS A 305     -22.825  58.960  -2.187  1.00 55.26      A C
ATOM   2199  NE2 HIS A 305     -22.663  57.670  -2.425  1.00 55.25      A N
ATOM   2200  C   HIS A 305     -22.543  58.423  -8.226  1.00 53.63      A C
ATOM   2201  O   HIS A 305     -23.322  57.790  -8.977  1.00 53.81      A O
ATOM   2202  OXT HIS A 305     -21.874  59.418  -8.591  1.00 54.41      A O
TER          1       HIS A 305                                          A
HET    2203  O   HOH W   1       5.028  44.768   8.332  1.00 30.17      W O
HET    2204  O   HOH W   2       8.189  38.473   7.347  1.00 29.96      W O
HET    2205  O   HOH W   3     -15.166  38.011   6.469  1.00 38.94      W O
HET    2206  O   HOH W   4      -2.980  38.949   5.561  1.00 14.04      W O
HET    2207  O   HOH W   5       5.819  34.261   9.032  1.00 32.20      W O
HET    2208  O   HOH W   6       2.651  36.873  -7.927  1.00 21.87      W O
HET    2209  O   HOH W   7      -8.247  33.214   2.755  1.00 16.11      W O
HET    2210  O   HOH W   8     -17.539  45.069   9.101  1.00 42.43      W O
HET    2211  O   HOH W   9       0.205  38.625 -11.274  1.00 27.72      W O
HET    2212  O   HOH W  10       8.601  39.365 -15.205  1.00 19.93      W O
HET    2213  O   HOH W  12     -12.178  27.032   6.042  1.00 34.29      W O
HET    2214  O   HOH W  13     -14.652  33.066   5.890  1.00 28.78      W O
HET    2215  O   HOH W  14       5.504  37.244   9.057  1.00 48.44      W O
HET    2216  O   HOH W  15     -10.014  53.379 -17.265  1.00 41.36      W O
HET    2217  O   HOH W  16     -11.733  55.657 -11.556  1.00 31.86      W O
HET    2218  O   HOH W  18      -9.067  42.492 -13.410  1.00 31.57      W O
HET    2219  O   HOH W  19      -3.301  54.461  10.306  1.00 29.67      W O
HET    2220  O   HOH W  20       4.634  47.588   9.605  1.00 26.06      W O
HET    2221  O   HOH W  21     -15.737  35.886   4.408  1.00 30.22      W O
HET    2222  O   HOH W  22       1.740  48.969  10.693  1.00 17.77      W O
HET    2223  O   HOH W  23      -2.124  37.491   0.591  1.00 18.68      W O
HET    2224  O   HOH W  24      -7.503  59.204  -2.056  1.00 24.14      W O
HET    2225  O   HOH W  25      14.691  42.500  -3.819  1.00 27.42      W O
HET    2226  O   HOH W  26      -5.015  58.805 -12.772  1.00 37.56      W O
HET    2227  O   HOH W  27     -12.893  49.920   5.111  1.00 27.25      W O
HET    2228  O   HOH W  28     -10.526  49.970   6.159  1.00 30.61      W O
HET    2229  O   HOH W  29     -10.579  55.841   1.956  1.00 37.09      W O
HET    2230  O   HOH W  30       8.174  55.239   3.025  1.00 35.98      W O
HET    2231  O   HOH W  31      -4.703  54.860 -13.350  1.00 34.79      W O
HET    2232  O   HOH W  33      -2.521  59.537   3.727  1.00 32.97      W O
HET    2233  O   HOH W  34      -6.902  39.184 -10.274  1.00 37.92      W O
HET    2234  O   HOH W  35     -25.018  22.780   4.471  1.00 38.82      W O
HET    2235  O   HOH W  37      11.110  45.626  -8.454  1.00 63.51      W O
```

FIGURE 3A-41

| | | | | | | | | | | | |
|---|---|---|---|---|---|---|---|---|---|---|---|
| HET | 2236 | O | HOH | W | 38 | 3.233 | 26.257 | 7.352 | 1.00 | 49.82 | W O |
| HET | 2237 | O | HOH | W | 39 | -8.993 | 46.605 | -16.788 | 1.00 | 36.24 | W O |
| HET | 2238 | O | HOH | W | 40 | -4.624 | 36.022 | -3.347 | 1.00 | 30.42 | W O |
| HET | 2239 | O | HOH | W | 42 | -8.156 | 51.431 | 10.620 | 1.00 | 53.74 | W O |
| HET | 2240 | O | HOH | W | 44 | 8.873 | 50.024 | 9.599 | 1.00 | 26.09 | W O |
| HET | 2241 | O | HOH | W | 46 | 15.002 | 39.397 | -12.496 | 1.00 | 50.24 | W O |
| HET | 2242 | O | HOH | W | 48 | 9.190 | 23.988 | 1.721 | 1.00 | 38.24 | W O |
| HET | 2243 | O | HOH | W | 49 | -29.966 | 30.019 | -6.829 | 1.00 | 46.18 | W O |
| HET | 2244 | O | HOH | W | 50 | -8.357 | 50.437 | -18.165 | 1.00 | 28.28 | W O |
| HET | 2245 | O | HOH | W | 51 | -31.637 | 29.667 | -3.497 | 1.00 | 37.94 | W O |
| HET | 2246 | O | HOH | W | 52 | -0.812 | 35.480 | -0.610 | 1.00 | 24.16 | W O |
| HET | 2247 | O | HOH | W | 55 | 7.743 | 65.356 | -13.441 | 1.00 | 51.25 | W O |
| HET | 2248 | O | HOH | W | 56 | -19.349 | 16.749 | 3.307 | 1.00 | 58.24 | W O |
| HET | 2249 | O | HOH | W | 59 | -25.068 | 57.066 | 8.935 | 1.00 | 43.95 | W O |
| HET | 2250 | O | HOH | W | 60 | -6.064 | 61.348 | -2.514 | 1.00 | 30.32 | W O |
| HET | 2251 | O | HOH | W | 61 | -2.366 | 34.318 | 16.286 | 1.00 | 40.09 | W O |
| HET | 2252 | O | HOH | W | 63 | 10.473 | 43.256 | -8.863 | 1.00 | 33.73 | W O |
| HET | 2253 | O | HOH | W | 64 | -1.891 | 37.597 | 3.438 | 1.00 | 27.48 | W O |
| HET | 2254 | O | HOH | W | 65 | 8.073 | 35.702 | 2.455 | 1.00 | 42.54 | W O |
| HET | 2255 | O | HOH | W | 67 | -7.043 | 63.544 | -4.235 | 1.00 | 41.47 | W O |
| HET | 2256 | O | HOH | W | 69 | 1.372 | 36.509 | -1.864 | 1.00 | 26.24 | W O |
| HET | 2257 | O | HOH | W | 71 | -18.454 | 24.863 | -4.559 | 1.00 | 62.61 | W O |
| HET | 2258 | O | HOH | W | 72 | -19.939 | 24.139 | -2.665 | 1.00 | 44.21 | W O |
| HET | 2259 | O | HOH | W | 74 | -0.878 | 62.275 | -3.204 | 1.00 | 31.73 | W O |
| HET | 2260 | O | HOH | W | 76 | 9.361 | 61.465 | -14.860 | 1.00 | 39.25 | W O |
| HET | 2261 | O | HOH | W | 77 | -13.726 | 57.212 | -10.884 | 1.00 | 35.78 | W O |
| HET | 2262 | O | HOH | W | 78 | 10.067 | 52.729 | -10.435 | 1.00 | 35.42 | W O |
| HET | 2263 | O | HOH | W | 79 | 7.053 | 43.341 | 4.431 | 1.00 | 23.74 | W O |
| HET | 2264 | O | HOH | W | 80 | -15.738 | 58.872 | 6.089 | 1.00 | 50.27 | W O |
| HET | 2265 | O | HOH | W | 83 | -11.985 | 33.169 | -3.657 | 1.00 | 48.41 | W O |
| HET | 2266 | O | HOH | W | 84 | -17.971 | 23.353 | -0.678 | 1.00 | 52.72 | W O |
| HET | 2267 | O | HOH | W | 85 | 1.104 | 51.366 | 9.124 | 1.00 | 19.42 | W O |
| HET | 2268 | O | HOH | W | 86 | 0.430 | 27.592 | -5.525 | 1.00 | 26.70 | W O |
| HET | 2269 | O | HOH | W | 87 | 0.645 | 36.162 | 3.793 | 1.00 | 31.58 | W O |
| HET | 2270 | O | HOH | W | 88 | 10.165 | 38.535 | 5.436 | 1.00 | 44.92 | W O |
| HET | 2271 | O | HOH | W | 89 | 12.085 | 47.218 | 4.404 | 1.00 | 34.05 | W O |
| HET | 2272 | O | HOH | W | 90 | -5.602 | 49.658 | 10.949 | 1.00 | 31.77 | W O |
| HET | 2273 | O | HOH | W | 91 | 0.406 | 34.678 | 1.571 | 1.00 | 47.69 | W O |
| HET | 2274 | O | HOH | W | 92 | -23.782 | 29.350 | -10.256 | 1.00 | 42.70 | W O |
| HET | 2275 | O | HOH | W | 93 | -19.758 | 41.777 | -7.221 | 1.00 | 28.35 | W O |
| HET | 2276 | O | HOH | W | 94 | 6.066 | 32.502 | 15.452 | 1.00 | 50.39 | W O |
| HET | 2277 | O | HOH | W | 96 | 9.202 | 39.065 | -17.522 | 1.00 | 25.41 | W O |
| HET | 2278 | O | HOH | W | 97 | -19.149 | 31.406 | -9.369 | 1.00 | 35.00 | W O |
| HET | 2279 | O | HOH | W | 99 | -3.415 | 29.086 | 2.112 | 1.00 | 44.42 | W O |
| HET | 2280 | O | HOH | W | 100 | -11.244 | 32.868 | 17.778 | 1.00 | 46.43 | W O |
| HET | 2281 | O | HOH | W | 101 | -6.371 | 60.625 | -9.318 | 1.00 | 20.35 | W O |
| HET | 2282 | O | HOH | W | 102 | -14.821 | 49.463 | 6.812 | 1.00 | 50.68 | W O |
| HET | 2283 | O | HOH | W | 103 | -20.628 | 43.673 | -10.854 | 1.00 | 39.24 | W O |
| HET | 2284 | O | HOH | W | 104 | -3.499 | 32.121 | -10.335 | 1.00 | 46.91 | W O |
| HET | 2285 | O | HOH | W | 105 | -4.206 | 30.482 | -8.410 | 1.00 | 41.69 | W O |
| HET | 2286 | O | HOH | W | 106 | -2.517 | 34.615 | -2.667 | 1.00 | 48.27 | W O |
| HET | 2287 | O | HOH | W | 107 | -19.491 | 49.493 | 5.239 | 1.00 | 54.59 | W O |
| HET | 2288 | O | HOH | W | 108 | 11.670 | 23.954 | 3.270 | 1.00 | 59.77 | W O |
| HET | 2289 | O | HOH | W | 110 | 10.956 | 50.968 | -5.659 | 1.00 | 37.53 | W O |
| HET | 2290 | O | HOH | W | 112 | -4.243 | 62.123 | -7.733 | 1.00 | 31.89 | W O |
| HET | 2291 | O | HOH | W | 113 | 2.869 | 29.235 | -14.985 | 1.00 | 58.33 | W O |

FIGURE 3A-42

```
HET  2292  O  HOH W 114    4.970  56.477  11.644  1.00 37.38      W O
HET  2293  O  HOH W 115   -2.277  27.663  -5.123  1.00 53.27      W O
HET  2294  O  HOH W 116  -25.920  44.829  -3.971  1.00 39.10      W O
HET  2295  O  HOH W 117   -2.918  28.265  10.863  1.00 34.48      W O
HET  2296  O  HOH W 118    1.093  31.480  16.111  1.00 38.19      W O
HET  2297  O  HOH W 119  -22.414  42.136  -7.347  1.00 46.41      W O
HET  2298  O  HOH W 120    4.651  43.405 -15.563  1.00 30.39      W O
HET  2299  O  HOH W 121  -10.047  32.408  -0.635  1.00 45.93      W O
HET  2300  O  HOH W 122  -19.404  36.073  -8.436  1.00 52.65      W O
HET  2301  O  HOH W 124  -15.398  22.505  -4.803  1.00 41.66      W O
HET  2302  O  HOH W 125  -25.154  42.786   7.198  1.00 35.04      W O
HET  2303  O  HOH W 126    9.795  42.939   4.202  1.00 41.67      W O
HET  2304  O  HOH W 127   10.504  46.370 -12.440  1.00 45.18      W O
HET  2305  O  HOH W 128  -16.449  49.115   8.910  1.00 32.05      W O
HET  2306  O  HOH W 129  -28.785  28.143   2.251  1.00 50.49      W O
HET  2307  O  HOH W 130    9.581  56.962 -13.351  1.00 36.93      W O
HET  2308  O  HOH W 131    0.326  23.925   0.259  1.00 42.39      W O
HET  2309  O  HOH W 132  -31.287  42.433   0.878  1.00 42.32      W O
HET  2310  O  HOH W 133  -25.630  42.964  -0.961  1.00 42.68      W O
HET  2311  O  HOH W 134  -10.529  48.443   9.728  1.00 27.22      W O
HET  2312  O  HOH W 135   13.634  43.596  -6.888  1.00 48.18      W O
HET  2313  O  HOH W 136  -21.363  29.135  -9.356  1.00 30.28      W O
HET  2314  O  HOH W 137    5.433  29.626  15.277  1.00 46.55      W O
HET  2315  O  HOH W 138  -21.620  32.893 -10.535  1.00 47.34      W O
HET  2316  O  HOH W 140    1.071  27.588  10.155  1.00 40.25      W O
HET  2317  O  HOH W 141   13.495  30.308   3.209  1.00 43.20      W O
HET  2318  O  HOH W 142  -21.940  38.568  -7.406  1.00 56.63      W O
HET  2319  O  HOH W 143   -0.195  29.774  10.882  1.00 45.91      W O
HET  2320  O  HOH W 144  -11.723  29.261  -5.968  1.00 52.48      W O
HET  2321  O  HOH W 145   11.930  51.561  -8.676  1.00 44.58      W O
HET  2322  O  HOH W 146  -22.617  58.131   9.053  1.00 39.70      W O
HET  2323  O  HOH W 148   13.187  48.467   2.191  1.00 50.09      W O
HET  2324  O  HOH W 149   11.065  34.327   3.436  1.00 50.72      W O
HET  2325  O  HOH W 150   16.314  37.631   3.591  1.00 44.33      W O
HET  2326  O  HOH W 151  -14.021  29.234   2.475  1.00 45.35      W O
HET  2327  O  HOH W 152   -2.913  25.549   3.115  1.00 50.75      W O
HET  2328  O  HOH W 153  -32.162  36.933  -0.013  1.00 49.96      W O
HET  2329  O  HOH W 154  -25.176  57.274  11.637  1.00 35.83      W O
HET  2330  O  HOH W 155   -1.236  62.037   3.918  1.00 52.89      W O
HET  2331  O  HOH W 163  -16.465  38.705  -9.317  1.00 48.95      W O
HET  2332  O  HOH W 164   -9.019  53.609   9.223  1.00 43.37      W O
HET  2333  O  HOH W 165    7.069  43.104   7.087  1.00 35.53      W O
HET  2334  O  HOH W 167   -2.964  56.739 -13.195  1.00 42.67      W O
HET  2335  O  HOH W 168   -0.674  26.977   7.333  1.00 58.51      W O
HET  2336  O  HOH W 169    2.022  62.269 -12.389  1.00 38.09      W O
HET  2337  O  HOH W 160    3.143  33.371  17.461  1.00 35.83      W O
HET  2338  O  HOH W 161   -8.159  47.886 -18.897  1.00 39.24      W O
HET  2362  O  HOH W 162  -25.035  50.827   7.036  1.00 32.68      W O
HET  2363  O  HOH W 163  -24.161  50.362   4.702  1.00 48.13      W O
HET  2364  O  HOH W 164   -0.982  59.064 -13.992  1.00 44.83      W O
HET  2365  O  HOH W 165    8.657  40.987   7.676  1.00 56.40      W O
ATOM    1  C1  LY2 Z   1  -22.659  39.798  -1.719  1.00 32.19      Z C
ATOM    2  C2  LY2 Z   1  -21.941  39.896  -2.932  1.00 31.95      Z C
ATOM    3  C3  LY2 Z   1  -20.613  39.421  -3.017  1.00 31.81      Z C
ATOM    4  C4  LY2 Z   1  -20.004  38.847  -1.880  1.00 31.38      Z C
ATOM    5  C5  LY2 Z   1  -20.712  38.742  -0.656  1.00 31.06      Z C
```

FIGURE 3A-43

```
ATOM      6  C6  LY2 Z   1     -22.045  39.222  -0.584  1.00 31.30      Z C
ATOM      7  C7  LY2 Z   1     -20.042  38.138   0.544  1.00 30.43      Z C
ATOM      8  C8  LY2 Z   1     -19.224  37.014   0.442  1.00 30.47      Z C
ATOM      9  C9  LY2 Z   1     -18.558  36.496   1.562  1.00 30.52      Z C
ATOM     10  C10 LY2 Z   1     -18.711  37.093   2.824  1.00 30.59      Z C
ATOM     11  C11 LY2 Z   1     -19.545  38.214   2.945  1.00 30.25      Z C
ATOM     12  C12 LY2 Z   1     -20.200  38.731   1.814  1.00 29.93      Z C
ATOM     13  O1  LY2 Z   1     -19.087  36.376  -0.778  1.00 30.87      Z O
ATOM     14  C13 LY2 Z   1     -18.362  35.240  -0.950  1.00 30.75      Z C
ATOM     15  C14 LY2 Z   1     -17.643  34.713   0.063  1.00 30.61      Z C
ATOM     16  C15 LY2 Z   1     -17.682  35.335   1.401  1.00 30.77      Z C
ATOM     17  O2  LY2 Z   1     -16.987  34.834   2.277  1.00 31.56      Z O
ATOM     18  N1  LY2 Z   1     -18.471  34.638  -2.293  1.00 30.52      Z N
ATOM     19  C16 LY2 Z   1     -18.695  35.645  -3.345  1.00 30.70      Z C
ATOM     20  C17 LY2 Z   1     -19.209  34.942  -4.608  1.00 31.40      Z C
ATOM     21  O3  LY2 Z   1     -18.262  33.963  -5.029  1.00 31.87      Z O
ATOM     22  C18 LY2 Z   1     -18.027  32.974  -4.029  1.00 31.23      Z C
ATOM     23  C19 LY2 Z   1     -17.486  33.642  -2.755  1.00 30.58      Z C
END
```

CRYSTAL STRUCTURE OF HUMAN PIM-1 KINASE PROTEIN COMPLEXES AND BINDING POCKETS THEREOF, AND USES THEREOF IN DRUG DESIGN

This application is a continuation of PCT application No. PCT/US2004/010345, filed Apr. 1, 2004, which claims benefit of U.S. Provisional Application No. 60/460,843, titled CRYSTAL STRUCTURE OF HUMAN PIM-1 KINASE PROTEIN AND BINDING POCKETS THEREOF, filed Apr. 4, 2003, and U.S. Provisional Application No: 60/552,526 titled CRYSTAL STRUCTURE OF HUMAN PIM-1 KINASE PROTEIN COMPLEXES AND BINDING POCKETS THEREOF, AND USES THEREOF IN DRUG DESIGN, filed Mar. 12, 2004. The disclosures of PCT application No. PCT/US2004/010345 and U.S. provisional application Nos. 60/460,843 and 60/552,526 are hereby incorporated herein by reference.

TECHNICAL FIELD OF INVENTION

The present invention relates to the X-ray analysis of crystalline molecules or molecular complexes of human Pim-1. The present invention also relates to Pim-1-like binding pockets. The present invention provides a computer comprising a data storage medium encoded with the structure coordinates of such binding pockets. This invention also relates to methods of using the structure coordinates to solve the structure of homologous proteins or protein complexes. In addition, this invention relates to methods of using the structure coordinates to screen for and design compounds, including inhibitory compounds, that bind to Pim-1 protein, Pim-1 protein complexes, or homologues thereof. The invention also relates to crystallizable compositions and crystals comprising Pim-1 protein, Pim-1 protein complexes with adenosine, staurosporine or 2-(4-morpholinyl)-8-phenyl-4H-1-benzopyran-4-one and methods to produce these crystals.

BACKGROUND OF THE INVENTION

Pim-1 is an oncogene-encoded serine/threonine kinase primarily expressed in hematopoietic and germ cell lines. The Pim-1 oncogene was originally identified as a preferred site for proviral integration of the slow transforming Maloney murine Leukemia Virus (MuLV)-induced in lymphoblastic T-cells and is associated with multiple cellular functions such as proliferation, survival, differentiation, apoptosis and tumorigenesis (Wang et al., *J. Vet. Sci.* 2: 167-179 (2001)). Direct evidence for the oncogenic potential of the Pim-1 gene comes from the study of transgenic mice in which overexpression of Pim-1 produces a low but spontaneous rate of tumor incidence (Domen et al., *Leukemia* 7 (Suppl. 2):S108-112 (1993)). These mice are highly susceptible to chemical carcinogens, X-ray radiation and MuLV-induced lymphomagnesis. In most cases, this correlated with the upregulation of C- or N-myc genes suggesting synergism between the Pim-1 and myc genes in the development of lymphomas (Breuer et al., *Cancer Res.* 51: 958-963 (1991); van Lohuizen et al., *Cell* 56: 673-682 (1989)). Pim-1 knockout mice did not show any obvious phenotype suggesting in vivo functional redundancy of this highly conserved oncogene (Domen et al., *J. Exp. Med.* 178: 1665-1673 (1993)).

Since the initial report of the cloning of mouse Pim-1 gene (Selten et al., Cell, 46: 603-611 (1986)), Pim-1 has been cloned from human, rat, bovine and zebrafish cDNA libraries (Wang et al., *J. Vet. Sci.* 2: 167-179 (2001)). In humans, the Pim-1 gene is expressed mainly in the developing fetal liver and spleen (Amson et al., *Proc. Natl. Acad. Sci. U.S.A.* 86: 8857-8861 (1989)) and in hematopoietic malignancies (Nagarajan et al., *Proc. Natl. Acad. Sci. U.S.A.* 83: 2556-2560 (1986); Meeker et al., *Oncogene Res.* 1: 87-101 (1987)). Two homologues of the Pim-1 gene, pim-2 (Allen et al., *Oncogene* 15: 1133-1141 (1997); van der Lugt et al., *Embo J.* 14: 2536-2544 (1995)) and pim-3/kid-1 (Feldman et al., *J. Biol. Chem.* 273: 16535-16543 (1998)) have also been identified.

The expression of Pim-1 is tightly regulated and is induced by cytokines, mitogens and hormones: IL-2, IL-3, IL-5, IL-6, IL-7, IL-9, IL-12 and IL-15, granulocyte-macrophage colony-stimulating factor (GM-CSF), erythropoietin, ConA, PMA, interferon-γ and prolactin (Wang et al., *J. Vet. Sci.* 2: 167-179 (2001)). The JAK/STAT pathway may be one of several signaling pathways that mediate Pim-1 expression (Nagata et al., *Leukemia* 11(Suppl 3): 435-438 (1997); Sakai and Kraft, *J. Biol. Chem.* 272: 12350-12358 (1997); O'Farrell et al., *Blood* 87: 3655-3668 (1996); Kumenacker et al., *J. Neuroimmunol.* 113: 249-259 (2001)). However, results from a study by Krishnan and colleagues (Krishnan et al., *Endocrine* 20: 123-130 (2003)) do not support a role for the JAK/STAT signaling pathway, but, instead, implicate AKT activation as a component of prolactin-induced Pim-1 transcription. Also, mitogen-activated protein kinase (MAPK) and phosphatidylinositol-3-kinase (PI-3-kinase) pathways may mediate prolactin-induced Pim-1 expression (Kumenacker et al., supra).

The human Pim-1 gene encodes a 313 amino acid serine-threonine kinase (Padma et al., *Cancer Res.* 51: 2486-2489 (1991); Hoover et al., *J. Biol. Chem.* 266: 14018-14023 (1991)) and is associated with multiple cellular functions such as proliferation, differentiation, apoptosis and tumorigenesis (Wang et al., *J. Vet. Sci.* 2: 167-179 (2001)). Several cellular substrates of Pim-1 have been identified, including the transcription factors cMyb (Winn et al., *Cell Cycle* 2: 258-262 (2003)) and NFATc1 (Rainio et al., *J. Immunol.* 168: 1524-7 (2002)), transcriptional co-activator of cMyb p100 (Leverson et al., *Mol. Cell* 2: 417-425 (1998)), phosphatases Cdc25A (Mochizuki et al., *J. Biol. Chem.* 274: 18659-18666 (1999)), and PTPU2S (Wang et al., *J. Biol. Chem.* 274: 18659-18666 (2001)), Pim-1 associated protein 1 (PAP-1) (Maita et al., *Eur. J. Biochem.* 267: 5168-5178 (2000)), cell-cycle inhibitor p21/WAF1 (Wang et al., *Biochem. Biophys. Acta* 1593: 45-55 (2002)), heterochromatin protein 1 (HP1) (Koike et al., *FEBS Lett.* 467: 17-21 (2000)), TRAF2/SNX6 (Ishibashi et al., *FEBS Lett.* 506: 33-38 (2001)) and nuclear mitotic apparatus (Bhattacharya et al., *Chromosoma* 111: 80-95 (2002)).

The consensus sequence for Pim-1 substrate recognition is Lys/Arg-Lys/Arg-Arg-Lys/Arg-Leu-Ser/Thr-X (SEQ ID NO:1), where X is an amino acid with a small side chain (Friedmann et al., *Arch. Biochem. Biophys.* 298: 594-601 (1992); Palaty et al., *Biochem. Cell. Biol.* 75: 153-162 (1997)). A detailed analysis of the autophosphorylation sites of Xenopus Pim-3 (previously incorrectly identified as Pim-1) has also been reported (Palaty et al., *J. Biol. Chem.* 272: 10514-10521 (1997)).

Due to the lack of structural information about Pim-1, the detailed mechanism of the protein is not known. Without such structural information and knowledge of the mechanism, the progress in designing drugs as specific inhibitors is impeded.

Structural information on the unique features of the active site of Pim-1 would facilitate drug discovery and the treatment of cancer.

SUMMARY OF THE INVENTION

The present invention provides for the first time the crystal structures of Pim-1-adenosine, Pim-1 staurosporine and Pim-1-LY294002 (2-(4-morpholinyl)-8-phenyl-4H-1-benzopyran-4-one) complexes. These structures present a rationale for the structure-based design of small molecule Pim-1 inhibitors as therapeutic agents, thus addressing the need for novel drugs for the treatment of cancer.

The present invention also provides molecules comprising Pim-1 binding pockets, or Pim-1-like binding pockets that have similar three-dimensional shapes. In one embodiment, the molecules are Pim-1 protein complexes or homologues thereof. In another embodiment, the molecules are in crystalline form.

The invention also provides crystallizable compositions and crystal compositions comprising phosphorylated Pim-1 kinase, complexes thereof, or homologues thereof.

The invention provides a computer comprising a machine-readable storage medium, comprising a data storage material encoded with machine-readable data, wherein the data defines the Pim-1 or Pim-1-like binding pocket or protein according to the structure coordinates of FIG. 1A, 2A, or 3A. Such storage medium when read and utilized by a computer programmed with appropriate software can display, on a computer screen or similar viewing device, a three-dimensional graphical representation of such binding pockets. In one embodiment, the structure coordinates of said binding pocket or protein are produced by homology modeling of at least a portion of the coordinates of FIGS. 1A, 2A or 3A.

The invention also provides methods for designing, selecting, evaluating and identifying and/or optimizing compounds which bind to the molecules or molecular complexes or their binding pockets. Such compounds are potential inhibitors of Pim-1 or its homologues.

The invention also provides a method for determining at least a portion of the three-dimensional structure of molecules or molecular complexes which contain at least some structurally similar features to Pim-1, particularly Pim-1 homologues. This is achieved by using at least some of the structure coordinates obtained from the Pim-1 protein.

BRIEF DESCRIPTION OF THE FIGURES

The following abbreviations are used in FIGS. 1A, 2A and 3A:

"Atom type" refers to the element whose coordinates are measured. The first letter in the column defines the element.

"Resid" refers to the amino acid residue in the molecular model.

"X, Y, Z" define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in the molecules.

"Mol" refers to a molecule in the asymmetric unit. Mol A, W and Z are Pim-1 protein, water and adenosine, respectively.

Residue "PSR", "ADE", STO" and "LY2" represent phosphorylated serine, adenosine, staurosporine and LY294002, respectively.

FIG. 1 (1A-1 to 1A-42) lists the atomic structure coordinates in Protein Data Bank (PDB)-like form for phosphorylated human Pim-1 in complex with adenosine (Pim-1-adenosine complex), as derived by X-ray diffraction from a crystal of the complex. The structure model includes human Pim-1 kinase amino acid residues 33-305, excluding residues 80-83, of SEQ ID NO:2). Glu79 was built as Ala because electron density was weak for the side chain of this amino acid residue. Ser261 is phosphorylated.

FIG. 2 (2A-1 to 2A-43) lists the atomic structure coordinates in Protein Data Bank (PDB)-like form for phosphorylated Pim-1 in complex with staurosporine (Pim-1-staurosporine complex), as derived by X-ray diffraction from a crystal of the complex. The structure model includes human Pim-1 kinase amino acid residues 33-305, excluding residues 80-83, of SEQ ID NO:2). Glu79 was built as Ala because electron density was weak for the side chain of this amino acid residue. Ser261 is phosphorylated.

FIG. 3 (3A-1 to 3A-43) lists the atomic structure coordinates in Protein Data Bank (PDB)-like form for phosphorylated Pim-1 in complex with LY294002 (Pim-1-LY294002 complex), as derived by X-ray diffraction from a crystal of the complex. The structure model includes human Pim-1 kinase amino acid residues 33-305, excluding residues 80-83, of SEQ ID NO:2). Glu79 was built as Ala because electron density was weak for the side chain of this amino acid residue. Ser261 is phosphorylated.

Figure 4:
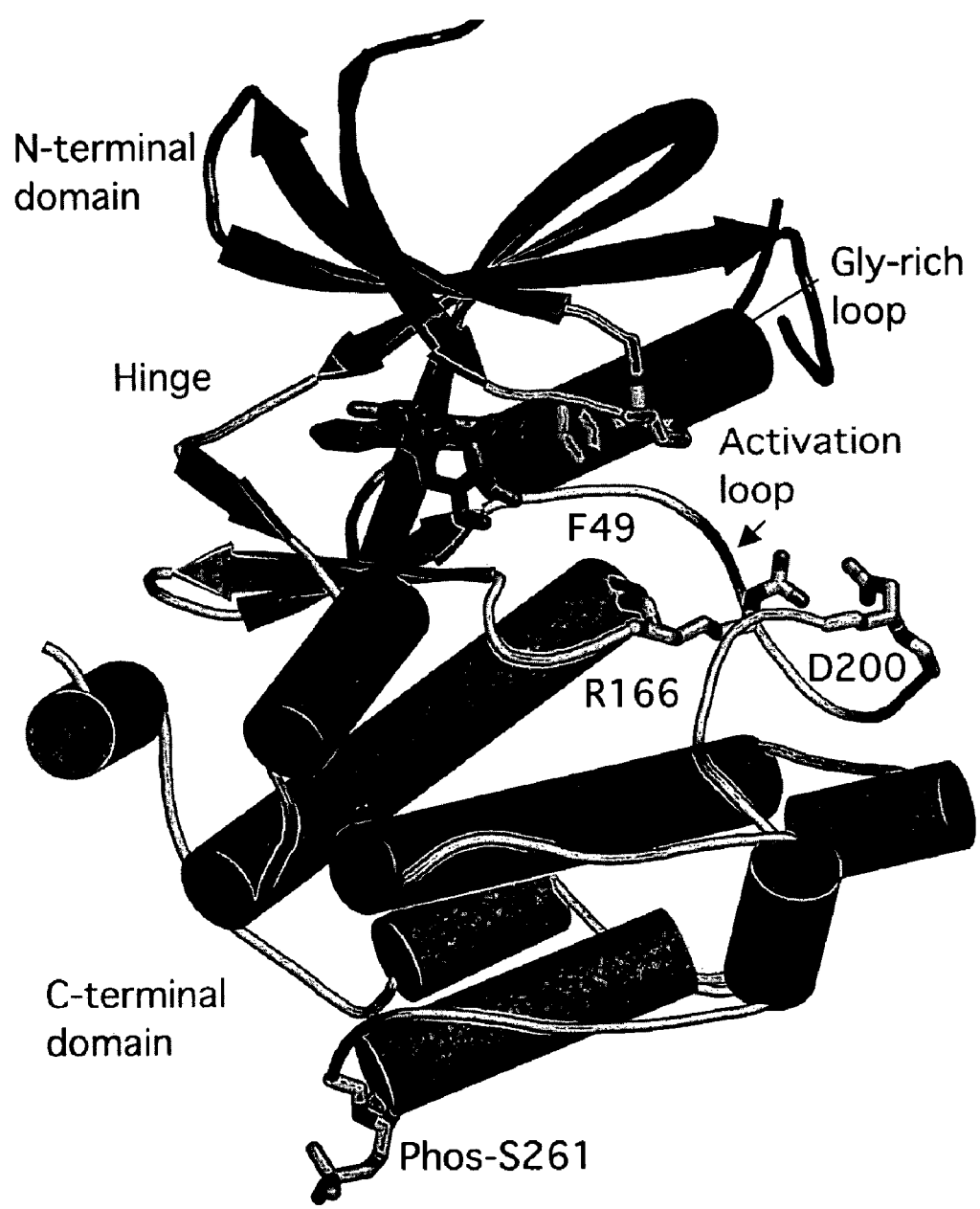

FIG. 4 depicts a ribbon diagram of the overall fold of the Pim-1-staurosporine complex. The structure is shown with β-strands as arrows and the α-helices as cylinders. The N-terminal domain is in dark grey with an arrow pointing to the glycine rich loop. The hinge connecting the two domains is labeled. The C-terminal domain is shown in light grey with an arrow indicating the activation loop. Staurosporine (represented in stick format) is shown in the active site, bound between Phe49 (glycine rich loop) and the hinge region. The salt bridge stabilizing the conformation of the activation loop is formed by residues Asp200 and Arg166. The site of phosphorylation, Ser261 is shown. All structural figures were prepared with Pymol (DeLano, DeLano Scientific, San Carlos, Calif., USA (2002)).

FIGS. 5A-5D depict Pim-1, PKA, and PI3K bound to staurosporine, adenosine and ATP. The Pim-1, PKA and PI3K structures were aligned to optimize the superposition of residues adjacent to the hinge regions. In each panel, the Pim-1 structure, carbon, nitrogen, oxygen and other atoms are shown in different shades of grey and amino acid residues are labeled in black type. PKA and PI3K complex structures are drawn in solid color and amino acid residues are labeled in light grey type. Hydrogen bonds are depicted as dotted lines.

FIG. 5A depicts the superposition of PKA-staurosporine complex (Protein Data Bank (PDB) accession number 1STO) and the Pim-1-staurosporine complex. Pim-1 amino acid residues are labeled.

FIG. 5B depicts the superposition of Pim-1-staurosporine and PI3K-staurosporine complexes (PDB accession number 1E8Z). The view is rotated approximately 90° from FIG. 4. In this orientation, the glycine-rich loop lies above and in the plane of the page. PI3K amino acid residues are labeled.

FIG. 5C depicts the same overlay as panel B seen from the side to illustrate the relative tilt in the staurosporine ring systems. Pim-1 amino acid residues are labeled.

FIG. 5D depicts the superposition of Pim-1-adenosine and PKA-adenosine complexes (PDB accession number 1FMO).

The view is rotated approximately 90° from FIG. 4. In this orientation, the glycine-rich loop lies above and in the plane of the page. PKA amino acid residues are labeled.

FIG. 5E depicts the superposition of Pim-1-adenosine and PI3K-ATP complexes (PDB accession number 1E8X). The view is rotated approximately 90° from FIG. 4. In this orientation, the glycine-rich loop lies above and in the plane of the page.

FIG. 5F shows a sequence alignment of hinge regions of Pim-1 (amino acid residues 116-132 of SEQ ID NO: 2), amino acid residues 116-131 of PKA (SEQ ID NO: 3), amino acid residues 76-90 of CDK-2 (SEQ ID NO: 4) and amino acid residues 875-891 of PI3K (SEQ ID NO: 5). Residues which accept and donate hydrogen bonds to the adenine ring of ATP are enclosed in boxes.

FIG. 6A depicts the binding site of the Pim-1-LY294002 complex. As drawn, the glycine rich loop would lie above and in the plane of the page. The Fo-Fc electron density map is drawn around the compound at 2.5 sigma level. A water molecule is drawn as a sphere with hydrogen bonds to the chromone oxygen and the Asp186 amide.

FIG. 6B depicts a similar orientation to that in FIG. 6A of the binding site of the PI3K-LY294002 complex (PDB accession number 1E7V).

Figure 7:
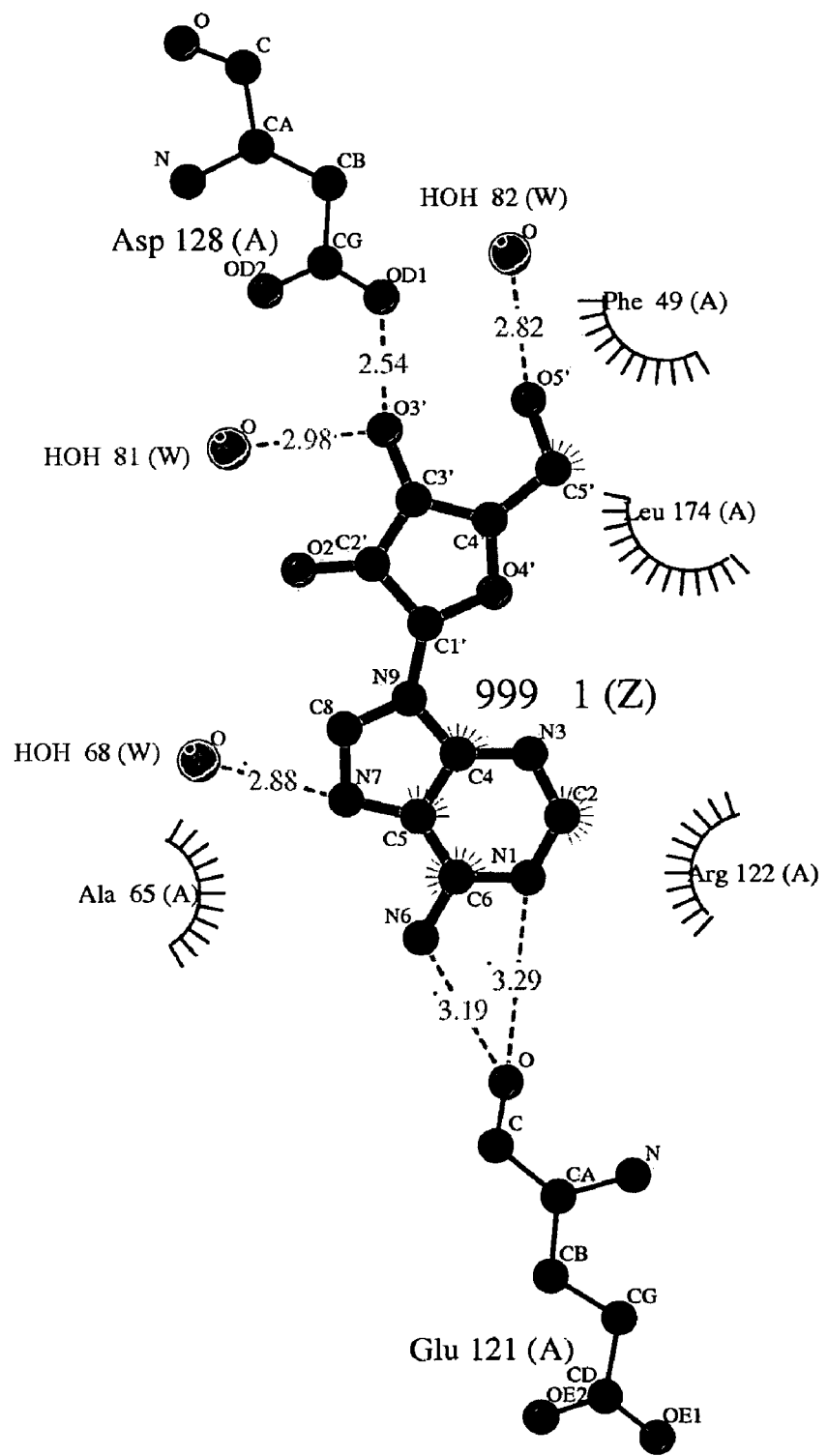
Figure 8:
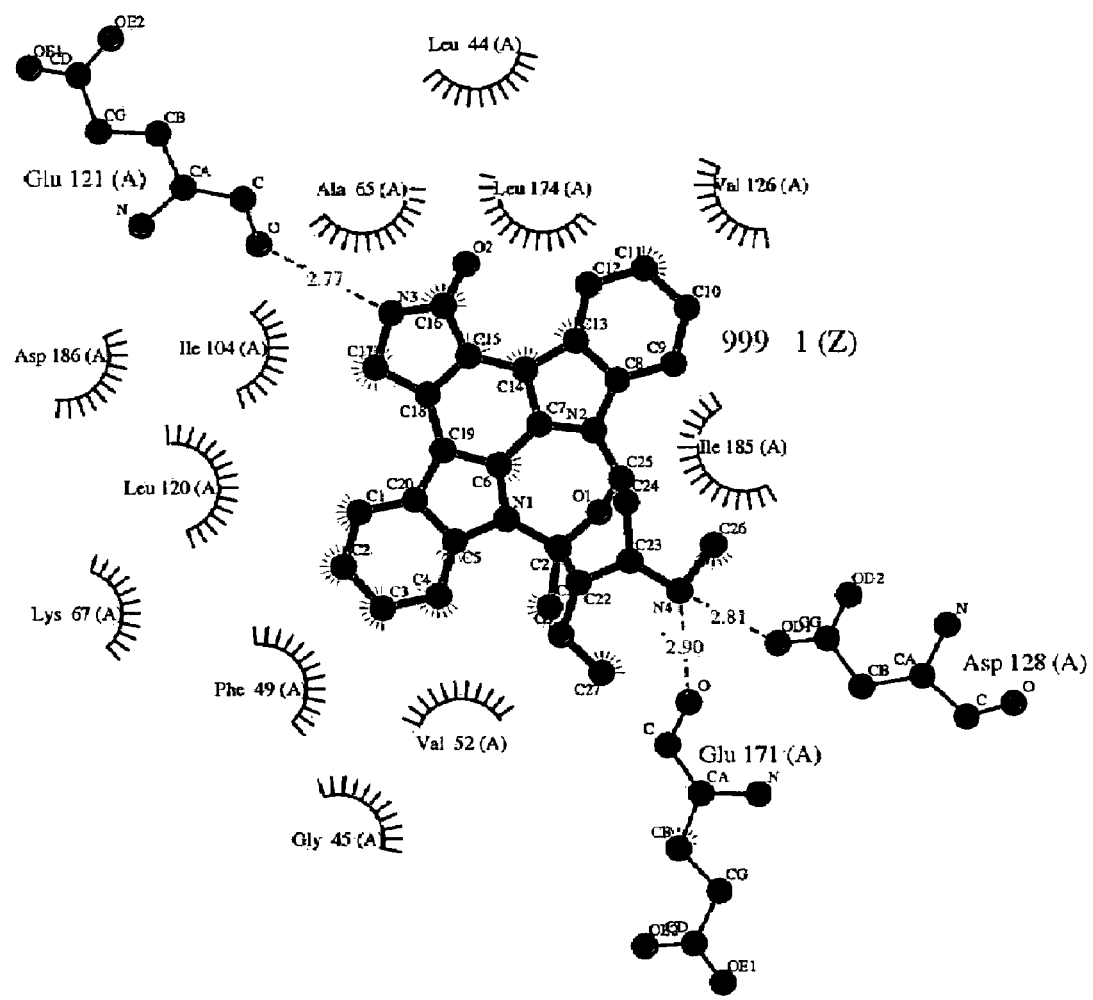
Figure 9:
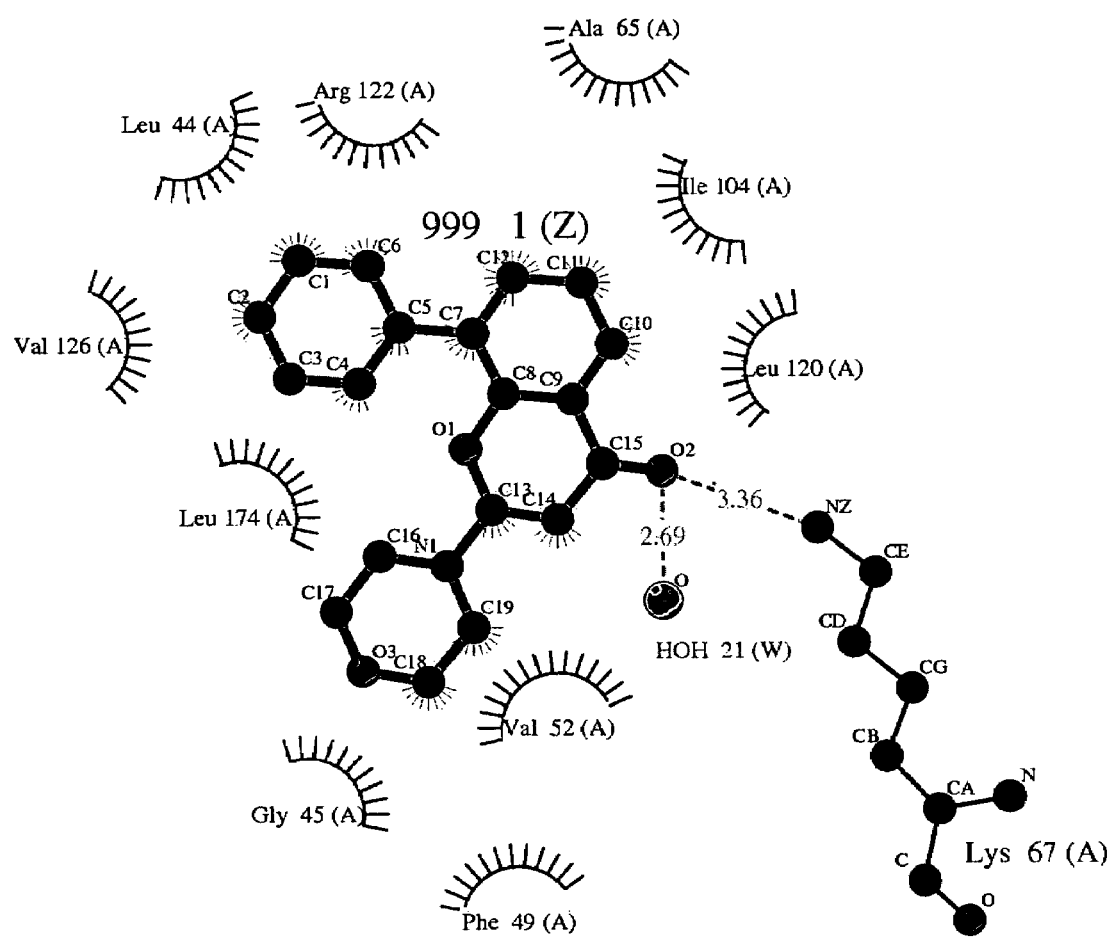

For FIGS. 7-9: thick lines connecting atoms (represented as spheres) depict ligand bonds. Thin lines connecting atoms depict non-ligand bonds. Hydrogen bonds are represented by light grey dashed lines. Non-ligand residues involved in hydrophobic contact(s) are depicted by semicircles with lines radiated outwards in the direction of contact. Ligand atoms that are involved in hydrophobic contact(s) are depicted as solid spheres with lines radiating outward in the direction of contact.

FIG. 7 shows a detailed representation of the active site of Pim-1 with adenosine. Hydrogen bonds are shown as dashed lines with the bond length indicated. Atoms and amino acid residues are identified with labels. Molecules labeled A, W and Z are Pim-1 protein, water and adenosine, respectively.

FIG. 8 shows a detailed representation of the active site of Pim-1 with staurosporine. Hydrogen bonds are shown as dashed lines with the bond length indicated. Atoms and amino acid residues are identified with labels. Molecules labeled A, W and Z are Pim-1 protein, water and staurosporine, respectively.

FIG. 9 shows a detailed representation of the active site of Pim-1 with LY294002. Hydrogen bonds are shown as dashed lines with the bond length indicated. Atoms and amino acid residues are identified with labels. Molecules labeled A, W and Z are Pim-1 protein, water and LY294002, respectively.

Figure 10:
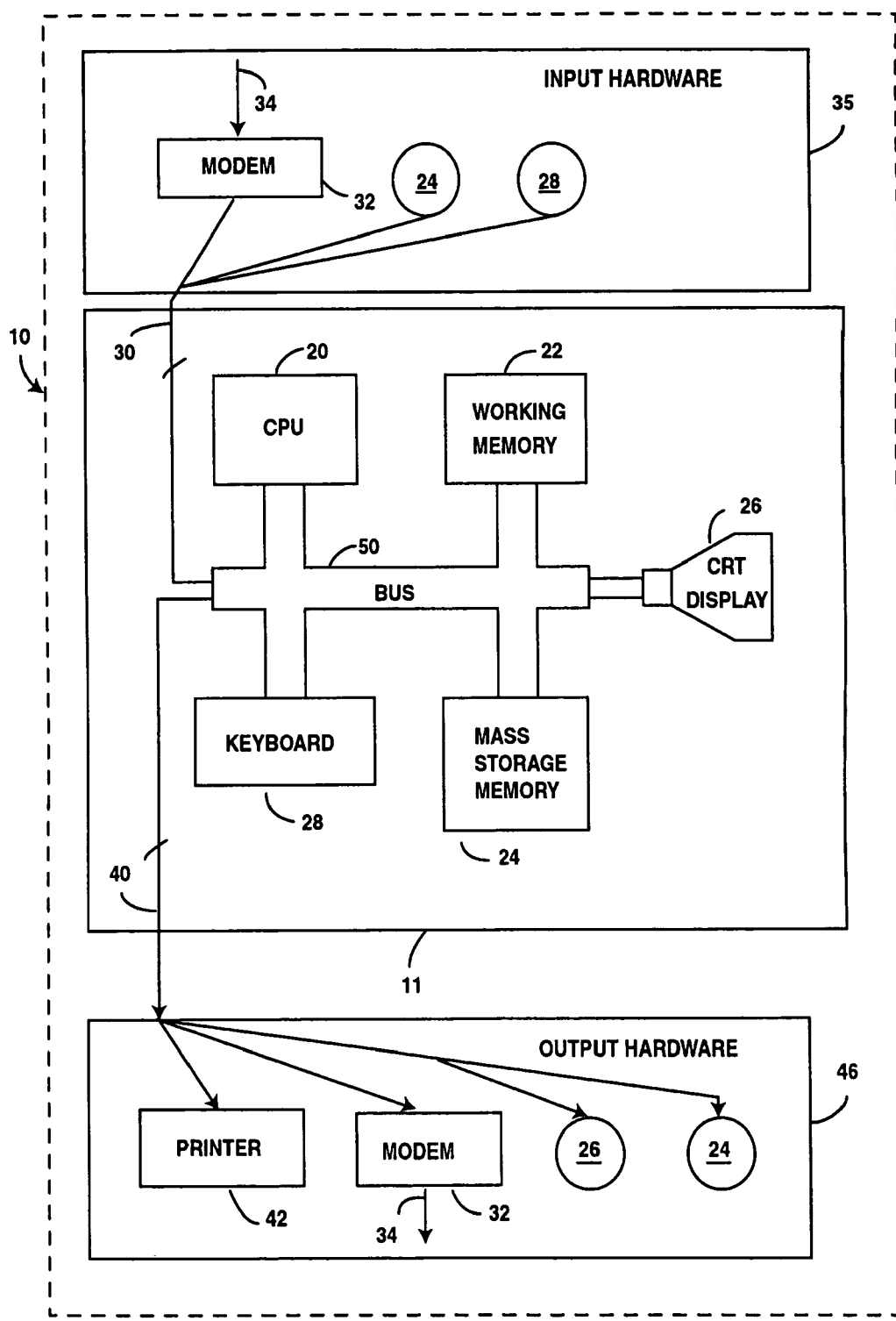
Figure 11:
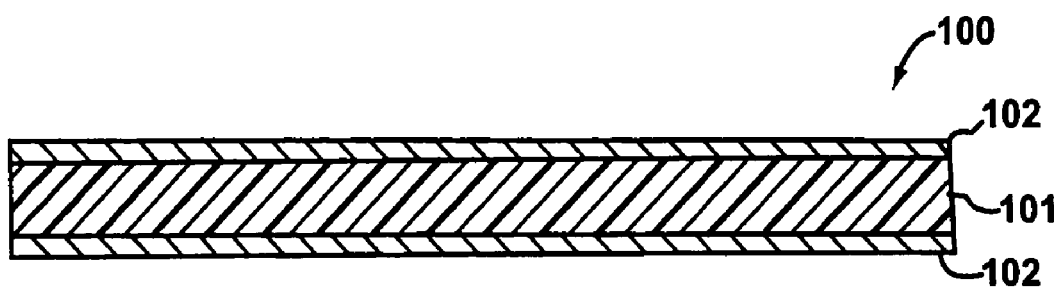
Figure 12:
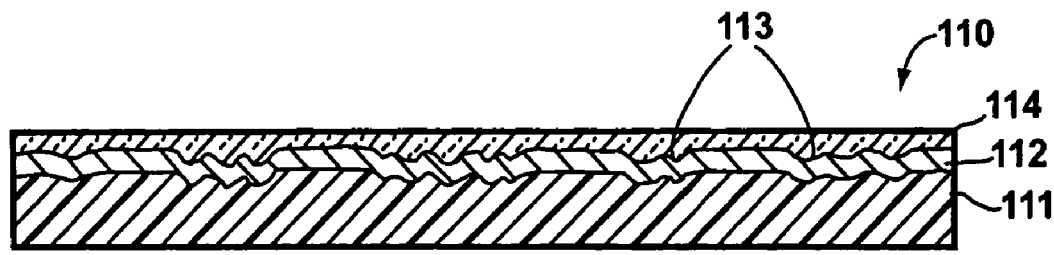

FIG. 10 shows a diagram of a system used to carry out the instructions encoded by the storage medium of FIGS. 11 and 12.

FIG. 11 shows a cross section of a magnetic storage medium.

FIG. 12 shows a cross section of a optically-readable data storage medium.

DESCRIPTION OF THE INVENTION

In order that the invention described herein may be more fully understood, the following detailed description is set forth.

Throughout the specification, the word "comprise", or variations such as "comprises" or "comprising" will be understood to imply the inclusion of a stated integer or groups of integers but not exclusion of any other integer or groups of integers.

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

Other abbreviations that are used throughout the application include: ADE (for adenosine), STO (for staurosporine), LY2 (for LY294002), PSR (for phosphorylation of Ser261) and CME (for 2-mercaptoethanol modification of Cys161).

As used herein, the following definitions shall apply unless otherwise indicated.

The term "about" when used in the context of root mean square deviation (RMSD) values takes into consideration the standard error of the RMSD value, which is ±0.1 Å.

The term "associating with" refers to a condition of proximity between a chemical entity or compound, or portions thereof, and a binding pocket or binding site on a protein. The association may be non-covalent—wherein the juxtaposition is energetically favored by hydrogen bonding, hydrophobic, van der Waals or electrostatic interactions—or it may be covalent.

The term "ATP analogue" refers to a compound derived from adenosine-5'-triphosphate (ATP). The compound can be adenosine, AMP, ADP, or a non-hydrolyzable analogue, such as, but not limited to AMP-PNP. The analogue may be in complex with magnesium or manganese ions.

The term "binding pocket" refers to a region of a molecule or molecular complex, that, as a result of its shape, favorably associates with another chemical entity. The term "pocket" includes, but is not limited to, a cleft, channel or site. Pim-1, Pim-1-like molecules or homologues thereof may have binding pockets which include, but are not limited to, peptide or substrate binding sites, and ATP-binding sites. The shape of a binding pocket may be largely pre-formed before binding of a chemical entity, may be formed simultaneously with binding of a chemical entity, or may be formed by the binding of another chemical entity to a different binding pocket of the molecule, which in turn induces a change in shape of the binding pocket.

The term "catalytic active site" or "active site" refers to the portion of the protein kinase to which nucleotide substrates bind. For example, the catalytic active site of Pim-1 is at the interface between the N-terminal and C-terminal domains.

The term "catalytic domain", "kinase catalytic domain", "protein kinase catalytic domain" or "catalytic kinase domain" refers to the kinase domain of a kinase protein. The kinase domain includes the catalytic active site.

The term "chemical entity" refers to chemical compounds, complexes of at least two chemical compounds, and fragments of such compounds or complexes. The chemical entity can be, for example, a ligand, substrate, nucleotide triphosphate, nucleotide diphosphate, phosphate, nucleotide, agonist, antagonist, inhibitor, antibody, peptide, protein or drug. In one embodiment, the chemical entity is an inhibitor or substrate for the active site.

The term "conservative substitutions" refers to residues that are physically or functionally similar to the corresponding reference residues. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure* 5: 345-352 (1978 & Supp.), which is incorporated herein by reference. Examples of conservative substitutions are substitutions including but not limited to the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

The term "contact score" refers to a measure of shape complementarity between the chemical entity and binding pocket, which is correlated with an RMSD value obtained from a least square superimposition between all or part of the atoms of the chemical entity and all or part of the atoms of the ligand bound (for example, adenosine, staurosporine or LY294002) in the binding pocket according to FIG. 1A, 2A or 3A. The docking process may be facilitated by the contact score or RMSD values. For example, if the chemical entity moves to an orientation with high RMSD, the system will resist the motion. A set of orientations of a chemical entity can be ranked by contact score. A lower RMSD value will give a higher contact score. See Meng et al. *J. Comp. Chem.* 4: 505-524 (1992).

The term "correspond to" or "corresponding amino acid" when used in the context of amino acid residues that correspond to Pim-1 amino acid residues refers to particular amino acid residues or analogues thereof in a Pim-1 protein or homologue thereof that corresponds to amino acid residues in the human Pim-1 protein. The corresponding amino acid may be an identical, mutated, chemically modified, conserved, conservatively substituted, functionally equivalent or homologous amino acid residue when compared to the Pim-1 amino acid residue to which it corresponds. For example, the following are examples of Pim-1 amino acid residues that correspond to PI3K amino acid residues: P125:D884 and V126:A885 (the identity of the Pim-1 residue is listed first; its position is indicated using Pim-1 sequence numbering; and the identity of PI3K residue is given at the end).

Methods for identifying a corresponding amino acid are known in the art and are based upon sequence, structural alignment, its functional position, or a combination thereof as compared to the Pim-1 kinase. For example, corresponding amino acids may be identified by superimposing the backbone atoms of the amino acids in Pim-1 and the protein using well known software applications, such as QUANTA (Accelrys, San Diego, Calif. ©2001, 2002). The corresponding amino acids may also be identified using sequence alignment programs such as the "bestfit" program or CLUSTAL W Alignment Tool (Higgins et al., *Methods Enzymol.* 266: 383-402 (1996)).

The term "crystallization solution" refers to a solution that promotes crystallization comprising at least one agent, including a buffer, one or more salts, a precipitating agent, one or more detergents, sugars or organic compounds, lanthanide ions, a poly-ionic compound and/or a stabilizer.

The term "docking" refers to orienting, rotating, translating a chemical entity in the binding pocket, domain, molecule or molecular complex or portion thereof based on distance geometry or energy. Docking may be performed by distance geometry methods that find sets of atoms of a chemical entity that match sets of sphere centers of the binding pocket, domain, molecule or molecular complex or portion thereof.

See Meng et al. *J. Comp. Chem.* 4: 505-524 (1992). Sphere centers are generated by providing an extra radius of given length from the atoms (excluding hydrogen atoms) in the binding pocket, domain, molecule or molecular complex or portion thereof. Real-time interaction energy calculations, energy minimizations or rigid-body minimizations (Gschwend et al., *J. Mol. Recognition* 9:175-186 (1996)) can be performed while orienting the chemical entity to facilitate docking. For example, interactive docking experiments can be designed to follow the path of least resistance. If the user in an interactive docking experiment makes a move to increase the energy, the system will resist that move. However, if that user makes a move to decrease energy, the system will favor that move by increased responsiveness. (Cohen et al., *J. Med. Chem.* 33:889-894 (1990)). Docking can also be performed by combining a Monte Carlo search technique with rapid energy evaluation using molecular affinity potentials. See Goodsell and Olson, *Proteins: Structure, Function and Genetics* 8:195-202 (1990). Software programs that carry out docking functions include but are not limited to MATCHMOL (Cory et al., *J. Mol. Graphics* 2: 39 (1984); MOLFIT (Redington, *Comput. Chem.* 16: 217 (1992)) and DOCK (Meng et al., supra).

The term "generating a three-dimensional structure" or "generating a three-dimensional representation" refers to converting the lists of structure coordinates into structural models or graphical representation in three-dimensional space. This can be achieved through commercially or publicly available software. A model of a three-dimensional structure of a molecule or molecular complex can thus be constructed on a computer screen by a computer that is given the structure coordinates and that comprises the correct software. The three-dimensional structure may be displayed or used to perform computer modeling or fitting operations. In addition, the structure coordinates themselves, without the displayed model, may be used to perform computer-based modeling and fitting operations.

The term "homologue of Pim-1" or "Pim-1 homologue" refers to a full-length Pim protein other than full-length human Pim-1, or a full-length Pim protein with mutations, conservative substitutions, additions, deletions or a combination thereof, which retains Pim kinase activity. In one embodiment, the additions or deletions are at the N- or C-terminal of the protein, preferably up to 40, 30, 20 or 10 amino acids. In one embodiment, the homologue is at least 95%, 96%, 97%, 98% or 99% identical in sequence to the full-length Pim-1 protein, and has conservative substitutions as compared to the Pim-1 protein. In one embodiment, the homologue is at least 95%, 96%, 97%, 98% or 99% identical in sequence to amino acid residues 33-305 of SEQ ID NO:2, and has conservative substitutions thereof. Examples of homologues include but are not limited to the following: other human Pim proteins such as human Pim-2, Pim-3 or isoforms thereof, or the foregoing or human Pim-1 with mutations, conservative substitutions, additions, deletions or a combination thereof or Pim-1, Pim-2, Pim-3 from another species, with mutations, conservative substitutions, additions, deletions or a combination thereof. Such animal species include, but are not limited to, mouse, rat, a primate such as monkey or other primates.

The term "homology model" refers to a structural model derived from known three-dimensional structure(s). Generation of the homology model, termed "homology modeling", can include sequence alignment, residue replacement, residue conformation adjustment through energy minimization, or a combination thereof The term "interaction energy" refers to the energy determined for the interaction of a chemical entity and a binding pocket, domain, molecule or molecular complex or portion thereof. Interactions include but are not limited to one or more of covalent interactions, non-covalent interactions such as hydrogen bond, electrostatic, hydrophobic, aromatic, van der Waals interactions, and non-complementary electrostatic interactions such as repulsive charge-charge, dipole-dipole and charge-dipole interactions. As interaction energies are measured in negative values, the lower the value the more favorable the interaction.

The term "motif" refers to a group of amino acid residues in the Pim-1 kinase or homologue that defines a structural compartment or carries out a function in the protein, for example, catalysis, structural stabilization or phosphorylation. The motif may be conserved in sequence, structure and function. The motif can be contiguous in primary sequence or three-dimensional space. Examples of a motif include, but are not limited to, a binding pocket, activation loop, the glycine-rich loop, and the DFG loop (See, Xie et al., *Structure* 6: 983-991 (1998)).

The term "part of a binding pocket" refers to less than all of the amino acid residues that define the binding pocket. The structure coordinates of amino acid residues that constitute part of a binding pocket may be specific for defining the chemical environment of the binding pocket, or useful in designing fragments of an inhibitor that may interact with those residues. For example, the portion of amino acid residues may be key residues that play a role in ligand binding, or may be residues that are spatially related and define a three-dimensional compartment of the binding pocket. The amino acid residues may be contiguous or non-contiguous in primary sequence. In one embodiment, part of the binding pocket has at least two amino acid residues, preferably at least three, six, eight, ten, fourteen or fifteen amino acid residues.

The term "part of a Pim-1 protein" or "part of a Pim-1 homologue" refers to less than all of the amino acid residues of a Pim-1 protein or homologue. In one embodiment, part of the Pim-1 protein or homologue defines the binding pockets, domains, sub-domains, and motifs of the protein or homologue. The structure coordinates of amino acid residues that constitute part of a Pim-1 protein or Pim-1 homologue may be specific for defining the chemical environment of the protein, or useful in designing fragments of an inhibitor that interact with those residues. The portion of amino acid residues may also be residues that are spatially related and define a three-dimensional compartment of the binding pocket, motif or domain. The amino acid residues may be contiguous or non-contiguous in primary sequence. For example, the portion of amino acid residues may be key residues that play a role in ligand or substrate binding, peptide binding, antibody binding, catalysis, structural stabilization or degradation.

The term "Pim" refers to the kinases from the Pim kinase family. Examples of this family of kinases include but are not limited to Pim-1, Pim-2, Pim-3.

The term "Pim-1 ATP-binding pocket" refers to a binding pocket of a molecule or molecular complex defined by the structure coordinates of a certain set of amino acid residues present in the Pim-1 structure, as described below. In general, the ligand for the ATP-binding pocket is a nucleotide such as ATP. This binding pocket is in the catalytic active site of the catalytic domain. In the protein kinase family, the ATP-binding pocket is generally located at the interface of the N-terminal and C-terminal domains, and is bordered by the glycine rich loop and the hinge (See, Xie et al., *Structure* 6: 983-991 (1998), incorporated herein by reference).

The term "Pim-1 inhibitor-binding pocket" refers to that portion of the Pim-1 enzyme active site to which the inhibitor binds. The inhibitor-binding pocket is defined by the structure coordinates of a certain set of amino acid residues present in the Pim-1-inhibitor structure, as described below.

The term "Pim-1-like" refers to all or a portion of a molecule or molecular complex that has a commonality of shape to all or a portion of the Pim-1 protein. For example, in the Pim-1-like inhibitor-binding pocket, the commonality of shape is defined by a root mean square deviation of the structure coordinates of the backbone atoms between the amino acids in the Pim-1-like inhibitor-binding pocket and the Pim-1 amino acids in the Pim-1 inhibitor-binding pocket as set forth in FIGS. 1A, 2A and 3A. Compared to the amino acids of the Pim-1 inhibitor-binding pocket, the corresponding amino acid residues in the Pim-1-like binding pocket may or may not be identical. Depending on the set of Pim-1 amino acid residues that define the Pim-1 inhibitor-binding pocket, one skilled in the art would be able to locate the corresponding amino acid residues that define a Pim-1-like binding pocket in a protein based on sequence or structural homology.

The term "Pim-1 protein" or "full-length Pim-1 protein" refers to human Pim-1 protein (amino acid residues 1 to 313; SwissProt entry P11309; SEQ ID NO:2).

The term "Pim-1 protein complex" or "Pim-1 homologue complex" refers to a molecular complex formed by associating the Pim-1 protein or Pim-1 homologue with a chemical entity, for example, a ligand, a substrate, nucleotide triphosphate, nucleotide diphosphate, phosphate, an agonist or antagonist, inhibitor, antibody, drug or compound.

The term "protein complex", "complex" or "molecular complex" refers to a protein or section of a protein associated with a chemical entity.

The term "quantified association" refers to calculations of distance geometry and energy. Energy can include but is not limited to interaction energy, free energy and deformation energy. See Cohen, supra.

The term "root mean square deviation" or "RMSD" means the square root of the arithmetic mean of the squares of the deviations from the mean. It is a way to express the deviation or variation from a trend or object. For purposes of the invention, the "root mean square deviation" defines the variation in the backbone atoms of Pim-1, a binding pocket, a motif, a domain, or portion thereof, as defined by the structure coordinates of Pim-1 described herein. It would be apparent to the skilled worker that the calculation of RMSD involves a standard error of ±0.1 Å.

The term "soaked" refers to a process in which the crystal is transferred to a solution containing the compound of interest.

The term "structure coordinates" refers to Cartesian coordinates derived from mathematical equations related to the patterns obtained on diffraction of a monochromatic beam of X-rays by the atoms (scattering centers) of a protein or protein complex in crystal form. The diffraction data are used to calculate an electron density map of the repeating unit of the crystal. The electron density maps are then used to establish the positions of the individual atoms of the molecule or molecular complex.

The term "sub-domain" refers to a portion of the domain.

The term "substantially all of a Pim-1 binding pocket" or "substantially all of a Pim-1 protein" refers to all or almost all of the amino acids in the Pim-1 binding pocket or protein. For example, substantially all of a Pim-1 binding pocket can be 100%, 95%, 90%, 80%, or 70% of the residues defining the Pim-1 binding pocket or protein.

The term "substrate binding pocket" refers to the binding pocket for a substrate of Pim-1 or homologue thereof. A substrate is generally defined as the molecule upon which an enzyme performs catalysis. Natural substrates, synthetic substrates or peptides, or mimics of a natural substrates of Pim-1 or homologue thereof may associate with the substrate binding pocket.

The term "sufficiently homologous to Pim-1" refers to a protein that has a sequence identity of at least 25% compared to Pim-1 protein. In other embodiments, the sequence identity is at least 40%. In other embodiments, the sequence identity is at least 50%, 60%, 70%, 80%, 90%, 95%, 96%, 97%, 98% or 99%.

The term "three-dimensional structural information" refers to information obtained from the structure coordinates. Structural information generated can include the three-dimensional structure or graphical representation of the structure. Structural information can also be generated when subtracting distances between atoms in the structure coordinates, calculating chemical energies for a Pim-1 molecule or molecular complex or homologues thereof, calculating or minimizing energies for an association of a Pim-1 molecule or molecular complex or homologues thereof to a chemical entity.

Crystallizable Compositions and Crystals of Pim-1 Protein and Complexes Thereof

According to one embodiment, the invention provides a crystal or crystallizable composition comprising Pim-1 protein, Pim-1 protein complex or homologues thereof. In one embodiment, the Pim-1 protein or homologue is phosphorylated. In another embodiment, the chemical entity is an ATP analogue, nucleotide triphosphate, nucleotide diphosphate, phosphate, adenosine, stauropsorine, LY294002, or active site inhibitor. In one embodiment the chemical entity is adenosine, staurosporine or LY294002.

The Pim-1 protein homologue in the crystal may be a truncated Pim-1 protein comprising amino acid residues 33 to 305 of SEQ ID NO:2, or full length or truncated Pim-1 protein with conservative substitutions.

```
        10          20          30  SEQ ID NO:2
   MLLSKINSLA  HLRAAPCNDL  HATKLAPGKE  (SwissProt
                                       entry P11309)
        40          50          60
   KEPLESQYQV  GPLLGSGGFG  SVYSGIRVSD 70          80          90
   NLPVAIKHVE  KDRISDWGEL  PNGTRVPMEV 100         110         120
   VLLKKVSSGF  SGVIRLLDWF  ERPDSFVLIL 130         140         150
   ERPEPVQDLF  DFITERGALQ  EELARSFFWQ 160         170         180
   VLEAVRHCHN  CGVLHRDIKD  ENILIDLNRG 190         200         210
   ELKLIDFGSG  ALLKDTVYTD  FDGTRVYSPP 220         230         240
   EWIRYHRYHG  RSAAVWSLGI  LLYDMVCGDI 250         260         270
   PFEHDEEIIR  GQVFFRQRVS  SECQHLIRWC 280         290         300
   LALRPSDRPT  FEEIQNHPWM  QDVLLPQETA

310
   EIHLHSLSPG              PSK
```

The crystallizable compositions may further comprise a crystallization solution of 0.025 to 1.5 M $(NH_4)_2HPO_4$, 0-200 mM citrate buffer at pH 4.0 and 7.5, and 0-300 mM NaCl. In one embodiment, the crystallizable compositions comprise a crystallization solution of equal volumes of Pim-1 protein (12 mg/ml protein in 20 mM HEPES at pH 8, 100 mM NaCl and 5 mM DTT) and a solution of 1.0 M $(NH_4)_2HPO_4$, 100 mM citrate buffer at pH 5.5, and 100 mM NaCl.

According to one embodiment, the invention provides for a crystal with unit cell dimensions of a=98.27 Å b=98.27 Å, c=80.39 Å, $\alpha=\beta=90$, $\gamma=120°$ and space group $P6_5$. Preferably, the crystal comprises the Pim-1-adenosine complex.

In another embodiment, the invention provides for a crystal with unit cell dimensions a=97.73 Å b=97.73 ÅA, c=80.51 Å, $\alpha=\beta=90$, $\gamma=120$ and space group $P6_5$. Preferably, the crystal comprises the Pim-1-staurosporine complex.

According to another embodiment, the invention provides for a crystal with unit cell dimensions a=97.65 Å b=97.65 Å, c=80.72 Å, $\alpha=\beta=90$, $\gamma=120°$ and space group $P6_5$. Preferably, the crystal comprises the Pim-1-LY294002 complex.

It will be readily apparent to those skilled in the art that the unit cells of the crystal compositions may deviate up to ±1-2 Å from the above cell dimensions depending on the deviation in the unit cell calculations or conformational change in the protein.

The Pim-1 protein or homologue thereof may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products. In one embodiment, the protein is overexpressed from an *E. coli* system.

Methods of Obtaining Crystals of Pim-1 Protein, Complexes Thereof or Homologues Thereof The invention also relates to a method of obtaining a crystal of Pim-1 protein or Pim-1 homologue thereof, comprising the steps of:
  a) producing and purifying a Pim-1 protein or homologue thereof;
  b) combining a crystallizable solution with said Pim-1 protein or homologue thereof to produce a crystallizable composition; and
  c) subjecting said crystallizable composition to conditions which promote crystallization and obtaining said crystals.

The invention also relates to a method of obtaining a crystal of a Pim-1 protein complex or Pim-1 homologue complex, further comprising the step of:
  d) soaking said crystal in a buffer solution comprising a chemical entity.

The invention also relates to a method of obtaining a crystal of a Pim-1 protein complex or Pim-1 homologue complex, comprising the steps of:
  a) producing and purifying a Pim-1 protein or homologue thereof;
  b) combining a crystallizable solution with said Pim-1 protein or homologue thereof in the presence of a chemical entity to produce a crystallizable composition; and c) subjecting said crystallizable composition to conditions which promote crystallization and obtaining said crystals.

In one embodiment, the chemical entity is selected from the group consisting of an ATP analogue, nucleotide triphosphate, nucleotide diphosphate, phosphate, adenosine, staurosporine, substrate inhibitor, or active site inhibitor. In another embodiment, the crystallization solution is as described previously. In another embodiment, the crystallizable composition is treated with micro-crystals of Pim-1 or Pim-1 complexes or homologues thereof.

In certain embodiments, the method of making crystals of Pim-1 protein complexes or homologues thereof includes the use of a device for promoting crystallizations. Devices for promoting crystallization can include but are not limited to the hanging-drop, sitting-drop, dialysis or microtube batch devices. (U.S. Pat. Nos. 4,886,646, 5,096,676, 5,130,105, 5,221,410 and 5,400,741; Pav et al., *Proteins: Structure, Function, and Genetics* 20: 98-102 (1994), incorporated herein by reference). The hanging-drop, sitting-drop, and some adaptations of the microbatch methods (D'Arcy et al., *J. Cryst. Growth* 168: 175-180 (1996) and Chayen, *J. Appl. Cryst.* 30: 198-202 (1997)) produce crystals by vapor diffusion. The hanging drop and sitting drop containing the crystallizable composition is equilibrated in a reservoir containing a higher or lower concentration of the precipitant. As the drop approaches equilibrium with the reservoir, the saturation of protein in the solution leads to the formation of crystals.

Microseeding or seeding may be used to increase the size and quality of crystals. In this instance, micro-crystals are crushed to yield a stock seed solution. The stock seed solution is diluted in series. Using a needle, glass rod, micro-pipet, micro-loop or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

It would be readily apparent to one of skill in the art to vary the crystallization conditions disclosed above to identify other crystallization conditions that would produce crystals of Pim-1 homologue, Pim-1 homologue complex, Pim-1 protein or other Pim-1 protein complexes. Such variations include, but are not limited to, adjusting pH, protein concentration and/or crystallization temperature, changing the identity or concentration of salt and/or precipitant used, using a different method of crystallization, or introducing additives such as detergents (e.g., TWEEN 20 (monolaurate), LDAO, Brij 30 (4 lauryl ether)), sugars (e.g., glucose, maltose), organic compounds (e.g., dioxane, dimethylformamide), lanthanide ions or polyionic compounds that aid in crystallization. High throughput crystallization assays may also be used to assist in finding or optimizing the crystallization condition.

Binding Pockets of Pim-1 Protein or Homologues Thereof

As disclosed herein, applicants have provided the three-dimensional X-ray structures of Pim-1-adenosine, Pim-1-staurosporine and Pim-1-LY294002 complexes. The atomic coordinates for the structures of Pim-1-adenosine, Pim-1-staurosporine and Pim-1-LY294002 complexes are presented in FIGS. 1A, 2A and 3A, respectively.

To use the structure coordinates generated for the Pim-1 complexes or one of their binding pockets or homologues thereof, it may be necessary to convert the structure coordinates, or portions thereof, into a three-dimensional shape (i.e., a three-dimensional representation of these complexes or binding pockets). This is achieved through the use of a computer and commercially available software that is capable of generating the three-dimensional representations or structures of molecules or molecular complexes, or portions thereof, from a set of structural coordinates. These three-dimensional representations may be displayed on a computer screen.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or part of the binding pocket. An understanding of such associations will help lead to the design of drugs having more favorable associations with their target receptor or enzyme, and thus, improved biological effects. Therefore, this information is valuable in designing potential inhibitors of the binding pockets of biologically important targets. The binding pockets of this invention will be important for drug design.

The conformations of Pim-1 and other proteins at a particular amino acid site, along the polypeptide backbone, can be compared using well-known procedures for performing sequence alignments of the amino acids. Such sequence alignments allow for the equivalent sites on these proteins to be compared. Such methods for performing sequence alignment include, but are not limited to, the "bestfit" program and CLUSTAL W Alignment Tool, Higgins et al., supra.

Figure 5:
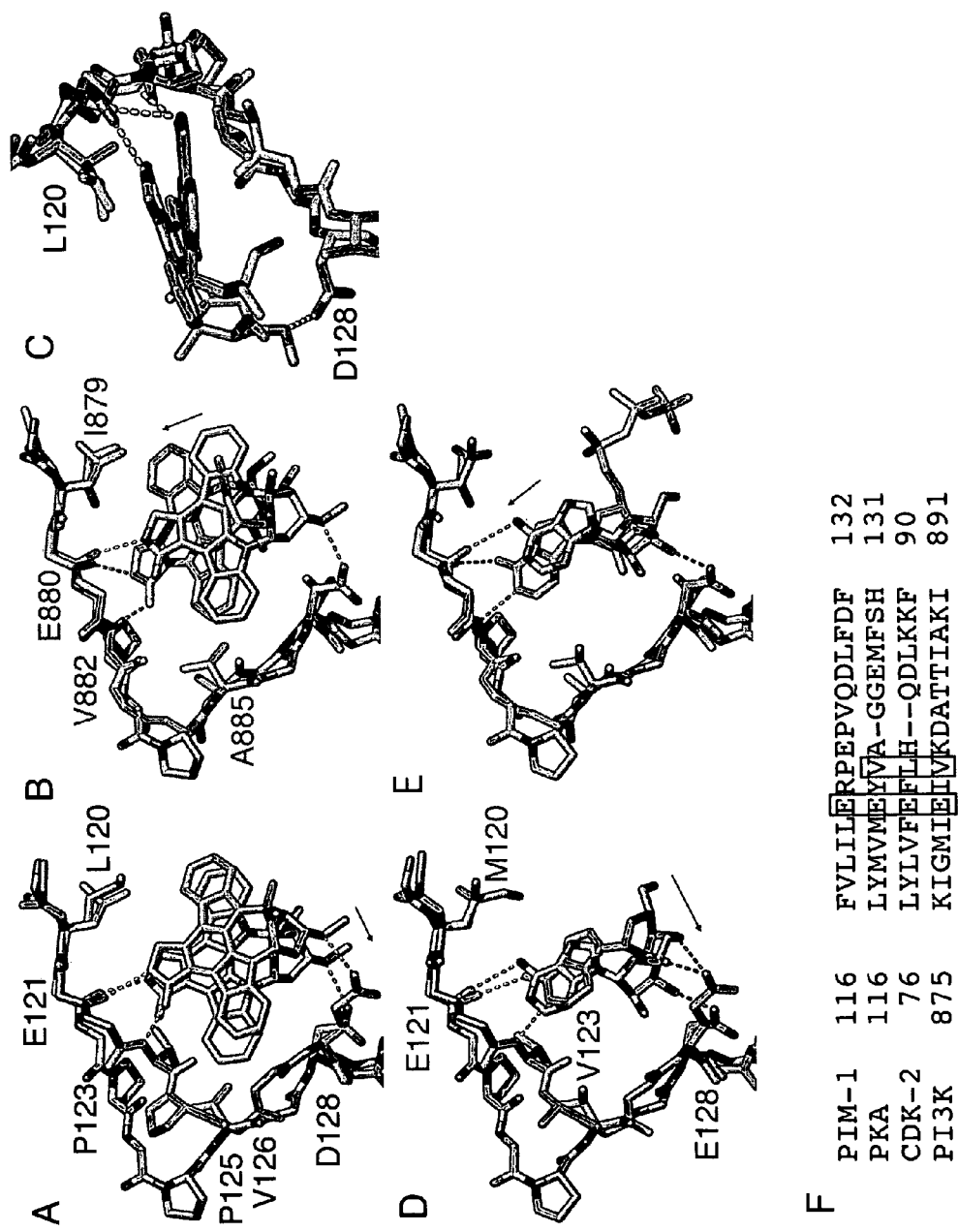
Figure 6:
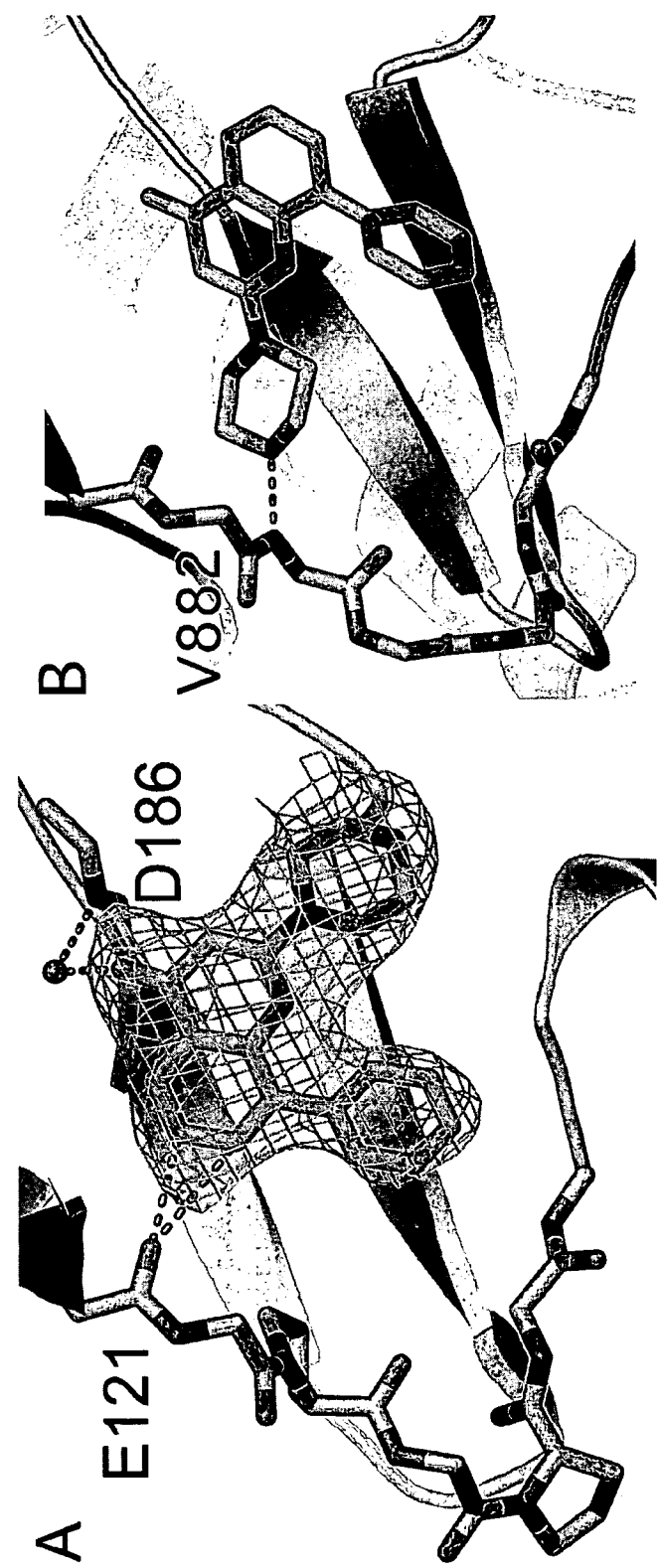

FIGS. 5, 6 and 7 show a detailed representation of the active sites of Pim-1-adenosine, Pim-1-staurosporine and Pim-1-LY294002 complexes, respectively. Pim-1 amino acids Phe49, Ala65, Glu121, Arg122, Asp128, and Leu174 form an inhibitor-binding pocket through their contacts with adenosine in the Pim-1-adenosine complex (FIG. 7). Pim-1 amino acids Leu44, Gly45, Phe49, Val52, Ala65, Lys67, Ile104, Leu120, Glu121, Val126, Asp128, Glu171, Leu174, Ile185 and Asp186 form an inhibitor-binding pocket through their contacts with staurosporine in the Pim-1-staurosporine complex (FIG. 8). Pim-1 amino acids Leu44, Gly45, Phe49, Val52, Ala65, Lys67, Ile104, Leu120, Arg122, Val126, Leu174 and Asp186 form an inhibitor-binding pocket through their contacts with LY294002 in the Pim-1-LY294002 complex (FIG. 9). Asp186 makes a water-mediated contact in the Pim-1-LY294002 complex. Pim-1 amino acid residues Phe49, Ala65 and Leu174 are found to contact the inhibitors in all three complex structures in FIG. 1A, 2A or 3A.

Pro123 and Val126 are residues unique to Pim-1 as discussed in Example 8. Accordingly, in one embodiment, an inhibitor-binding pocket comprises Pim-1 amino acid residues Phe49, Ala65, Pro123, Val126 and Leu174 according to the structure of Pim-1 protein in FIG. 1A, 2A or 3A. In another embodiment, an inhibitor-binding pocket comprises Pim-1 amino acid residues Phe49, Ala65, Val 126 and Leu174 according to the structure of Pim-1 protein in FIG. 1A, 2A or 3A.

In another embodiment, the inhibitor-binding pocket comprises amino acid residues Leu44, Gly45, Phe49, Val52, Ala65, Ile104, Leu120, Glu121, Arg122, Pro123, Val126, Asp128, Asp131, Glu171, Leu174, and Ile185 according to the structure of the Pim-1-adenosine complex in FIG. 1A. In another embodiment, the inhibitor-binding pocket comprises amino acid residues Leu44, Gly45, Ser46, Phe49, Val52, Ala65, Lys67, Glu89, Ile104, Leu120, Glu121, Arg122, Pro123, Val126, Asp128, Glu171, Asn172, Leu174, Ile185 and Asp186 according to the structure of the Pim-staurosporine complex in FIG. 2A. In another embodiment, the inhibitor-binding pocket comprises amino acid residues Leu44, Gly45, Ser46, Phe49, Val52, Ala65, Lys67, Ile104, Leu120, Glu121, Arg122, Val126, Leu174, Ile185 and Asp186 according to the structure of Pim-1-LY294002 in FIG. 3A. These amino acid residues are within 1 Å("5 Å sphere of amino acids") of adenosine, staurosporine or LY294002 bound in the inhibitor-binding pockets as identified using the program Swiss-Pdb Viewer (Guex, N. and Peitsch, M. C. (1997) "SWISS-MODEL and the Swiss-PdbViewer: An environment for comparative protein modeling", *Electrophoresis* 18: 2714-2723).

In one embodiment, the inhibitor-binding pocket comprises amino acid residues Leu44, Gly45, Phe49, Val52, Ala65, Ile104, Leu120, Glu121, Arg122, Val126, Leu174, and Ile185 according to the structure of the Pim-1-inhibitor complex in FIG. 1A, 2A or 3A. These are the common amino acid residues within 5 Å of the inhibitor in the three complex structures.

In another embodiment, the inhibitor-binding pocket comprises amino acid residues Leu43, Leu44, Gly45, Ser46, Gly47, Phe49, Gly50, Ser51, Val52, Tyr53, Ser54, Pro63, Val64, Ala65, Ile66, Lys67, Val103, Ile104, Arg105, Leu118, Ile119, Leu120, Glu121, Arg122, Pro123, Glu124, Val126, Gln127, Asp128, Leu129, Phe130, Asp131, Lys169, Asp170, Glu171, Asn172, Ile173, Leu174, Ile175, Lys183, Leu184, Ile185 and Asp186 according to the structure of the Pim-1-adenosine complex in FIG. 1A. In another embodiment, the inhibitor-binding pocket comprises amino acid residues Leu43, Leu44, Gly45, Ser46, Gly47, Gly48, Phe49, Gly50, Ser51, Val52, Tyr53, Ser54, Pro63, Val64, Ala65, Ile66, Lys67, Val69, Glu89, Leu93, Ile104, Arg105, Leu118, Ile119, Leu120, Glu121, Arg122, Pro123, Glu124, Pro125, Val126, Gln127, Asp128, Leu129, Phe130, Asp131, Asp167, Lys169, Asp170, Glu171, Asn172, Ile173, Leu174, Ile175, Lys183, Leu184, Ile185, Asp186, Phe187 and Gly188 according to the structure of the Pim-staurosporine complex in FIG. 2A. In another embodiment, the inhibitor-binding pocket comprises amino acid residues Leu43, Leu44, Gly45, Ser46, Gly47, Gly48, Phe49, Gly50, Ser51, Val52, Tyr53, Ser54, Gly55, Val64, Ala65, Ile66, Lys67, Glu89, Leu93, Val103, Ile104, Arg105, Leu118, Ile119, Leu120, Glu121, Arg122, Pro123, Glu124, Pro125, Val126, Gln127, Asp128, Asp131, Glu171, Asn172, Ile173, Leu174, Ile175, Lys183, Leu184, Ile185, Asp186, Phe187 and Gly188 according to the structure of Pim-1-LY294002 in FIG. 3A. These amino acid residues are within 8 Å ("8 Å sphere of amino acids") of adenosine, staurosporine or LY294002 bound in the inhibitor-binding pockets as identified using the program Swiss-Pdb Viewer (Guex, N. and Peitsch, M. C. (1997) "SWISS-MODEL and the Swiss-PdbViewer: An environment for comparative protein modeling", *Electrophoresis* 18: 2714-2723).

In one embodiment, the inhibitor-binding pocket comprises amino acid residues Leu43, Leu44, Gly45, Ser46, Gly47, Phe49, Gly50, Ser51, Val52, Tyr53, Ser54, Val64, Ala65, Ile66, Lys67, Ile104, Arg105, Leu118, Ile119, Leu120, Glu121, Arg122, Pro123, Glu124, Val126, Gln127, Asp128, Asp131, Glu171, Asn172, Ile173, Leu174, Ile175, Lys183, Leu184, Ile185 and Asp186 according to the structure of Pim-1-inhibitor complex in FIG. 1A, 2A or 3A. These are the common amino acid residues within 8 Å of the inhibitor in the three complex structures.

It will be readily apparent to those of skill in the art that the numbering of amino acid residues in homologues of human Pim-1 may be different than that set forth for human Pim-1. Corresponding amino acids in Pim-1 homologues are easily identified by visual inspection of the amino acid sequences or by using commercially available homology software programs. Homologues of Pim-1 include, for example, Pim-1 from other species, such as non-humans primates, mouse, rat, etc.

Those of skill in the art understand that a set of structure coordinates for an enzyme or an enzyme-complex, or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The variations in coordinates discussed above may be generated because of mathematical manipulations of the Pim-1-adenosine structure coordinates. For example, the structure coordinates set forth in FIG. 1A, 2A or 3A may undergo crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal may also account for variations in structure coordinates. If such variations are within a certain root mean square deviation as compared to the original coordinates, the resulting three-dimensional shape is considered encompassed by this invention. Thus, for example, a ligand that bound to the inhibitor-binding pocket of Pim-1 would also be expected to bind to another binding pocket whose structure coordinates defined a shape that fell within the RMSD value.

Various computational analyses may be necessary to determine whether a molecule or binding pocket, or portion thereof, is sufficiently similar to the binding pockets above-described. Such analyses may be carried out in well known software applications, such as ProFit (A. C. R. Martin, ProFit version 1.8, http://www.bioinf.org.uk/software), Swiss-Pdb Viewer (Guex et al., *Electrophoresis* 18: 2714-2723 (1997)), the Molecular Similarity application of QUANTA (Accelrys, San Diego, Calif. © 2001, 2002) and as described in the accompanying User's Guide, which are incorporated herein by reference.

The above programs permit comparisons between different structures, different conformations of the same structure, and different parts of the same structure. The procedure used in QUANTA (Accelrys, San Diego, Calif. ©2001, 2002) and Swiss-Pdb Viewer (Guex and Peitsch, *Electrophoresis* 18: 2714-2723 (1997) to compare structures is divided into four steps: 1) load the structures to be compared; 2) define the atom equivalences in these structures; 3) perform a fitting operation on the structures; and 4) analyze the results.

The procedure used in ProFit to compare structures includes the following steps: 1) load the structures to be compared; 2) specify selected residues of interest; 3) define the atom equivalences in the selected residues; 4) perform a fitting operation on the selected residues; and 5) analyze the results.

Each structure in the comparison is identified by a name. One structure is identified as the target (i.e., the fixed structure); all remaining structures are working structures (i.e., moving structures). Since atom equivalency within QUANTA (Accelrys, San Diego, Calif. ©2001, 2002) is defined by user input, for the purposes of this invention, we will define equivalent atoms as protein backbone atoms N, O, C and Cα for all corresponding amino acid residues between two structures being compared.

The corresponding amino acids may be identified by sequence alignment programs such as the "bestfit" program available from the Genetics Computer Group which uses the local homology algorithm described by Smith and Waterman in *Advances in Applied Mathematics* 2: 482 (1981), which is incorporated herein by reference. A suitable amino acid sequence alignment will require that the proteins being aligned share minimum percentage of identical amino acids. Generally, a first protein being aligned with a second protein should share in excess of about 35% identical amino acids (Hanks et al., *Science* 241: 42 (1988); Hanks and Quinn, *Methods in Enzymology* 200: 38 (1991)). The identification of equivalent residues can also be assisted by secondary structure alignment, for example, aligning the α-helices, β-sheets in the structure. The program Swiss-Pdb viewer (Guex and Peitsch, *Electrophoresis* 18: 2714-2723 (1997) utilizes a best fit algorithm that is based on secondary sequence alignment.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by the above programs. The Swiss-Pdb Viewer (Guex and Peitsch, *Electrophoresis* 18: 2714-2723 (1997) program sets an RMSD cutoff for eliminating pairs of equivalent atoms that have high RMSD values. An RMSD cutoff value can be used to exclude pairs of equivalent atoms with extreme individual RMSD values. In the program ProFit, the RMSD cutoff value can be specified by the user.

For the purpose of this invention, any molecule, molecular complex, binding pocket, motif, domain thereof or portion thereof that is within a root mean square deviation for backbone atoms (N, Cα, C, O) when superimposed on the relevant backbone atoms described by structure coordinates listed in FIG. 1A, 2A or 3A are encompassed by this invention.

The RMSD values of all backbone atoms between Pim-1-adenosine and Pim-1-staurosporine complexes, and Pim-1-LY294002 complex were 0.47 Å and 0.31 Å, respectively. RMSD values of the binding pockets comprising amino acid residues Leu43, Leu44, Gly45, Ser46, Gly47, Phe49, Gly50, Ser51, Val52, Tyr53, Ser54, Val64, Ala65, Ile66, Lys67, Ile104, Arg105, Leu118, Ile119, Leu120, Glu121, Arg122, Pro123, Glu124, Val126, Gln127, Asp128, Asp131, Glu171, Asn172, Ile173, Leu174, Ile175, Lys183, Leu184, Ile185 and Asp186 in the Pim-1-adenosine and Pim-1-staurosporine complexes, and Pim-1-LY294002 complex were 0.44 Å and 0.37 Å, respectively. The RMSD values between the binding pockets comprising amino acid residues Leu44, Gly45, Phe49, Val52, Ala65, Lys67, Ile104, Leu120, Arg122, Val126, and Leu174 Asp186 in the Pim-1-adenosine and Pim-1-staurosporine complexes, and the Pim-1-LY294002 complex were 0.48 Å and 0.42 Å, respectively. The RMSD values between the binding pockets comprising amino acid residues Phe49, Ala65, Val126, and Asp186 in the Pim-1-adenosine and Pim-1-staurosporine complexes, and the Pim-1-LY294002 complex were 0.61 Å and 0.55 Å, respectively. All RMSD values were calculated by comparing the backbone atoms (N, Cα, C, O) of structures.

One embodiment of this invention provides a crystalline molecule or molecular complex comprising a protein defined by structure coordinates of a set of amino acid residues that are identical to Pim-1 amino acid residues according to FIG. 1A, 2A or 3A, wherein the RMSD between said set of amino acid residues and said human Pim-1 kinase amino acid residues is not more than about 3.0 Å. In other embodiments, the RMSD between said set of amino acid residues and said human Pim-1 kinase amino acid residues is not greater than about 2.0 Å, not greater than about 1.0 Å, or not greater than about 0.5 Å.

In one embodiment, the present invention provides a crystalline molecule or molecular complex comprising all or part of a binding pocket defined by a set of amino acid residues which are identical to human Pim-1 kinase amino acid residues Leu43, Leu44, Gly45, Ser46, Gly47, Phe49, Gly50, Ser51, Val52, Tyr53, Ser54, Val64, Ala65, Ile66, Lys67, Ile104, Arg105, Leu118, Ile119, Leu120, Glu121, Arg122, Pro123, Glu124, Val126, Gln127, Asp128, Asp131, Glu171, Asn172, Ile173, Leu174, Ile175, Lys183, Leu184, Ile185 and Asp186 according to FIG. 1A, 2A or 3A, wherein the RMSD of the backbone atoms between said human Pim-1 kinase amino acid residues and said amino acid residues which are identical is not greater than about 2.0 Å. In other embodiments, the RMSD is not greater than about 1.5 Å, 1.0 Å, 0.8 Å, 0.5 Å, 0.3 Å, or 0.2 Å. In other embodiments, the binding pocket is defined by a set of amino acid residues comprising at least twelve, fourteen, sixteen, eighteen, nineteen, twenty-one, twenty-three or twenty-five amino acid residues which are identical to said human Pim-1 kinase amino acid residues.

In one embodiment, the present invention provides a crystalline molecule or molecular complex comprising all or part of a binding pocket defined by a set of amino acid residues which are identical to human Pim-1 kinase amino acid residues Leu44, Gly45, Phe49, Val52, Ala65, Lys67, Ile104, Leu120, Arg122, Val126, and Leu174 according to FIG. 3A, wherein the RMSD of the backbone atoms between said human Pim-1 kinase amino acid residues and said set of amino acid residues which are identical is not greater than about 2.0 Å. In other embodiments, the RMSD is not greater than about 1.5 Å, 1.0 Å, 0.8 Å, 0.5 Å, 0.3 Å, or 0.2 Å. In other embodiments, the binding pocket is defined by a set of amino acid residues comprising at least eight, nine, ten or eleven amino acid residues which are identical to said human Pim-1 kinase amino acid residues.

In one embodiment, the present invention provides a crystalline molecule or molecular complex comprising all or part of a binding pocket defined by a set of amino acid residues which are identical to human Pim-1 kinase amino acid residues Phe49, Ala65, Val126, and Leu174 according to FIG. 1A, 2A or 3A, wherein the RMSD of the backbone atoms between said human Pim-1 kinase amino acid residues and said set of amino acid residues which are identical is not greater than about 2.0 Å. In other embodiments, the RMSD is not greater than about 1.5 Å, 1.0 Å, 0.8 Å, 0.5 Å, 0.3 Å, or 0.2 Å.

Computer Systems

According to another embodiment, this invention provides a machine-readable data storage medium, comprising a data storage material encoded with machine-readable data, wherein said data defines the above-mentioned molecules or molecular complexes. In one embodiment, the data defines the above-mentioned binding pockets by comprising the structure coordinates of said amino acid residues according to FIG. 1A, 2A or 3A. To use the structure coordinates generated for Pim-1, homologues thereof, or one of its binding pockets, it is at times necessary to convert them into a three-dimensional shape or to extract three-dimensional structural information from them. This is achieved through the use of commercially or publicly available software that is capable of generating a three-dimensional structure or a three-dimensional representation of molecules or portions thereof from a set of structure coordinates. In one embodiment, three-dimensional structure or representation may be displayed graphically.

Therefore, according to another embodiment, this invention provides a machine-readable data storage medium comprising a data storage material encoded with machine readable data. In one embodiment, a machine programmed with instructions for using said data is capable of generating a three-dimensional structure or three-dimensional representation of any of the molecules, or molecular complexes or binding pockets thereof, that are described herein.

This invention also provides a computer comprising:
(a) a machine-readable data storage medium, comprising a data storage material encoded with machine-readable data, wherein said data defines any one of the above molecules or molecular complexes;
(b) a working memory for storing instructions for processing said machine-readable data;
(c) a central processing unit (CPU) coupled to said working memory and to said machine-readable data storage medium for processing said machine readable data and means for generating three-dimensional structural information of said molecule or molecular complex; and
(d) output hardware coupled to said central processing unit for outputting three-dimensional structural information of said molecule or molecular complex, or information produced by using said three-dimensional structural information of said molecule or molecular complex.

In one embodiment, the data defines the binding pocket of the molecule or molecular complex.

Three-dimensional data generation may be provided by an instruction or set of instructions such as a computer program or commands for generating a three-dimensional structure or graphical representation from structure coordinates, or by subtracting distances between atoms, calculating chemical energies for a Pim-1 molecule or molecular complex or homologues thereof, or calculating or minimizing energies for an association of a Pim-1 molecule or molecular complex or homologues thereof to a chemical entity. The graphical representation can be generated or displayed by commercially available software programs. Examples of software programs include but are not limited to QUANTA (Accelrys, San Diego, Calif. ©2001, 2002), O (Jones et al., *Acta Crystallogr.* A47: 110-119 (1991)) and RIBBONS (Carson, *J. Appl. Crystallogr.* 24: 958-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described in the Rational Drug Design section.

Information of said binding pocket or information produced by using said binding pocket can be outputted through display terminals, touchscreens, facsimile machines, modems, CD-ROMs, printers, a CD or DVD recorder, ZIP™ or JAZ™ drives or disk drives. The information can be in graphical or alphanumeric form.

In one embodiment, the computer is executing an instruction such as a computer program for generating three-dimensional structure or docking. In another embodiment, the computer further comprises a commercially available software program to display the information as a graphical representation. Examples of software programs include but as not limited to, QUANTA (Accelrys, San Diego, Calif. ©2001, 2002), O (Jones et al., *Acta Crystallogr.* A47: 110-119 (1991)) and RIBBONS (Carson, *J. Appl. Crystallogr.* 24: 958-961 (1991)), all of which are incorporated herein by reference.

FIG. 10 demonstrates one version of these embodiments. System (10) includes a computer (11) comprising a central processing unit ("CPU") (20), a working memory (22) which may be, e.g., RAM (random-access memory) or "core" memory, mass storage memory (24) (such as one or more disk drives, CD-ROM drives or DVD-ROM drives), one or more cathode-ray tube ("CRT") display terminals (26), one or more keyboards (28), one or more input lines (30), and one or more output lines (40), all of which are, interconnected by a conventional bi-directional system bus (50).

Input hardware (35), coupled to computer (11) by input lines (30), may be implemented in a variety of ways. Machine-readable data of this invention may be inputted via the use of a modem or modems (32) connected by a telephone line or dedicated data line (34). Alternatively or additionally, the input hardware (35) may comprise CD-ROM or DVD-ROM drives or disk drives (24). In conjunction with display terminal (26), keyboard (28) may also be used as an input device.

Output hardware (46), coupled to computer (11) by output lines (40), may similarly be implemented by conventional devices. By way of example, output hardware (46) may include CRT display terminal (26) for displaying a graphical representation of a binding pocket of this invention using a program such as QUANTA (Accelrys, San Diego, Calif. ©2001, 2002) as described herein. Output hardware may also include a printer (42), so that hard copy output may be produced, or a disk drive (24), to store system output for later use. Output hardware may also include a display terminal, touchscreens, facsimile machines, modems, a CD or DVD recorder, ZIP™ or JAZ™ drives, disk drives, or other machine-readable data storage device.

In operation, CPU (20) coordinates the use of the various input and output devices (35), (46), coordinates data accesses from mass storage (24) and accesses to and from working memory (22), and determines the sequence of data processing steps. A number of programs may be used to process the machine-readable data of this invention. Such programs are discussed in reference to the computational methods of drug discovery as described herein. Specific references to components of the hardware system (10) are included as appropriate throughout the following description of the data storage medium.

FIG. 11 shows a cross section of a magnetic data storage medium (100) which can be encoded with a machine-readable data that can be carried out by a system such as system (10) of FIG. 10. Medium (100) can be a conventional floppy diskette or hard disk, having a suitable substrate (101), which may be conventional, and a suitable coating (102), which may be conventional, on one or both sides, containing magnetic domains (not visible) whose polarity or orientation can be altered magnetically. Medium (100) may also have an opening (not shown) for receiving the spindle of a disk drive or other data storage device (24).

The magnetic domains of coating (102) of medium (100) are polarized or oriented so as to encode in manner which may be conventional, machine readable data such as that described herein, for execution by a system such as system (10) of FIG. 10.

FIG. 12 shows a cross section of an optically-readable data storage medium (110) which also can be encoded with such a machine-readable data, or set of instructions, which can be carried out by a system such as system (10) of FIG. 10.

Medium (110) can be a conventional compact disk read only memory (CD-ROM) or a rewritable medium such as a magneto-optical disk which is optically readable and magneto-optically writable. Medium (100) preferably has a suitable substrate (111), which may be conventional, and a suitable coating (112), which may be conventional, usually of one side of substrate (111).

In the case of CD-ROM, as is well known, coating (112) is reflective and is impressed with a plurality of pits (113) to encode the machine-readable data. The arrangement of pits is read by reflecting laser light off the surface of coating (112). A protective coating (114), which preferably is substantially transparent, is provided on top of coating (112).

In the case of a magneto-optical disk, as is well known, coating (112) has no pits (113), but has a plurality of magnetic domains whose polarity or orientation can be changed magnetically when heated above a certain temperature, as by a laser (not shown). The orientation of the domains can be read by measuring the polarization of laser light reflected from coating (112). The arrangement of the domains encodes the data as described above.

In one embodiment, the structure coordinates of said molecules or molecular complexes are produced by homology modeling of at least a portion of the structure coordinates of FIGS. 1A, 2A or 3A. Homology modeling can be used to generate structural models of Pim-1 homologues or other homologous proteins based on the known structure of Pim-1. This can be achieved by performing one or more of the following steps: performing sequence alignment between the amino acid sequence of a molecule (possibly an unknown molecule) against the amino acid sequence of Pim-1; identifying conserved and variable regions by sequence or structure; generating structure coordinates for structurally conserved residues of the unknown structure from those of Pim-1; generating conformations for the structurally variable residues in the unknown structure; replacing the non-conserved residues of Pim-1 with residues in the unknown structure; building side chain conformations; and refining and/or evaluating the unknown structure.

Software programs that are useful in homology modeling include XALIGN (Wishart et al., *Comput. Appl. Biosci.* 10: 687-88 (1994)) and CLUSTAL W Alignment Tool, Higgins et al., supra. See also, U.S. Pat. No. 5,884,230. These references are incorporated herein by reference.

To perform the sequence alignment, programs such as the "bestfit" program available from the Genetics Computer Group (Waterman in *Advances in Applied Mathematics* 2: 482 (1981), which is incorporated herein by reference) and CLUSTAL W Alignment Tool (Higgins et al., supra, which is incorporated by reference) can be used. To model the amino acid side chains of homologous molecules, the amino acid residues in Pim-1 can be replaced, using a computer graphics program such as "O" (Jones et al., (1991) *Acta Cryst. Sect. A* 47: 110-119), by those of the homologous protein, where they differ. The same orientation or a different orientation of the amino acid can be used. Insertions and deletions of amino acid residues may be necessary where gaps occur in the sequence alignment. However, certain portions of the active site of Pim-1 and its homologues are highly conserved with essentially no insertions and deletions.

Homology modeling can be performed using, for example, the computer programs SWISS-MODEL available through Glaxo Wellcome Experimental Research in Geneva, Switzerland; WHATIF available on EMBL servers; Schnare et al., *J. Mol. Biol.* 256: 701-719 (1996); Blundell et al., *Nature* 326: 347-352 (1987); Fetrow and Bryant, *Bio/Technology* 11:479-484 (1993); Greer, *Methods in Enzymology* 202: 239-252 (1991); and Johnson et al., *Crit. Rev. Biochem. Mol. Biol.* 29:1-68 (1994). An example of homology modeling can be found, for example, in Szklarz G. D., *Life Sci.* 61: 2507-2520 (1997). These references are incorporated herein by reference.

Thus, in accordance with the present invention, data capable of generating the three-dimensional structure or three-dimensional representation of the above molecules or molecular complexes, or binding pockets thereof, can be stored in a machine-readable storage medium, which is capable of displaying structural information or a graphical three-dimensional representation of the structure. In one embodiment, the means of generating three-dimensional information is provided by the means for generating a three-dimensional structural representation of the binding pocket or protein of a molecule or molecular complex.

Rational Drug Design

The Pim-1 structure coordinates or the three-dimensional graphical representation generated from these coordinates may be used in conjunction with a computer for a variety of purposes, including drug discovery.

For example, the structure encoded by the data may be computationally evaluated for its ability to associate with chemical entities. Chemical entities that associate with Pim-1 may inhibit or activate Pim-1 or its homologues, and are potential drug candidates. Alternatively, the structure encoded by the data may be displayed in a graphical three-dimensional representation on a computer screen. This allows visual inspection of the structure, as well as visual inspection of the structure's association with chemical entities.

In one embodiment, the invention provides for a method of using a computer for selecting an orientation of a chemical entity that interacts favorably with a binding pocket or protein comprising the steps of:
 (a) providing the structure coordinates of said binding pocket or protein on a computer comprising the means for generating three-dimensional structural information from said structure coordinates;
 (b) employing computational means to dock a first chemical entity in the binding pocket or protein;
 (c) quantifying the association between said chemical entity and all or part of the binding pocket or protein for different orientations of the chemical entity; and
 (d) selecting the orientation of the chemical entity with the most favorable interaction based on said quantified association.

In one embodiment, the docking is facilitated by said quantified association.

In one embodiment, the above method further comprises the following steps before step (a):
 (e) producing a crystal of a molecule or molecular complex comprising Pim-1 or homologue thereof;
 (f) determining the three-dimensional structure coordinates of the molecule or molecular complex by X-ray diffraction of the crystal; and
 (g) identifying all or part of a binding pocket that corresponds to said binding pocket.

Three-dimensional structural information in step (a) may be generated by instructions such as a computer program or commands that can generate a three-dimensional representation; subtract distances between atoms; calculate chemical energies for a Pim-1 molecule, molecular complex or homologues thereof; or calculate or minimize the chemical energies of an association of Pim-1 molecule, molecular complex or homologues thereof to a chemical entity. These types of computer programs are known in the art. The graphical representation can be generated or displayed by commercially available software programs. Examples of software programs include but are not limited to QUANTA (Accelrys, San Diego, Calif. ©2001, 2002), O (Jones et al., *Acta Crystallogr.* A47: 110-119 (1991)) and RIBBONS (Carson, *J. Appl. Crystallogr.* 24: 958-961 (1991)), which are incorporated herein by reference. Certain software programs may imbue this representation with physico-chemical attributes which are known from the chemical composition of the molecule, such as residue charge, hydrophobicity, torsional and rotational degrees of freedom for the residue or segment, etc. Examples of software programs for calculating chemical energies are described below.

The above method may further comprise the following step after step (d): outputting said quantified association to a suitable output hardware, such as a CRT display terminal, a CD or DVD recorder, ZIP™ or JAZ™ drive, a disk drive, or other machine-readable data storage device, as described previously. The method may further comprise generating a three-dimensional structure, graphical representation thereof, or both, of the molecule or molecular complex prior to step (b).

One embodiment of this invention provides for the above method, wherein energy minimization, molecular dynamics simulations, or rigid body minimizations are performed simultaneously with or following step (b).

The above method may further comprise the steps of:
(e) repeating steps (b) through (d) with a second chemical entity; and
(f) selecting at least one of said first or second chemical entity that interacts more favorably with said binding pocket or protein based on said quantified association of said first or second chemical entity.

In another embodiment, the invention provides for the method of using a computer for selecting an orientation of a chemical entity with a favorable shape complementarity in a binding pocket comprising the steps of:
(a) providing the structure coordinates of said binding pocket and all or part of the ligand bound therein on a computer comprising the means for generating three-dimensional structural information from said structure coordinates;
(b) employing computational means to dock a first chemical entity in the binding pocket;
(c) quantitating the contact score of said chemical entity in different orientations; and
(d) selecting an orientation with the highest contact score.

In one embodiment, the docking is facilitated by the contact score.

The method above may further comprise the step of generating a three-dimensional graphical representation of the binding pocket and all or part of the ligand bound therein prior to step (b).

The method above may further comprise the steps of:
(e) repeating steps (b) through (d) with a second chemical entity; and
(f) selecting at least one of said first or second chemical entity that has a higher contact score based on said quantitated contact score of said first or second chemical entity.

In another embodiment, the invention provides a method for screening a plurality of chemical entities to associate at a deformation energy of binding of less than −7 kcal/mol with said binding pocket:
(a) employing computational means, which utilize said structure coordinates to dock one of said plurality of chemical entities in said binding pocket;
(b) quantifying the deformation energy of binding between the chemical entity and the binding pocket;
(c) repeating steps (a) and (b) for each remaining chemical entity; and
(d) outputting a set of chemical entities that associate with the binding pocket at a deformation energy of binding of less than −7 kcal/mol to a suitable output hardware.

In another embodiment, the method comprises the steps of:
(a) constructing a computer model of a binding pocket of a molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a Pim-1 protein, or homologue thereof;
(c) employing computational means to dock said chemical entity to be evaluated in said binding pocket in order to provide an energy-minimized configuration of said chemical entity in the binding pocket; and
(d) evaluating the results of said docking to quantify the association between said chemical entity and the binding pocket.

Alternatively, the structure coordinates of the Pim-1 binding pockets may be utilized in a method for identifying a candidate inhibitor of a molecule or molecular complex comprising a binding pocket of Pim-1. This method comprises the steps of:
(a) using a three-dimensional structure of the binding pocket or protein to design, select or optimize a plurality of chemical entities;
(b) contacting each chemical entity with the molecule and molecular complex;
(c) monitoring the inhibition to the catalytic activity of the molecule or molecular complex by the chemical entity; and
(d) selecting a chemical entity based on the effect of the chemical entity on the activity of the molecule or molecular complex.

In one embodiment, the three-dimensional structure is displayed as a graphical representation.

In another embodiment, the method comprises the steps of:
(a) constructing a computer model of a binding pocket of the molecule or molecular complex;
(b) selecting a chemical entity to be evaluated by a method selected from the group consisting of assembling said chemical entity; selecting a chemical entity from a small molecule database; de novo ligand design of said chemical entity; and modifying a known agonist or inhibitor, or a portion thereof, of a Pim-1 protein or homologue thereof;
(c) employing computational means to dock said chemical entity to be evaluated and said binding pocket in order to provide an energy-minimized configuration of said chemical entity in the binding pocket; and
(d) evaluating the results of said docking to quantify the association between said chemical entity and the binding pocket;
(e) synthesizing said chemical entity; and
(f) contacting said chemical entity with said molecule or molecular complex to determine the ability of said chemical entity to activate or inhibit said molecule.

In one embodiment, the invention provides a method of designing a compound or complex that associates with all or part of the binding pocket comprising the steps of:

(a) providing the structure coordinates of said binding pocket or protein on a computer comprising the means for generating three-dimensional structural information from said structure coordinates;
(b) using the computer to dock a first chemical entity in part of the binding pocket or protein;
(c) docking a second chemical entity in another part of the binding pocket or protein;
(d) quantifying the association between the first and second chemical entity and part of the binding pocket or protein;
(e) repeating steps (b) to (d) with another first and second chemical entity, selecting a first and a second chemical entity based on said quantified association of all of said first and second chemical entity;
(f) optionally, visually inspecting the relationship of the first and second chemical entity to each other in relation to the binding pocket or protein on a computer screen using the three-dimensional graphical representation of the binding pocket or protein and said first and second chemical entity; and
(g) assembling the first and second chemical entity into a compound or complex that interacts with said binding pocket by model building.

For the first time, the present invention permits the use of molecular design techniques to identify, select and design chemical entities, including inhibitory compounds, capable of binding to Pim-1 or Pim-1-like binding pockets, motifs and domains.

Applicants' elucidation of binding pockets on Pim-1 provides the necessary information for designing new chemical entities and compounds that may interact with Pim-1 substrate, active site, ligand binding pockets or Pim-1-like substrate, active site or ligand binding pockets, in whole or in part.

Throughout this section, discussions about the ability of a chemical entity to bind to, interact with or inhibit Pim-1 binding pockets refer to features of the entity alone.

The design of compounds that bind to or inhibit Pim-1 binding pockets according to this invention generally involves consideration of two factors. First, the chemical entity must be capable of physically and structurally associating with parts or all of the Pim-1 binding pockets. Non-covalent molecular interactions important in this association include hydrogen bonding, van der Waals interactions, hydrophobic interactions and electrostatic interactions.

Second, the chemical entity must be able to assume a conformation that allows it to associate with the Pim-1 binding pockets directly. Although certain portions of the chemical entity will not directly participate in these associations, those portions of the chemical entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of a chemical entity comprising several chemical entities that directly interact with the Pim-1 or Pim-1-like binding pockets.

The potential inhibitory or binding effect of a chemical entity on Pim-1 binding pockets may be analyzed prior to its actual synthesis and testing by the use of computer modeling techniques. If the theoretical structure of the given entity suggests insufficient interaction and association between it and the Pim-1 binding pockets, testing of the entity is obviated. However, if computer modeling indicates a strong interaction, the molecule may then be synthesized and tested for its ability to bind to a Pim-1 binding pocket. This may be achieved by testing the ability of the molecule to inhibit Pim-1 using the assays described in Example 5 and Fox et al., *Protein Sci.* 7: 2249-2255 (1998), which is incorporated herein by reference.

A potential inhibitor of a Pim-1 binding pocket may be computationally evaluated by means of a series of steps in which chemical entities or fragments are screened and selected for their ability to associate with the Pim-1 binding pockets.

One skilled in the art may use one of several methods to screen chemical entities or fragments or moieties thereof for their ability to associate with the binding pockets described herein. This process may begin by visual inspection of, for example, any of the binding pockets on the computer screen based on the Pim-1 structure coordinates FIGS. 1A, 2A or 3A, or other coordinates which define a similar shape generated from the machine-readable storage medium. Selected chemical entities, or fragments or moieties thereof may then be positioned in a variety of orientations, or docked, within that binding pocket as defined supra. Docking may be accomplished using software such as QUANTA (Accelrys, San Diego, Calif. ©2001, 2002) and Sybyl (Tripos Associates, St. Louis, Mo.), followed by, or performed simultaneously with, energy minimization, rigid-body minimization (Gshwend, supra) and molecular dynamics with standard molecular mechanics force fields, such as CHARMM and AMBER.

Specialized computer programs may also assist in the process of selecting fragments or chemical entities. These include:

1. GRID (Goodford, P. J., "A Computational Procedure for Determining Energetically Favorable Binding Sites on Biologically Important Macromolecules", *J. Med. Chem.* 28: 849-857 (1985)). GRID is available from Oxford University, Oxford, UK.
2. MCSS (Miranker et al., "Functionality Maps of Binding Sites: A Multiple Copy Simultaneous Search Method." *Proteins Struct. Funct. Genet.* 11: 29-34 (1991)). MCSS is available from Molecular Simulations, San Diego, Calif.
3. AUTODOCK (Goodsell et al., "Automated Docking of Substrates to Proteins by Simulated Annealing", *Proteins Struct. Funct. and Genet.* 8: 195-202 (1990)). AUTODOCK is available from Scripps Research Institute, La Jolla, Calif.
4. DOCK (Kuntz et al., "A Geometric Approach to Macromolecule-Ligand Interactions", *J. Mol. Biol.* 161: 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of Pim-1. This would be followed by manual model building using software such as QUANTA (Accelrys, San Diego, Calif. ©2001, 2002) or Sybyl (Tripos Associates, St. Louis, Mo.).

Useful programs to aid one of skill in the art in connecting the individual chemical entities or fragments include:

1. CAVEAT (Bartlett et al., "CAVEAT: A Program to Facilitate the Structure-Derived Design of Biologically Active Molecules", in *Molecular Recognition in Chemical and Biological Problems*, S. M. Roberts, Ed., Royal Society of Chemistry, Special Publication No. 78: pp. 182-196 (1989); Lauri, G. and Bartlett, P. A., "CAVEAT: A Program to Facilitate the Design of Organic Molecules", *J. Comp. Aid. Molec. Design* 8: 51-66 (1994)).

CAVEAT is available from the University of California, Berkeley, Calif.

2. 3D Database systems such as ISIS (MDL Information Systems, San Leandro, Calif.). This area is reviewed in Martin, Y. C., "3D Database Searching in Drug Design", *J. Med. Chem.* 35: 2145-2154 (1992).

3. HOOK (Eisen et al., "HOOK: A Program for Finding Novel Molecular Architectures that Satisfy the Chemical and Steric Requirements of a Macromolecule Binding Site", *Proteins Struct. Funct. Genet.* 19: 199-221 (1994)). HOOK is available from Molecular Simulations, San Diego, Calif.

Instead of proceeding to build an inhibitor of a Pim-1 binding pocket in a step-wise fashion one fragment or chemical entity at a time as described above, inhibitory or other Pim-1 binding compounds may be designed as a whole or "de novo" using either an empty binding pocket or optionally including some portion(s) of a known inhibitor(s). There are many de novo ligand design methods including:

1. LUDI (Böhm, H.-J., "The Computer Program LUDI: A New Method for the De Novo Design of Enzyme Inhibitors", *J. Comp. Aid. Molec. Design* 6: pp. 61-78 (1992)). LUDI is available from Molecular Simulations Incorporated, San Diego, Calif.

2. LEGEND (Nishibata et al., *Tetrahedron* 47: 8985-8990 (1991)). LEGEND is available from Molecular Simulations Incorporated, San Diego, Calif.

3. LeapFrog (available from Tripos Associates, St. Louis, Mo.).

4. SPROUT (Gillet et al., "SPROUT: A Program for Structure Generation)", *J. Comp. Aid. Molec. Design* 7:127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, *J. Med. Chem.* 33: 883-894 (1990); see also, Navia, M. A. and Murcko, M. A., "The Use of Structural Information in Drug Design", Current Opinions in Structural Biology 2: 202-210 (1992); Balbes et al., "A Perspective of Modern Methods in Computer-Aided Drug Design", in *Reviews in Computational Chemistry*, K. B. Lipkowitz and D. B. Boyd, Eds., VCH Publishers, New York, 5: pp. 337-379 (1994); see also, Guida, W. C., "Software For Structure-Based Drug Design", *Curr. Opin. Struct. Biology* 4: 777-781 (1994)).

Once a chemical entity has been designed or selected by the above methods, the efficiency with which that entity may bind to any of the above binding pockets may be tested and optimized by computational evaluation. For example, an effective binding pocket inhibitor must preferably demonstrate a relatively small difference in energy between its bound and free states (i.e., a small deformation energy of binding). Thus, the most efficient binding pocket inhibitors should preferably be designed with a deformation energy of binding of not greater than about 10 kcal/mole, more preferably, not greater than 7 kcal/mole. Binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

A chemical entity designed or selected as binding to any one of the above binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Accelrys, San Diego, Calif. ©2001, 2002); Insight II/Discover (Molecular Simulations, Inc., San Diego, Calif. ©1998); DelPhi (Molecular Simulations, Inc., San Diego, Calif. ©1998); and AMSOL (Quantum Chemistry Program Exchange, Indiana University). These programs may be implemented, for instance, using a Silicon Graphics workstation such as an Indigo2 with "IMPACT" graphics. Other hardware systems and software packages will be known to those skilled in the art.

Another approach enabled by this invention is the computational screening of small molecule databases for chemical entities or compounds that can bind in whole, or in part, to any of the above binding pocket. In this screening, the quality of fit of such entities to the binding pocket may be judged either by shape complementarity or by estimated interaction energy (Meng et al., *J. Comp. Chem.* 13: 505-524 (1992)).

Another particularly usefil drug design technique enabled by this invention is iterative drug design. Iterative drug design is a method for optimizing associations between a protein and a chemical entity by determining and evaluating the three-dimensional structures of successive sets of protein/chemical entity complexes.

In iterative drug design, crystals of a series of protein or protein complexes are obtained and then the three-dimensional structures of each crystal is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. High throughput crystallization assays may be used to find a new crystallization condition or to optimize the original protein crystallization condition for the new complex. Alternatively, a pre-formed protein crystal may be soaked in the presence of an inhibitor, thereby forming a protein/compound complex and obviating the need to crystallize each individual protein/compound complex.

Any of the above methods may be used to design peptide or small molecule which may have inhibitory effects on full-length Pim-1 protein or fragments thereof, or on full-length Pim-1 protein which is mutated in or fragments of the mutated protein thereof.

Structure Determination of Other Molecules

The structure coordinates set forth in FIGS. 1A, 2A or 3A can also be used in obtaining structural information about other crystallized molecules or molecular complexes. This may be achieved by any of a number of well-known techniques, including molecular replacement.

According to one embodiment, the machine-readable data storage medium comprises a data storage material encoded with a first set of machine readable data which comprises the Fourier transform of at least a portion of the structure coordinates set forth in FIGS. 1A, 2A or 3A or homology model thereof, and which, when using a machine programmed with instructions for using said data, can be combined with a second set of machine readable data comprising the X-ray diffraction pattern of a molecule or molecular complex to determine at least a portion of the structure coordinates corresponding to the second set of machine readable data.

In another embodiment, the invention provides a computer for determining at least a portion of the structure coordinates corresponding to X-ray diffraction data obtained from a molecule or molecular complex having an unknown structure, wherein said computer comprises:

(a) a machine-readable data storage medium comprising a data storage material encoded with machine-readable data, wherein said data comprises at least a portion of the structure coordinates of Pim-1 according to FIGS. 1A, 2A or 3A or homology model thereof;

(b) a machine-readable data storage medium comprising a data storage material encoded with machine-readable data, wherein said data comprises X-ray diffraction data obtained from said molecule or molecular complex having an unknown structure; and (c) instructions for performing a Fourier transform of the machine-readable data of (a) and for processing said machine-readable data of (b) into structure coordinates.

For example, the Fourier transform of at least a portion of the structure coordinates set forth in FIGS. 1A, 2A or 3A or homology model thereof may be used to determine at least a portion of the structure coordinates of the molecule or molecular complex.

Therefore, in another embodiment this invention provides a method of utilizing molecular replacement to obtain structural information about a molecule or a molecular complex of unknown structure, wherein the molecule or molecular complex is sufficiently homologous to Pim-1, comprising the steps of:

(a) crystallizing said molecule or molecular complex of unknown structure;

(b) generating X-ray diffraction data from said crystallized molecule or molecular complex;

(c) applying at least a portion of the Pim-1 structure coordinates set forth in one of FIGS. 1A, 2A or 3A or a homology model thereof to the X-ray diffraction data to generate a three-dimensional electron density map of at least a portion of the molecule or molecular complex whose structure is unknown; and (d) generating a structural model of the molecule or molecular complex from the three-dimensional electron density map.

In one embodiment, the method is performed using a computer. In another embodiment, the molecule is selected from the group consisting of Pim-1 protein and Pim-1 protein homologues. In another embodiment, the molecular complex is Pim-1 protein complex or homologue thereof.

By using molecular replacement, all or part of the structure coordinates of Pim-1 as provided by this invention (and set forth in FIGS. 1A, 2A or 3A) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure may provide a satisfactory estimate of the phases for the unknown structure.

Thus, this method involves generating a preliminary model of a molecule or molecular complex whose structure coordinates are unknown, by orienting and positioning the relevant portion of Pim-1 protein according to FIG. 1A, 2A or 3A within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (E. Lattman, "Use of the Rotation and Translation Functions", in *Meth. Enzymol.* 115: 55-77 (1985); M. G. Rossmann, ed., "The Molecular Replacement Method", Int. Sci. Rev. Ser. No. 13, Gordon & Breach, New York (1972)).

The structure of any portion of any crystallized molecule or molecular complex that is sufficiently homologous to any portion of the structure of human Pim-1 protein can be resolved by this method.

In one embodiment, the method of molecular replacement is utilized to obtain structural information about a Pim-1 homologue. The structure coordinates of Pim-1 as provided by this invention are particularly useful in solving the structure of Pim-1 complexes that are bound by ligands, substrates and inhibitors.

Furthermore, the structure coordinates of Pim-1 as provided by this invention are useful in solving the structure of Pim-1 proteins that have amino acid substitutions, additions and/or deletions (referred to collectively as "Pim-1 mutants", as compared to naturally occurring Pim-1). These Pim-1 mutants may optionally be crystallized in co-complex with a chemical entity. The crystal structures of a series of such complexes may then be solved by molecular replacement and compared with that of wild-type Pim-1. Potential sites for modification within the various binding pockets of the enzyme may thus be identified. This information provides an additional tool for determining the most efficient binding interactions, for example, increased hydrophobic interactions, between Pim-1 and a chemical entity or compound.

The structure coordinates are also particularly useful in solving the structure of crystals of Pim-1 or homologues co-complexed with a variety of chemical entities. This approach enables the determination of the optimal sites for interaction between chemical entities, including candidate Pim-1 inhibitors. For example, high resolution X-ray diffraction data collected from crystals exposed to different types of solvent allows the determination of where each type of solvent molecule resides. Small molecules that bind tightly to those sites can then be designed and synthesized and tested for their Pim-1 inhibition activity.

All of the complexes referred to above may be studied using well-known X-ray diffraction techniques and may be refined using 1.5-3.4 Å resolution X-ray data to an R value of about 0.30 or less using computer software, such as X-PLOR (Yale University, ©1992, distributed by Molecular Simulations, Inc.; see, e.g., Blundell & Johnson, supra; *Meth. Enzy-* mol. vol. 114 & 115, H. W. Wyckoff et al., eds., Academic Press (1985)) or CNS (Brunger et al., *Acta Cryst.* D54: 905-921, (1998)).

In order that this invention be more fully understood, the following examples are set forth. These examples are for the purpose of illustration only and are not to be construed as limiting the scope of the invention in any way.

EXAMPLE 1

Cloning and Expression of Pim-1

Full-length Pim-1 (residues M1-K313) was cloned in two parts by PCR from a human IMAGE Consortium clone (GenBank GI 1845036), and from a human bone marrow cDNA library (BD Biosciences, Clontech, Palo Alto, Calif.). The pieces were fused by PCR and inserted into the NdeI and EcoRI sites of the dual promoter vector pBEV1, encoding a protein with an N-terminal HexaHis tag and thrombin cleavage site. The amino acid sequence of this Pim-1 clone is identical to SwissProt entry P11309.

BL21/DE3 pLysS *E. coli* cells were transformed with the construct encoding full-length human Pim-1 kinase, using a standard transformation protocol (Stratagene, La Jolla, Calif.). Freshly transformed cells were grown at 37° C. in Brain Heart Infusion Medium (DIFCO laboratories, Detroit, Mich.) supplemented with 100 µg/ml carbenicillin and 35 µg/ml chloramphenicol. Cells were grown at 37° C. to an optical density of 0.75 at 600 nm, and expression was induced at 28° C. with 1 mM IPTG. Cells were harvested via centrifugation 4 hours post-induction and flash frozen at −80° C. prior to purification.

EXAMPLE 2

Purification of Pim-1

Frozen cell pellets (~30 g) were thawed in 7 volumes of Buffer A (50 mM HEPES 7.8, 300 mM NaCl, 10% (v/v) glycerol, 3 mM β-mercaptoethanol) containing 0.1% (v/v) Tween-20, 50 µM DFP, 1 µg/ml E-64, 1 µg/ml leupeptin and 10 µg/ml pepstatin (Roche Diagnostics Corp, Indianapolis, Ind.) and lysed in a microfluidizer (Microfluidics, Newton, Mass.). The lysate was centrifuged at 54,000×g for 45 min and the supernatant was incubated with 1 ml of TALON™ metal affinity resin (BD Biosciences, Clontech) per 5 mg of protein overnight at 4° C. The resin was washed with 20 column volumes of Buffer A and the Pim-1 protein was eluted with Buffer A containing 100 mM imidazole. Fractions containing Pim-1 were pooled and concentrated by ultrafiltration using a 30 KDa molecular weight cut-off (MWCO) membrane in an Amicon stirred-cell concentrator (Millipore, Billerica, Mass.).

The concentrated fractions of Pim-1 was then loaded onto a Superdex 200 column (90×2.6 cm, Amersham Bioscience Corp, Uppsala, Sweden) that was equilibrated in Buffer B (50 mM HEPES pH 7.8, 200 mM NaCl, 10% (v/v) glycerol, and 5 mM β-mercaptoethanol). Fractions were pooled based on SDS-PAGE, diluted to 25 mM NaCl with 50 mM HEPES, pH 7.8, 10% (v/v) glycerol and 5 mM dithiothreitol (DTT), and loaded onto a Pharmacia 8 ml pre-packed MonoQ (HR 10/10) anion-exchange column (Amersham Bioscience Corp, Uppsala, Sweden) that was equilibrated in Buffer C (50 mM HEPES pH 7.8, 20 mM NaCl, 10% (v/v) glycerol, 5 mM DTT). Pim-1 was eluted using a gradient of 0-40% Buffer D (buffer C plus 1 M NaCl) over 60 column volumes. Peak fractions were collected as four separate pools (I-IV) based on the elution chromatogram. Pim-1 was dialyzed into 20 mM Tris pH 8.0 (25° C.), 100 mM NaCl, 5 mM DTT and concentrated to 10 mg/ml using a 10 KDa MWCO Vivaspin concentrator (Vivascience, Hanover, Germany). The identity of the purified Pim-1 was confirmed by N-terminal amino acid sequencing.

After sequential purification with affinity and size exclusion chromatography, the Pim-1 protein was >98% pure, but was heterogeneous with respect to phosphorylation states. Typically, preparations contained a mixture of species with 0-5 phosphoryl groups, which were partially resolved by anion exchange chromatography. Purified Pim-1 had a monomer:dimer ratio of 80:20 (Kd 23 µM; apparent molecular weight of the monomer 44,023 Da) as determined by analytical ultracentrifugation and was completely free of higher molecular weight oligomers.

Pim-1 crystallized from different MonoQ pools gave similar crystal forms. Phosphoamino acid analysis revealed that Pim-1 purified from *E. coli* was extensively phosphorylated in the HexaHis tag (MGSSHHHHHHSSGLVPRGSH) (SEQ ID NO: 6) and the four MonoQ pools differed mainly in the degree of phosphorylation in this region. Dephosphorylation of Pim-1 with Lambda phosphatase (New England Biolabs) followed by autophosphorylation showed that Pim-1 readily autophosphorylates in the HexaHis tag region. Ser261 was the major phosphorylation site observed in Pools III and IV. Other minor phosphorylation sites, Ser8, Thr23 and Ser98 were present to varying degrees in each pool.

Kinase activity of MonoQ pools I-IV was tested using S6 peptide as a substrate. All four pools showed very similar kinetic parameters ($k_{cat}$=4±0.4 s$^{-1}$; peptide $K_m$=51±2 µM and ATP $K_m$=120±16 µM), despite of the fact that they were phosphorylated to a different degree at several sites. A panel of kinase inhibitors was evaluated for their ability to inhibit Pim-1. Staurosporine and structurally similar compounds, such as K-252a and bisindolyl-maleimides-I and -IX, were found to inhibit Pim-1 with sub-micromolar potency (Table 1). These compounds are non-specific inhibitors of Ser/Thr and Tyr kinases (Dumas, J., *J. Exp. Opin. Ther. Patents* 11: 405-429 (2001); Cohen, P. *Nat. Rev. Drug Discov.* 1: 309-315 (2002); Hashimoto et al., *Biochem. Biophys. Res. Commun.* 181: 423-429 (1991); Harris et al., *Biochem. Biophys. Res. Commun.* 227: 672-676 (1996); Davies et al., *Biochem. J.* 351: 95-105 (2000); Berg et al., *J. Biol. Chem.* 267: 13-16 (1992); Mizuno et al., *FEBS Lett.* 330: 114-116 (1993)). LY294002 was found to be a potent inhibitor of Pim-1 with $IC_{50}$=4 µM. This compound was originally described as a specific inhibitor of PI3K with 1.4 µM $IC_{50}$ (Mizuno et al., *FEBS Lett.* 330: 114-116 (1993)). Later, Davies et al (Davies et al., supra) reported that LY294002 inhibits PI3K and Casein kinase 2 with a similar potency (10 µM and 6.9 µM, respectively).

EXAMPLE 3

Analytical Ultracentrifugation Sedimentation Velocity Data Acquisition and Analysis All sedimentation velocity experiments were performed with the Beckman Coulter Optima XL-I using an An60 Ti rotor and charcoal-filled Epon double-sector cells. A 400 µl aliquot of Pim-1 was loaded into the sample channel and 430 µl of buffer into the reference channel. Experiments were performed at 42,000 rpm for 8 h at 20° C. Radial absorbance scans were collected in continuous scan mode at 280 nm every 10 min at a spacing of 0.001 cm. Velocity data were analyzed using DCDT+ (version 1.14) (Philo, J. S., *Anal.*

Biochem. 279: 151-163 (2000)) and SVEDBERG (version 6.39) (Philo, J. S., Biophys. J. 72: 435-444 (1997)).

EXAMPLE 4

Mass Spectrometric Analysis of Purified Pim-1

The overall phosphorylation state of each of the MonoQ purified pools I-IV of Pim-1 was determined by electrospray mass spectrometry of thrombin cleaved Pim-1. Electrospray mass spectra of protein samples were collected using a Micromass Quattro II triple quadrupole mass spectrometer (Waters Corp., Milford, Mass.) (Fox et al., FEBS Lett. 461: 323-328 (1999)).

The phosphorylation sites of Pim-1 were identified from tryptic digests of the MonoQ purified pools I-IV to LC/MSMS on a QSTAR Pulsar quadrupole time-of-flight tandem mass spectrometer (AB/MDS-Sciex, Toronto, Canada) equipped with a nanoelectrospray ion source (MDS Protana, Odese, Denmark). Data were analyzed using the Mascot search engine (Matrix Science, London, UK).

EXAMPLE 5

Kinase Assays

A coupled-enzyme assay (Fox et al., Protein Sci. 7: 2249-2255 (1998)) was used to quantify the ADP generated in the kinase reaction with S6 peptide (RRRLSSLRA) (SEQ ID NO: 7) as a substrate. The assay was carried out in a total volume of 100 µl in 0.1 M HEPES buffer (pH 7.6) containing 10 mM $MgCl_2$, 2.5 mM phosphoenolpyruvate, 0.2 mM NADH, 30 µg/ml pyruvate kinase, 10 µg/ml lactate dehydrogenase (Roche Diagnostics Corp., Indianapolis, Ind.) and 2 mM DTT in a 96-well plate, and read at 340 nm at 30° C. on a Spectramax spectrophotometer (Molecular Devices, Sunnyvale, Calif.). Pim-1 concentration was 25 nM in all assays. The reaction was started by addition of ATP after 10 minutes pre-incubation of the reaction mixture at 30° C. Substrate concentrations were 1 mM S6 peptide, 2 mM ATP for activity assays and 40 µM S6 peptide, 100 µM ATP for $IC_{50}$ determinations. Inhibitors were dissolved in DMSO and added to the reaction to 2.5% DMSO final at the beginning of pre-incubation period. Kinetic analysis was performed by non-linear regression fitting using the program Prism (GraphPad software, San Diego, Calif., USA).

EXAMPLE 6

Crystallization of Pim-1-adenosine Complex

Pim-1 crystals were grown by the vapor diffusion method at 22° C. Equal volumes of protein (12 mg/ml protein, 20 mM HEPES pH 8, 100 mM NaCl, 5 mM DTT) and well solution (1 M $(NH_4)_2HPO_4$, 100 mM citrate buffer pH 5.5, 200 mM NaCl) were mixed and suspended over 1 ml of well solution. Over 4 days, the crystals reached a final size of approximately 250×40×40 µm. Crystals were harvested and flash-frozen in a solution composed of the well solution with 30% (v/v) glycerol. A complex of Pim-1 with either staurosporine (Sigma-Aldrich, St. Louis, Mo.) or the inhibitor LY294002 (Calbiochem, La Jolla, Calif.) was made by soaking apo crystals (grown as above) with 500 µM compound and 5% DMSO (final concentration) for 24 hours at room temperature. The adenosine-Pim-1 complex was made by adding adenosine (2 mM) to the protein prior to crystallization.

EXAMPLE 7

X-ray Data Collection and Structure Determination

For the staurosporine and LY294002 complexes, X-ray diffraction data were recorded using a RU-200 X-ray generator and RaxisV++ detector (Rigaku, The Woodlands, Texas), and intensities were integrated and scaled using the program d*TREK (CrystalClear: An Integrated Program for the Collection and Processing of Area Detector Data, R. C., © 1997-2002; Pflugrath, Acta Crystallogr. D55: 1718-1725 (1999)). Diffraction data for the adenosine complex crystals were recorded at Beamline 5.0.2 at the Advanced Light Source (Lawrence Berkeley Laboratories, Berkeley, Calif.). Intensities were integrated and scaled using the programs DENZO and SCALEPACK (Otwinowski, supra) and d*TREK (CrystalClear: An Integrated Program for the Collection and Processing of Area Detector Data, R. C., © 1997-2002; Pflugrath, Acta Crystallogr. D55: 1718-1725 (1999)). Table 2 summarizes data collection.

The structure was determined by molecular replacement using homology models based upon phosphorylase kinase (PDB accession code 1PHK) (Owen et al., supra) and death-associated protein kinase (PDB accession code 1JKK) (Tereshko et al., supra). The molecular replacement solution was determined using AMoRe (Navaza, CCP4 distribution) (CCP4 (Collaborative Computational Project, N., Acta Crystallogr. D50: 760-763 (1994)). The crystals belong to the space group $P6_5$, and a single protein monomer comprises the asymmetric unit. The protein model was built using QUANTA (Accelrys, San Diego, Calif. ©2001, 2002) and refined with both CNX (Accelrys, San Diego, Calif.) (Pannu, N. S., and Read, R. J., Acta Crystallogr. A 52: 659-668 (1996); Rice, L. M., and Brunger, A. T., Proteins 19: 277-290 (1994)) and BUSTER (Global Phasing Inc., Cambridge, UK) (Roversi et al., Acta Crystallogr. D Biol. Crystallogr. 56 (Pt 10): 1316-1323 (2000)).

Table 2 summarizes the Refinement Statistics. The refined models consist of the protein kinase catalytic domain. While full-length protein was used for crystallization (313 residues), 32 residues at the N-terminus, 8 residues at the C-terminus, and 4 residues in one loop (80-83) could not be built into the electron density. Glu79 was built as Ala because electron density was weak for the side chain of this amino acid residue. Phosphorylation of Ser261 is clearly visible in the electron density map. The phosphoserine side chain participates in both intra- and intermolecular interactions, and may be important in formation of the crystal packing interactions. Also, the electron density map reveals additional density adjacent to the sulfur of Cys161 indicating an adduct at this residue. The electron density was large enough to accommodate four non-hydrogen atoms; it was modeled as a mercaptoethanol adduct, however it is also consistent with a partially ordered DTT adduct. Both DTT and β-mercaptoethanol were used in the purification.

EXAMPLE 8

Overview of Crystal Structure of Pim-1-Inhibitor Complexes

The structure of Pim-1 reveals a global fold typical of protein serine/threonine kinases, consisting of two domains linked by a hinge region (FIG. 4). The smaller, N-terminal domain (residues 33-121) consists primarily of β-strands with one α-helix, and the C-terminal domain (residues 128-305) is largely α-helical. The active site is formed by a groove at the interface between these two domains, and is enclosed by the hinge region (residues 122-127), the glycine rich loop (residues 44-52), and the activation loop (residues 186-210). The Pim-1 structure was compared to several other protein kinases with high sequence homology such as c-AMP dependent kinase (PKA) and phosphorylase kinase (PHK). Pim-1 shares the same secondary and tertiary structure as other protein kinases. When secondary structural elements are aligned, a root mean square difference (RMSD) of 1.3 Å for C-α atom positions is observed between Pim-1 and both PKA or PHK (using 213 residues from PDB accession code 1PHK (Owen et al., supra) and 220 residues from PDB accession code 1ATP (Zheng et al., *Biochemistry* 32: 2154-2161 (1993)), respectively).

Among kinase structures, the conformation of the activation loop varies widely (reviewed in Huse, M., and Kuriyan, J., *Cell* 109: 275-282 (2002)). Many kinases are activated by phosphorylation in this region, causing a conformational change consistent with substrate binding. The Pim-1 activation loop is in a similar conformation to the active, peptide-bound form of PKA and the constitutively active kinase PHK. In PKA, Thr197 is phosphorylated and the conformation of the activated state is stabilized by a salt bridge to Arg165. In both Pim-1 and PHK, a similar salt bridge is observed, however, an acidic side chain takes the place of the phosphothreonine (Asp200-Arg166 in Pim-1, Glu182-Arg148 in PHK).

The positions and side chain rotamers of the catalytic residues resemble that observed in the PKA-ATP-peptide complex. In PKA, Asn171 forms a hydrogen bond to Asp166 and thus orients Asp166, which in turn forms a hydrogen bond with the substrate Ser or Thr hydroxyl group. The corresponding residues in Pim-1, Asn172 and Asp167, have the same position and side chain rotamers. Likewise, the residues of PKA which interact with the ATP phosphate or $Mg^{2+}$ atoms (Lys72, Asn171, Asp184) are conserved both in sequence and position in Pim-1 (Lys67, Asn172, Asp186). The conformation of the glycine rich loop (residues 45-52) in this structure differs from that of the PKA structures. The Pim-1 glycine rich loop moves toward the C-terminal domain and Phe49 adopts a rotamer in which the side chain points toward the hinge region, thereby filling the space usually occupied by ATP phosphates (FIG. 6). A similar conformation has been observed in GSK-3β where Phe67 contacts the phosphate binding portion of the glycine rich loop (Bax et al., *Structure, (Camb)* 9: 1143-1152 (2001)).

The N- and C-terminal domains are connected by a hinge region, which forms important interactions with the adenine ring of ATP. Typically, the adenosine N1 nitrogen accepts a hydrogen bond from a main chain amide while the N6-amino atom donates a hydrogen bond to a main chain carbonyl. In the hinge region of Pim-1, however, the residue closest to the adenine Ni is a proline (Pro 123), so a main chain amide is not available for this hydrogen bonding. A proline at this position is extremely rare: in fact, none of the kinases for which the structure is known has a similarly placed proline. Sequence alignments in the hinge region can be difficult because of low homology. The only other human kinases with a proline at this position are Pim-2, Pim-3, SgK069 and PRP4 (Manning et al., *Science* 298: 1912-1934 (2002)). This implies that the hydrogen bond to N1 of ATP is not necessary for substrate binding or catalysis in these kinases, and that other interactions are sufficient to correctly position ATP. Likewise, a kinase inhibitor optimized for Pim-1 selectivity would lack a hydrogen bond acceptor at the position corresponding to N1 of ATP, and might instead interact with the hinge via a van der Waal's contact.

The Pim-1 hinge sequence is also unusual due to a two-residue insertion relative to kinases such as CDK-2 (De Bondt et al., *Nature* 363: 595-602 (1993)) and JNK-3 (Xie et al., *Structure* 6: 983-991 (1998)), and a single residue insertion relative to PKA and Aurora (Cheetham et al., *J. Biol. Chem.* 277: 42419-42422 (2002)). A comparison of the hinge regions of Pim-1 and PKA is shown in FIG. 5. Residues before and after the insertion superimpose well (Pim-1 residues 117-122 with PKA 117-122; Pim-1 128-131 with PKA 127-130). At the point of insertion (Pro125), the hinge bulges away from the ATP binding site by up to 4 Å. Some of the additional space created by the change in main chain position is occupied by the Val126 side chain which is oriented toward the ATP binding pocket and interacts with Pro123. This unique hinge conformation could be utilized for the design of specific Pim-1 inhibitors, and creates a space for substitution at the position corresponding to C2 of ATP. For instance, polar interactions with the carbonyl oxygen of Pro123 or hydrophobic contacts with the side chain of Val126 would be unique to PIM.

One kinase which shares this two residue insertion is phosphoinositide 3-kinase (PI3K) (Walker et al., *Nature* 402: 313-320 (1999)). Overall, the structures of protein kinases and PI3K share many structural features, especially with respect to the ATP binding pocket. While there is little sequence homology in the hinge region between PI3K and Pim-1, the main chain conformations are remarkably similar (0.86 Å RMSD over 13 C-α positions). The PI3K and Pim-1 hinge conformation differ most at Pro125 (Asp884 in PI3K) (FIG. 5).

Staurosporine Complex

The position of staurosporine bound to Pim-1 is similar to that found in other kinases. The compound is sandwiched between hydrophobic residues from the glycine rich loop (Ala65, Leu44, Val52, Phe49), the C-terminal domain (Ile104, Leu174, Ile185), and the hinge (Val126). A hydrogen bond is observed between the pyrrolidinone nitrogen and the Glu121 main chain carbonyl atom. The amino group of the staurosporine sugar moiety makes two hydrogen bonds: one to the main chain carbonyl of Glu171 and the other to the side chain oxygen of Asp128. Unlike other kinase-staurosporine complexes, no hydrogen bond is observed to the pyrrolidinone oxygen due to the presence of a proline at position 123. Compared to the PKA-staurosporine complex (PDB accession code 1STC) (Prade et al., *Structure* 5: 1627-1637 (1997)), the staurosporine is rotated about 100 (about an axis perpendicular to the plane of the pyrrolidinone ring) toward the hinge, and into the additional space formed by the proline insertion in the hinge (FIG. 5B). The aromatic rings of staurosporine in the Pim-1 and PKA structures are approximately coplanar. The relative position of the staurosporine in the two structures is, in part, fixed by the length of the side chain to which the sugar moiety forms a hydrogen bond (Asp128 in Pim-1, Glu128 in PKA).

A comparison of the staurosporine position in the Pim-1 and the PI3K complexes (PDB accession code 1E8Z) (Walker et al., supra; Pacold et al., *Cell* 103: 931-943 (2000)), reveals a shift and a rotation. In PI3K, two hydrogen bonds are made between the pyrrolidinone and the PI3K main chain, typical of other staurosporine complexes. Staurosporine bound to PI3K is shifted toward the outermost edge of the hinge by about 2.5 Å relative to the Pim-1 structure (FIG. 5C). Also, the staurosporine is tilted about 30° about an axis parallel to the main chain of the hinge (between I879 and V882), such that the pyrrolidinone ring lies below (towards the C-terminal domain) the same ring in the Pim-1 structure (FIG. 5D).

While the conformations of the Pim-1 and PI3K hinges are similar, specific interactions with active site side chains bring about the difference in positions. For instance, in Pim-1, the side chain of Ala65 lies above the plane of the staurosporine pyrrolidinone ring. In PI3K, Ile831 occupies the same location in the active site, and the larger side chain causes the ring to tilt downwards, away from the glycine rich loop. Likewise, in Pim-1, the C-α carbon of Pro123 and the side chains of Ile104 and Val126 prevent staurosporine from adopting the same position seen in PI3K.

Adenosine Complex

In the Pim-1-adenosine complex, only a single hydrogen bond is observed with the hinge main chain: between the N6-amino group and the main chain carbonyl of Glu121. Relative to the PKA-adenosine complex (PDB accession code 1FMO) (Narayana et al., *Biochemistry* 36: 4438-4448 (1997)), the adenosine in Pim-1 rotates by approximately 20° toward the hinge (rotation axis perpendicular to the plane of the adenine ring, see FIG. 5E). As with the staurosporine complex, the extent of the rotation is determined by the hydrogen bond acceptor at position 128.

In the PI3K-ATP complex structure (PDB accession code 1E8X), the adenine ring makes two hydrogen bonds to the main chain as seen in other protein kinases. However, the ATP bound to PI3K moves toward the hinge (FIG. 5F) and tilts such that the adenine ring lies below the plane of the adenine ring in the Pim-1-adenosine complex (closer to the C-terminal domain). As described above, in Pim-1, the C-α of Pro123 prevents the adenine from moving to the position seen in PI3K.

LY294002 Complex

The structure of PI3K inhibitor LY294002 bound to Pim-1 (FIG. 6A) was pursued based upon the observation of the compound's inhibitory activity in the Pim-1 in vitro assay as well as the conformational similarity between the Pim-1 and PI3K hinges. When bound to PI3K, the morpholine oxygen of LY294002 accepts a hydrogen bond from the amide nitrogen of Val882, making the same interaction as seen with N1 of ATP (PDB accession code 1E7V) (FIG. 6B). The structure of the Pim-1-LY294002 complex reveals that compound orientation is quite different. Relative to the PI3K structure, the LY294002 compound rotates about 180° about the bond common to the 2 rings in the chromone. In this case, the only interaction with the hinge is a pair of hydrogen bonds between the main chain carbonyl of Glu121 and two aromatic hydrogens of the chromone (2.6 and 2.9 Å O to H distance). The chromone carbonyl oxygen makes a hydrogen bond to a solvent molecule, which in turn interacts with the main chain amide of Asp186. The phenyl group of LY294002 packs against the side chains of Arg122, Val 126 and Leu174, while the morpholine group interacts with Phe49 in the glycine-rich loop.

Phosphorylation of Pim-1

Pim-1 purified from *E. coli* was phosphorylated at Ser261 as well as multiple sites in the His-tag region. Palaty et al. (Palaty et al., *J. Biol. Chem.* 272: 10514-10521 (1997)) have identified Ser190 in Xenopus Pim-3 as the major autophosphorylation site and showed that Ser190Ala and Ser190Glu mutants are 7-fold less active than the wild type Pim-3. The equivalent residue in human Pim-1, Ser189, was not phosphorylated in the *E. coli* purified preparations. The fact that all four MonoQ Pim-1 pools exhibit very similar kinetic parameters indicates that the enzyme is constitutively active and that the phosphorylation state does not affect enzymatic activity.

The specific activity (5±0.2 μmol/min/mg) observed here is much higher than previously reported (Hoover et al., supra; Friedmann et al., supra; Palaty et al., *Biochem. Cell. Biol.* 75: 153-162 (1997); Palaty et al., *J. Biol. Chem.* 272: 10514-10521 (1997)). It is 60-fold greater than that reported by Friedman et al. for human GST-Pim-1 using a histone H1 peptide (KRRASGP) (Friedmann et al., supra; SEQ ID NO:8) and over $10^4$-fold greater than that reported by Palaty et al. for GST fusions of human Pim-1 using S6 peptide (AKRRRLSS-LRA) (Palaty et al., *Biochem. Cell. Biol.* 75: 153-162 (1997); SEQ ID NO:9). Since both studies utilized GST fusions for expression and purification, it is possible that this large protein tag had a detrimental effect on enzyme activity, either by interfering with substrate access to the active site, or with overall protein folding. Human Pim-1 described herein with a small HexaHis tag exhibited a substantially higher and physiologically relevant level of kinase activity.

Comparisons of Structures of Pim-1-inhibitor Complexes to Structures of Other Kinases The overall structure and position of the catalytic residues of the Pim-1-adenosine complex represents the active state of the enzyme. The conformation of the activation loop resembles that of active kinases (PHK and phosphorylated PKA), consistent with the fact that Pim-1 is constitutively active. However, the structure of a Pim-1-ATP complex is likely to differ from the Pim-1-adenosine structures in the conformation of the glycine-rich loop and in the position of the adenosine. In the three ligand structures presented here, the side chain of Phe49 blocks the region of the active site normally occupied by the ATP phosphates. It is likely that ATP would displace Phe49, and the loop would adopt a more typical conformation. In GSK-3β, for instance, the corresponding phenylalanine residue is observed both within the active site pointing toward the hinge (Bax et al., supra) and, in another structure, outside the active site, pointing away from the hinge (ter Haar et al., *Nat. Struct. Biol.* 8: 593-596 (2001)).

The sequence and the conformation of the hinge region of Pim-1 differ from that found in other protein kinases: a conserved main chain hydrogen bond donor is replaced by a proline, and an insertion causes the hinge to bulge away from the adenine binding pocket. Nonetheless, Pim-1 is an active enzyme and binds compounds which also bind to other protein kinases (staurosporine, adenosine). Since the catalytic residues of Pim-1 are in the same position as in other protein kinases, and correct positioning of the phosphates of ATP is needed for catalysis, one would expect the position of the adenine and ribose to resemble that found in other kinases. Indeed, while the hinge conformation differs, the adenosine is bound in a similar way as in PKA. It is likely that when Pim-1 binds ATP, as opposed to adenosine, interactions between the phosphates and catalytic residues would fix the position of ATP in a manner similar to PKA and other protein kinases.

While the hinge conformations between Pim-1 and PI3K are very similar, the positions of adenosine and staurosporine differ. In fact, the orientation of the ligands in Pim-1 more closely resembles that found in other protein kinases. The PI3K binding mode, characterized by the shift towards the hinge and tilt down toward the C-terminal domain, is sterically hindered in Pim-1. The presence of the C-α atom of Pro123 and the larger side chain at position 126 (valine instead of alanine), prevent the shift toward the hinge. The tilt toward the C-terminal domain is hindered by the side chain of Ile104 in Pim-1. In the absence of the conserved pair of hydrogen bonds to the hinge, a number of van der Waal's contacts constrain the position of the ligands.

The fact that LY294002 binds to Pim-1, a protein with a PI3K-like hinge, appears to be coincidental, since the compound orientation is quite different. While the proteins have structural similarities, none of the features in common contribute to the binding of LY294002. In fact, superposition of the two complexes reveals that the PI3K binding mode is sterically hindered by Pro123 in Pim-1. Also, the Pim-1 binding mode is incompatible with the PI3K structure: Trp182 in PI3K packs against the phenyl and the morpholine rings of LY294002, but would collide with the phenyl ring if the compound bound in the Pim-1 orientation.

The contacts between the Pim-1 hinge and LY294002 are quite unusual. Typically, ligands interact with the hinge via hydrogen bonds, where the donor hydrogen is bonded to either oxygen or nitrogen. In this case, only hydrogens bonded to aromatic carbon atoms interact with the hinge. If indeed these interactions were important for LY294002 binding, we would expect the arrangement of the atoms to be favorable for hydrogen bonding. The ideal (C)H to O distance is approximately 2.6-2.7 Å, and the distance between the Glu121 carbonyl and the LY294002 hydrogens is 2.6 and 2.9 Å. The ideal O—CH angle is 180°, but not less than 90°. The angles observed with LY294002 in Pim-1 are 140 and 130°. Further, the hydrogen and the peptide should be coplanar, which is the case in the Pim-1-LY294002 complex. It is likely, therefore, that a pair of aromatic CH hydrogen bonds are formed between LY294002 and the Pim-1 hinge (Pierce et al., *Proteins,* 49: 567-576 (2002)).

The compound LY294002 is commonly used to assess the role of PI3K in cell signaling, and does not significantly inhibit most kinases (Davies et al., supra). For instance, PKA activity is reduced by only 9% (±5%) in the presence of 50 μM LY294002, so we would not expect the structure of PKA to easily accommodate LY294002 binding. Indeed, both the Pim-1 and PI3K binding modes are sterically hindered by Thr183 and Val123, respectively, in PKA. One kinase inhibited by LY294002 is casein kinase 2 (CK2) (IC50 6.9 μM). The structures of CK2 and Pim-1 were aligned to predict how LY294002 might bind to CK2. The PI3K binding mode is blocked by the side chain of Val116 in CK2. However, the CK2 active site will accommodate LY294002 in the Pim-1 binding mode, with a 0.5 Å translation to avoid a close contact with Ile66.

In addition to kinases, LY294002 has also been observed to bind to proteins with unrelated sequences and functions. For instance, through a PI3K-independent mechanism, the compound has been shown to alter intracellular calcium concentrations in bronchial smooth muscle cells (Ethier, M. F., and Madison, J. M., *Cell, Calcium* 32: 31-38 (2002)), block the Kv2.1 and Kv1.4 channels (El-Kholy et al., *Faseb J.* 17: 720-722 (2003)), and also bind to and inhibit estrogen receptor (Pasapera Limon et al., *Mol. Cell. Endocrinol.* 200: 199-202 (2003)). This may be due to the fact that LY294002 is a relatively small, planar, and unelaborated molecule with several hydrogen bonding opportunities. It is likely that there are other, as yet, unidentified targets of this compound, and therefore LY294002 should be used with caution in cellular assays.

In protein kinases, the hinge conformation and the hydrogen bonds to ATP are highly conserved. The Pim-1 structure reveals how fairly standard substrate binding is achieved even when the hinge is unusual in both sequence and conformation. The structures of the adenosine and staurosporine complexes show how van der Waal's contacts play the same role as a conserved hydrogen bond in positioning the substrate. While the Pim-1 hinge closely resembles the analogous region in the active site of PI3K, the compound LY294002 interacts with the hinges of the two proteins in very different ways. The Pim-1/LY294002 structure explains how LY294002 might inhibit other protein kinases, and this structure can be used to aid in the design of specific inhibitors, which utilize unique features of the Pim-1 active site.

While we have described a number of embodiments of this invention, it is apparent that our basic constructions may be altered to provide other embodiments which utilize the products, processes and methods of this invention.

TABLE 1

IC$_{50}$ determination of some common kinase inhibitors

| Inhibitor | IC$_{50}$ (μM) | Reported Inhibition Targets |
|---|---|---|
| Staurosporine 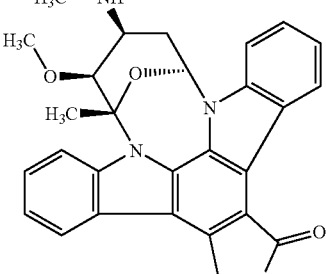 | 0.01 | Broad-spectrum Ser/Thr and Tyr kinases (Cohen, supra; Hashimoto et al., supra) |
| K-252a 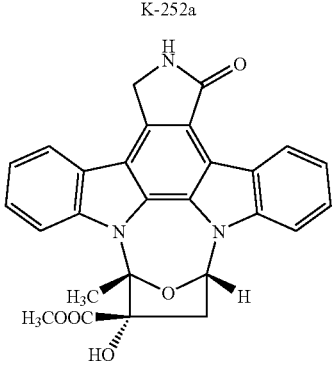 | .15 | Broad-spectrum Ser/Thr and Tyr kinases (Hashimoto et al., supra; Berg et al., supra; Mizuno et al., supra) |
| Bisindolyl-maleimide IX 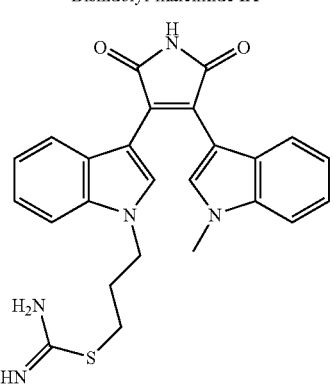 | 0.01 | PKC, GSK3, MAPKAP-K1b, SGK, p70S6K (Harris et al., supra; Davies et al., supra) |

TABLE 1-continued

IC50 determination of some common kinase inhibitors

| Inhibitor | IC50 (µM) | Reported Inhibition Targets |
|---|---|---|
| Bisindolyl-maleimide I 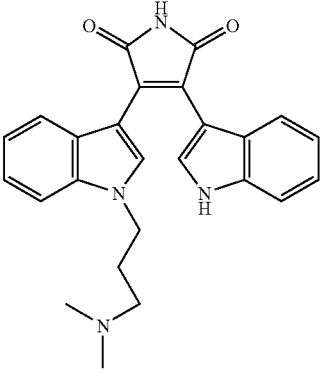 | 0.15 | PKC, MAPKAP-K1b, MSK1, p70S6K, GSK3 (Davies et al., supra) |
| LY294002 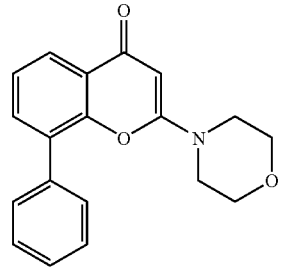 | 4 | PI3K, CK2 (Davies et al., supra; Vlahos et al., Davies et al., supra) |

TABLE 2

Data Collection and Refinement Statistics

| Data set | Staurosporine | Adenosine | LY294002 |
|---|---|---|---|
| Data collection | | | |
| X-ray source | Rigaku RU-H3R | ALS 5.0.2 | Rigaku RU-H3R |
| Space group | $P6_5$ | $P6_5$ | $P6_5$ |
| Unit cell parameters (Å) | a = b = 97.73 c = 80.51 | a = b = 98.27 c = 80.39 | a = b = 97.65 c = 80.73 |
| Resolution (Å) | 20 – 2.15 | 20 – 2.4 | 20 – 2.5 |
| Unique reflections | 22615 | 16430 | 14445 |
| Redundancy | 3.6 | 5.2 | 3.1 |
| Completeness (%)* | 94.9 (74.8) | 94.3 (96.1) | 94.9 (87.6) |
| $R_{merge}$* | 0.050 (0.250) | 0.060 (0.361) | 0.072 (0.336) |
| $<I/\sigma>$* | 10.6 (2.3) | 14.7 (3.9) | 12.0 (2.6) |
| Refinement | | | |
| Reflections used | 22526 | 16152 | 14206 |
| Test reflections | 1706 | 1268 | 1097 |
| R-factor | 0.205 | 0.210 | 0.208 |
| Free R-factor (% data) | 0.233 (7.6) | 0.246 (7.9) | 0.259 (7.7) |
| RMS deviation | | | |
| Bond lengths (Å) | 0.015 | 0.007 | 0.009 |
| Bond angles (°) | 1.7 | 1.3 | 1.2 |
| Dihedral angles (°) | 23.1 | 22.8 | 22.2 |
| Protein atoms | 2202 | 2202 | 2202 |
| Solvent atoms | 142 | 81 | 136 |

*Values for the highest resolution shell are shown in parentheses.
$R_{merge} = \Sigma_{hkl} \Sigma_i |I(hkl)_i - <I(hkl)>|/\Sigma_{hkl}\Sigma_i <I(hkl)_i>$ over i observations of reflection hkl.
R-factor = $\Sigma ||F_{obs}| - |F_{calc}||/\Sigma |F_{obs}|$ where $F_{obs}$ and $F_{calc}$ are the observed and calculated structure factors, respectively. Free R-factor is calculated from a randomly chosen subset of reflections not used for refinement.

We claim:

1. A crystal comprising a protein in complex with staurosporine, wherein said protein consists of SEQ ID NO:6 and SEQ ID NO:2, wherein SEQ ID NO:6 is directly joined at its C-terminus to the N-terminus of SEQ ID NO:2, and wherein said crystal is in space group $P6_5$ and has unit cell parameters of $a=97.73\pm2$ Å, $b=97.73\pm2$ Å, $c=80.51\pm2$ Å, $\alpha=\beta=90°$, $\gamma=120°$.

* * * * *

SEQUENCE LISTING

```
<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: PIM-1
      substrate recognition peptide
<220> FEATURE:
<221> NAME/KEY: MOD_RES
<222> LOCATION: (1)..(2)
<223> OTHER INFORMATION: Lys or Arg
<220> FEATURE:
<221> NAME/KEY: MOD_RES
<222> LOCATION: (4)
<223> OTHER INFORMATION: Lys or Arg
<220> FEATURE:
<221> NAME/KEY: MOD_RES
<222> LOCATION: (6)
<223> OTHER INFORMATION: Ser or Thr
<220> FEATURE:
<221> NAME/KEY: MOD_RES
<222> LOCATION: (7)
<223> OTHER INFORMATION: any amino acid with a small side chain
```

-continued

```
<400> SEQUENCE: 1

Xaa Xaa Arg Xaa Leu Xaa Xaa
 1               5

<210> SEQ ID NO 2
<211> LENGTH: 313
<212> TYPE: PRT
<213> ORGANISM: Homo sapiens

<400> SEQUENCE: 2

Met Leu Leu Ser Lys Ile Asn Ser Leu Ala His Leu Arg Ala Ala Pro
 1               5                  10                  15

Cys Asn Asp Leu His Ala Thr Lys Leu Ala Pro Gly Lys Glu Lys Glu
                20                  25                  30

Pro Leu Glu Ser Gln Tyr Gln Val Gly Pro Leu Leu Gly Ser Gly Gly
            35                  40                  45

Phe Gly Ser Val Tyr Ser Gly Ile Arg Val Ser Asp Asn Leu Pro Val
        50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                85                  90                  95

Ser Ser Gly Phe Ser Gly Val Ile Arg Leu Leu Asp Trp Phe Glu Arg
            100                 105                 110

Pro Asp Ser Phe Val Leu Ile Leu Glu Arg Pro Glu Pro Val Gln Asp
        115                 120                 125

Leu Phe Asp Phe Ile Thr Glu Arg Gly Ala Leu Gln Glu Glu Leu Ala
    130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Glu Ile Ile Arg Gly Gln Val Phe Phe Arg
                245                 250                 255

Gln Arg Val Ser Ser Glu Cys Gln His Leu Ile Arg Trp Cys Leu Ala
            260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 3
<211> LENGTH: 16
<212> TYPE: PRT
<213> ORGANISM: Homo sapiens
```

-continued

```
<400> SEQUENCE: 3

Leu Tyr Met Val Met Glu Tyr Val Ala Gly Gly Glu Met Phe Ser His
1               5                   10                  15

<210> SEQ ID NO 4
<211> LENGTH: 15
<212> TYPE: PRT
<213> ORGANISM: Homo sapiens

<400> SEQUENCE: 4

Leu Tyr Leu Val Phe Glu Phe Leu His Gln Asp Leu Lys Lys Phe
1               5                   10                  15

<210> SEQ ID NO 5
<211> LENGTH: 17
<212> TYPE: PRT
<213> ORGANISM: Homo sapiens

<400> SEQUENCE: 5

Lys Ile Gly Met Ile Glu Ile Val Lys Asp Ala Thr Thr Ile Ala Lys
1               5                   10                  15

Ile

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence:
      Illustrative His-tagged peptide

<400> SEQUENCE: 6

Met Gly Ser Ser His His His His His His Ser Ser Gly Leu Val Pro
1               5                   10                  15

Arg Gly Ser His
            20

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: S6 peptide
      fragment

<400> SEQUENCE: 7

Arg Arg Arg Leu Ser Ser Leu Arg Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Histone H1
      peptide fragment

<400> SEQUENCE: 8

Lys Arg Arg Ala Ser Gly Pro
1               5

<210> SEQ ID NO 9
<211> LENGTH: 11
<212> TYPE: PRT
```

-continued

```
<213> ORGANISM: Artificial Sequence
<220> FEATURE:
<223> OTHER INFORMATION: Description of Artificial Sequence: S6 peptide
      fragment

<400> SEQUENCE: 9

Ala Lys Arg Arg Arg Leu Ser Ser Leu Arg Ala
 1               5                   10
```